(12) United States Patent
Guney et al.

(10) Patent No.: US 11,452,834 B2
(45) Date of Patent: Sep. 27, 2022

(54) PATIENT INTERFACE

(71) Applicant: ResMed Pty Ltd, Bella Vista (AU)

(72) Inventors: Memduh Guney, Sydney (AU);
Rupert Christian Scheiner, Sydney (AU); David Anthony Pidcock, Sydney (AU); Gerard Michael Rummery, Woodford (AU); Matthew Eves, Sydney (AU); Craig David Edwards, Sydney (AU); Melanie Lucia Cariola, Sydney (AU); Muditha Pradeep Dantanarayana, Sydney (AU); Michael Fu Pin Chen, Malmo (SE); Christopher Scott Skipper, Sydney (AU); Karthikeyan Selvarajan, Sydney (AU); Steven John Lubke, Sydney (AU); Bruce David Gregory, Sydney (AU); Joel Edward Gibson, Sydney (AU); Andrew David Cameron, Sydney (AU); Philip Rodney Kwok, Sydney (AU)

(73) Assignee: ResMed Pty Ltd, Bella Vista (AU)

( * ) Notice: Subject to any disclaimer, the term of this patent is extended or adjusted under 35 U.S.C. 154(b) by 0 days.

(21) Appl. No.: 17/689,102

(22) Filed: Mar. 8, 2022

(65) Prior Publication Data

US 2022/0193362 A1 Jun. 23, 2022

Related U.S. Application Data

(63) Continuation of application No. 16/872,442, filed on May 12, 2020, which is a continuation of application
(Continued)

(30) Foreign Application Priority Data

| Jan. 11, 2008 | (AU) | 2008900134 |
| Jan. 11, 2008 | (AU) | 2008900136 |

(Continued)

(51) Int. Cl.
*A61M 16/06* (2006.01)
*A61M 16/08* (2006.01)
*A61M 16/20* (2006.01)

(52) U.S. Cl.
CPC .... *A61M 16/0666* (2013.01); *A61M 16/0611* (2014.02); *A61M 16/0616* (2014.02);
(Continued)

(58) Field of Classification Search
CPC .............. A61M 16/06; A61M 16/0605; A61M 16/0611; A61M 16/0666; A61M 16/0672; A61M 16/0683
See application file for complete search history.

(56) References Cited

U.S. PATENT DOCUMENTS

| 443,191 A | 12/1890 | Illing |
| 1,081,745 A | 12/1913 | Johnston |

(Continued)

FOREIGN PATENT DOCUMENTS

| AU | 199651130 | 10/1996 |
| AU | 2005100738 | 11/2005 |

(Continued)

OTHER PUBLICATIONS

Proceeding Correspondence mailed Nov. 23, 2021 in corresponding NZ Application 754622, including Opponent's Nov. 22, 2021 correspondence (6 pages).
(Continued)

*Primary Examiner* — Joseph D. Boecker
(74) *Attorney, Agent, or Firm* — Nixon & Vanderhye P.C.

(57) ABSTRACT

A patient interface for delivering breathable gas to a patient includes a nasal prong assembly including a pair of nasal (Continued)

prongs structured to sealingly communicate with nasal passages of a patient's nose in use and headgear to maintain the nasal prong assembly in a desired position on the patient's face. The headgear includes side straps and rigidizers provided to respective side straps. Each rigidizer includes a first end portion that provides a connector structured to engage a respective end of the nasal prong assembly and an inwardly curved protrusion in the form of a cheek support that curves inwardly of the connector. The cheek support is adapted to follow the contour of the patient's cheek and guide a respective end portion of the side strap into engagement with the patient's cheek to provide a stable cheek support.

30 Claims, 250 Drawing Sheets

Related U.S. Application Data

No. 15/288,510, filed on Oct. 7, 2016, now Pat. No. 10,675,428, which is a continuation of application No. 12/219,852, filed on Jul. 29, 2008, now Pat. No. 9,480,809.

(60) Provisional application No. 61/071,512, filed on May 2, 2008, provisional application No. 61/064,818, filed on Mar. 28, 2008, provisional application No. 61/006,409, filed on Jan. 11, 2008, provisional application No. 60/996,160, filed on Nov. 5, 2007, provisional application No. 60/935,179, filed on Jul. 30, 2007.

(30) Foreign Application Priority Data

| Jan. 11, 2008 | (AU) | ............................... | 2008900137 |
| Jan. 11, 2008 | (AU) | ............................... | 2008900138 |
| Jan. 11, 2008 | (AU) | ............................... | 2008900139 |
| Jan. 11, 2008 | (AU) | ............................... | 2008900140 |
| Jan. 11, 2008 | (AU) | ............................... | 2008900141 |
| Feb. 25, 2008 | (AU) | ............................... | 2008900891 |

(52) U.S. Cl.
CPC .... *A61M 16/0622* (2014.02); *A61M 16/0683* (2013.01); *A61M 16/0816* (2013.01); *A61M 16/0825* (2014.02); *A61M 16/0875* (2013.01); *A61M 16/208* (2013.01); *A61M 2205/42* (2013.01); *A61M 2207/00* (2013.01)

(56) References Cited

U.S. PATENT DOCUMENTS

| 1,125,542 A | 1/1915 | Humphries |
| 1,192,186 A | 7/1916 | Greene |
| 1,229,050 A | 6/1917 | Donald |
| 1,282,527 A | 10/1918 | Bidonde |
| 1,362,766 A | 12/1920 | McGargill |
| 1,445,010 A | 2/1923 | Feinberg |
| 1,610,793 A | 12/1926 | Kaufman |
| 1,873,160 A | 8/1932 | Sturtevant |
| 2,353,643 A | 7/1944 | Bulbulian |
| 2,415,846 A | 2/1947 | Randall |
| 2,433,565 A | 12/1947 | Korman |
| 2,625,155 A | 1/1953 | Engelder |
| 2,706,983 A | 4/1955 | Matheson et al. |
| 2,998,818 A | 5/1956 | Tabor |
| 2,931,356 A | 4/1960 | Schwarz |
| 3,013,556 A | 12/1961 | Galleher |
| 3,670,726 A | 3/1972 | Mahon et al. |
| 3,682,171 A | 8/1972 | Dali et al. |
| 3,739,774 A | 6/1973 | Gregory |
| 3,754,552 A | 8/1973 | King |
| 3,861,385 A | 1/1975 | Carden |
| 3,902,486 A | 9/1975 | Guichard |
| 3,905,361 A | 9/1975 | Hewson et al. |
| 3,938,614 A | 2/1976 | Ahs |
| 3,972,321 A | 8/1976 | Proctor |
| 4,006,744 A | 2/1977 | Steer |
| 4,142,527 A | 3/1979 | Garcia |
| 4,153,051 A | 5/1979 | Shippert |
| 4,156,426 A | 5/1979 | Gold |
| 4,248,218 A | 2/1981 | Fischer |
| 4,263,908 A | 4/1981 | Mizerak |
| 4,264,743 A | 4/1981 | Maruyama et al. |
| 4,266,540 A | 5/1981 | Panzik et al. |
| 4,267,845 A | 5/1981 | Robertson, Jr. et al. |
| 4,273,124 A | 6/1981 | Zimmerman |
| 4,312,359 A | 1/1982 | Olson |
| 4,367,735 A | 1/1983 | Dali |
| 4,367,816 A | 1/1983 | Wilkes |
| 4,406,283 A | 9/1983 | Bir |
| 4,414,973 A | 11/1983 | Matheson et al. |
| 4,422,456 A | 12/1983 | Teip |
| 4,449,526 A | 5/1984 | Elam |
| 4,455,675 A | 6/1984 | Bose et al. |
| 4,493,614 A | 1/1985 | Chu et al. |
| 4,548,200 A | 10/1985 | Wapner |
| 4,549,542 A | 11/1985 | Chein |
| 4,572,323 A | 2/1986 | Randall |
| 4,587,967 A | 5/1986 | Chu et al. |
| 4,601,465 A | 7/1986 | Roy |
| 4,617,637 A | 11/1986 | Chu et al. |
| 4,630,604 A | 12/1986 | Montesi |
| 4,641,647 A | 2/1987 | Behan |
| 4,660,555 A | 4/1987 | Payton |
| 4,671,271 A | 6/1987 | Bishop et al. |
| 4,676,241 A | 6/1987 | Webb et al. |
| 4,699,139 A | 10/1987 | Marshall et al. |
| 4,706,664 A | 11/1987 | Snook et al. |
| 4,711,636 A | 12/1987 | Bierman |
| 4,713,844 A | 12/1987 | Westgate |
| D293,613 S | 1/1988 | Wingler |
| 4,753,233 A | 6/1988 | Grimes |
| 4,767,411 A | 8/1988 | Edmunds |
| 4,774,946 A | 11/1988 | Ackerman et al. |
| 4,782,832 A | 11/1988 | Trimble et al. |
| 4,790,829 A | 12/1988 | Bowden et al. |
| 4,802,857 A | 2/1989 | Laughlin |
| 4,803,981 A | 2/1989 | Vickery |
| 4,811,730 A | 3/1989 | Milano |
| 4,830,138 A | 5/1989 | Palmaer et al. |
| 4,838,878 A | 6/1989 | Kalt et al. |
| 4,899,740 A | 2/1990 | Napolitano |
| 4,907,584 A | 3/1990 | McGinnis |
| 4,915,105 A | 4/1990 | Lee |
| 4,919,128 A | 4/1990 | Kopala et al. |
| 4,919,654 A | 4/1990 | Kalt |
| 4,944,310 A | 7/1990 | Sullivan |
| 4,945,907 A | 8/1990 | Tayebi |
| 4,960,121 A | 10/1990 | Nelson et al. |
| 4,966,590 A | 10/1990 | Kalt |
| 4,969,880 A | 11/1990 | Zamierowski |
| 4,971,051 A | 11/1990 | Toffolon |
| 4,976,698 A | 12/1990 | Stokley |
| 4,989,599 A | 2/1991 | Carter |
| 4,996,983 A | 3/1991 | Amrhein |
| 5,000,173 A | 3/1991 | Zalkin et al. |
| 5,005,571 A | 4/1991 | Dietz |
| 5,020,163 A | 6/1991 | Aileo et al. |
| 5,022,900 A | 6/1991 | Bar-Yona et al. |
| 5,023,955 A | 6/1991 | Murphy, II et al. |
| 5,025,805 A | 6/1991 | Nutter |
| 5,038,772 A | 8/1991 | Kolbe et al. |
| 5,042,478 A | 8/1991 | Kopala et al. |
| 5,046,200 A | 9/1991 | Feder |
| 5,046,491 A | 9/1991 | Derrick |
| 5,074,297 A | 12/1991 | Venegas |
| 5,113,857 A | 5/1992 | Dickerman et al. |
| 5,117,818 A | 6/1992 | Palfy |

(56) References Cited

U.S. PATENT DOCUMENTS

| | | |
|---|---|---|
| 5,121,745 A | 6/1992 | Israel |
| 5,127,397 A | 7/1992 | Kohnke |
| 5,137,017 A | 8/1992 | Salter |
| 5,138,722 A | 8/1992 | Urella et al. |
| D333,015 S | 2/1993 | Farmer et al. |
| 5,188,101 A | 2/1993 | Tumolo |
| 5,207,665 A | 5/1993 | Davis et al. |
| 5,220,699 A | 6/1993 | Farris |
| 5,243,709 A | 9/1993 | Sheehan et al. |
| 5,243,971 A * | 9/1993 | Sullivan ............... A61M 16/06 128/207.18 |
| 5,245,995 A | 9/1993 | Sullivan et al. |
| 5,261,893 A | 11/1993 | Zamierowski |
| 5,263,939 A | 11/1993 | Wortrich |
| 5,265,592 A | 11/1993 | Beaussant |
| 5,265,595 A | 11/1993 | Rudolph |
| 5,267,557 A | 12/1993 | Her-Mou |
| 5,269,296 A | 12/1993 | Landis |
| 5,271,391 A | 12/1993 | Graves |
| 5,304,146 A | 4/1994 | Johnson et al. |
| 5,299,599 A | 5/1994 | Farmer et al. |
| 5,335,656 A | 8/1994 | Bowe et al. |
| 5,349,949 A | 9/1994 | Schegerin |
| 5,355,878 A | 10/1994 | Griffiths et al. |
| 5,355,893 A | 10/1994 | Mick et al. |
| 5,364,367 A | 11/1994 | Banks et al. |
| 5,372,130 A | 12/1994 | Stem et al. |
| 5,372,388 A | 12/1994 | Gargiulo |
| 5,372,389 A | 12/1994 | Tam et al. |
| 5,372,390 A | 12/1994 | Conway et al. |
| 5,372,391 A | 12/1994 | Bast et al. |
| 5,375,593 A | 12/1994 | Press |
| 5,385,141 A | 1/1995 | Granatiero |
| 5,394,568 A | 3/1995 | Brostrom et al. |
| 5,396,885 A | 3/1995 | Nelson |
| 5,398,676 A | 3/1995 | Press et al. |
| 5,400,776 A | 3/1995 | Bartholomew |
| 5,419,318 A | 5/1995 | Tayebi |
| 5,425,359 A | 6/1995 | Liou |
| 5,429,683 A | 7/1995 | Le Mitouard |
| 5,437,267 A | 8/1995 | Weinstein et al. |
| 5,441,046 A | 8/1995 | Starr et al. |
| 5,462,528 A | 10/1995 | Roewer |
| 5,477,852 A | 12/1995 | Landis et al. |
| 5,526,806 A | 1/1996 | Sansoni |
| 5,488,948 A | 2/1996 | Dubruille et al. |
| 5,509,409 A | 4/1996 | Weatherholt |
| 5,513,634 A | 5/1996 | Jackson |
| 5,513,635 A | 5/1996 | Bedi |
| 5,524,300 A | 6/1996 | Chiang |
| 5,533,506 A | 7/1996 | Wood |
| 5,538,000 A | 7/1996 | Rudolph |
| 5,538,001 A | 7/1996 | Bridges |
| 5,560,354 A | 10/1996 | Berthon-Jones et al. |
| 5,570,684 A | 11/1996 | Behr |
| 5,592,938 A | 1/1997 | Scarberry et al. |
| 5,623,923 A | 4/1997 | Bertheau et al. |
| 5,647,357 A | 7/1997 | Barnett et al. |
| 5,653,228 A | 8/1997 | Byrd |
| 5,655,527 A | 8/1997 | Scarberry et al. |
| 5,662,101 A | 9/1997 | Ogden et al. |
| 5,682,881 A | 11/1997 | Winthrop et al. |
| 5,704,345 A | 1/1998 | Berthon-Jones et al. |
| 5,707,342 A | 1/1998 | Tanaka |
| 5,724,965 A | 3/1998 | Handke et al. |
| 5,735,272 A | 4/1998 | Dillon et al. |
| 5,740,799 A | 4/1998 | Nielson |
| 5,752,511 A | 5/1998 | Simmons et al. |
| 5,794,619 A | 8/1998 | Edeiman et al. |
| 5,807,341 A | 9/1998 | Heim |
| 5,842,469 A | 12/1998 | Rapp et al. |
| 5,906,203 A | 5/1999 | Klockseth et al. |
| 5,918,598 A | 7/1999 | Belfer et al. |
| 5,921,239 A | 7/1999 | McCall et al. |
| 5,954,049 A | 9/1999 | Foley et al. |
| 5,975,079 A | 11/1999 | Hellings et al. |
| 6,019,101 A | 2/2000 | Cotner et al. |
| 6,026,811 A | 2/2000 | Settle |
| 6,044,844 A | 4/2000 | Kwok et al. |
| 6,082,360 A | 7/2000 | Rudolph et al. |
| 6,086,118 A | 7/2000 | McNaughton et al. |
| 6,095,996 A | 8/2000 | Steer et al. |
| 6,098,205 A | 8/2000 | Schwartz et al. |
| 6,109,263 A | 8/2000 | Feuchtgruber |
| 6,112,746 A | 9/2000 | Kwok et al. |
| 6,119,693 A | 9/2000 | Kwok et al. |
| 6,119,694 A | 9/2000 | Correa et al. |
| 6,123,071 A | 9/2000 | Berthon-Jones et al. |
| 6,123,082 A | 9/2000 | Berthon-Jones |
| 6,139,787 A | 10/2000 | Harrison |
| 6,152,137 A | 11/2000 | Schwartz et al. |
| 6,193,914 B1 | 2/2001 | Harrison |
| 6,196,223 B1 | 3/2001 | Belfer et al. |
| 6,211,263 B1 | 4/2001 | Cinelli et al. |
| 6,231,548 B1 | 5/2001 | Bassett |
| 6,241,930 B1 | 6/2001 | Harrison |
| 6,258,066 B1 | 7/2001 | Urich |
| 6,295,366 B1 | 9/2001 | Haller et al. |
| 6,328,038 B1 | 12/2001 | Kessler et al. |
| 6,341,606 B1 | 1/2002 | Bordewick et al. |
| 6,347,631 B1 | 2/2002 | Hansen et al. |
| 6,357,441 B1 | 3/2002 | Kwok et al. |
| 6,358,279 B1 | 3/2002 | Tahi et al. |
| 6,374,826 B1 | 4/2002 | Gunaratnam et al. |
| 6,412,487 B1 | 7/2002 | Gunaratnam et al. |
| 6,412,488 B1 | 7/2002 | Barnett et al. |
| 6,412,593 B1 | 7/2002 | Jones |
| 6,419,660 B1 | 7/2002 | Russo |
| 6,422,238 B1 | 7/2002 | Lithgow |
| 6,423,036 B1 | 7/2002 | Van Huizen |
| 6,431,172 B1 | 8/2002 | Bordewick |
| 6,434,796 B1 | 8/2002 | Speirs |
| 6,439,234 B1 | 8/2002 | Curti et al. |
| 6,448,303 B1 | 9/2002 | Paul |
| 6,467,482 B1 | 10/2002 | Boussignac |
| 6,467,483 B1 | 10/2002 | Kopacko et al. |
| 6,470,887 B1 | 10/2002 | Martinez |
| 6,478,026 B1 | 11/2002 | Wood |
| 6,482,178 B1 | 11/2002 | Andrews et al. |
| 6,491,034 B1 | 12/2002 | Gunaratnam et al. |
| 6,513,526 B2 | 2/2003 | Kwok et al. |
| 6,530,373 B1 | 3/2003 | Patron et al. |
| 6,532,961 B1 | 3/2003 | Kwok et al. |
| 6,536,435 B1 | 3/2003 | Fecteau et al. |
| 6,561,188 B1 | 5/2003 | Ellis |
| 6,561,190 B1 | 5/2003 | Kwok et al. |
| 6,561,192 B2 | 5/2003 | Palmer |
| 6,561,193 B1 | 5/2003 | Noble |
| 6,571,798 B1 | 6/2003 | Thornton |
| 6,579,267 B2 | 6/2003 | Lynch et al. |
| 6,581,601 B2 | 6/2003 | Ziaee |
| 6,581,602 B2 | 6/2003 | Kwok et al. |
| 6,584,975 B1 | 7/2003 | Taylor |
| 6,595,214 B1 | 7/2003 | Hecker et al. |
| 6,595,215 B2 | 7/2003 | Wood |
| 6,607,516 B2 | 8/2003 | Cinelli et al. |
| 6,627,289 B1 | 9/2003 | Dilnik et al. |
| 6,631,718 B1 | 10/2003 | Lovell |
| 6,634,358 B2 | 10/2003 | Kwok et al. |
| 6,637,434 B2 | 10/2003 | Noble |
| 6,644,315 B2 | 11/2003 | Ziaee |
| 6,655,385 B1 | 12/2003 | Curti et al. |
| 6,663,600 B2 | 12/2003 | Bierman et al. |
| 6,669,712 B1 | 12/2003 | Cardoso |
| D485,905 S | 1/2004 | Moore et al. |
| 6,679,257 B1 | 1/2004 | Robertson et al. |
| 6,679,265 B2 | 1/2004 | Strickland et al. |
| 6,701,927 B2 | 3/2004 | Kwok et al. |
| 6,710,099 B2 | 3/2004 | Cinelli et al. |
| 6,766,800 B2 | 7/2004 | Chu et al. |
| 6,766,817 B2 | 7/2004 | da Silva |
| 6,776,162 B2 | 8/2004 | Wood |
| 6,776,163 B2 | 8/2004 | Dougill et al. |
| 6,789,543 B2 | 9/2004 | Cannon |

(56) References Cited

U.S. PATENT DOCUMENTS

| | | |
|---|---|---|
| 6,805,117 B1 | 10/2004 | Ho et al. |
| 6,807,967 B2 | 10/2004 | Wood |
| 6,817,362 B2 | 11/2004 | Gelinas et al. |
| 6,820,617 B2 | 11/2004 | Robertson et al. |
| 6,823,865 B2 | 11/2004 | Drew et al. |
| 6,823,869 B2 | 11/2004 | Raje et al. |
| 6,834,650 B1 | 12/2004 | Fini |
| 6,840,238 B1 | 1/2005 | Van Hegelsom |
| 6,860,270 B2 | 3/2005 | Sniadach |
| 6,895,965 B2 | 5/2005 | Scarberry et al. |
| 6,907,882 B2 | 6/2005 | Ging et al. |
| 6,918,404 B2 | 7/2005 | Dias da Silva |
| 6,926,004 B2 | 8/2005 | Schumacher |
| 6,938,620 B2 | 9/2005 | Payne, Jr. |
| 6,968,844 B2 | 11/2005 | Liland |
| 6,972,003 B2 | 12/2005 | Bierman et al. |
| 6,986,352 B2 | 1/2006 | Frater et al. |
| 6,997,177 B2 | 2/2006 | Wood |
| 7,011,090 B2 | 3/2006 | Drew et al. |
| 7,018,362 B2 | 3/2006 | Bierman et al. |
| 7,052,127 B2 | 5/2006 | Harrison |
| 7,066,586 B2 | 6/2006 | da Silva |
| 7,076,282 B2 | 7/2006 | Munro et al. |
| 7,080,645 B2 | 7/2006 | Genger et al. |
| 7,101,359 B2 | 9/2006 | Kline et al. |
| 7,107,989 B2 | 9/2006 | Frater et al. |
| 7,146,976 B2 | 12/2006 | McKown |
| 7,152,599 B2 | 12/2006 | Thomas |
| 7,152,601 B2 | 12/2006 | Barakat et al. |
| 7,178,525 B2 | 2/2007 | Matula, Jr. et al. |
| 7,191,781 B2 | 3/2007 | Wood |
| 7,207,328 B1 | 4/2007 | Altemus |
| 7,210,481 B1 | 5/2007 | Lovell et al. |
| 7,237,551 B2 | 7/2007 | Ho et al. |
| 7,243,723 B2 | 7/2007 | Surjaatmadja |
| D550,836 S | 9/2007 | Chandran et al. |
| D552,733 S | 10/2007 | Criscuolo et al. |
| 7,285,255 B2 | 10/2007 | Kadlec et al. |
| 7,302,950 B2 | 12/2007 | Berthon-Jones et al. |
| 7,318,437 B2 | 1/2008 | Gunaratnam et al. |
| 7,353,826 B2 | 4/2008 | Sleeper et al. |
| 7,523,754 B2 | 4/2009 | Lithgow |
| 7,640,934 B2 | 1/2010 | Zollinger et al. |
| 7,658,189 B2 | 2/2010 | Davidson |
| 7,874,291 B2 | 1/2011 | Ging et al. |
| 9,480,809 B2 | 11/2016 | Guney et al. |
| 9,974,915 B2 | 5/2018 | Haskard |
| 10,675,428 B2 | 6/2020 | Guney et al. |
| 2001/0020474 A1 | 9/2001 | Hecker et al. |
| 2002/0005198 A1 | 1/2002 | Kwok et al. |
| 2002/0029780 A1 | 3/2002 | Frater et al. |
| 2002/0046755 A1 | 4/2002 | Devoss |
| 2002/0053347 A1 | 5/2002 | Ziaee |
| 2002/0066452 A1 | 6/2002 | Kessler et al. |
| 2002/0069872 A1 | 6/2002 | Gradon et al. |
| 2002/0096178 A1 | 7/2002 | Ziaee |
| 2002/0124849 A1 | 9/2002 | Billette De Villemeur |
| 2002/0143296 A1 | 10/2002 | Russo |
| 2002/0157673 A1 | 10/2002 | Kessler et al. |
| 2002/0174868 A1 | 11/2002 | Kwok et al. |
| 2002/0185134 A1 | 12/2002 | Bishop |
| 2003/0000526 A1 | 1/2003 | Goebel |
| 2003/0019495 A1 | 1/2003 | Palkon et al. |
| 2003/0079749 A1 | 5/2003 | Strickland et al. |
| 2003/0089373 A1 | 5/2003 | Gradon et al. |
| 2003/0111080 A1 | 6/2003 | Olsen et al. |
| 2003/0154980 A1 | 8/2003 | Berthon-Jones et al. |
| 2003/0168063 A1 | 9/2003 | Gambone et al. |
| 2003/0196656 A1 | 10/2003 | Moore et al. |
| 2003/0196658 A1* | 10/2003 | Ging .............. A61M 16/0683 128/201.22 |
| 2004/0025882 A1 | 2/2004 | Madaus et al. |
| 2004/0025885 A1 | 2/2004 | Payne, Jr. |
| 2004/0045551 A1 | 3/2004 | Eaton et al. |
| 2004/0065328 A1 | 4/2004 | Amarasinghe et al. |
| 2004/0106891 A1 | 6/2004 | Langan et al. |
| 2004/0111104 A1 | 6/2004 | Schein et al. |
| 2004/0112377 A1 | 6/2004 | Amarasinghe |
| 2004/0112384 A1 | 6/2004 | Lithgow et al. |
| 2004/0118406 A1 | 6/2004 | Lithgow et al. |
| 2004/0127856 A1 | 7/2004 | Johnson |
| 2004/0211428 A1 | 10/2004 | Jones |
| 2004/0221850 A1 | 11/2004 | Ging et al. |
| 2004/0226564 A1 | 11/2004 | Persson |
| 2004/0226566 A1* | 11/2004 | Gunaratnam ..... A61M 16/0622 128/207.18 |
| 2005/0011523 A1 | 1/2005 | Aylsworth et al. |
| 2005/0028822 A1 | 2/2005 | Sleeper et al. |
| 2005/0033247 A1 | 2/2005 | Thompson |
| 2005/0039757 A1 | 2/2005 | Wood |
| 2005/0051171 A1 | 3/2005 | Booth |
| 2005/0051176 A1 | 3/2005 | Riggins |
| 2005/0056286 A1 | 3/2005 | Huddart et al. |
| 2005/0061326 A1 | 3/2005 | Payne, Jr. |
| 2005/0101933 A1 | 5/2005 | Marrs et al. |
| 2005/0126573 A1 | 6/2005 | Jaffre et al. |
| 2005/0150495 A1 | 7/2005 | Rittner et al. |
| 2005/0155604 A1 | 7/2005 | Ging et al. |
| 2005/0211252 A1 | 9/2005 | Lang et al. |
| 2005/0241644 A1 | 11/2005 | Gunaratnam et al. |
| 2005/0284481 A1 | 12/2005 | Meyer |
| 2006/0060200 A1 | 3/2006 | Ho et al. |
| 2006/0081250 A1 | 4/2006 | Bordewick et al. |
| 2006/0095008 A1 | 5/2006 | Lampropoulos et al. |
| 2006/0095009 A1 | 5/2006 | Lampropoulos et al. |
| 2006/0118117 A1 | 6/2006 | Berthon-Jones |
| 2006/0124131 A1* | 6/2006 | Chandran .......... A61M 16/0666 128/206.28 |
| 2006/0137690 A1 | 6/2006 | Gunaratnam et al. |
| 2006/0174887 A1* | 8/2006 | Chandran .......... A61M 16/0816 128/207.18 |
| 2006/0196511 A1 | 9/2006 | Lau et al. |
| 2006/0207597 A1 | 9/2006 | Wright |
| 2006/0213520 A1 | 9/2006 | Frater et al. |
| 2006/0231103 A1 | 10/2006 | Matula et al. |
| 2006/0237017 A1 | 10/2006 | Davidson et al. |
| 2006/0283461 A1* | 12/2006 | Lubke ............... A61M 16/0825 128/201.19 |
| 2007/0017525 A1 | 1/2007 | Madaus et al. |
| 2007/0023044 A1 | 2/2007 | Kwok et al. |
| 2007/0125385 A1* | 6/2007 | Ho .................... A61M 16/0683 128/206.26 |
| 2007/0125387 A1* | 6/2007 | Zollinger ........... A61M 16/0611 128/207.18 |
| 2007/0144525 A1 | 6/2007 | Davidson et al. |
| 2007/0186930 A1 | 8/2007 | Davidson et al. |
| 2007/0272249 A1 | 11/2007 | Chandran et al. |
| 2007/0282272 A1 | 12/2007 | Bannon et al. |
| 2008/0004573 A1 | 1/2008 | Kaufmann et al. |
| 2008/0006277 A1 | 1/2008 | Worboys et al. |
| 2008/0047560 A1 | 2/2008 | Veliss et al. |
| 2008/0060649 A1 | 3/2008 | Veliss et al. |
| 2008/0065022 A1 | 3/2008 | Kyvik et al. |
| 2008/0110469 A1 | 5/2008 | Weinberg |
| 2008/0200880 A1 | 8/2008 | Kyvik et al. |
| 2008/0257354 A1 | 10/2008 | Davidson et al. |
| 2009/0044808 A1 | 2/2009 | Guney et al. |
| 2009/0126739 A1 | 5/2009 | Ng et al. |
| 2009/0277452 A1 | 11/2009 | Lubke et al. |
| 2010/0000534 A1 | 1/2010 | Kooij et al. |
| 2010/0000537 A1* | 1/2010 | McAuley .......... A61M 16/0666 128/205.25 |
| 2010/0018534 A1 | 1/2010 | Veliss et al. |
| 2011/0232649 A1* | 9/2011 | Collazo ............. A61M 16/0605 128/207.18 |
| 2017/0021121 A1 | 1/2017 | Guney et al. |

FOREIGN PATENT DOCUMENTS

| | | |
|---|---|---|
| CN | 1750854 A | 3/2006 |
| CN | 1901961 | 1/2007 |
| DE | 185017 | 5/1907 |
| DE | 30 11 900 | 10/1980 |

(56) References Cited

FOREIGN PATENT DOCUMENTS

| | | |
|---|---|---|
| DE | 146 688 | 2/1981 |
| DE | 37 19 009 | 12/1988 |
| DE | 39 27 038 | 2/1991 |
| DE | 297 23 101 | 7/1998 |
| DE | 197 03 526 | 8/1998 |
| DE | 199 44 242 | 3/2001 |
| DE | 100 02 571 | 7/2001 |
| DE | 102 13 905 | 10/2002 |
| DE | 10 2004 055 433 | 11/2004 |
| EP | 0 288 937 | 11/1988 |
| EP | 0 427 474 | 5/1991 |
| EP | 0 466 960 | 1/1992 |
| EP | 0 303 090 | 4/1992 |
| EP | 0 658 356 | 6/1995 |
| EP | 0 776 679 | 6/1997 |
| EP | 1 099 452 | 5/2001 |
| EP | 1 258 266 | 11/2002 |
| EP | 1 481 702 | 12/2004 |
| EP | 1 721 630 A2 | 11/2006 |
| EP | 2 027 880 A1 | 2/2009 |
| EP | 2 140 902 A1 | 1/2010 |
| FR | 2 720 280 | 12/1995 |
| GB | 532 214 | 1/1941 |
| GB | 2 176 404 | 12/1986 |
| GB | 2 368 533 | 8/2003 |
| GB | 2 385 533 | 8/2003 |
| JP | 2006-518230 | 8/2006 |
| JP | 2006-518231 | 8/2006 |
| JP | 2008-541955 | 11/2008 |
| NZ | 570059 A | 8/2010 |
| NZ | 582559 | 4/2011 |
| WO | WO 1982/003548 | 10/1982 |
| WO | WO 1987/001950 | 4/1987 |
| WO | WO 1992/020392 | 11/1992 |
| WO | WO 1992/020395 | 11/1992 |
| WO | WO 1996/028207 | 9/1996 |
| WO | WO 1998/004310 | 2/1998 |
| WO | WO 1998/012965 | 4/1998 |
| WO | WO 1998/023305 | 6/1998 |
| WO | WO 1999/016327 | 4/1999 |
| WO | WO 1999/025410 | 5/1999 |
| WO | WO 1999/043375 | 9/1999 |
| WO | WO 1999/061088 | 12/1999 |
| WO | WO 2000/020072 | 4/2000 |
| WO | WO 2000/038772 | 7/2000 |
| WO | WO 2000/050121 | 8/2000 |
| WO | WO 2000/069521 | 11/2000 |
| WO | WO 2000/072905 | 12/2000 |
| WO | WO 2000/074758 | 12/2000 |
| WO | WO 2000/076568 | 12/2000 |
| WO | WO 2000/078384 | 12/2000 |
| WO | WO 2001/062326 | 8/2001 |
| WO | WO 2001/095965 | 12/2001 |
| WO | WO 2001/097892 | 12/2001 |
| WO | WO 2001/097893 | 12/2001 |
| WO | WO 2002/038221 | 5/2002 |
| WO | WO 2002/045784 | 6/2002 |
| WO | PCT/AU2003/00458 | 4/2003 |
| WO | WO 2003/090827 | 11/2003 |
| WO | WO 2003/105921 | 12/2003 |
| WO | WO 2004/022146 | 3/2004 |
| WO | WO 2004/041342 | 5/2004 |
| WO | WO 2004/073778 | 9/2004 |
| WO | WO 2004/078230 | 9/2004 |
| WO | WO 2005/053781 | 6/2005 |
| WO | WO 2005/063326 | 7/2005 |
| WO | WO 2005/063328 | 7/2005 |
| WO | WO 2005/086943 | 9/2005 |
| WO | WO 2005/099801 | 10/2005 |
| WO | WO 2005/110220 | 11/2005 |
| WO | WO 2005/118040 | 12/2005 |
| WO | PCT/AU2006/000031 | 1/2006 |
| WO | PCT/AU2006/000417 | 3/2006 |
| WO | PCT/AU2006/000770 | 6/2006 |
| WO | WO 2006/069415 | 7/2006 |
| WO | WO 2006/074513 | 7/2006 |
| WO | WO 2006/074516 | 7/2006 |
| WO | WO 2006/099658 | 9/2006 |
| WO | WO 2006/130903 | 12/2006 |
| WO | WO 2007/009182 | 1/2007 |
| WO | WO 2007/041751 | 4/2007 |
| WO | WO 2007/041786 | 4/2007 |
| WO | WO 2007/048174 | 5/2007 |
| WO | WO 2007/053878 | 5/2007 |
| WO | PCT/AU2007/001051 | 7/2007 |
| WO | PCT/AU2007/001936 | 12/2007 |
| WO | WO 2007/143772 | 12/2007 |
| WO | WO 2007/145534 | 12/2007 |
| WO | WO 2008/007985 | 1/2008 |
| WO | WO 2008/011682 | 1/2008 |
| WO | WO 2008/011683 | 1/2008 |
| WO | WO 2008/014543 | 2/2008 |
| WO | WO 2008/040050 | 4/2008 |
| WO | WO 2008/070929 | 6/2008 |
| WO | WO 2009/059353 | 5/2009 |
| WO | WO 2009/108994 | 9/2009 |
| WO | WO 2009/109004 | 9/2009 |
| WO | WO 2010/028425 | 3/2010 |

OTHER PUBLICATIONS

Proceeding Correspondence mailed Jan. 28, 2022 in corresponding NZ Application 754622, including First Amended Counterstatement dated Dec. 22, 2021, and Opponent's Dec. 23, 2021 comments (21 pages).
Notice of Opposition to Grant of Patent mailed Jun. 28, 2021 in corresponding NZ Application 754622 (3 pages).
Extension of Time Granted mailed Jun. 28, 2021 in corresponding NZ Application 754622 (1 page).
Statement of Case mailed Aug. 27, 2021 in corresponding NZ Application 754622 (11 pages).
Deadline for Counterstatement mailed Aug. 27, 2021 in corresponding NZ Application 754622 (2 pages).
First Examination Report dated Jan. 21, 2021 in corresponding NZ Application 771895 (2 pages).
Communication pursuant to Article 94(3) EPC dated Feb. 5, 2021 in corresponding EP Application 17176525.8 (6 pages).
NZ First Examination Report dated Aug. 8, 2019 in corresponding NZ Application 754622.
A Counterstatement issued in corresponding New Zealand Application No. 722816 dated Dec. 5, 2018, with proposed claim amendments (29 pages).
A Letter to Iponz filed by Baldwins on behalf of Fisher & Paykel Healthcare Limited in corresponding New Zealand Application No. 722816 dated Dec. 18, 2018, (4 pages).
A Proceeding Correspondence issued in corresponding New Zealand Application No. 722816, dated Jan. 28, 2019 (1 page).
A Statement of Case issued Aug. 23, 2018 in a corresponding New Zealand Application No. 722816, (20 pages).
A Deadline for Counterstatement issued Sep. 12, 2018 in a corresponding New Zealand Application No. 722816 (1 page).
An Extended European Search Report dated Apr. 24, 2018, in a corresponding European Patent Application No. 17176525.8 (8 pages).
A Notice of Opposition to Grant of Patent (Section 21) dated Jun. 22, 2018, issued in a corresponding New Zealand Patent Application No. 722816 (2 pages).
A Third Office Action dated Jun. 7, 2017 in a corresponding Chinese Application No. 201410757943.9 (5 pages), and an English translation thereof (4 pages).
Deadline for Counterstatement issued May 15, 2017 in a corresponding New Zealand Application No. 706053 (2 pages), forwarding a Second Notice of Opposition (2 pages) and a Statement of Case dated Apr. 28, 2017 (12 pages).
U.S. Appl. No. 10/385,701, filed Aug. 2003, Berthon-Jones et al.
U.S. Appl. No. 10/533,928, filed Jul. 2005, Berthon-Jones.
U.S. Appl. No. 10/584,711, filed Dec. 2004, Davidson.
U.S. Appl. No. 10/655,622, filed Sep. 2003, Lithgow.
U.S. Appl. No. 10/781,929, filed Jan. 2008, Gunaratnam et al.

(56) References Cited

OTHER PUBLICATIONS

U.S. Appl. No. 10/871,929, filed Feb. 2004, Surjaatmadja.
U.S. Appl. No. 11/080,446, filed Jul. 2005, Ging et al.
U.S. Appl. No. 11/447,295, filed Jun. 2006, Lubke et al.
U.S. Appl. No. 11/474,415, filed Jun. 2006, Davidson et al.
U.S. Appl. No. 11/491,016, filed Feb. 2007, Kwok et al.
U.S. Appl. No. 11/597,909, filed Jul. 2007, Worboys.
U.S. Appl. No. 11/703,082, filed Feb. 2007, Davidson.
U.S. Appl. No. 11/878,932, filed Jul. 2007, Veliss et al.
U.S. Appl. No. 11/878,933, filed Jul. 2007, Veliss et al.
U.S. Appl. No. 12/081,696, filed Apr. 2008, Davidson et al.
U.S. Appl. No. 12/085,191, filed May 2008, Kwok et al.
U.S. Appl. No. 12/309,696, filed Jan. 2009, Kwok et al.
U.S. Appl. No. 12/382,517, filed Mar. 2009, Lithgow.
U.S. Appl. No. 12/448,250, filed Jun. 2009, Veliss et al.
U.S. Appl. No. 12/461,448, filed Aug. 2009, Berthon-Jones.
U.S. Appl. No. 12/478,537, filed Jun. 2009, Kooij et al.
U.S. Appl. No. 12/656,466, filed Jan. 2010, Biener et al.
U.S. Appl. No. 12/700,878, filed Feb. 2010, Davidson et al.
U.S. Appl. No. 60/424,686, filed Nov. 2002, Lithgow.
U.S. Appl. No. 60/483,622, filed Jul. 2003, Kwok et al.
U.S. Appl. No. 60/533,214, filed Dec. 2003, Drew.
U.S. Appl. No. 60/634,802, filed Dec. 2004, Chandran.
U.S. Appl. No. 60/645,672, filed Jan. 2005, Chandran.
U.S. Appl. No. 60/795,615, filed Apr. 2006, Wdson et al.
U.S. Appl. No. 60/833,841, filed Jul. 2006, Veliss.
U.S. Appl. No. 60/835,442, filed Aug. 2006, Selvarajan et al.
U.S. Appl. No. 60/852,649, filed Oct. 2006, Selvarajan et al.
U.S. Appl. No. 60/874,968, filed Dec. 2006, Kwok et al.
U.S. Appl. No. 60/907,856, filed Apr. 2007, Davidson et al.
U.S. Appl. No. 60/924,241, filed May 2007, Kwok et al.
U.S. Appl. No. 60/929,393, filed Jun. 2007, Kwok et al.
U.S. Appl. No. 60/935,336, filed Aug. 2007, Davidson et al.
U.S. Appl. No. 61/213,326, filed May 2009, Dravitzki et al.
U.S. Appl. No. 61/222,711, filed Jul. 2009, Dravitzki et al.
U.S. Appl. No. 61/263,175, filed Nov. 2009, Dravitzki et al.
U.S. Appl. No. 61/272,162, filed Aug. 2009, Dravitzki et al.
U.S. Appl. No. 61/272,250, filed Sep. 2009, Dravitzki et al.
Notice of Opposition to Grant of Patent (Section 21) (2 pages), Application Under Regulation 168 for Extension of Time (1 page), and Grant of extension of time (1 page), issued Feb. 28, 2017 in a corresponding New Zealand Application No. 706053.
A Second Office Action dated Dec. 9, 2016 in a corresponding Chinese Application No. 201410757943.9 (8 pages), and an English translation thereof (8 pages).
Further Examination Report dated Jun. 30, 2016 in a corresponding New Zealand Application No. 706053 (3 pages).
Notification of the First Office Action dated Mar. 25, 2016 in a corresponding Chinese Patent Application No. 201410757943.9 (5 pages), and an English translation thereof (7 pages).
Sixth Office Action dated Apr. 30, 2015 in a corresponding Chinese Application No. 200810129969.3, and English translation thereof (8 pages).
First Examination Report dated Mar. 30, 2015 issued in a corresponding New Zealand Application No. 706053 (2 pages).
Decision to Refuse a European Patent Application issued in corresponding European Application No. 11 191 742.3-1662, dated Feb. 11, 2015.
Minutes of the Oral Proceedings issued in corresponding European Application No. 11 191 742.3-1662, dated Feb. 11, 2015.
Further Examination Report dated Jan. 21, 2015 issued in corresponding New Zealand Application No. 615814 (2 pages).
Decision of Rejection dated Aug. 26, 2014 in corresponding Chinese Application No. 200810129969.3, with English translation thereof.
Office Action issued in corresponding Chinese Application No. 200810129969.3, dated Apr. 25, 2014, with English translation thereof.
Further Examination Report dated in corresponding New Zealand Application No. 599563 dated May 6, 2014.
Summons to Attend Oral Proceedings issued in corresponding European Application No. 11191742.3 dated Jun. 10, 2014.
Fourth Office Action issued in corresponding Chinese Patent Application No. 200810129969.3 dated Jan. 8, 2014 with English-language translation.
Communication dated Jul. 18, 2013 in European Application No. 11 191 742.3 (4 pages).
Communication dated Aug. 9, 2013 in European Application No. 11 191 782.9 (5 pages).
Notification of the Second Office Action dated Dec. 3, 2012, in Chinese Application No. 200810129969.3, with English Translation (8 pages).
Patent Examination Report No. 1 dated Aug. 24, 2012 in Australian Application No. 2008203372 (4 pages).
Extended European Search Report dated Apr. 18, 2012 in European Application No. 11191742.3 (6 pages).
Office Action issued in related Chinese Application No. 200810129969.3 (dated Feb. 14, 2012).
Office Action issued in a related European Application No. 08161249.1 (dated May 10, 2011).
"Ear Loop Face Mask".
Adam J. Singer MD et al. "The Cyanoacrylate Topical Skin Adhesives," American Journal of Emergency Medicine, vol. 26, 2008, pp. 490-496.
Webster's Third New International Dictionary, 1993, Dictionary definition for adjustable, bendable, and mild steel.
ComfortLite™, Respironics, http://comfortlite.respironics.com.
ComfortLite™ 2, Respironics, http://comfortlite2.respironics.com.
If You Hate CPAP! You Need CPAP Pro®, www.cpappro.com.
Webster's New World Dictionary, Third College Edition 1988, definition for engaged and flexible.
EP Supplementary Search Report issued in EP Application 03793493, dated Dec. 2, 2009.
European Search Report filed on Jul. 27, 2009 in EP Application No. 07784697.0.
Examination Report filed in New Zealand Application 539836, dated Aug. 25, 2005.
Examiner's Report No. 3 dated Nov. 18, 2009 in New Zealand Application No. 2003275762.
Extended European Search Report dated Sep. 3, 2009 in corresponding EP Application No. 09161984.1.
Extended European Search Report. Application No. EP 08154854, dated Nov. 27, 2008.
Fisher and Paykel Col.—Product Family—http://www.fphcare.com/osa/products.asp/.
Hans Rudolph, Inc.—Mask Products—http:/www.rudolphke.com/products.php?category=MASKS.
International Preliminary Report on Patentability for PCT/AU2004/001832, dated Jul. 3, 2006.
International Search Report for PCT/AU2005/000803, dated Jun. 30, 2005.
International Search Report filed in PCT/AU2006/000770, dated Aug. 3, 2006.
International Search Report for PCT/AU2007/001052, dated Oct. 9, 2007.
International Search Report for PCT/AU2007/001051, dated Nov. 5, 2007.
International Search Report for PCT/AU2004/0018 32, dated Mar. 24, 2005.
International Search Report for PCT/AU2007/001936, dated Mar. 4, 2008.
Joel W. Beam, "Tissue Adhesives for Simple Traumatic Lacerations," Journal of Athletic Training, 2008, vol. 43, No. 2, pp. 222-224.
Merriam-Webster Online Dictionary definition of moveable from the 14th century.
Office Action dated Dec. 22, 2009 in European Appln. No. 04802133.1.
ResMed Co.—Mask Products—httg://resmed.com/portal_/site/ResMedUS/index._jsp? . . . .
Respironics Co.—Mask Family—http:/masksfamily.respironics.com/.

(56) References Cited

OTHER PUBLICATIONS

Snapp Nasal Interface, Tiara Medical Systems, Inc.—http://www.tiaramed.com/asp_shops/shopdisplayproducts.asp?id=109&cat=SNAPP%2A+Nasal+Interface.
Subbu Venkatraman et al., "Review Skin Adhesives and Skin Adhesion a. Transdermal Drug Delivery Systems," Biomaterials, vol. 19, 1998, pp. 1119-1136.
Supplementary European Search Report dated Sep. 8, 2009 in European Appln. No. 04802133.1.
Supplementary Search Report issued in European Appln. 05746824.1, dated Dec. 17, 2009.
Supplementary European Search Report dated Dec. 18, 2009 in European Application No. 03810331.3.
Unsolicited email from Elson Silva, PhD, dated Mar. 28, 2008, "Requesting IDS of U.S. Pat. No. 6,766,817 for patents on fluids moving on porosity by Unsaturated Hydraulic Flow," (email provided in both HTML and plain text format).
International Search Report PCT/AU2003/001163, dated Nov. 4, 2003.
International Search Report PCT/AU2003/001471, dated Feb. 12, 2004.
International Search Report PCT/AU2009/000240, dated May 21, 2009.
International Search Report PCT/AU2009/000262, dated Jun. 9, 2009.
International Search Report PCT/AU2009/001144, dated Dec. 18, 2009.
EP Summons to Oral Proceedings Pursuant to Rule 115(1) EPC in Appeal No. T1813/15-3.2.02 mailed Apr. 23, 2020 in EP Application 11191742.3.
Office Action dated Jul. 14, 2022 issued in European Application No. 17176525.8 (4 pages).

\* cited by examiner

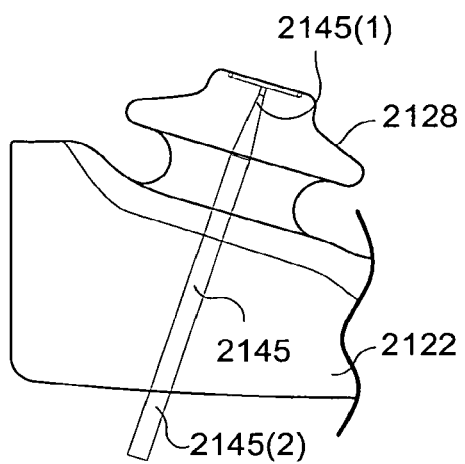 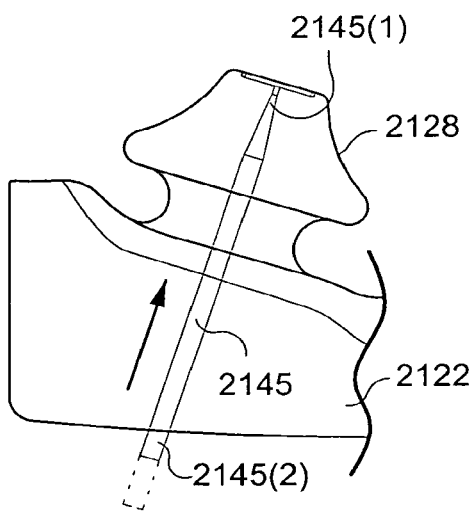
FIG. 5-19-1  FIG. 5-19-2
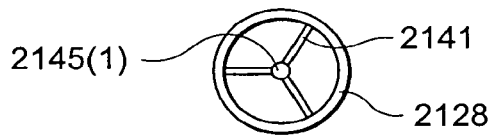
FIG. 5-19-3
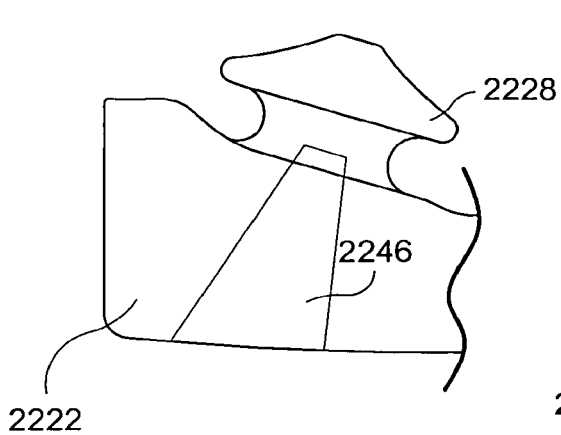 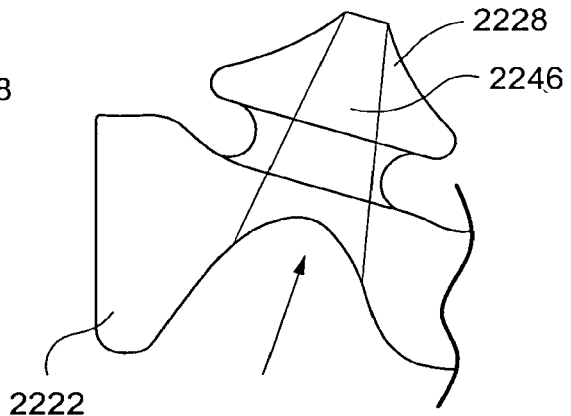
FIG. 5-20-1  FIG. 5-20-2

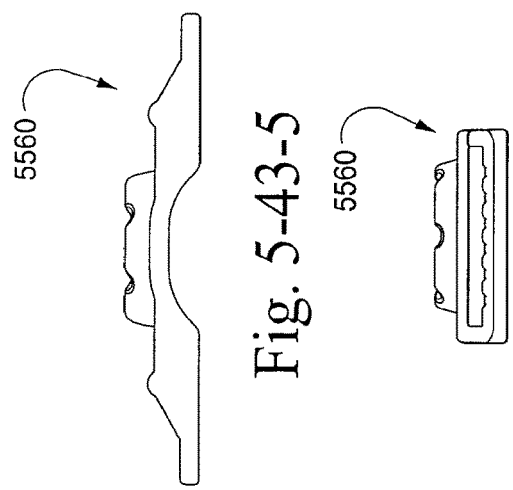
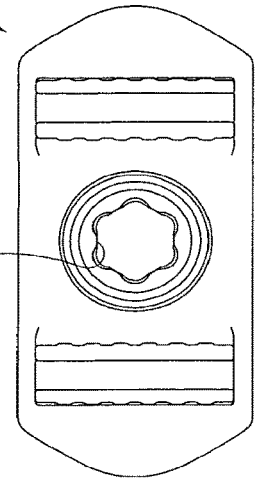
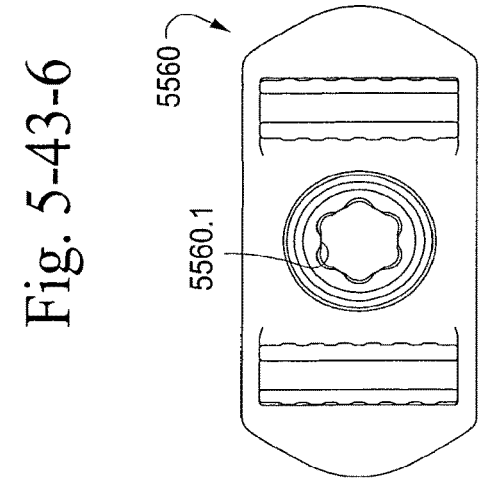
Fig. 5-43-5
Fig. 5-43-6
Fig. 5-43-7
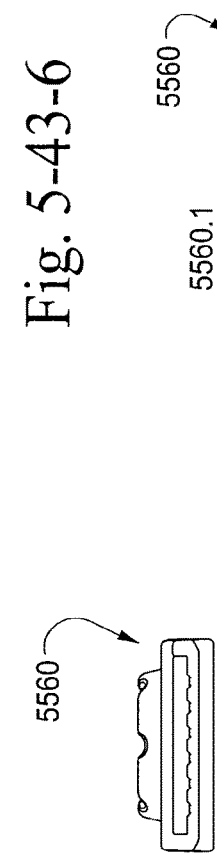
Fig. 5-43-3
Fig. 5-43-4
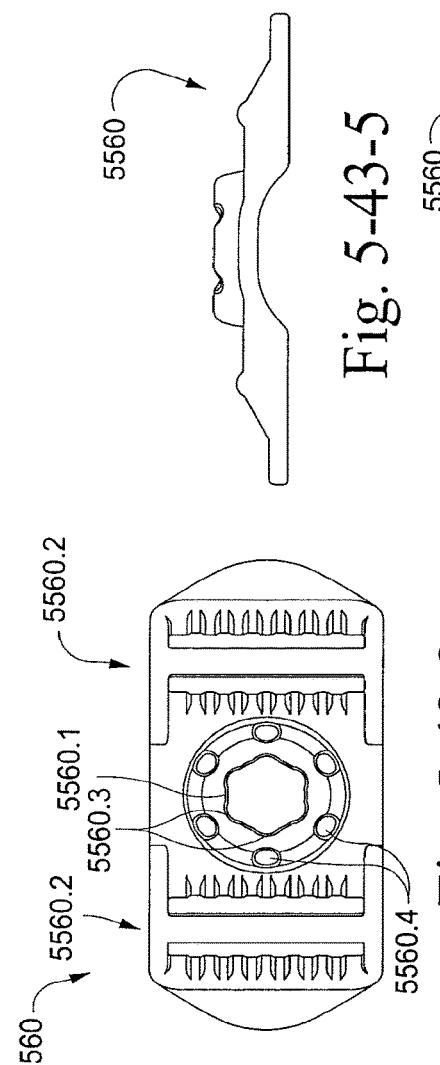
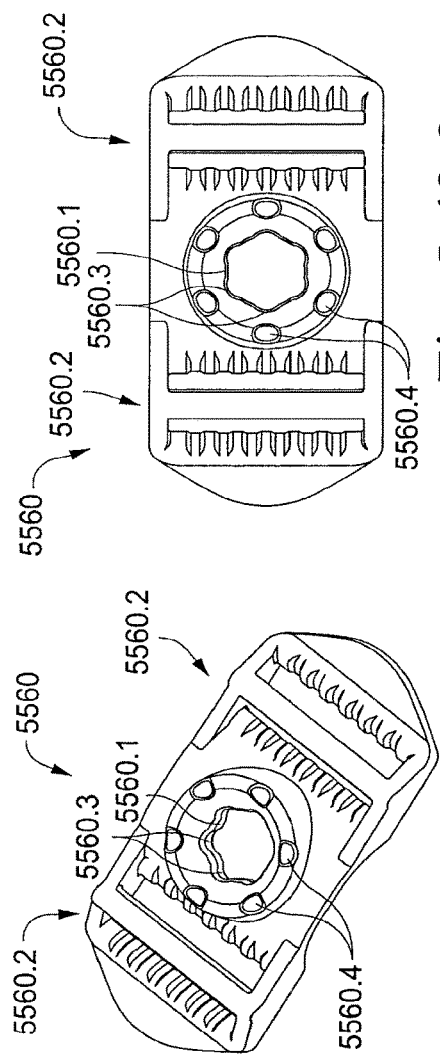
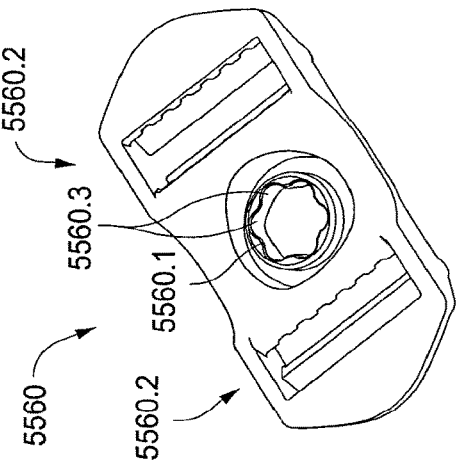
Fig. 5-43-1
Fig. 5-43-2

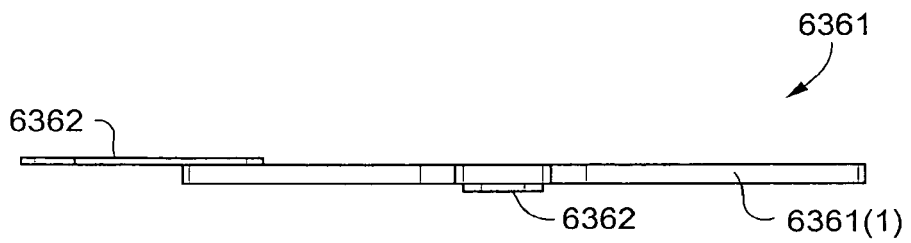
Fig. 5-47-3
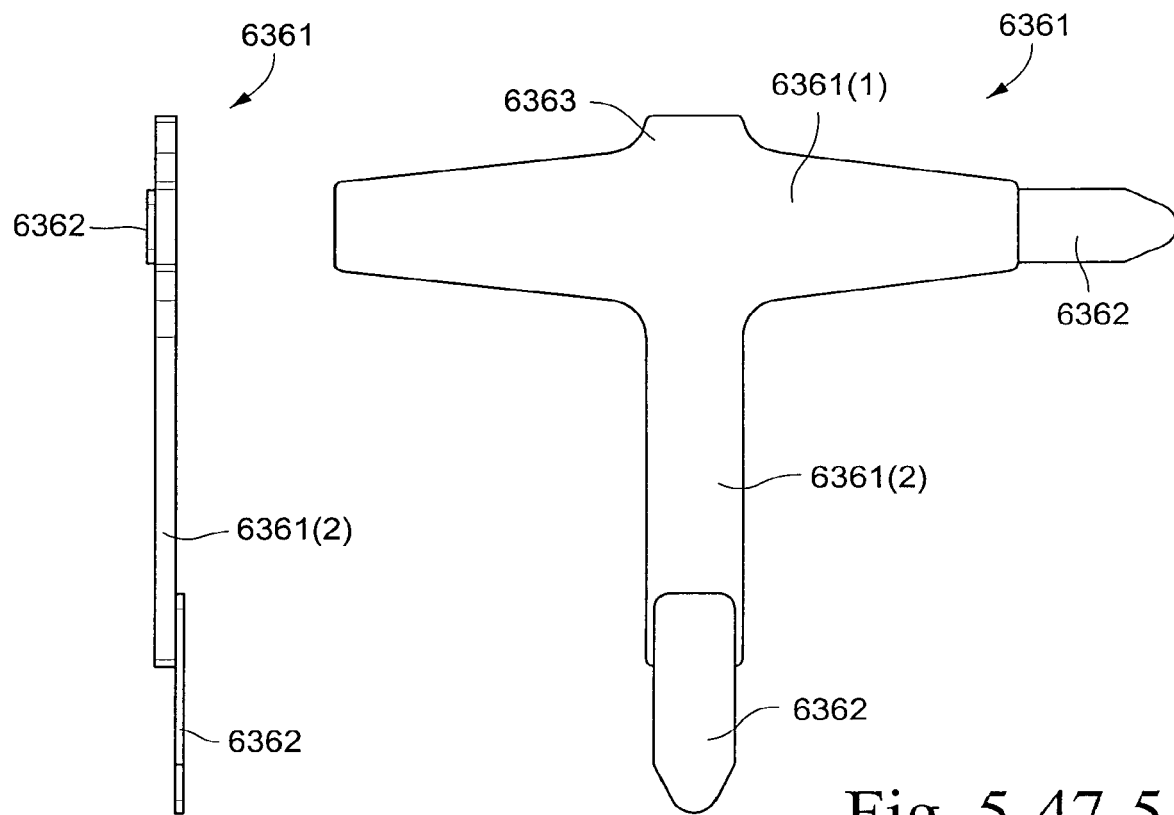
Fig. 5-47-5
Fig. 5-47-4
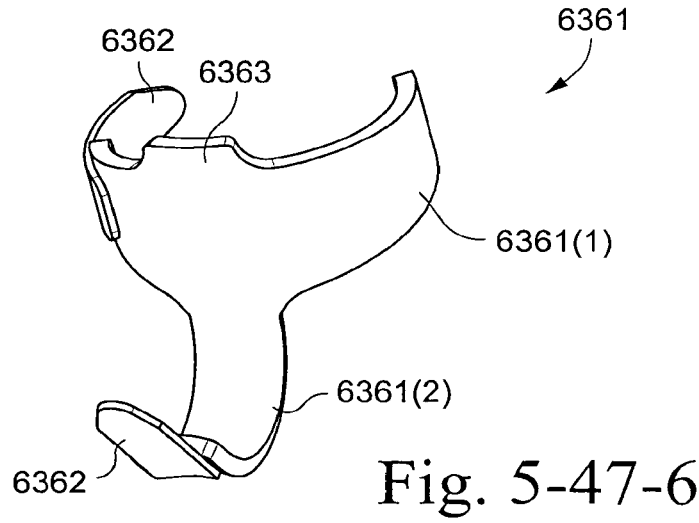
Fig. 5-47-6

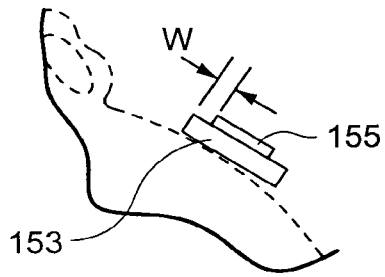
FIG. 10-3-2
(Prior Art)
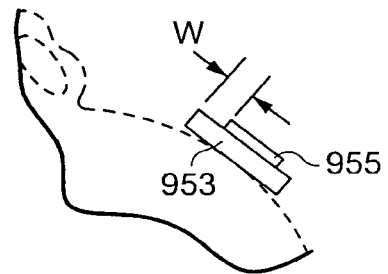
FIG. 10-4
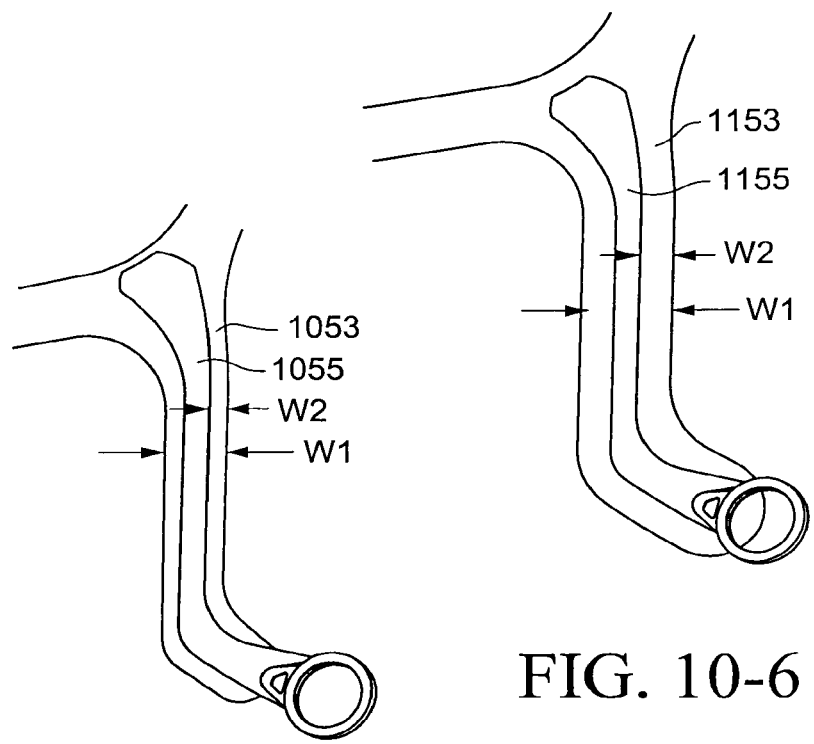
FIG. 10-5
FIG. 10-6

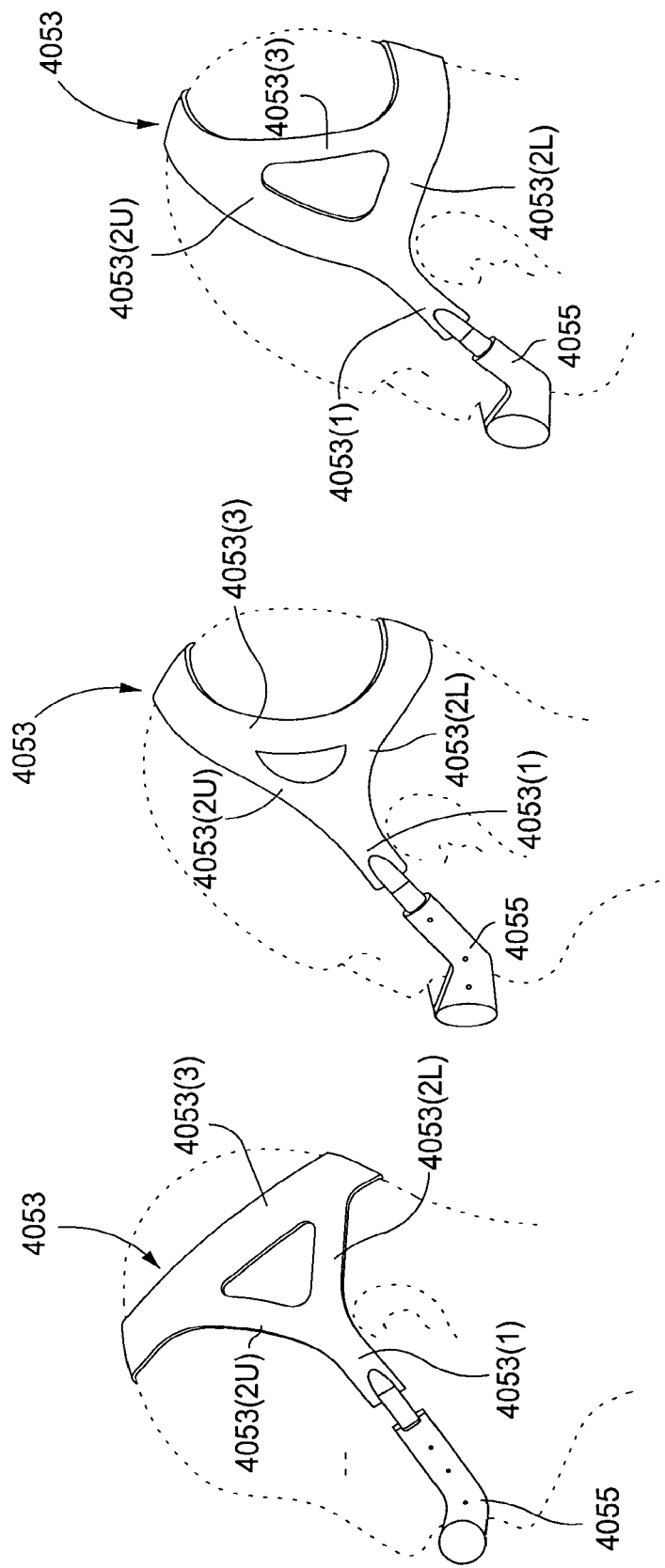

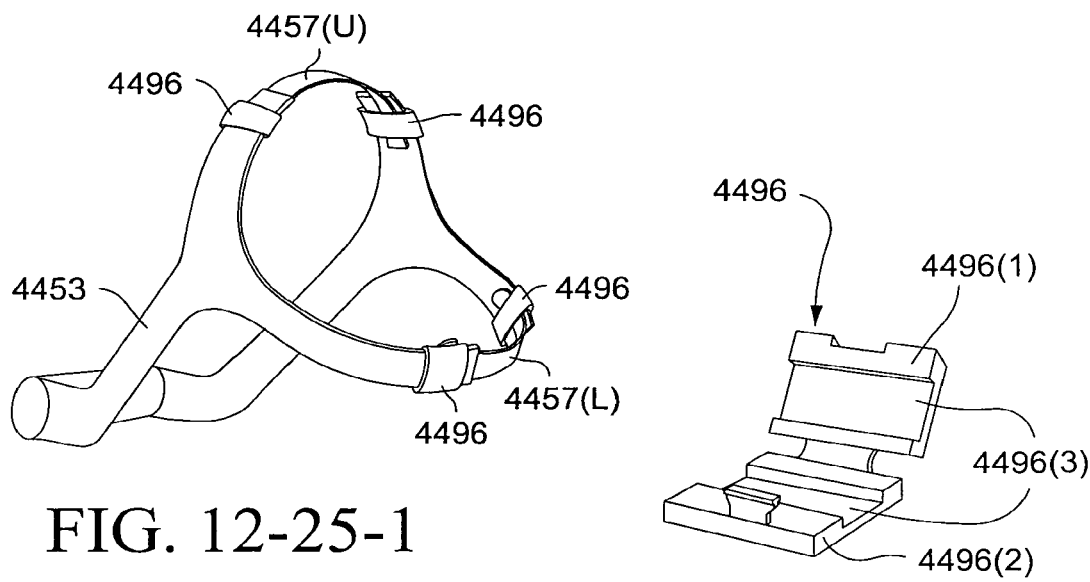
FIG. 12-25-1
FIG. 12-25-2
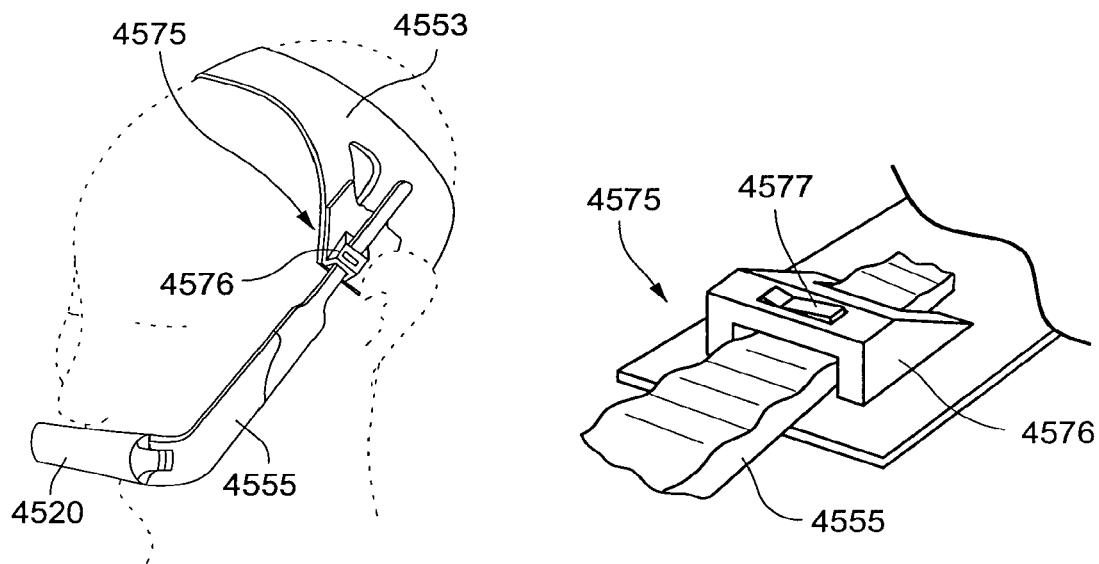
FIG. 12-26-1
FIG. 12-26-2

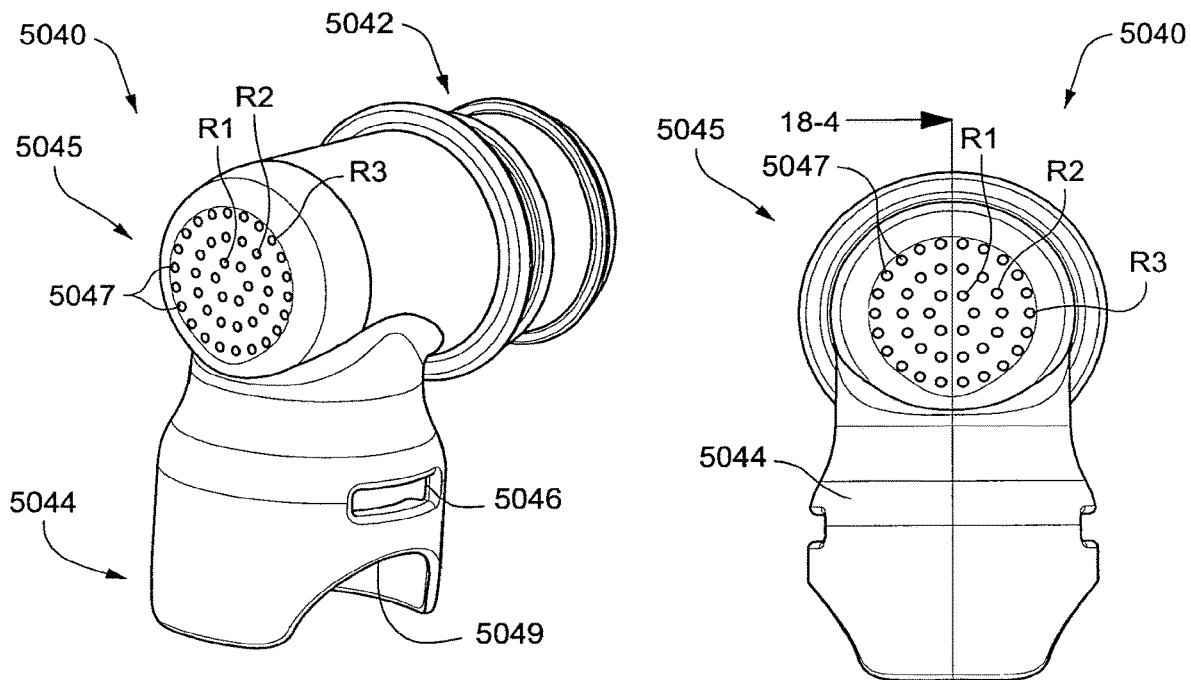
Fig. 18-1
Fig. 18-2
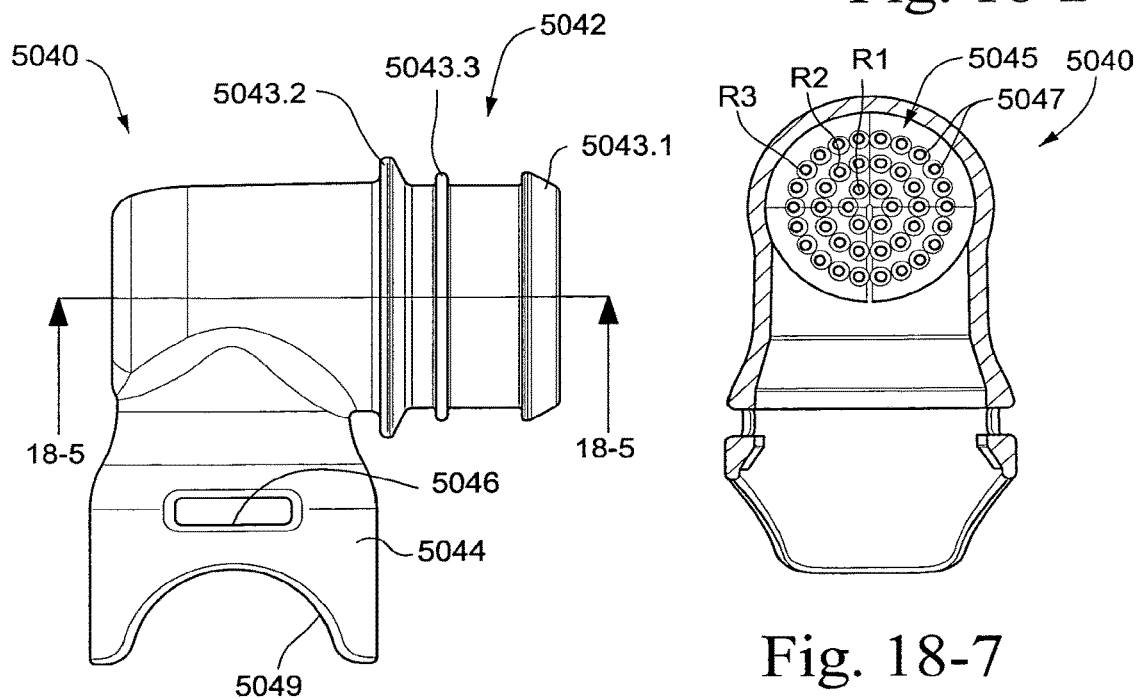
Fig. 18-3
Fig. 18-7

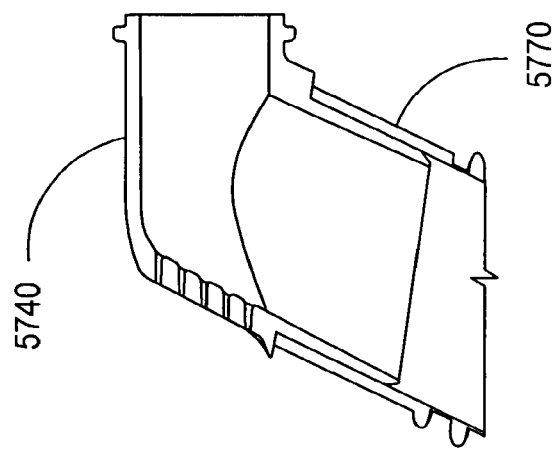
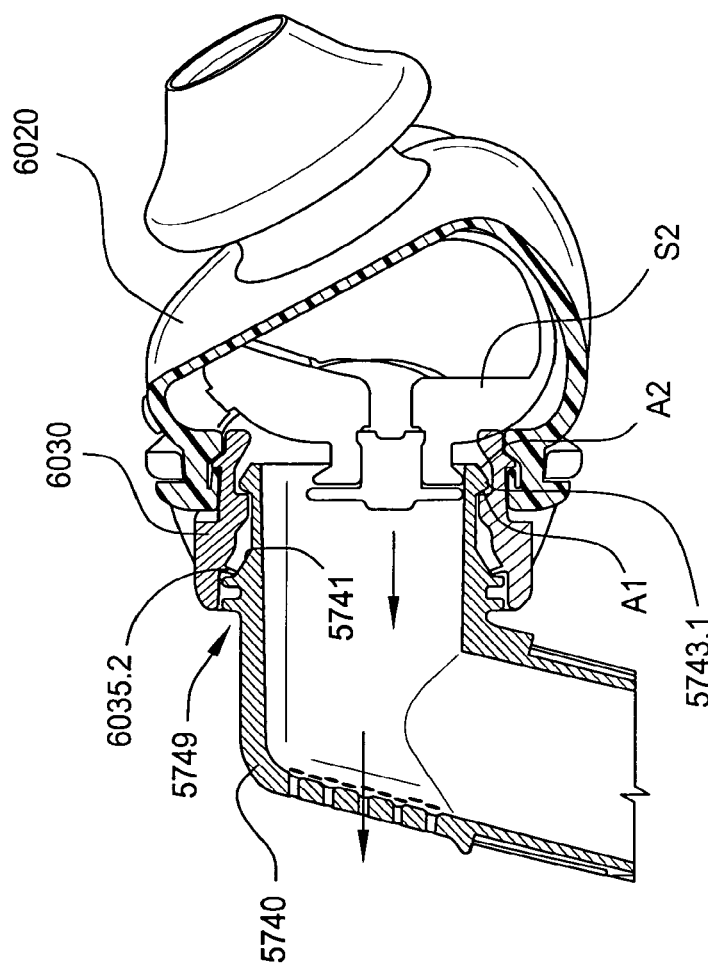
Fig. 18-8-17
Fig. 18-8-16

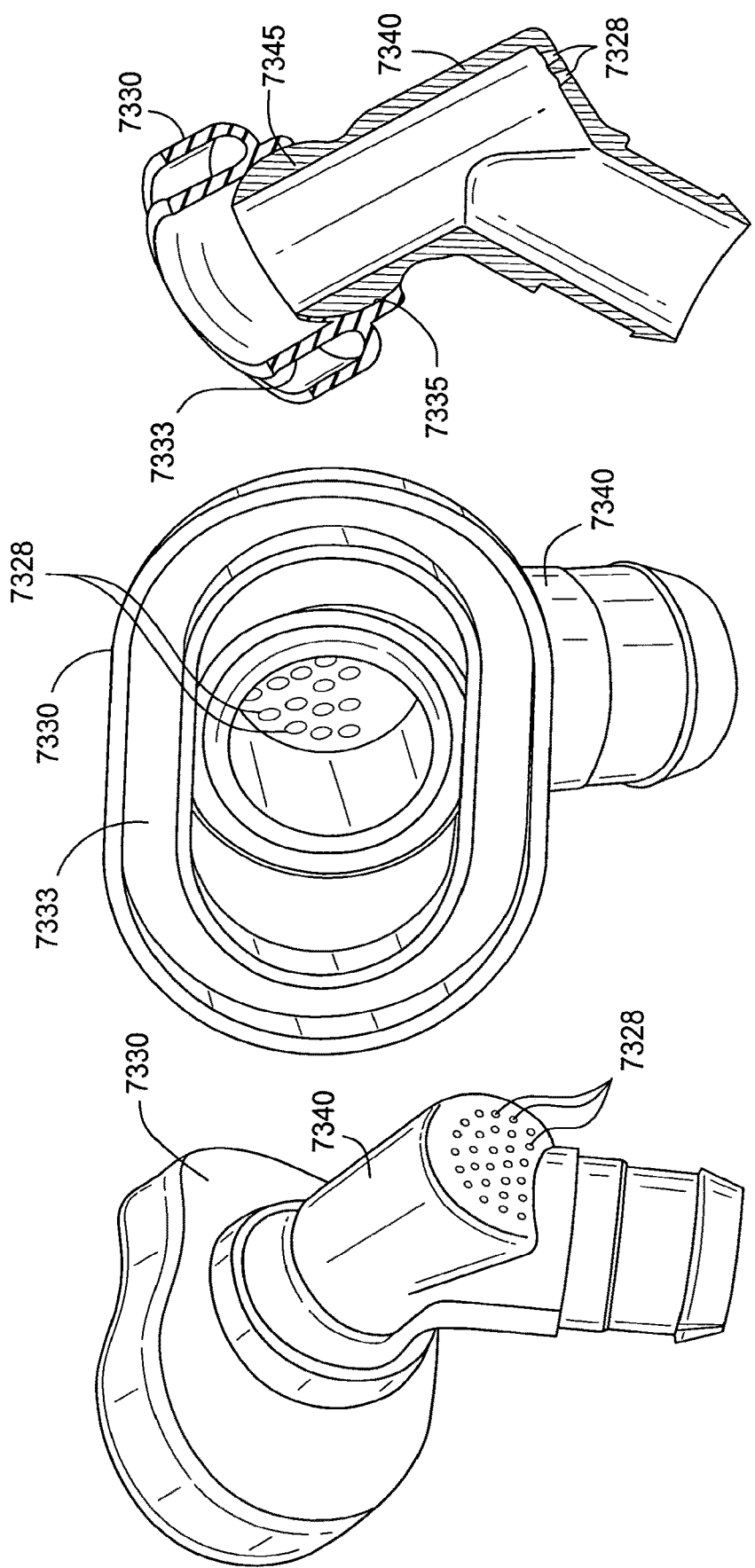

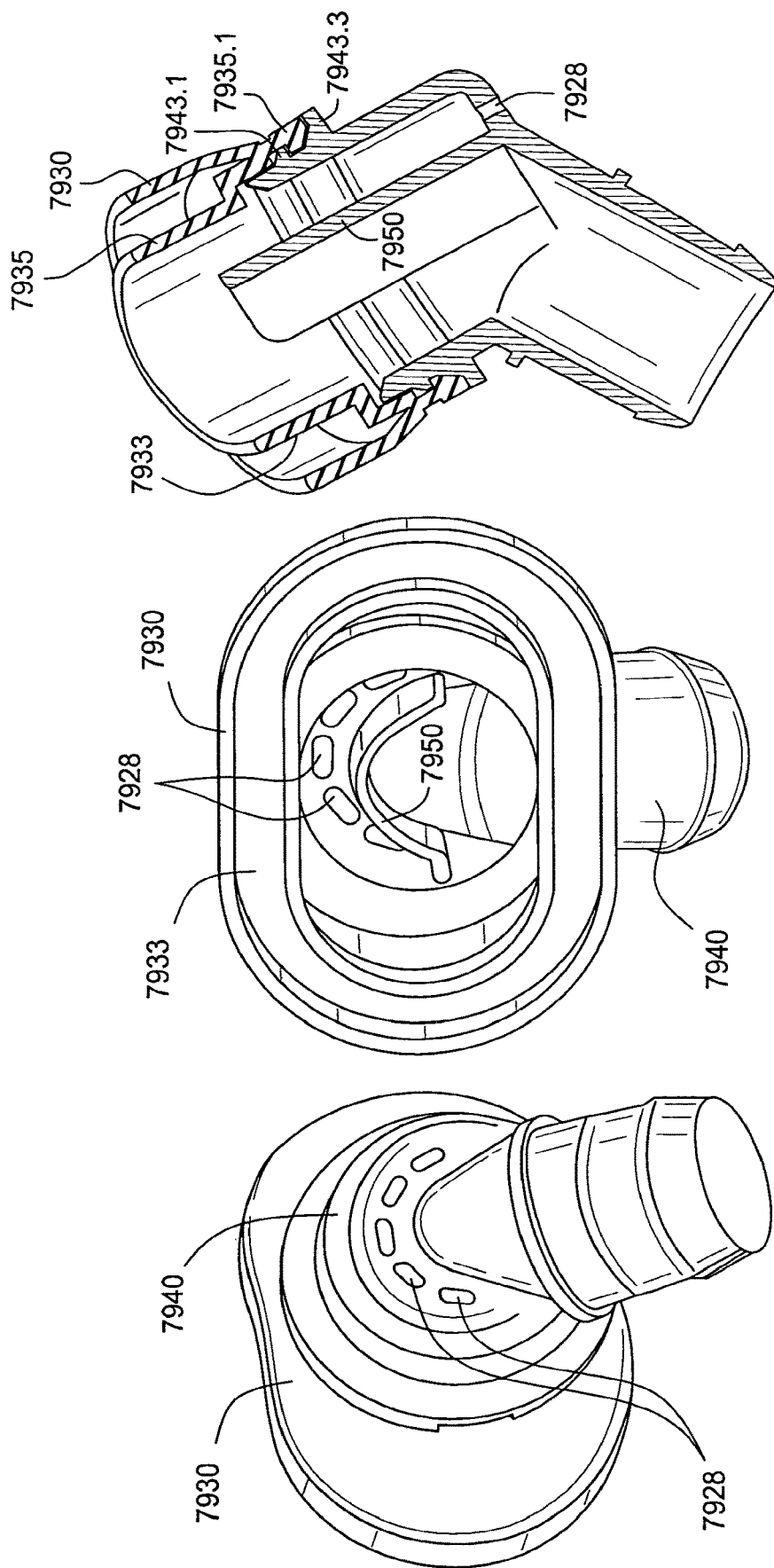

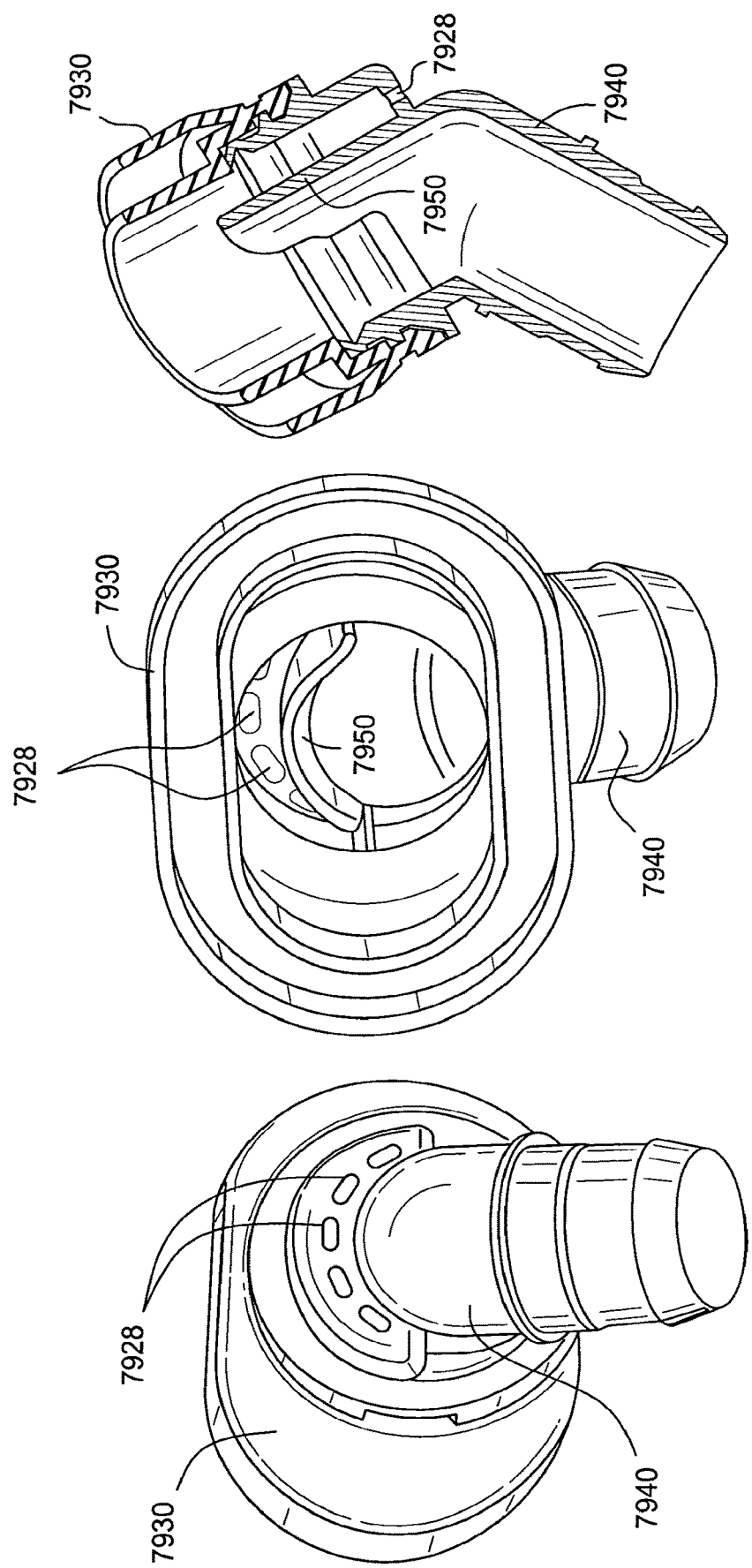

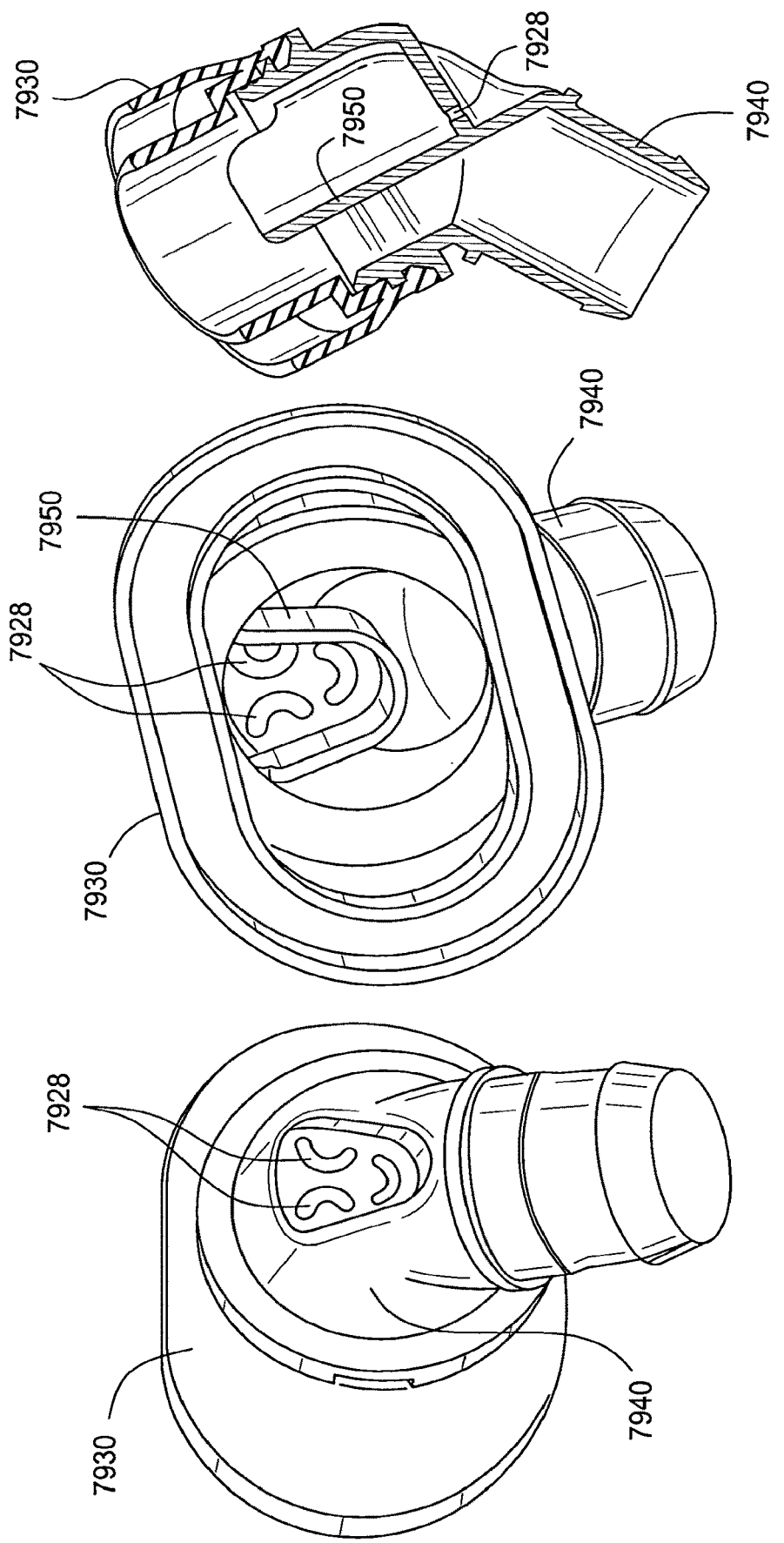

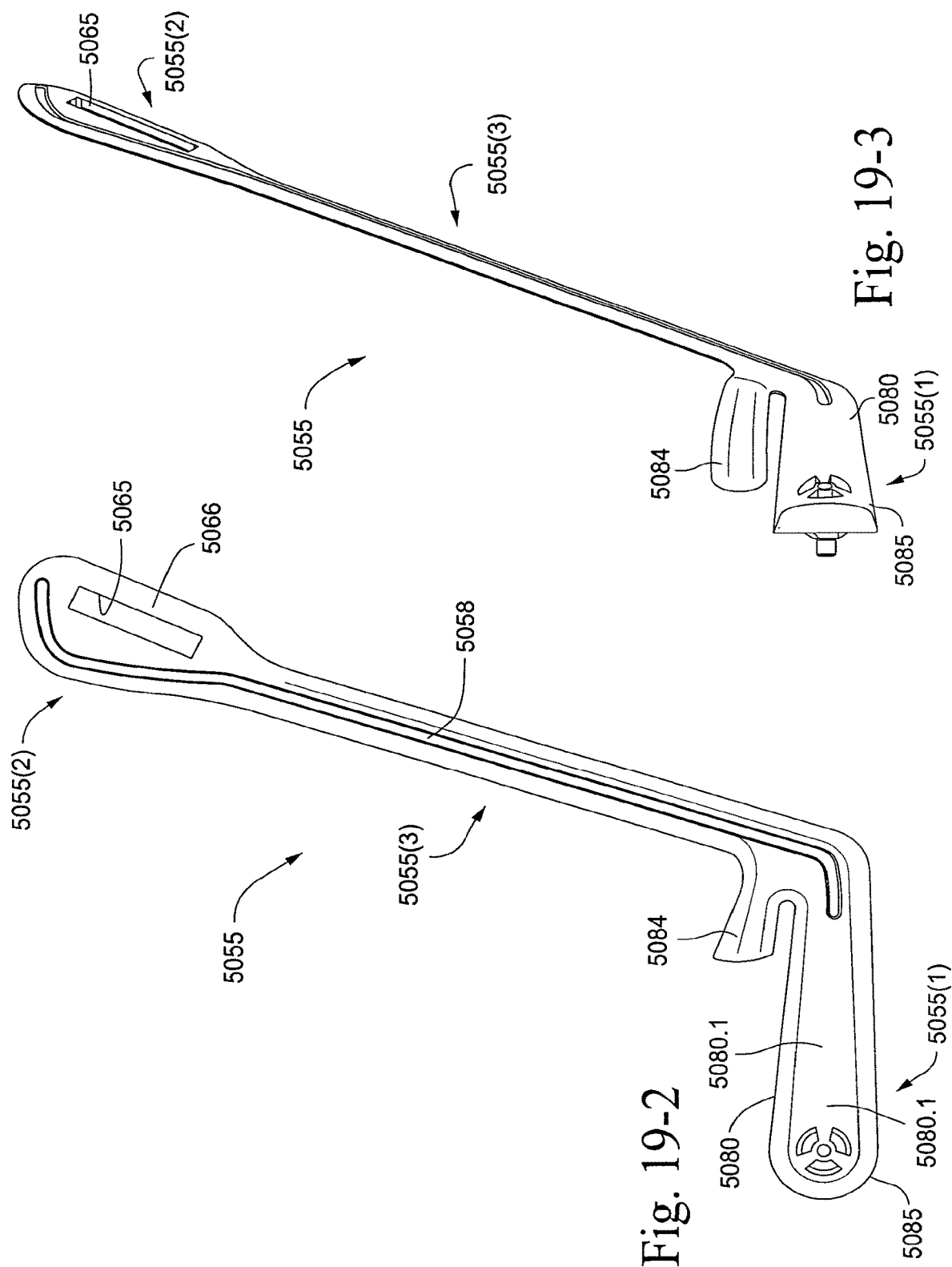

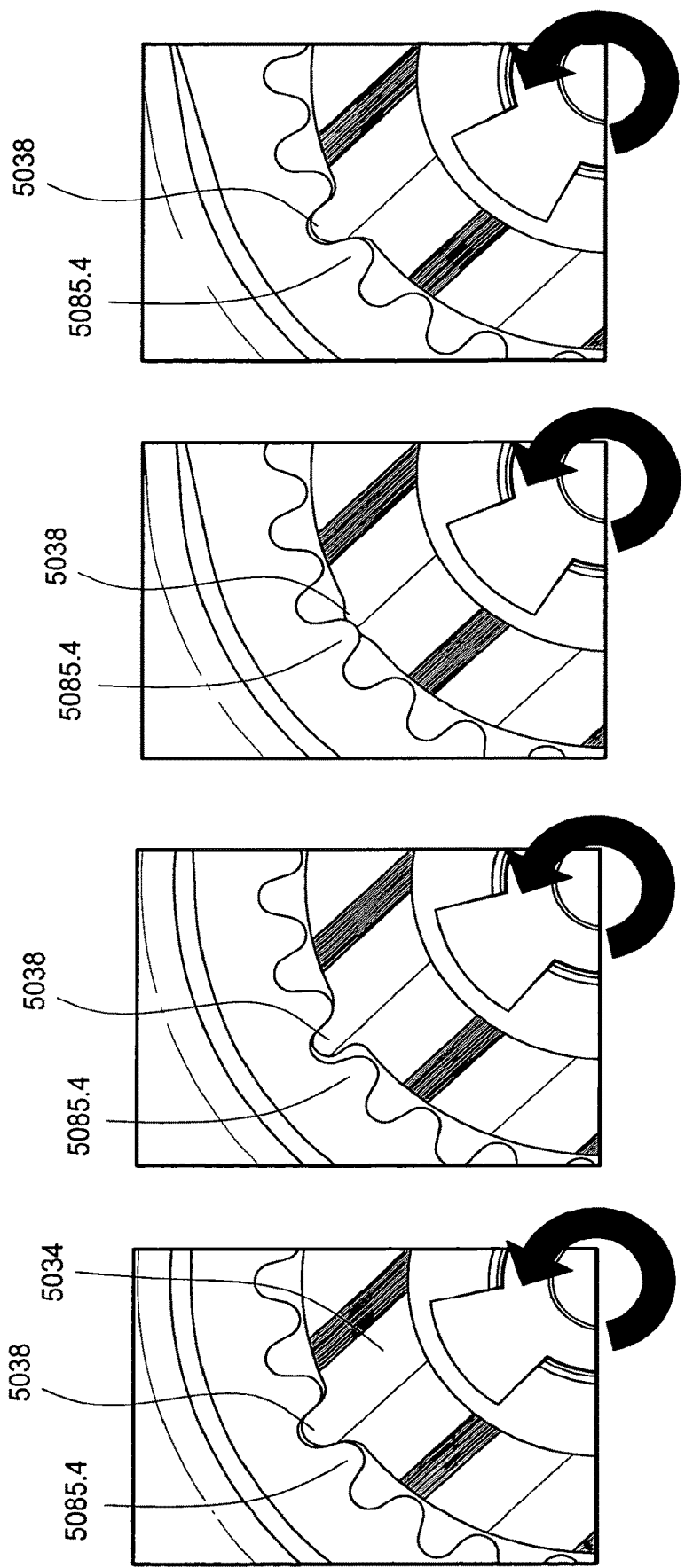

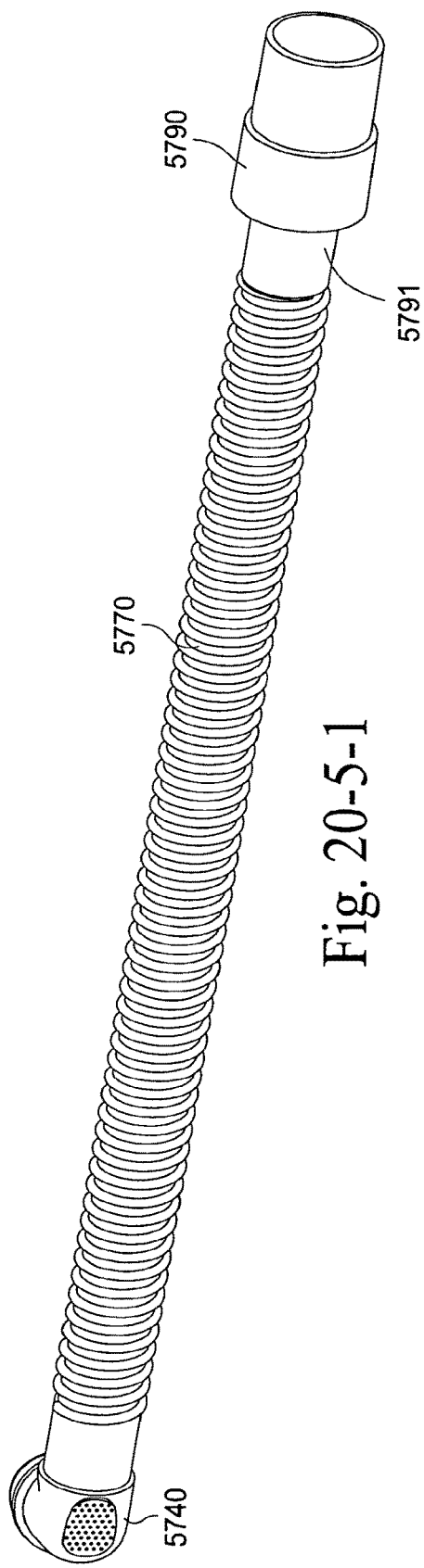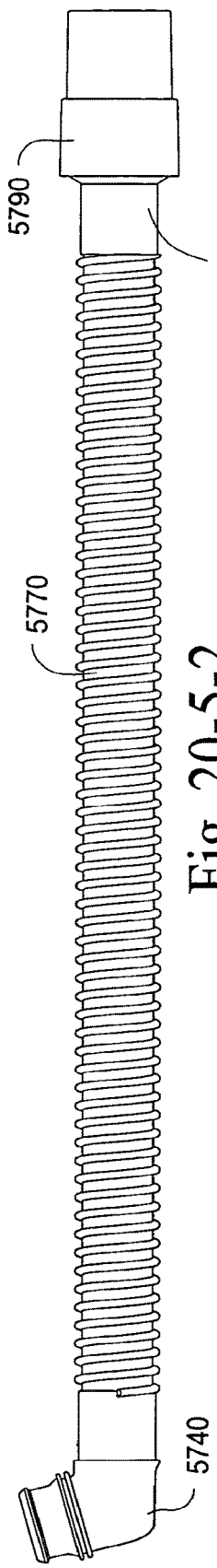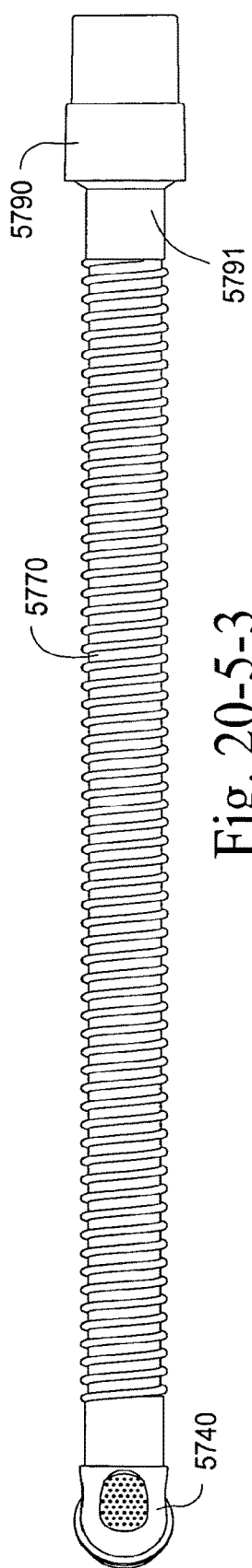
Fig. 20-5-1  Fig. 20-5-2  Fig. 20-5-3

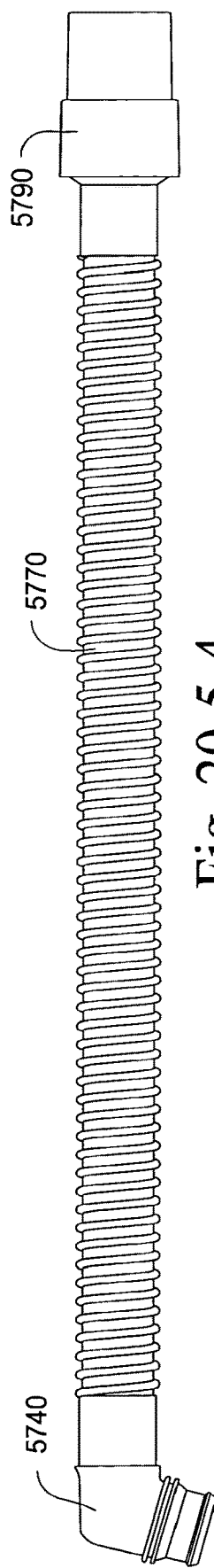
Fig. 20-5-4
Fig. 20-5-6
Fig. 20-5-5

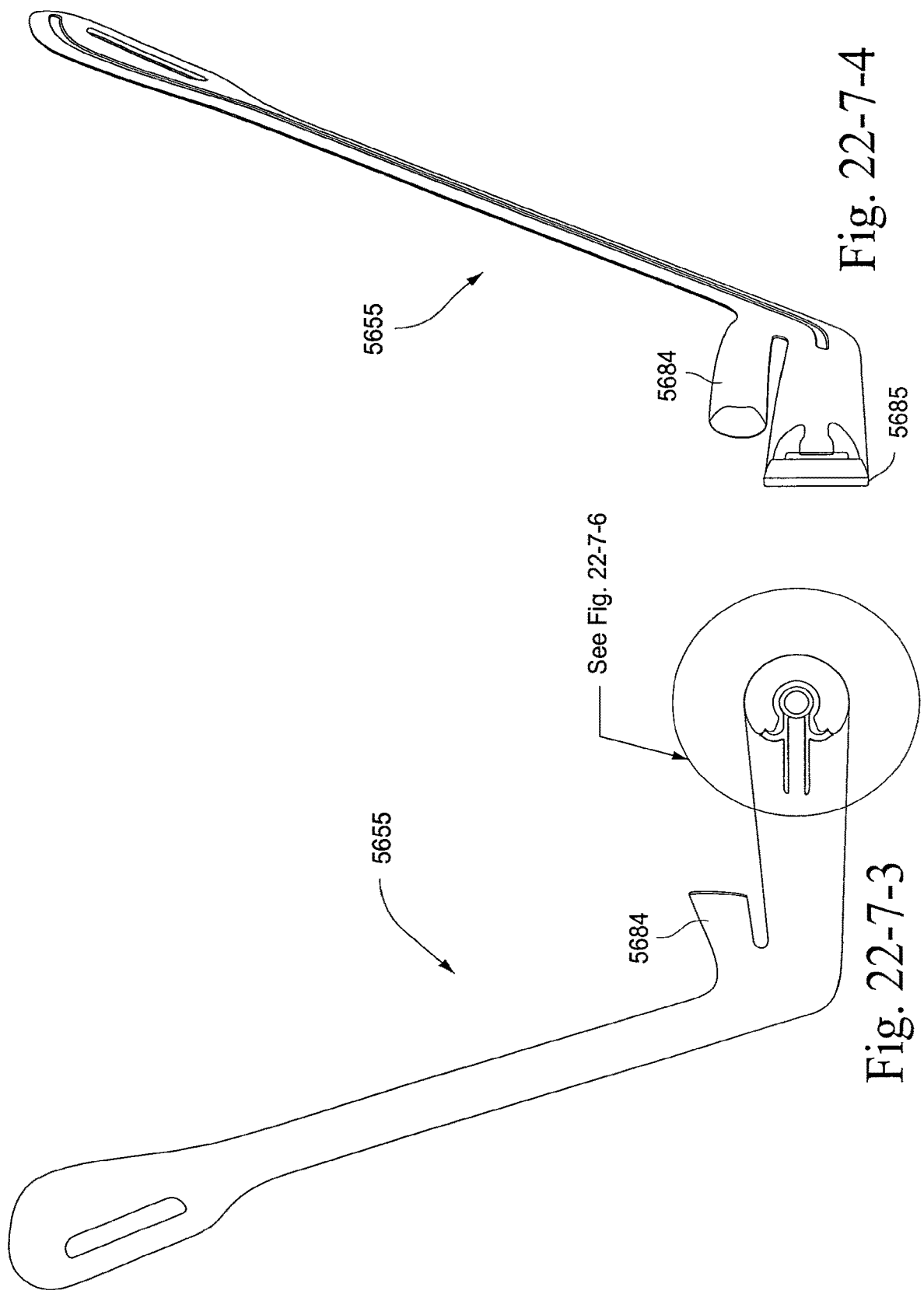

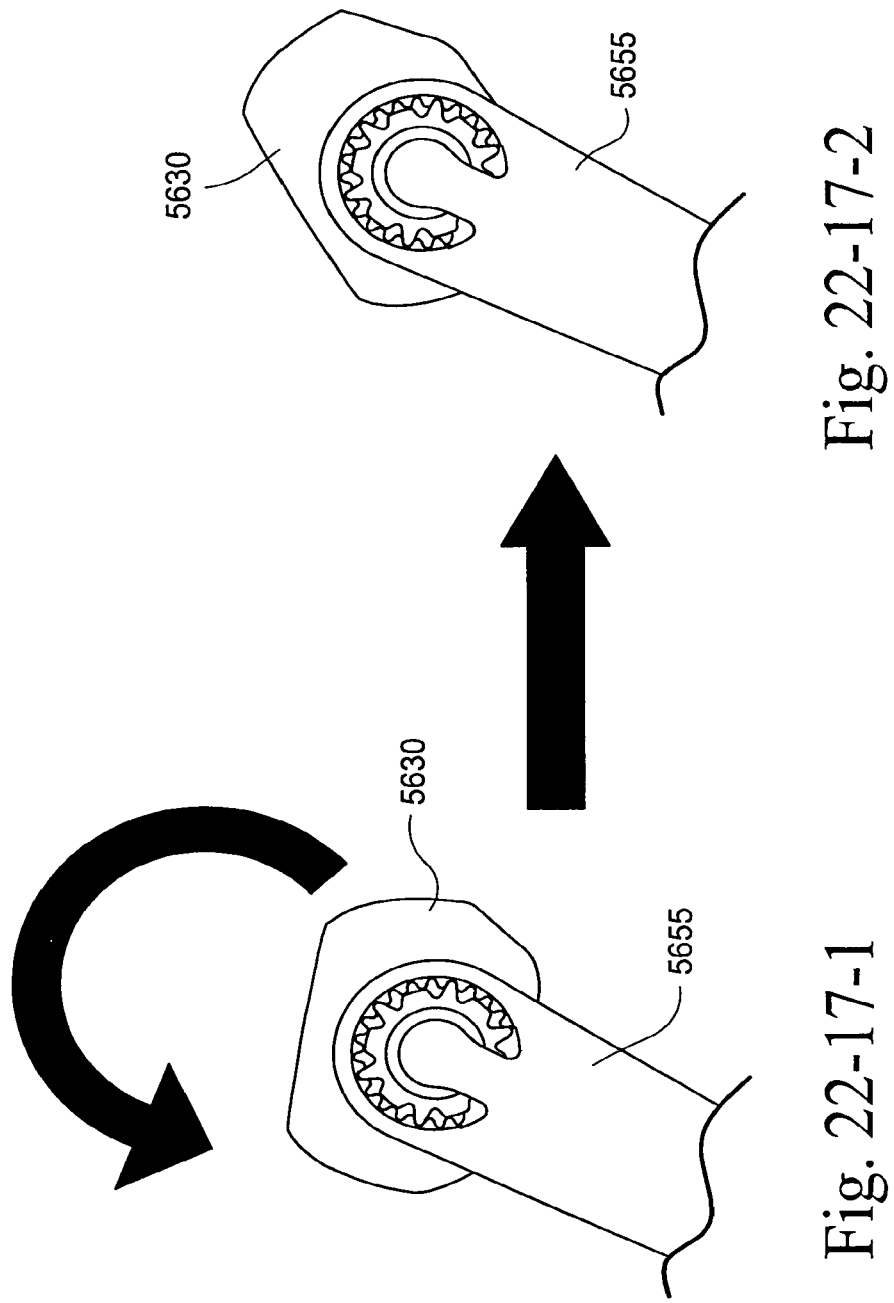

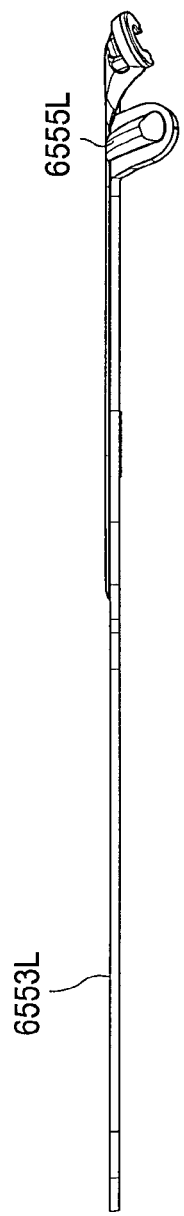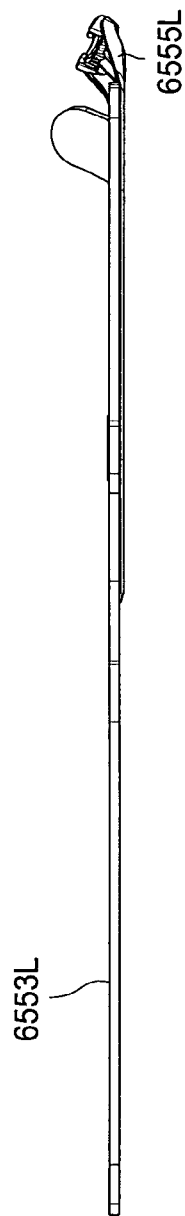
Fig. 22-21-3          Fig. 22-21-4

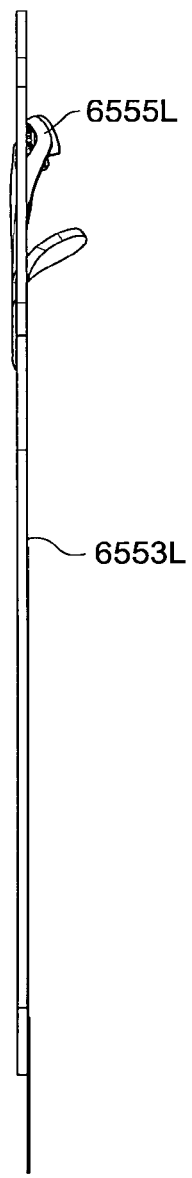
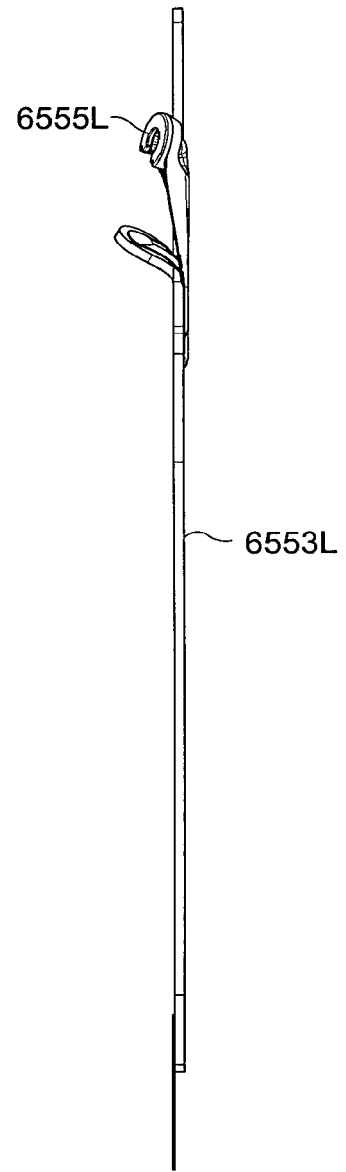
Fig. 22-21-6     Fig. 22-21-7

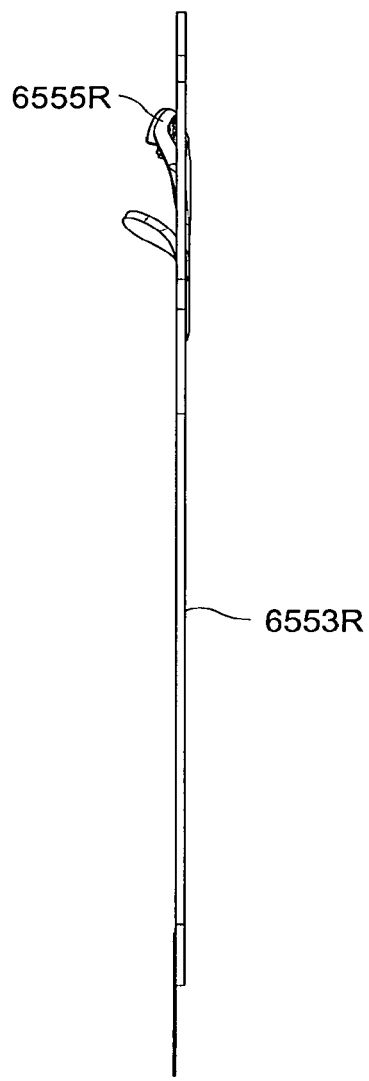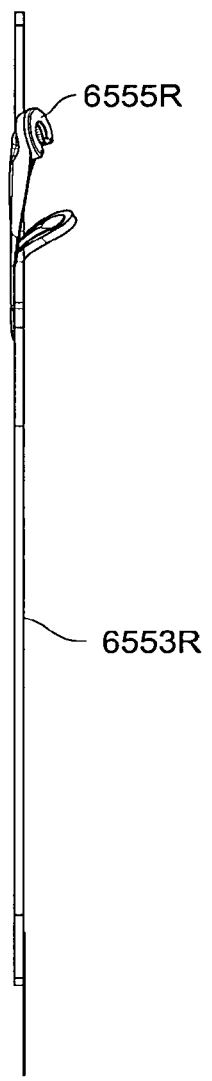
Fig. 22-22-6    Fig. 22-22-7

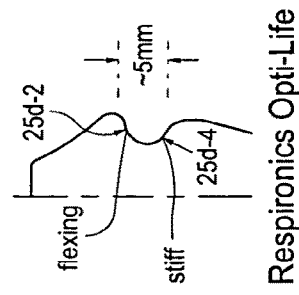
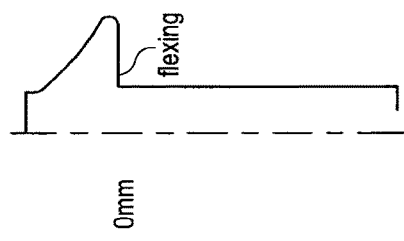
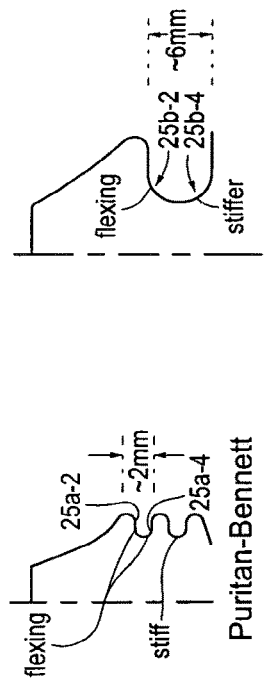
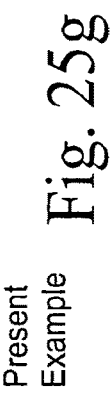
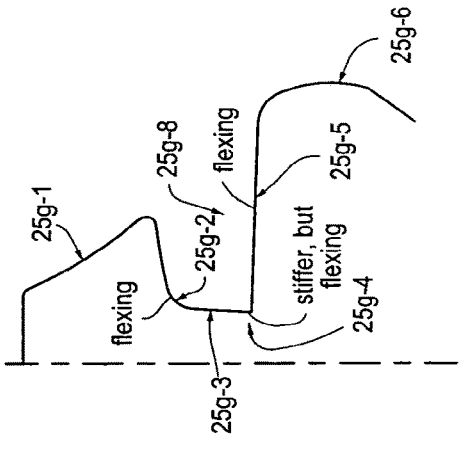
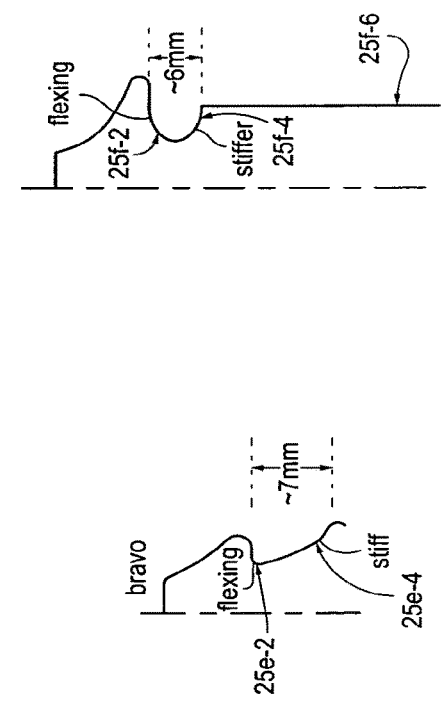

|   | Region name | SWIFT stiffness vs Present Example stiffness |
|---|---|---|
| 1 | Wall of pillow | > |
| 2 | Attachment of pillow to stalk | ~= |
| 3 | Stalk | ~= |
| 4 | Attachment of pillow to platform | < |
| 5 | Platform | > |
| 6 | Gusset/Base region | >> |

DETAIL B

SECTION C-C

SECTION B-B

PATIENT INTERFACE

CROSS-REFERENCE TO APPLICATION

This application is a continuation of U.S. application Ser. No. 16/872,442, filed May 12, 2020, now pending, which is a continuation of U.S. application Ser. No. 15/288,510, filed Oct. 7, 2017, now U.S. Pat. No. 10,675,428, which is a continuation of U.S. application Ser. No. 12/219,852, filed Jul. 29, 2008, now U.S. Pat. No. 9,480,809, which claimed the benefit of U.S. Provisional Application Nos. 60/935,179, filed Jul. 30, 2007, 60/996,160, filed Nov. 5, 2007, 61/006, 409, filed Jan. 11, 2008, 61/064,818, filed Mar. 28, 2008, and 61/071,512, filed May 2, 2008, and Australian Provisional Application Nos. AU 2008900891, filed Feb. 25, 2008, AU 2008900134, filed Jan. 11, 2008, AU 2008900136, filed Jan. 11, 2008, AU 2008900137, filed Jan. 11, 2008, AU 2008900138, filed Jan. 11, 2008, AU 2008900139, filed Jan. 11, 2008, AU 2008900140, filed Jan. 11, 2008, and AU 2008900141, filed Jan. 11, 2008, each of which is hereby incorporated herein by reference in its entirety.

FIELD OF THE INVENTION

The present invention relates to a patient interface for delivery of respiratory therapy to a patient. Examples of such therapies are Continuous Positive Airway Pressure (CPAP) treatment, Non-Invasive Positive Pressure Ventilation (NIPPY), and Variable Positive Airway Pressure (VPAP). The therapy is used for treatment of various respiratory conditions including Sleep Disordered Breathing (SDB) such as Obstructive Sleep Apnea (OSA).

BACKGROUND OF THE INVENTION

Mask systems form an interface between a patient and apparatus providing a supply of pressurized air or breathing gas and are hence sometimes referred to as patient interfaces. In this specification, the words mask system and patient interface will be used interchangably. Mask systems in the field of the invention differ from mask systems used in other applications such as aviation and safety in particular because of their emphasis on comfort. This high level of comfort is desired because patients must sleep wearing the masks for hours, possibly each night for the rest of their lives. Mask systems typically, although not always, comprise (i) a rigid or semi-rigid portion often referred to as a shell or frame, (ii) a soft, patient contacting portion often referred to as a cushion, and (iii) some form of headgear to hold the frame and cushion in position. Mask systems often include a mechanism for connecting an air delivery conduit. The air delivery conduit is usually connected to a blower or flow generator.

A range of patient interfaces are known including nasal masks, nose & mouth masks, full face masks and nasal prongs, pillows, nozzles & cannulae. Masks typically cover more of the face than nasal prongs, pillows, nozzles and cannulae. In this specification, all will be collectively referred to as patient interfaces or mask systems. Nasal prongs, nasal pillows, nozzles and cannulae all will be collectively referred to as nasal prongs.

SUMMARY OF THE INVENTION

A first aspect of the invention relates to a patient interface for delivering breathable gas to a patient. A mask system in accordance with an embodiment of the invention provides improved seal, fit, comfort, stability, adjustability and ease of use compared to prior art mask systems. Other aspects of the invention include providing a small, lightweight, unobtrusive mask system. Another aspect is to provide a mask system that fits a wide range of different faces.

One aspect of improved seal is provided through the use of dual walled nasal pillows in accordance with an embodiment of the invention. Another aspect is the ability of a mask system in accordance with an embodiment of the invention to maintain a seal despite tube drag, side-sleeping, and other disruptions. Another aspect of improved seal and fit is through the adjustability provided by a mask in accordance with an embodiment of the invention which allows adjustment to better suit an individual patient's face.

A mask system in accordance with an embodiment of the invention is flexible and can fit a wide variety of facial shapes. An aspect of flexibility of a mask system in accordance with an embodiment of the invention is provided through the use of a semi-rigid frame. The use of a semi-rigid frame also leads to an improved seal with an elbow, and a reduction in the overall number of parts.

A mask system in accordance with an embodiment of the invention provides improved comfort through improved seal, meaning patients do not need to overtighten headgear straps to get a seal. Another aspect of improved comfort comes from removal of a rear buckle when compared to otherwise similar prior art mask systems. Another aspect of the invention providing improved comfort is through the improved attachment mechanism of stiffening portions of the interface stabilizing arrangement, for example, across the cheek regions. Another aspect of improved comfort of the present invention results from a more comfortable strap and or padding arrangement in the cheek region that leads to a reduction in "cheek mark" when compared to the prior art.

An aspect of improved stability provided to a mask in accordance with an embodiment of the invention is through support features that engage with the front of the face generally in the region of the maxilla and or zygoma, depending on the size of the patient's face.

An aspect of the present invention relates to a patient interface including a nasal prong assembly including a pair of nasal prongs structured to sealingly communicate with nasal passages of a patient's nose in use and headgear to maintain the nasal prong assembly in a desired position on the patient's face. The headgear includes side straps and rigidizers provided to respective side straps. Each rigidizer includes a first end portion that provides a connector structured to engage a respective end of the nasal prong assembly and a curved protrusion in the form of a cheek support that curves forward of the connector. The cheek support is adapted to follow the contour of the patient's cheek and guide a respective end portion of the side strap into engagement with the patient's cheek to provide a stable cheek support.

Another aspect of the invention relates to a patient interface for delivering breathable gas to a patient. The patient interface includes a nasal seal to sealingly communicate with the patient's nose in use and headgear to maintain the nasal seal in a desired position on the patient's face. The headgear includes side straps. Each side strap includes a curved protrusion in the form of a cheek support adapted to follow the contour of the patient's cheek and guide a respective end portion of the side strap into engagement with the patient's cheek to provide a stable cheek support.

Another aspect of the invention relates to a patient interface for delivering breathable gas to a patient. The patient interface includes a nasal seal to sealingly communicate with the patient's nose in use and headgear to maintain the nasal seal in a desired position on the patient's face. The headgear includes side straps each having a rigidizer with a slotted connector portion and a rear or back strap having ends that connect to a respective slotted connector portion.

Another aspect of the invention relates to a patient interface for delivering breathable gas to a patient. The patient interface includes a frame, a nasal prong assembly provided to the frame and adapted to provide an effective seal or interface with the patient's nose, an elbow provided to the frame and adapted to be connected to an air delivery tube that delivers breathable gas to the patient, and headgear adapted to support the patient interface in a desired position on the patient's head. The frame is relatively harder than the nasal prong assembly and relatively softer and more flexible than the elbow. In an embodiment, the frame is relatively softer and more flexible than the elbow and/or headgear yokes of the headgear. In an embodiment, the nasal prong assembly includes a gusset that allows a range of axial and lateral movement while maintaining a sufficient seal. In an embodiment, the headgear yoke of the headgear includes a yoke to frame interface structured to retain the headgear yoke to the frame, provide rotation relative to the frame, and provide a friction element to provide sufficient rotational torque (e.g., to reduce tube drag, to provide tactile/audible feedback).

Another aspect of the invention relates to a patient interface for delivering breathable gas to a patient. The patient interface includes a frame, a nasal prong assembly provided to the frame and adapted to provide an effective seal or interface with the patient's nose, an elbow provided to the frame and adapted to be connected to an air delivery tube that delivers breathable gas to the patient, and headgear adapted to support the patient interface in a desired position on the patient's head. The headgear includes side straps and rigidizers provided to respective side straps. Each rigidizer includes a frame interface structured to retain the rigidizer to the frame, provide rotation relative to the frame, and provide a friction element to provide sufficient rotational torque.

Another aspect of the invention relates to a patient interface for delivering breathable gas to a patient. The patient interface includes a pair of nasal prongs adapted to provide an effective seal or interface with the patient's nose and a support arrangement to support the nasal prongs in an operative position on the patient's face. The support arrangement is structured to provide a range of rotational, axial, and lateral movement to the nasal prongs while maintaining a sufficient seal and resisting the application of tube drag and headgear tension to the nasal prongs.

Another aspect of the invention relates to a headgear link member for connecting two or more straps of a headgear assembly for securing a respiratory mask to a patient. The link member is flexible and has connector portions for adjustable connection to said two or more straps.

Another aspect of the invention relates to a headgear assembly for securing a respiratory mask to a patient including a pair of rear headgear straps located in use at a rear portion of the patient's head and a headgear link member connecting the rear headgear straps. The straps and link member are configured such that each strap passes through the link member in a single U-shape and is secured back to itself.

Another aspect of the invention relates to headgear for a patient interface including a pair of side straps. Each of the side straps includes an upper strap portion adapted to pass over the top of the patient's head, a front strap portion adapted to pass along the side of the patient's head, and a rear strap portion adapted to pass around a rear portion of the patient's head. The free end of each rear strap portion includes a tab of hook material, and one side of each rear strap portion is coated with un-broken loop material which allows the tab of hook material to fasten anywhere along its length.

Another aspect of the invention relates to a patient interface for delivering breathable gas to a patient including a frame and a nasal prong assembly provided to the frame. The nasal prong assembly includes a pair of nasal prongs adapted to provide an effective seal or interface with the patient's nose. The nasal prong assembly includes a frame contacting portion that is adapted to be inserted and retained within a frame channel provided to the frame. The frame contacting portion includes an external protrusion that is adapted to protrude through a corresponding opening provided in the frame channel.

Another aspect of the invention relates to a tube retainer for retaining an air delivery tube to a headgear strap of headgear. The tube retainer includes a first strap portion adapted to loop around a headgear strap of headgear and a second strap portion provided to the first strap portion and adapted to loop around an air delivery tube. The first and second strap portions are integrally formed in one-piece from a soft and flexible material with the second strap portion extending transverse to the first strap portion. Each strap portion includes a hook and loop arrangement adapted to secure the respective strap portion in position.

Another aspect of the invention relates to a tube retaining assembly for retaining air delivery tubing including a headgear buckle including opposing locking portions adapted to be removably and adjustably coupled with respective headgear straps of headgear and a tube retainer provided to the headgear buckle. The tube retainer includes a pair of arcuate arms adapted to retain air delivery tubing.

Other aspects, features, and advantages of this invention will become apparent from the following detailed description when taken in conjunction with the accompanying drawings, which are a part of this disclosure and which illustrate, by way of example, principles of this invention.

BRIEF DESCRIPTION OF THE DRAWINGS

The accompanying drawings facilitate an understanding of the various embodiments of this invention. In such drawings:

FIGS. 2-1 and 2-2 are perspective views of a nasal prong assembly for a patient interface according to an embodiment of the present invention;

FIGS. 2-3 and 2-4 are top and front views of a nasal prong assembly for a patient interface and showing exemplary dimensions according to an embodiment of the present invention;

FIG. 3-1 is a perspective view of dual wall nasal prongs according to an embodiment of the present invention;

FIG. 4-1 is a schematic view of a trampoline-like suspension system for a nasal prong and showing exemplary dimensions according to an embodiment of the present invention;

FIG. 4-2 is a schematic view of a trampoline-like suspension system for a nasal prong according to another embodiment of the present invention;

FIGS. 5-1 to 5-40 illustrate nasal prongs and nasal prong assemblies according to alternative embodiments of the present invention;

FIG. 5-41 illustrates a nasal prong assembly and air delivery conduit according to another embodiment of the present invention;

FIGS. 5-42-1 to 5-42-6 are various views of a tube retainer according to an embodiment of the present invention;

FIGS. 5-43-1 to 5-43-7 are various views of a headgear buckle according to an embodiment of the present invention;

FIGS. 5-44-1 to 5-44-4 are respectively side, top, cross-section (along line 5-44-3 of FIG. 5-44-2), and bottom orthogonal views of a link according to an embodiment of the present invention;

FIG. 5-44-5 is an isometric view of the link shown in FIGS. 5-44-1 to 5-44-4;

FIG. 5-45 is a cross-section showing the connection between the headgear straps and the link shown in FIGS. 5-44-1 to 5-44-4;

FIG. 5-46 shows a portion of a prior art headgear buckle and strap assembly in use;

FIGS. 5-47-1 to 5-47-6 are various views of a tube retainer according to an embodiment of the present invention;

FIG. 5-48 is an isometric view of a buckle according to an embodiment of the present invention;

FIG. 5-49 is an isometric view of a buckle according to another embodiment of the present invention;

FIG. 5-50 is a side view of a buckle according to another embodiment of the present invention;

FIG. 5-51 is a side view of a buckle according to another embodiment of the present invention;

FIG. 5-52 is an isometric view of a buckle according to another embodiment of the present invention;

FIG. 5-53 is an isometric view of a buckle according to another embodiment of the present invention;

FIG. 5-54 is a top view of a buckle according to another embodiment of the present invention;

FIG. 5-55 is a top view of a buckle according to another embodiment of the present invention;

FIG. 5-56 is a top view of a buckle according to another embodiment of the present invention;

FIG. 5-57 is a top view of a buckle according to another embodiment of the present invention;

FIG. 5-58 is a top view of a buckle according to another embodiment of the present invention;

FIG. 5-59 is a top view of a buckle according to another embodiment of the present invention;

FIG. 5-60 is a top view of a buckle according to another embodiment of the present invention;

FIG. 5-61 is a top view of a buckle according to another embodiment of the present invention;

FIG. 5-62 is a top view of a buckle according to another embodiment of the present invention;

FIG. 5-63 is a top view of a buckle according to another embodiment of the present invention;

FIG. 5-64 is a top view of a buckle according to another embodiment of the present invention;

FIG. 5-65 is a top view of a buckle according to another embodiment of the present invention;

FIG. 5-66 is an isometric view of the keyhole of a buckle according to an embodiment of the present invention;

FIG. 5-67 is a top view of a buckle according to another embodiment of the present invention;

FIG. 5-68 is an isometric view of a tube retainer according to another embodiment of the present invention;

FIG. 5-69 is an isometric view of a tube retainer according to another embodiment of the present invention;

FIG. 5-70 is an isometric view of a tube retainer according to another embodiment of the present invention;

FIG. 5-71 is an isometric view of a tube retainer according to another embodiment of the present invention;

FIG. 5-72 is a front view of a tube retainer according to another embodiment of the present invention;

FIG. 5-73 is a front view of a tube retainer according to another embodiment of the present invention;

FIG. 5-74 is a front view of a tube retainer according to another embodiment of the present invention;

FIG. 5-75 is a front view of a tube retainer according to another embodiment of the present invention;

FIG. 5-76 is an isometric view of a tube retainer according to another embodiment of the present invention;

FIG. 5-77 is an isometric view of a tube retainer according to another embodiment of the present invention;

FIG. 5-78 is an isometric view of a tube retainer according to another embodiment of the present invention;

FIG. 5-79 is a front view of a tube retainer according to another embodiment of the present invention;

FIG. 5-80 is a front view of a tube retainer according to another embodiment of the present invention;

FIG. 5-81 is an isometric view of a tube retainer according to another embodiment of the present invention;

FIG. 5-82 is an isometric view of a tube retainer according to another embodiment of the present invention;

FIG. 5-83 is an isometric view of the tab of a tube retainer according to an embodiment of the present invention;

FIG. 5-84 is an isometric view of the tab of a tube retainer according to another embodiment of the present invention;

FIG. 5-85 is an isometric view of the tab of a tube retainer according to another embodiment of the present invention;

FIG. 5-86 is an isometric view of the tab of a tube retainer according to another embodiment of the present invention;

FIGS. 6-1 to 6-5 illustrate headgear yoke for headgear according to an embodiment of the present invention;

FIG. 7-1 schematically illustrates headgear tension on ResMed's Mirage Swift headgear;

FIG. 7-2 schematically illustrates headgear tension on headgear according to an embodiment of the present invention;

FIGS. 8-1 to 8-4 schematically illustrate headgear yoke according to alternative embodiments of the present invention;

FIG. 9 illustrates a rear strap for headgear according to an embodiment of the present invention;

FIGS. 10-1 illustrates a headgear strap section including a headgear strap and headgear yoke according to an embodiment of the present invention;

FIGS. 10-2-1 and 10-2-2 illustrate foam headgear straps according to an embodiment of the present invention;

FIG. 10-3-1 illustrates a cheek mark region with respect to ResMed's Swift headgear;

FIG. 10-3-2 illustrates a known headgear strap section;

FIG. 10-4 illustrates a headgear strap section according to an embodiment of the present invention;

FIGS. 10-5 and 10-6 illustrate headgear straps and headgear yokes according to alternative embodiments of the present invention;

FIGS. 10-7-1 to 10-7-3 illustrate headgear including a friction pad according to an embodiment of the present invention;

FIGS. 10-8-1 to 10-8-3 illustrate a nasal prong assembly including wings according to an embodiment of the present invention;

FIGS. 10-9-1 to 10-9-3 illustrate headgear including foam padding according to an embodiment of the present invention;

FIG. 10-9-4 illustrates headgear with yoke and wing without foam padding according to another embodiment of the present invention;

FIGS. 11-1 and 11-2 illustrate cutting profiles for headgear straps according to embodiments of the present invention;

FIGS. 12-1 to 12-26-2 illustrate headgear according to alternative embodiments of the present invention;

FIGS. 13-1 to 13-4 illustrate various views of a patient interface on a patient's head according to an embodiment of the present invention;

FIG. 13-5 is a schematic view illustrating headgear vectors according to an embodiment of the present invention;

FIGS. 14-1 to 14-2 illustrate various views of the patient interface shown in FIGS. 13-1 to 13-4 with the headgear straps removed;

FIGS. 15-1 to 15-12 illustrate various views of the frame of the patient interface shown in FIGS. 13-1 to 13-4;

FIGS. 16-1 to 16-12 illustrate various views of the nasal prong assembly of the patient interface shown in FIGS. 13-1 to 13-4;

FIGS. 16-13-1 to 16-13-7 illustrate a nasal prong assembly according to an embodiment of the present invention;

FIG. 16-14-1 illustrates an assembled view of a nasal prong assembly and frame according to another embodiment of the present invention;

FIG. 16-14-2 illustrates an unassembled view of the nasal prong assembly and frame shown in FIG. 16-14-1;

FIG. 16-14-3 is a perspective view of a patient interface including the nasal prong assembly and frame of FIG. 16-14-1;

FIGS. 16-15-1 to 16-15-10 illustrate various views of the nasal prong assembly of FIG. 16-14-1;

FIGS. 16-16-1 to 16-16-8 illustrate various views of the frame of FIG. 16-14-1;

FIG. 16-17 is a perspective view of a nasal prong assembly and frame according to another embodiment of the present invention;

FIG. 16-18-1 is a perspective view of a nasal prong assembly and frame according to another embodiment of the present invention;

FIG. 16-18-2 illustrates an unassembled view of the nasal prong assembly and frame shown in FIG. 16-18-1;

FIG. 16-18-3 illustrates a frame according to an embodiment of the present invention;

FIG. 16-19 is a perspective view of a nasal prong assembly and frame according to another embodiment of the present invention;

FIG. 16-20 is a cross-sectional view of a frame contacting portion of a nasal prong assembly and a frame according to an embodiment of the present invention;

FIG. 16-21 is a cross-sectional view of a frame according to an embodiment of the present invention;

FIG. 16-22 is a cross-sectional view of a frame according to another embodiment of the present invention;

FIG. 16-23 is a cross-sectional view of a frame according to another embodiment of the present invention;

FIG. 16-24 is a cross-sectional view of a frame according to another embodiment of the present invention;

FIG. 16-25 is a cross-sectional view of a frame contacting portion of a nasal prong assembly according to an embodiment of the present invention;

FIG. 16-26 is a cross-sectional view of a frame contacting portion of a nasal prong assembly and a frame according to an embodiment of the present invention;

FIG. 16-27 is a cross-sectional view of a frame contacting portion of a nasal prong assembly and a frame according to another embodiment of the present invention;

FIG. 16-28 is a cross-sectional view of a frame contacting portion of a nasal prong assembly and a frame according to another embodiment of the present invention;

FIG. 16-29 is a cross-sectional view of a frame contacting portion of a nasal prong assembly and a frame according to another embodiment of the present invention;

FIG. 16-30 is a cross-sectional view of a frame contacting portion of a nasal prong assembly and a frame according to another embodiment of the present invention;

FIG. 16-31 is a cross-sectional view of a frame contacting portion of a nasal prong assembly and a frame according to another embodiment of the present invention;

FIG. 16-32 is a cross-sectional view of a frame contacting portion of a nasal prong assembly and a frame according to another embodiment of the present invention;

FIG. 16-33 is a cross-sectional view of a frame contacting portion of a nasal prong assembly and a frame according to another embodiment of the present invention;

FIG. 16-34-1 is a cross-sectional view of a frame contacting portion of a nasal prong assembly according to an embodiment of the present invention;

FIG. 16-34-2 is a cross-sectional view of a frame contacting portion of a nasal prong assembly according to an embodiment of the present invention;

FIG. 16-35 is a rear view of a frame and frame channel according to an embodiment of the present invention;

FIG. 16-36 is a rear view of a frame and frame channel according to another embodiment of the present invention;

FIG. 16-37 is a perspective view of a nasal prong assembly including a frame contacting portion according to an embodiment of the present invention;

FIG. 16-38 is a rear view of a frame and frame channel according to another embodiment of the present invention;

FIG. 16-39 is a cross-sectional view of a frame contacting portion of a nasal prong assembly according to another embodiment of the present invention;

FIG. 17 is a cross-sectional view of the patient interface shown in FIGS. 13-1 to 13-4;

FIGS. 18-1 to 18-7 illustrate various views of the elbow of the patient interface shown in FIGS. 13-1 to 13-4;

FIGS. 18-8-1 to 18-8-9 illustrate various views of an elbow according to another embodiment of the present invention;

FIG. 18-8-10 is a cross-sectional view through line 18-8-10-18-8-10 of FIG. 18-8-5;

FIG. 18-8-11 is an enlarged portion of FIG. 18-8-10;

FIG. 18-8-12 is a cross-sectional view through line 18-8-12-18-8-12 of FIG. 18-8-10;

FIG. 18-8-13 is an enlarged portion of FIG. 18-8-12;

FIG. 18-8-14 is a cross-sectional view similar to FIG. 18-8-10 in perspective;

FIG. 18-8-15 is an enlarged portion of FIG. 18-8-14;

FIG. 18-8-16 shows the elbow attached to the frame and nasal prong assembly according to an embodiment of the present invention;

FIG. 18-8-17 shows the interface between the elbow and the short tube according to an embodiment of the present invention;

FIGS. 18-9-1 to 18-9-3 are various views of an elbow to frame attachment according to an embodiment of the present invention;

FIGS. 18-10-1 to 18-10-3 are various views of an elbow to frame attachment according to another embodiment of the present invention;

FIGS. 18-11-1 to 18-11-3 are various views of an elbow to frame attachment according to another embodiment of the present invention;

FIGS. 18-12-1 to 18-12-3 are various views of an elbow to frame attachment according to another embodiment of the present invention;

FIGS. 18-13-1 to 18-13-3 are various views of an elbow to frame attachment according to another embodiment of the present invention;

FIGS. 18-14-1 to 18-14-3 are various views of an elbow to frame attachment according to another embodiment of the present invention;

FIGS. 18-15-1 to 18-15-3 are various views of an elbow to frame attachment according to another embodiment of the present invention;

FIGS. 18-16-1 to 18-16-3 are various views of an elbow to frame attachment according to another embodiment of the present invention;

FIGS. 18-17-1 to 18-17-3 are various views of an elbow to frame attachment according to another embodiment of the present invention;

FIGS. 18-18-1 to 18-18-3 are various views of an elbow to frame attachment according to another embodiment of the present invention;

FIGS. 19-1 to 19-5 illustrate various views of headgear yoke of the patient interface shown in FIGS. 13-1 to 13-4;

Figure 1:
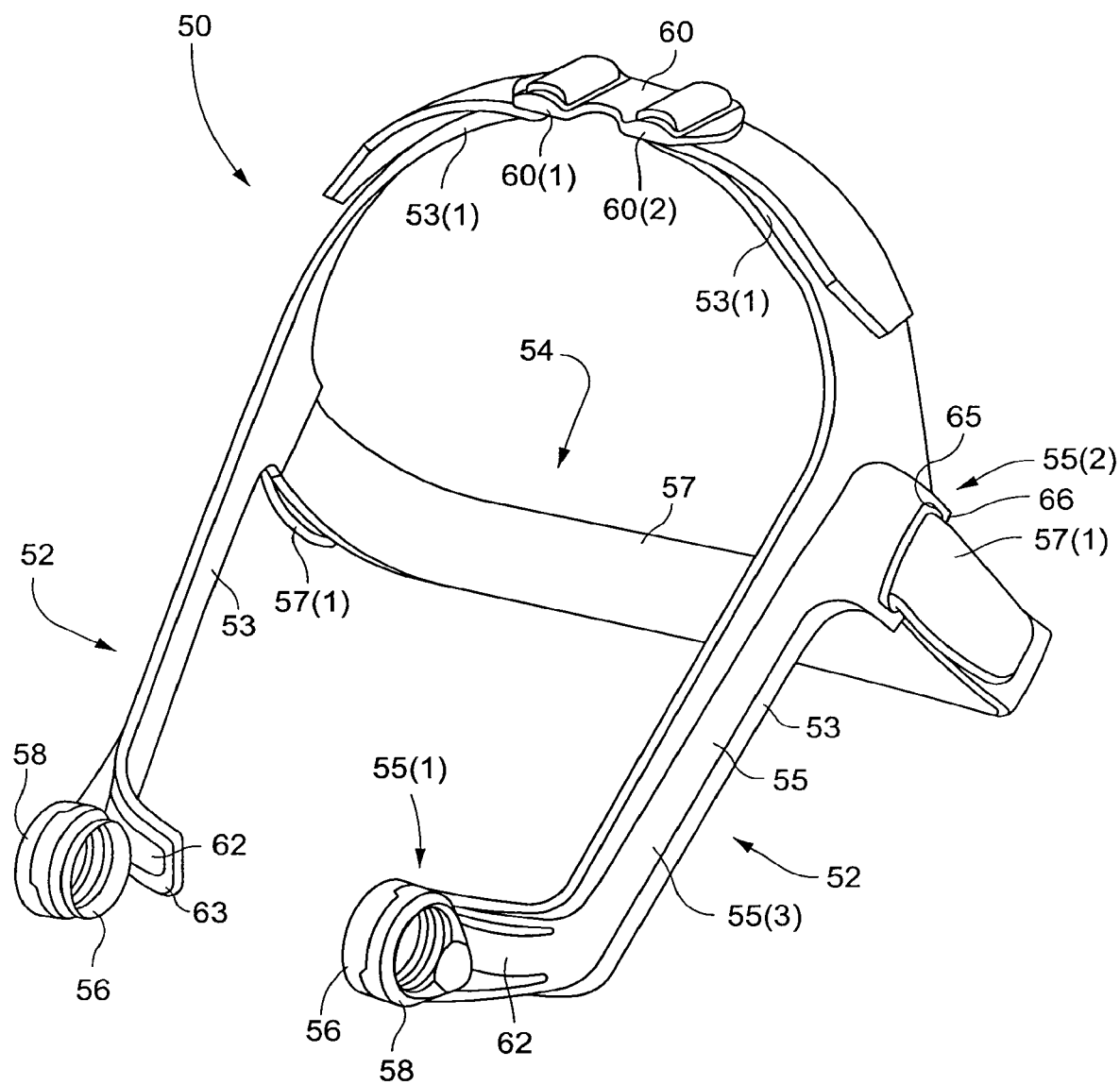
FIG. 1-1 is a perspective view of headgear for a patient interface according to an embodiment of the present invention.
Figures 1, 2:
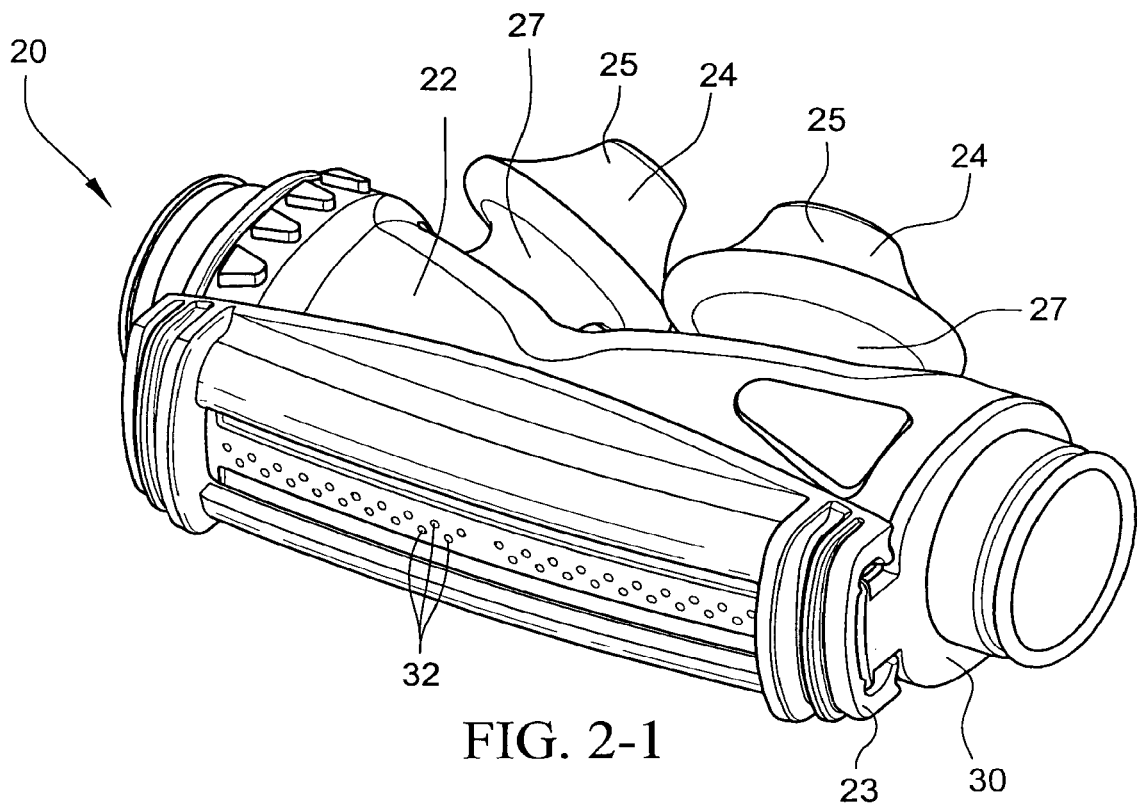
Figure 2:
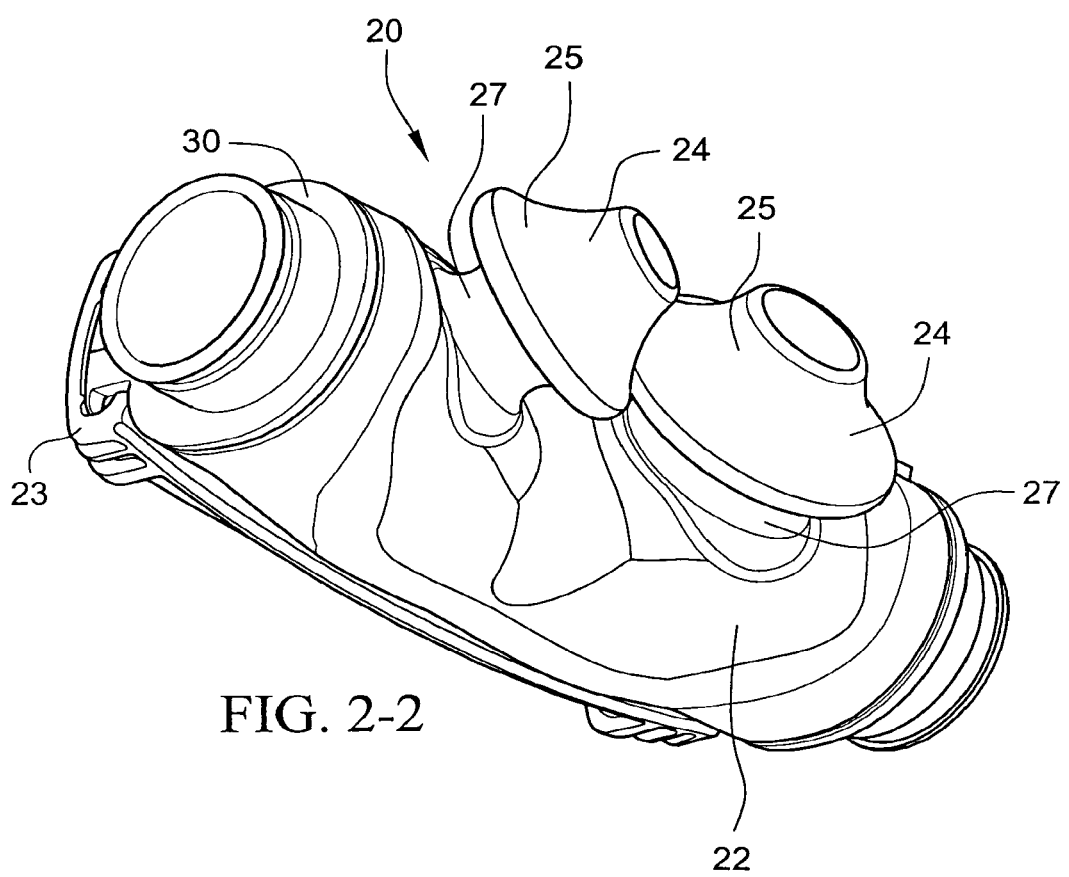
Figures 2, 3:
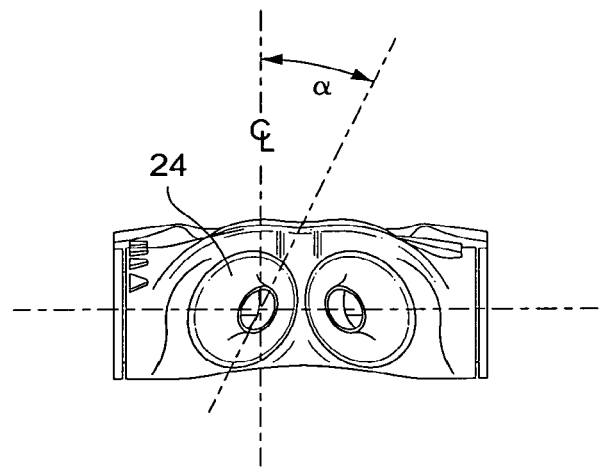
Figures 2, 3, 4:
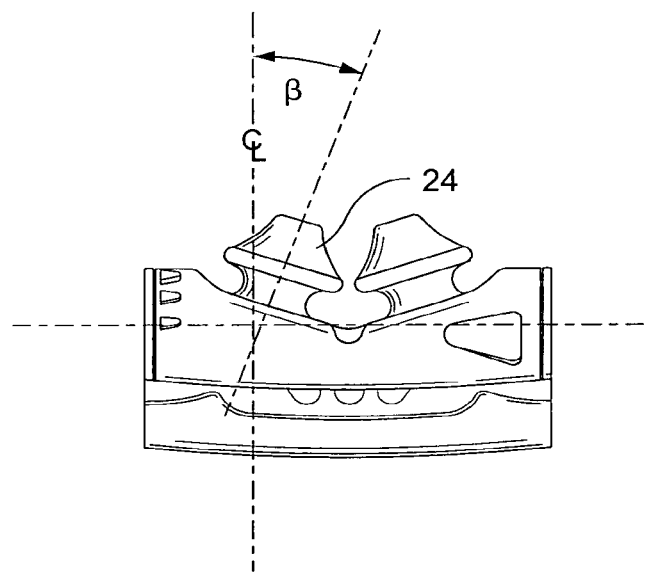
Figures 1, 3:
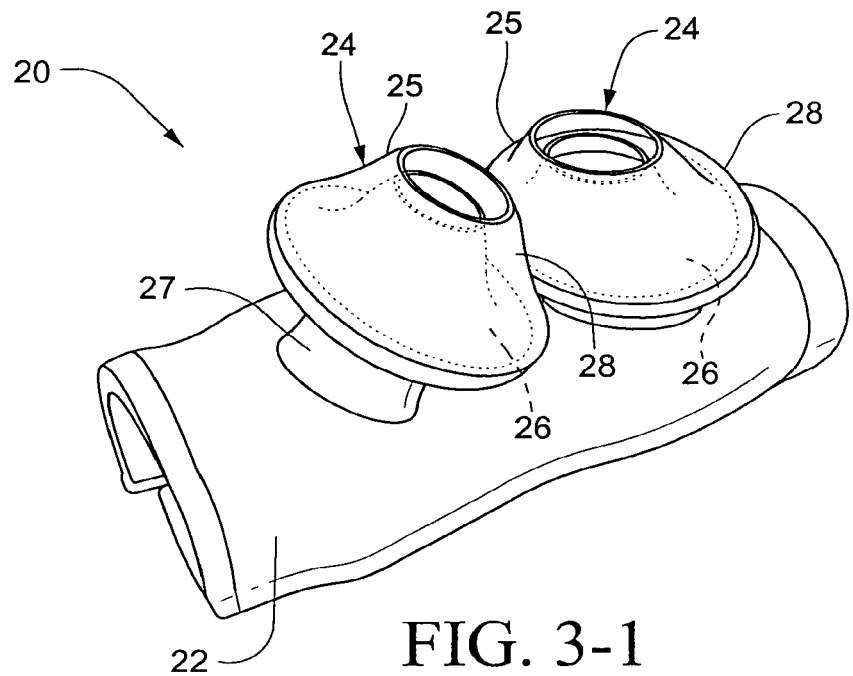
Figures 1, 4:
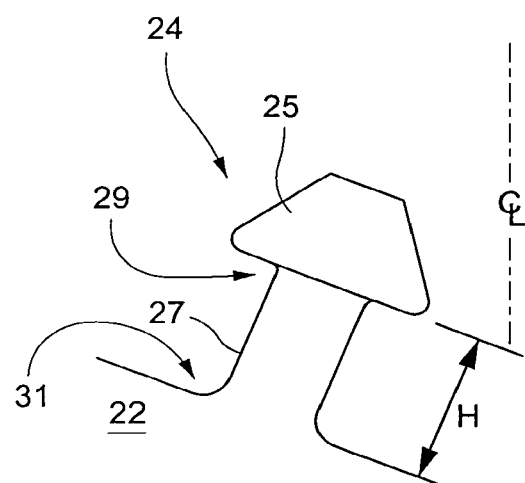
Figures 2, 4:
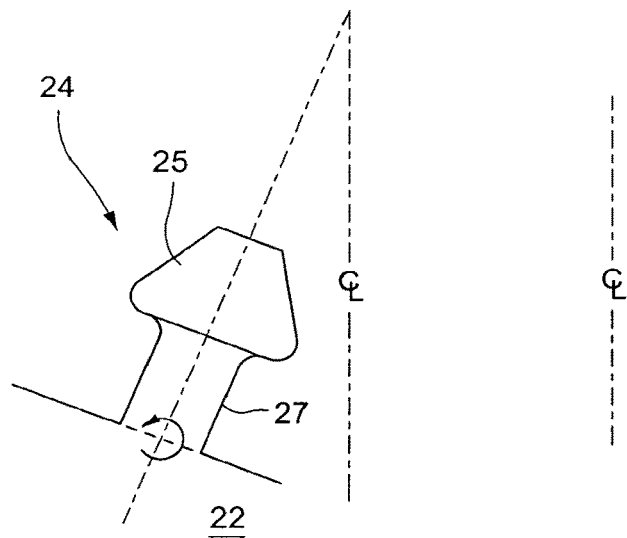
Figures 1, 5:
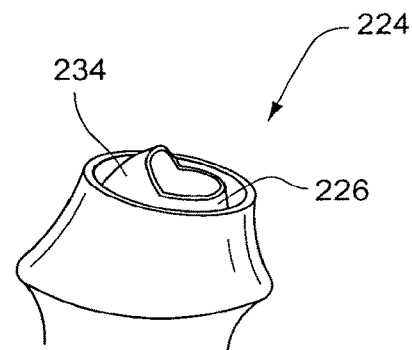
Figures 2, 5:
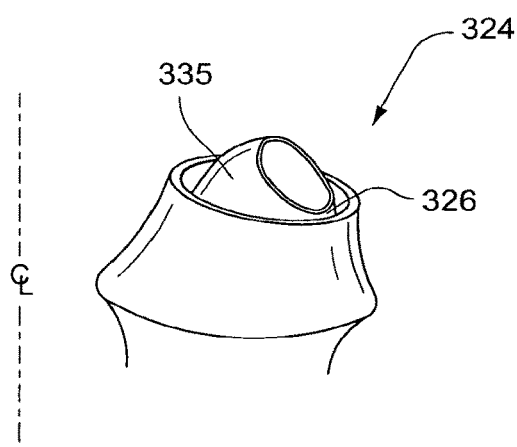
Figures 3, 5:
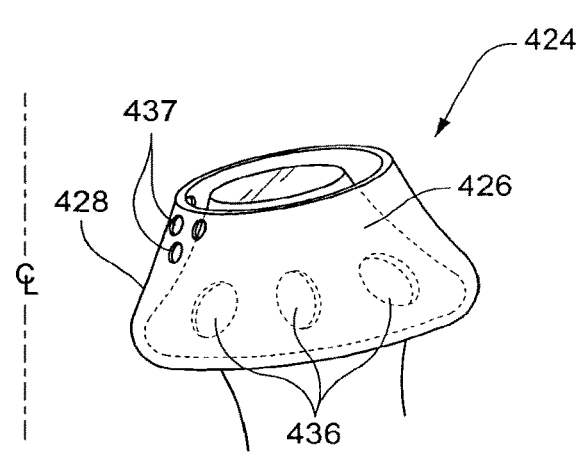
Figures 4, 5:
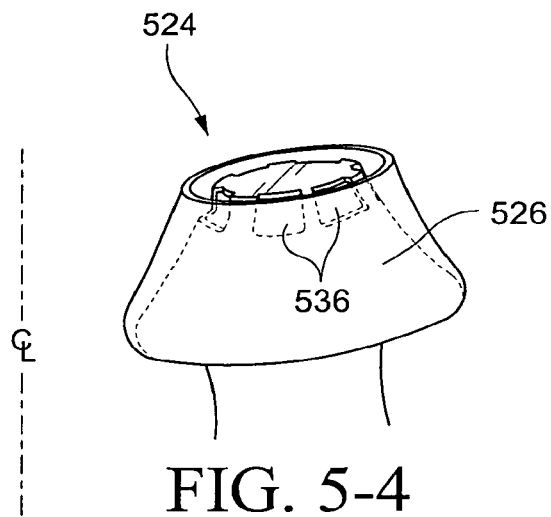
Figure 5:
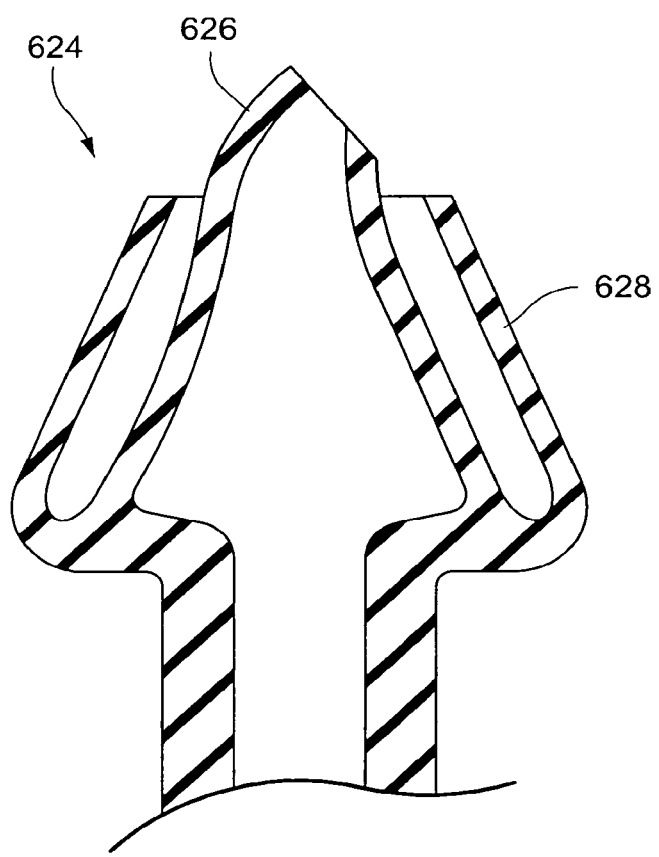
Figures 5, 6:
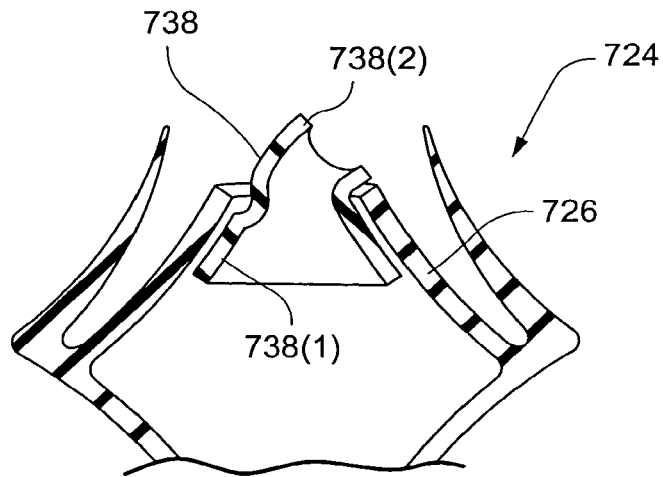
Figures 1, 5, 6, 7:
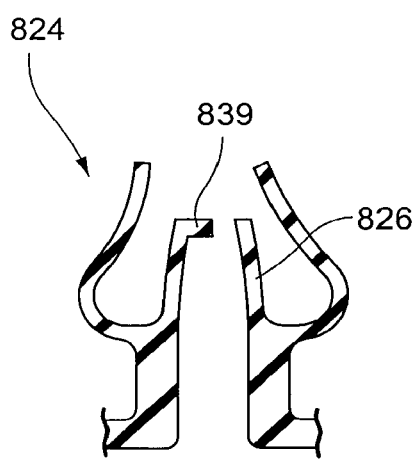
Figures 2, 5, 6, 7:
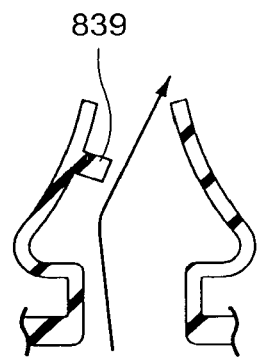
Figures 5, 6, 7, 8:
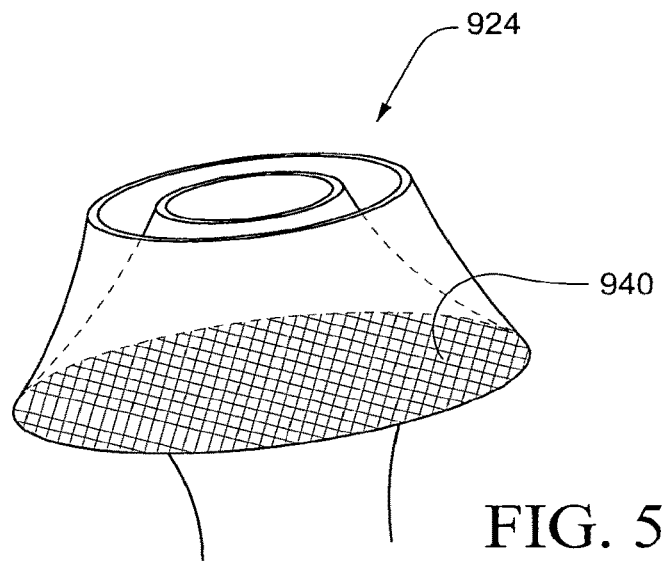
Figures 1, 5, 6, 7, 8, 9:
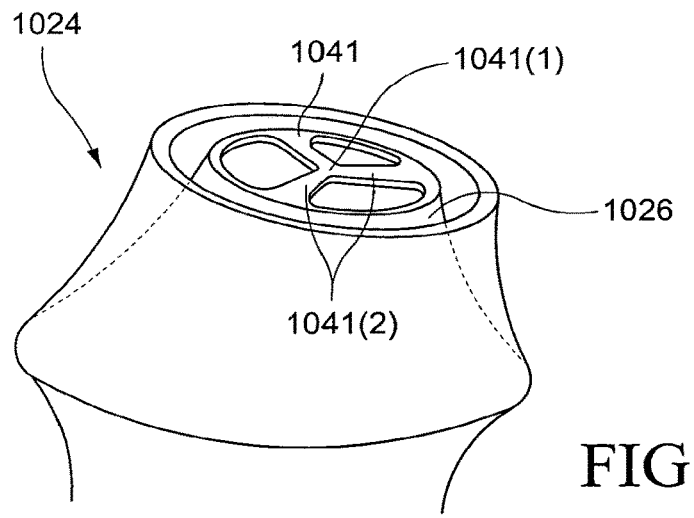
Figures 2, 5, 6, 7, 8, 9:
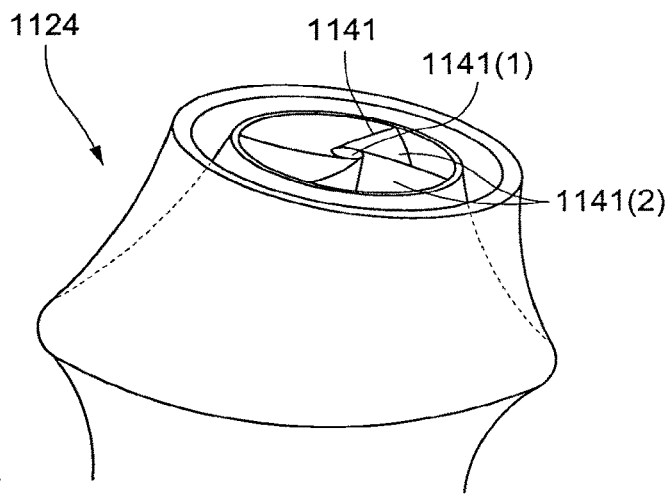
Figures 5, 6, 7, 8, 9, 10:
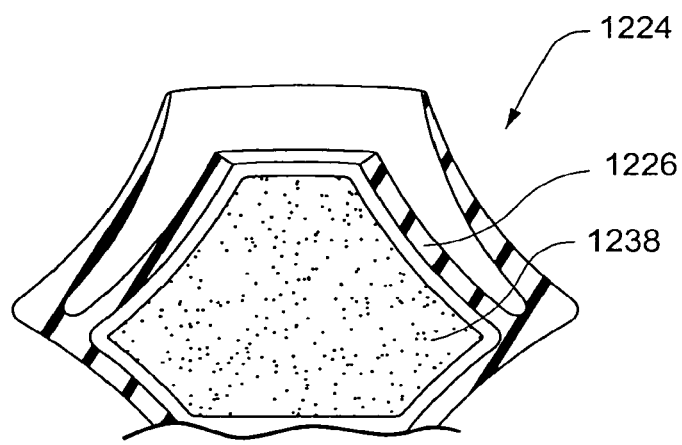
Figures 5, 6, 7, 8, 9, 10, 11:
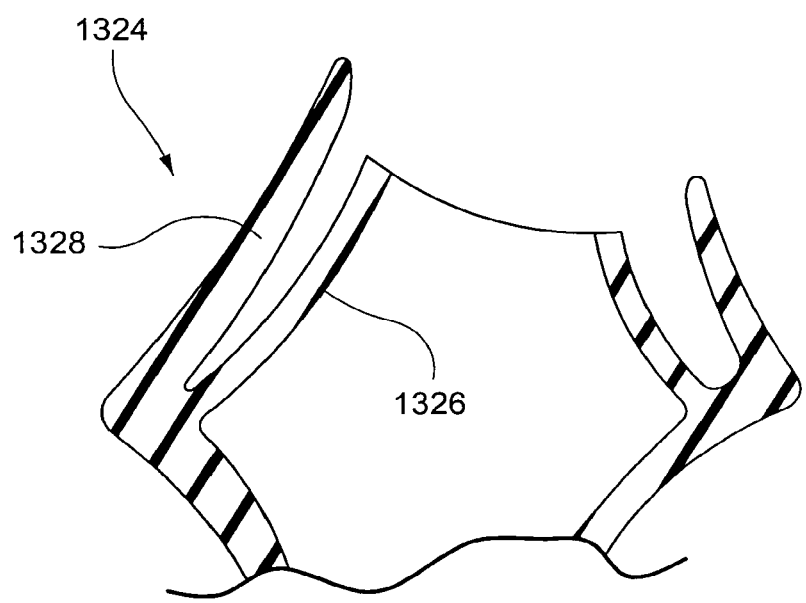
Figures 1, 5, 6, 7, 8, 9, 10, 11, 12:
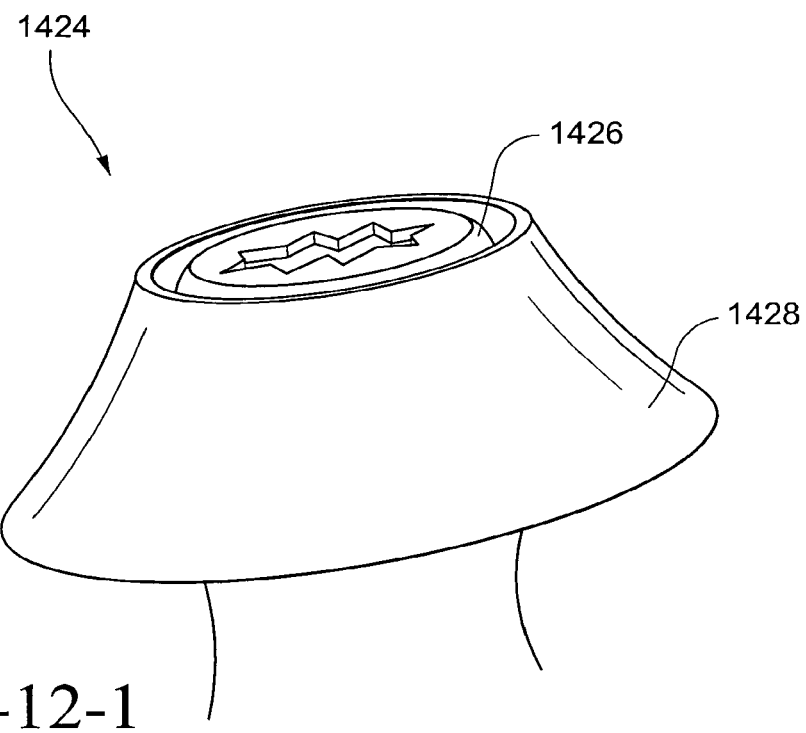
Figures 2, 5, 6, 7, 8, 9, 10, 11, 12:
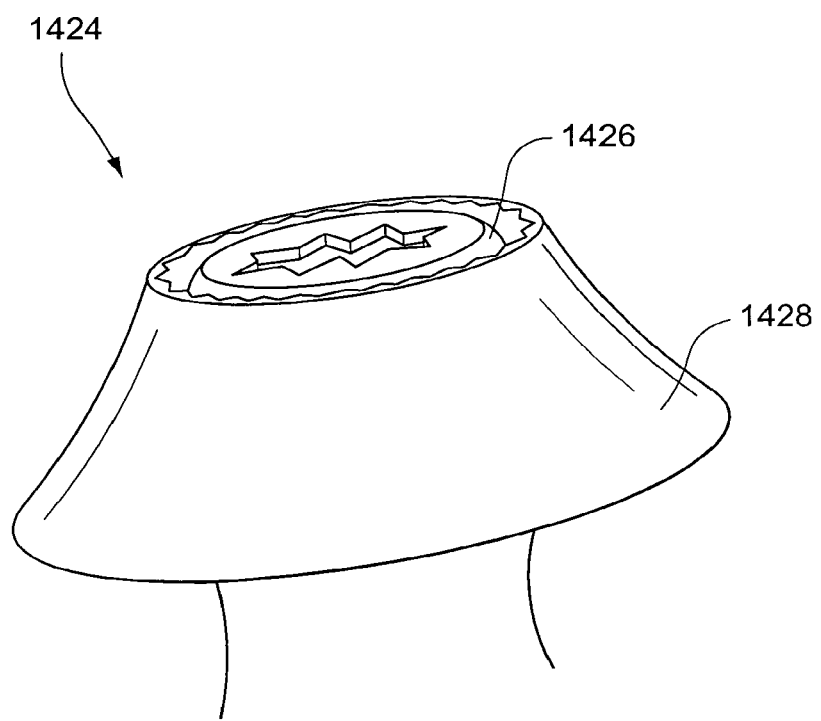
Figures 3, 5, 6, 7, 8, 9, 10, 11, 12:
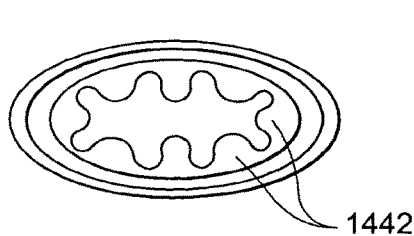
Figures 4, 5, 6, 7, 8, 9, 10, 11, 12:
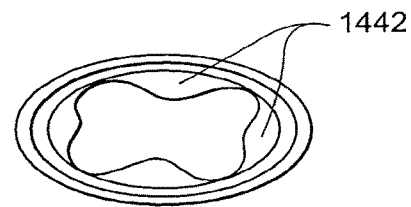
Figures 1, 2, 5, 6, 7, 8, 9, 10, 11, 12, 13:
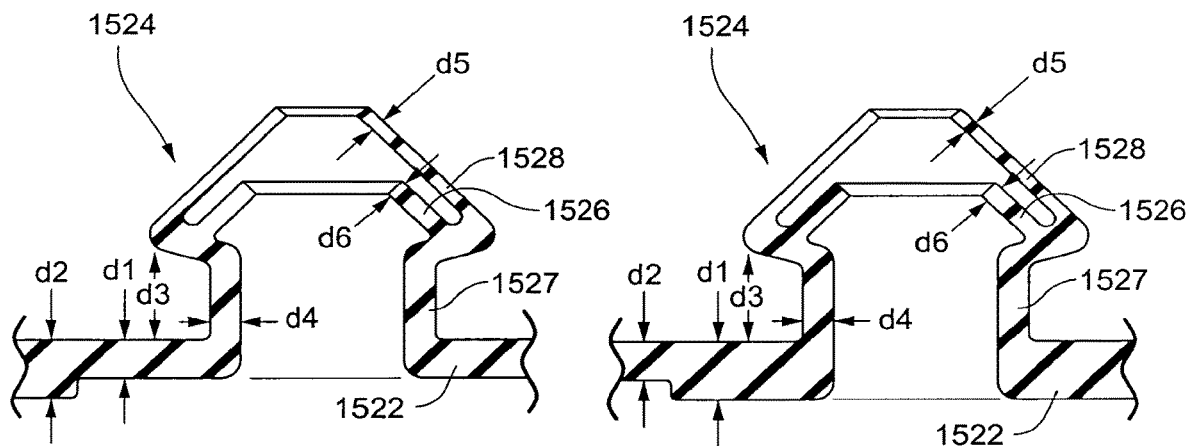
Figures 3, 5, 6, 7, 8, 9, 10, 11, 12, 13:
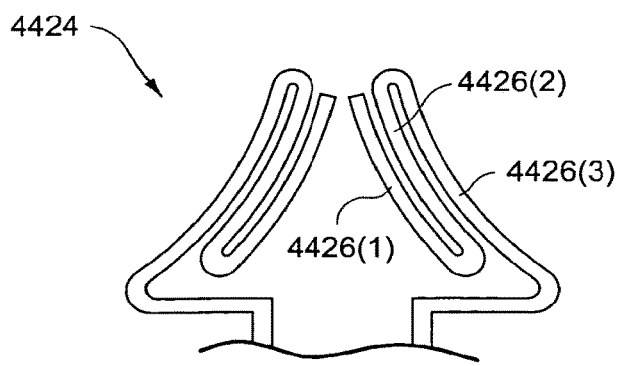
Figures 1, 5, 6, 7, 8, 9, 10, 11, 12, 13, 14:
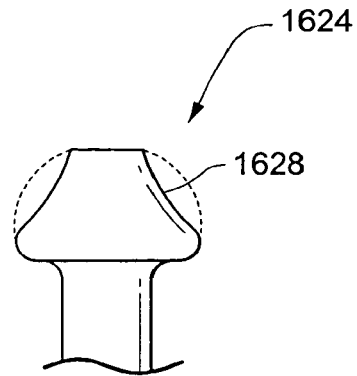
Figures 2, 5, 6, 7, 8, 9, 10, 11, 12, 13, 14:
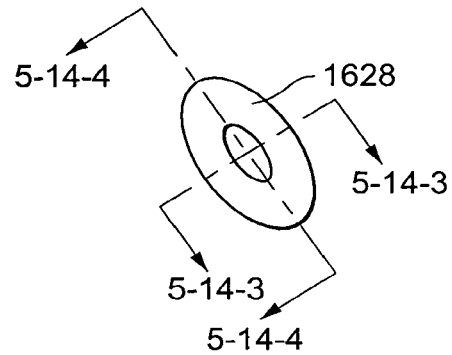
Figures 3, 5, 6, 7, 8, 9, 10, 11, 12, 13, 14:
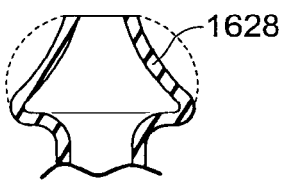
Figures 4, 5, 6, 7, 8, 9, 10, 11, 12, 13, 14:
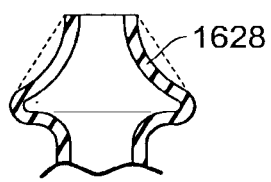
Figures 1, 5, 6, 7, 8, 9, 10, 11, 12, 13, 14, 15:
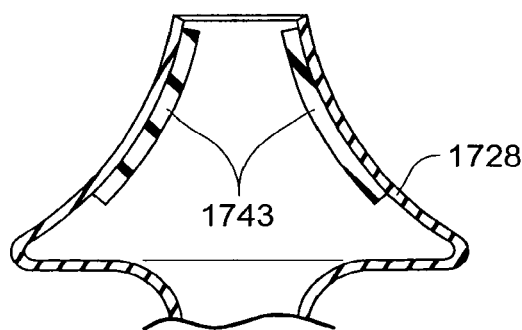
Figures 2, 5, 6, 7, 8, 9, 10, 11, 12, 13, 14, 15:
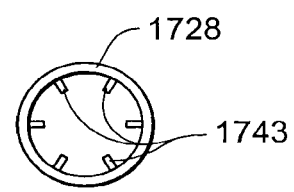
Figures 5, 6, 7, 8, 9, 10, 11, 12, 13, 14, 15, 16:
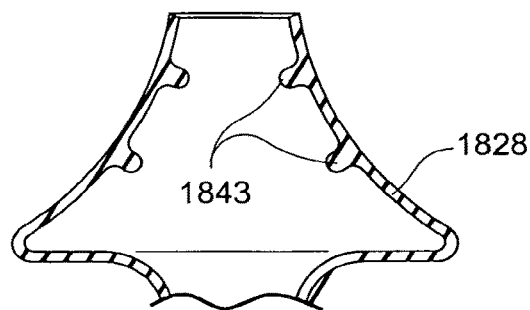
Figures 5, 6, 7, 8, 9, 10, 11, 12, 13, 14, 15, 16, 17:
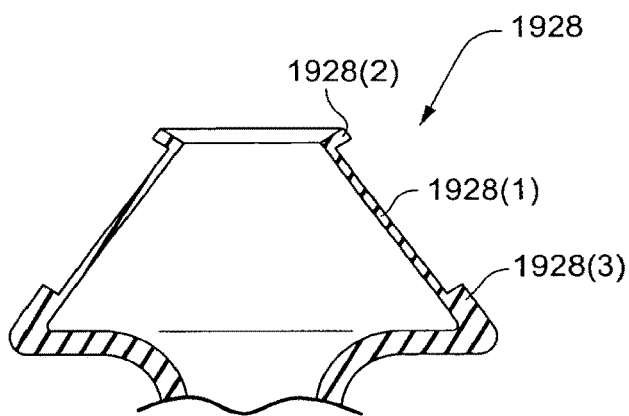
Figures 5, 6, 7, 8, 9, 10, 11, 12, 13, 14, 15, 16, 17, 18:
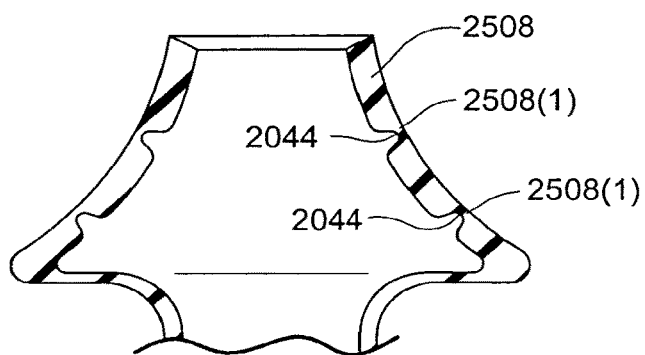
Figures 5, 6, 7, 8, 9, 10, 11, 12, 13, 14, 15, 16, 17, 18, 19, 20, 21:
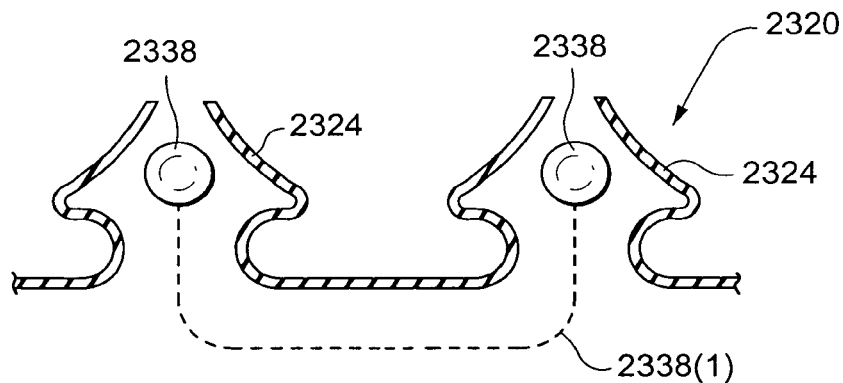
Figures 1, 5, 6, 7, 8, 9, 10, 11, 12, 13, 14, 15, 16, 17, 18, 19, 20, 21, 22:
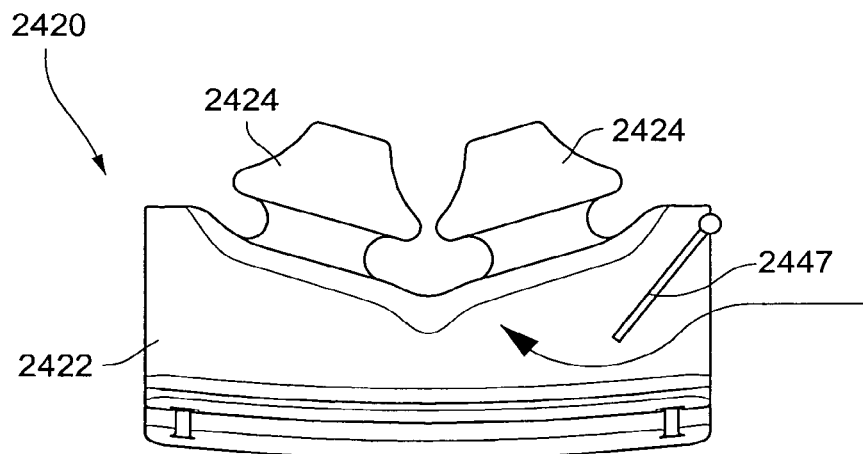
Figures 2, 5, 6, 7, 8, 9, 10, 11, 12, 13, 14, 15, 16, 17, 18, 19, 20, 21, 22:
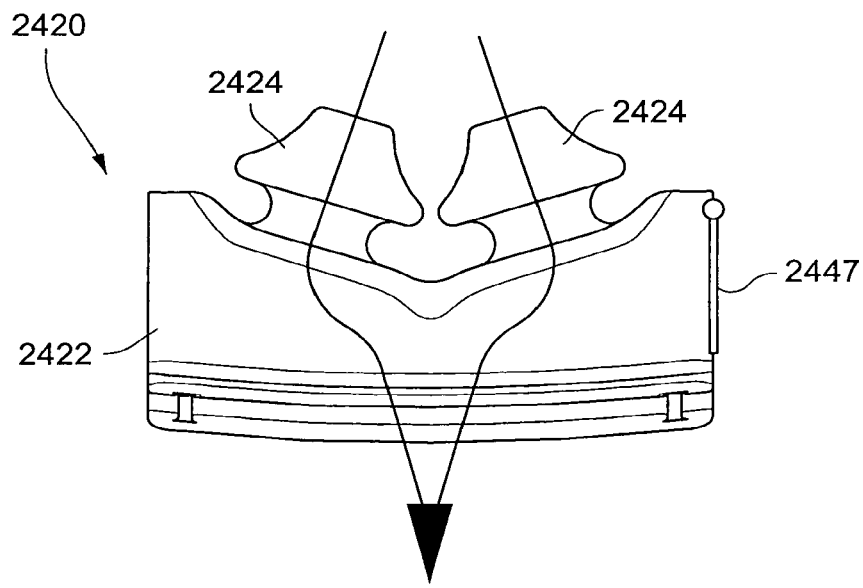
Figures 1, 5, 6, 7, 8, 9, 10, 11, 12, 13, 14, 15, 16, 17, 18, 19, 20, 21, 22, 23:
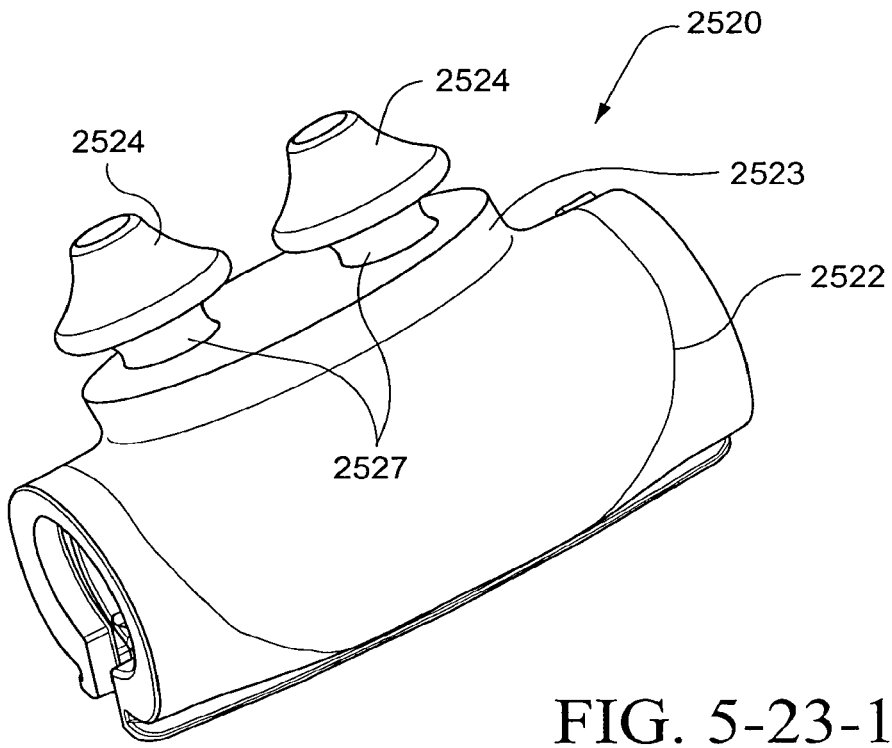
Figures 2, 5, 6, 7, 8, 9, 10, 11, 12, 13, 14, 15, 16, 17, 18, 19, 20, 21, 22, 23:
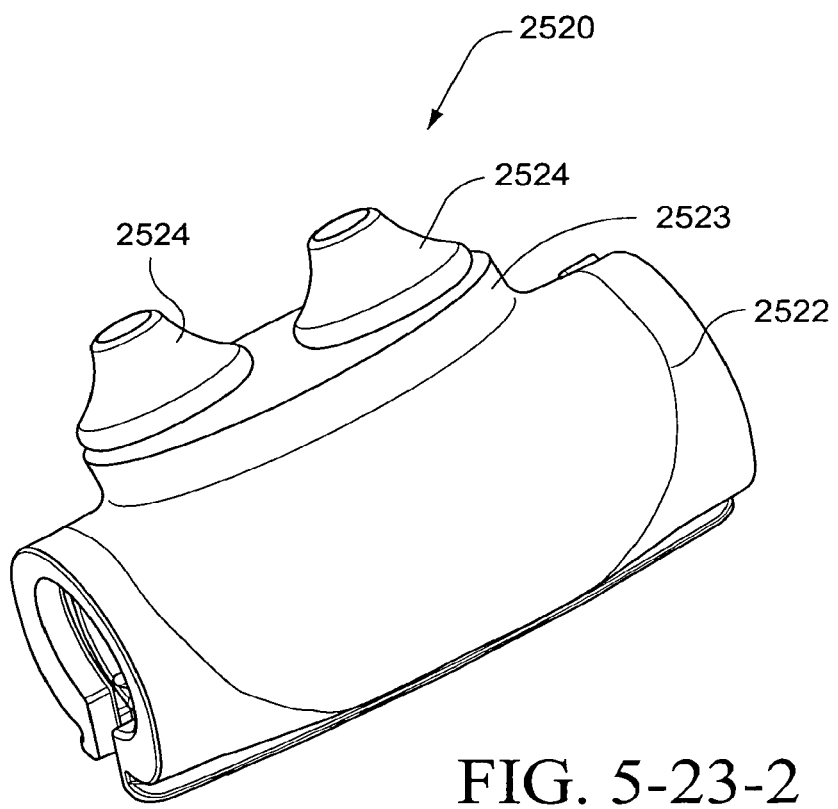
Figures 1, 5, 6, 7, 8, 9, 10, 11, 12, 13, 14, 15, 16, 17, 18, 19, 20, 21, 22, 23, 24:
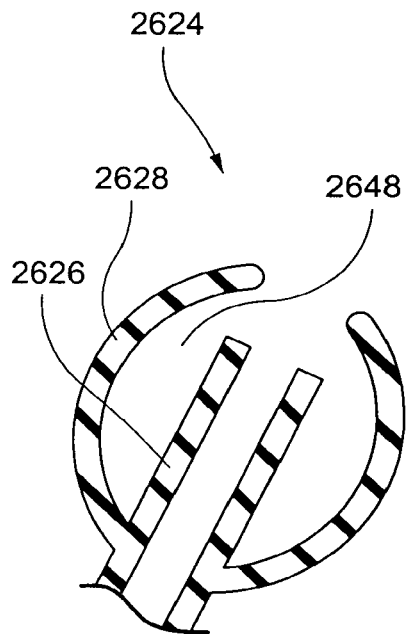
Figures 2, 5, 6, 7, 8, 9, 10, 11, 12, 13, 14, 15, 16, 17, 18, 19, 20, 21, 22, 23, 24:
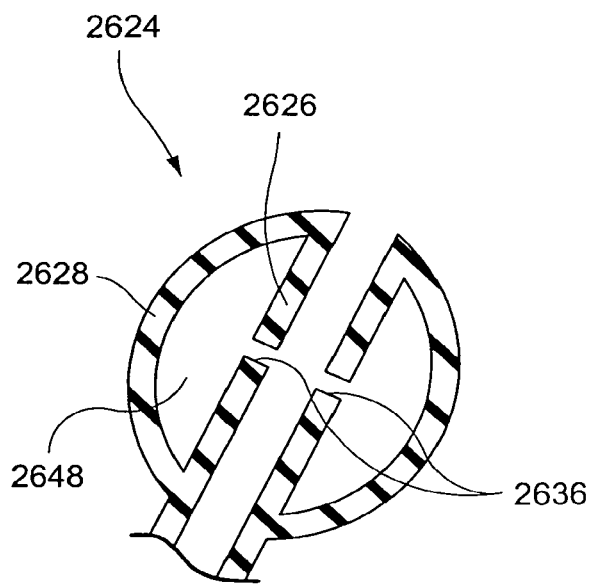
Figures 5, 6, 7, 8, 9, 10, 11, 12, 13, 14, 15, 16, 17, 18, 19, 20, 21, 22, 23, 24, 25:
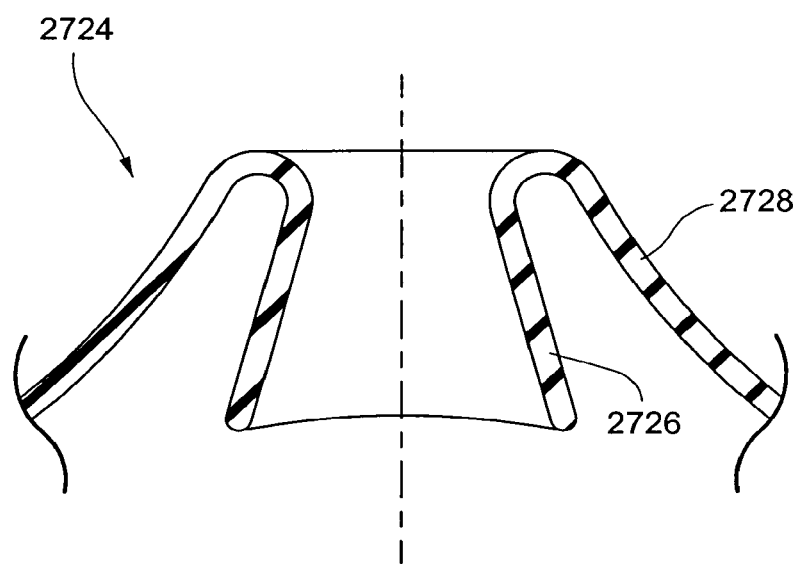
Figures 5, 6, 7, 8, 9, 10, 11, 12, 13, 14, 15, 16, 17, 18, 19, 20, 21, 22, 23, 24, 25, 26:
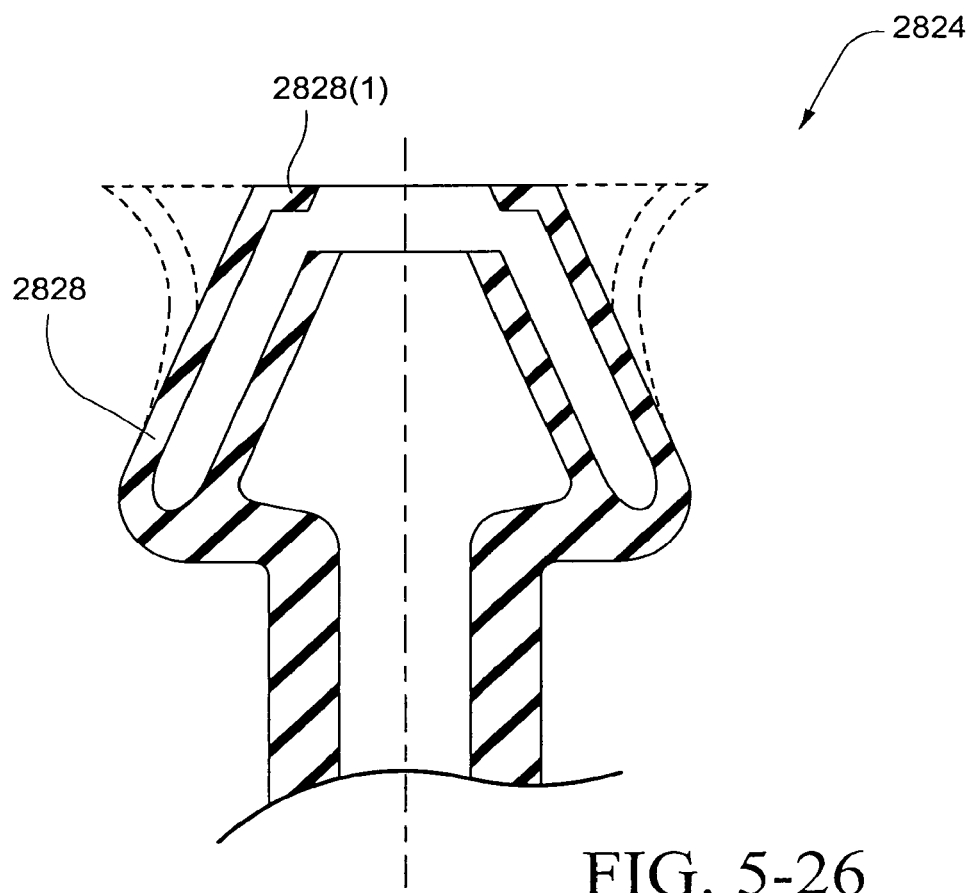
Figures 5, 6, 7, 8, 9, 10, 11, 12, 13, 14, 15, 16, 17, 18, 19, 20, 21, 22, 23, 24, 25, 26, 27:
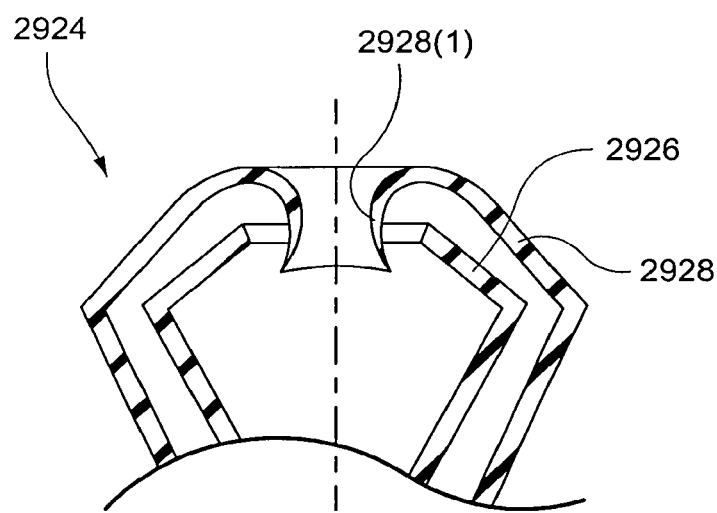
Figures 5, 6, 7, 8, 9, 10, 11, 12, 13, 14, 15, 16, 17, 18, 19, 20, 21, 22, 23, 24, 25, 26, 27, 28:
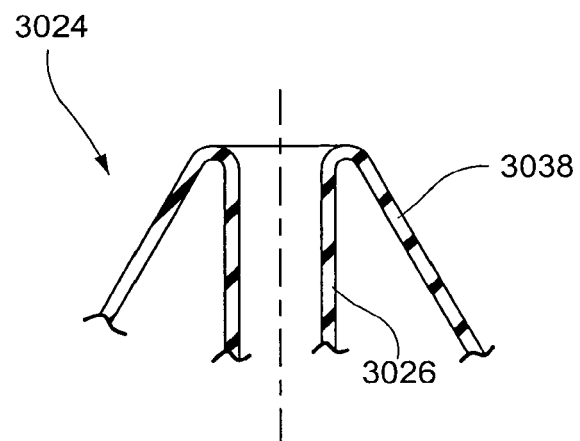
Figures 5, 6, 7, 8, 9, 10, 11, 12, 13, 14, 15, 16, 17, 18, 19, 20, 21, 22, 23, 24, 25, 26, 27, 28, 29:
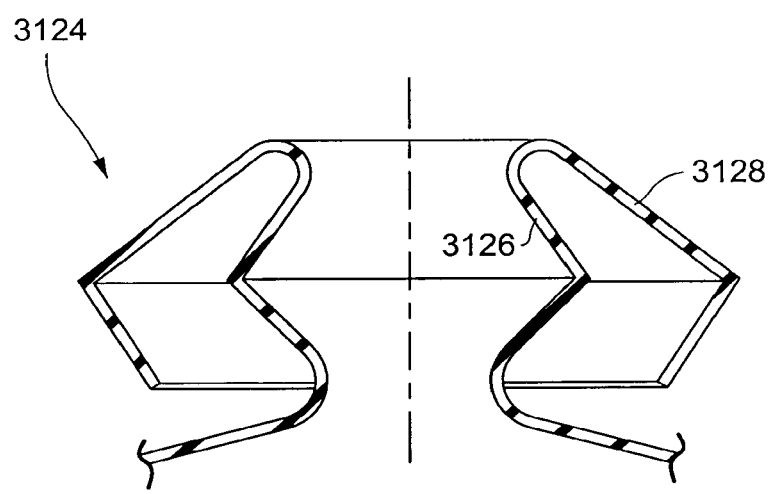
Figures 5, 6, 7, 8, 9, 10, 11, 12, 13, 14, 15, 16, 17, 18, 19, 20, 21, 22, 23, 24, 25, 26, 27, 28, 29, 30:
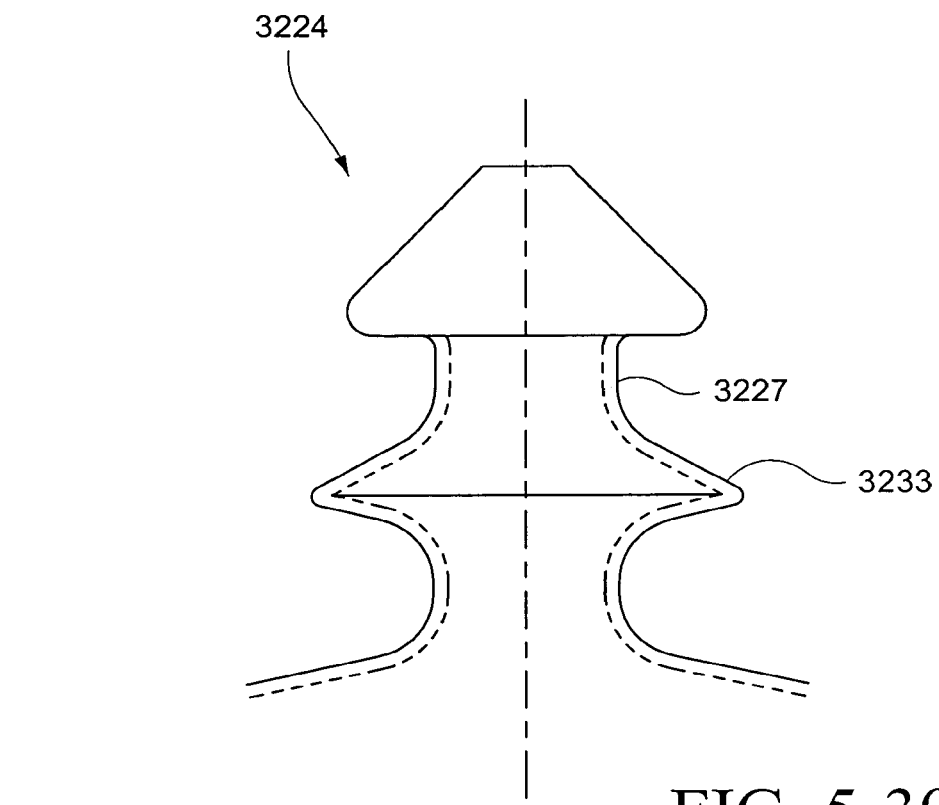
Figures 5, 6, 7, 8, 9, 10, 11, 12, 13, 14, 15, 16, 17, 18, 19, 20, 21, 22, 23, 24, 25, 26, 27, 28, 29, 30, 31:
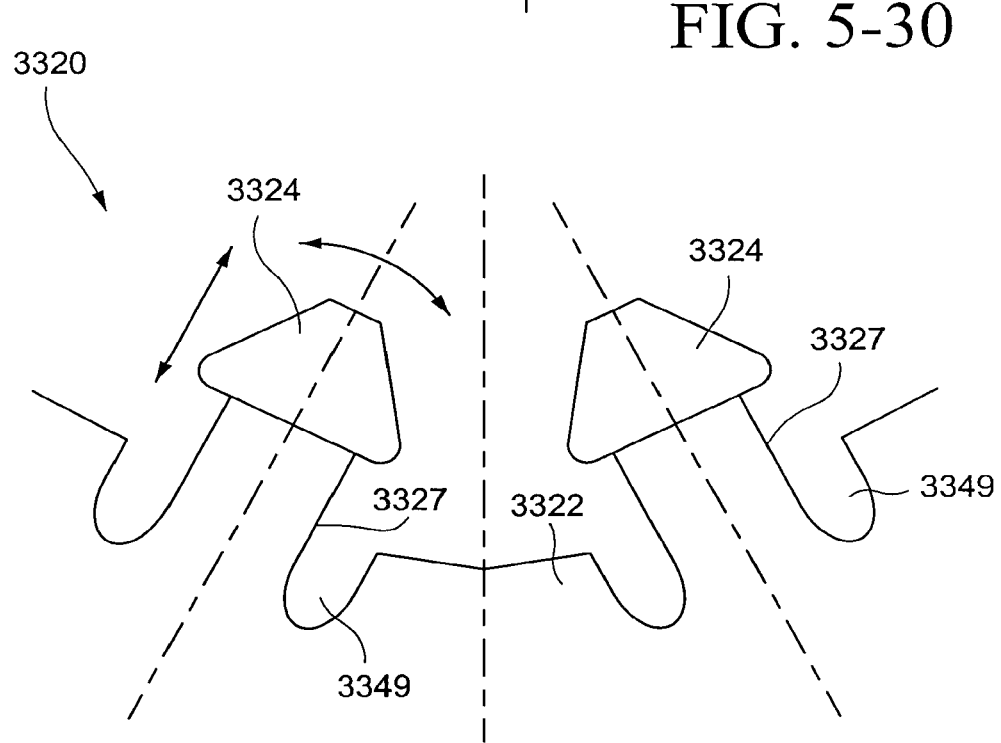
Figures 1, 5, 6, 7, 8, 9, 10, 11, 12, 13, 14, 15, 16, 17, 18, 19, 20, 21, 22, 23, 24, 25, 26, 27, 28, 29, 30, 31, 32:
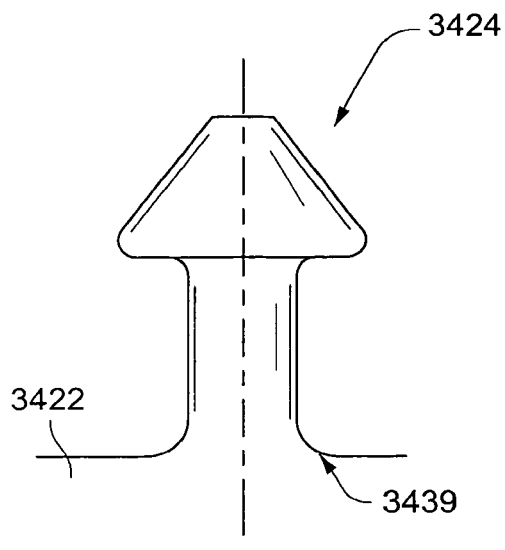
Figures 2, 5, 6, 7, 8, 9, 10, 11, 12, 13, 14, 15, 16, 17, 18, 19, 20, 21, 22, 23, 24, 25, 26, 27, 28, 29, 30, 31, 32:
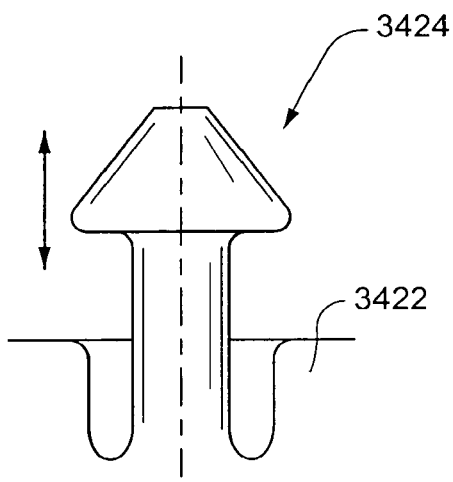
Figures 3, 5, 6, 7, 8, 9, 10, 11, 12, 13, 14, 15, 16, 17, 18, 19, 20, 21, 22, 23, 24, 25, 26, 27, 28, 29, 30, 31, 32:
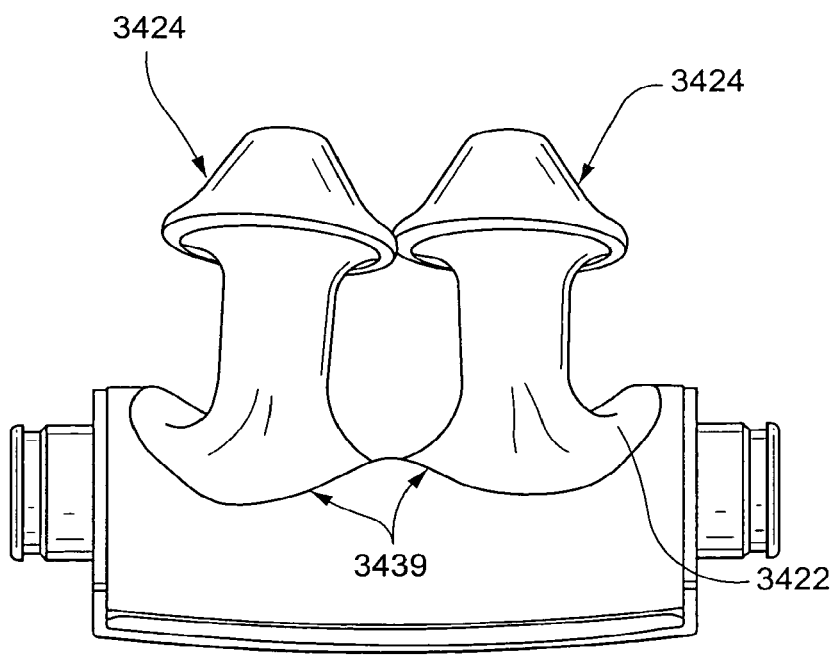
Figures 4, 5, 6, 7, 8, 9, 10, 11, 12, 13, 14, 15, 16, 17, 18, 19, 20, 21, 22, 23, 24, 25, 26, 27, 28, 29, 30, 31, 32:
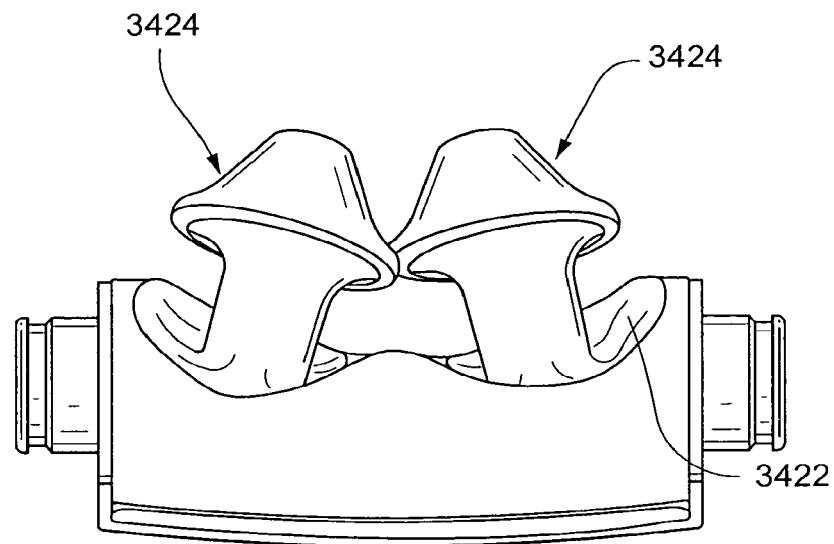
Figures 5, 6, 7, 8, 9, 10, 11, 12, 13, 14, 15, 16, 17, 18, 19, 20, 21, 22, 23, 24, 25, 26, 27, 28, 29, 30, 31, 32:
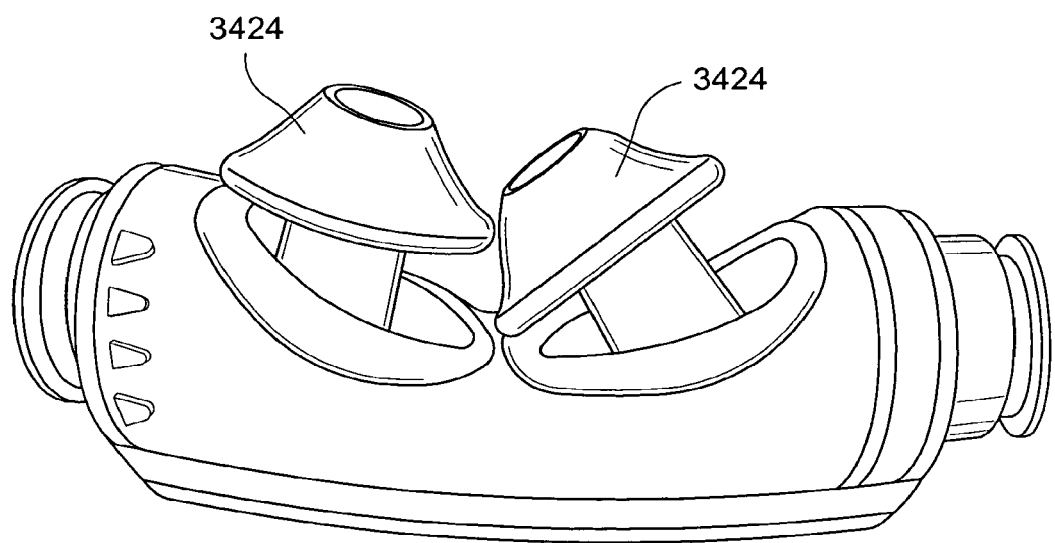
Figures 5, 6, 7, 8, 9, 10, 11, 12, 13, 14, 15, 16, 17, 18, 19, 20, 21, 22, 23, 24, 25, 26, 27, 28, 29, 30, 31, 32, 33:
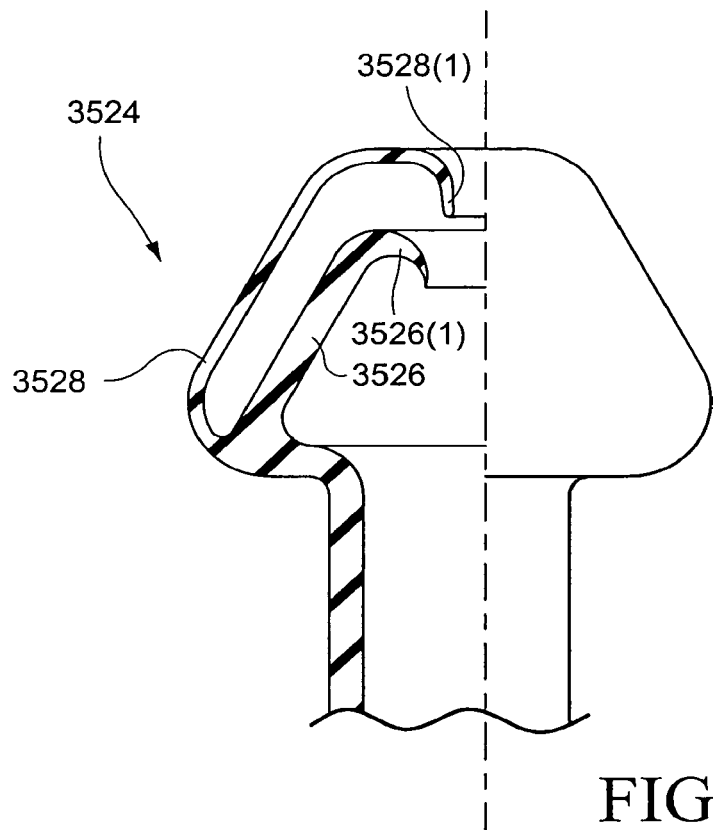
Figures 5, 6, 7, 8, 9, 10, 11, 12, 13, 14, 15, 16, 17, 18, 19, 20, 21, 22, 23, 24, 25, 26, 27, 28, 29, 30, 31, 32, 33, 34:
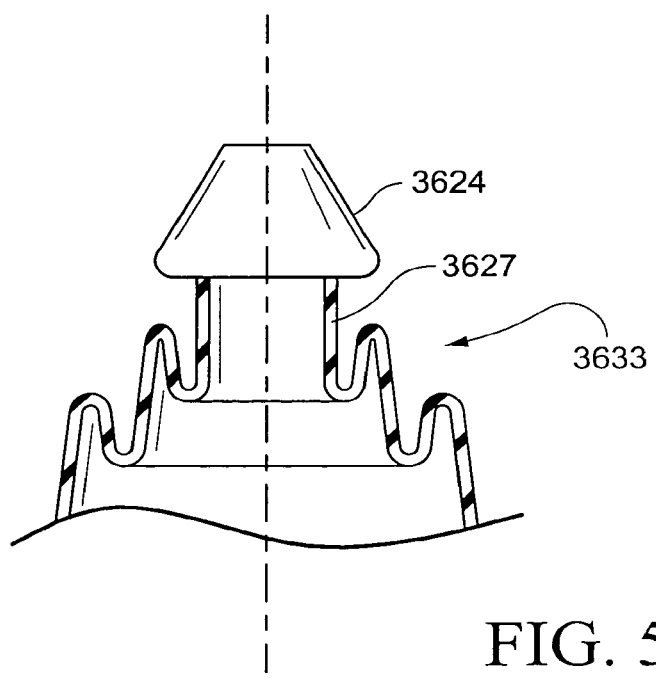
Figures 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35:
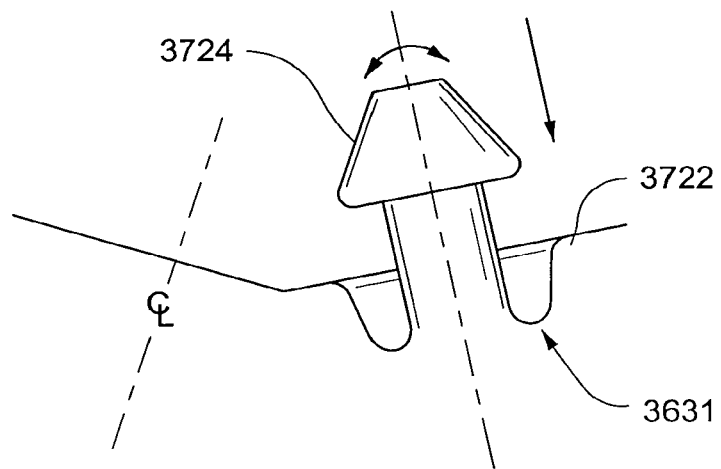
Figures 1, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36:
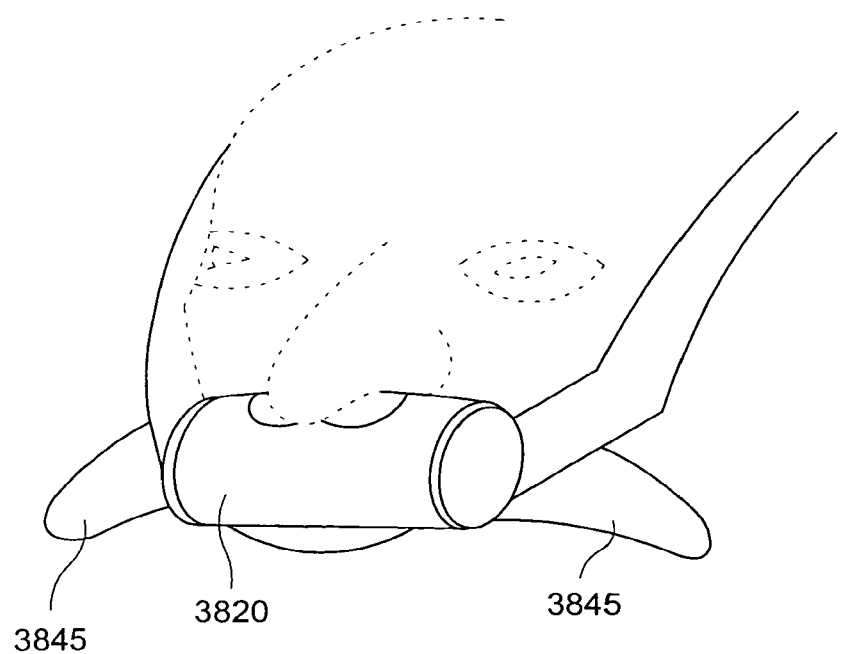
Figures 2, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36:
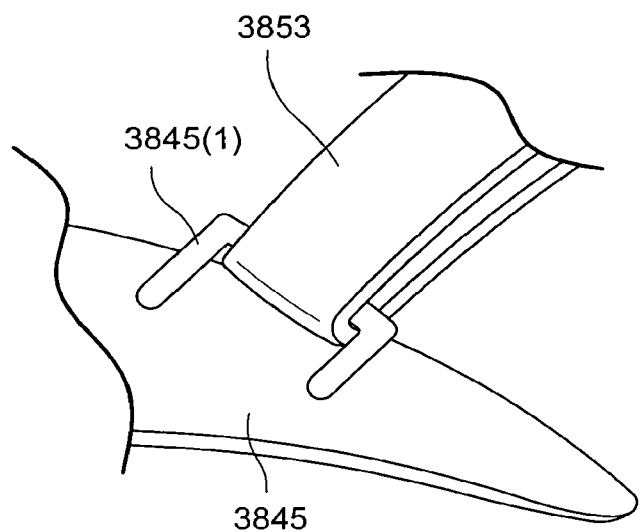
Figures 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37:
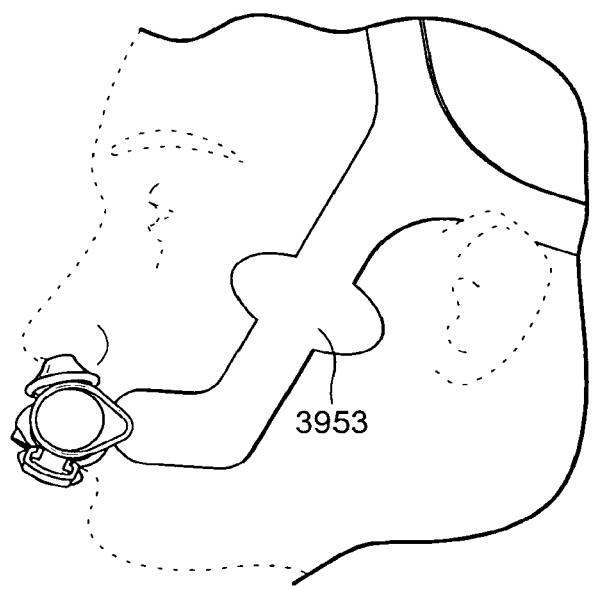
Figures 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38:
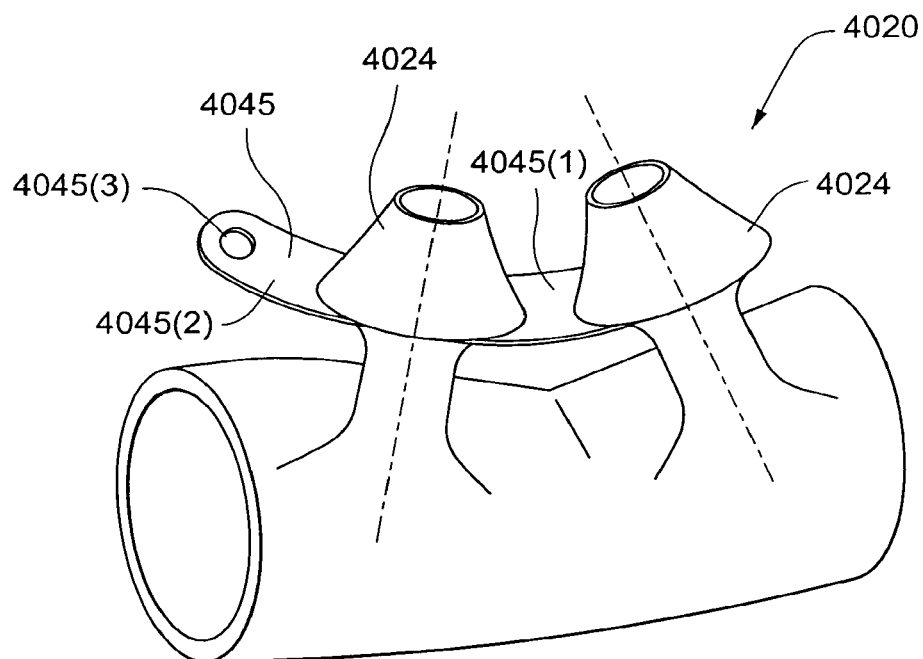
Figures 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39:
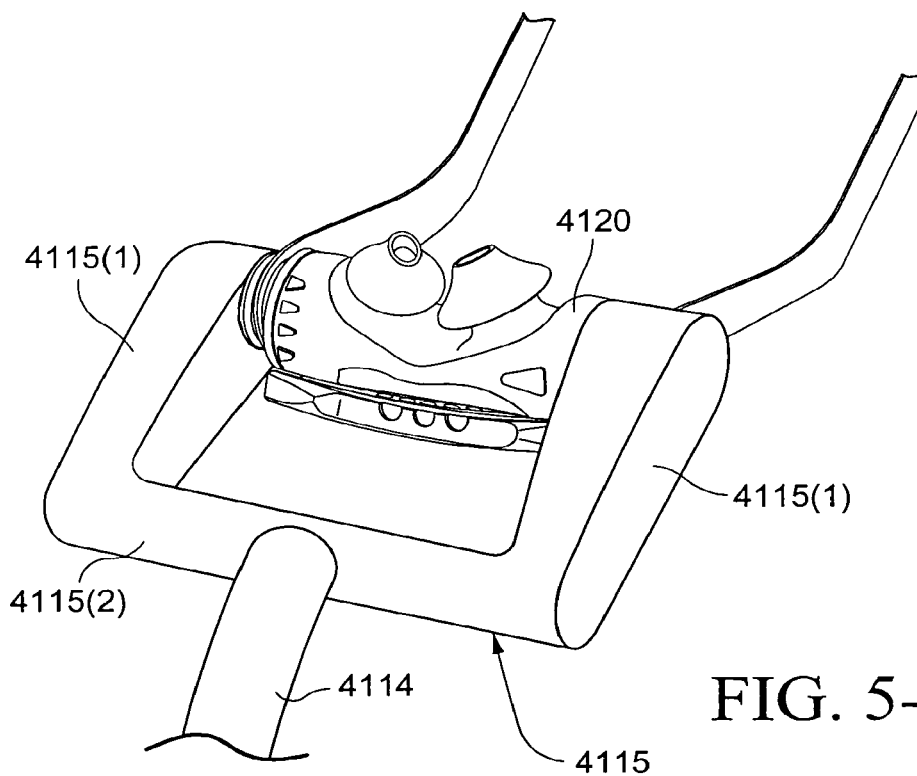
Figures 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40:
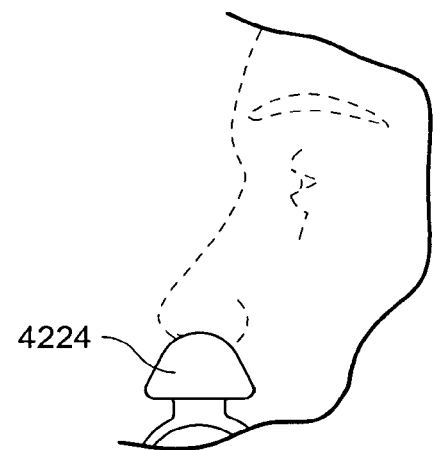
Figures 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41:
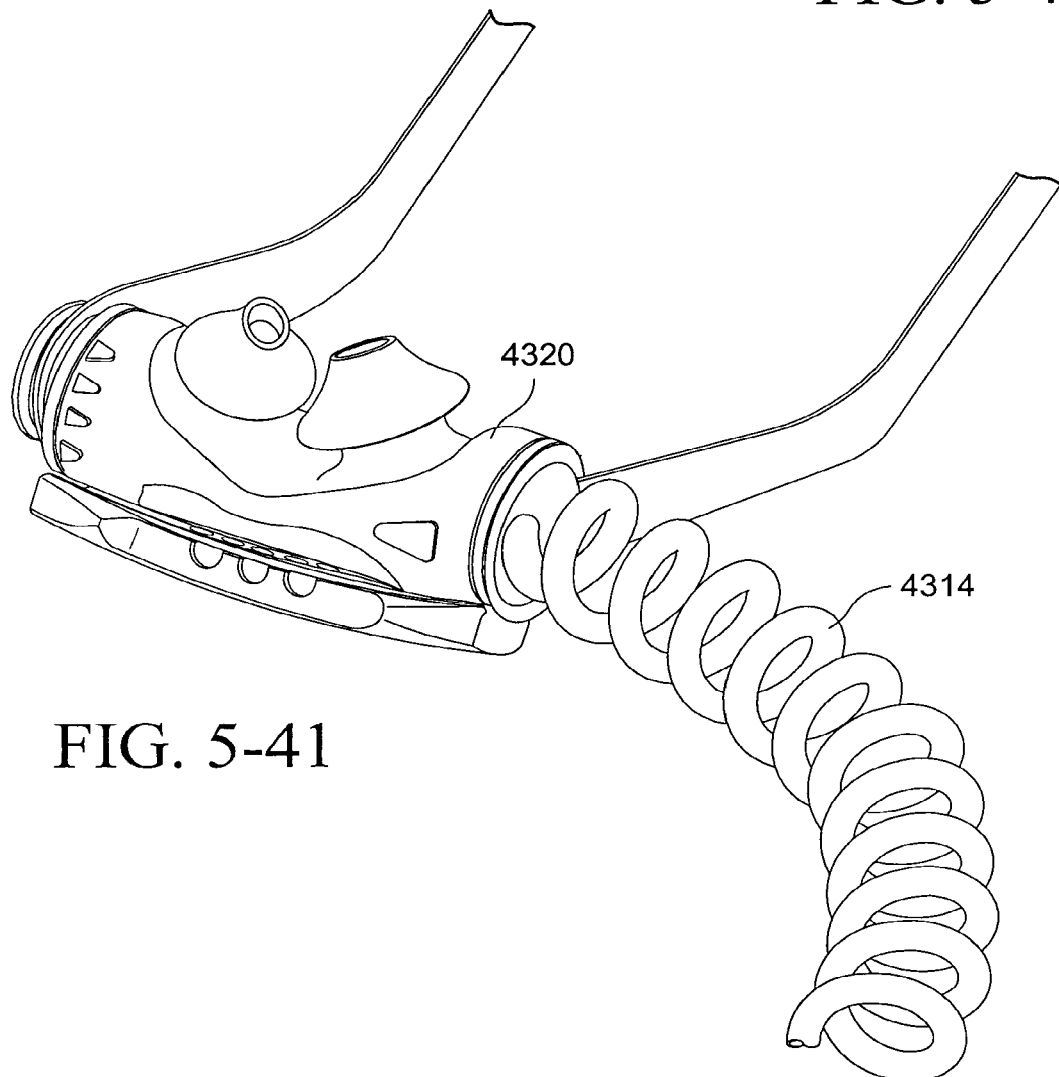
Figures 3, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42:
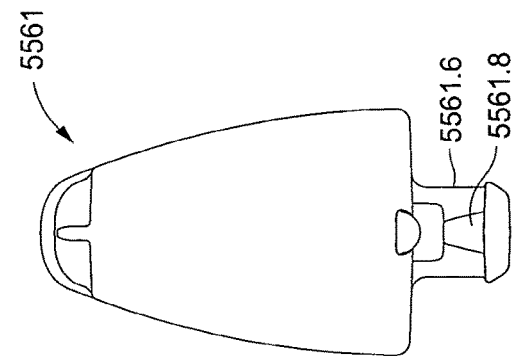
Figures 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42:
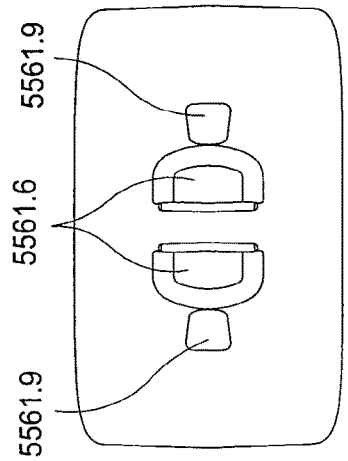
Figures 1, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42:
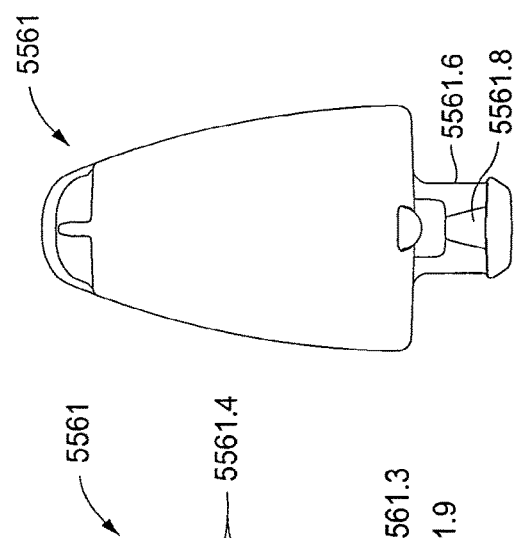
Figures 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42:
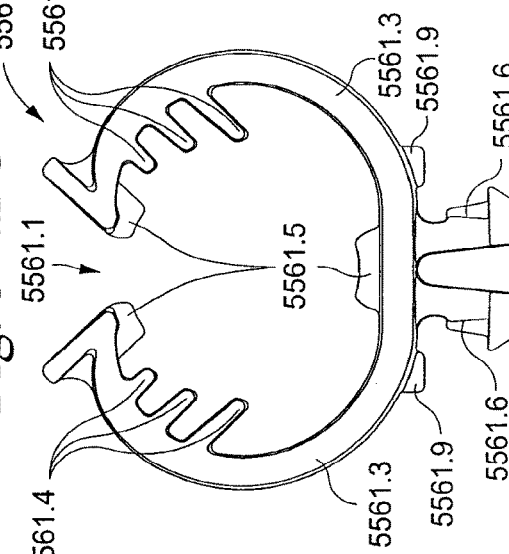
Figures 2, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42:
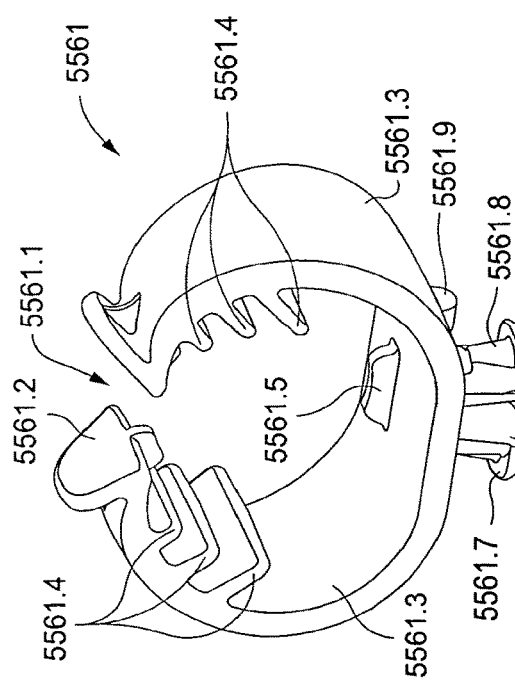
Figures 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42:
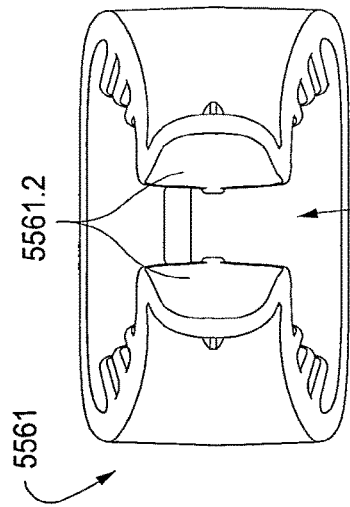
Figures 3, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44:
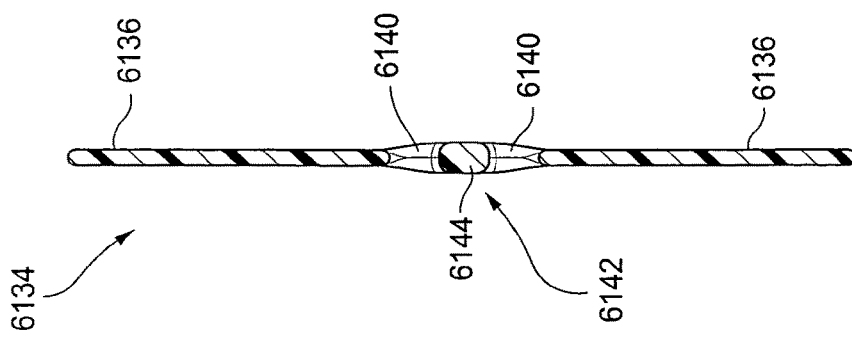
Figures 2, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44:
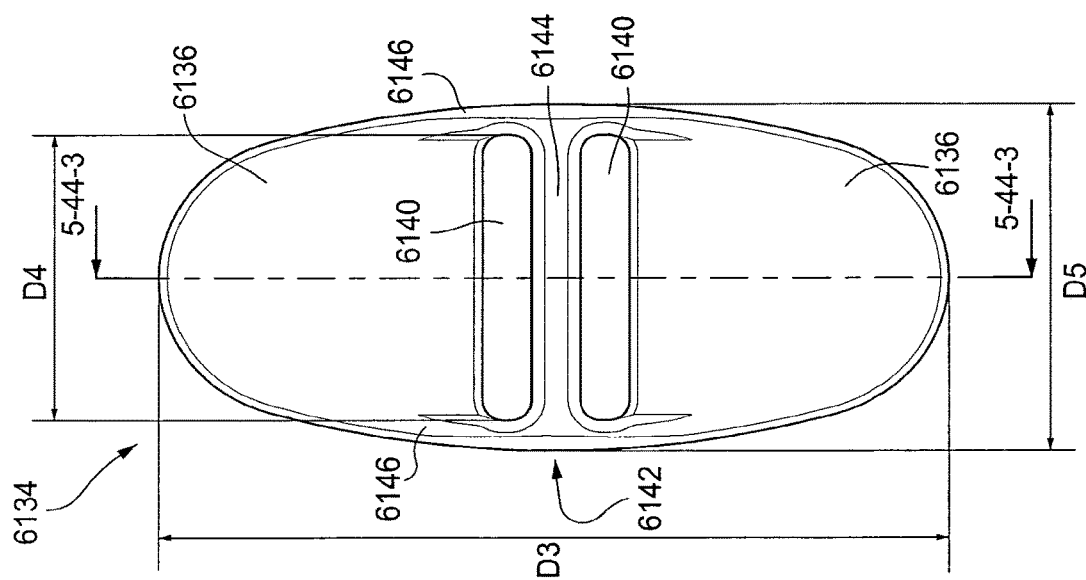
Figures 1, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44:
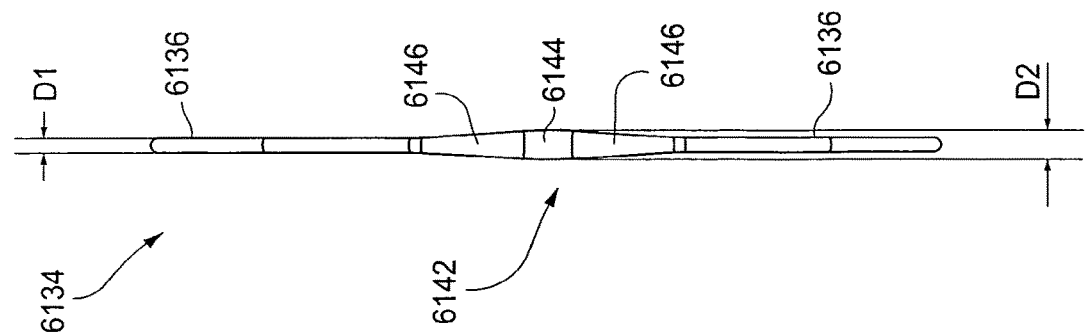
Figures 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44:
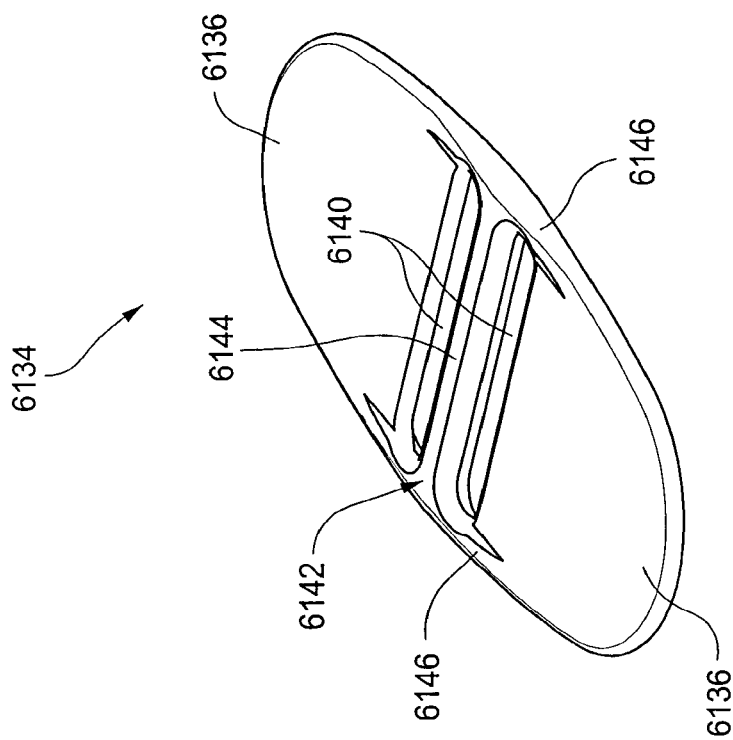
Figures 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44:
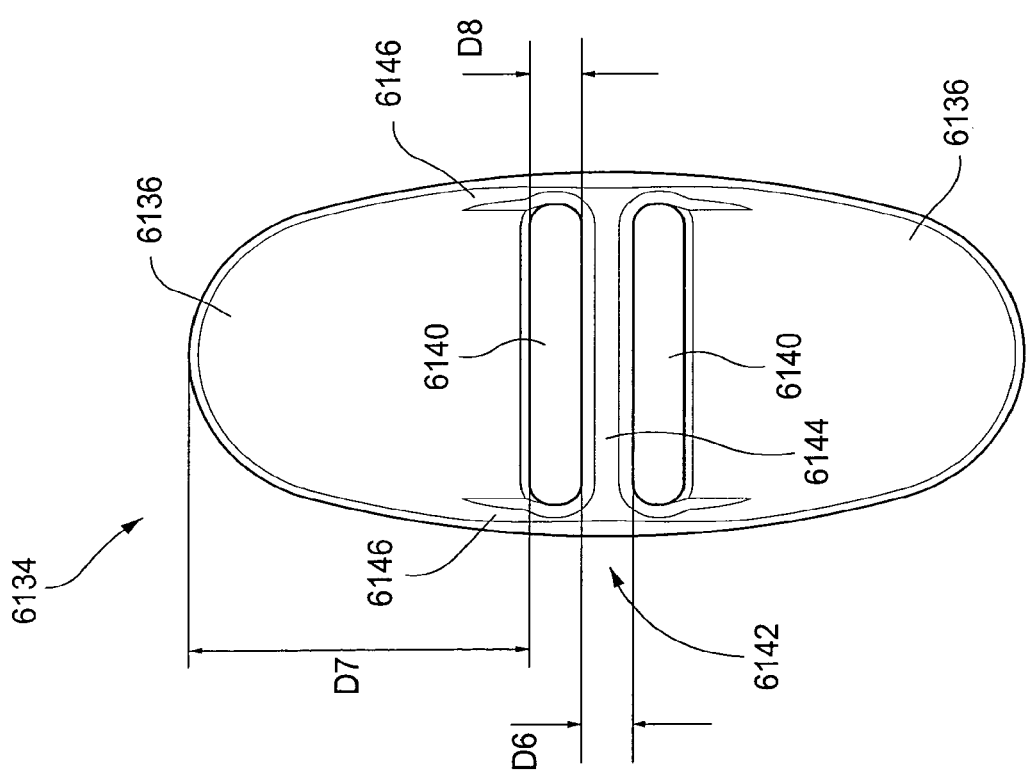
Figures 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45:
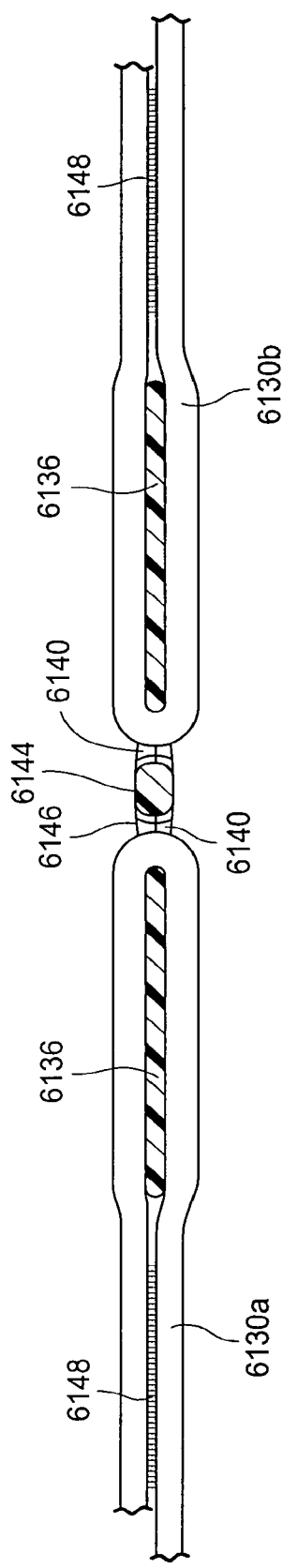
Figures 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46:
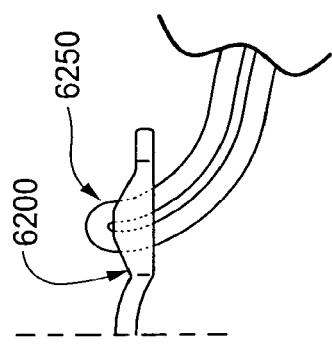
Figures 1, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47:
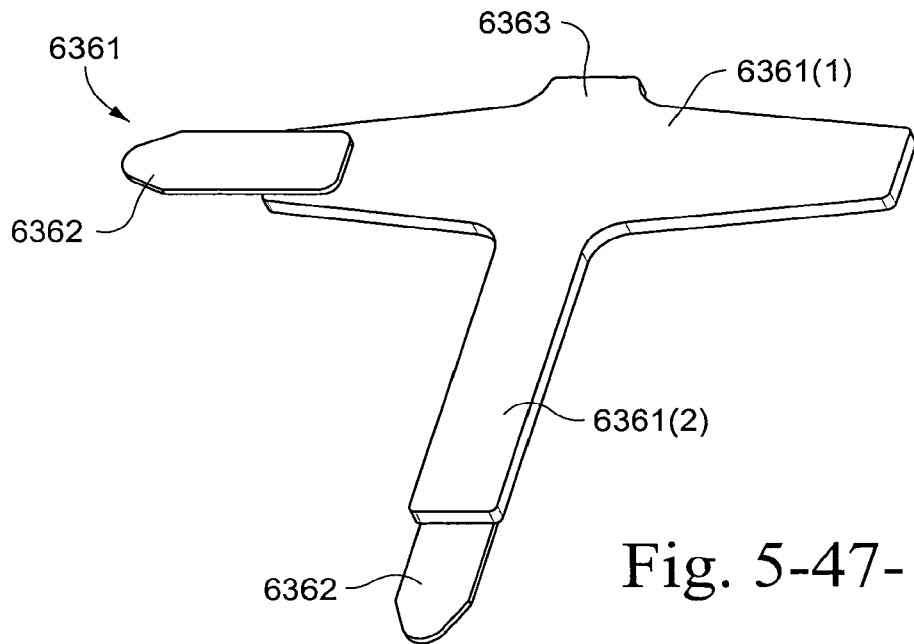
Figures 2, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47:
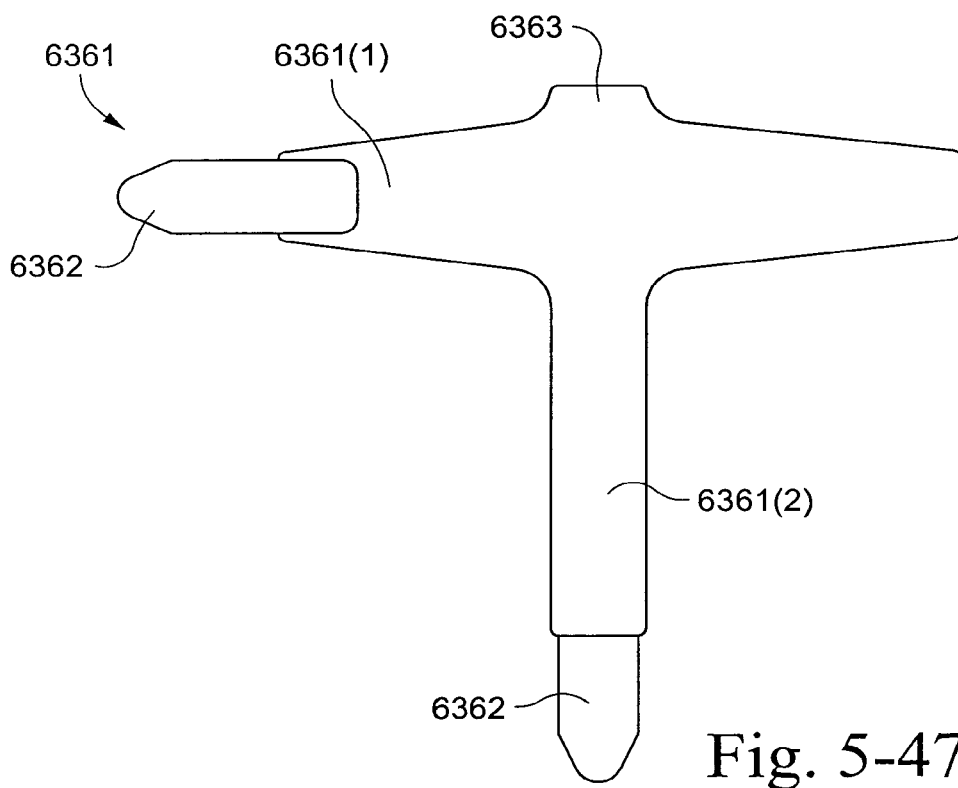
Figures 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48:
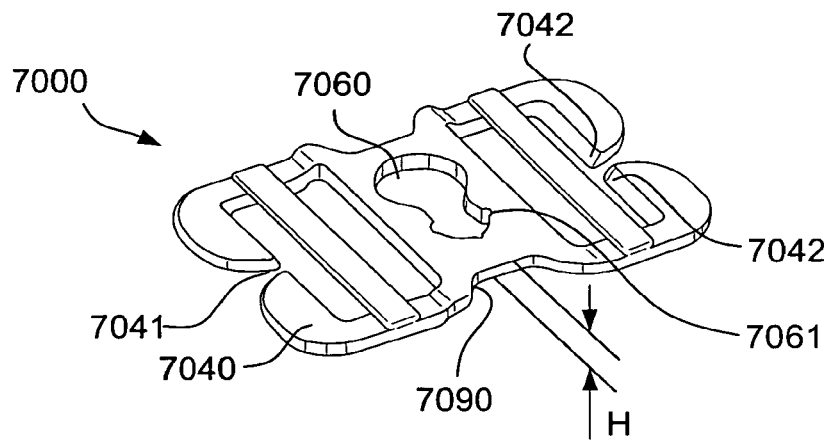
Figures 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49:
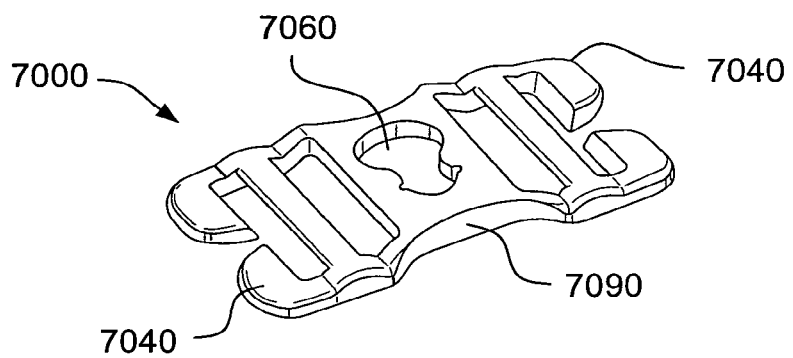
Figures 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50:
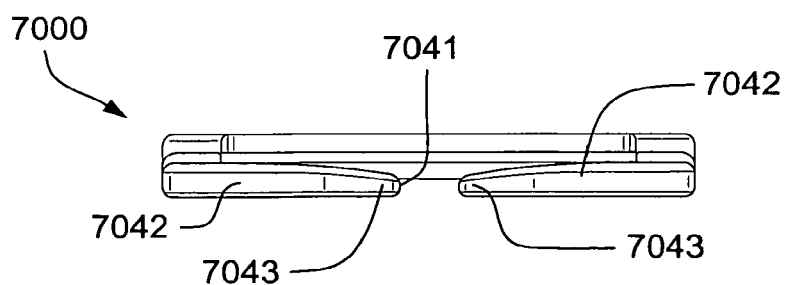
Figures 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51:
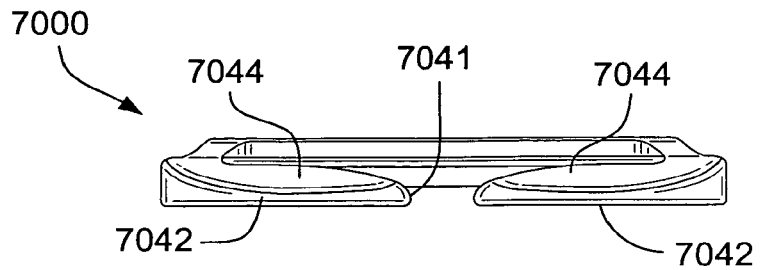
Figures 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52:
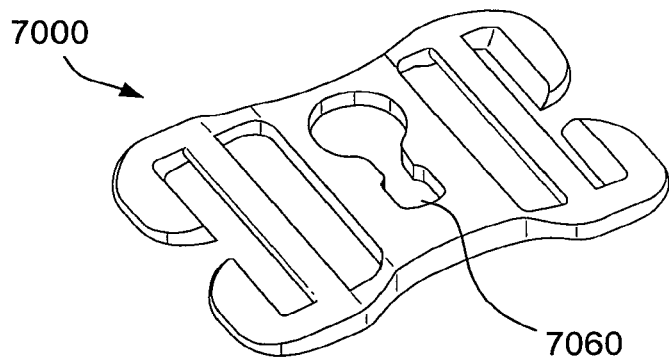
Figures 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53:
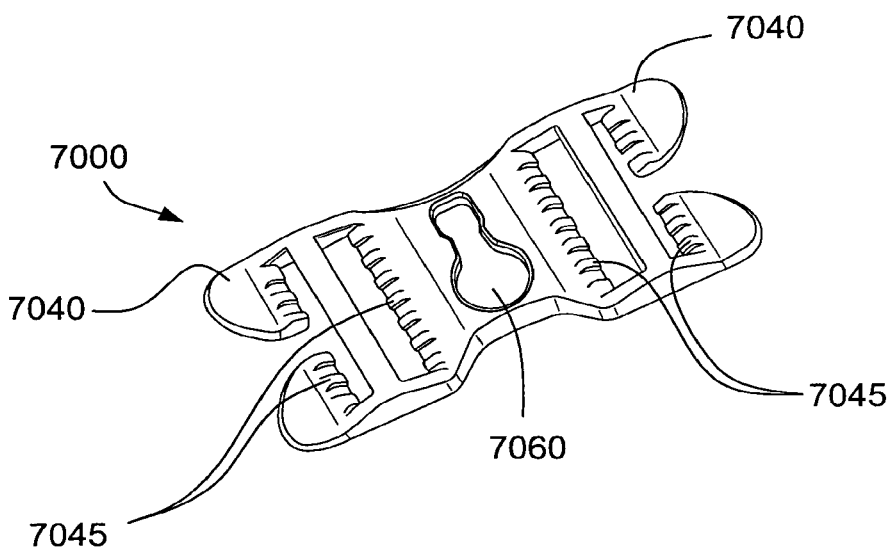
Figures 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54:
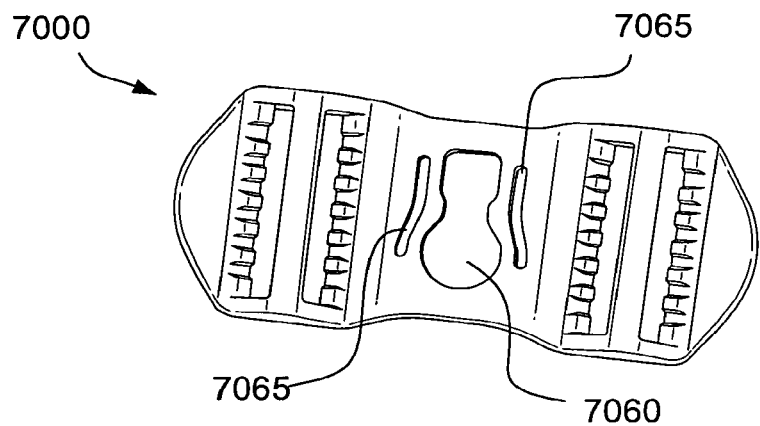
Figures 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55:
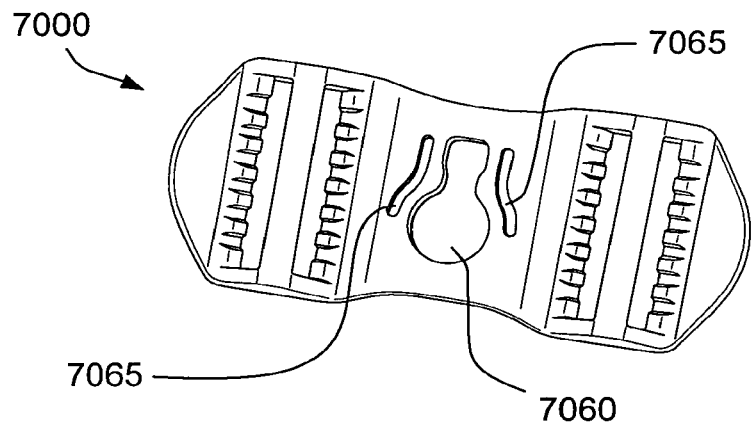

FIGS. 19-6 and 19-7 are enlarged views of the yoke to frame interface of the headgear yoke shown in FIGS. 19-1 to 19-5;

FIG. 19-8 is a cross-sectional view illustrating the yoke to frame interface attached to a respective frame connector according to an embodiment of the present invention;

FIGS. 19-9-1 to 19-9-6 are sequential views illustrating attachment of the yoke to frame interface to a respective frame connector according to an embodiment of the present invention;

FIGS. 19-10 to 19-13 illustrate exemplary dimensions of the headgear yoke according to an embodiment of the present invention;

FIG. 19-14 is a side view illustrating rotational movement of the patient interface according to an embodiment of the present invention;

FIGS. 19-15-1 to 19-15-5 are sequential views illustrating rotational adjustment of the headgear yoke with respect to the frame according to an embodiment of the present invention;

FIG. 19-16 is a top view of the patient interface on a patient's head according to an embodiment of the present invention;

FIGS. 19-17-1 to 19-17-4 illustrate various cross-sections through the headgear yoke according to an embodiment of the present invention;

FIG. 19-18 is a perspective view of the patient interface showing exemplary dimensions according to an embodiment of the present invention;

FIG. 19-19 is a cross-sectional view of the headgear yoke showing exemplary dimensions according to an embodiment of the present invention;

FIG. 19-20 is a cross-sectional view illustrating headgear yoke attached to a headgear strap according to an embodiment of the present invention;

FIGS. 19-21-1 to 19-21-3 illustrate a yoke to frame rotation indicator according to an embodiment of the present invention;

FIGS. 19-22-1 to 19-22-4 illustrate a yoke to frame rotation indicator according to another embodiment of the present invention;

FIGS. 19-23-1 to 19-23-4 illustrate a yoke to frame rotation indicator according to another embodiment of the present invention;

FIG. 20-1 is a perspective view of a short tube according to an embodiment of the present invention;

FIGS. 20-2 to 20-4 are various views illustrating attachment of the short tube to a swivel according to an embodiment of the present invention;

FIGS. 20-5-1 to 20-5-6 illustrate a short tube with elbow and swivel according to another embodiment of the present invention;

FIGS. 21-1 and 21-2 illustrate Velcro tabs for a headgear strap according to embodiments of the present invention;

FIGS. 22-1-1 to 22-1-8 are various views of a frame according to an embodiment of the present invention;

FIGS. 22-1-9 and 22-1-10 illustrate rotation of the yoke relative to the frame according to an embodiment of the present invention;

FIGS. 22-2 and 22-3 illustrate assembly of headgear yoke to a frame according to an embodiment of the present invention;

FIGS. 22-4 to 22-6 and 22-7-1 to 22-7-8 are various views of a headgear yoke according to an embodiment of the present invention;

FIGS. 22-8 to 22-13 are various views illustrate attachment of headgear yoke to a frame according to an embodiment of the present invention;

FIGS. 22-14 and 22-15 illustrate a ratchet arrangement between headgear yoke and frame according to an embodiment of the present invention;

FIG. 22-16 illustrates a fully assembled frame and headgear yoke according to an embodiment of the present invention;

FIGS. 22-16-1 and 22-16-2 illustrate an interference fit between the yoke and the frame according to an embodiment of the present invention;

FIGS. 22-17-1 to 22-17-2 illustrate relative movement between the frame and headgear yoke according to an embodiment of the present invention;

FIGS. 22-18-1 to 22-18-3 illustrate a mold for molding a frame according to an embodiment of the present invention;

FIGS. 22-19-1 to 22-19-7 illustrate headgear yoke attached to a headgear strap according to an embodiment of the present invention;

FIGS. 22-20-1 to 22-20-5 illustrate a fully assembled patient interface according to an embodiment of the present invention;

FIGS. 22-20-6 and 22-20-7 illustrate a back strap for a patient interface according to an embodiment of the present invention;

FIGS. 22-21-1 to 22-21-8 illustrate a left-hand-side (LHS) side strap with headgear yoke according to an embodiment of the present invention;

FIGS. 22-22-1 to 22-22-8 illustrate a right-hand-side (RHS) side strap with headgear yoke according to an embodiment of the present invention;

FIGS. 22-22-9 and 22-22-10 illustrate under-side and top-side views of a tab of hook material according to an embodiment of the present invention;

FIGS. 22-23-1 to 22-23-7 illustrate a fully assembled patient interface according to an embodiment of the present invention;

FIG. 22-24 is a perspective view showing a yoke engaged with a frame via a ball and socket joint according to an embodiment of the present invention;

FIG. 22-25 is a cross-sectional view showing the ball and socket joint of FIG. 22-24;

FIG. 23 illustrates the difference in compression before bottoming out between prior art nasal pillow mask systems (Puritan-Bennett Breeze), related art nasal pillow system (ResMed Swift II) and an embodiment of the present invention;

FIG. 24 illustrates the difference in lateral movement that can be obtained in accordance with an embodiment of the present invention when compared to ResMed Swift nasal pillows;

FIG. 25*a* to FIG. 25*g* show cross-sectional profiles of a range of prior and related nasal pillow systems, as well as an embodiment of the present invention;

FIG. 26 shows a table comparing relative properties of the ResMed SWIFT mask and an embodiment of the present invention;

FIG. 27*a* to FIG. 27*l* show a range of views of a nasal pillow and gusset assembly in accordance with another embodiment of the present invention, FIG. 27 is similar to FIG. 16;

FIG. 28 is a sketch illustrating how the nasal pillows and gusset align with the face in use;

FIG. 29 is a sketch comparing a nasal pillow of an embodiment of the present invention and a prior art nasal pillow when subject to a compression force;

FIG. 30 is a cross-section of headgear material according to an embodiment of the present invention;

FIGS. 31-1 and 31-2 are perspective views of a mask system according to another embodiment of the present invention;

FIGS. 32-1 and 32-2 are perspective views of a mask system according to another embodiment of the present invention;

FIGS. 33-1 and 33-2 are side and front views of a mask system according to another embodiment of the present invention;

FIG. 34 is a perspective view of a mask system according to another embodiment of the present invention;

FIG. 35 is an exploded view of a mask system according to another embodiment of the present invention;

FIG. 36 is a perspective view of a mask system according to another embodiment of the present invention;

FIG. 37 is a perspective view of a mask system according to another embodiment of the present invention;

FIG. 38 is a perspective view of a mask system according to another embodiment of the present invention;

FIGS. 39-1 and 39-2 are perspective views of a mask system according to another embodiment of the present invention;

FIG. 40 is a cross-sectional view of a mask system according to another embodiment of the present invention;

FIG. 41-1 illustrates a nasal prong assembly having a width and FIG. 41-2 illustrates a nasal prong assembly having a smaller width according to an embodiment of the present invention;

FIG. 41-3 is a cross-sectional view of the nasal prong assembly shown in FIG. 41-2;

FIG. 42 is a cross-sectional view of a mask system according to another embodiment of the present invention;

FIG. 43 is a cross-sectional view of a mask system according to another embodiment of the present invention;

FIG. 44 is a cross-sectional view of a mask system according to another embodiment of the present invention; and FIG. 45-1 illustrates a nasal prong assembly having a central axis and FIG. 45-2 illustrates a nasal prong assembly having a shifted central axis according to an embodiment of the present invention.

DETAILED DESCRIPTION OF ILLUSTRATED EMBODIMENTS

In broad terms, a patient interface in accordance with an embodiment of the invention may comprise three functional aspects: (i) interfacing, (ii) a positioning and stabilizing, and (iii) air delivery. These three functional aspects may be constructed from one or more structural components, with a given structural component potentially fulfilling more than one function. For example, a mask frame may serve as part of a positioning and stabilizing function and allow the supply of air.

In addition, a patient interface in accordance with an embodiment of the invention may perform other functions including venting of exhaled gases, decoupling of potentially seal disruptive forces and adjustment for different sized faces. Venting may be performed by different structures, such as a frame, an elbow and/or a conduit.

The following description is provided in relation to several embodiments which may share common characteristics and features. It is to be understood that one or more features of any one embodiment may be combinable with one or more features of the other embodiments. In addition, any single feature or combination of features in any of the embodiments may constitute additional embodiments.

In this specification, the word "comprising" is to be understood in its "open" sense, that is, in the sense of "including", and thus not limited to its "closed" sense, that is the sense of "consisting only of". A corresponding meaning is to be attributed to the corresponding words "comprise", "comprised" and "comprises" where they appear.

The term "air" will be taken to include breathable gases, for example air with supplemental oxygen. It is also acknowledged that the positive airway pressure (PAP) devices or flow generators described herein may be designed to pump fluids other than air.

Each illustrated embodiment includes features that may be used with the embodiments and/or components described in U.S. Patent Application Publication Nos. 2004-0226566, 2006-0137690, and 2005-0241644, PCT Application Publication Nos. WO 2005/063328, WO 2006/130903, and WO 2007/053878, and U.S. Provisional Application Nos. 60/835,442, filed Aug. 4, 2006, and 60/852,649, filed Oct. 19, 2006, as would be apparent to those of ordinary skill in the art. Each of the above noted applications are incorporated herein by reference in its entirety. However, it should be appreciated that any single feature or combination of features in any of the embodiments may be applied to other suitable mask arrangements, e.g., full-face, etc.

1 Interfacing 1.1 Introduction

In one form of the invention, the interfacing function is provided by a pair of nasal prongs (or "nasal pillows") that are placed at an entrance to the patient's nares. Each prong is structured to form an adequate seal with its respective naris and is shaped, oriented, sized and constructed so as provide a fit with a range of differently shaped and located nares.

As shown in FIGS. 2-1 to 2-2, the nasal prong assembly 20 includes a base 22 and a pair of nasal prongs 24 provided to the base 22. Each nasal prong 24 includes a generally conical, "volcano", or mushroom-shaped head portion 25 adapted to seal and/or sealingly communicate with a respective patient nasal passage (e.g., concave and oval prong designed to fit into the patients nares and seal against the rim of the nares) and a column or stalk 27 that interconnects the head portion 25 with the base 22. The nasal prong assembly 20 is structured to be removably and replaceably attached to a substantially rigid frame 30 and be retained to the frame 30 by a clip 23 (such as that described in WO 2007/053878, which is incorporated herein by reference in its entirety). One or more vent openings 32 may be provided in the frame and/or base for $CO_2$ washout.

The nasal prong assembly 20 may be integrally formed in one-piece, e.g., by silicone in an injection molding process (e.g., LSR (liquid silicone rubber) and CMSR (compression molded silicon rubber) molding technology). However, the nasal prong assembly 20 may be formed in other suitable processes.

In an embodiment, one end of the nasal prong assembly is provided with a plug and the other end is provided with an elbow (e.g., swivel elbow). The positions of the elbow and the plug may be interchanged, according to preference, e.g., the typical sleeping position of the patient. In an alterative embodiment, both ends of the nasal prong assembly may be provided with an elbow. An air delivery tube is joined to the elbow or elbows to deliver a source of pressurized gas (e.g., 2-30 cmH2O).

In an embodiment, the nasal prong assembly may include a "low flow" version with a different pressure flow requirement.

The nasal prong assembly provides a lightweight, unobtrusive arrangement for delivering positive airway pressure as a means of therapy, e.g., for OSA.

The following discussion in the "Interfacing" section of this detailed description principally relates to the cone-shaped portion of the prong, other aspects of the prong—such as the stalk—will be discussed in more detail in subsequent sections.

1.2 Shape, Geometry and Anthropometrical Features

The nasal prongs may include geometry and/or anthropometrical features similar to the nasal prongs described in U.S. Patent Application Publication Nos. 2004-0226566, 2006-0137690 and PCT Application Publication Nos. WO 2006/130903, and WO 2007/053878, each of which is incorporated herein by reference in its entirety.

Also, rotating the nasal prong assembly in relation to the headgear can physically rotate the prongs in an anterior/posterior direction in relation to the nose. This flexibility effectively sets the prongs into an "exact" comfortable position for an individual user.

Further, the prong's stalk provides a flexible point to allow prong alignment and seal maintenance.

1.3 Orientation

For example, the orientation of the nasal prongs is designed to present the exit holes and the conical sealing surfaces as square to the nostril openings as possible. This increases the effectiveness of the seal. The prongs have been angled and rotated in relation to the base in order to provide this orientation for average anthropometry.

As shown in top view FIG. 2-3 (nostril angle), the rotation angle $\alpha$ of the prong 24 with respect to centerline CL may about 20-35 degrees, e.g., 27 degrees. As shown in front view FIG. 2-4 (alar angle), the inward rotation angle $\beta$ of the prong 24 with respect to centerline CL may be about 15-20 degrees, e.g., 17 degrees. However, other suitable angles are possible.

1.4 Sizing

In combination with this orienting geometry, the prongs can be adapted to nasal geometry variations from patient to patient in a number of ways. Firstly, the prongs may be available in multiple sizes (e.g., extra small, small, medium, large, extra large). The variant geometry between sizes may be the diameters of the oval prong profile.

1.5 Spacing

Spacing of the pillows is illustrated in FIG. 16-8 described below.

1.6 Construction

1.6.1 Dual-Wall Nasal Prongs

In an embodiment, the nasal prongs 24 may be similar to nasal prongs those described in WO 2006/130903, which is incorporated herein by reference in its entirety.

For example, as shown in FIG. 3-1, the head portion 25 of each nasal prong 24 may include a dual or double-wall arrangement including an inner wall 26 (inner membrane or support membrane) and an outer wall 28 (outer membrane or sealing membrane) that surrounds the inner wall 26. The outer wall 28 may be relatively thin (e.g., 0.35 mm) to conform to the shape of the patient's nose and provide a more compliant seal. In addition, the thin outer wall effectively finds its own seal with very little tweaking, which reduces the time for set-up. In an embodiment, the dual-wall prongs 24 may be manufactured in a manner as described in WO 2006/130903, e.g., fold or invert one wall with respect to the other wall.

One of the advantages of dual wall nasal prongs that may be used to improve jetting performance is that it is possible to reorient the inner exit hole at any angle while retaining a "square" sealing orientation for the outer wall.

One aspect of dual pillows construction is that the inner surface of the outer membrane may be frosted to facilitate removal from the molding tool. Also, the outer surface of the outer membrane may be frosted, e.g., for comfort and for improving fitting to nose because less sticking.

1.6.2 Alternative Nasal Prong Embodiments

The following embodiments describe alternative prong arrangements that are structured to improve sealing comfort and/or fitting. In embodiments, the prong arrangements may be structured to reduce and/or eliminate the air jetting effect, e.g., redirect air flow direction (e.g., away from sensitive regions such as the septum), diffuse air flow or create turbulence, and/or change the prong orifice in order to reduce and/or eliminate air jetting effects. Reducing and/or eliminating the air jetting effect may provide increased comfort across a wider pressure range and/or reduced concentrated dryness and cold burning sensation. In addition, adding turbulence may reduce noise.

Additional prong arrangements to improve comfort and fitting are described in U.S. Provisional Application Nos. 60/835,442, filed Aug. 4, 2006, and 60/852,649, filed Oct. 19, 2006, each of which is incorporated herein by reference in its entirety.

The nasal prong embodiments described below include a dual or double-wall head portion. While embodiments described below relate to dual-wall nasal prongs, it should be appreciated that embodiments of the invention may be adapted for use with single-wall nasal prongs and/or multi-wall nasal prongs (e.g., 2 or more walls).

Dual Wall with Hood

FIG. 5-1 illustrates a nasal prong 224 according to another embodiment of the present invention. In the illustrated embodiment, the inner wall 226 includes a hood 234 (e.g., integrally formed with the inner wall) adapted to reorient the exit hole and change the air flow direction to reduce and/or eliminate the air jetting effect, e.g., direct flow away from the septum.

As illustrated, the hood 234 is provided to anterior and medial portions (i.e., front and middle portions) of the inner wall 226 along the perimeter of the orifice. The hood 234 is structured to direct the air posteriorly, e.g., towards the rear, rather than straight up the nasal passage. In addition, the hood 234 is structured to direct the air laterally, e.g., towards the side, rather than towards the septum. Thus, the hood 234 is structured to change the air flow in two planes such that the hood 234 directs the air flow away from the septum and avoids direct contact with sensitive areas of the anterior nose.

Dual Wall with Dome

FIG. 5-2 illustrates a nasal prong 324 according to another embodiment of the present invention. In the illustrated embodiment, the inner wall 326 includes a dome 335 (e.g., integrally formed with the inner wall) adapted to change the air flow direction to reduce and/or eliminate the air jetting effect, e.g., direct flow away from the septum. The dome 335 may also reduce pressure drop and/or impedance.

As illustrated, the dome 335 has a hemispherical shape that extends over the orifice of the inner wall 326 and provides an eccentrically placed exit hole to direct the air away from sensitive regions of the patient's nose, e.g., septum. In an embodiment, the exit hole may be positioned to direct air similar to the hood described above, e.g., direct the air posteriorly and laterally.

Dual Wall with Blocked Orifice and Holes on Inner and Outer Walls

FIG. 5-3 illustrates a nasal prong 424 according to another embodiment of the present invention. In the illustrated embodiment, the orifice of the inner wall 426 is blocked and the inner wall 426 includes one or more holes 436. As illustrated, the holes 436 are provided to a posterior side of the inner wall 426. However, the holes 436 may be provided along any suitable portion of the inner wall 426. Also, each hole 436 has a generally circular or oval shape. In alternative embodiments, each hole 436 may have any other suitable shapes, e.g., non-circular such as elongated slots or square or rectangular openings. In addition, the inner wall 426 may have any suitable number of holes 436, e.g., 1, 2, 3, or more holes.

Further, the outer wall 428 may optionally include one or more holes 437. In the illustrated embodiment, the holes 437 are provided to an upper region of the outer wall (e.g., near the orifice) on a medial portion of the outer wall which is oriented towards the patient's face in use (e.g., near the patient's top lip). Similar to the holes 436 in the inner wall, the holes 437 in the outer wall may be provided to other suitable portions of the outer wall, may be have other suitable shapes, and may have any suitable number of holes, e.g., 1, 2, 3, or more holes.

In the illustrated embodiment, the holes 436 in the inner wall are larger than the holes 437 in the outer wall. However, other suitable sizes are possible.

In use, the holes 436, 437 disperse air as it passes through the prong 424, e.g., to create turbulence and/or reduce impedance.

Dual Wall with Blocked Orifice and Castellated Openings

FIG. 5-4 illustrates a nasal prong 524 according to another embodiment of the present invention. In the illustrated embodiment, the orifice of the inner wall 526 is blocked and the inner wall 526 includes one or more openings 536 around the perimeter or rim of the inner wall 526 adjacent the blocked orifice. As illustrated, the openings 536 each include a generally square or rectangular shape to provide a castellated-type arrangement at the top of the inner wall 526. However, the openings 526 may have other suitable shapes and may be provided in any suitable number, e.g., 5, 6, 7, or more openings.

In use, the openings 536 direct the flow laterally from the blocked orifice to disperse and/or diffuse air as it passes through the prong, e.g., to create turbulence.

In an alternative embodiment, the orifice of the inner wall 526 may not be blocked and the top of the inner wall 526 may include the castellated-type arrangement to disperse air.

Dual Wall with Elongated Inner Wall

FIG. 5-5 illustrates a nasal prong 624 according to another embodiment of the present invention. In the illustrated embodiment, the inner wall 626 is elongated or extended so that the orifice of the inner wall 626 is substantially higher than the orifice of the outer wall 628. In addition, the inner wall 626 has a tube-like configuration with the orifice of the inner wall 626 oriented to change the air flow direction to reduce and/or eliminate the air jetting effect, e.g., direct flow away from the septum. In an embodiment, the orifice may be oriented to direct air similar to the hood described above, e.g., direct the air posteriorly and laterally. For example, the inner wall 626 extends further inside the patient's nostril to direct flow away from the inner septum.

Dual Wall with Insert

FIG. 5-6 illustrates a nasal prong 724 according to another embodiment of the present invention. In the illustrated embodiment, an insert 738 (i.e., formed separately from the prong) is provided to the inner wall 726 that is adapted to change the air flow direction to reduce and/or eliminate the air jetting effect, e.g., direct flow away from the septum.

As illustrated, the insert 738 includes a base 738(1) adapted to support the insert 738 in a operative position adjacent the orifice of the inner wall 726 and a head 738(2) that provides an exit opening to change the air flow direction. The length of the head 738(2) may be changed, e.g., customized length for particular patient, to provide a longer or shorter exit from the inner wall 726. In the illustrated embodiment, the wall of the insert 738 may be constructed of a foam or silicone material. Alternatively, the entire volume of the insert 738 may be constructed of foam, e.g., similar to the foam insert described below.

The insert 738 is secured to the inner wall 726 to prevent removal and possible inhalation in use. In an embodiment, the inner wall 726 may include an annular flange or shoulder around the orifice adapted to support or secure the insert 738 in position. However, the insert 738 may be supported in its operative position in other suitable manners, e.g., adhesive, friction fit, mechanical interlock, etc. In an embodiment, a connector may be provided between inserts of adjacent prongs to prevent discharge of an insert through the orifice, e.g., during inspiration.

In an embodiment, the insert 738 may be retrofitted to an existing nasal prong in order to direct flow in a similar manner to a hood. For example, the exit opening of the insert 738 may be positioned to direct air in a similar manner to the hood described above, e.g., direct the air posteriorly and laterally. Thus, the insert 738 may be made as a "spare part" or separate accessory and used only when the patient is suffering from jetting effect with an existing nasal prong assembly.

Dual Wall with Internal Ledge

FIG. 5-7-1 illustrates a nasal prong 824 according to another embodiment of the present invention. In the illustrated embodiment, the prong 824 includes an internal ledge or shelf 839 that extends inwardly from the inner wall 826 to block at least a portion of the flow exiting the orifice of the inner wall 826. In an embodiment, the ledge or shelf 839 is positioned on a medial portion of the inner wall 826 so that the ledge or shelf 839 is adapted to block flow nearest to the patient's septum in use. However, the ledge or shelf 839 may be provided at other portions of the inner wall 826 to block air flow directed at sensitive regions.

As illustrated, the ledge or shelf 839 extends inwardly from the edge of the orifice. In an alternative embodiment, the ledge or shelf 839 may be spaced downwardly from the edge of the orifice, e.g., to reduce impedance.

In yet another alternative, as shown in FIG. 5-7-2, a ledge or shelf 839 may be provided to a single wall prong. For example, the ledge or shelf 839 may extend inwardly from the wall of the prong to block at least a portion of the flow exiting the orifice, e.g., block flow nearest to the patient's septum.

Dual Wall with Mesh or Gauze

FIG. 5-8 illustrates a nasal prong 924 according to another embodiment of the present invention. In the illustrated embodiment, the prong 924 includes mesh or gauze 940 constructed of a suitable mesh or gauze material (e.g., auxetic materials possible) to diffuse the flow of air. As illustrated, the mesh or gauze 940 is provided at the base of the head portion. However, the mesh or gauze 940 may be provided at other suitable locations along the prong, e.g., at the base of the stalk. In an embodiment, the mesh or gauze 940 may be provided as an insert that is retrofit to an existing nasal prong.

In use, the mesh or gauze 940 increases the dispersion and turbulence of the air as it exits the prong orifice and enters the patient's nasal passage.

In an alternative embodiment, the mesh or gauze 940 may be designed as an anti-asphyxia valve (AAV) style flap adapted to cover the prong orifice on inspiration and fall open on expiration to reduce impedance.

Dual Wall with Exit Gate

FIG. 5-9-1 illustrates a nasal prong 1024 according to another embodiment of the present invention. In the illustrated embodiment, the prong 1024 includes a pinwheel-shaped or star-shaped gate 1041, e.g., integrally formed with the prong, provided at the rim or exit orifice of the inner wall 1026. As illustrated, the pinwheel-shaped or star-shaped gate 1041 includes a hub 1041(1) and a plurality of vanes or legs 1041(2) extending radially from the hub 1041(1). Each vane 1041(2) tapers from the rim to the hub.

In use, the gate 1041 increases the dispersion and turbulence of the air as it exits the orifice and enters the patient's nasal passage.

It should be appreciated that the gate 1041 may be provided at other suitable locations along the prong (e.g., at the outer wall, along the stalk, etc.), and the gate 1041 may have other suitable shapes and orientations. In addition, the gate 1041 may have any suitable number of vanes 1041(2), e.g., 3, 4, 5, or more vanes.

For example, FIG. 5-9-2 illustrates a prong 1124 with a gate 1141 according to another embodiment of the present invention. As illustrated, the gate 1141 includes a hub 1141(1) and a plurality of vanes 1141(2) extending radially from the hub 1141(1). Each vane 1141(2) is helical or in the shape of a propeller blade to disperse the air and create turbulence as it exits the orifice.

In yet another alternative, such a pinwheel-shaped or star-shaped gate may be provided to a single wall prong, e.g., at the exit orifice of the prong.

Dual Wall with Foam Insert

FIG. 5-10 illustrates a nasal prong 1224 according to another embodiment of the present invention. In the illustrated embodiment, the prong 1224 includes a foam insert 1238 constructed of a foam material, e.g., low density foam material, to diffuse the flow of air. As illustrated, the foam insert 1238 is provided within the cavity defined by the inner wall 1226. However, the foam insert 1238 may be provided at other suitable locations along the prong, e.g., within the stalk. In an embodiment, the foam insert 1238 may be provided as a "spare part" that is adapted to be retrofitted to an existing nasal prong.

The foam insert 1238 may be supported by the inner wall 1226 in its operative position in any suitable manner, e.g., adhesive, friction fit, mechanical interlock, etc. For example, the foam insert 1238 may be squeezed into the cavity and then allowed to resiliently expand into engagement with the inner wall 1226. In an embodiment, a connector may be provided between foam inserts of adjacent prongs to prevent discharge of an insert through the orifice, e.g., during inspiration.

In use, air passes through the thickness of the foam insert 1238 which increases the dispersion and turbulence of the air as it exits the prong orifice and enters the patient's nasal passage.

In another alternative embodiment, each prong may include an insert constructed of a silicone material and provided with relatively small channels through the interior to diffuse the flow of air in use. Inserts constructed of other suitable materials are also possible, e.g., Gore-Tex.

In yet another embodiment, the insert (e.g., foam or silicone insert) may provide a mechanical valve type arrangement. For example, the insert may be adapted to cover the orifice and act as a diffuser on inspiration, and open or uncover the orifice on expiration. In an embodiment, the insert may include a cone-shape with a hollow center to facilitate movement between covering and uncovering positions.

Dual Wall with Cut Inner Wall

FIG. 5-11 illustrates a nasal prong 1324 according to another embodiment of the present invention. In the illustrated embodiment, the orifice of the inner wall 1326 and/or the orifice of the outer wall 1328 is cut at an angle, e.g., 45° angle, to direct air flow. The angled orifice(s) changes the air flow direction to reduce and/or eliminate the air jetting effect, e.g., direct flow away from the septum. In addition, the angled orifice(s) increase the size of the orifice(s) (e.g., with respect to a non-cut or non-angled orifice) to provide lower impedance. The prong orifice(s) may be cut at any suitable angle, e.g., angle may be dependent on the shape of the patient's nostrils.

Dual Wall with Chevron-Pattern Exit Hole

FIGS. 5-12-1 and 5-12-2 illustrate nasal prongs 1424 according to another embodiment of the present invention. In the illustrated embodiment, the orifice of the inner wall 1426 and/or the orifice of the outer wall 1428 includes a chevron-pattern or toothed arrangement around its perimeter. In FIG. 5-12-1, the prong includes a chevron-pattern around the orifice of the inner wall, 1426. In FIG. 5-12-2, the prong includes a chevron-pattern around the orifice of the inner and outer walls 1426, 1428.

However, the orifice may have other suitable shapes or patterns around its perimeter. For example, FIGS. 5-12-3 and 5-12-4 are tope top views of prongs including orifices with a series of contours or lobes 1442, e.g., 3, 4, 5, 6, or more contours or lobes.

In use, the non-oval-shaped orifice increases the dispersion and turbulence of the air as it exits the orifice and enters the patient's nasal passage.

Dual Wall with Alternative Base

FIGS. 5-13-1 and 5-13-2 illustrate a nasal prong 1524 and base 1522 according to alternative embodiments of the present invention. In the illustrated embodiment, the base 1522 that supports the prong 1524 may include different thicknesses to vary a trampoline or bounce effect provided by the base 1522. For example, FIG. 5-13-1 illustrates a base 1522 wherein d1 is about 0.6 mm and d2 is about 0.75-0.85 mm, and FIG. 5-13-2 illustrates a base 1522 wherein d1 is about 0.85 mm and d2 is about 0.75 mm. In each embodiment, the stalk 1527 may have a length d3 of about 5.2 mm and a thickness d4 of about 0.6-1.0 mm. Also, in each embodiment, the outer wall 1528 may have a thickness d5 of about 0.1 to 0.5 mm, or about 0.35±0.1 mm, or about 0.3±0.1 mm, or about 0.45 mm. The relatively thin outer wall 1528 may be more comfortable and compliant. The inner wall 1526 may have a thickness d6 of about 0.4 to 1.0 mm.

It is to be understood that these dimensions and ranges are merely exemplary and other dimensions and ranges are possible depending on application. Also, such base may be provided to a nasal prong having a single wall configuration.

Manufacturing

In an embodiment, the dual-wall prong may be molded into its operative dual wall construction. In an alternative embodiment, one of the inner and outer walls may be molded in an open position and then inverted or folded to form the dual wall construction.

In yet another embodiment, as shown in FIG. 5-13-3, a prong 4424 may include a multi-wall construction (e.g., triple-wall construction) in which two or more walls 4426(1), 4426(2) are molded in an open position and then inverted or folded with respect to another wall 4426(3) to form the multi wall construction (e.g., three wall concentric arrangement). Exemplary folded wall arrangements are described in WO 2006/130903, which is incorporated herein by reference in its entirety.

Thin Wall Thickness

FIG. 5-14-1 illustrates a nasal prong 1624 according to another embodiment of the present invention. In the illustrated embodiment, the outermost wall 1628 (e.g., the outer wall of a multi-wall prong or the single wall of a single wall prong has a relatively thin wall thickness (e.g., thickness less than about 0.45 mm (e.g., 0.35 mm)) so that the outermost wall is adapted to bulge outwardly or slightly inflate (as indicated in dashed lines in FIG. 5-14-1) in use to accommodate and/or conform to the patient's nose in use.

For example, FIG. 5-14-2 is a plan view of the outermost wall 1628 to illustrate its generally oval or elliptical shape, and FIGS. 5-14-3 and 5-14-4 are cross-sectional views through minor and major axes of the outermost wall respectively. As illustrated, the sides of the wall are structured to bulge more outwardly than the ends of the wall in use. Specifically, the sides of the wall are adapted to move from a generally concave shape to a generally convex shape in use (see FIG. 5-14-3), and the ends are adapted to move from a generally concave shape to a generally straight or linear shape in use (see FIG. 5-14-4). Such arrangement facilitates sealing and compliance of the prong with the patient's nose in use as the thin wall is able to conform to the patient's nasal contours.

Support of Thin Outer Wall

A support structure may be provided to a thin outer wall (such as that described above in FIGS. 5-14-1 to 5-14-4) to add rigidity and/or facilitate alignment and engagement of the thin outer wall with the patient's nose before use. In addition, the support structure may be constructed and arranged to create turbulence in use.

For example, as shown in FIGS. 5-15-1 and 5-15-2, the thin outer wall 1728 may include one or more ribs 1743 that extend along an interior surface of the outer wall, e.g., integrally formed with the thin outer wall.

In another embodiment, as shown in FIG. 5-16, the thin outer wall 1828 may include a plurality of ribs 1843 that form concentric ribs or rings along an interior surface of the outer wall 1828, e.g., integrally formed with the outer wall. The ribs 1843 may extend around the entire interior perimeter of the outer wall and/or the ribs 1843 may extend around portions of the interior perimeter of the outer wall.

In another embodiment, as shown in FIG. 5-17, the outer wall 1928 may include a thin region 1928(1) positioned between a thicker rim 1928(2) along the orifice and a thicker base 1928(3).

In another embodiment, as shown in FIG. 5-18, the outer wall 2028 may include a plurality of notches 2044 that form thinned sections 2028(1) along the outer wall 2028. The thinned sections 2028(1) may extend around the entire interior perimeter of the outer wall and/or the thinned sections 2028(1) may extend around portions of the interior perimeter of the outer wall.

In another embodiment, a dual wall prong may be provided and the inner wall may be substantially rigid (e.g., thickness greater than about 0.4 mm (e.g., 0.4 to 0.8 mm)) in order to support and guide the thin outer wall into engagement with the patient's nose before use. That is, the thin outer wall provides a seal-forming thinner wall and the inner wall provides a structure-defining thicker wall that adds stiffness to the thin outer wall as it is engaged and aligned with the patient's nose before use. In use, pressurized air causes the outer wall to bulge outwardly into conformance with the patient's nose, e.g., pressure supported seal.

In another embodiment, as shown in FIGS. 5-19-1 to 5-19-3, a support rod 2145 may be operatively engaged with the outer wall 2128 of the prong in order to support and guide the outer wall 2128 thereof into engagement with the patient's nose before use. As shown in FIG. 5-19-3, each prong includes a pinwheel-shaped or star-shaped gate 2141 provided at the rim of the outer wall 2128. The support rod 2145 includes a first end 2145(1) engaged with the hub of the gate 2141 and a second end 2145(2) that extends through the base 2122 supporting the prongs. In use, the patient can slidably move the support rod 2145 via the exposed first end 2145(2) in order to hold the outer wall in a sufficiently taut or extended position for engagement with the patient's nose before use (see FIG. 5-19-2).

In another embodiment, as shown in FIGS. 5-20-1 to 5-20-2, support projections 2246 may be provided to the base 2222 supporting the prongs that is adapted to operatively engage with the outer wall 2228 of a respective prong in order to support and guide the outer wall thereof into engagement with the patient's nose before use. As illustrated, each support projection 2246 is provided to the lower wall of the base 2222 in alignment with a respective prong and includes a generally cone-like shape. In use, the patient can deflect or deform the base 2222 so that each support projection 2246 moves from an initial position (FIG. 5-20-1) into an engaged position (FIG. 5-20-2) with the outer wall 2228 of a respective prong. In the engaged position of FIG. 5-20-2, the support projection 2246 supports or holds the outer wall 2228 in a sufficiently taut or extended position for engagement with the patient's nose before use.

1.6.3 Ball-Type Insert

FIG. 5-21 illustrates a nasal prong assembly 2320 according to another embodiment of the present invention. In the illustrated embodiment, a ball-type insert 2338 (e.g., silicone or plastic ball) is provided to the interior of each prong 2324. The ball-type insert 2338 has a diameter that is sufficiently larger than the diameter of the prong orifice to prevent discharge of the ball-type insert 2338 through the orifice, e.g., during inspiration. In use, the ball-type insert 2338 moves or rotates freely within the prong interior to introduce variable direction air flow, e.g., random diffuse of air, to reduce and/or eliminate the air jetting effect, e.g., reduce air flow time with specific areas of the patient's nose (e.g., septum).

In an embodiment, the ball-type insert 2338 may have a sphere-like shape and may include one or more perforations, grooves, dimples, or detents along its exterior surface. However, the ball-type insert 2338 may have other suitable shapes, e.g., non sphere-like.

In an embodiment, a connector 2338(1) may be provided between ball-type inserts 2338 of adjacent prongs to prevent discharge of the inserts 2338 through respective orifices.

It should be appreciated that the ball-type insert 2338 may be adapted for use with dual-wall nasal prongs.

1.6.4 One-Way Valve

In another embodiment, a one-way valve may be provided to the vent arrangement of the nasal prong assembly to reduce the pressure of exhalation and allow easier nose breathing. The one-way valve is adapted to pivot or otherwise move between (1) an open position that uncovers the vent arrangement to allow venting during exhalation, and (2) a closed position that covers at least a portion of the vent arrangement during inhalation. The valve may provide variable vent flow in the closed position, e.g., depending on closed portion of vent arrangement. The threshold pressure may be set at therapy pressure, such that the valve moves to the open position during exhalation as added pressure from the patient's lungs exceeds therapy pressure.

1.6.5 Blocking Flap

FIGS. 5-22-1 and 5-22-2 illustrate a nasal prong assembly 2420 according to another embodiment of the present invention. As illustrated, the nasal prong assembly 2420 includes a base 2422 and a pair of nasal prongs 2424 provided to the base.

In the illustrated embodiment, a blocking flap or valve 2447 may be provided to one or both ends of the base 2422 (e.g., depending on whether air enters the base via one or both ends) to control the flow of air entering the base 2422 and hence the pair of nasal prongs 2424. As illustrated, the blocking flap or valve 2447 is adapted to pivot or otherwise move between (1) an open or partially open position that uncovers at least a portion of the end of the base to allow pressurized air to enter the base during inhalation (see FIGS. 5-22-1), and (2) a closed position that blocks or covers the end of the base to prevent pressurized air from entering the base during exhalation and venting (see FIG. 5-22-2). This arrangement is adapted to block incoming flow from the PAP device on exhalation to reduce the pressure of exhalation and allow easier nose breathing.

In an alternative embodiment, a vibratable flap may be provided along the flow path to introduce random diffuse of air.

1.6.6 Change Frequency

In another embodiment, the prong may be configured to change frequency, e.g., like jet engine.

1.6.7 Common Stalk

FIGS. 5-23-1 and 5-23-2 illustrate a nasal prong assembly 2520 according to alternative embodiments of the present invention. As illustrated, each nasal prong assembly 2520 includes a base 2522, a pair of nasal prongs 2524, and a common support or stalk 2523 that interconnects the prongs 2524 with the base 2522.

In FIG. 5-23-1, each prong 2524 includes a relatively short stalk 2527 provided to the common stalk 2523. In use, the common stalk 2523 and/or the relatively short stalk 2527 may provide a trampoline or bounce effect.

In an alternative embodiment, as shown in FIG. 5-23-2, the relatively short stalk may be eliminated and each prong 2524 may be directly coupled to the common stalk 2523. In such embodiment, the common stalk 2523 may provide a trampoline or bounce effect.

1.6.8 Nasal Insert

FIGS. 5-24-1 and 5-24-2 illustrate nasal inserts 2624 according to alternative embodiments of the present invention. In use, the nasal insert 2624 is inserted into the patient's nasal passage and retained therein by inflation of the outer wall 2628.

As illustrated, the nasal insert 2624 includes a dual or double-wall arrangement with an inner wall 2626 and an outer wall 2628 that surrounds the inner wall 2626. An air pocket 2648 is provided between the inner and outer walls 2626, 2628. In use, air enters the pocket 2648 to inflate the outer wall 2628 or cause the outer wall 2628 to bulge more outwardly. Such arrangement allows the outer wall 2628 to seal and conform within the patient's nasal passage.

As shown in FIG. 5-24-1, the insert 2624 may provide an open ended pocket wherein air is adapted to enter the pocket 2648 via the opening between free ends of the inner and outer walls 2626, 2628.

Alternatively, as shown in FIG. 5-24-2, the insert 2624 may provide a closed pocket wherein air is adapted to enter the pocket 2648 via one or more openings 2636 provided through an intermediate portion of the inner wall 2626.

1.6.9 Alternative Embodiments

The following figures illustrate embodiments structured to improve seal, stability, and/or comfort, for example.

FIG. 5-25 illustrates a nasal prong 2724 according to another embodiment of the present invention. As illustrated, the nasal prong 2724 includes a dual or double-wall head portion. Specifically, the head portion includes an outer wall 2728 and an inner wall 2726 that is inverted internally or looped over at the top of the outer wall 2728 to form the dual wall construction. This arrangement provides a rounded top to strengthen the top which may facilitate insertion of the prong 2724 into engagement with the patient's nostril. That is, this arrangement provides one continuous wall that is engaged with the nostril, rather than two separate walls such as embodiments of the dual wall configurations described above. Such arrangement may also enhance the seal of the head portion and may reduce the time of mask set-up as the dual wall configuration provides more ability to seal.

FIG. 5-26 illustrates a dual wall nasal prong 2824 according to another embodiment of the present invention. As noted above, the outer wall may be relatively thin to enhance conformance to the patient's nasal contours. In the illustrated embodiment, the rim 2828(1) of the outer wall 2828 may be thicker or more rigid to stiffen the top of the outer wall 2828, e.g., to prevent creeping out of the outer wall as indicated in dashed lines. However, the outer wall 2828 may include other support structures or mechanisms to stiffen the outer wall and/or enhance the seal, e.g., ribs as described above.

FIG. 5-27 illustrates a dual wall nasal prong 2924 according to another embodiment of the present invention. In the illustrated embodiment, the outer wall 2928 loops over or rolls over the inner wall 2926. That is, the outer wall 2928 provides a rolled edge 2928(1) that rolls or curls inwardly and at least partially into the orifice of the inner wall 2926. A gap is provided between the free ends of the inner and outer walls 2926, 2928. The rolled edge 2928(1) may taper towards its free end. This arrangement provides a rounded top to strengthen the top to facilitate insertion in use, e.g., similar to the prong shown in FIG. 5-25. Also, this arrangement holds the outer wall 2928 and prevents pulling side-to-side.

FIG. 5-28 illustrates a dual wall nasal prong 3024 according to another embodiment of the present invention. As illustrated, the outer wall 3028 is inverted externally or looped over at the top of the inner wall 3026 to form the dual wall construction. This arrangement provides a rounded top to strengthen the top to facilitate insertion in use, e.g., similar to the prong shown in FIG. 5-25. In an alternative embodiment, the outer wall 3028 may be inverted internally. Pressurized air may help to maintain the form of the prong in use.

FIG. 5-29 illustrates a dual wall nasal prong 3124 according to another embodiment of the present invention. As illustrated, the outer wall 3128 is inverted externally or folded outwards over the outside of the inner wall 3126 to form the dual wall construction. This arrangement provides a rounded top or rolled over end to facilitate insertion in use. In the illustrated embodiment, the inner and outer walls 3126, 3128 are bent and/or contoured along their length to provide flexibility in use. Pressurized air may help to pull the inner wall 3126 into the patient's nose in use.

FIG. 5-30 illustrates a nasal prong 3224 according to another embodiment of the present invention. As illustrated, the stalk 3227 of the nasal prong includes a gusset portion or flexing detail 3233 to add flexibility and articulation of the nasal prong in use. That is, the gusset portion 3233 may facilitate bending, stretching, and/or compressing of the nasal prong in use. Such arrangement may improve seal and stability of the prong in use. Pressurized air may expand the gusset portion 3233 so that it increases the projected surface area on the patient's nose, e.g., to improve seal.

FIG. 5-31 illustrates a nasal prong assembly 3320 according to another embodiment of the present invention. As illustrated, the stalk 3327 of each prong 3324 is sunken, recessed, or inset into the base 3322 to define a recess 3349 surrounding the stalk 3327. Such arrangement increases the length/height of the prongs 3324 (e.g., add extra length to the stalks 3327) without increasing the overall height of the prongs 3324 with respect to the base 3322. In addition, the interface between each stalk 3327 and the base 3322 provides a trampoline or bounce effect. This arrangement allows greater extension, compression, and rotation of each prong to facilitate sealing in use. In addition, extension, compression, and rotation of the prongs (as indicated by the arrows in FIG. 5-31) acts as a form of "suspension" so that the base 3322 can move away from the prongs without disrupting the seal. Further, the recessed suspension arrangement allows the patient's fingers to reach underneath the prongs 3324 in order to adjust them in the nose in use.

In an embodiment, the prongs may be molded in one piece with the base, and the recess surrounding each prong is exposed to the molding tool's open and shut direction, e.g., to avoid an undercut.

FIGS. 5-32-1 to 5-32-5 illustrate a nasal prong 3424 according to another embodiment of the present invention. As illustrated, the prong 3424 may be formed using an "over-the-center" molding technique wherein the prong 3424 is molded in an extended position (as shown in FIGS. 5-32-1 and 5-32-3) with a detail or over-the-center feature 3439 (e.g., thin wall) that allows the prong 3424 to sink or be recessed into the base 3422 (as shown in FIGS. 5-32-2 and 5-32-4). That is, the prong 3424 is structured to hold the position shown in FIGS. 5-32-2 and 5-32-4 when assembled, which is similar to the prongs shown in FIG. 5-31. As noted above, such arrangement provides a long stalk length and trampoline base to allow greater articulation (e.g., extension, compression and rotation) of each prong in use (e.g., as shown by the rotated prong in FIG. 5-32-5). Also, the recess surrounding each prong 3424 does not include an undercut.

FIG. 5-33 illustrates a dual wall nasal prong 3524 according to another embodiment of the present invention. As illustrated, the outer wall 3528 surrounds and loops over the inner wall 3526. In the illustrated embodiment, both the inner and outer walls 3526, 3528 provide a rolled edge 3526(1), 3528(1) respectively that rolls or curls inwardly. The rolled edge 3526(1), 3528(1) may taper towards its free end. This arrangement facilitates insertion into the patient's nostrils, and may provide a seal with the patient's nostrils that is similar to the seal provided by dual wall nasal or mouth cushions, e.g., see ResMed's Mirage® mask.

FIG. 5-34 illustrates a nasal prong 3624 according to another embodiment of the present invention. As illustrated, the nasal prong 3624 includes an compression and extension mechanism 3633 to improve flexibility and comfort of the nasal prong 3624 in use. In the illustrated embodiment, the compression and extension mechanism 3633 is provided to the stalk 3627 and includes a bellows or accordion-like configuration with multiple pleats that allow compression and extension of the prong in use. Such arrangement provides maximum extensions in a small area.

FIG. 5-35 illustrates a nasal prong 3724 according to another embodiment of the present invention. As illustrated, the nasal prong 3724 includes a recessed trampoline base 3631 such as that shown in FIG. 4-1 described below. In such embodiment, when the prong 3724 has been fully compressed, the patient's nose may be supported on nose support areas provided by the base 3722, which provides extra stability in use. That is, when the prongs 3724 have been fully compressed, the prongs will travel with the patient's nose, e.g., if there is mask movement. As illustrated, each prong has an axis that is angled with respect to a centerline CL of the base.

FIG. 5-36-1 illustrates a nasal prong assembly 3820 according to another embodiment of the present invention. As illustrated, a support structure, e.g., silicone wings 3845, may extend from the nasal prong assembly 3820 to stabilize or support the nasal prong assembly 3820 against the patient's cheek and/or chin.

In an embodiment, as shown in FIG. 5-36-2, a headgear strap 3853 may be coupled to each wing 3845, e.g., via cross-bar 3845(1) or other headgear attachment point provided to the wing, so that tension of the headgear strap 3853 may press or force the wing 3845 into the patient's face. Moreover, the headgear load or tension is applied to the wing 3845 in order to take the load off the prongs, i.e., decouple headgear from the prongs. This arrangement facilitates adjustment and improves comfort in the patient's nostrils.

In an embodiment, headgear straps of headgear may be structured to utilize skeletal features of the patient's face to achieve stability (e.g., increase surface area of straps). For example, as shown in FIG. 5-37, the side strap 3953 of headgear and/or a silicone pad provided to the side strap 3953 may be profiled or contoured to capture the cheek bone of the patient's face in use.

FIG. 5-38 illustrates a nasal prong assembly 4020 according to another embodiment of the present invention. As illustrated, a strap 4045 is provided to the nasal prongs 4024 to link the nasal prongs 4024 and facilitate adjustment of the nasal prongs 4024 in use. In the illustrated embodiment, the strap 4045 includes a linking member 4045(1) that links the prongs 4024 so that the prongs are connected and support one another. Also, the strap 4045 includes a finger tab 4045(2) that protrudes outwardly from one of the prongs 4024. The free end of the finger tab 4045(2) may include one or more gripping protrusions 4045(3). In use, the finger tab 4045(2) may pulled and/or pushed to adjust the position of the prongs 4024 in the patient's nose.

In the illustrated embodiment, the strap 4045 extends along the base of the head portion of the prongs 4024. However, the strap may engage the prongs at other suitable locations. In an embodiment, the strap 4045 may be integrally formed in one piece with the prongs 4024. In an alternative embodiment, the strap 4045 be formed separately from the prongs (e.g., from a silicone material with sufficient rigidity to allow pulling/pushing) and attached or retrofit to the prongs 4024. For example, the strap 4045 may include spaced openings for receiving respective prongs 4024 therethrough.

Also, the strap 4045 adds stability to the prongs 4024 by preventing tube drag from pulling prongs out of engagement with the patient's nose. That is, the linking member allows the prong that normally wants to draw out of the patient's nose due to tube drag to be held in place by the other prong.

FIG. 5-39 illustrates a nasal prong assembly 4120 according to another embodiment of the present invention. In the illustrated embodiment, a generally U-shaped inlet tube adaptor 4115 is provided (e.g., retrofit) to the nasal prong assembly 4120 to center the inlet tube 4114 and remove the asymmetric nature of the interface (e.g., inlet tube typically provided to only one side of the nasal prong assembly). As illustrated, the inlet tube adaptor 4115 includes side portions 4115(1) adapted to connect to respective ends of the nasal prong assembly 4120 and an intermediate portion 4115(2) adapted to connect to the inlet tube 4114. In use, gas flows from the inlet tube 4114, into the intermediate portion 4115(2), into the side portions 4115(1), and into respective ends of the nasal prong assembly 4120. Such arrangement provides a symmetrical configuration to improve stability, e.g., with respect to an asymmetric arrangement wherein an inlet tube is connected to one end of the nasal prong assembly. In addition, such arrangement provides flexibility to accommodate different sleep positions, e.g., side of head, back of head, etc.

In an alternative embodiment, the tube entry point may be relocated to the front of the frame for the nasal prong assembly, which may eliminate the need for plugs, seal rings, etc. In yet another embodiment, a central soft tube connection may be incorporated into the nasal prong assembly. The soft tube connection may be structured to accommodate flexibility and movement (e.g., increased decoupling of forces) and may be molded to avoid kinking or reduction of airflow.

FIG. 5-40 illustrates a nasal prong 4224 according to another embodiment of the present invention. As illustrated, the nasal prong 4224 is one size larger than the typically recommended size. The next larger size prong 4224 may be used by educated patients to improve stability as the prong is larger (larger head portion and/or stalk) and requires more force to bend or deform it. In addition, the next larger size prong 4224 may improve seal and may improve comfort as the next larger size prong provides a suspension system that allows looser headgear. In an embodiment, at least the head portion of the prong 4224 may include a frosted surface finish to improve comfort, e.g., frosted surface finish like a lubricated joint that allows sliding.

FIG. 5-41 illustrates a nasal prong assembly 4320 and air delivery conduit 4314 according to another embodiment of the present invention. In the illustrated embodiment, the air delivery conduit 4314 is in the form of spiral tubing, e.g., similar to spiral configuration of a telephone cord. The use of such spiral tubing 4314 may improve stability and help reduce the drag of the tubing on the nasal prong assembly 4320 in use.

In the illustrated embodiment, the spiral tubing 4314 is provided to one end of the nasal prong assembly 4320 for delivering pressurized breathable gas. In an embodiment, the spiral tubing 4314 may be spring loaded or biased to keep the tubing compact and neat and to prevent tangling.

The spiral tubing 4314 may be particularly advantageous for use with such nasal prong assembly 4320. Specifically, because tubing for the nasal prong assembly is asymmetric or provided to only one side of the nasal prong assembly, typical elongated tubing (e.g., 2 m elongate tubing) may provide enough pass to pull the nasal prong arrangement sideways (e.g., when the patient moves around in bed) which may break the seal between the nasal prongs and the patient's nares. However, the spiral tubing 4314 provides a flexible arrangement that allows sufficient extension and retraction of the tubing in use. This arrangement reduces tube drag and effectively decouples the tubing from the nasal prong assembly to prevent breaking of the seal.

1.6.10 Foam Prong

In an alternative embodiment, at least a portion of the prong may be constructed of a foam material. For example, the entire head portion of the prong may be constructed of a foam material, and provide a foam contact surface to interface with the patient's nasal passages. The foam head portion may provide grip, warming sensation, and/or improved comfort in use.

1.6.11 Question-Mark Shaped Prong

In an alternative embodiment, side walls of the prong may include a question-mark or sickle shaped configuration.

Alternative Embodiment Nasal Prongs

As shown in FIGS. 16-1 to 16-12, each nasal prong 5024 of nasal prong assembly 5020 includes a head portion 5025 adapted to seal and/or sealingly communicate with a respective patient nasal passage and a column or stalk 5027 that interconnects the head portion 5025 with a gusset 5022.

In the illustrated embodiment, each head portion 5025 includes a dual or double-wall arrangement including an inner wall 5026 (inner membrane or support membrane) and an outer wall 5028 (outer membrane or sealing membrane) that surrounds the inner wall 5026. The outer wall 5028 may be relatively thin (e.g., 0.35 mm) with respect to the inner wall 5026 (e.g., 0.75 mm) to conform to the shape of the patient's nose and provide a more compliant seal.

The stalk 5022 may be relatively short (e.g., about 2-8 mm, e.g., 5.1 mm), e.g., due to flexibility provided by the gusset 5022.

1.7 Other Forms of Interfacing Structure

In other forms of the invention, alternative interfacing structures may be used. For example, a nasal cradle as described in International Patent Application PCT/AU2007/001051, the contents of which are hereby incorporated by cross-reference.

Other alternative forms of interfacing structure could be as described in U.S. Pat. No. 4,782,832 (Trimble et al.), U.S. Pat. No. 5,724,965 (Handke et al.), U.S. Pat. No. 6,119,694 (Correa et al.), U.S. Pat. No. 6,431,172 (Bordewick), and International Patent Application WO 2000/74758 (Lovell et al.), the contents of each of which is hereby incorporated by cross-reference.

2 Positioning, Suspension & Stabilising

2.1 Introduction

A patient interface in accordance with an embodiment of the invention provides a structure for suitable positioning, suspension and stabilizing of the interfacing portion of the patient interface at an entrance to the airways of the patient. This structure includes the stalks of the nasal prongs, the gusset portion, the frame and headgear with stabilizers. The structure as a whole may be regarded as positioning the interfacing portions. The stalks of the nasal prongs, and the gusset portion together function as a form of suspension system. The headgear and stabilizers form a structure that resists bending (for example from tube drag) and yet is flexible to conform to different facial geometries, or to move in response to other potentially disruptive forces. In combination with the suspension system, a greater range of movement of a mask system in accordance with an embodiment of the invention can be accommodated without disrupting the seal than in prior art mask systems.

A frame in accordance with an embodiment of the present invention serves a number of functions, including serving as a connection point to which the gusset, headgear stabilizers and elbow may be connected. A given functional feature may reside in different structures. For example, the stabilizing portion of headgear may be formed as part of a frame either additionally or alternatively.

2.2 Suspension System

Stalks

As shown in FIG. 4-1, each prong 24 may include a trampoline-like suspension system at both ends of the stalk 27, such as described in WO 2006/130903. Specifically, each prong 24 may include an upper trampoline-like suspension system 29 between the head portion 25 and the stalk 27, and a lower trampoline-like suspension system 31 between the stalk 27 and the base 22. The upper and lower trampoline-like suspension systems 29, 31 act as a universal mechanism to articulate and align the head portion 25 to the patient's alar and nasolabial angles, self-adjust the stalk length to suit the patient's nasolabial height, and/or provide a comfortable sealing force to the nares. That is, the upper and lower trampoline-like suspension systems 29, 31 allow rotation of the stalk 27 relative to both the head portion 25 and the base 22, and allow reduction in height of the head portion 25 relative to the base 22. For example, a relatively thin base may allow the stalk to sink into the base and/or rotate relative to the base (e.g., like a ball joint), and the head portion may deform and sink into the stalk (e.g., like a ball joint). Such compliance and flexibility in rotation and height allows the range of overall length to be effectively increased or decreased a great deal to allow for accommodation of different geometries.

In an embodiment, the height H of the stalk 27 may be between 5-15 mm, e.g., 7 mm, 8 mm, 9 mm, 12 mm, etc.

In an alternative embodiment, as shown in FIG. 4-2, the lower trampoline-like suspension system 31 may include a square edge, e.g., square edge between bottom of stalk 27 and base 22, to provide a suitable collapsing point for the prong 24 on the base 22. The square edge may bring the center of articulation down towards the base, which may provide more articulation for a particular height of stalk 27.

Gusset

As best shown in FIGS. 16-5, 16-9, and 16-12, the gusset 5022 of nasal prong assembly 5020 includes a base 5023.1 adapted to support the nasal prongs 5024, lateral side walls 5023.2, an outer side wall 5023.3 (adapted to face away from the patient's face in use), and an inner side wall 5023.4 (adapted to face towards and/or contact the patient's face in use).

The gusset 5022 provides structure that creates an axial force to enhance axial or vertical movement (e.g., gusset and prongs (e.g., prong compression) together can move axially or vertically up to about 17 mm), and provide contact with the patient's upper lip, and create an axial force to enhance the nasal prong seal. The gusset also allows lateral movement to enhance stability while maintaining a sufficient seal with an acceptable amount of leak to maintain a sufficient seal (e.g., gusset and prongs (e.g., prong flexibility and dual wall movement) together can move laterally up to about 7-10 mm total with less than 0.5 L/min leak), provides a trampoline like base due to a relatively thin base (e.g., 0.75 mm) which allows articulation and extra flexibility of the nasal prongs, provides compressibility, and provides a wide range of movement of fit a large range of patients.

The dual wall nasal prongs in combination with the gusset enhances the lateral movement of the nasal prong assembly. Also, each nasal prong may include an upper trampoline-like suspension system between the head portion and the stalk, and a lower trampoline-like suspension system between the stalk and the gusset base, which allows rotation of the stalk relative to both the head portion and the gusset base, and allow reduction in height of the head portion relative to the gusset base (e.g., thin gusset base allows retraction of the stalk into the base).

The gusset increases the range of adjustability to substantially prevent overtightening of the headgear, e.g., gusset can compress axially to absorb headgear tension.

As illustrated in FIGS. 16-5, 16-9, and 16-12, the upper portion of the gusset (e.g., base) includes a relatively thinner wall thickness than the lower portion of the gusset (e.g., lower portion of the side walls). In an exemplary embodiment, the wall thickness of the upper portion of the gusset is about 0.75 mm, and the wall thickness of the lower portion of the gusset is about 1.5 mm. However, other suitable wall thicknesses of the gusset are possible, e.g., to adjust rigidity or springiness. For example, in an alternative embodiment, the gusset may include 0.75 mm overall wall thickness, with selected portions of the gusset including stiffening members (e.g., ribs) to add rigidity.

As shown in the side view of FIG. 16-9, the gusset 5022 provides a wedge like cross-section (e.g., wedge angle α of about 15-45° (e.g., 30°) as shown in FIG. 16-9) in which the inner side wall 5023.4 includes a larger surface area than the outer side wall 5023.3. The larger surface area of the inner side wall 5023.4 is structured to contact with the patient's upper lip and tilt the frame and elbow away from the patient's chin and mouth. In addition, this arrangement moves the harder frame edge away from the patient's lip and moves the seal into the patient's nose. The inner side wall 5023.4 may be contoured to match the contour of the patient's upper lip. However, the gusset may have other suitable shapes.

As shown in the front view of FIGS. 16-4 and 16-12, the gusset 5022 provides a generally V-shaped cross-section in order to angle the prongs in the correct orientation with respect to the patient's nose.

Combination of Pillows and Gusset

A suspension system combination of pillows and gusset in accordance with an embodiment of the present invention provides significant improvement over related and prior pillows. To facilitate an understanding of the nature of the improvement, it is helpful to consider the following:

To effect an adequate seal against a surface, a system can present an interfacing component (e.g. the top portion or head of the pillow) against the face (or surface of the nose) with an appropriate force that restricts the flow of air between the surface of the face and that of the interfacing component. An unnecessarily high level of force is both uncomfortable and unhealthy—with a range of symptoms from red marks to sores and skin necrosis. Most mask systems use a flexible cushioning material positioned against the skin and located between the skin and more rigid components of the mask. The cushioning component may be modeled mechanically as one or more springs.

Generally the spring arrangements of cushions in consideration have a range of possible compression before they are fully compressed or "bottomed out". Once fully compressed, a cushion will generally have little "cushioning" effect, and simply transfer to the face whatever force has been established through headgear tension. We have discovered that it is desirable for improved comfort and seal to provide for significantly more movement before a cushion is fully compressed. As will be presently described, prior nasal pillow arrangements in masks of the presently contemplated type (e.g., Puritan Bennett Adam's Circuit, ResMed Mirage Swift, Innomed Bravo, Respironics Optilife, Fisher & Paykel Opus) provide from about 1 mm to about 6 mm vertical movement, whereas a nasal pillows system according to an embodiment of the present invention can provide up to about 10 mm vertical movement before fully compressing the pillows.

FIG. 23 illustrates the difference between different nasal pillow mask systems. Three mask systems are shown. Each mask system tested generally provides two regions, a flatter region and a steep region. In the first, flatter region, the force on the face transmitted through the pillow increases gradually as the spring is further compressed. Once the spring is fully compressed, the force on the face has a much more significant rate of increase. Of the nasal pillow masks tested, the Puritan-Bennet BREEZE mask system allows approximately 2 mm of compression before the pillow is fully compressed and the force on the face starts to significantly increase. The ResMed SWIFT II allows approximately 6-7 mm of compression before the force on the face starts to increase more significantly. Other mask systems tested lie between the BREEZE and SWIFT masks. A mask system in accordance with an embodiment of the present invention allows approximately 9-10 mm compression before the force on the face starts to increase more significantly.

We have also discovered that comfort and seal of a nasal pillows mask system can be improved if it can accommodated greater lateral movement (e.g., left to right, right to left) without breaking a seal than that provided by known nasal pillows mask systems. For example, providing greater lateral movement facilitates side sleeping. A mask system in accordance with an embodiment of the present invention provides approximately five times the lateral movement of SWIFT II without unacceptably leaking.

FIG. 24 shows the amount of leak measured for the present example and the ResMed SWIFT nasal pillow system when subject to lateral movement. The amount of leak increases with the amount of lateral movement. However, since the present example is much more accommodating of movement than the SWIFT, at a leak level of approximately 2 L/min, approximately 5 mm of total lateral movement can be accommodated with the present example compared to approximately 1 mm for the SWIFT mask. The values determined in this test are dependent on the test rig, and in another test rig, different values may result. Furthermore, the choice of 2 L/min to measure the amount of movement is somewhat arbitrary and intended merely to illustrate the advantages of the present example.

FIGS. 25a to 25g show portions of nasal pillow systems including a range of prior art nasal pillows and the present example (FIG. 25g). In particular, they illustrate the portions of the pillows that provide (vertical) compression and lateral movement. As discussed above, the performance of the different nasal pillows may be modeled as a number of mechanical springs. The spring constant for a particular spring may be, amongst other things, a function of the material's inherent resilience, the thickness of the part, a radius of curvature, a configuration (e.g., is the spring a being bent like a cantilever or compressed along its length) as well as the properties of surrounding components. In the following commentary, the shortcomings of prior nasal pillows will be discussed as well as how the present example leads to an improved result.

FIG. 25a shows a portion of a nasal pillow from the Puritan-Bennet BREEZE mask. The pillow includes three apparent corrugations as shown, however, the pillow is mounted in a rigid frame between the bottom two corrugations, hence the only movement possible in use is that which is afforded by the flexibility of the regions between the top two corrugations, marked as "flexing" in FIG. 25a. We estimate that approximately 2 mm of compression can be provided by the BREEZE pillow before it is fully compressed. It is noted that the radius of curvature of the first curve 25a-2 and second curve 25a-4 is approximately similar.

It is noted that U.S. Pat. No. 6,431,172 (Bordewick) appears to illustrate a nasal pillow similar to the BREEZE nasal pillow, however instead of being mounted on a rigid support, it is mounted on an inflatable plenum chamber. As far as we are aware, no commercial sample was ever produced and hence we are unable to test it. Since the base region is described as "entirely flaccid" and "not effective in transmitting forces between nares elements and rigid support" we expect it not to have any "springiness" (or a spring constant with a value of zero).

FIG. 25b shows a cross-sectional profile of the ResMed SWIFT I and SWIFT II nasal pillows system. As illustrated, the "head" of the pillow can compress approximately 6 mm before it reaches the base. The first curved region 25b-2 has a generally similar radius as the second curved region 25b-4, however because the second curved region 25b-4 is adjacent a much stiffer platform (not shown), the first curved region 25b-2 is more flexible than the second curved region 25b-4.

FIG. 25c illustrates the Fisher & Paykel OPUS nasal pillow. This nasal pillow has a relatively inflexible stalk region. The only compression that is provided is by collapse and buckling of the pillow head or collapse of the stalk base. Because collapse and buckling are unpredictable, this pillow seals very poorly.

FIG. 25d illustrates the Respironics OPTILIFE nasal pillow. The corresponding first and second curved regions of this pillow 25d-2 and 25d-4 have approximately similar radii. The first (25d-2) of these two regions is more flexible, in use, very little flexing of the second region 25d-4 appears to occur. Approximately 5 mm compression may be achieved before the stalk is fully compressed. Since the rest of the OPTILIFE pillow is relatively stiff, further compression leads to a significant increase in force. Note that the sidewall of the pillow base region is located below the head region hence, once the stalk region is compressed (~5 mm) further compression may only be obtained by buckling the pillow.

FIG. 25e illustrates the Innomed BRAVO nasal pillow. This pillow appears to provide approximately 7 mm of compression before bottoming out. The pillow has two curved regions 25e-2 and 25e-4. The second of these two curved regions appears to have a larger radius than the first and we would expect that the region with the larger radius would be more flexible—everything else being equal. However, since the base region to which the pillow is connected is relatively stiff, flexing only occurs at the first region 25e-2. Other parts (not shown) of the BRAVO nasal pillows mask adjacent the base of the pillows are constructed from a rigid polycarbonate.

A portion of the pillows of the Fisher & Paykel OPUS 2 mask is shown in FIG. 25f. The stalk/neck region of the pillow has two curved portions 25f-2 and 25f-4. Both curved regions appear to have approximately the same radius. The pillow appears to provide approximately 6 mm of compression before bottoming out. Furthermore, it is noted that the base region 25f-6 of the pillow, is similarly configured to the Respironics OPTILIFE nasal pillow. Hence, upon compression of the pillow beyond that provided by the neck region of the stalk can only be provided by buckling the pillow, or at least attempting to compress it along its length.

FIG. 25g shows a portion of a nasal pillow in accordance with an example of the invention. First curved region 25g-2 provides compression of the pillow. Second curved region 25g-4 has a reduced curvature compared to region 25g-2 and hence is stiffer than region 25g-2. Nevertheless, flexing can still occur at region 25g-4. Unlike all the prior art nasal pillow regions discussed thus far, the nasal pillow in accordance with an embodiment of the present invention also includes an additional flexing region 25g-5 located on a flatter, top or "platform" region 25g-8 of the gusset. The platform region 25g-8 of the gusset extends approximately 5 to 10 mm from the point of connection of the stalk to the gusset. When the pillow is compressed, this additional flexing region 25g-5 can bend somewhat like a cantilever. This contrasts with the other nasal pillows which may be subject to buckling forces when further compressed.

As shown in FIG. 25g, six flexing regions have been enumerated. These may be named as follows: 25g-1 "single wall pillow", 25g-2 "attachment of pillow to stalk", 25g-3 "stalk", 25g-4 "attachment of stalk to platform", 25g-5 "platform" & 25g-6 "gusset" or "base region". By way of comparison of corresponding regions between the SWIFT and the present example, the relative stiffness of the different regions is shown in FIG. 26. For example, the stiffness of region 2, the attachment of the pillow to stalk, is approximately the same in the present example and the ResMed SWIFT. However, in region 4, the attachment of the stalk to platform is less stiff in the SWIFT than in the present example. While the SWIFT does not have a gusset, a comparison can be made between the barrel/base region of the SWIFT and the gusset of the present example and the result is that the gusset of the present example is significantly less stiff than the barrel/base portion of the SWIFT. There is a direct inverse correspondence between the amount of movement provided by stiffness—the stiffer a spring, the less movement is provided for a given force.

FIG. 27a to FIG. 27l show a nasal pillow and gusset assembly in accordance with an embodiment of the invention. Some illustrative dimensions are shown. However, it should be noted that the principles of the invention may be applied to other sizes and shapes. A preferred platform region in accordance with an embodiment of the invention has a thickness of approximately 0.75 mm and is molded from 40 Shore A hardness silicone. Other dimensions are as shown.

For example, as shown in FIGS. 27a to 27l, D1 may be about 3 mm, D2 may be about 1 mm, D3 may be about 1 mm, D4 may be about 5 mm, D5 may be about 2 mm, D6 may be about 3 mm, D7 may be about 4 mm, D8 may be about 5 mm, D9 may be about 6 mm, D10 may be about 0.6 mm at the tip, D11 may be about 20 mm, D12 may be about 7 mm, D13 may be about 5 mm, D14 may be about 9 mm, D15 may be about 10 mm, D16 may be about 25 mm, D17 may be about 14 mm, D18 may be about 27°, D19 may be about 32 mm, D20 may be about 2 mm, D21 may be about 21 mm, D22 may be about 30°, D23 (the average outer membrane thickness) may be about 0.35 mm, D24 (the average inner membrane thickness) may be about 0.75 mm, D25 (the average thickness of the stalk) may be about 0.75 mm, D26 (the average platform thickness) may be about 0.75 mm, D27 may be about 9 mm, D28 may be about 11 mm, D29 may be about 5 mm, D30 may be about 73°, D31 may be a radius of about 12 mm, D32 may be a radius of about 5 mm, D33 may be about 54 mm, and D34 may be about 29 mm Although specific dimensions are indicated, it is to be understood that these dimensions are merely exemplary and other dimensions are possible depending on application. For example, the exemplary dimensions may vary by 10-20% or more or less depending on application.

Figure 27B:
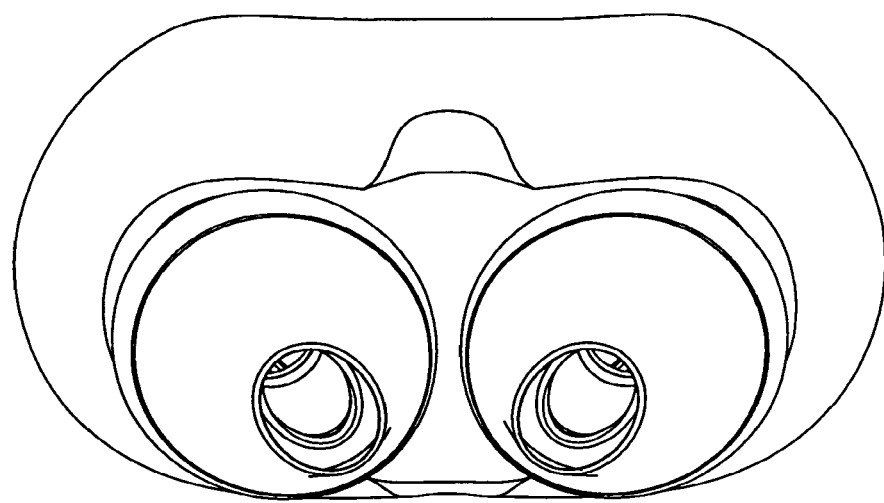
Figure 27C:
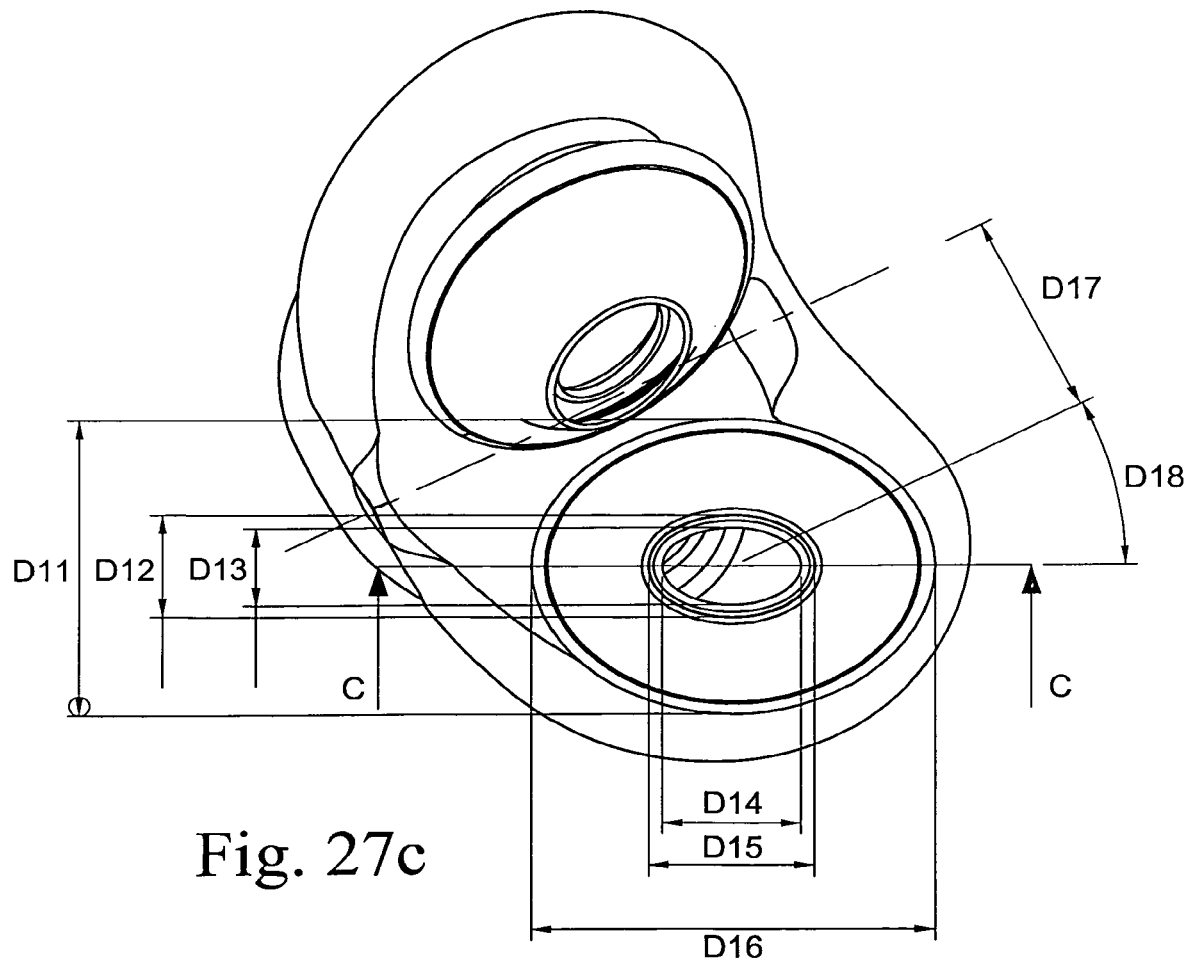
Figure 27D:
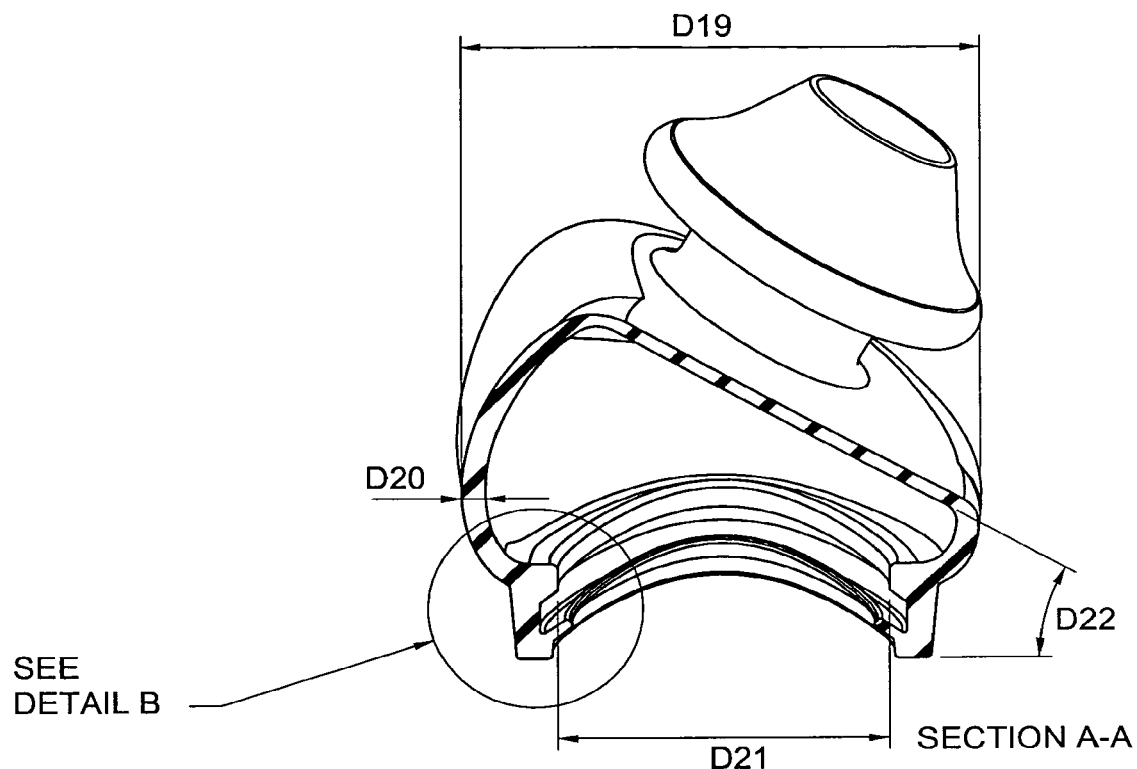
Figure 27E:
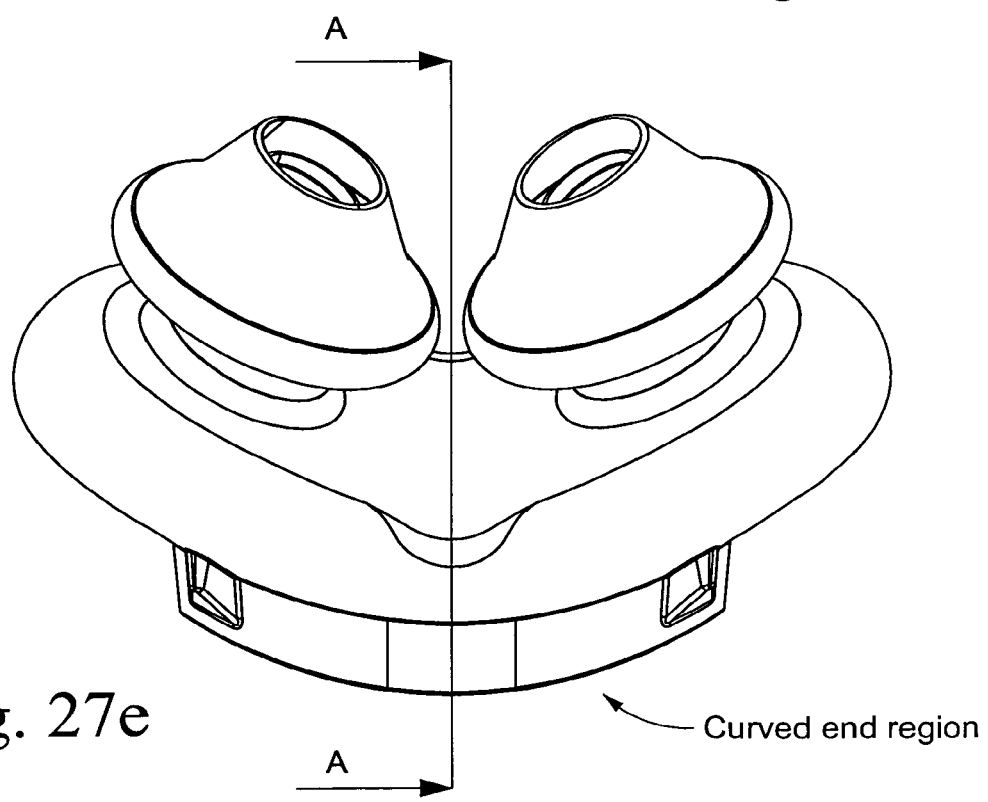
Figure 27F:
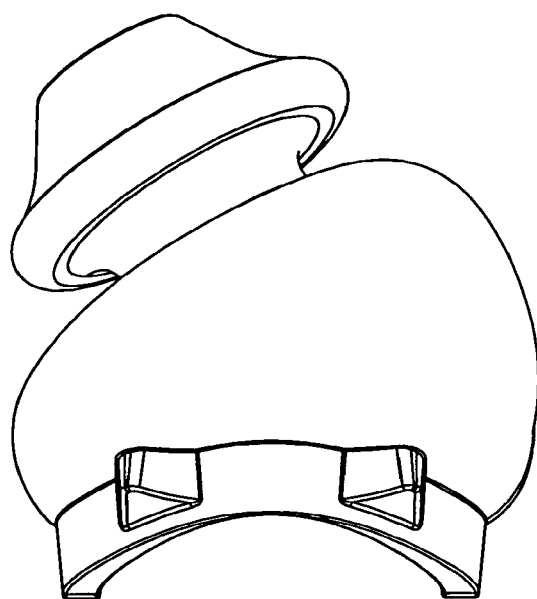
Figure 27G:
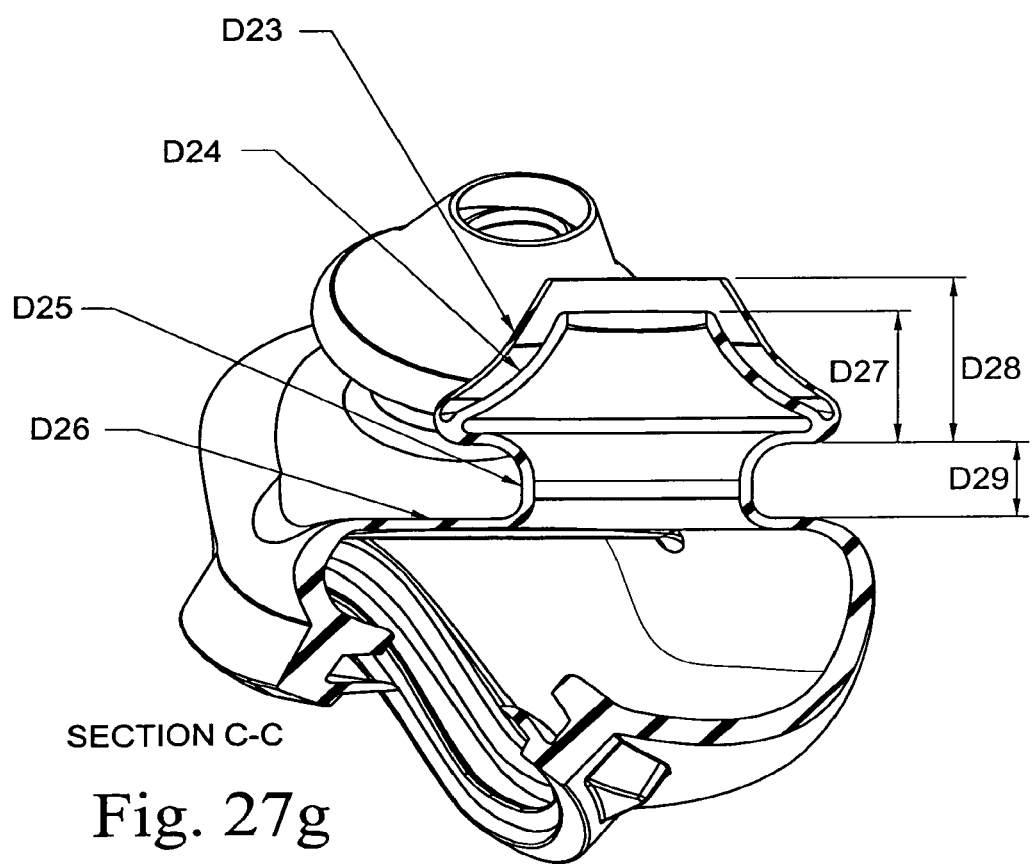
Figure 27H:
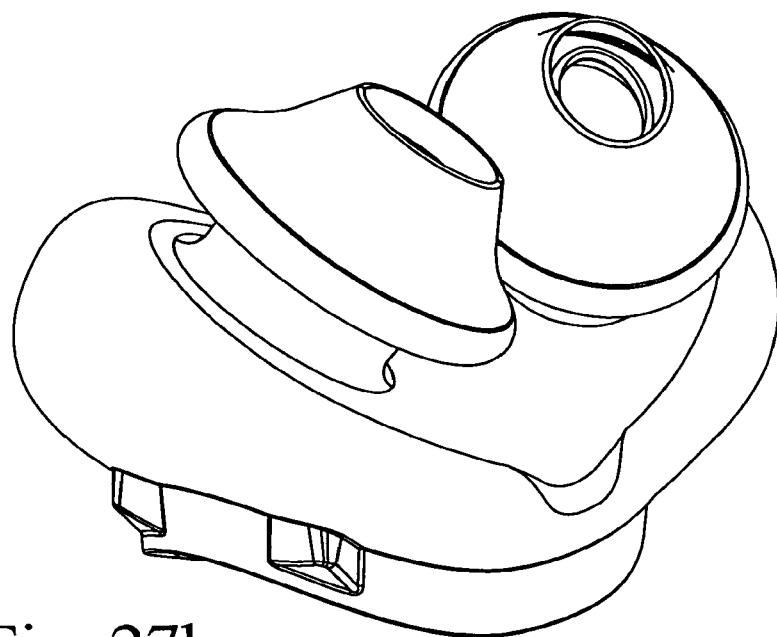
Figure 27I:
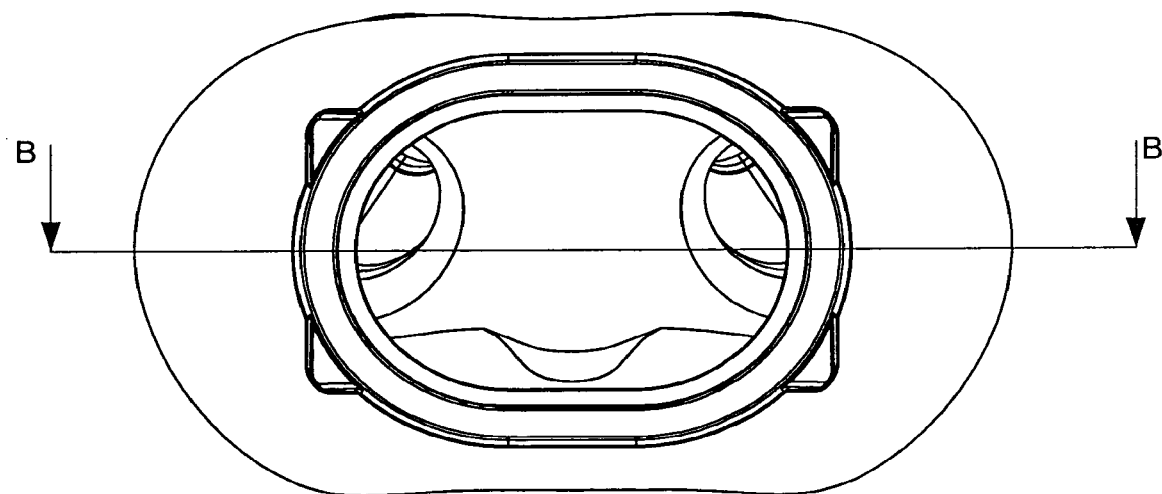
Figure 27J:
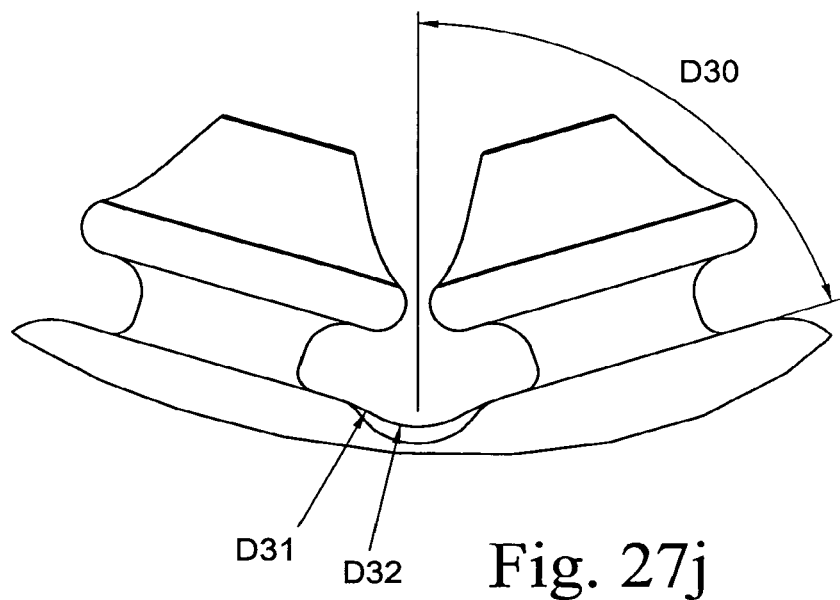
Figure 27K:
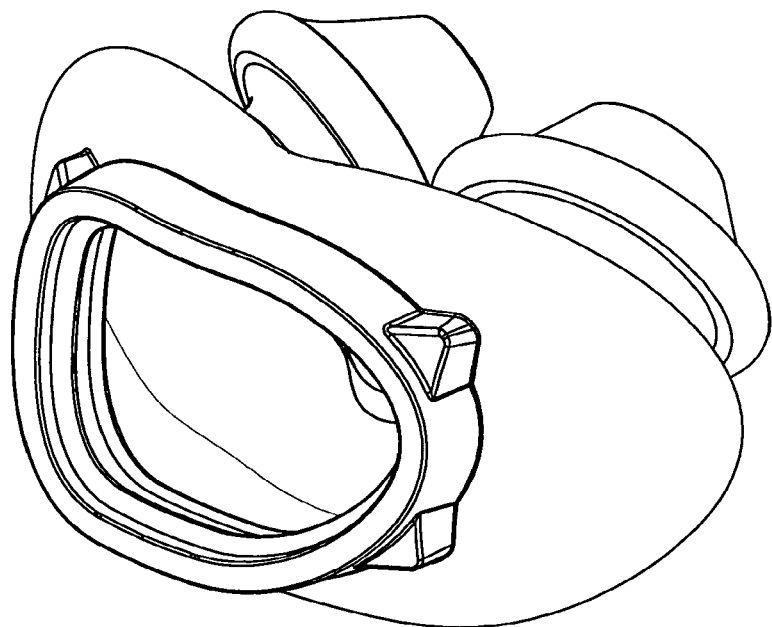
Figure 271:
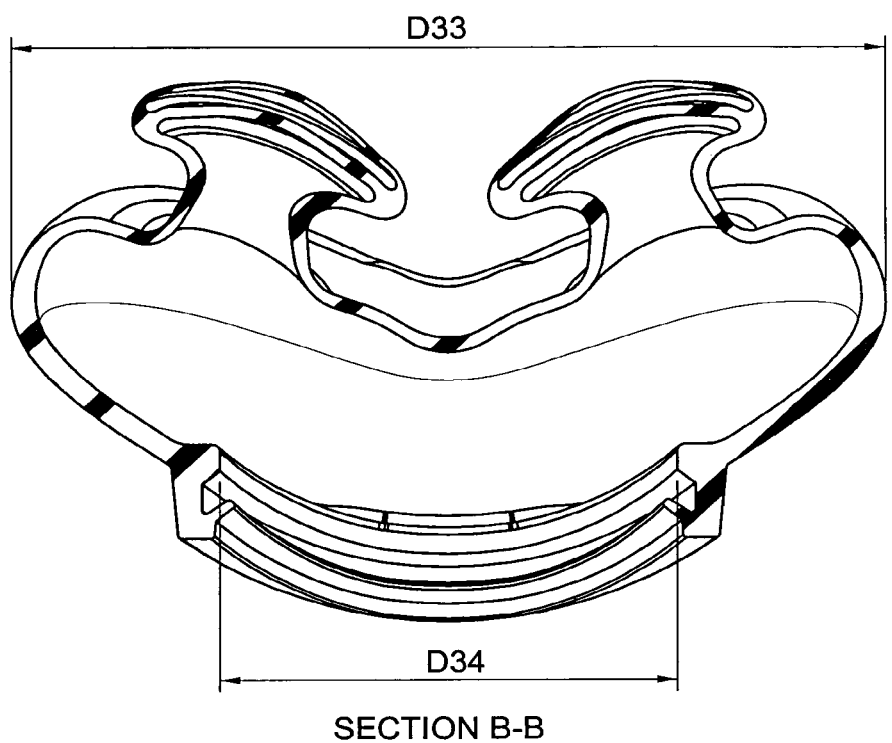
Figure 28:
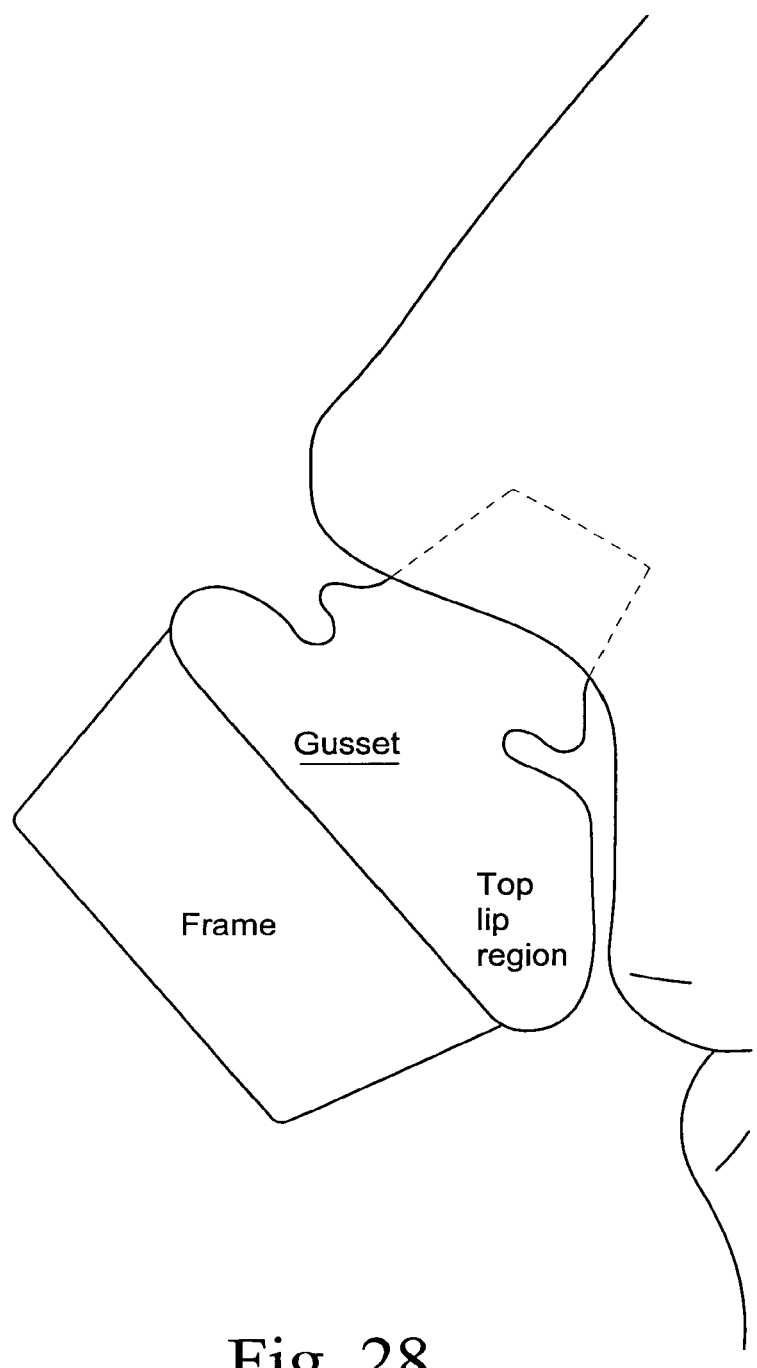
Figure 29:
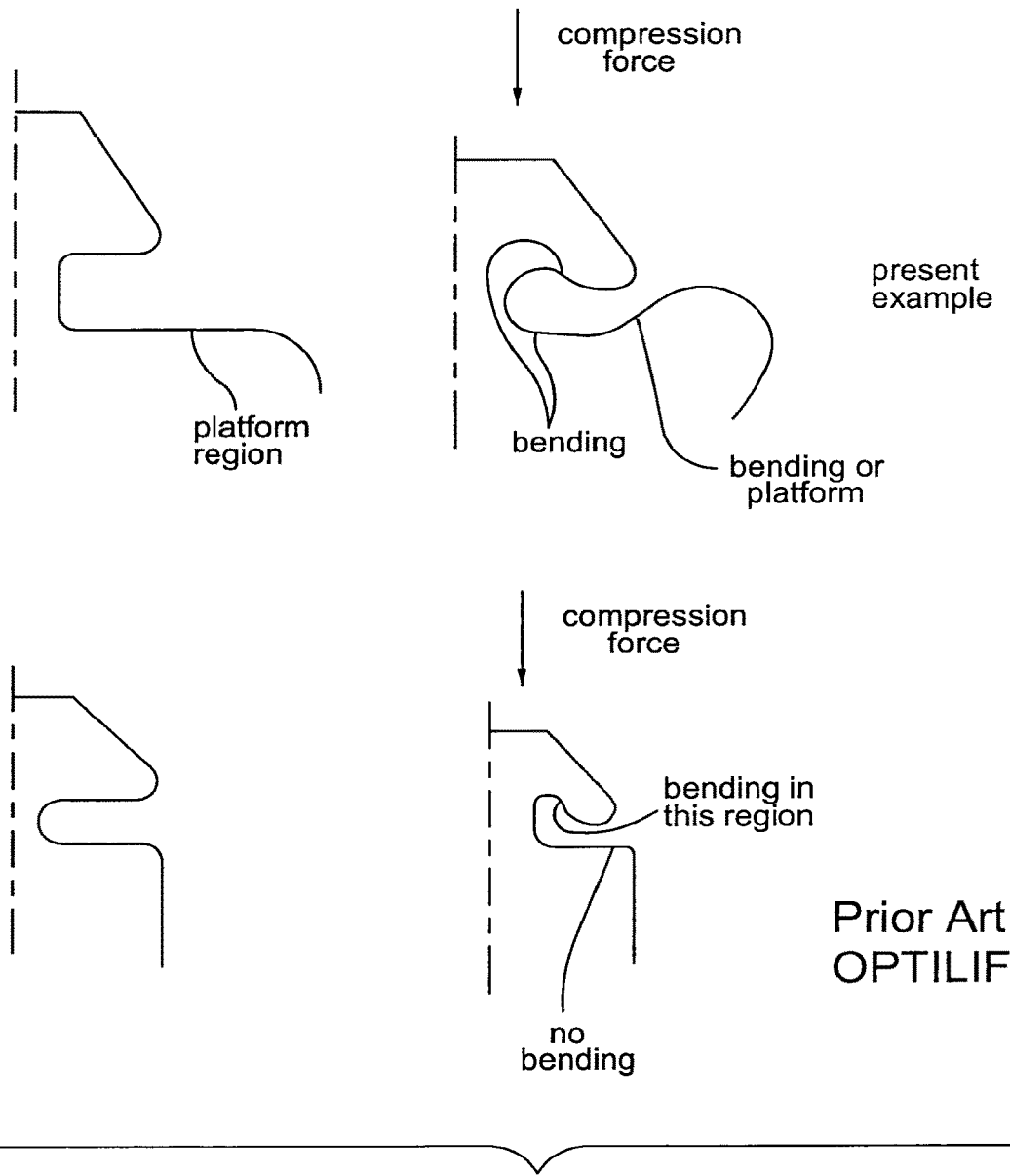
Figure 30:
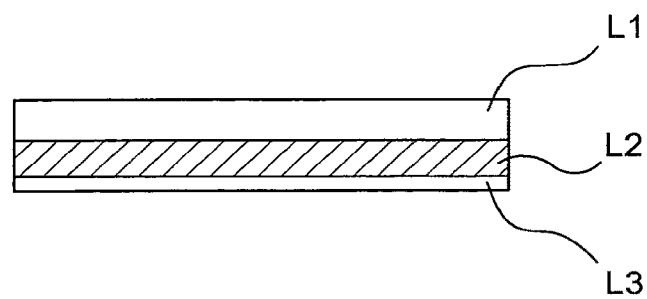
Figures 1, 31:
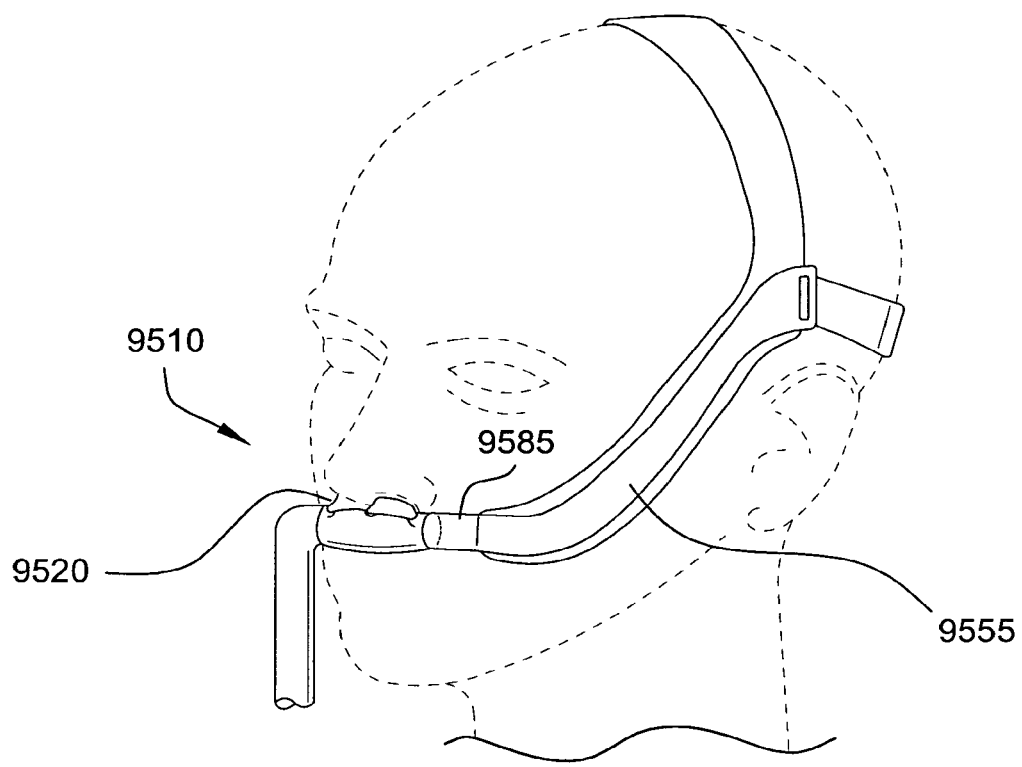
Figures 2, 31:
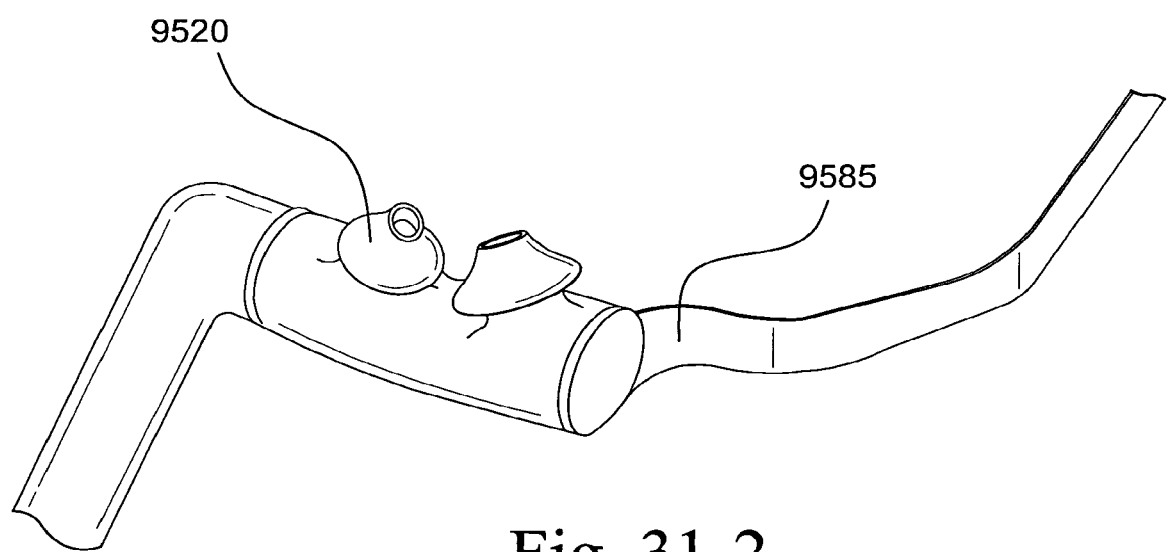
Figures 1, 32:
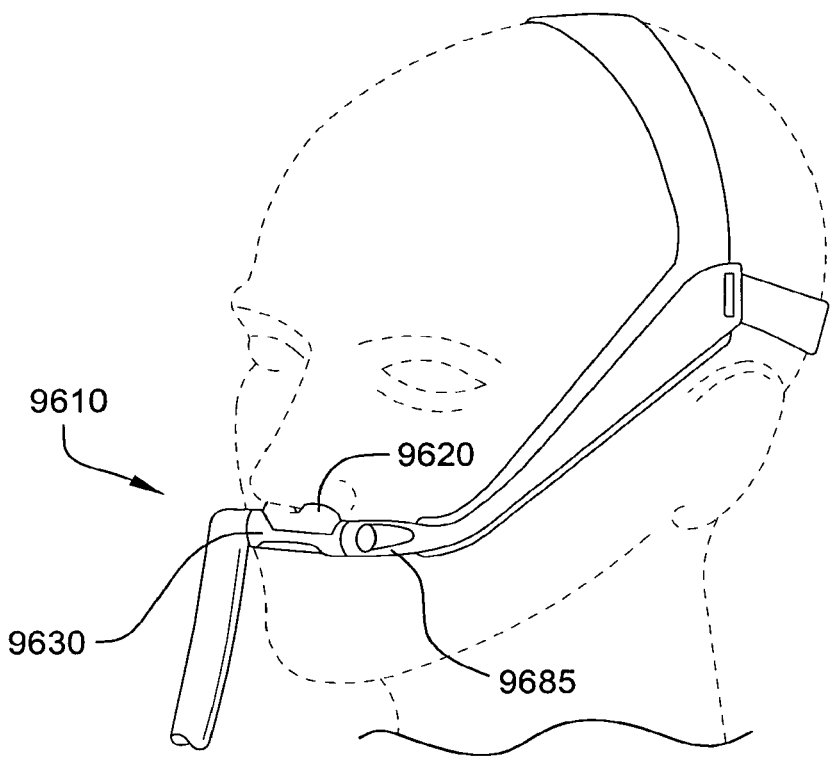
Figures 2, 32:
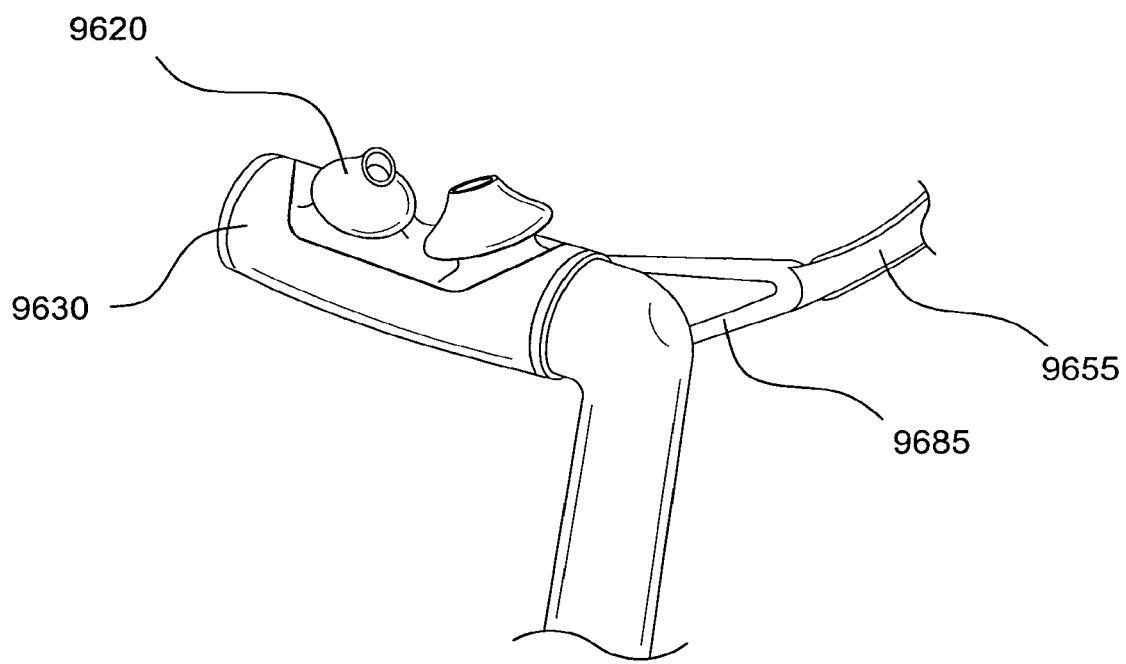
Figures 1, 33:
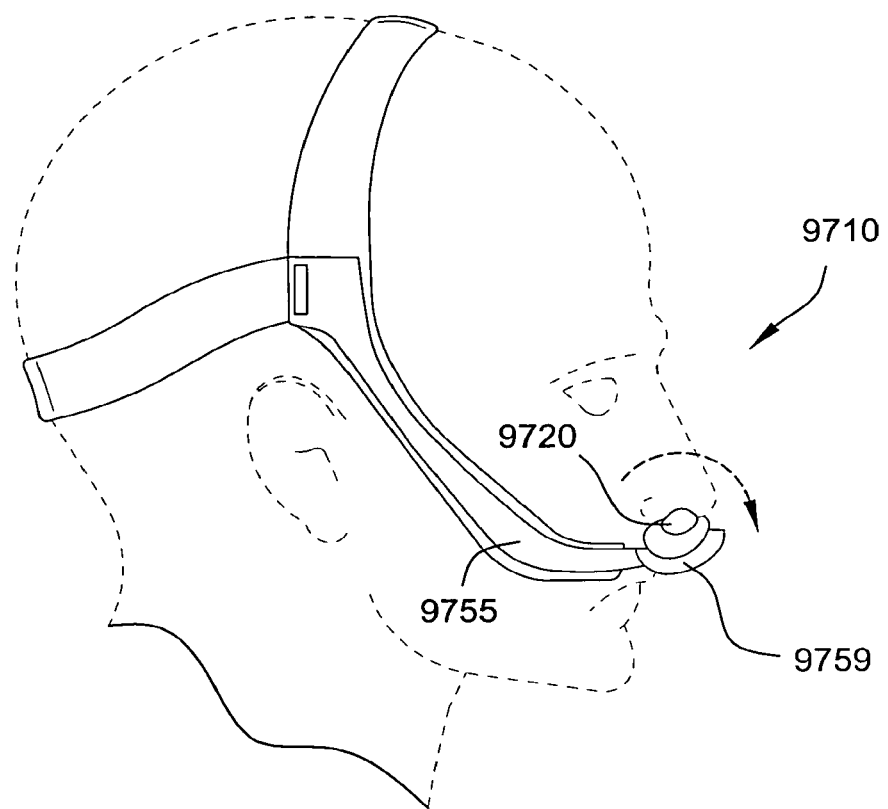
Figures 2, 33:
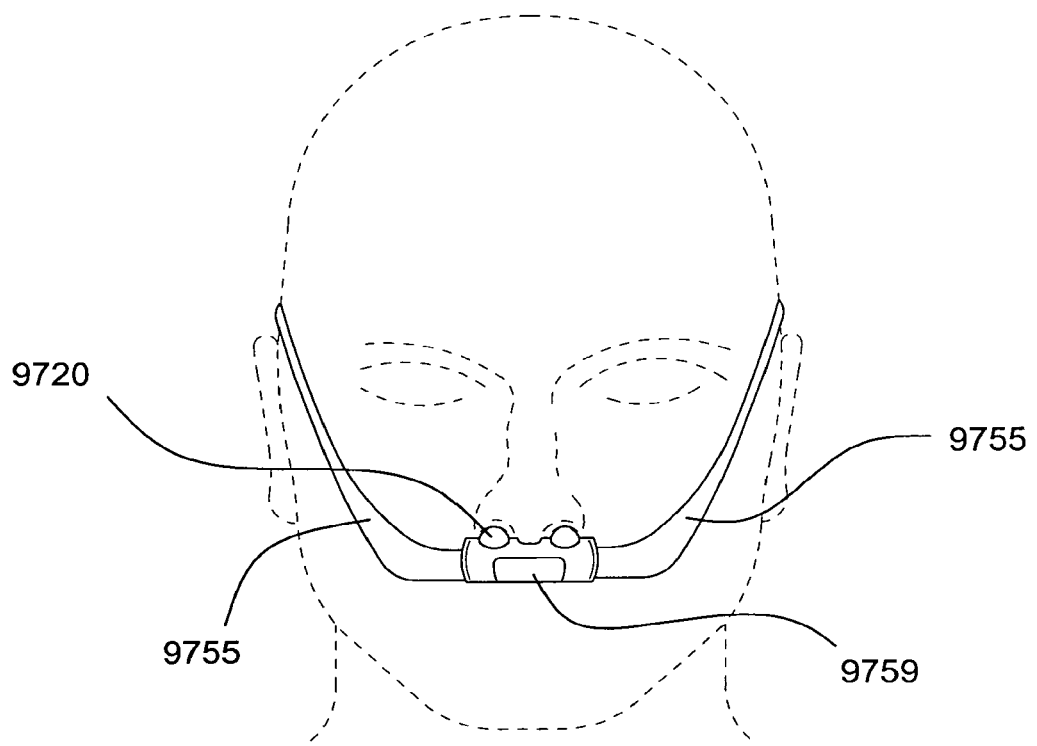
Figure 34:
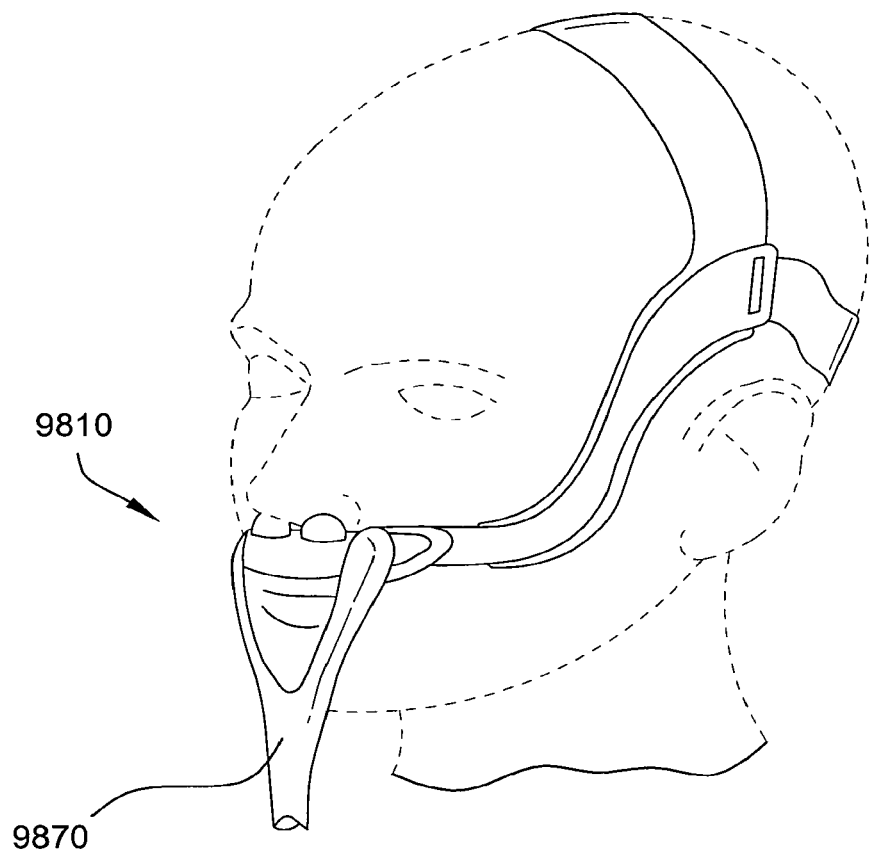
Figure 35:
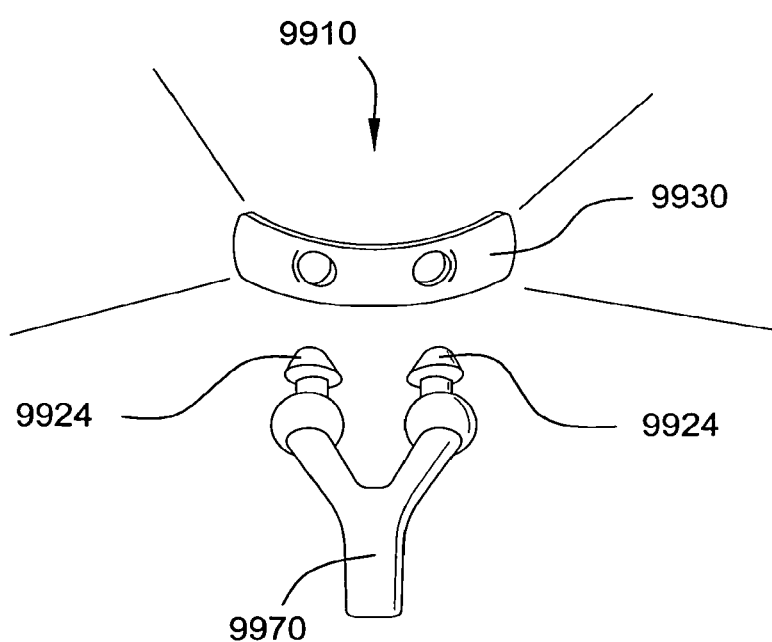
Figure 36:
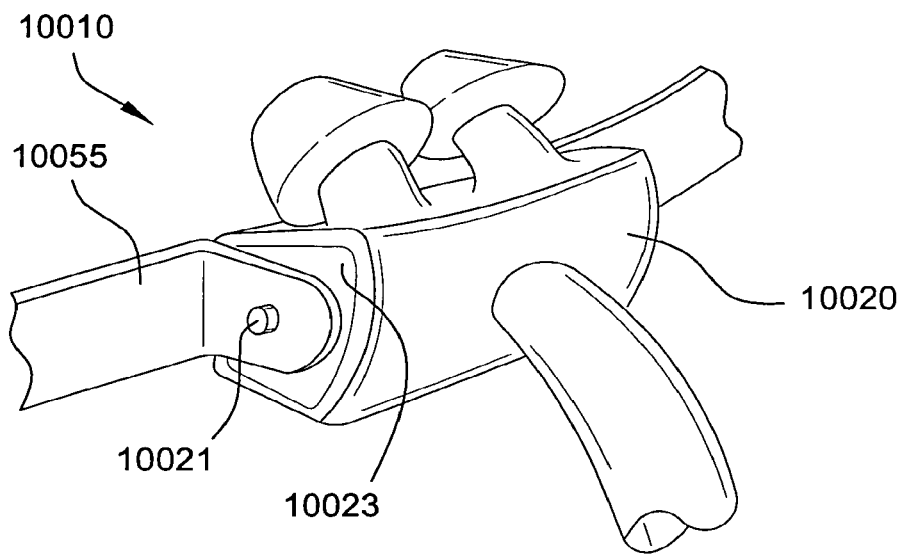
Figure 37:
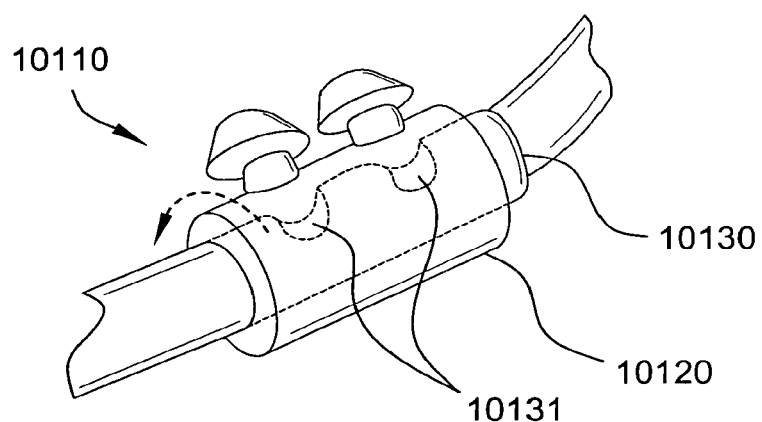
Figure 38:
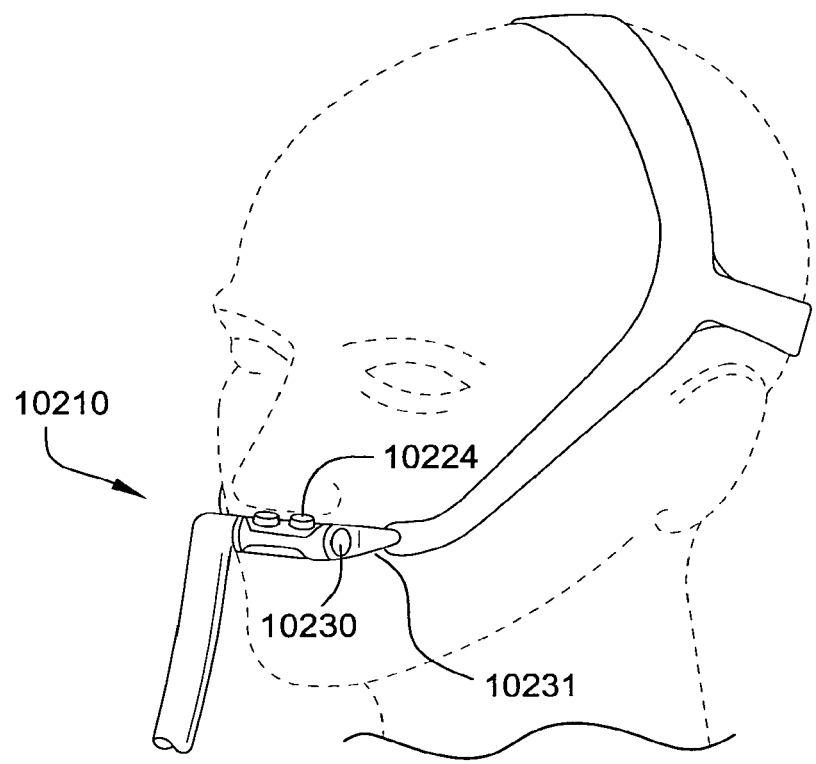
Figures 1, 39:
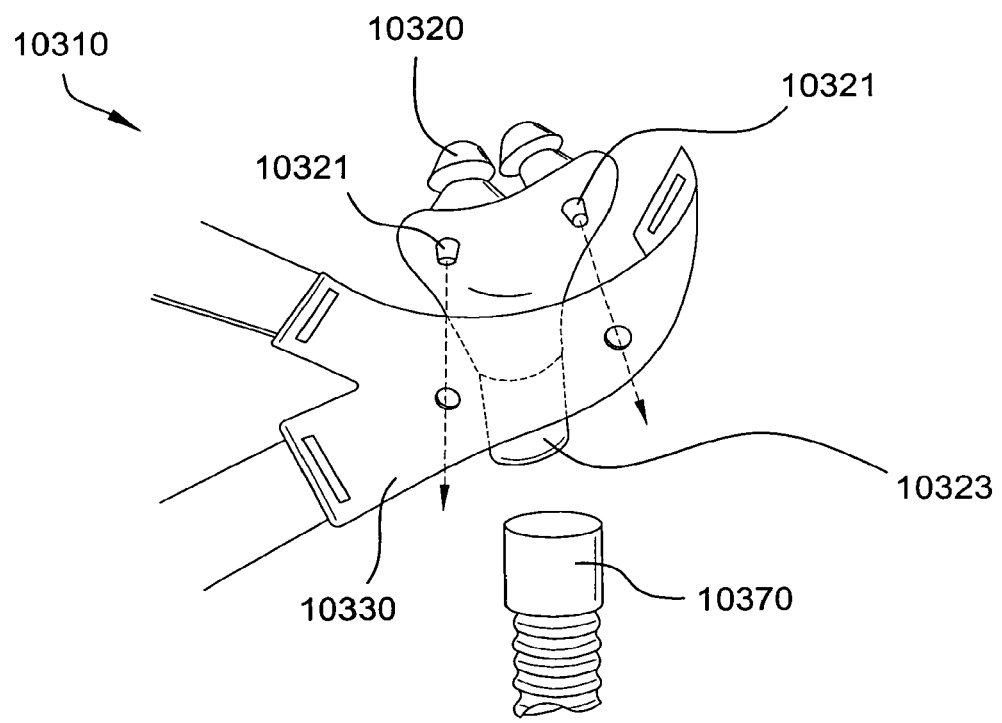
Figures 2, 39:
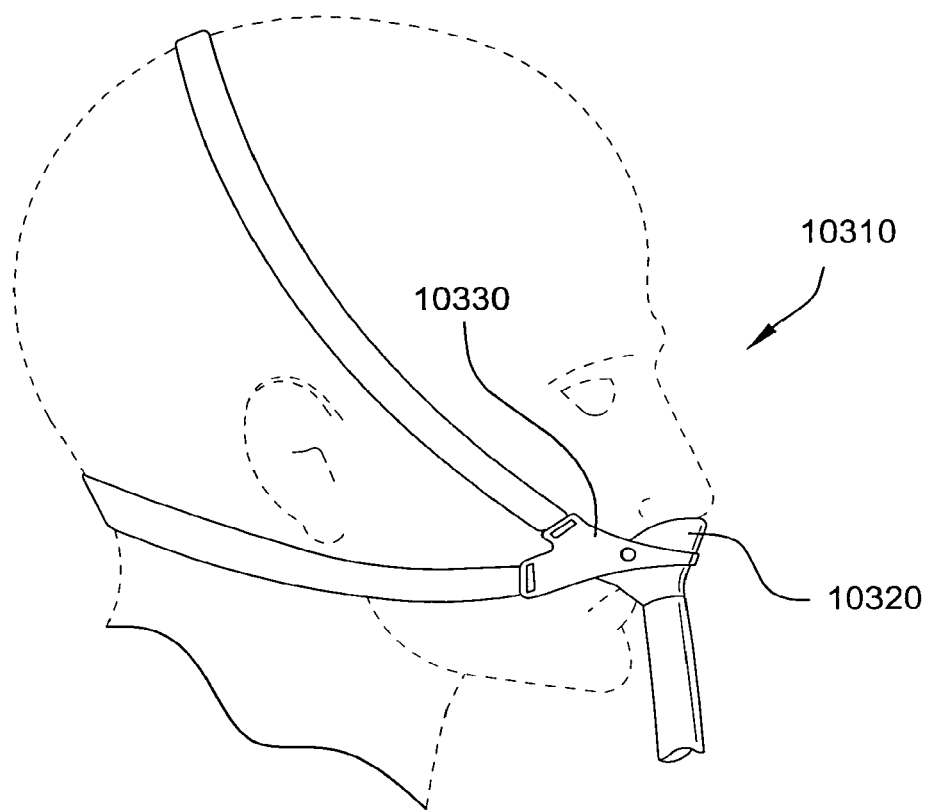
Figure 40:
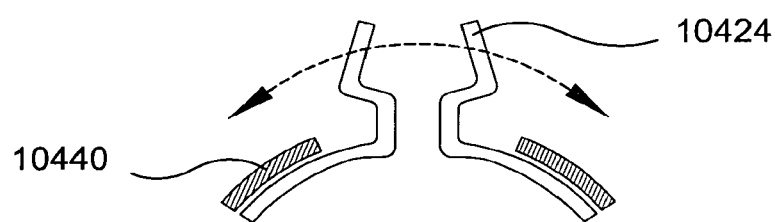
Figures 1, 41:
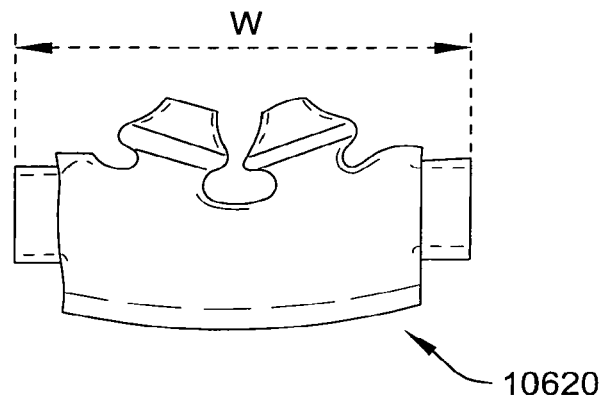
Figures 2, 41:
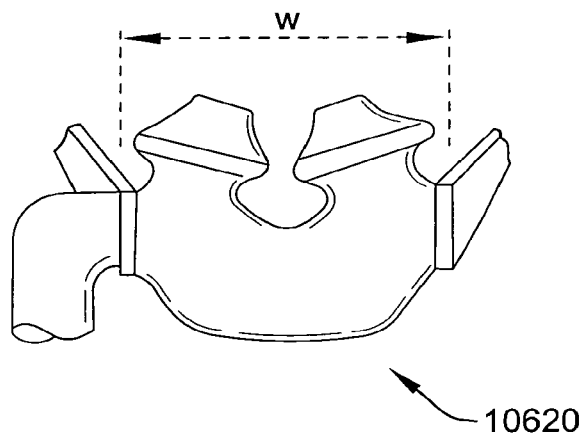
Figures 3, 41:
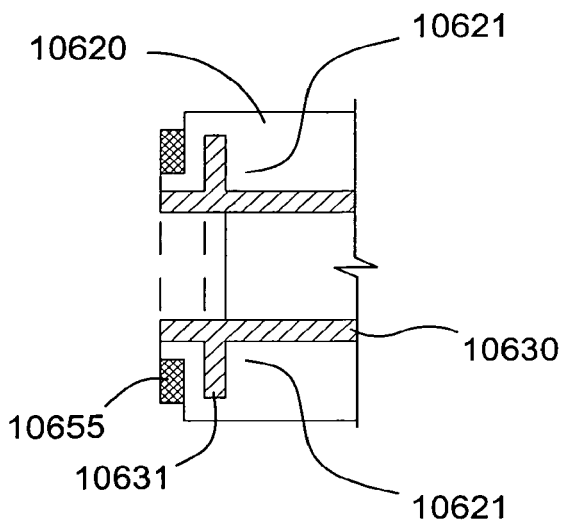
Figure 42:
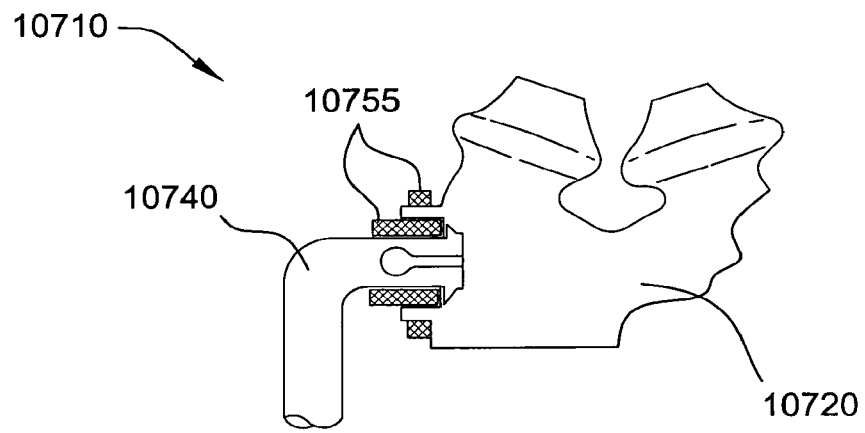
Figure 43:
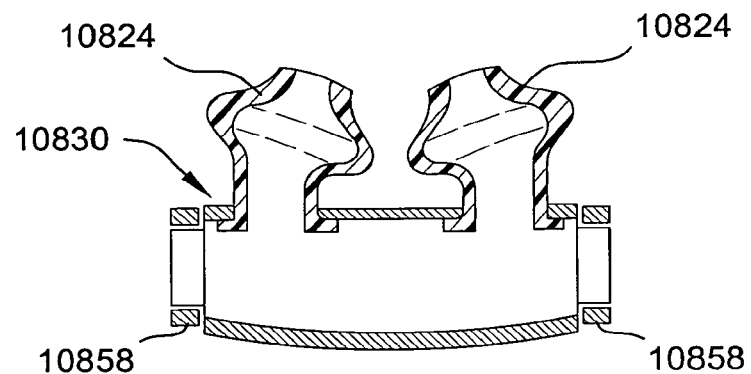
Figure 44:
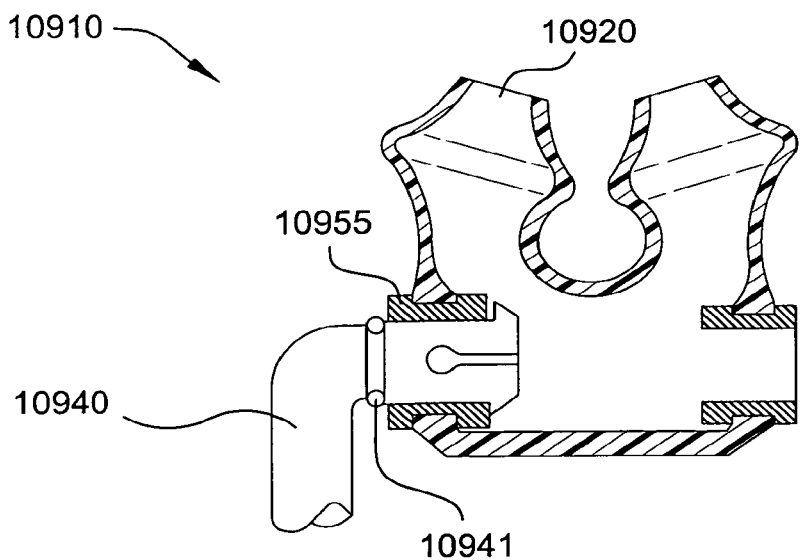
Figures 1, 45:
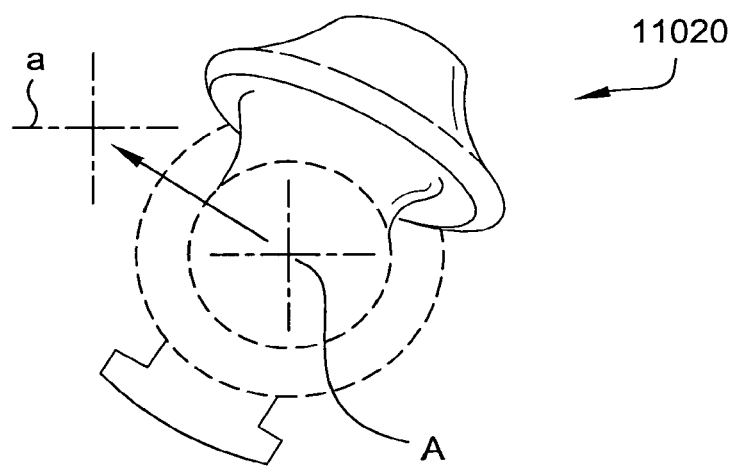
Figures 2, 45:
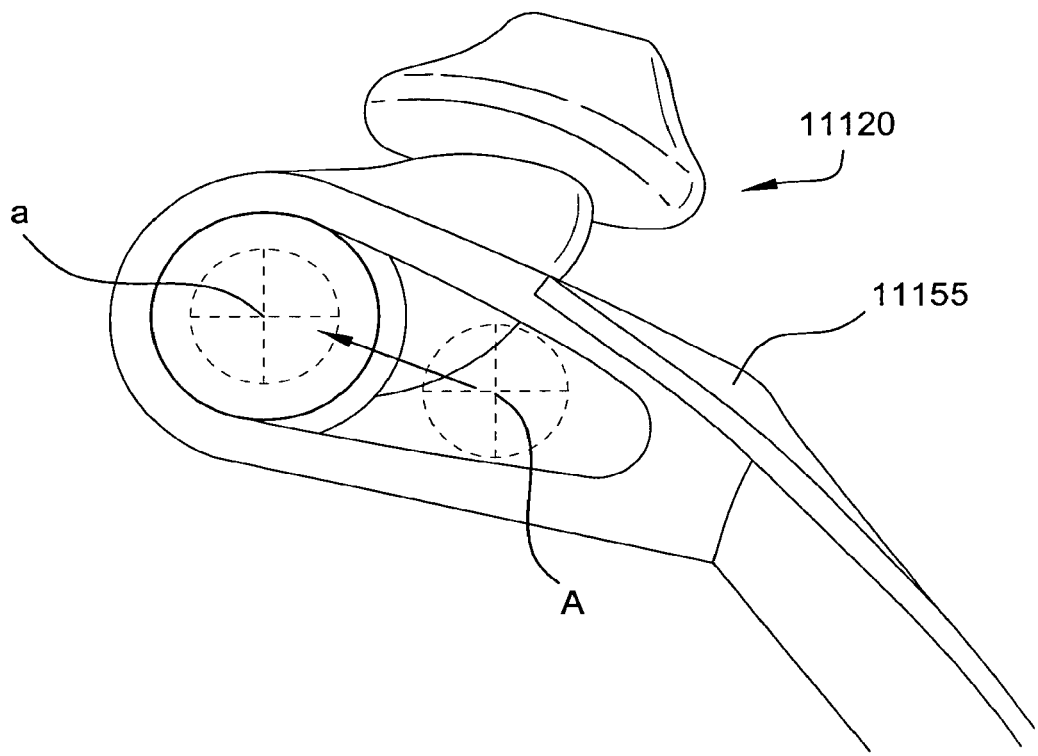

As shown in FIG. 27*d*, the gusset includes a top lip stability region. This portion of the gusset lightly rests on the top lip of the patient in use to aid stability of the system. The area is approximately 5 cm$^2$. When compared to the ResMed SWIFT mask (approximately 3.5 cm$^2$), OPUS 1 (approximately 2 cm$^2$) and OPUS 2 (approximately 2.5 cm$^2$), this region has a relatively larger area, which leads to less pressure on the top lip, and less force concentrations. The exact area in contact with a patient's lip depends on how the mask is positioned in use.

As shown in FIG. 27*d*, the platform region of the gusset is angled at approximately 30° with respect to the base of the gusset. See also FIG. 28 which is a sketch illustrating the pillows and gusset in use. By adopting this angled configuration, the risk of frame contacting the top lip is reduced, improving comfort.

FIG. 29 illustrates a nasal pillow according to an embodiment of the invention (top row) and a prior art arrangement (2nd row). When subject to a compression force (right hand side), as in when in use, a number of regions of the present example, such as the platform region begin to bend and flex. However, the same force on the prior art mask assembly only results in bending of the region the top of the stalk and the head of the pillow.

Another known form of nasal pillow is described in International Patent Application No. PCT/AU2006/000770 (Lubke et al., assigned to ResMed) published as WO 2006/130903. This nasal pillow is particularly suited for an oro-nasal mask. Because the oro-nasal mask includes nasal pillows extending from a mouth cushion, they have a significantly longer stalk region than the nasal pillows discussed above. This long stalk arrangement also provides a significant amount of flexibility and articulation, however this long-stalk arrangement is a different configuration to the present example. In the present example, significant articulation and movement is provided in relatively short stalks when compared to the oro-nasal mask of WO 2006/130903. Furthermore, the corresponding top region of the mouth cushion to which the long-stalk pillows are connected is relatively stiff compared to the top region of the present example.

Gusset to Frame Attachment

As shown in FIGS. 16-1 to 16-12, the nasal prong assembly 5020 includes a frame contacting portion 5029 that extends from the lower end of the gusset 5022, and is structured to be removably and replaceably attached to a frame 5030 (e.g., see FIGS. 15-1 to 15-12), e.g., push-in type fit, tongue/groove mechanical interlock. As illustrated, the frame channel 5033 of the frame 5030 is provided along a curve (e.g., see FIG. 15-7).

As best shown in FIGS. 16-5 and 16-6, the frame contacting portion 5029 includes an end portion 5029.1 with a sealing lip 5029.2. The end portion 5029.1 is adapted to be easily inserted and retained within the frame channel 5033 (end portion 5029.1 may be tapered to facilitate insertion). The sealing lip 5029.2 provides a seal around the perimeter of the frame channel 5033 and also in conjunction with the bead 5033.1 (see FIGS. 15-9 and 15-12) around the frame channel 5033 retains the nasal prong assembly 5020 onto the frame 5030 during use, as shown in FIG. 17. In addition, such arrangement allows the nasal prong assembly to be easily disassembled from the frame, e.g., for cleaning or replacement.

It is noted that, without the sealing lip 5029.2 or bead 5033.1, the end portion 5029.1 would still be able to provide a seal just by interference of the end portion 5029.1 and the frame. However, the sealing lip and bead arrangement are structured to allow quite a bit of disassembly of the nasal prong assembly from the frame without any increase in leak. For example, FIG. 16-6-1 illustrates the end portion 5029.1 engaged with the frame 5030 (ideal sealed assembly), and FIG. 16-6-2 illustrates the end portion 5029.1 partly disassembled from the frame 5030 but the sealing lip 5029.2 remains engaged with the bead 5033.1 to maintain seal. In an embodiment, this arrangement may allow the sides of the nasal prong assembly to lift out of the frame a little while the external catches 6029.3 remain fully engaged with the frame 6030 (e.g., see FIG. 16-14-1 described below).

In one form the frame bead 5033.1 has a protrusion in the range of 0.4 mm to 1.2 mm, preferably 0.8 mm. The angle of the underside of the bead is preferably in the range 85° to 95°, preferably 90°. Other protrusion values and angles are possible. More than one bead may also be used.

As shown in FIG. 17, the sealing lip 5029.2 seals along the inner wall of the frame channel 5033 closest to the internal volume of the frame 5030. Any air pressure between the end portion 5029.1 and the inner wall of the frame channel 5033 will enhance the seal as the air pressure will force the sealing lip 5029.2 into the inner wall of the frame channel 5033.

In an embodiment, the end portion 5029.1 of the frame contacting portion 5029 may be sufficiently long (e.g., D23 is about 5 mm long) to help locate the end portion 5029.1 in the frame channel 5033 before an insertion force is applied to secure the end portion 5029.1 in position. In addition, the end portion 5029.1 may provide only a slight taper so that the end portion 5029.1 is sufficiently thick to aid insertion and/or to create interference in the channel, increasing retention. The end portion 5029.1 may also be very long, e.g., the whole depth of the frame channel, to increase retention. This length may vary around the perimeter of the end portion, e.g., only at the front and back, between protrusions 5629.1 (described below), etc.

In an embodiment, the frame contacting portion 5029 and frame channel 5033 may provide locating features to properly align the nasal prong assembly 5020 with respect to the frame 5030 and prevent askew assembly. For example, the frame contacting portion 5029 may include one or more corners/protrusions (example described below) that are adapted to fit into corresponding recesses provided in the frame channel 5033. However, other suitable locating arrangements are possible.

FIGS. 16-13-1 to 16-13-7 illustrate a nasal prong assembly 5620 including a frame contacting portion 5629 with one or more protrusions 5629.1 (e.g., four protrusions). When assembled to the frame, the one or more protrusions 5629.1 are adapted to fit into corresponding recesses provided in the frame channel to align the nasal prong assembly 5620 with respect to the frame (e.g., see recesses 5633.1 in frame 5630 in FIGS. 22-1-2 and 22-1-4 described in greater detail below).

FIGS. 16-14-1 to 16-14-3 illustrate a nasal prong assembly 6020 and frame 6030 according to another embodiment of the present invention. In this embodiment, the frame contacting portion 6029 of the nasal prong assembly 6020 includes an external catch or protrusion 6029.3 on opposing sides thereof. When assembled to the frame 6030, the external catches 6029.3 are adapted to interlock with corresponding openings 6033.1 provided in the frame channel 6033 of the frame 6030. Such arrangement is structured to improve retention of the nasal prong assembly 6020 to the frame 6030. In addition, the user can visually confirm that the frame/nasal prong assembly are properly connected. Disassembly is relatively easy because the parts are flexible and soft, e.g., disassemble by peeling/pulling nasal prong assembly out of frame. Also, assembly is relatively easy because the frame is sufficiently rigid, the external catches 6029.3 are sufficiently thick, the frame "window" bar 6033.2 (including thickness t1 plus t2 (see FIG. 16-14-2)) is sufficiently flexible and rigid to stretch and snap into place over the external catch 6029.3 (e.g., see FIGS. 16-14-2, 16-16-1, and 16-16-7). As shown in FIG. 16-16-7, the bar 6033.2 may include a chamfer c to aid insertion/location of the nasal prong assembly.

FIGS. 16-15-1 to 16-15-10 illustrate the nasal prong assembly 6020. As illustrated, the nasal prong assembly 6020 includes the gusset 6022, the pair of nasal prongs 6024 provided to the gusset 6022, and the frame contacting portion 6029 extending from the lower end of the gusset 6022. The frame contacting portion 6029 includes four alignment protrusions 6029.1 and a sealing lip 6029.2 around its perimeter as described above. In addition, opposing sides of the frame contacting portion 6029 include the external catch 6029.3 which protrudes outwardly from the bottom edge.

FIGS. 16-16-1 to 16-16-8 illustrate the frame 6030. As illustrated, the frame 6030 includes a main body 6032 with a channel 6033 to retain the nasal prong assembly 6020 and a tube portion 6035 to retain the elbow. Cylindrical connectors 6034 are provided to respective sides of the main body 6032 for assembling headgear yoke. Yoke to frame assembly and elbow to frame assembly is described in greater detail below.

Opposing sides of the frame channel 6033 include the opening 6033.1, which extends from the channel to the frame exterior. When the frame contacting portion 6029 is inserted and retained within the frame channel 6033, the external catches 6029.3 protrude through respective openings 6033.1 to the frame exterior. As illustrated, recessed portions 6032.1 are provided to the frame exterior adjacent each opening 6033.1, e.g., for tooling. The recessed portions 6032.1 also allow visual feedback of complete assembly and facilitate access to the catches 6029.1 for assembly, e.g., if the catches get stuck.

As shown in FIG. 16-16-7, dimension d is sufficient to allow clearance for the contacting portion 6029 of the nasal prong assembly. This allows the nasal prong assembly to be pushed in far enough for the catch 6029.3 to snap past the window bar 6033.2. For the same reason, the catch 6029.3 has been design with enough clearance between it and the gusset 6022.

FIG. 16-14-3 illustrates a patient interface 6010 including frame 6030, nasal prong assembly 6020, elbow 6040, and headgear including headgear yoke 6055 and straps 6053 (headgear described in greater detail below).

In an embodiment, the nasal prong assembly may be attached to the frame in either of two orientations (180° with respect to one another) and then the headgear must be correctly attached to ensure correct orientation of the nasal prong assembly with respect to the patient's face in use (e.g., headgear and frame/nasal prong assembly may include marking to ensure proper assembly/orientation). However, if the headgear is first attached to the frame, then the nasal prong assembly must be correctly oriented and attached to the frame (same markings apply).

In an alternative embodiment, the patient interface may be structured such that the nasal prong assembly may be attached to the frame in only one way and the headgear may be attached to the frame in only one way in order to ensure correct assembly/orientation (e.g., use mechanical constraints such that left side frame to left side yoke only and right side frame to right side yoke only).

The curved end of the gusset portion (see for example FIGS. 16-4 and 27e) result in the centre of gravity of the nasal mask system being closer to the face of the patient, making the system more stable.

Other gusset to frame mechanisms may be used. See for example the disclosure of International Patent Application PCT/AU03/00458 published as WO 03/090827. Other mechanisms may also be used, for example that used in the cushion-to-frame mechanism of the Fisher & Paykel OPUS. In this case, the orientation of the bead may be perpendicular to the orientation of the illustrated embodiment. In another form, the cushion and frame may be comolded and hence no gusset/cushion to frame mechanism would be required.

FIGS. 16-17 to 16-39 illustrate gusset-to-frame attachment mechanisms according to alternative embodiments of the present invention.

FIG. 16-17 illustrates an arrangement similar to that shown in FIGS. 16-14-1 to 16-16-8, i.e., nasal prong assembly 8020 including external catch 8029.3 adapted to interlock with corresponding opening 8033.1 in frame 8030. In contrast, the frame 8030 includes little to no recessed portion 8032.1 (e.g., unlike elongated recessed portion 6032.1 in FIGS. 16-14-1 to 16-14-3) adjacent each opening 8033.1.

FIGS. 16-18-1 and 16-18-2 illustrate a nasal prong assembly 8120 including two external catches 8129.3 on each opposing side thereof that are adapted to interlock with corresponding openings 8133.1 in the frame 8130. As shown in FIG. 16-18-3, the frame 8130 may include ribs 8136 along the frame channel 8133 (e.g., on opposing ends and sides of the channel), e.g., to add rigidity to the frame.

FIG. 16-19 illustrates a single internal catch arrangement. In the illustrated embodiment, the nasal prong assembly 8220 includes a catch on opposing sides thereof (not visible) that are adapted to interlock with a corresponding internal recess in the frame 8230 (only a protrusion 8238 providing such internal recess being shown).

FIG. 16-20 illustrates the frame contacting portion 8329 of a nasal prong assembly including an end portion 8329.1 with a sealing lip 8329.2. As illustrated, the end portion 8329.1 is sufficiently wide to always provide an interference fit in the channel 8333 of the frame 8330. The bead 8333.1 around the frame channel 8333 also helps retain the nasal prong assembly onto the frame 8330. In addition, the thickness of the outer wall 8339 may be increased to enhance interference with the frame contacting portion. In an embodiment, the frame contacting portion 8329 may provide about 0.4 mm of interference with the channel 8333.

FIG. 16-21 illustrates a frame 8430 in which an inner wall portion 8435 is thickened around its perimeter, e.g., to add rigidity or stiffness. As illustrated, the frame undercut or elbow-to-frame cutout 8437 for retaining the elbow 8440 (e.g., with a snap fit) is maintained where necessary. In an embodiment, a clearance c of about 0.2-0.3 mm may be provided between the elbow 8440 and frame 8430 when connected.

FIG. 16-22 illustrates a frame 8530 in which the snap length of the elbow 8540 is increased to stiffen the inner wall 8535 of the frame 8530. That is, the location of the frame undercut or elbow-to-frame cutout 8537 for retaining the elbow 8540 (e.g., with a snap fit) is moved further into the frame 8530.

FIG. 16-23 illustrates a frame 8630 in which the height of the inner wall 8635 is increased to match the height of the frame contacting portion 8629 of a nasal prong assembly. In an embodiment, the height of the inner wall may be increased in selected portions of the frame, e.g., only at opposing front and back portions of the frame.

FIG. 16-24 illustrates a frame 8730 in which the height of the inner wall 8735 is increased to greater than the height of the frame contacting portion 8729 of a nasal prong assembly. In addition, a hook portion 8739 is provided to the inner wall 8735 that is adapted to lock the frame contacting portion 8729 within the frame channel. In an embodiment, the increased height of the inner wall and hook portion may be provided in selected portions of the frame, e.g., only at opposing front and back portions of the frame.

FIG. 16-25 illustrates a frame contacting portion 8829 of a nasal prong assembly in which the stiffness of the sealing lip 8829.2 is increased by thickening the lip. For example, the sealing lip 8829.2 may be thickened along inner portion A, along upper end portion B, and/or along lower portion C. In another embodiment, the stiffness of the sealing lip 8829.2 may be increased by reducing the length of the lip from the frame contacting portion.

FIG. 16-26 illustrates a frame contacting portion 8929 in which the length is increased and the sealing lip 8929.2 is moved downwards, e.g., to lower the engagement point with the frame 8930. To accommodate such frame contacting portion, the bead 8933.1 around the frame channel 8933 is moved downwards, and any frame ribs within the channel are removed or lowered.

FIG. 16-27 illustrates a frame contacting portion 9029 with two sealing lips 9029.2 in series adapted to interface with respective beads 9033.1 along the inner wall of the frame 9030.

FIG. 16-28 illustrates a frame contacting portion 9129 with a sealing lip 9129.2 adapted to interface with a bead 9133.1 along an inner wall of the frame 9130 and a recessed portion 9129.5 adapted to interface with a bead 9133.2 along an outer wall of the frame 9130. The positioning and/or configuration of each lip, recessed portion, and bead may vary.

For example, in FIG. 16-29, the bead 9133.2 along an outer wall of the frame 9130 may be positioned more downwards within the frame channel and the corresponding recessed portion 9129.5 may be positioned more downwards along the frame contacting portion 9129. In FIG. 16-30, the frame contacting portion 9129 includes a sealing lip 9129.2 adapted to interface with a bead 9133.1 along an inner wall of the frame 9130 and a second sealing lip 9129.3 adapted to interface with a bead 9133.2 along an outer wall of the frame 9130. In FIG. 16-31, the frame contacting portion 9129 includes a sealing lip 9129.2 adapted to interface with an inner wall of the frame 9130 and a recessed portion 9129.5 adapted to interface with a bead 9133.2 along an outer wall of the frame 9130.

FIGS. 16-32 and 16-33 illustrates a frame contacting portion 9229 with a sealing lip 9229.2 adapted to interface with a bead 9233.1 along an inner wall of the frame 9230 and a non-slip interface 9229.5 adapted to interface with an outer wall of the frame 9230. The non-slip interface may be barbed (FIG. 16-32), ribbed (FIG. 16-33), or zig-zag, for example.

In another embodiment, vertical ribs along the channel of the frame and/or along the frame contacting portion of the nasal prong assembly may be used to create interference for securing the frame contacting portion within the frame channel.

FIG. 16-34-1 illustrates a frame contacting portion 9329 in which the flange length or end portion 9329.1 is extended, e.g., to aid insertion into the frame channel, to create interference in the frame channel, to increase retention in the frame channel. This extended length may vary around the perimeter of the frame contacting portion, e.g., to accommodate frame ribs within the frame channel. In an embodiment, the extended end portion 9329.1 may include a second sealing lip 9329.3 as shown in FIG. 16-34-2.

FIG. 16-35 illustrates a frame 9330 including a frame channel 9333 adapted to accommodate a frame contacting portion of a nasal prong assembly. As illustrated, opposing frame ribs A, B, C, and D are provided at the base of the frame channel 9333, e.g., to add rigidity to the frame. In an embodiment, one or more of the opposing frame ribs A, B, C, and D may be removed so that the frame channel can accommodate an extended frame contacting portion 9329 such as that shown in FIG. 16-34-1 or 16-34-2. Alternatively, the frame contacting portion 9329 may be structured to accommodate one or more of the opposing frame ribs A, B, C, and D.

For example, the frame may only include opposing frame ribs A, and the frame contacting portion may be extended around its perimeter except where the opposing frame ribs A would be located. In another embodiment, the frame may only include opposing frame ribs A and C (see FIG. 16-36 showing frame 9330 with frame ribs A and C only), and the frame contacting portion may be extended around its perimeter except where the opposing frame ribs A and C would be located (see FIG. 16-37 showing frame contacting portion 9329 with cutouts or spaces to accommodate frame ribs A and C). In another embodiment, the frame may only include opposing frame ribs A, B, and D (see FIG. 16-38 showing frame 9330 with frame ribs A, B, and D only), and the frame contacting portion may be extended around its perimeter except where the opposing frame ribs A, B, and D would be located. In this embodiment, the outer wall of the frame may be thickened where opposing frame ribs C are removed further down into the frame channel. In yet another embodiment, the frame may not include any frame ribs, and the frame contacting portion may be extended around its entire perimeter.

FIG. 16-39 illustrates a frame contacting portion 9429 of a nasal prong assembly in which the stiffness of the sealing lip 9429.2 is increased by filling a gap with silicone 9429.8.
Assembly of Prongs and Gusset As shown in FIGS. 16-1 to 16-12, the nasal prong assembly 5020 (e.g., constructed of silicone (e.g., 40 shore A silicone)) includes a gusset 5022 and a pair of nasal prongs 5024 provided to the gusset 5022. The gusset 5022 provides a trampoline-like base which allows movement or flexibility to isolate external forces from the seal (e.g., frame movement does not affect nasal prong seal) and enhance stability, seal, and comfort, as described.

In an embodiment, one or more portions of the exterior surface of the nasal prong assembly 5020 (e.g., the entire exterior surface) may have a frosted or fine surface finish (e.g., sand blasted) in order to reduce dust collection.

In an embodiment of the nasal prong assembly (see FIGS. 16-1 to 16-12), D1 may be about 25-35 mm, e.g., 32.3 mm, D2 may be about 15-25 mm, e.g., 20.6 mm, D3 may be about 1-2 mm, e.g., 1.5 mm, D4 may be about 25-35°, e.g., 30°, D5 may be about 10-20 mm, e.g., 13.63 mm, D6 may be about 20-30°, e.g., 27°, D7 may be about 5-10 mm, e.g., 7.98 mm, D8 may be about 5-15 mm, e.g., 10.29 mm, D9 may be about 15-25 mm, e.g., 20.1 mm, D10 may be about 5-10 mm, e.g., 6.99 mm, D11 may be about 3-8 mm, e.g., 4.63 mm, D12 may be about 20-30 mm, e.g., 25.1 mm, D13 may be about 5-10 mm, e.g., 8.87 mm, D14 may be about 5-15 mm, e.g., 11.14 mm, D15 may be about 2-8 mm, e.g., 5.1 mm, D16 may be about 0.5-1 mm, e.g., 0.75 mm, D17 may be about 0.5-1 mm, e.g., 0.75 mm, D18 may be about 65-75°, e.g., 72.5°, D19 may be about 50-60 mm, e.g., 54.37 mm, and D20 may be about 25-35 mm, e.g., 28.6 mm, D21 may be about 2-3 mm, e.g., 2.2 mm, D22 may be about 2-4 mm, e.g., 3 mm, and D23 may be about 4-5 mm, e.g., 4.8 mm Although specific dimensions and ranges are indicated, it is to be understood that these dimensions and ranges are merely exemplary and other dimensions and ranges are possible depending on application. For example, the exemplary dimensions may vary by 10-20% or more or less depending on application.

In an embodiment, the nasal prong assembly may be provided in multiple sizes, e.g., small, medium, and large.

2.3 Frame

As shown in FIGS. 15-1 to 15-12, the frame 5030 includes a main body 5032 and tubular connectors 5034 provided to respective sides of the main body 5032. As illustrated, the frame 5030 provides a relatively a narrow width across the patient's face, e.g., about 45-55 mm (e.g., 48 or 49 mm).

Referring to FIGS. 15-8 and 15-10, the main body 5032 includes a channel 5033 structured to retain the nasal prong assembly 5020 and an open-ended tube portion 5035 structured to retain the elbow 5040. The open-ended tube portion 5035 protrudes from a frame opening rearwards into an internal volume of the frame. Attachment of the elbow 5040 to the frame 5030 is described in greater detail below.

Each connector 5034 of the frame includes a cavity 5036 having structure to retain respective headgear yoke 5055 of the headgear 5050. In addition, the exterior surface of each connector 5034 includes one or more locking bumps 5038 (e.g., three locking bumps or six locking bumps) adapted to engage ratchet teeth of respective yoke 5055. Attachment of the headgear yoke 5055 to the frame 5030 is described in greater detail below.

The frame 5030 is constructed of a relatively semi-rigid or soft plastic material (e.g., hard silicone (e.g., 30-80 shore A silicone, preferably 70 shore A silicone, or about 60 or 80 shore A silicone), TPE, thermoplastic polyurethanes). As a result, the frame 5030 is relatively softer and more flexible than the relatively hard plastic material of the elbow 5040 and the yokes 5055 of the headgear 5050. The flexibility of the frame may be adjusted, e.g., frame may have different degrees of flexibility. However, it should be appreciated that the frame may be constructed of other suitable materials, e.g., harder plastic material. In addition, the frame may have thicker wall section to add hardness. For example, the hardness of the frame material could extend to the Shore D hardness scale in the range of 45 to 85, or on the Rockwell R scale in the range of 50 to 100. It could be made from rubbers, polyurethanes, polyesters, PTFE, polypropylenes and other plastics.

A frame constructed of silicone provides an arrangement that is easier to seal (e.g., with the elbow), and provides no squeak in use (e.g., when elbow/yokes rotated with respect to frame), without requiring an additional part and with reduced leak (e.g., effectively zero leak).

In an embodiment of the frame (see FIGS. 15-1 to 15-12), D1 may be about 25-35 mm, e.g., 31.7 mm, D2 may be about 15-25 mm, e.g., 19.7 mm, D3 may be about 45-55 mm, e.g., 48 mm, D4 may be about 35-45 mm, e.g., 39 mm, D5 may be about 25-35 mm, e.g., 28 mm, D6 may be about 20-30 mm, e.g., 26.76 mm, D7 may be about 10-20 mm, e.g., 16.9 mm, and D8 may be about 15-25 mm, e.g., 21.06 mm Although specific dimensions and ranges are indicated, it is to be understood that these dimensions and ranges are merely exemplary and other dimensions and ranges are possible depending on application. For example, the exemplary dimensions may vary by 10-20% or more or less depending on application.

Flexibility of the frame allows a given mask system to accommodate a range of different facial geometries, for example ranging from narrower, pointed faces (the so-called "crocodile" or "alligator" shape) to the wider, flatter shape (the so-called "panda" shape). The soft frame is also aesthetically nicer and soft to touch. The outside surface finish conceals internal details (ribs) and reduces dust. A surface finish may be applied to inside surfaces also.

2.4 Adjustment

Naso-Labial Angular Adjustment/Yoke to Frame

2.4.1 Headgear/Yoke to Frame Interface

In an illustrated embodiment, headgear is attached to the frame 5030 via headgear yoke 5055 (e.g., see FIGS. 19-1 to 19-5). The headgear yoke 5055 includes a yoke to frame interface 5085 that is structured to provide easy assembly to and disassembly from the frame 5030 (e.g., clear and intuitive assembly, tactile feedback of engagement, easy disassembly for cleaning), retain the frame 5030 during use (e.g., prevent accidental disassembly during use), provide rotation relative to the frame 5030, and provide a friction element to provide sufficient rotational torque (e.g., to reduce tube drag, provide tactile/audible feedback). In addition, rotation of the frame relative to the yokes does not effect impedance.

The frame and nasal prong assembly attached thereto may be rotated with respect to the yokes positioned on the patient's head to allow adjustment to suit the nasolabial angle for a large range of patients. In addition, such adjustment allows movement of the nasal prongs to avoid air jetting. Because the rotation point RP (see FIG. 13-2) of the yoke to frame interface is spaced sufficiently outwardly from the patient's nose (e.g., with respect to the yoke 55/frame interface described above), a degree of rotation of the frame may not effect an equal degree of rotation of the nasal prongs, e.g., not 1:1 rotation. For example, a 5° rotation of the frame may effect a 2° rotation of the nasal prongs.

As best shown in FIGS. 19-5 to 19-7, the yoke to frame interface 5085 includes a rear wall 5085.1, an annular side wall 5085.2, and a central hub 5085.3. The inner edge of the side wall 5085.2 includes a plurality of ratchet teeth 5085.4 to provide friction and tactile feedback with respect to the frame. The central hub 5085.3 is tubular with its interior cored out/vented. The central hub 5085.3 provides snap fingers 5085.5 to retain the interface to the frame 5030 (e.g., three snap fingers), bearing surfaces 5085.6, and a tip extension 5085.7. Supporting ribs 5085.8 extend between the central hub 5085.3 and the side wall 5085.2. In addition, windows 5085.9 are provided in the rear wall 5085.1 to allow molding of the snap fingers 5085.5.

2.4.2 Frame Attachment

As shown in FIG. 19-8, the yoke to frame interface 5085 is structured to attach to a respective connector 5034 of the frame 5030. Each connector 5034 of the frame includes a cavity 5036 having structure to retain respective headgear yoke 5055, i.e., an annular engagement lip 5037.1, yoke snap clearance 5037.2 and yoke tip extension hole 5037.3 to accommodate the yoke to frame interface 5085, and a bearing surface 5037.4. In addition, the exterior surface of each connector 5034 includes one or more locking bumps 5038 (e.g., three locking bumps) adapted to engage the ratchet teeth 5085.4 of the yoke to frame interface 5085.

FIGS. 19-9-1 to 19-9-6 illustrate attachment of the yoke to frame interface 5085 to a respective connector 5034 of the frame 5030. In FIG. 19-9-1, the tip extension 5085.7 of the yoke to frame interface is inserted past the engagement lip 5037.1 on the frame to begin alignment. In FIG. 19-9-2, the yoke snap fingers 5085.5 and frame engagement lip 5037.1 contact slightly before contact of the frame bumps 5038 and yoke ratchet teeth 5085.4, and the connector 5034 may pull in a little (as indicated by the arrows). In FIG. 19-9-3, as the yoke is inserted further, the frame engagement lip 5037.1 is displaced down and the connector 5034 expands (as indicated by the arrows). Also, the ratchet teeth 5084.4 engage with the frame bumps 5038. In FIG. 19-9-4, the frame engagement lip 5037.1 is folded down almost flat inside the yoke snap clearance 5037.2, and expansion of the frame connector 5034 is limited by the surrounding yoke side wall 5085.2 (as indicated by the arrows). In FIG. 19-9-5, the front face of the yoke snap fingers 5085.5 and tip extension 5085.7 bottom out inside the yoke tip extension hole 5037.3 (e.g., yoke compressed inwards about 1.6 mm beyond nominal position), which provides sufficient space to allow the frame engagement lip 5037.1 to relax or resiliently recover to its original position (as indicated by the arrows). That is, the yoke snap clearance 5037.2 and the yoke tip extension hole 5037.2 is sufficiently long to provide sufficient space for the frame engagement lip 5037.1 to recover to its nominal position following a natural arc, e.g., resiliently pivot back to its nominal position. In FIG. 19-9-6, the yoke to frame interface 5085 springs back out to a nominal position when the engagement lip 5037.1 relaxes. As shown in FIG. 19-10, a clearance Cl of at least about 0.5 mm is provided between an outer edge of the frame connector 5034 and the yoke to frame interface 5085.

The snap fingers 5085.5 and tip extension 5085.7 are structured to retain the yoke to the frame, e.g., axial retention and lever retention. In an embodiment, as shown in FIGS. 19-11 and 19-12, the tip extension 5085.7 has a length D1 of about 2-4 mm, e.g., 3 mm, each snap finger 5085.5 has a diameter D2 of about 6-8 mm, e.g., 7 mm, each snap finger 5085.5 has width D3 of about 2-5 mm, e.g., 4 mm, and each snap finger 5085.5 provides an engagement face of about 5-15°, e.g., 10°. Although specific dimensions and ranges are indicated, it is to be understood that these dimensions and ranges are merely exemplary and other dimensions and ranges are possible depending on application. For example, the exemplary dimensions may vary by 10-20% or more or less depending on application.

In an embodiment, the yoke 5055 may be pivoted with respect to the frame 5030 without disassembly by an angle D1 of about 5-15°, e.g., due to lever retention and/or frame flexibility.

As shown in FIG. 19-14, the locking bumps 5038 of the frame 5030 and the ratchet teeth 5085.4 of the yoke to frame interface 5085 provide a ratcheting arrangement to lock the frame/nasal prong assembly in an operative position. In addition, the ratcheting arrangement provides a rotation and sufficient torque arrangement to resist tube drag, and prevent the nasal prongs from being rotated out of the patient's nose, rotate relative to the frame and allow adjustment to suit nasolabial angle, and provide tactile feedback to the user with adjustments.

For example, such arrangement allows 360° rotation of the yoke with respect to the frame, provides position locks at 15° increments, and the soft to hard interface (relatively soft frame engages relatively hard yoke) provides tactile feedback to the user with each adjustment. However, the ratchet teeth/locking bumps may be structured to provide other suitable incremental position locks.

The size of the ratchet teeth 5085.4 and locking bumps 5038 may be determined by fitting a maximum number of increments (e.g., 6 to 72 teeth at 60° to 5° increments, e.g., 24 teeth at 15° increments) around a minimum diameter. In an embodiment, the length of tooth engagement (i.e., contact length between locking bump and ratchet tooth) may be determined by the shallowest point of yoke contacting frame on assembly (e.g., about 2 mm).

FIGS. 19-15-1 to 19-15-5 illustrate rotation of the yoke 5055 with respect to the frame 5030, e.g., angle adjustment. FIGS. 19-15-1 and 19-15-2 illustrate a nominal position of the yoke 5044 and frame 5030. In FIG. 19-15-3, the yoke 5055 is rotated about 3.25° from nominal, and the frame locking bumps 5038 are deformed sideways and compressed inwards. In FIG. 19-15-4, the yoke 5055 is rotated about 10.75° from nominal, and the frame locking bumps 5038 are significantly deformed flat by the respective ratchet tooth 5085.4. In FIG. 19-15-5, the yoke 5055 is rotated about 15° from nominal, and the frame locking bumps 5038 spring back to original form in the next ratchet tooth 5085.4.

It should be appreciated that the torque (e.g., to resist tube drag) may be adjusted, e.g., torque increased by adding more locking bumps 5038 to frame connectors 5034. Also, instead of a ratcheting type arrangement, other suitable torque arrangements may be provided, e.g., friction-type, magnetic, etc.

In alternative embodiment, the one or more locking bumps of the frame may be separated by truncated or squared-off teeth to allow for easier rotation of the yoke with respect to the frame. For example, FIGS. 22-1-1 to 22-1-8 illustrate a frame 5630 and each connector 5634 of the frame 5630 includes locking bumps 5638 (e.g., six locking bumps) separated by truncated teeth 5639 (e.g., see FIG. 22-1-7).

The indents 5639.1 between the locking bumps and the truncated teeth make the locking bumps 5638 longer, meaning that the stress and thus wear on these elements is lower. In addition, as shown in FIGS. 22-1-9 and 22-1-10, as the yoke 5655 rotates relative to the frame 5630, each locking bump 5638 is displaced sideways. The indent 5639.1 defines a spring relief feature that provides clearance allowing the locking bump 5638 to completely flex over on itself. This reduces wear on the semi-rigid locking bump 5638 over time. The number of locking bumps 5638 may be adjusted for desired torque. The cavity 5636 of the connector 5634 may be cut out (e.g., by 1 mm) to allow for a snap lock with the central hub 5685.1 of the headgear yoke 5655 for tactile connectivity. Attachment of the headgear yoke 5655 to the frame 5630 is described in greater detail below.

As shown in FIGS. 22-2 and 22-3, the first end portion 5655(1) of each headgear yoke 5655 includes a support arm 5680, a yoke to frame interface 5685 provided to an end of the support arm 5680 and adapted to engage a respective connector 5634 of the frame 5630, and a cheek support 5684 (also referred to as a stability arm).

The yoke to frame interface 5685 is structured to provide easy assembly to and disassembly from the frame 5630 (e.g., clear and intuitive assembly, tactile feedback of engagement, easy disassembly for cleaning), retain the frame 5630 during use (e.g., prevent accidental disassembly during use), provide rotation relative to the frame 5630, and provide a friction element to provide sufficient rotational torque (e.g., to reduce tube drag, provide tactile/audible feedback). Torque is also provided by interference on the "shaft" between the yoke and the frame, not just the ratchet teeth. For example, FIGS. 22-16-1 and 22-16-2 illustrate an embodiment in which the yoke 5655 is structured to have an interference fit on the shaft 5634.1 of the frame 5630 to provide torque additional to the ratchet teeth. In an embodiment, the interference fit may be about 0.4 mm on diameter on the frame shaft, e.g., each d about 0.2 mm in FIG. 22-16-2.

The yoke connection involved in the yoke to frame interface 5685 consists primarily of an annular side wall 5685.2, rear wall 5685.3 and central hub 5685.1 (e.g., see FIGS. 22-4 to 22-7-8).

The inner radius of side wall 5685.2 has multiple ratchet teeth 5685.4 (e.g., 3, 4, 5, or more teeth) to provide friction while allowing for some rotation of the frame with respect to the yoke (e.g., see FIGS. 22-6 and 22-7-8). It should be appreciated that there can be multiple embodiments of ratchet teeth/locking bumps on the yoke/frame, e.g., 24 teeth/bumps on frame or yoke adapted to engage 3 or more teeth/bumps on the other of the frame or yoke. The rotation means the headgear can adapt more readily to the movement of the patient during sleep. Additionally, on the interfacing side of the yoke (i.e., the side of the yoke that sits closest to the patient's skin), the side wall 5685.2 extends radially inwards (e.g., by 3 mm) to form a generally C-shaped engagement lip 5685.5 (e.g., see FIGS. 22-4, 22-6, and 22-7-6). This is to allow for a locked horizontally sliding connection with the frame connector 5634 (direction of sliding connection shown in FIG. 22-2) that inhibits lateral movement of the yoke and frame so as to prevent the accidental disassembly of the yoke to frame interface 5685 during use. The tips 5685.5(1) of the C-shaped engagement lip 5685.5 are convexly curved to provide a lead-in for the frame connector shaft or base 5634.1, thereby enabling alignment during assembly (e.g., see FIGS. 22-4 and 22-7-6). The width between these two tips 5685.5(1) can be adjusted to vary the force required to assemble to frame and yoke (e.g., if the force for assembly needed to be adjusted downwards, the distance between the tips 5685.5(1) could be increased).

The central hub 5685.1 (e.g., shown in FIGS. 22-4 to 22-6) is generally circular and may have a hollow core. The central hub 5685.1 locks with the cavity 5636 of the frame connector 5634 (e.g., see FIG. 22-12). This allows for greater stability when slidingly connected with the frame and also aids disconnection of the interlocking pieces. When the frame connector 5634 engages with the central hub 5685.1, there is a snapping sound that aims to provide tactile feedback to the user that the parts are assembled correctly. The central hub 5685.1 is connected to the rear wall 5685.3 via an arm 5685.6 (e.g., see FIGS. 22-4). The posterior side of the arm 5685.6 can have multiple ribs 5685.6(1) (e.g., 2 or 3 ribs) as shown in FIG. 22-4, that are elevated from the rear wall 5685.3 by, e.g., 2 mm Ribs 5685.6(1) act to guide the frame into the yoke and thus ensure correct assembly of the parts.

The rear wall 5685.3 has a window 5685.7 to allow for unimpeded rotation of the frame with respect to the yoke (e.g., see FIGS. 22-5 and 22-6). It also enables the patient to visually assess if the assembly is correct. In addition, the window 5685.7 is provided to mold the ratchet teeth.

FIGS. 22-8 to 22-16 illustrate the attachment of the yoke to frame interface 5685 to a respective connector 5634 of the frame 5630. In FIGS. 22-8 and 22-9, the frame connector base 5634.1 is inserted past the tips 5685.5(1) of engagement lip 5685.5 on the yoke to begin alignment. Ribs 5685.6(1) are also guiding the frame connector 5634 in position on the anterior side of the connector. FIG. 22-9 demonstrates the interaction of the central hub 5685.1 with the anterior surface of the frame connector 5634 when the parts are not fully engaged. The central hub 5685.1 is flexed outwards about arm 5685.6. FIG. 22-10 is a photograph of this arrangement.

In FIGS. 22-11 and 22-12, the frame connector base 5634.1 has passed through the tips 5685.5(1) of engagement lip 5685.5 on the yoke. The central hub 5685.1 has engaged with cavity 5636 and snapped back from its flexed position to its original position (as shown in FIG. 22-12). This creates a tactile connection that enables patients to hear when the assembly is correctly joined. Once the connector 5634 has slotted into the yoke, the locking bumps 5638 engage with the ratchet teeth 5685.4 (e.g., demonstrated by FIGS. 22-14 and 22-15). The cavity 5636 of the frame connector 5634 includes a yoke snap clearance 5636.1 that provides sufficient space for the central hub 5685.1 to relax or resiliently recover to its original position. Similar to window 5685.7, the yoke snap clearance 5636.1 is designed to ensure that there is no impedance on the rotational motion of the yoke to frame interface 5685 (see FIG. 22-12).

FIGS. 22-13 and 22-16 are photographs that show the fully assembled frame 5630 and yoke 5655. Also, FIGS. 22-17-1 and 22-17-2 illustrate the frame 5630 being rotated relative to the yoke 5655.

FIGS. 22-18-1 to 22-18-3 are various views of a mold M for molding the frame 5630 according to an embodiment of the present invention. As illustrated, the mold M may include upper and lower molds UM, LM for molding the main body of the frame 5630 and side molds SM for molding the frame connectors 5634 of the frame 5630. As illustrated, the frame 5630 may include draft features (angled surfaces) to facilitate removal from the mold M.

FIGS. 22-19-1 to 22-19-7 illustrate the headgear yoke 5655 attached to a headgear strap 5653, e.g., via stitching, according to an embodiment of the present invention. FIGS. 22-20-1 to 22-20-5 illustrate a fully assembled patient interface 5610 according to an embodiment of the present invention. As illustrated, the patient interface 5610 includes a frame 5630 (as described in reference to FIGS. 22-1-1 to 22-1-8), a nasal prong assembly 5620 (as described in reference to FIGS. 16-13-1 to 16-13-7), an elbow 5740, short tube 5770, and swivel 5790 (as described in reference to FIGS. 18-8-1 to 18-8-7 and FIGS. 20-5-1 to 20-5-6), headgear including headgear yoke 5655 and straps 5653 (as described in reference to FIGS. 22-2 to 22-19-7), and tube retainer 5561 and headgear buckle 5560 (as described in reference to FIGS. 5-42-1 to 5-42-6 and FIGS. 5-43-1 to 5-43-7).

FIGS. 22-20-6 and 22-20-7 illustrate the rear or back strap 5657 of the patient interface 5610. As illustrated, the back strap 5657 includes thinner end portions 5657(1) (e.g., 19 mm width) adapted to engage a respective slotted connector portion of the headgear yoke 5655 and a wider intermediate portion 5657(2) (e.g., 38 mm width). The wider intermediate portion 5657(2) includes a slot 5658 which spreads the intermediate portion apart so that it can act like two smaller width straps (e.g., 2×19 mm straps), e.g., slot allows the intermediate portion to conform to the back of the patient's head in use. Stress release holes 5659 are provided on each of the slot 5658, e.g., so the back strap does not tear. In an embodiment, the slot 5658 is formed by a relatively straight cut between the holes 5659. Also, the back strap 5657 may be constructed of a Breathoprene headgear material including an un-broken loop (UBL) side 5660(1) and a Lycra side 5660(2).

FIGS. 22-24 and 22-25 illustrate a yoke to frame attachment mechanism according to another embodiment of the present invention. In this embodiment, at least one yoke and optimally both yokes 7255 are engaged with the frame 7230 via a ball and socket joint 7285.

The ball and socket joint 7285 allows greater axial rotational and some lateral rotation. A high degree of rotation at the yoke to frame interface allows the respiratory mask to better accommodate a larger range of face shapes and sizes. Also, infinite adjustment allows the patient to have a larger range of motion when using the respiratory mask, while maintaining a comfortable and effective seal. The ball and socket joint 7285 is a familiar mechanism and visually simple to assemble so therefore more likely to be utilized effectively by patients.

In the illustrated embodiment, the socket 7210 is provided to the yoke 7255 (e.g., integrally formed in one piece therewith) and the ball 7240 is provided to the frame 7230 (e.g., integrally formed in one piece therewith). However, it should be appreciated that the opposite arrangement is possible, i.e., socket on frame and ball on yoke.

As illustrated, the socket 7210 on yoke 7255 is a cavity with a generally rounded profile. In an embodiment, the socket 7210 is in the shape of a hemisphere. In another embodiment, the socket 7210 is part of a hemisphere. The socket 7210 may have a lip 7215 on its outer edge as shown in FIG. 22-25, which lip 7215 aids in securely fastening the ball 7240 to the socket 7210. The lip 7215 also limits the movement of the frame 7230 beyond desirable limits so that the respiratory mask is able to maintain its seal. In an alternative embodiment, the socket 7210 may include a lead-in to facilitate connection of the joint.

In an embodiment, the ball 7240 on frame 7230 may be generally spherical, elliptical, or any other rounded shape. In another embodiment, the ball 7240 may be part of a sphere or any rounded shape, e.g., a hemisphere. In yet another embodiment, the ball 7240 may be hollow or partly hollow.

In the illustrated embodiment, the ball 7240 may be engaged with the socket 7210 by a push fit. In an alternative embodiment, the ball 7240 may be engaged with the socket 7210 by a sliding connection. In an embodiment, the ball 7240 has the same or larger diameter D than that of socket 7210 for an interference fit (e.g., FIG. 22-25 illustrates an embodiment where ball 7240 and socket 7210 have the same diameter D).

In another alternative embodiment, the frame and yoke may be integrally formed in one piece. In an embodiment, the frame and yoke may include different colors or transparencies with respect to one another.

2.4.3 Yoke to Frame Rotation Indicator

In an embodiment, rotation indicators may be provided on the frame and/or yokes to indicate to the user that the frame can rotate relative to the yokes. In addition, the rotation indicators may function as position markings to indicate the frame's position with respect to the yokes, e.g., used as a reference for preferred naso-labial rotation angle.

For example, a series of markings (e.g., dots, arrows, combination of dots/arrows, etc.) may be provided on the frame that align with a position mark (e.g., line, dot, arrow, etc.) provided on the yokes to indicate the frame's position.

In FIGS. 19-21-1 to 19-21-3, the frame 5030 includes a series of dots 5002 with a center one of the dots (having a larger size) aligned with a horizontal axis of the frame 5030 (e.g., see FIGS. 19-21-3). In this embodiment, the dots 5002 are provided on only one side of the frame 5030. The adjacent yoke 5055 includes a line 5004 to align with a selected one of the dots 5002 on the frame 5030.

In FIGS. 19-22-1 to 19-22-4, the frame 5030 includes a series of dots 5002 with a center one of the dots (having a larger size) offset from a horizontal axis of the frame (e.g., see FIG. 19-22-4). In this embodiment, the dots 5002 are provided on both sides of the frame 5030. The adjacent yoke 5055 includes a line 5004 to align with a selected one of the dots 5002 on the frame 5030. The intent of off-center dots in FIGS. 19-22-1 to 19-22-4 is that the nominal yoke position is indicated by the large, center one of the dots.

In FIGS. 19-23-1 to 19-23-4, the frame 5030 includes a dot 5002(1) aligned with a horizontal axis of the frame (e.g., see FIG. 19-23-4) and arrows 5002(2) provided on each side of the dot 5002(1). In this embodiment, the dot/arrows are provided on only one side of the frame 5030. The adjacent yoke 5055 includes an arrow 5004 to align with a selected dot/arrow on the frame 5030.

In each embodiment, the markings on the frame and yoke may be printed, molded, etched, polished, etc. Also, the markings on the frame and/or yoke may include other configurations (e.g., color-coded, numbered, varying sizes, bands with ascending heights, etc.). Markings may be provided on one or both sides of the frame, and markings may be provided on one or both of the yokes. In addition, any suitable number of markings may be provided on the frame and yoke, and the markings may have any suitable spacing.

2.4.4 Yoke to Nasal Prong Assembly Rotation Indicator

In an embodiment, rotation indicators may be provided on the nasal prong assembly and/or yokes to indicate to the user that the nasal prong assembly/frame can rotate relative to the yokes. In addition, the rotation indicators may function as position markings to indicate the nasal prong assembly's position with respect to the yokes, e.g., used as a reference for preferred naso-labial rotation angle.

For example, a series of markings (e.g., dots, arrows, combination of dots/arrows, etc.) may be provided on the nasal prong assembly that align with a position mark (e.g., line, dot, arrow, etc.) provided on the yokes to indicate the nasal prong assembly's position.

As best shown in FIGS. 16-15-4 to 16-15-6, the gusset 6022 of the nasal prong assembly 6020 includes a series of dots 6025, e.g., 2, 3, 4 or more dots. The dots may vary in size, e.g., a center one of the dots (having a larger size) aligned with a horizontal axis of the nasal prong assembly. In this embodiment, the dots 6025 are provided on only one side of the nasal prong assembly 6020. As best shown in FIG. 22-23-7, the adjacent yoke 6555 includes a protrusion or dot 6504 (may also be in the form of a line or other suitable alignment indicator) to align with a selected one of the dots 6025 on the cushion 6020.

Similar to the concepts shown in FIGS. 19-21-1 to 19-23-3, the dots 6025 featured on the nasal prong assembly 6020 can align with the dot 6504 on yoke 6555 to indicate the position of the nasal prong assembly with respect to the yoke. This re-positions the patient interface so that it can have the same settings each time. In an embodiment, the alignment dot or marker on the yoke may be positioned at any suitable location along the arm of the yoke, e.g., closer to the yoke's interface with the frame. Also, in an embodiment, as the yoke is rotated relative to the nasal prong assembly, the yoke may cover one or more of the dots 6025 (i.e., instead of alignment markers on the nasal prong assembly and yoke meeting, one may adjust the system until a certain number of dots are visible, e.g., only 1 or 2 alignment dots are visible).

Another advantage of this alignment concept is it indicates to the user that the nasal prong assembly should be positioned in the frame in such a way that the adjacent yoke 6555 with dot 6504 is aligned with dots 6025. This therefore indicates that the nasal prong assembly will be oriented so that it interfaces with the nares of the patient correctly, i.e., nasal prong assembly placed in the frame in the right direction. For example, if the patient interface was completely disassembled, it is obvious that the headgear straps are to be placed along the side of the face with the yokes facing outwards. The user would then proceed to connect the frame to the yokes (which can be put in either way and still work). The alignment dots on the nasal prong assembly can then be positioned so that they are on the side of the yoke with the alignment dot. This means the nasal prong assembly is in the right direction, i.e., with the largest side of the gusset touching the face of the user and the company logo facing outwards. Should the user attempt to align the nasal prong assembly in such a way that the alignment dots on the nasal prong assembly are over the yoke that does not have an alignment dot, the nasal prong assembly will be facing the wrong way, i.e., company logo touching the face of the user.

In each embodiment, the markings on the nasal prong assembly and yoke may be printed, molded, etched, polished, etc. Also, the markings on the nasal prong assembly and/or yoke may include other configurations (e.g., color-coded, numbered, varying sizes, bands with ascending heights, etc.). Markings may be provided on one or both sides of the nasal prong assembly, and markings may be provided on one or both of the yokes. In addition, any suitable number of markings may be provided on the nasal prong assembly and yoke, and the markings may have any suitable spacing.

First End Portion, First Embodiment

FIGS. 6-1 to 6-4 illustrate an embodiment of headgear yoke 55. As illustrated, the first end portion 55(1) includes a yoke ring 56 (also referred to as a retaining member or connector) that is adapted to engage a respective end or connector portion of the frame of the nasal prong assembly 20 (e.g., see FIGS. 2-1 and 2-2). In addition, a seal ring or seal portion 58 (see FIG. 1-1) is provided to the yoke ring 56 and is adapted to sealingly engage a plug or elbow. Further details of such yoke ring 56 and seal ring 58 (and attachment to a plug or elbow) are described in U.S. Patent Application Publication Nos. 2004-0226566, 2006-0137690, and 2005-0241644, each of which are incorporate herein by reference in its entirety.

First End Portion Alternative Embodiment

In the embodiment of headgear yoke 5055 shown in FIGS. 19-1 to 19-5, the first end portion 5055(1) includes a support arm 5080, a yoke to frame interface 5085 provided to an end of the support arm 5080 and adapted to engage a respective connector 5034 of the frame 5030, and a cheek support 5084 (also referred to as a stability arm).

Second End Portion, First Embodiment

As shown in FIGS. 1-1, 6-1 to 6-2, and 6-5 for the embodiment of headgear yoke 55, the second end portion 55(2) provides a slotted connector portion including a slot 65 that defines a cross-bar 66 that is adapted to engage a respective end of the rear strap 57. Specifically, a respective end 57(1) of the rear strap 57 may be wrapped around the cross-bar 66 of the yoke, in a known manner. The free end of the rear strap 57 may be tapered (e.g., to aid threading through the slot 65) and secured to the remainder of the strap by a hook and look arrangement, e.g., Velcro®.

The use of Velcro attachment at the headgear yokes eliminates the use of a rear buckle to adjust the rear strap 57. This arrangement improves comfort by removing discomfort and irritation caused by the patient lying on a rear buckle in use.

Second End Portion Alternative Embodiment

As shown in FIGS. 13-1 to 13-4 and 19-1 to 19-4 for the embodiment of headgear yoke 5055, the second end portion 5055(2) provides a slotted connector portion including a slot 5065 that defines a cross-bar 5066 that is adapted to engage a respective end of the rear strap 5057. Specifically, a respective end 5057(1) of the rear strap 5057 may be wrapped around the cross-bar 5066 of the yoke, in a known manner. The free end of the rear strap 5057 may be tapered and/or locally thinned (e.g., to aid threading through the slot 5065) and secured to the remainder of the strap by a hook and look arrangement, e.g., Velcro®.

In an embodiment, the slot may have a width of about 3-5 mm, e.g., 4 mm, and a length of about 15-25 mm, e.g., 21 mm. However, these dimensions and ranges are merely exemplary and other dimensions and ranges are possible depending on application.

Adjustment of Strap Length

Headgear Buckle

As shown in FIG. 1-1, the headgear buckle 60 is adapted to be centrally located on the patient's head to allow symmetrical adjustment of the headgear 50, e.g., adjustment of strap tension can be accomplished by pulling loose tabs on the top of the patient's head in opposite directions. Specifically, the headgear buckle 60 includes a first locking portion 60(1) and a second locking portion 60(2). The first locking portion 60(1) is adapted to be removably and adjustably coupled with one of the upper strap portions 53(1) and the second locking portion 60(2) is adapted to be removably and adjustably coupled with the other of the upper strap portions 53(1). Each of the upper strap portions 53(1) may be wrapped around the cross-bar of the associated locking portion of the buckle, in a known manner. The free ends of the upper strap portions 53(1) may be tapered (e.g., to aid threading through respective locking portions) and secured to the remainder of the strap by a hook and look arrangement, e.g., Velcro®.

The headgear buckle 60 joins the headgear straps and yokes to form the headgear, allows fine and infinite adjustments of the headgear straps, allows quick and easy adjustments and loosening of the headgear straps, and/or allows the straps to pull symmetrically against the head to minimize dislodgement of the nasal prong assembly during adjustment.

As noted above, the rear strap eliminates the use of a rear buckle and uses Velcro fasteners, e.g., to improve comfort. Alternative embodiments to eliminate or reduce discomfort that may be caused by a headgear buckle include: using an isolated highly elastic section that allows the user to easily stretch the headgear over the head to remove/replace it; reducing the overall height of the buckle (e.g., low profile buckle); adding padding to the buckle; allowing the user to customize the position of the buckle so that it can be located on an area of the head that will not cause irritation to the user (e.g., positioned along side regions of the head rather than at the back); and/or introducing a textile buckle that provides the same function as a plastic buckle; introducing a headgear material that provides the same function as a buckle.

Soft and Flexible Link

In an alternative embodiment, the headgear buckle may be in the form of a soft and flexible link (also referred to as a linking element, link element or link member). Such a link is disclosed in Australian Provisional Application No. AU 2008900891, filed Feb. 25, 2008, which is incorporated herein by reference in its entirety. The link provides a more comfortable linking element for headgear straps and has sufficient strength in tension to secure a mask to a patient's face under pressure.

FIGS. 5-44-1 to 5-44-5 are respectively side, top, longitudinal cross-section, bottom, and isometric views of a link 6134 according to an embodiment of the invention.

In an embodiment of the link (see FIGS. 5-44-1 to 5-44-5), D1 may be about 0.5-1.5 mm, e.g., 1.0 mm, D2 may be about 1-3 mm, e.g., 2.0 mm, D3 may be about 45-50 mm, e.g., 48 mm, D4 may be about 15-25 mm, e.g., 19 mm, D5 may be about 20-25 mm, e.g., 23.0 mm, D6 may be about 2-4 mm, e.g., 3.0 mm, D7 may be about 17-22 mm, e.g., 19.5 mm, and D8 may be about 2-4 mm, e.g., 3.0 mm Although specific dimensions and ranges are indicated, it is to be understood that these dimensions and ranges are merely exemplary and other dimensions and ranges are possible depending on application. For example, the exemplary dimensions may vary by 10-20% or more or less depending on application.

The illustrated link 6134 is formed of a relatively soft and flexible material, preferably an elastomer, e.g., thermoplastic elastomer (TPE), and more preferably a thermoplastic polyester elastomer such as Hytrel™ by DuPont Corporation. Alternatively, the link may be constructed from a nylon or other material with sufficient strength and flexibility. The link may be made by any suitable method, for example by molding.

The illustrated link 6134 may be elongate in the dimension which is adapted to lie parallel to the strap length, and may be approximately elliptical in plan view as illustrated (see FIG. 5-44-2).

The link is thin (e.g., less than about 3 mm, and more preferably about 0.75 to 2.5 mm thick) in its smallest transverse dimension, and mostly generally planar in its unflexed state. Preferably, the link is symmetrical both end-to-end and about a central longitudinal plane, to facilitate assembly and reassembly of the headgear without needing to have regard to the orientation of the link. In an embodiment, the link has a thickness less than the strap thickness.

The link 6134 has opposed end portions 6136, a pair of transverse strap-receiving slots 6140 and a central portion 6142 between and adjacent the slots. By including a pair of slots 6140 rather than a single slot, the headgear straps are less prone to skewing in use.

The link of FIGS. 5-44-1 to 5-44-5 is adapted to cooperate with a fabric and foam headgear strap of approximate width 19 mm and approximate thickness 2.7 mm. The illustrated link is approximately 48 mm long by 23 mm wide by 1 mm to 2 mm thick. The edges of the link may be rounded.

In the illustrated embodiment, the end portions 6136 (which correspond substantially with that part of the link which is overlaid by the strap in use) are approximately 1 mm thick.

The illustrated link further includes a pair of parallel 19 mm by 3 mm transverse slots 6140 spaced apart by about 3 mm, and a reinforced central portion 6142 adjacent the slots.

It should be appreciated that the link may be adapted for use with headgear straps of other suitable length, width, and thickness, e.g., size of slots in link may be sized accordingly to accommodate any suitable size headgear strap.

In the illustrated embodiment, the central portion 6142 is strengthened by being thickened relative to the end portions 6136. The reinforced central portion 6142 may comprise an I-shaped thicker region of 2 mm thickness. The center bar 6144 of the I-shape is located between the two slots and the cross bars 6146 of the I-shape are located between the ends of the slots 6140 and the side edge of the link, and taper down in thickness towards their ends.

It will be appreciated that the central portion 6142 may strengthened in ways other than by increased thickness, for example by co-molding with different materials, or attachment or inclusion of reinforcing members.

The thickest portion of the link and straps in use is a double thickness of strap together with a thickness of the end portions 6136. By providing a reinforced, thickened central portion 6142, the linking element is strengthened without contributing to the overall thickness of the assembly of straps and link, since the straps do not wrap around the central portion in use. See FIG. 5-45.

FIG. 5-45 is a schematic section of the link 6134 (similar to FIG. 5-44-3), showing the location of the rear strap portions 6130a, 6130b when connected to the link.

As can be seen in FIG. 5-45, the slots 6140 in the link are sized to allow threading of the straps therethrough by the user to adjust the headgear fit and tension, with the strap ends being doubled back onto themselves and secured, for example by the use of a hook material 6148 (e.g., Velcro™ or similar) stitched or otherwise attached to the end portion of the strap. The strap surface facing the hook tape may have a complementary loop material attached, or alternatively the hook tape may be secured against the outer fabric layer of the strap itself.

The link 6134 and strap 6130 are thus adapted to connect together by the strap making a single pass through the link and forming a U-shape with both legs of the U parallel to the adjacent surface of the patient's head.

The thicker portion 6144 of the link 6134 preferably has a thickness of less than two strap thicknesses, and does not protrude beyond the combined thickness of the doubled-over strap connected to the link.

In this arrangement, the overall thickness of the strap arrangement is approximately a double thickness of strap. This contrasts with prior art arrangements where more than a double thickness of strap is located on the head, for example using a ladder lock, leading to an uncomfortable bulk to lie on. See FIG. 5-46, which shows one end of a prior art ladder lock-type headgear buckle 6200 and strap 6202. Tests have shown that the pressure on a typical head are approximately halved from about 13 $g/mm^2$ to about 6 $g/mm^2$ when using a link according to an embodiment of the present invention.

In accordance with a preferred form of the present invention, a length of hook & loop material (e.g., Velcro™) is used to secure an end of a strap to itself and to retain the strap in tension.

The rounded corners of the linking element (see for example FIGS. 5-44-2 and 5-44-4) reduce the likelihood of a sharp corner impinging on the patient's head, and lead to improved comfort.

The illustrated arrangement is intended to allow a lower link profile and provide increased comfort to the patient, while retaining the ease of adjustment of current link member designs.

While the illustrated embodiment of the invention is a flexible linking element, other forms may be more rigid, or completely rigid.

Such flexible linking element may be used to removably and adjustably couple upper or top strap portions of headgear (e.g., similar to buckle 60 in FIG. 1-1). Also, such flexible linking element may be used to removably and adjustably couple rear strap portions of headgear (e.g., see FIGS. 22-23-1 to 22-23-6 described below).

2.5 Side & Rear Stabilising Portions

2.5.1 Headgear

2.5.1.1 Introduction

A mask assembly in accordance with an embodiment of the invention provides stability to the interface through a combination of components referred to as "headgear". The headgear may be broadly described as comprising a pair of side portions including cheek & upper/crown portions and a rear portion. In the preferred embodiment, the cheek portions include stabilizing features or "yokes". Furthermore, as discussed above naso-labial angular adjustment is provided via a yoke to frame connection mechanism.

As shown in FIG. 1-1, the headgear 50 includes two side portions 52 with a rear portion 54 connecting the side portions 52. Each side portion 52 includes a side strap 53 (e.g., constructed of Breathoprene) and a headgear yoke 55 (e.g., constructed of a molded plastic such as nylon) attached to the side strap 53. The headgear yoke 55 (also referred to as a rigidizer, rigidizing element, stabilizer, stabilizing element, stiffened headgear element) acts as a stiffener or rigidizer to add rigidity to the headgear and add stability to the sides. The rear portion 54 includes a rear strap 57 (e.g., constructed of Breathoprene) that passes around a rear portion of the patient's head (e.g., below the occiput).

Each side strap 53 includes an upper strap portion 53(1) that passes over the top of the patient's head. The upper strap portions 53(1) of the side straps 53 are coupled to one another by a headgear buckle 60. The rear strap 57 includes end portions 57(1) coupled to respective headgear yoke 55.

The upper strap portions 53(1) are structured to adjust the sealing force because they pull the nasal prong assembly 20 up into the patient's nose. The rear strap 57 is structured to adjust the stability of the nasal prong assembly 20 because it pulls the nasal prong assembly 20 back into the patient's face on the top lip of the patient.

The headgear 50 captures the crown of the patient's head (when assembled) while avoiding the base of the neck, accommodates a sufficient range of adjustment to cover a broad range of the target population, and/or provides sufficient flexibility for removal of the interface without requiring readjustment. In an embodiment, the headgear 50 may be provided in multiple sizes (e.g., small, medium, large).

In another embodiment as shown in FIGS. 13-1 to 13-4, the headgear 5050 includes two side portions 5052 with a rear portion 5054 connecting the side portions 5052. The headgear 5050 is structured to stabilize the patient interface on the patient's head and apply sufficient force for sealing. In addition, the headgear is structured to provide one or more of the functions described below, e.g., unobtrusive, comfortable, easy to use, etc.

Each side portion 5052 includes a side strap 5053 (e.g., constructed of Breathoprene) and a headgear yoke 5055 (e.g., constructed of hard plastic such as Nylon, Hytrel) attached to the side strap 5053. The headgear yoke 5055 (also referred to as a rigidizer, rigidizing element, stabilizer, stabilizing element, stiffener, stiffened headgear element) acts as a stiffener or rigidizer to add rigidity to the headgear and add stability to the sides. The rear portion 5054 includes a rear strap 5057 (e.g., constructed of Breathoprene) that passes around a rear portion of the patient's head (e.g., below the occiput).

Each side strap 5053 includes an upper strap portion 5053(1) that passes over the top of the patient's head. The upper strap portions 5053(1) of the side straps 5053 are coupled to one another by a headgear buckle 5060 (e.g., constructed of hard plastic such as Nylon, Hytrel). The rear strap 5057 includes end portions 5057(1) coupled to respective headgear yoke 5055.

FIGS. 22-21-1 to 22-23-6 illustrate headgear according to another embodiment of the present invention. In this embodiment, a rear strap portion is incorporated into each side strap.

Specifically, FIGS. 22-21-1 to 22-21-8 shows a left-hand-side (LHS) side strap 6553L with headgear yoke 6555L and FIGS. 22-22-1 to 22-22-8 shows a right-hand-side (RHS) side strap 6553R with headgear yoke 6555R. Each of the side straps 6553L, 6553R includes an upper strap portion 6553(1) adapted to pass over the top of the patient's head, a front strap portion 6553(2) adapted to pass along the side of the patient's head, and a rear strap portion 6553(3) adapted to pass around a rear portion of the patient's head. As illustrated, each side strap 6553L, 6553R has a general Y-shape configuration, e.g., similar to headgear in ResMed's Swift II mask.

FIG. 13-5 is a schematic view illustrating headgear vectors according to an embodiment of the present invention (e.g., in relation to FIGS. 13-1 to 13-4 but also applicable to FIGS. 22-21-1 to 22-21-8 for example). In an embodiment, A1 is about 152°, A2 is about 124°, and A3 is about 84°. However, other dimensions are possible, e.g., depending on application. Such headgear vectors provide stability to the nasal prongs in order to maintain seal and provide sufficient ear clearance for comfort.

The headgear yoke 6555L, 6555R is substantially similar to the headgear yoke 5655 described above (e.g., see FIGS. 22-7-1 to 27-7-8). In contrast, the stitching groove 6559 of the headgear yoke 6555L, 6555R loops around the edge of the second end portion 6555(2) thereof.

In the illustrated embodiment, the upper strap portion 6553(1) and the front strap portion 6553(2) are formed in one piece, and the rear strap portion 6553(3) is attached to the upper and front strap portions by stitching (e.g., stitch joint indicated at 6556). However, the rear strap portion 6553(3) may be provided to the upper and front strap portions in other suitable manners, e.g., formed in one piece therewith, attached via adhesive, attached via mechanical connector, etc.

As illustrated, the free end of each rear strap portion 6553(3) includes a Velcro® fastener or tab of hook material 6557. In addition, one side of each rear strap portion 6553(3) is coated with un-broken loop (UBL) material 6558 (e.g., instead of lycra) which allows the tab of hook material 6557 to fasten anywhere along its length. The tab of hook material 6557 provides an "easy peel" arrangement wherein only a portion of the tab of hook material 6557 engages with the UBL material 6558 making it easier to grip.

FIGS. 22-22-9 and 22-22-10 illustrate under-side and top-side views of the tab of hook material 6557. The under-side view of FIG. 22-22-9 shows the UBL side 6558 of the Breathoprene headgear material, Velcro hooks 6557(1) of the hook material, and an area 6557(2) with the hooks 6557(1) removed, e.g., to facilitate gripping or peeling the tab. The hooks may be removed in area 6557(2) through shaving off, ultrasonic removal, or other suitable removal means. The top-side view of FIG. 22-22-10 shows the Lycra side 6560 of the Breathoprene headgear material (opposite side of UBL) and the attachment area 6557(3) of the tab to the Lycra side 6560. In an embodiment, the tab may be ultrasonically welded to the Lycra side 6560.

In use, the upper strap portions 6553(1) of the side straps 6553L, 6553R may coupled to one another by a top headgear buckle or link, and the rear strap portions 6553(3) of the side straps 6553L, 6553R may be coupled to one another by a rear headgear buckle or link.

For example, FIGS. 22-23-1 to 22-23-6 illustrate a fully assembled patient interface 6510 with the upper strap portions 6553(1) coupled by tube retainer 5561 and headgear buckle 5560 (as described in reference to FIGS. 5-42-1 to 5-42-6 and FIGS. 5-43-1 to 5-43-7) and the rear strap portions 6553(3) coupled by linking member 6134 (as described above in reference to FIGS. 5-44-1 to 5-45). In addition, the patient interface 6510 includes a frame 6030 and nasal prong assembly 6020 (as described in reference to FIGS. 16-14-1 to 16-16-8).

In the illustrated embodiment, the headgear yoke is formed separately from the frame and attached thereto. In an alternative embodiment, the headgear yoke may be integrally formed with the frame so that the frame and headgear yoke provide a one-piece structure.

The headgear may provide one or more of the following functions: support and stabilize the nasal prong assembly on the user in a manner that maintains the integrity of the nasal prong seal around the naris region during the delivery of pressurized air; allow the user to adjust and set the nasal prong to a desired position to obtain and maintain an "exact fit" with a good nasal prong seal around the naris region during the delivery of pressurized air; accommodate an anthropometrically diverse range of users (e.g., 95% of male and female population); accommodate a range of different sleeping positions and transitions in sleeping positions including the ability to support different tube mounting configurations (e.g., allow patient to sleep on side without the barrel-like base and/or prongs being dislodged); allow the user to remove and replace the interface without significant loosening of the adjustment mechanisms; ergonomically comfortable and not a source of marking or irritation to the user; unobtrusive and both visually and physically minimal avoiding the user feeling stifled or claustrophobic; allow the user to wear glasses with the interface; aesthetically pleasing, high quality and stylish; provide a region, or regions, for the application of branding; allow user to easily assemble/disassemble from the nasal prong assembly; and/or allow user to easily fit and remove from head.

2.5.1.2 Headgear Strap Material

In the illustrated embodiment, each of the headgear straps may be constructed of Breathoprene including an open cell polyurethane laminated between Lycra outer layers. In alternative embodiments, the nap of the outer layer material may be altered, the density of the core material may be altered, and/or the color of the individual materials may be altered.

For example, each of the straps may be constructed of micro-fiber nylon (e.g., Tattel), which may provide a relatively soft edge and feel.

However, other suitable materials are possible. In an embodiment, the straps have a material thickness of about 2-3 mm, e.g., 2.5 mm.

In another embodiment, the straps may be constructed of a more elastic headgear material to increase decoupling of headgear forces such that shifts in the headgear position does not significantly influence the seal region.

FIG. 30 is a cross-section of Breathoprene material according to an embodiment of the present invention. As illustrated, the material includes a layer L1 of Nylon/Spandex Loop, a layer L2 of Open-cell Polyurethane, and a layer L3 of Polyester/Lycra jersey. The material has the benefits of being soft, light, flexible and comfortable. Moisture is allowed to escape through the material from the skin, and air is allowed through to maximize heat dispersion and breath-ability, making the headgear more comfortable to wear for longer periods.

2.5.1.3 Headgear Strap Dimensions and Angles

In an embodiment, an intermediate strap portion 5053(2) of each side strap 5053 (e.g., see FIG. 13-2) has a width of about 17-21 mm, e.g., 19 mm, and an upper strap portion 5053(1) of each side strap 5053 (e.g., see FIG. 13-4) has a width of about 17-21 mm, e.g., 19.8 mm. Also, the rear strap 5057 may include a central portion with an increased width such that the end portions 5057(1) of the rear strap 5057 (e.g., see FIG. 13-3) have a width of about 17-21 mm, e.g., 19 mm, and the central portion 5057(2) of the rear strap 5057 (e.g., see FIG. 13-3) has a width of about 36-40 mm, e.g., 38 mm. The wider, central portion 5057(2) is adapted to sit further down the back of the patient's head.

As best shown in FIGS. 13-1 and 13-4, the upper strap portion 5053(1) of each side strap 5053 is sufficiently long so that the largest patient can be fitted to the headgear, which results in the upper strap portion 5053(1) overhanging at least a portion of the yoke 5055 when fitted to a smaller person. In an exemplary embodiment, the strap length of the upper strap portion 5053(1) (measured from the top of the yoke) may be about 180-230 mm, e.g., 193 mm.

As best shown in FIG. 13-3, the end portions 5057(1) of the rear strap 5057 are sufficiently long so that the largest patient can be fitted to the headgear, which results in overhang of the end portions 5057(1) when fitted to a smaller person. In addition, a gap may be provided between the free ends of the end portions 5057(1). In an exemplary embodiment, the strap length of the rear strap 5057 may be about 530-560 mm, e.g., 545 mm.

Velcro Tab

As shown in FIGS. 21-1 and 21-2, a Velcro tab 5059 (hook material) is provided to the end of each rear strap end portion 5057(1) (see FIGS. 13-1 to 13-4) to secure the strap in position. Such Velcro arrangement improves comfort and usability (locating, pealing, and reattaching). In addition, such Velcro arrangement is not visible when the Velcro is attached onto the back strap. In an embodiment, the Velcro provides an effective engagement area of about 300-500 mm$^2$, e.g., 375 mm$^2$. In an embodiment, the rear strap end portion and Velcro tab may have a tapered or triangular shape. In such embodiment, the rear strap may be wider at the yoke connection, e.g., for stiffness and minimal vertical movement. The central portion 5057(2) may have a reduced thickness with respect to the remainder of the rear strap, e.g., for increasing pressure for better grip.

In an embodiment, the Velcro tab 5059 may be ultrasonically welded to the rear strap. For example, the Velcro tab 5059 may be ultrasonically welded in two locations (see FIG. 21-1) or the Velcro tab 5059 may be ultrasonically welded in an enclosed pattern (see FIG. 21-2). However, other suitable attachment methods are possible.

2.5.2 Stabilising Element (Yoke)

Each headgear yoke 55 is constructed from a rigid or semi-rigid material (e.g., injection molded from nylon, polypropylene, polycarbonate, etc.) and attached to a respective side strap 53. The yokes 55 retain at least a partial portion of the basic shape of the headgear 50, which may facilitate donning of the headgear 50.

As shown in FIGS. 1-1 and 6-1 to 6-5, each yoke 55 includes a first end portion 55(1) adapted to secure a respective end of the nasal prong assembly 20 in an operative position, a second end portion 55(2) adapted to engage a respective end of the rear strap 57, and an intermediate portion 55(3) between the first and second end portions 55(1), 55(2) adapted to add rigidity to a respective side strap 53.

The headgear yokes 55 provide rigidity for stabilizing the interface and flexibility for comfort (when assembled), provide a flexible stiffening section for the headgear straps, form a retaining interface with the first end portion (yoke ring), and/or provide alignment markers to correspond to the correct front-to-back orientation of the nasal prong assembly.

Yoke to Strap Attachment

Each yoke 55 may be attached to a respective side strap 53, e.g., via stitching, welding, gluing, or otherwise mechanically affixed.

In an embodiment, each yoke 55 may be attached to a respective strap 53 with glue, e.g., Loctite (e.g. 4011 medical grade). In such arrangement, the glue may be provided along a glue path that is spaced inwardly from the side edges of the strap 53 (e.g., 1-5 mm).

In other embodiments, each yoke 55 may be attached to a respective strap 53 with double-sided tape, hot melt glue, and/or the application of heat (non glue).

In another embodiment, a sleeve may be created in the side strap 53, and the yoke 55 may be inserted into such sleeve.

In yet another embodiment, a yoke or rigidizing section may be provided to a respective strap by a manufacturing process. For example, a thermoforming process may be used to form a one-piece strap with a rigidizing section. In such embodiment, a relatively thick strap may be provided, and then pressure and/or heat may be applied to the strap in certain sections to add the desired rigidity. In an embodiment, the strap may be constructed of a foam material that would allow features to be created in the foam during manufacturing, e.g., seal ring, branding, etc.

In a further illustrated embodiment, each yoke 5055 is attached to a respective side strap 5053 via stitching. As shown in FIGS. 13-1 to 13-4 and 19-2, a stitching groove 5058 is provided along a length of the yoke 5055 to receive the stitching. As illustrated, the stitching groove 5058 is provided along an intermediate portion of the yoke 5055 (e.g., spaced inwardly from the edges).

The stitching groove 5058 locates the stitching making it flush with the top surface of the yoke, improves aesthetics by providing an overall cleaner appearance, provides a single stitching line to improve comfort levels through reducing edge stiffness of the headgear strap edge (e.g., potentially reducing facial marks), and provides path having sufficient level of attachment and stability. Also, the recessed structure of the stitching groove 5058 provides a thinner yoke wall section (e.g., see FIG. 19-20) for the stitching needle to punch through, which provides reduced part deformation.

FIG. 19-19 illustrates exemplary dimensions for an embodiment of the stitching groove 5058. As illustrated, D1 may be about 1-2 mm, e.g., 1.5 mm, D2 may be about 0.25-0.75 mm, e.g., 0.4 mm, D3 may be about 1-2 mm, e.g., 1.2 mm, and D4 may be about 25-75°, e.g., 45°. Although specific dimensions and ranges are indicated, it is to be understood that these dimensions and ranges are merely exemplary and other dimensions and ranges are possible depending on application. For example, the exemplary dimensions may vary by 10-20% or more or less depending on application.

It should be appreciated that each yoke 5055 may be attached to a respective side strap 5053 in other suitable manners, e.g., via welding, gluing, or otherwise mechanically affixed.

Yoke Width

In the illustrated embodiment, the yoke 55 includes a width that is less than a width of the respective side strap 53, e.g., intermediate portion 55(3) narrower than side strap 53.

If stitching is not used to attach the yoke 55 to the respective strap 53 (e.g., yoke attached via welding or gluing), the intermediate portion 55(3) may be even narrower.

However, in an alternative embodiment, the intermediate portion 55(3) may have a width that is substantially the same as the respective strap 53.

In alternative embodiments, the width of the yoke may be tapered or contoured along its length. For example, FIG. 8-1 illustrates yoke 255 that tapers from a smaller width w to a larger width W. FIG. 8-2 illustrates yoke 355 that has a convex edge 359 along its length, and FIG. 8-3 illustrates yoke 455 that has a concave edge 459 along its length.

In yet another embodiment, as shown in FIG. 8-4, one or more slots 561 may be provided along a portion of a yoke 555 (e.g., along inner radius of curved portion of the yoke) to reduce the springboard effect provided by the yoke in use.

In a further illustrated embodiment, the yoke 5055 includes a width (e.g., about 9 mm) that is less than a width of the respective side strap 5053 (e.g., about 19 mm), e.g., intermediate portion 5055(3) narrower than side strap 5053. As described above, such arrangement may eliminate or reduce facial marks in use.

For example, FIG. 19-20 illustrates yoke 5055 attached to strap 5053 by a single stitch 5056. In an embodiment, the cantilever distance D1 is about 8.5-10.5, e.g., 9.5 mm.

Materials and Properties of Stabiliser/Yoke

First Forms

As noted above, each headgear yoke 55 is constructed from a rigid or semi-rigid material, e.g., nylon, polypropylene, polycarbonate.

In an embodiment, the yoke 55 is sufficiently soft and flexible so that it can bend or conform to suit the patient's head, and sufficiently rigid to efficiently transfer headgear forces/vectors for locating the nasal prong assembly 20 on the patient's face.

In another embodiment, the yoke 55 may be rubber like, e.g., constructed from Santoprene silicon material or thermoplastic. In another embodiment, silicon may be overmolded onto the yokes.

In yet another embodiment, headgear straps may not be provided along the yokes 55, e.g., straps only provided to cup the patient's head. Alternatively, yokes may not be provided.

In yet another embodiment, a flexible connection between the yoke and frame may be provided by an extension of the silicone seal rings, e.g., to increase decoupling of headgear forces.

In yet another embodiment, a metal component may be inserted in headgear straps around the yoke region to provide stiffness and to allow the user to customize the headgear region to the shape of the patient's face, e.g., in-molded stainless steel wire. In other forms this insert may be constructed from a malleable plastic or TPE.

Alternative Forms—Thermoformed Foam Yoke

FIGS. 12-12-1 to 12-13 illustrate headgear with thermoformed foam yoke.

In FIG. 12-12-1, the headgear includes headgear straps 3153 that cup the patient's occiput and yoke 3155 to couple the headgear straps 3153 with the nasal prong assembly. The yoke 3155 is constructed of a thermoformed foam material. Also, a molded plastic seal ring 3156 is provided to a proximal end of the yoke 3155, and a molded plastic buckle 3160 is provided to a distal end of the yoke 3155 to provide lateral adjustment with the headgear straps 3153 (see FIG. 12-12-2).

In an embodiment, the seal ring 3156 and buckle 3160 may be provided to the yoke 3155 via a thermoformed foam sandwich. For example, FIGS. 12-12-3 and 12-12-4 illustrate a thermoforming process for coupling the molded plastic sealing ring 3156 or buckle 3160 to the foam yoke 3155 with heat/pressure. As shown in FIG. 12-12-3, a separately molded relative hard plastic part (e.g., seal ring 3156 or buckle 3160) is positioned between two pieces of foam 3155(1), 3155(2), and the plastic ring 3156 or buckle 3160 and foam pieces 3155(1), 3155(2) are positioned in a molding tool having a top tool half T1 and a bottom tool half T2. The molding tool is heated up and top and bottom tool halves T1, T2 compress the foam pieces 3155(1), 3155(2) and plastic ring 3156 or buckle 3160 so that the foam pieces 3155(1), 3155(2) bond to one another and retain the plastic ring 3156 or buckle 3160 therebetween (see FIG. 12-12-4). In another embodiment, the seal ring may be integrated to the yoke.

This embodiment provides increased levels of usability (e.g., particularly during fitting and adjustment) for intuitive features such as single piece 3D shaped headgear and lateral headgear tension adjustments.

Also, this embodiment provides an increased level of aesthetics as it utilizes a thermoformed foam section, which provides broad opportunities for aesthetic styling. In FIG. 12-13, the headgear includes a thermoformed foam yoke 3255 with a thin breathoprene layer attached thereto (e.g., along surface adapted to engage the patient's head in use) for comfort. Similar to 12-12-1, this embodiment provides increased levels of usability (e.g., particularly during fitting and adjustment) for intuitive features such as single piece 3D shaped headgear and lateral headgear tension adjustments.

Branding

Branding may be molded and/or printed onto the yokes 55, and such branding may also function as an aid for correct alignment during assembly. The branding may include changes in color/tone.

Alternative Headgear Yoke

FIGS. 12-1 to 12-4 illustrate alternative arrangements of headgear yoke. Each embodiment may include one or more of the following features: localized thinning to adjust flexibility of the yoke, improved comfort, seal ring co-molded to yoke, improved aesthetics, branding (e.g., to show which side is inside/outside for assembly), and/or structured to fit more people.

In FIG. 12-1, the yoke 2055 has a streamlined arrangement in which the yoke 2055 includes localized thinning or tapers along its length, e.g., inner edge of the yoke tapers towards its distal end, to improve flexibility.

FIG. 12-2 illustrates another embodiment of a yoke 2155 having a streamlined arrangement in which the yoke 2155 includes localized thinning or tapers along its length, e.g., inner edge of the yoke tapers towards its distal end, to improve flexibility. In this embodiment, the yoke 2155 has a smaller width than that shown in FIG. 12-1.

In FIG. 12-3, the yoke 2255 has a geometric or symmetric arrangement in which the yoke 2255 has a substantially uniform thickness and shape along its length. In addition, the distal end of the yoke 2255 includes a section 2280 for branding, e.g., section includes branding cut-out.

In FIG. 12-4, the yoke 2355 has a contoured inner radius or surface and the distal end of the yoke 2355 includes a section 2380 for branding, e.g., bird logo for aesthetic cues. In an embodiment, a soft elastomeric material 2382, e.g., santoprene, may be co-molded to the yoke 2355 along the contoured surface. In addition, the branding may include a different surface finish than that of the yoke 2355, e.g., elastomeric surface. The embodiment of FIG. 12-4 provides an increased level of aesthetics as it utilizes branding as an aesthetic cue for the design of the yokes.

Flexible Yoke/Incorporated Seal Ring

FIGS. 12-8 to 12-11-2 illustrate headgear with flexible yoke and incorporated seal ring.

In FIG. 12-8, the headgear includes Breathoprene headgear straps 2753 and yoke 2755 molded of a thin thermoplastic/silicone material. As illustrated, the yoke 2755 has a varying profile along its length. Also, a yoke ring 2756 is integrated to the proximal end of the yoke 2755 and branding 2780 is incorporated into a distal end section thereof. In an embodiment, no headgear straps may be provided along the yoke and a slot may be provided at the distal end of the yoke for engaging straps that cup the patient's head.

In FIG. 12-9-1, the headgear includes Breathoprene headgear straps 2853 and yoke 2855 constructed of a thin thermoplastic/silicone material. As illustrated, the yoke 2855 has a general L-shape with a seal ring 2856 provided to the proximal end and branding 2880 incorporated into a distal end section. As shown in FIG. 12-9-2, the thermoplastic/silicone yoke 2855 may include corrugations, arcuate cut outs, thinned out localized section, or ridges 2888 to encourage bending or flexing so that the yoke 2855 can contour to the profile of the user's face (e.g., similar to swimming goggle straps). The thermoplastic/silicone yoke 2855 may maintain strength in the direction of the seal (e.g., into the patient' nose) which is essentially parallel to the direction of the force vector created by the straps.

In FIG. 12-10, the headgear includes Breathoprene headgear straps 2953 and yoke 2955 constructed of a thin thermoplastic/silicone material. As illustrated, the proximal end of the yoke 2955 includes a seal ring 2956 and the distal end of the yoke 2955 includes a Y-shaped configuration 2981. The Y-shaped distal end of the yoke 2955 provides a rigidizer along two different straps and hence in two different vectors. Also, the strap portion adjacent the distal end of the yoke 2955 may include surface texture 2980 for a branding feature.

In FIG. 12-11-1, the headgear includes headgear straps 3053 that cup the patient's occiput and yoke 3055 to couple the headgear straps 3053 with the nasal prong assembly. The yoke 3055 includes a narrow construction and may be formed of a silicone material. As illustrated, the proximal end of the yoke 3055 includes a seal ring 3056 and the distal end of the yoke 3055 includes a cross-bar 3066 for adjustable attachment with the headgear straps 3053. Also, a foam pad 3090 is provided to the yoke 3055 and adapted to contact the side of the patient's face. As shown in FIG. 12-11-2, the foam pad 3090 is molded with an undercut so that it can wrap over the yoke 3055. That is, the undercut of the foam pad 3090 naturally captures the yoke 3055 and holds the foam pad 3090 in place.

Foam Section Attached to Yoke

In FIG. 12-15-1, the headgear includes headgear straps 3453, molded plastic yokes 3455 that extend along respective sides of the patient's face, and a foam section or insert 3490 (e.g., constructed of viscoelastic foam) attached to the yoke 3455 and adapted to contact the side of the patient's face. As shown in FIG. 12-15-2, the foam section 3490 may be molded with an undercut shape so that it can wrap over or capture the yoke 3455. That is, the molded undercut of the foam section 3490 naturally captures the yoke 3455 and holds the foam section in place. In an embodiment, the undercut shape may be provided to only one side of the foam section 3490 such as that shown in FIG. 12-15-1.

The viscoelastic foam section 3490 provides a "high comfort" material around the sensitive cheek bone (zygomatic) region of the patient's face, which appears to be one of the primary sources of discomfort for headgear.

Also, this embodiment provides increased levels of usability (e.g., particularly during fitting and adjustment) for intuitive features such as single piece 3D shaped headgear and lateral headgear tension adjustments.

Silicone/Thermoplastic Foam Attached to Yoke

In FIG. 12-16-1, the headgear includes headgear straps 3553, molded plastic yokes 3555 that extend along respective sides of the patient's face, and a foam section or insert 3590 (e.g, injection molded of silicone/thermoplastic foam) attached to the yoke 3555 and adapted to contact the side of the patient's face. As shown in FIGS. 12-16-2 and 12-16-3, the silicone/thermoplastic foam section 3590 may be molded with an undercut shape so that it can wrap over or capture the yoke 3555. That is, the molded undercut of the foam section 3590 naturally captures or slips over the yoke 3555 and retains the foam section 3590 in position. In addition, this arrangement provides foam to both the inside and outside radii of the yoke 3555. In an embodiment, the foam may be visco elastic foam and/or may provide heat activated memory.

The silicone/thermoplastic foam section 3590 provides a "high comfort" material around the sensitive cheek bone (zygomatic) region of the patient's face, which appears to be one of the primary sources of discomfort for headgear.

Also, this embodiment provides increased levels of usability (e.g., particularly during fitting and adjustment) for intuitive features such as single piece 3D shaped headgear and lateral headgear tension adjustments.

2.5.3 Alternative Headgear Yoke

As shown in FIGS. 19-1 to 19-4, each yoke 5055 includes a first end portion 5055(1) adapted to engage a respective side of the frame 5030 and provide stability and support to the frame and nasal prong assembly during use, a second end portion 5055(2) adapted to engage a respective end of the rear strap 5057, and an intermediate portion 5055(3) between the first and second end portions 5055(1), 5055(2) adapted to add rigidity to a respective side strap 5053.

The yokes 5055 include one or more of the following functions: attach headgear to the frame, provide stability and support to the frame and nasal prong assembly during use, provide a yoke to frame interface, retain the frame during use, easy assembly/disassembly from the frame, rotate relative to the frame and allow adjustment to suit nasolabial angle, durability (e.g., 12 months or more), wide fit range (e.g., 95% of male and female population), visually minimal and unobtrusive, comfortable, provide a region, or regions, for the application of branding, and/or ease-of-use.

The yokes 5055 are structured and designed to improve visual integration and simple clean lines and forms. For example, the contoured form of each yoke breaks up flat faces to create highlight/shadow line and give an overall smaller impression. The single stitch and recessed groove used to attach the yoke to the respective strap provides a clean, streamlined form when assembled. The second end portion of the yoke is structured to leave minimum edges to lift away from the headgear strap if glued. The overall size of the yoke may be dictated by the various functions of the yoke to frame interface, e.g., minimum overall size and width while providing torque and rotation, retention of frame, and sufficient strength in area between yoke to frame and yoke to headgear strap.

2.5.4 Cheek Support

In accordance with an embodiment of the invention, cheek supports 62 are provided (e.g., see FIGS. 6-1 to 6-4). These function to enhance stability of the mask system on the face. In one aspect they enable headgear forces to be directed more onto the front of the face, e.g. the maxilla and or zygoma.

The first end portion 55(1) also includes a curved protrusion in the form of a cheek support 62 that curves forward or inwardly of the yoke ring 56. The cheek support 62 is attached to an end portion 63 of the side strap 53 (e.g., via stitching, glue, etc.) as shown in FIGS. 1-1 and 6-4. The cheek support 62 follows the cheek contour and is adapted to engage or hug the patient's cheek to provide stable cheek support. That is, the cheek support 62 stably supports the nasal prong assembly 20 in position and retains overall sealing stability.

The cheek support 62 provides a feature which both cushions against the cheeks and hugs the face evenly without introducing pressure points. This arrangement may reduce the strap tension required to maintain a seal and optimize patient comfort. Thus, the positioning of the cheek supports 62 on the headgear yokes 55 should discourage the user from applying excess headgear tension or over-tightening of the headgear, which can force the nasal prongs to compress into the naris region and affect sealing effectiveness.

The cheek supports 62 effectively takes the prongs' responsibility to provide stability to the mask system. The prongs can hence work almost independently to the supplied headgear tension, focusing on its own expansion to provide a secure seal.

FIG. 6-4 illustrates a version of the cheek support 62 with the strap portion 63 attached thereto. As illustrated, the strap 63 bends around the cheek support 62 to suit the contours of the patient's face. The cheek support 62 may be flexible or provide a lever action which flexes to suit the patient.

FIGS. 7-1 and 7-2 schematically illustrate how the supplied headgear tension has a different effect on the headgear 50 according to an embodiment of the present invention and ResMed's Mirage Swift headgear 150. On the Swift headgear 150, only a small section of the padded headgear is used to absorb the headgear tension in order to stabilize the mask. As a result, a large percentage of the headgear tension is applied directly through the prongs (see FIG. 7-1), pressing directly onto the septum and nostrils, which are very sensitive areas. For some patients, their minimum amount of securing headgear tension is sufficient to completely compress the pillows into the nose. In contrast, the cheek supports 62 on the headgear 50 transfers the bearing surface area from the prongs such that the headgear tension can be dispersed across the less sensitive cheek area and produce acceptable mask comfort. Beneficially, since mask stability is attributed to the entire headgear, sealing force is left attributed to the prongs. Thus, the cheek supports 62 take in most of the headgear tension, preventing the prongs from being compressed.

As shown in FIGS. 6-1 to 6-4, rib-strengthened brackets 64 support the yoke ring 56 on the yoke 55. Such brackets 64 add rigidity to the yoke ring 56 without affecting the flexibility of the yoke 55. That is, the brackets 64 help retain the yoke ring 56 and hence the frame of the nasal prong assembly 20 in position and prevent the frame from compressing the nasal prongs against the naris region when the headgear 50 is adjusted/tightened.

In addition, the cheek support 62 and/or brackets 64 may help to reduce tube drag which can cause undesired shifting of the frame and/or affect sealing stability.

As shown in FIGS. 13-1 to 13-4, 14-1, and 19-1 to 19-5, each cheek support 5084 curves forward of the yoke to frame interface 5085. The cheek support 5084 is attached to an end portion 5063 of the side strap 5053 (e.g., via stitching, glue, etc.). In an embodiment, the end portion 5063 of the side strap 5053 may overhang the cheek support 5084 by about 2.5 mm at the tip and about 4.0 mm at the upper and lower sides. However, the strap overhang may have other suitable dimensions, e.g., depending on application, patient comfort, etc.

The cheek support 5084 follows the cheek contour and is adapted to engage or hug the patient's cheek to provide a stable cheek support and hence provide additional support to the patient interface. That is, the cheek support 5084 stably supports the nasal prong assembly 4020 in position and retains overall sealing stability.

The cheek support 5084 is adapted to rest on the cheeks of the patient in use, e.g., below the cheek bone. Benefits of this location include one or more of the following: soft skin which is pliable, not sensitive, cheek bone support structure, and/or unobtrusive location.

The curvature of the cheek support 5084 may be determined from anthropometric analysis to provide a good fit for a wide range of patient head sizes. In the illustrated embodiment, the cheek support 5084 is raised vertically on the cheek (e.g., by about 2 mm with respect to the cheek support 62 described above) to provide preferred stability and comfort for this embodiment of the patient interface.

In an embodiment, the cheek support 5084 may be flexible in order to conform to the contours of the patient's face. Such flexibility may be provided by the selected material and/or thickness of the cheek support (e.g., 1.2 mm nylon material), and/or the cantilever arrangement of the cheek support (e.g., 22 mm cantilever arm) which may be locally narrowed to aid flexibility.

In an embodiment, as shown in FIG. 19-18, the distance D1 between cheek supports 5034 may be about 55 mm, which provides a distance D2 of about 50 mm with the headgear strap 5053 (e.g., 2.5 mm strap backing on each side). Such distance provides sufficient clearance to accommodate the width of the patient's nose for a wide range of patients, e.g., 97.5% male width is 39 mm (provides over 11 mm clearance). However, such distance may be increased, e.g., 60-65 mm distance between cheek supports.

The cheek supports 5084 provide a three-dimensional gripping mechanism, for sufficient comfort and mask stability, may allow less headgear tension to seal the nasal prongs, and/or may help to reduce tube drag which can cause undesired shifting of the frame and/or affect sealing stability. Moreover, the cheek supports 5084 isolate seal forces from stability forces, so that headgear tension is applied to the cheek supports rather than to the upper lip and/or to the prongs (preventing the prongs from being compressed).

In alternative embodiments, more than one cheek support may be provided, and/or the one or more cheek supports may be provided at different angles.

The support arm 5080 supports the yoke to frame interface 5085 on the yoke 5055. Moreover, the support arm 5080 provides support and stability of the frame 5030 and nasal prong assembly 5020 attached thereto.

As shown in FIG. 19-16, the lever length D1 of the yoke 5055 between attachment of headgear strap and frame has been increased (e.g., with respect to the yoke 55 described above). The increase in length provides sufficient clearance to accommodate the gusseted nasal prong assembly 5020.

As shown in FIGS. 19-1 to 19-5, the support arm 5080 is contoured or c-shaped to strengthen the support arm 5080 along its length. Specifically, the support arm 5080 has a generally C-shaped cross-sectional configuration along its length, which provides structural rigidity to the support arm 5080 and hence overall stability to the yoke 5055. As shown in FIGS. 19-17-1 to 19-17-4 which illustrate cross-sections along the length of the support arm 5080, the support arm 5080 transitions from a relatively flat section (FIG. 19-17-4) to the three-dimensional C-shaped section (FIG. 19-17-2). The flat section (FIG. 19-17-4) provides a flat contact surface for engaging the respective headgear strap. The depth of the upper and lower ribs (i.e., the depth of the upper and lower walls of the c-shaped section) may be determined by the width of the gusset 5022 of the nasal prong assembly 5020.

Along with the differing structural shape along its length, the wall section in the support arm 5080 is thicker than the wall section in the remaining portions of the yoke 5055 (e.g., wall section of support arm 5080 increases from about 1.2 mm (primary part wall thickness) to about 1.5 mm) to provide further rigidity.

The rounded, outwardly facing surface 5080.1 of the support arm 5080 (see FIG. 19-2) provides a branding surface for branding, e.g., lettering and/or logo. Such branding may be molded and/or printed onto the support arm. However, it should be appreciated that branding may be provided to other suitable portions of the yoke.

2.5.5 Increase Friction and Stability

The headgear 50 and/or nasal prong assembly 20 may include structure to improve stability. For example, such structure may increase friction with the patient's face, and the added friction enhances stability of the mask system on the patient's face in use.

Wider Headgear Straps

In an embodiment, the width of the headgear straps may be increased (e.g., with respect to ResMed's Swift mask) in order to increase the friction provided by the headgear straps. That is, the straps may be wider to increase the contact area with the patient's face, which provides more friction. The added friction increases stability which improves comfort. In addition, the wider straps may help to reduce irritation to the patient's cheeks.

FIG. 10-1 illustrates a headgear strap section including a headgear strap 753 and headgear yoke 755 provided the headgear strap 753 (e.g., via stitching). In such embodiment, the width w of the strap on each side of the yoke is about 5-9 mm. In contrast, known embodiments include a strap width on each side of the yoke of about 4.5-5 mm.

FIGS. 10-2-1 and 10-2-2 illustrate another embodiment including wider headgear straps. In this embodiment, the headgear straps 853 may be constructed of a foam material to further increase friction. In addition, the headgear strap 853 may include an extended portion 863 that extends between the nasal prong assembly 820 and the patient's cheek to improve stability.

In an alternative embodiment, the width of the yoke may be thinner in order to increase the width of the strap on each side of the yoke.

Reduction of Headgear Marking/Irritation

An increase in strap width on a side of the yoke may also help to reduce headgear "cheek mark".

In the illustrated embodiment, the headgear closely follows the profile of the patient's face and "hugs" the cheek region. The Breathoprene straps provide sufficient contact area and friction to stabilize the interface and the yokes function as a rigid element that retain the shape of the headgear.

A common side effect with known headgear is "cheek mark", which is a temporary marking left along the side of the patient's face and cheek region upon removing the interface, after an extended period of wearing. This region R is displayed in FIG. 10-3-1 with respect to ResMed's SWIFT headgear 150. As illustrated, the temporary marking appears to follow the profile of the headgear straps along the side of the face (e.g., swoosh mark). Also, yokes attached to the strap by stitching may leave a stitch mark and/or indentations along the perimeter of the yoke with stitching indentations on the inside face of the strap material.

According to an embodiment of the present invention, the amount of headgear strap material on a side of the yoke facing inwardly (i.e., towards the patient's nose) may be increased to reduce facial marks left by the headgear.

FIG. 10-3-2 illustrates a known embodiment in which the width w of the strap 153 on each side of the yoke 155 is about 5 mm. In such arrangement, the strap material 153 may cut into the patient's cheek and create a cheek mark.

FIG. 10-4 illustrates a headgear section according to an embodiment of the present invention in which the strap 953 on the side of the yoke 955 facing the patient's nose has a width w of about 8 mm Such arrangement increases the cantilever nature of the strap 953 so that the strap 953 becomes more flexible and does not substantially cut into the patient's cheek to create a mask.

FIGS. 10-5 and 10-6 illustrate alternative embodiments of headgear structured to reduce facial marks. In FIG. 10-5, the strap 1053 includes a total width w1 of about 20 mm and includes a width or overhang w2 of about 5.5 mm on each side of the yoke 1055. In FIG. 10-6, the strap 1153 includes a total width w1 of about 25 mm wide and includes a width or overhang w2 of about 8.5 mm on each side of the yoke 1155.

Alternative embodiments to eliminate or reduce facial marks occurring on the cheeks include: reducing the density of the headgear strap material; introducing a softer strap surface material; introducing a highly compliant element to the inside surface of the strap, removing the sharp 90° edge that sits up against the face (e.g., change profile of edge); improving lateral flexibility of the strap and yoke; altering the way in which the yokes interface with the frame; imbedding a component or material that provides the function of the yokes within a soft padded outer layer (e.g., a "sock" like padded outer layer); introducing a material that provides flexibility along a single plane/direction (e.g., it will flex and contour to the shape of the face while providing a rigidizer function along an adjustment plane); eliminating the stitching used to hold the yokes; adding a layer of 3 mm or 4 mm flocking to the inside of the strap; raising the headgear straps off of the face along the cheek region so that it is only making contact on the upper lip and side of head; introducing a molded foam component that is transfer molded to a plastic headgear component; reducing the overall material thickness of the headgear straps; using a thin textile, e.g., linen, rather than a plastic and foam component (e.g., this arrangement may reduce the overall height of the straps); and/or constructing the headgear from a thin textile that is stiffened in an isolated region to provide the rigidizing function currently fulfilled by the yokes (e.g., stiffening may be provided by impregnating the material with an epoxy (e.g., screen-printing)).

Also, alternative embodiments to eliminate or reduce marking/irritation occurring on the upper ear lobes include: introducing a lower density strap material; altering the geometry of the headgear to avoid the ears completely; using a softened rounded edge material or soft padded component where the headgear contacts the ears; providing headgear that sits over the sides of the ears (e.g., headphone style); incorporating a rotational adjustment for the back strap so that the strap can be positioned to clear the ears; using the ears as a point of location/stability (e.g., eye glasses) which may aid in correctly locating the interface or improving overall stability; and/or eliminating the back strap to avoid the ears.

Friction Pads Provided to Headgear

In another embodiment, a friction pad may be provided to the headgear to increase friction. For example, FIG. 10-7-1 illustrates a lower headgear strap section including a headgear strap 1253 and headgear yoke 1255 (including yoke ring 1256) provided the headgear strap 1253. As illustrated, a friction pad 1270 (e.g., constructed of silicone) may be provided to the yoke 1255 and adapted to contact the patient's cheek or cheekbone region to improve stability and provide additional support to the seal region.

In an embodiment, such friction pad 1270 may be retrofit to ResMed's Swift headgear. For example, FIGS. 10-7-2 and 10-7-3 illustrate friction pads 1270 provided to yokes 155 of ResMed's Swift headgear. In the illustrated embodiment, each friction pad 1270 may include a retainer 1271 sized and configured to be accepted in an opening provided in the yoke 155. As illustrated, the friction pads 1270 contour to the patient's face to improve stability.

Friction Pads Provided to Nasal Prong Assembly

In another embodiment, a friction pad may be provided to the nasal prong assembly to increase friction. For example, FIGS. 10-8-1 to 10-8-3 illustrate wings 1372 (e.g., constructed of silicone) provided to the base or body 1322 of the nasal prong assembly 1320 and adapted to contact the patient's cheeks or cheekbone region to improve stability and provide additional support to the seal region. As shown in FIG. 10-8-3, the wings 1372 contour to the patient's face in use.

In embodiments, the wings may extend from the base of the nasal prong assembly or the wings may extend from the frame.

Foam Padding Provided to Headgear

In another embodiment, foam padding may be provided to the headgear to increase friction. For example, FIG. 10-9-1 illustrates a lower headgear strap section including a headgear strap 1453 (e.g., constructed of Breathoprene) and headgear yoke 1455 (including yoke ring 1456) provided the headgear strap 1453. As illustrated, foam padding 1474 may be provided to the rear of the strap 1453 and between the strap 1453 and the yoke 1455.

As shown in FIGS. 10-9-2 and 10-9-3, the foam padding 1474 is suitably contoured so that the foam padding 1474 guides the strap 1453 along the curvature of the patient's face to increase surface area and facial contact provided by the strap 1453, and hence improve stability.

In an alternative embodiment, as shown in FIG. 10-9-4, foam padding may not be provided between the yoke and the strap. As illustrated, the strap 1453 may form a wing adapted to engage the patient's face in use.

Alternative Embodiments to Improve Stability

In alternative embodiments, additional support and stability to the seal region may be provided by wings or straps that sit under the mouth or below the chin in use (e.g., chin pad, chin strap).

For example, an exemplary chin strap may follow the plane of the headgear straps/yokes to run down and under the chin, and such chin strap may also support a secondary function of holding the mouth closed.

In another embodiment, a loop may contact the patient's face around the nose to provide addition support to the seal region.

Other embodiments to improve headgear stability includes: provide additional support through adhering the silicone nasal prongs to the skin; provide additional support through increasing contact between the prong and the patient's top lip; provide additional support through introducing an inflatable hood to the prongs that expands up against the walls of the nasal passage to hold the interface in place; provide additional support through a silicone skeleton that lies across the upper lip and cheek bone region which may eliminate all rigid plastic elements from the face (e.g., headgear may no longer have to function to hold the seal in as this is facilitated by the skeleton, rather the headgear functions only to hold the skeleton against the face); provide gel padding that sits against the face; and/or provide a mouthpiece that holds the frame in place.

Crown Portion

Crown Strap Style Headgear

FIGS. 12-19 to 12-21-3 illustrate headgear having a crown strap style.

In FIG. 12-19, the headgear includes an arrangement similar to that shown in WO 2006/130903, which is incorporated herein by reference in its entirety. As illustrated, the headgear includes headgear straps 3853 that cup the crown of the patient's head, and yokes 3855 provided between the headgear straps 3853 and the nasal prong assembly. The headgear straps 3853 include side strap portions 3853(1), bridge strap portions 3853(2), and crown strap portions 3853(3). The side strap portions 3853(1) may provide lateral Velcro adjustment with respect to the yokes 3855. Also, an additional adjustment buckle may be provided along the straps at the top of the patient's head. Each yoke 3855 includes a yoke ring 3856 to engage the nasal prong assembly and a cross bar 3866 to engage a respective side strap 3853(1).

In FIGS. 12-20-1 and 12-20-2, the headgear is similar to that shown in FIG. 12-19. In contrast, the headgear includes an extra bridge strap. Specifically, the headgear straps 3953 include side strap portions 3953(1), upper bridge strap portions 3953(2U), lower bridge strap portions 3953(2L), center strap portions 3953(4) between the upper and lower bridge strap portions, and crown strap portions 3953(3). The side strap portions 3953(1) may provide lateral Velcro adjustment with respect to the yokes 3955. In use, the extra bridge strap may help to balance headgear forces.

In FIGS. 12-21-1 to 12-21-3, the headgear is similar to that shown in FIGS. 12-20-1 and 12-20-2. In contrast, no center strap portion is provided between the upper and lower bridge strap portions. Thus, the headgear straps 4053 include side strap portions 4053(1), upper bridge strap portions 4053(2U), lower bridge strap portions 4053(2L), and crown strap portions 4053(3). The side strap portions 4053(1) may provide lateral Velcro adjustment with respect to the yokes 4055.

Rear Strap Portion

FIG. 9 illustrates another embodiment of a rear strap 657. As illustrated, the central portion of the rear strap 657 includes an increased width w with respect to the end portions. In addition, a hook material 668 is inset from respective ends of the strap 657 (e.g., attached by welding, stitching, etc.) so that the respective ends of the strap 657 provide a pull tab 669 to facilitate adjustment. The hook material 668 is adapted to engage remaining portions of the strap (e.g., loop type material) to secure the strap 657 in position.

Alternative Headgear Materials

FIGS. 12-5 to 12-7-2 illustrate alternative arrangements of headgear material.

In FIG. 12-5, headgear straps 2453 of the headgear are constructed of Breathoprene material with company branded microfibre 2484 on an inside surface (i.e., surface adapted to engage the patient's head in use). Similar to FIG. 12-3, the yoke 2455 may include a distal end section with a cut-out logo 2480.

In FIG. 12-6, headgear straps 2553 of the headgear are constructed of Breathoprene material, and at least a section of the material is perforated 2586. For example, selected portions of the headgear straps 2553 may include perforated Breathoprene material, or all the headgear straps 2553 may include perforated Breathoprene material. Also, a thermoformed rigidizer section 2555 may be provided to the headgear straps 2553, e.g., to secure the nasal prong assembly in position.

In FIG. 12-7-1, the headgear straps 2653 of the headgear are constructed of Breathoprene material, and a heat transfer label 2655 (e.g., constructed of foam) is provided to each side strap (e.g., label ironed onto strap) to provide a rigidizing function. As shown in FIG. 12-7-2, the heat transfer label 2655 may include corrugations or cut outs 2688 to encourage bending or flexing so that the heat transfer label 2655 can contour to the profile of the user's face. Also, the heat transfer label 2655 may provide an opportunity for a wide range of branding designs (e.g., branding printed to label). The seal ring that engages the frame of the nasal prong assembly may be constructed of strap material or silicone, for example, and provided to the end of the label. In an embodiment, selected portions of the label may be treated.

Removable Foam Sock

In FIG. 12-14-1, the headgear includes headgear straps 3353, molded plastic yokes 3355 that extend along respective sides of the patient's face, and a removable sock 3392 (e.g., constructed of foam) that encloses at least a portion of the yoke 3355. As shown in FIGS. 12-14-2 and 12-14-3, the foam sock 3392 may be constructed of open or closed cell foam and forms a sleeve that sheathes or encloses the yoke 3355. In the illustrated embodiment, the foam sock 3392 is generally L-shaped, and includes a cut-out 3393 to positively locate and properly position the foam sock 3392 with respect to the yoke 3355. The foam sock 3392 may be a closed cell extruded section or a thin slab of open cell foam rolled back on itself and glued to form the required section. Also, the foam sock 3392 may be available in a variety of colors and sizes, e.g., foam sock may extend along portions of the headgear straps and/or nasal prong assembly. In addition, the foam sock 3392 may provide various aesthetic and branding possibilities.

The foam sock 3392 provides a "high comfort" material around the sensitive cheek bone (zygomatic) region of the patient's face, which appears to be one of the primary sources of discomfort for headgear.

Tube Retainer

A tube retainer or retaining strap (not shown) may be provided to an upper strap portion 53(1) to retain the air delivery tube when in an upward position along the side of the patient's head (e.g., tube retainer wraps around both the tube and strap portion or buckle). An exemplary tube retainer is described in U.S. Pat. No. 7,318,437 and U.S. Patent Application Publication No. 2006-0137690, each of which is incorporated herein by reference in its entirety.

FIGS. 5-47-1 to 5-47-6 illustrate a soft-loop tube retainer 6361 according to an embodiment of the present invention. As illustrated, the tube retainer 6361 includes a first strap portion 6361(1) adapted to wrap or loop around one of the headgear straps and a second strap portion 6361(2) provided to the first strap portion 6361(1) and adapted to wrap or loop around the air delivery tube. The tube retainer 6361 may be provided to the headgear at any suitable position along the upper strap portions to retain the air delivery tube along the side or over the top of the patient's head. Also, the tube retainer 6361 may be structured to wrap or loop around two or more different size tubings, e.g., short tube and 2 m air delivery tube.

In the illustrated embodiment, the tube retainer 6361 is integrally formed in one-piece (e.g., cut from headgear material (e.g., Breath-O-Prene™) or other suitable soft and flexible material) with the second strap portion 6361(2) extending transverse to the first strap portion 6361(1). As illustrated, the second strap portion 6361(2) is thinner than the first strap portion 6361(1), and each strap portion includes a Velcro® tab 6362 adapted to secure the respective loop in position. The first strap portion 6361(1) tapers towards respective ends, and includes a tab 6363 to facilitate connection with the second strap portion 6361(2). FIG. 5-47-6 illustrates the orientation of looping of the first and second strap portions 6361(1), 6361(2).

In an alternative embodiment, a tube retainer or retaining strap may be provided to headgear to retain the air delivery tube in a position over the top of the patient's head (i.e., tube runs over the head as opposed to along the side of the head). This arrangement allows the patient to assume different sleep positions, e.g., sleeping on side head, back of head, etc.

For example, a tube retainer or retaining clip may be provided to a headgear buckle (e.g., in the position of headgear buckle 60 shown in FIG. 1-1 or headgear buckle 5060 shown in FIG. 13-4) to retain the air delivery tube when in an upward position along the top or side of the patient's head (e.g., tube retainer clips around the tube and locks into the strap portion). This arrangement allows the patient to assume different sleep positions, e.g., sleeping on side head, back of head, etc.

In the illustrated embodiment, the tube retainer 5561 (FIGS. 5-42-1 to 5-42-6) is structured to adjustably interlock with a headgear buckle 5560 (FIGS. 5-43-1 to 5-43-7). The tube retainer 5561 (e.g., constructed of plastic) is structured to retain at least two different sized tubings, interface with the headgear buckle 5560, rotate within the headgear buckle for desired positions for side sleeping, connect/disconnect from the headgear buckle, and does not allow tube slide until a certain tube drag limit to avoid tube damage. As illustrated, the tube retainer 5561 is generally round (e.g., circular or oval) with an opening 5561.1 at its proximal end. The air delivery tube may be passed through this opening 5561.1 via extension of the tube retainer 5561. Slides or guiding surfaces 5561.2 may be placed on either side of the opening 5561.1 to aid in the positioning and/or insertion of the air delivery tube. Also, each of the inner radial arms or walls 5561.3 of the tube retainer 5561 include multiple teeth 5561.4 (e.g., 3, 4 or 5 teeth, or more or less) to better support the air delivery tube once clipped into the tube retainer 5561. In addition, one or more teeth 5561.5 may be provided to support the air delivery tube. The arms or walls 5561.3 of the tube retainer 5561 are structured to flex to accommodate two or more different size tubings, e.g., short tube and 2 m air delivery tube (two different diameters), and do so over the lifetime of the product.

The tube retainer 5561 has two buttons 5561.6 at its distal end that may be resiliently pressed together to align the tongues 5561.7 together. Once aligned, the buttons 5561.6 may be engaged with the opening 5560.1 on the headgear buckle 5560 by releasing the buttons 5561.6 and allowing them to flex into the opening 5560.1. This mechanically locks the tube retainer 5561 with the headgear buckle 5560, and allows the tube retainer 5561 to rotate relative to the headgear buckle 5560. However, alternative methods of fixation may be used, e.g., buttons engaged with respective grooves on the buckle, adhesives.

As illustrated, the headgear buckle 5560 includes opposing locking portions 5560.2 adapted to be removably and adjustably coupled with respective headgear straps, e.g., headgear strap may be wrapped around the cross-bar of the associated locking portion in a known manner.

Also, the tube retainer 5561 may be rotated relative to the headgear buckle 5560 to adjust its position. A detent assembly assists in restraining the tube retainer 5561 at the desired position, and provides tactile feedback with the motion of the tube retainer 5561. Specifically, the opening 5560.1 of the buckle 5560 includes detents 5560.3 that interact with projections 5561.8 provided on each of the buttons 5561.6 of the tube retainer 5561. In addition, the buckle 5560 includes a series of recesses 5560.4 that interact with projections 5561.9 provided on the underside of the tube retainer 5561. As the tube retainer 5561 is rotated or adjusted, the projections 5561.8, 5561.9 of the tube retainer 5561 will move into and out of engagement with respective detents 5560.3/recesses 5560.4 of the buckle 5560. The projections 5561.8, 5561.9 will be seated within respective detents 5560.3/recesses 5560.4 to assist in restraining the tube retainer 5561 at the desired position.

Alternative Tube Retainers and Buckles

FIGS. 5-48 to 5-86 illustrate tube retainers 7100 and headgear buckles 7000 structured to manage tubing according to alternative embodiments of the present invention.

In each embodiment, the tube retainer is structured to stabilize the air delivery tube increasing the opportunity for an effective seal to form. The stabilization of the air delivery tube will also enhance patient comfort by allowing for a larger range of sleeping positions and reducing the incidence of irritation caused by tubing interference.

The tube retainer is a structure designed to maintain the air delivery tube in a fixed position. The tube retainer may be formed from any semi-rigid or rigid material such as Hytrel, HTPC.

The buckle is a joining member between two headgear straps that allows the tension in the headgear to be adjusted (e.g., in the position of headgear buckle 60 shown in FIG. 1-1 or headgear buckle 5060 shown in FIG. 13-4). The buckle may be formed from any semi-rigid or rigid material such as Hytrel, HTPC.

In the embodiments described below, each tube retainer 7100 (FIGS. 5-68 to 5-86) may be connected to each buckle 7000 (FIGS. 5-48 to 5-67). In an embodiment, each tube retainer 7100 may be easily and repeatedly connected to each buckle 7000. In an embodiment, each tube retainer 7100 may be rotated, either fixed or freely, once connected to the buckle 7000.

Buckle

As shown in FIGS. 5-48 to 5-67, each buckle 7000 includes two openings or strap locks 7040 (e.g., laddered strap lock) for engagement with upper strap portions of the headgear (e.g., headgear strap may be wrapped around the cross-bar of the associated strap lock in a known manner) and a cutout section or keyhole 7060 in the center for engagement with a tube retainer.

In an embodiment, each buckle 7000 may have a height H, e.g., 2 mm, as shown in FIG. 5-48. This embodiment may be considered a low profile buckle, which can be beneficial as it less obtrusive and more comfortable for the patient. In FIG. 5-48, the buckle includes a cutout 7090 along its outer edges on each side of the keyhole 7060. In an embodiment, such cutout 7090 may be more curved along its length as shown in FIG. 5-49, which soft curved edges increase comfort and add to the visual appeal of the headgear.

Strap Locks

In an embodiment, the strap locks 7040 on the buckle 7000 may have a cutout in the middle or anywhere along its longest side to form gap 7041 and teeth 7042 as demonstrated in FIGS. 5-48 to 5-53. The gap 7041 allows for easy engagement and disengagement of the upper strap portions of the headgear. In an alternative embodiment, the teeth 7042 may have tapered tips 7043 to enable the headgear straps to slide more readily through gap 7041, as shown in FIG. 5-50. In yet another embodiment, the teeth 7042 may have tapered edges 7044 to enable the headgear straps to slide more readily through gap 7041, as shown in FIG. 5-51. The strap locks 7040 may also have a ladder-lock profile 7045 as shown in FIG. 5-53.

Keyhole

The keyhole 7060 may be located in the center of the buckle 7000, however it may also be located at other suitable locations on the buckle, e.g., offset from the center of the buckle.

Figures 5, 56:
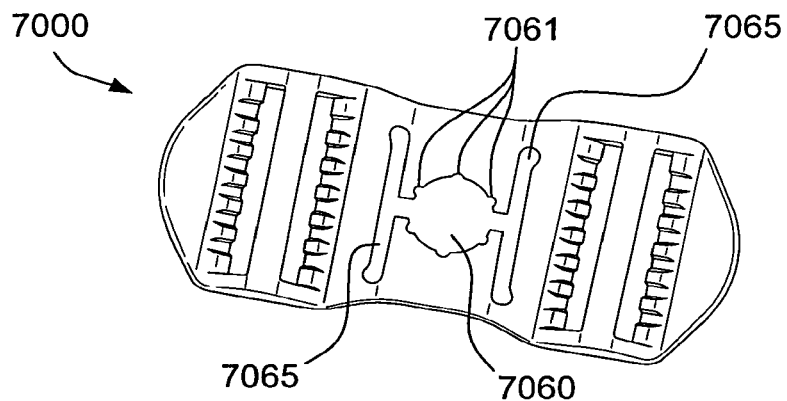
Figures 5, 57:
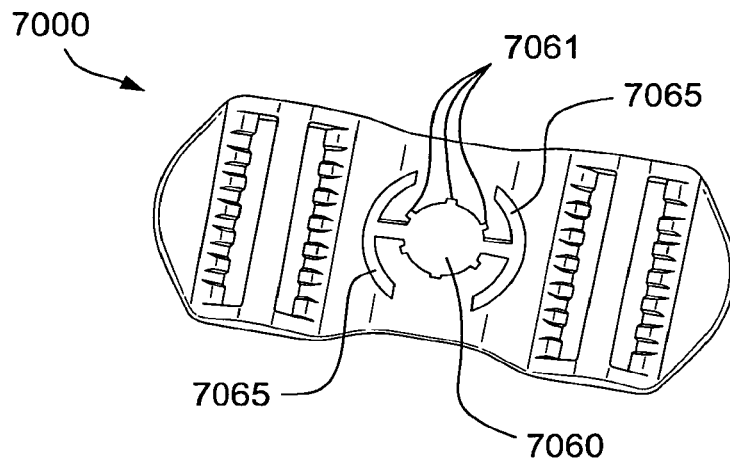
Figures 5, 58:
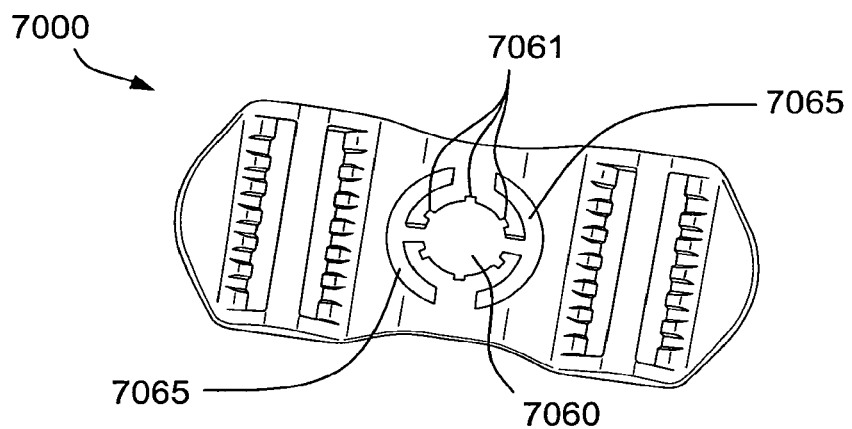
Figures 5, 59:
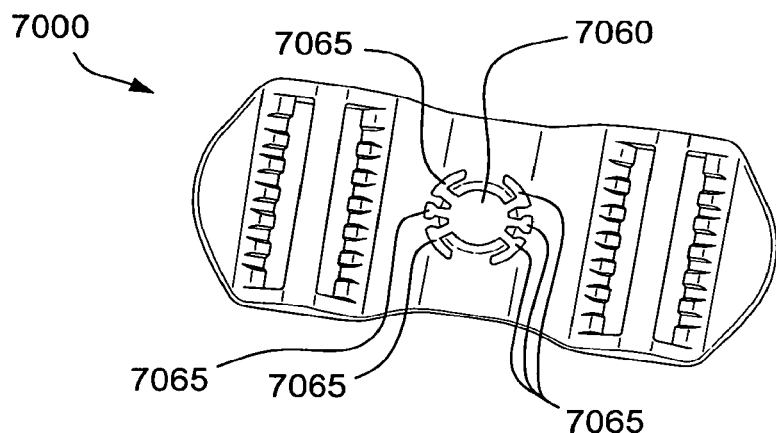
Figures 5, 60:
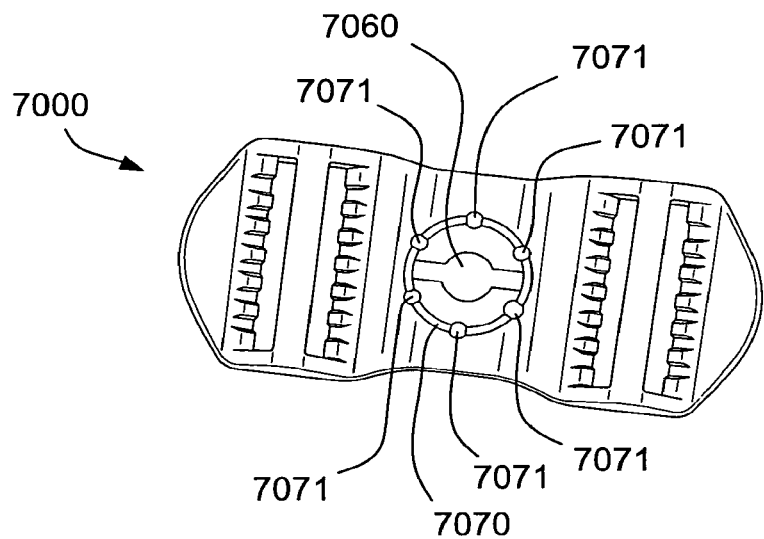
Figures 5, 61:
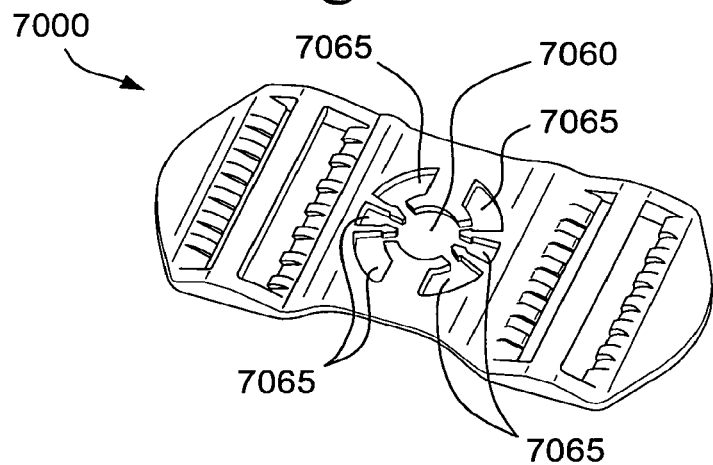

The keyhole 7060 may have a general key shape as shown in FIG. 5-52. Alternatively, the keyhole 7060 may assume other suitable shapes, e.g., generally circular shaped as shown in FIGS. 5-56 to 5-67. In embodiments, the keyhole 7060 may have shaped (e.g., square, circular, triangular) apertures 7061 (e.g., 1, 2, 3, or more shaped apertures) extending from the keyhole 7060. In an embodiment, the apertures 7061 may have a generally conical shape as shown in FIG. 5-66. These apertures 7061 can be evenly spaced (e.g., provided every 90°) or unevenly spaced. These apertures are to allow rotation and thus adjustment of the tube retainer when connected to the buckle. The keyhole 7060 may have a tapered entry 7062 as shown in FIG. 5-67. Tapered entry 7062 provides a lead-in for the tube retainer 7100 to ensure correct alignment of tube retainer 7100 with buckle 7000.

The keyhole 7060 may also have one or more additional holes 7065 about the keyhole 7060 as shown in FIGS. 5-54 to 5-63. In an embodiment, the additional holes 7065 may follow the general path of the keyhole 7060 (as shown in FIGS. 5-54 and 5-55) or the additional holes 7065 may follow a path unlike the keyhole 7060 (as shown in FIG. 5-56). In embodiments, the additional holes 7065 may be substantially the same length as keyhole 7060, longer than the keyhole 7060 (as shown in FIGS. 5-56 and 5-63), or shorter than the keyhole 7060 (as shown in FIGS. 5-54 and 5-55). The width of the additional holes 7065 may be relatively thin (e.g., 0.5 mm, see FIGS. 5-57 and 5-59) or relatively thick (e.g., 4 mm, see FIGS. 5-58 and 5-61) and the thickness may vary along its length. In another embodiment, the additional holes 7065 may vary in number, e.g., there may be 1, 2, 3, 4, or more additional holes (see FIG. 5-59). In yet another embodiment, the additional holes 7065 may adjoin keyhole 7060 (as shown in FIGS. 5-56 to 5-59) or may be separated from keyhole 7060 (as shown in FIGS. 5-54 and 5-55).

The additional holes 7065 are provided to allow spring or resilient flexibility during engagement of the tube retainer 7100 with the keyhole 7060 and also during rotation of the tube retainer 7100 when engaged with the keyhole 7060. Adjusting the length of holes 7065 will alter the spring properties and thus ease of engagement and disengagement and also rotation of the tube retainer 7100 with the buckle 7000.

Figures 5, 62:
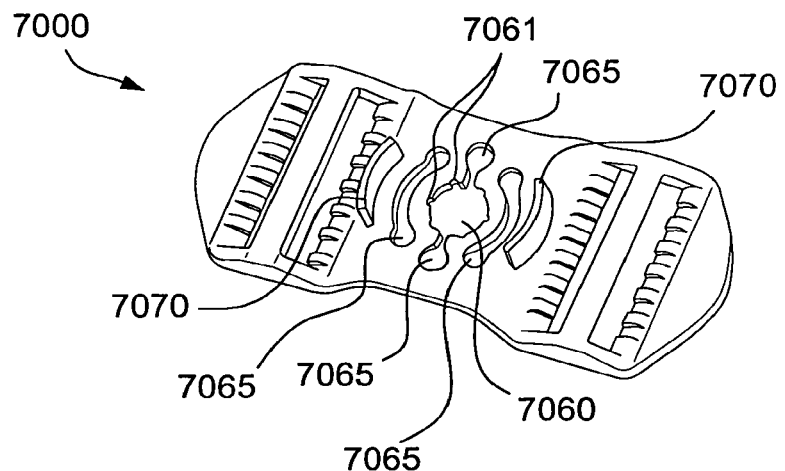
Figures 5, 63:
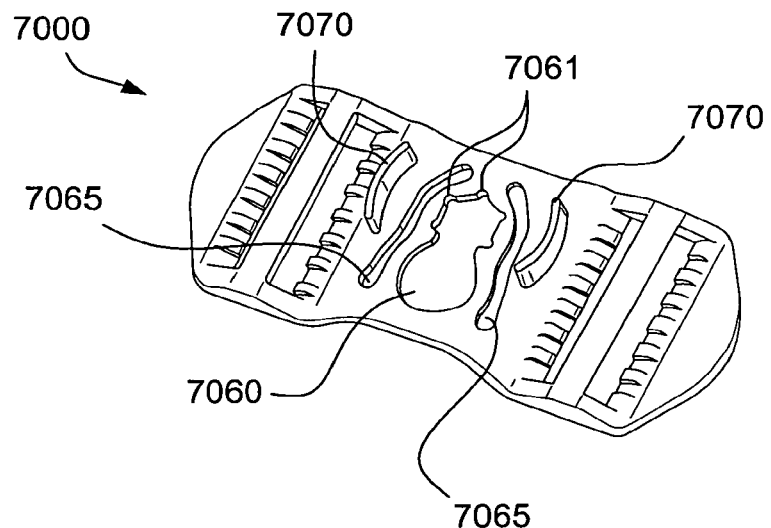
Figures 5, 64:
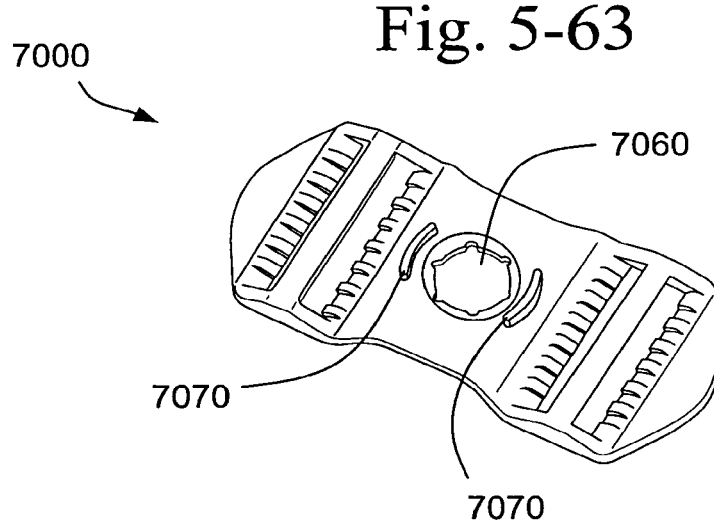
Figures 5, 65:
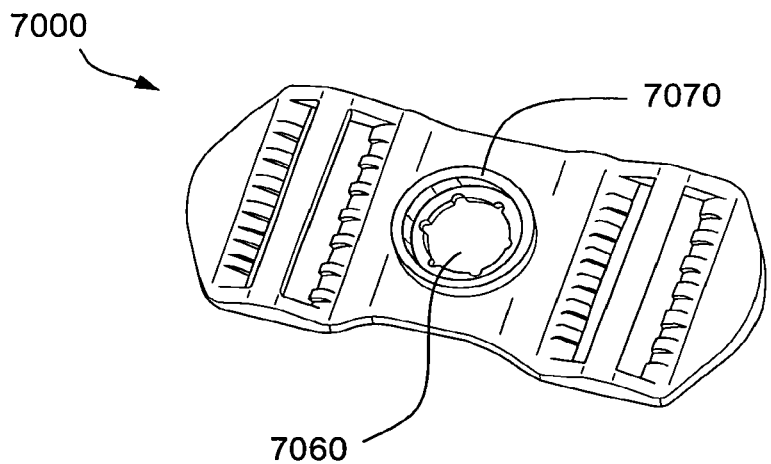
Figures 5, 66:
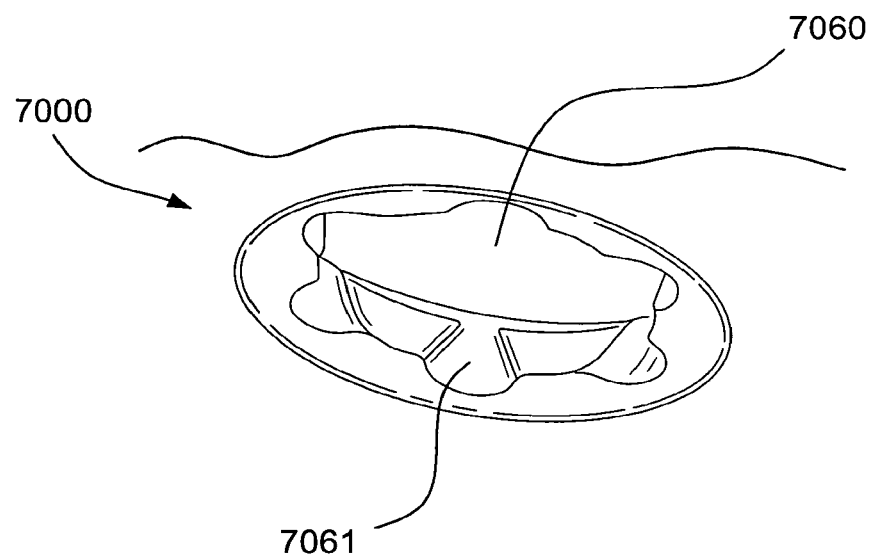
Figures 5, 67:
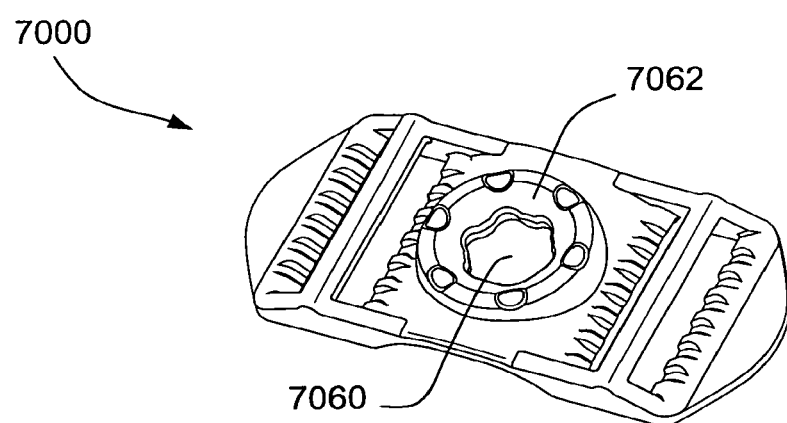

In an embodiment, a locking collar 7070 may be provided around keyhole 7060 (see FIG. 5-60) or around the keyhole 7060 and additional holes 7065 (see FIGS. 5-62 and 5-63). The locking collar 7070 may follow the path of the keyhole 7060, as shown in FIGS. 5-60 and 5-65. The locking collar 7070 may extend around the entire perimeter of the keyhole 7060 (see FIGS. 5-60 and 5-65) or may follow a portion or portions of the keyhole 7060 (see FIG. 5-64). Locking bumps 7071 may be provided along the locking collar 7070 (shown in FIG. 5-60) to allow for fixed rotation of the tube retainer 7100 with respect to the buckle 7000 (e.g., detent assembly). The locking bumps 7071 may be generally hemispherical (as shown in FIG. 5-60), conical, or any other suitable shape. The number of locking bumps 7071 may be varied (e.g., 3, 6, or other suitable number) to alter the number of fixed positions of the tube retainer 7100 with respect to the buckle 7000.

Tube Retainer

Figures 5, 68:
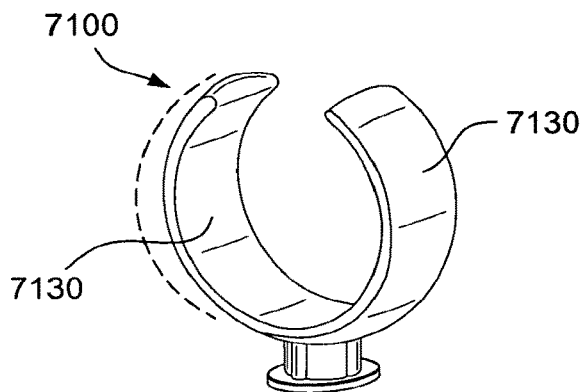
Figures 5, 69:
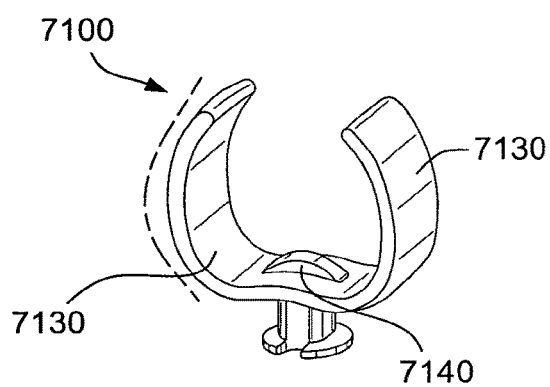
Figures 5, 70:
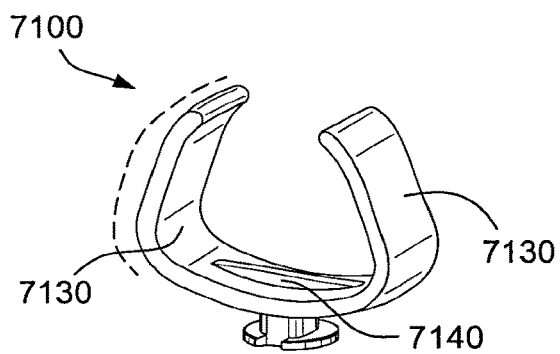
Figures 5, 71:
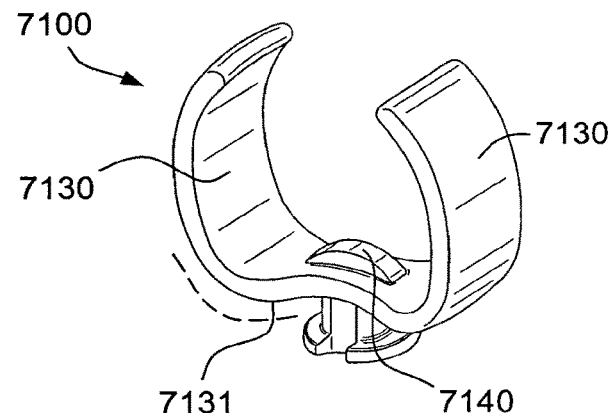
Figures 5, 72:
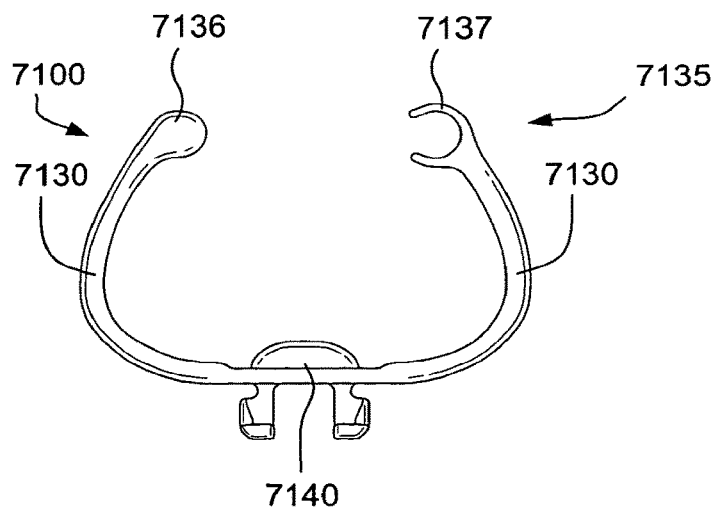
Figures 5, 73:
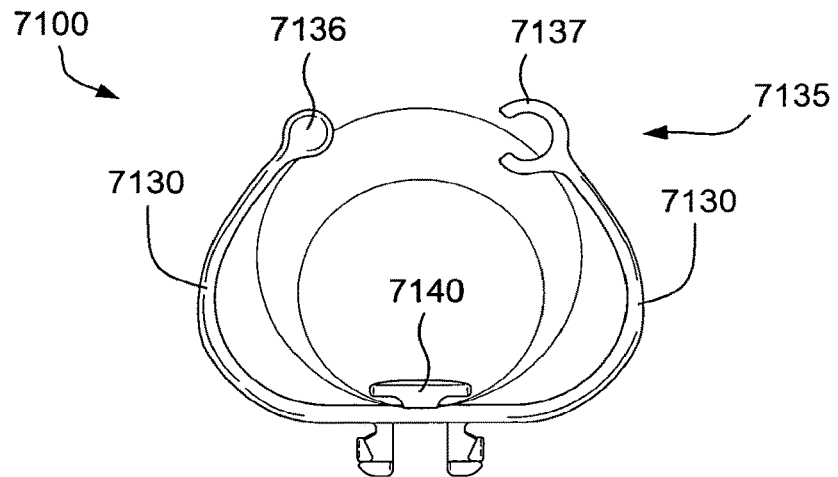
Figures 5, 74:
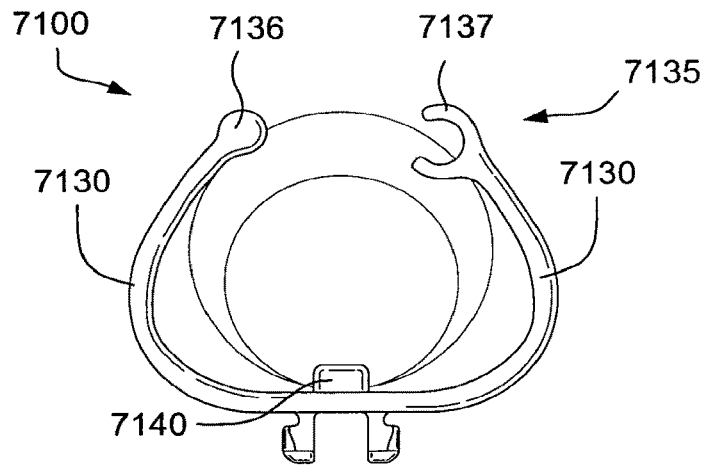
Figures 5, 75:
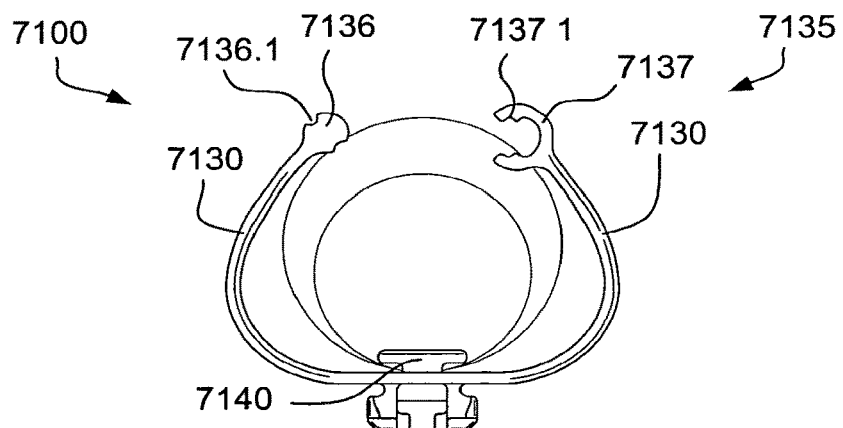
Figures 5, 76:
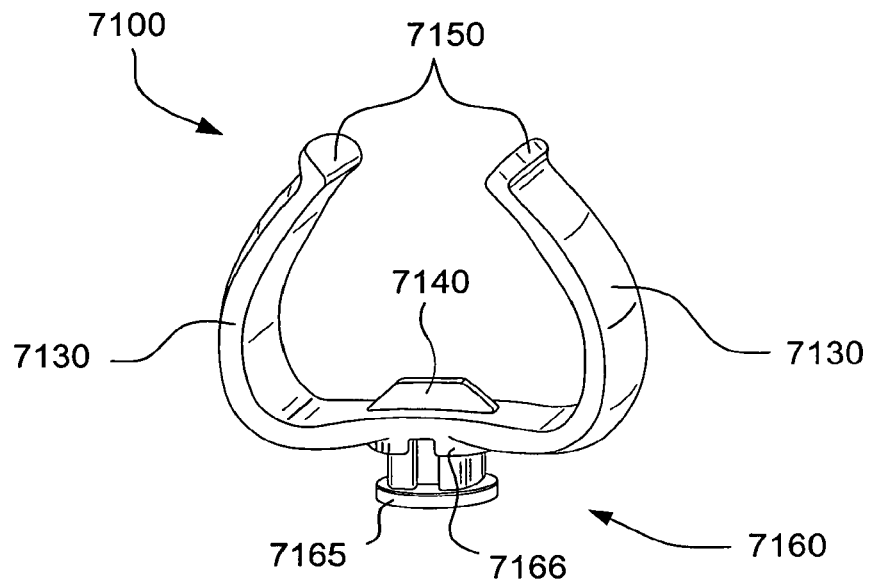
Figures 5, 77:
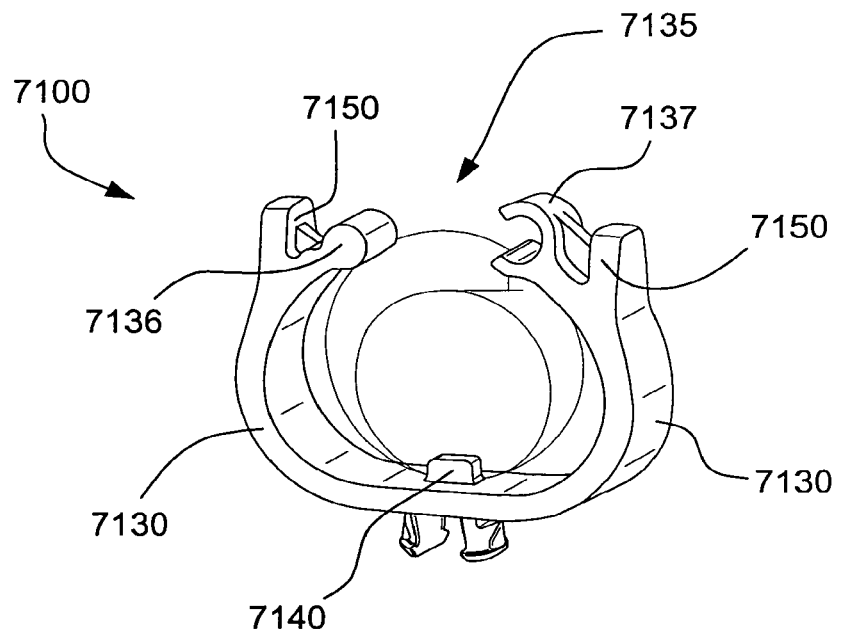
Figures 5, 78:
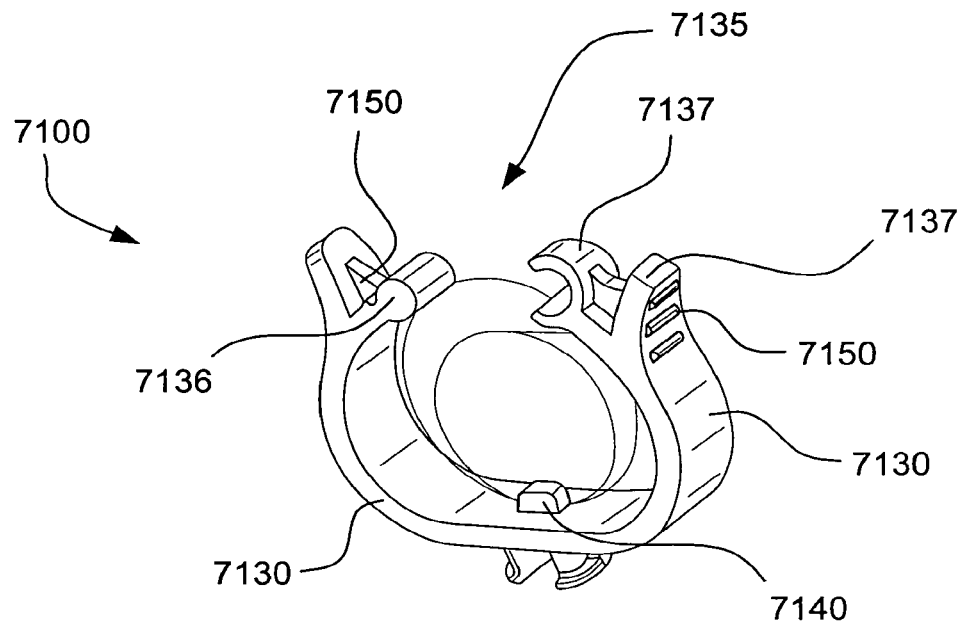
Figures 5, 79:
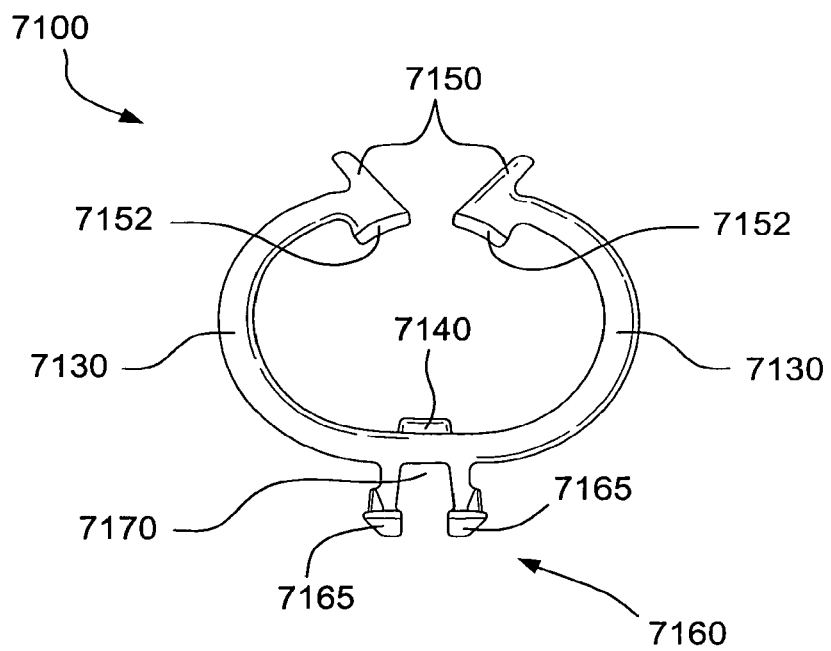
Figures 5, 80:
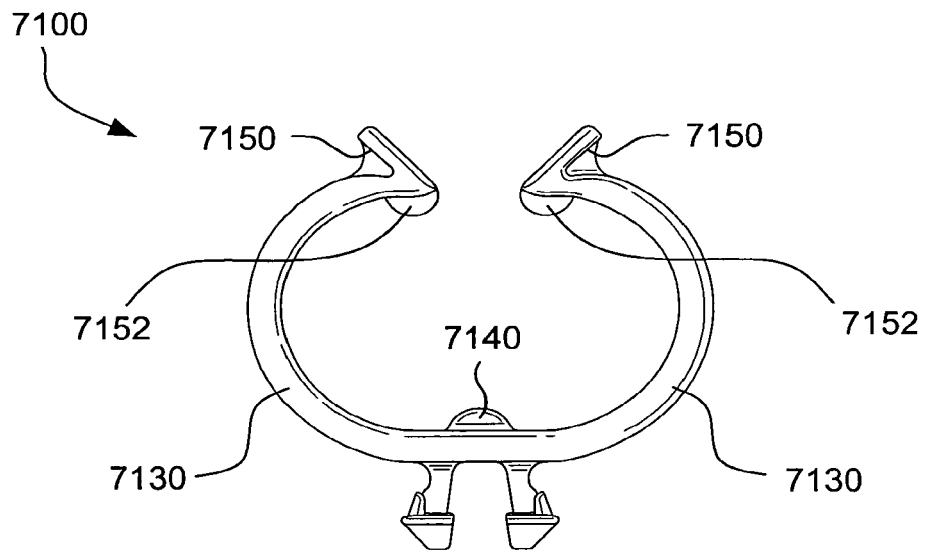
Figures 5, 81:
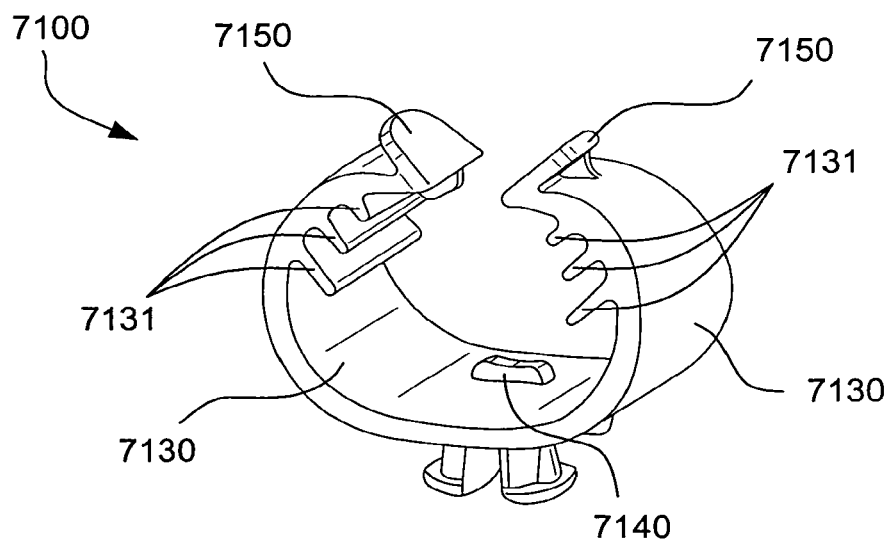
Figures 5, 82:
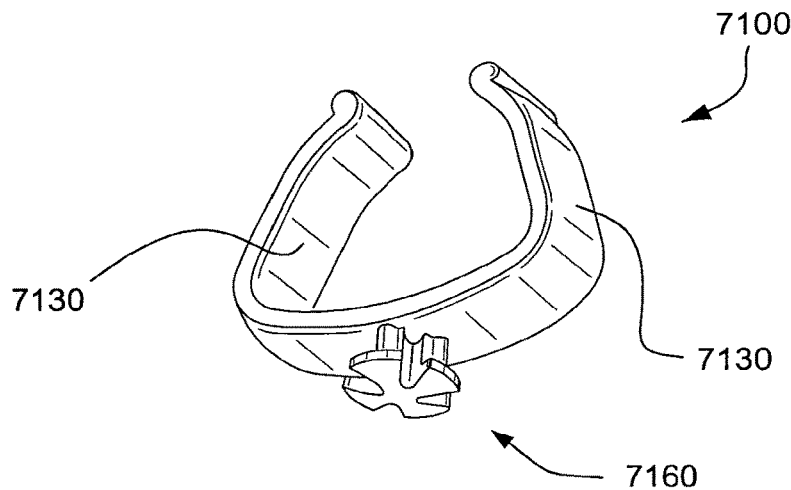

As shown in FIGS. 5-68 to 5-82, each tube retainer 7100 has a generally rounded curvature, an opening to allow a tube to pass through its circumference, and a tab adapted to engage with a buckle 7000.

Arms

In the illustrated embodiments, each tube retainer 7100 has two arms 7130 each with a generally rounded curvature. In an embodiment, the arms 7130 may be generally circular as shown in FIG. 5-68 or may be generally elliptical as shown in FIG. 5-69. In an alternative embodiment, the arms 7130 may be irregularly shaped as shown in FIG. 5-70. Furthermore, the lower portion of the arms 7130 may be recessed to increase flexibility (e.g., see recessed portion 7131 shown in FIG. 5-71).

In an embodiment, a rib 7140 may be provided to the base of the arms 7130 (as shown in FIGS. 5-69 to 5-74). In an embodiment, the rib 7140 may be generally hemispherical or curved as shown in FIGS. 5-69, 5-71 and 5-72. In an alternative embodiment, the rib 7140 may be generally rectangular (or square) as shown in FIGS. 5-70 and 5-74. In another embodiment, the rib 7140 may be raised from the surface of arms 7130 as shown in FIG. 5-73 (e.g., T-shaped). The rib 7140 prevents the air delivery tube from sliding erratically once engaged with tube retainer 7100, meaning that the headgear and air delivery tube can be held in a secure position.

In an embodiment, the arms 7130 may have a locking mechanism 7135 that operates with a ball and clasp type joint (e.g., see FIGS. 5-72 to 5-75, 5-77, and 5-78). As illustrated, the locking mechanism 7135 includes a ball 7136 on one of the arms 7130 and a clasp 7137 on the other of the arms 7130. In use, the ball 7137 and clasp 7137 can be pushed together and interlocked to close the arms 7130 around the air delivery tube. In an embodiment, the clasp 7137 may have one or more teeth 7137.1 on its inner radius that are adapted to engage with respective grooves 7136.1 on the ball 7136 as shown in FIG. 5-75. The teeth to grooves feature will further secure and retain the locking mechanism 7135 in its locking position.

In another embodiment, the upper ends of the arms 7130 may include a lead-in 7150 as shown in FIG. 5-76. The lead-in 7150 enables easier insertion of the air delivery tube through the gap between the arms 7130. The lead-in 7150 may also be combined with a locking mechanism 7135 as shown in FIGS. 5-77 and 5-78. In FIG. 5-78, ribbing 7151 may be provided to the under surface of each lead-in 7150. Ribbing 7151 enables the user to obtain a better grip when pulling the arms 7130 outward to remove the air delivery tube or when disengaging the locking mechanism 7135. In yet another embodiment, teeth 7152 may be provided to the inner surface of the lead-in 7150 to contact the air delivery tube and provide better stability of the air delivery tube, as shown in FIGS. 5-79 and 5-80. The teeth 7152 may be generally square (as shown in FIG. 5-79), may be generally round (as shown in FIG. 5-80), may have other suitable shapes.

The inner radius of the arms 7130 may also be provided with one or more ribs 7131 as shown in FIG. 5-81. In use, the ribs 7131 provide support for the air delivery tube in the lateral direction. There may be any suitable number of ribs 7131 (e.g., 2, 4, 7, or more) and these ribs may be spaced evenly or randomly. The ribs 7131 may also vary in size, e.g., the ribs may all be the same size or become longer to support different shaped tubes.

Tab

Figures 5, 83:
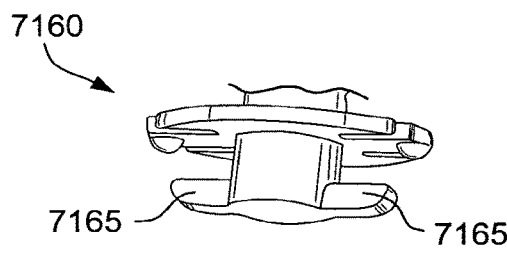
Figures 5, 84:
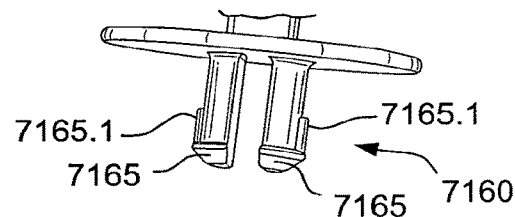
Figures 5, 85:
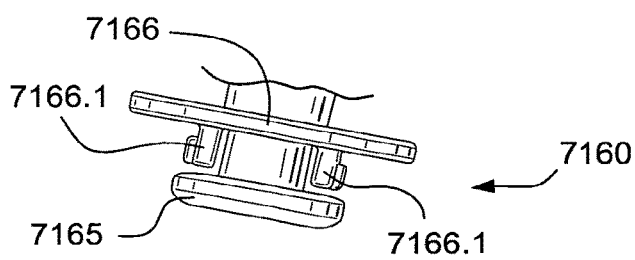
Figures 5, 86:
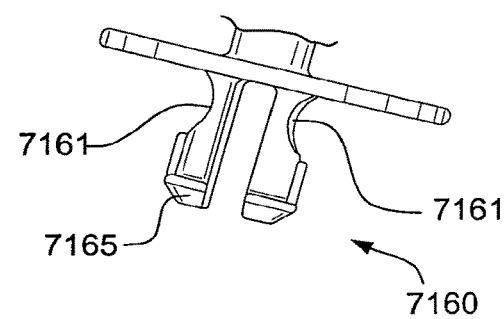
Figures 1, 6:
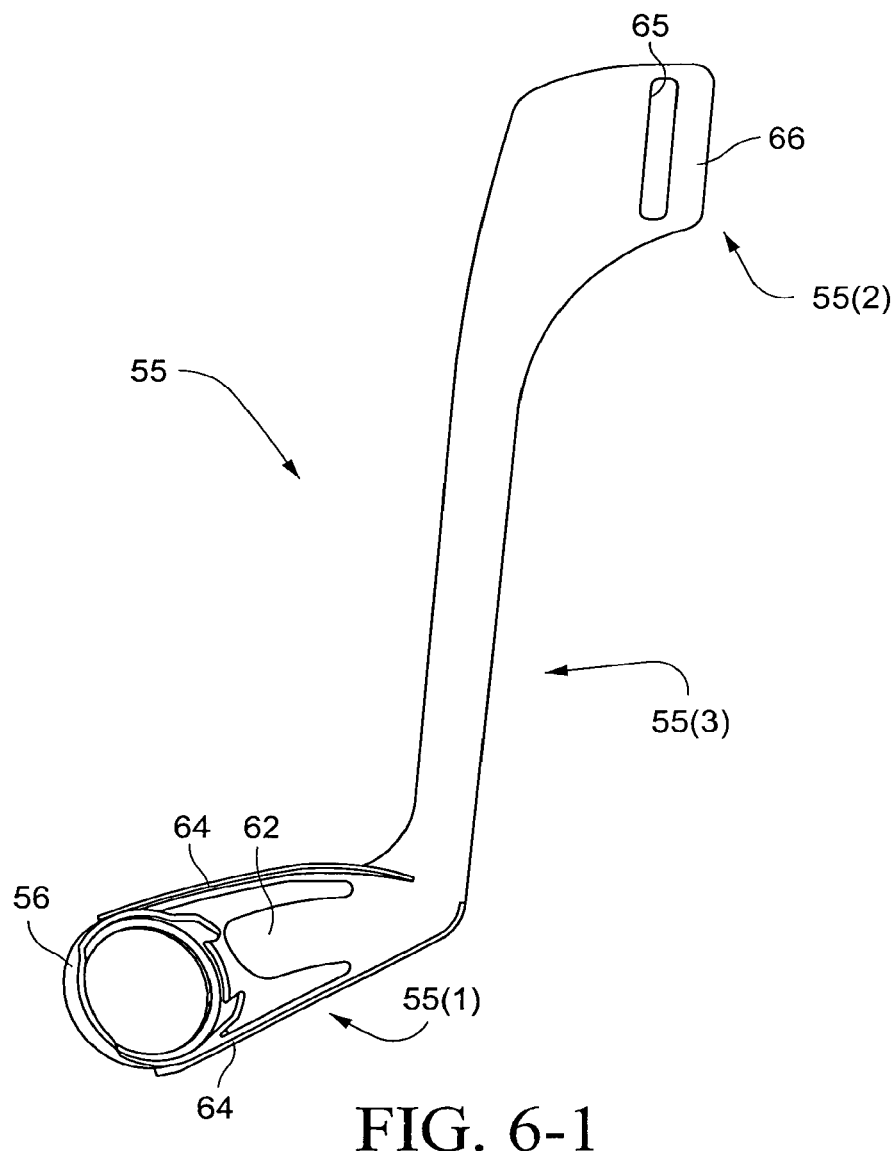
Figures 2, 6:
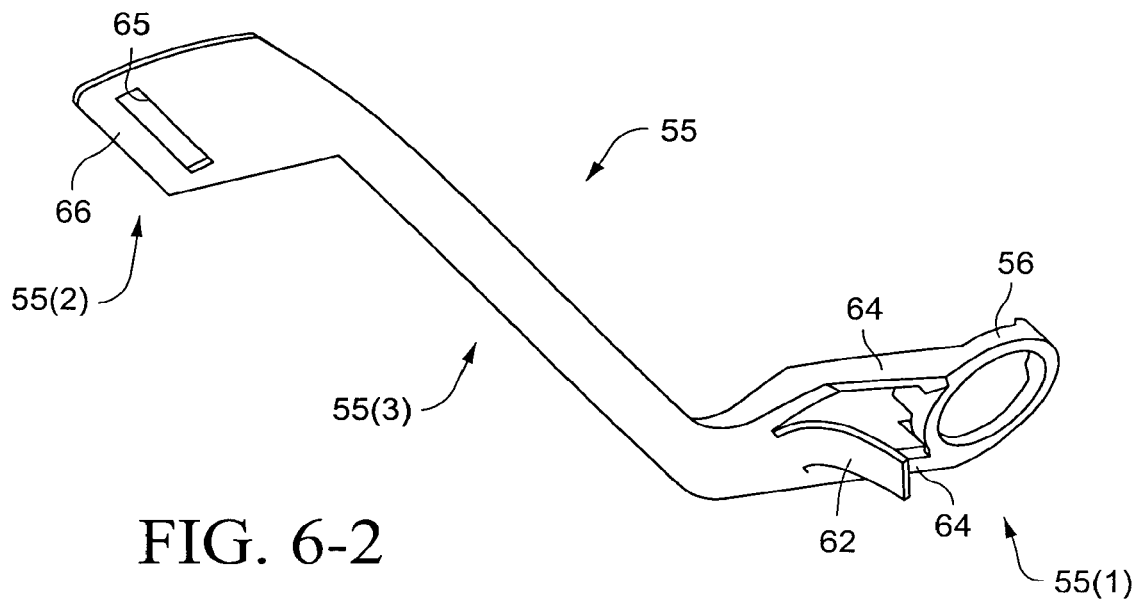
Figures 3, 6:
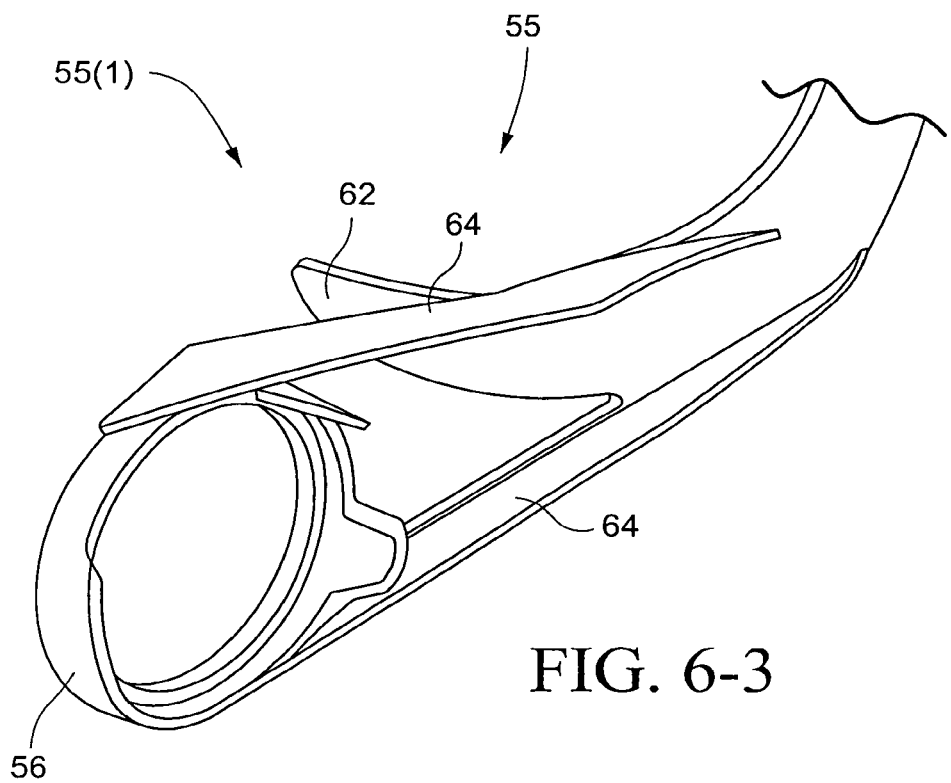
Figures 4, 6:
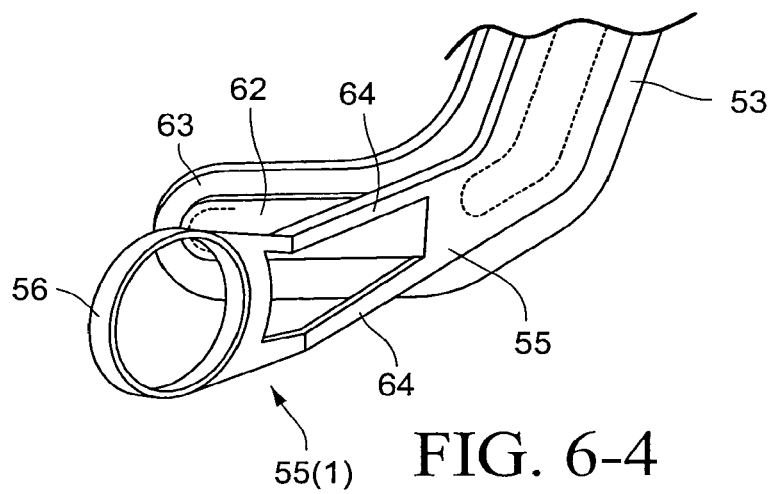
Figures 5, 6:
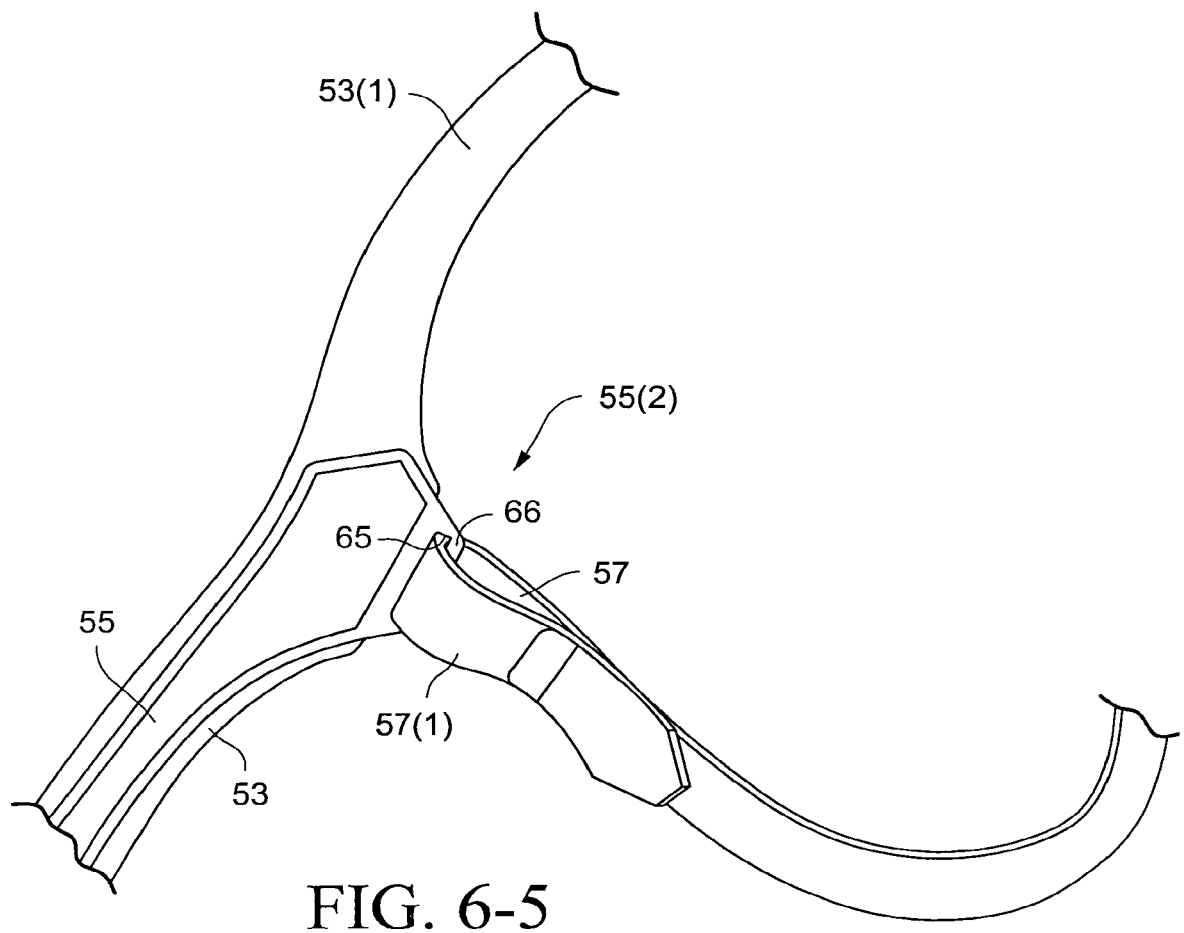
Figures 1, 7:
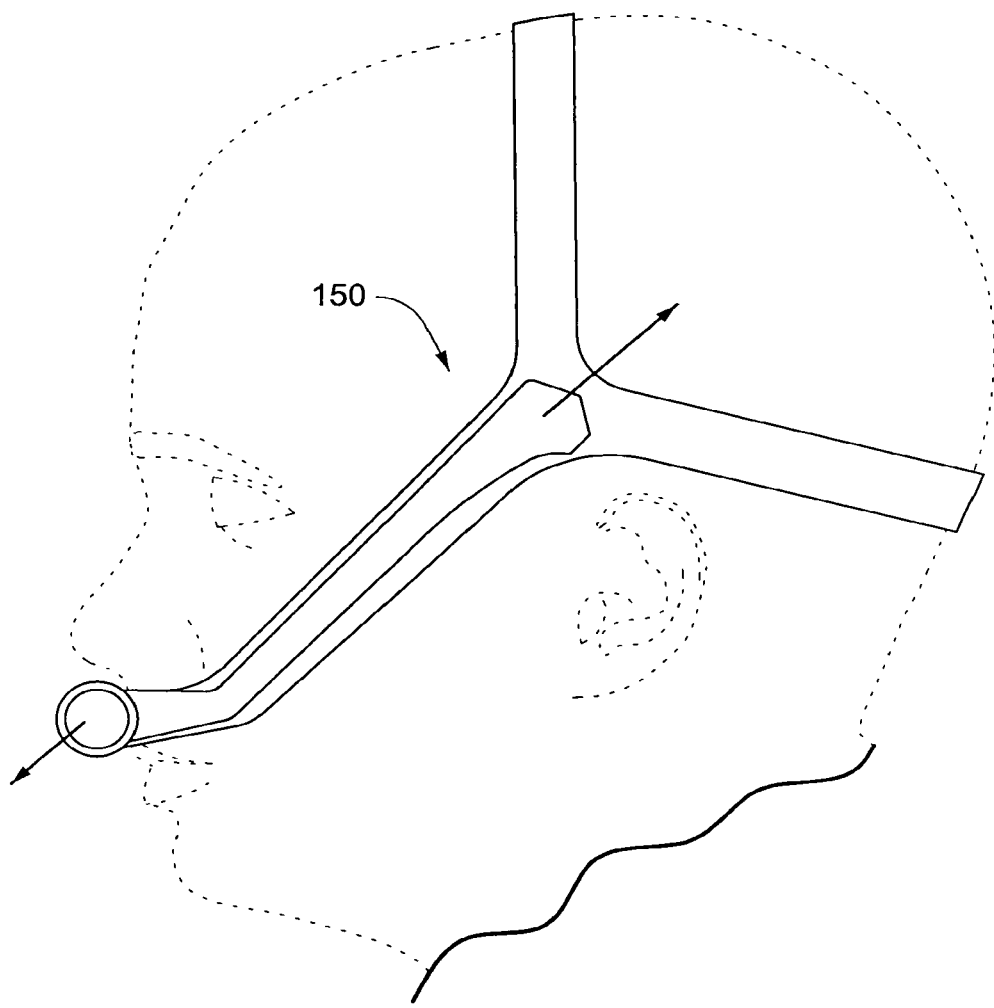
Figures 2, 7:
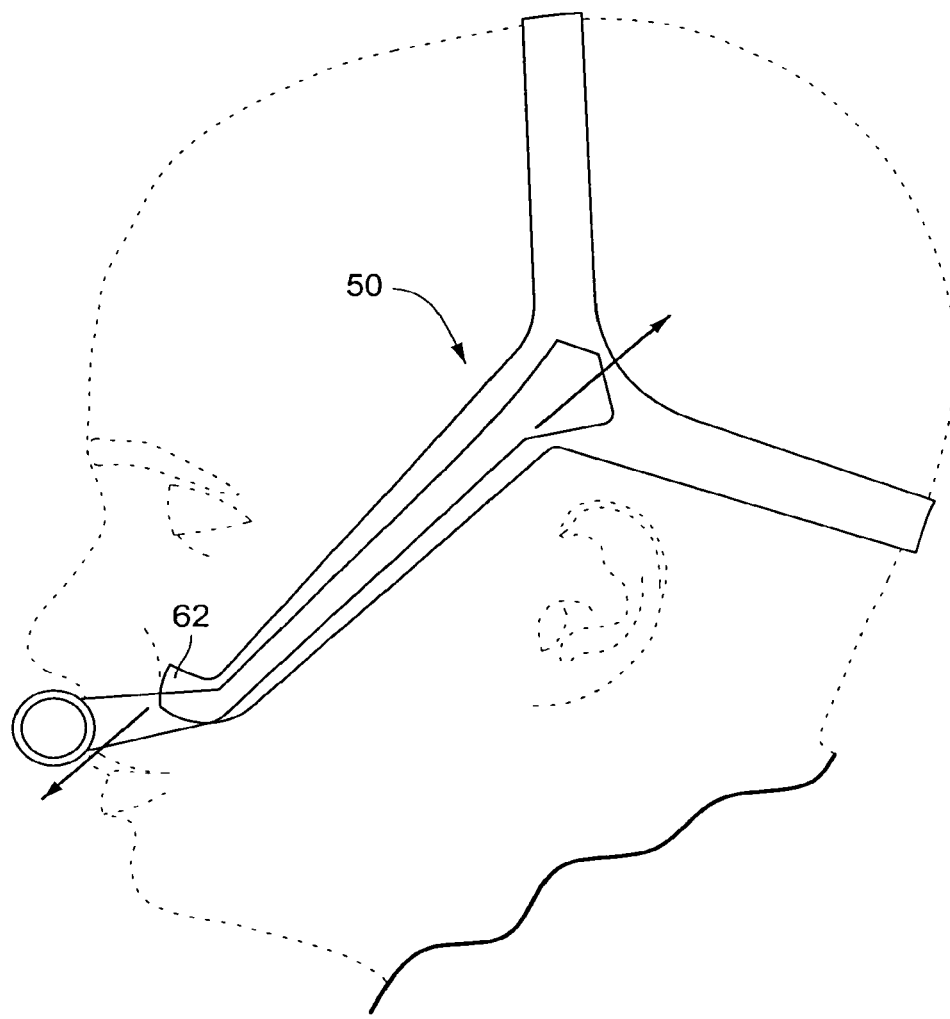
Figures 1, 8:
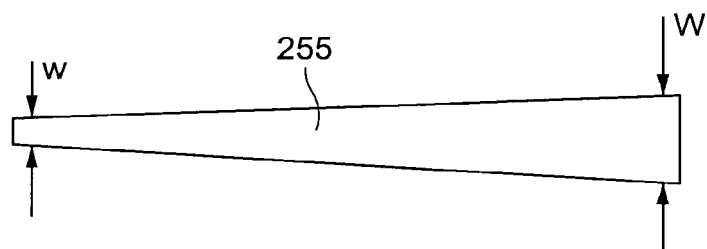
Figures 2, 8:
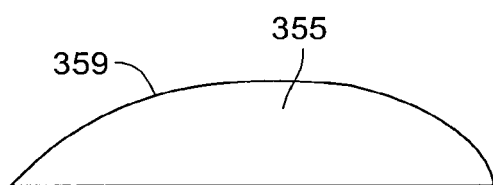
Figures 4, 8:
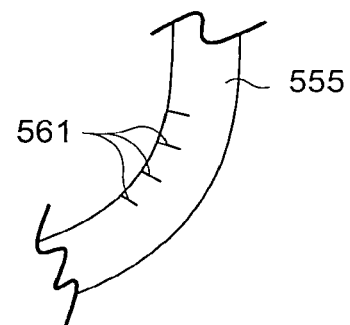
Figures 3, 8:
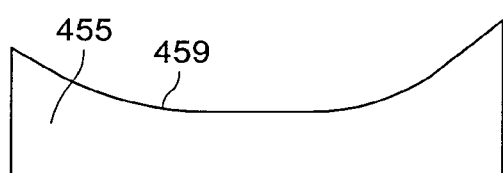
Figure 9:
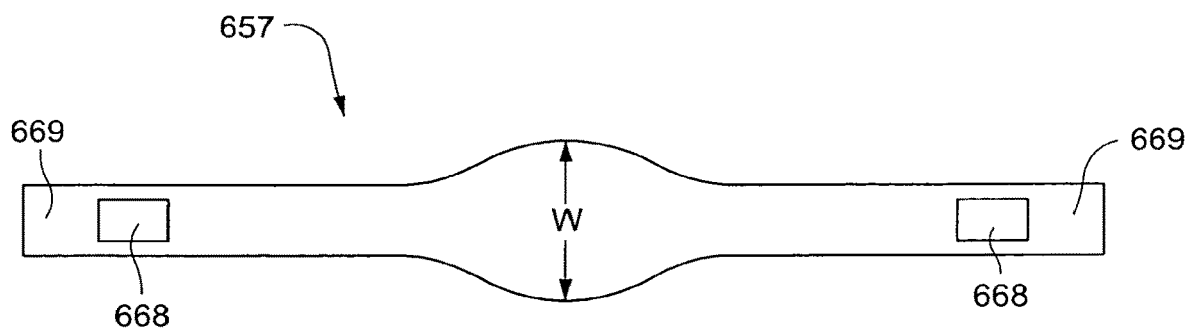
Figures 1, 10:
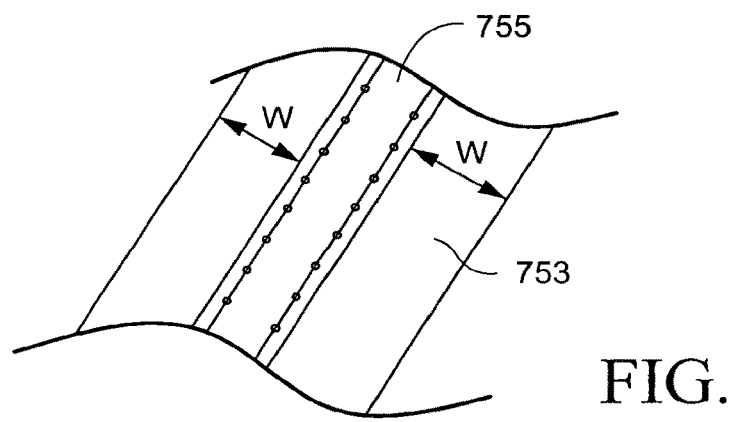
Figures 1, 2, 10:
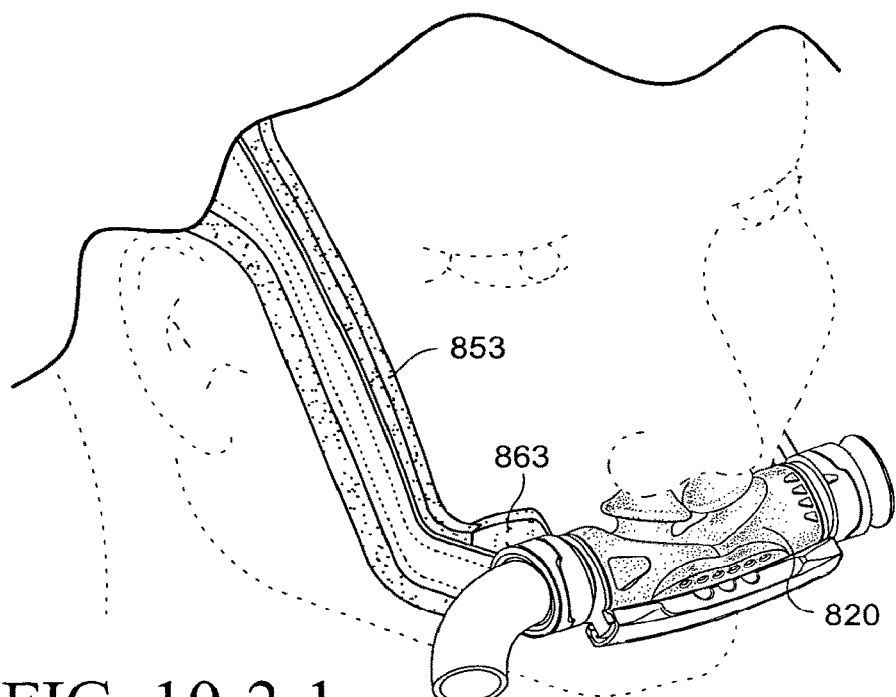
Figures 2, 10:
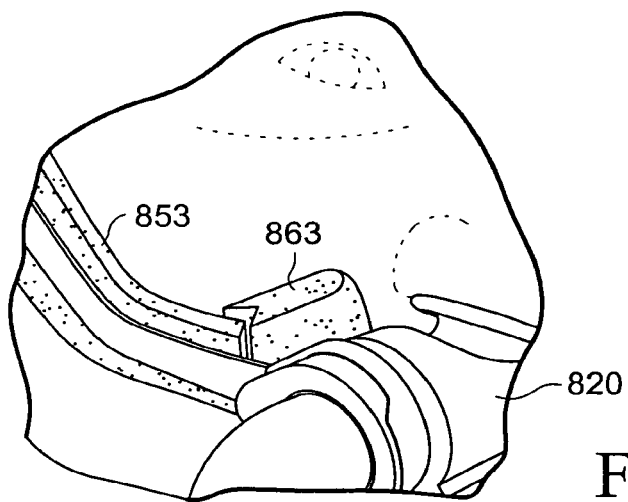
Figures 1, 3, 10:
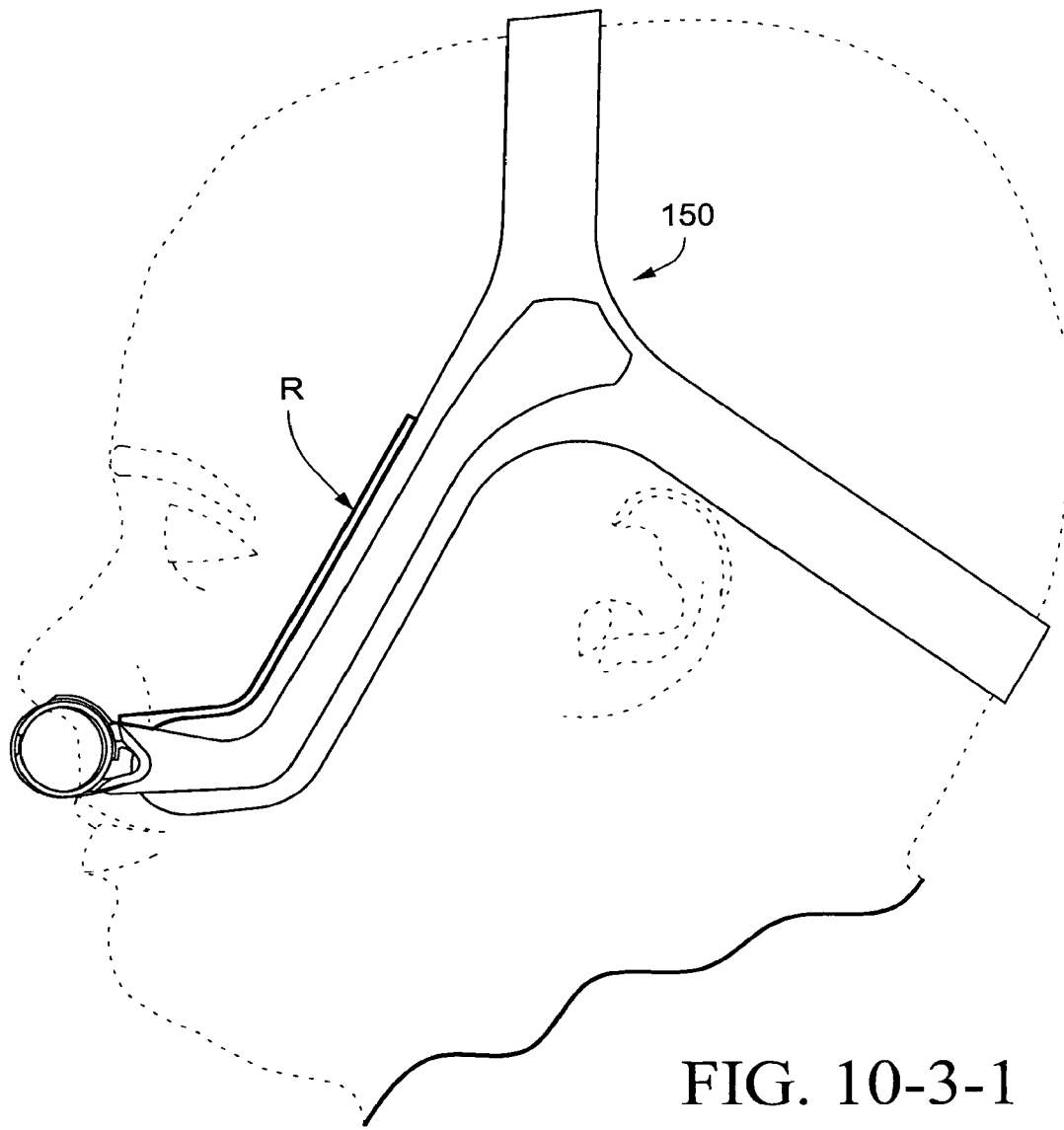
Figures 1, 7, 10:
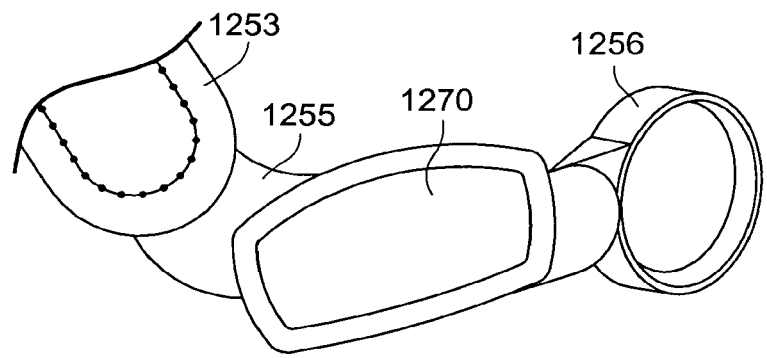
Figures 2, 7, 10:
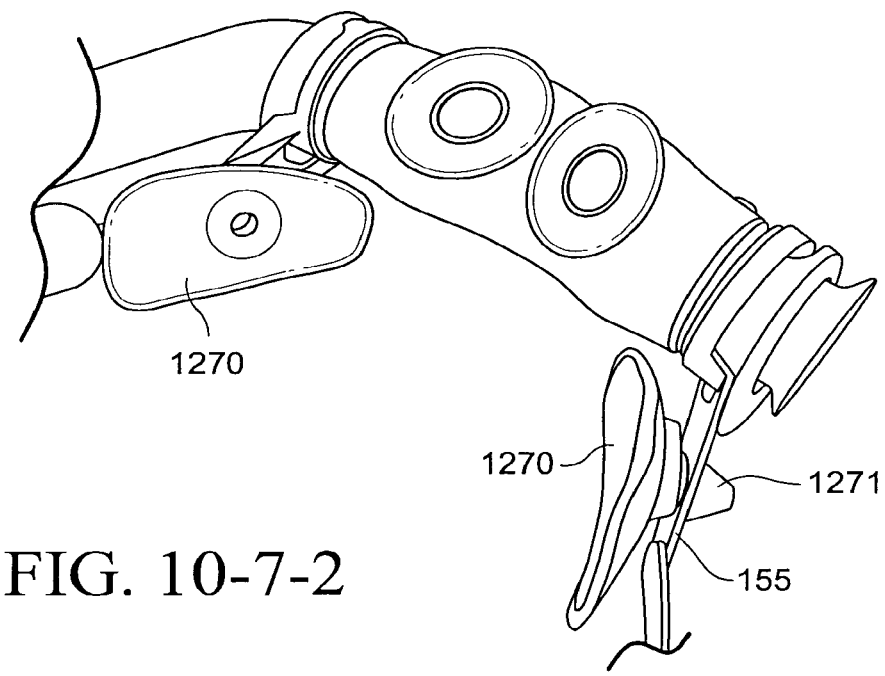
Figures 3, 7, 10:
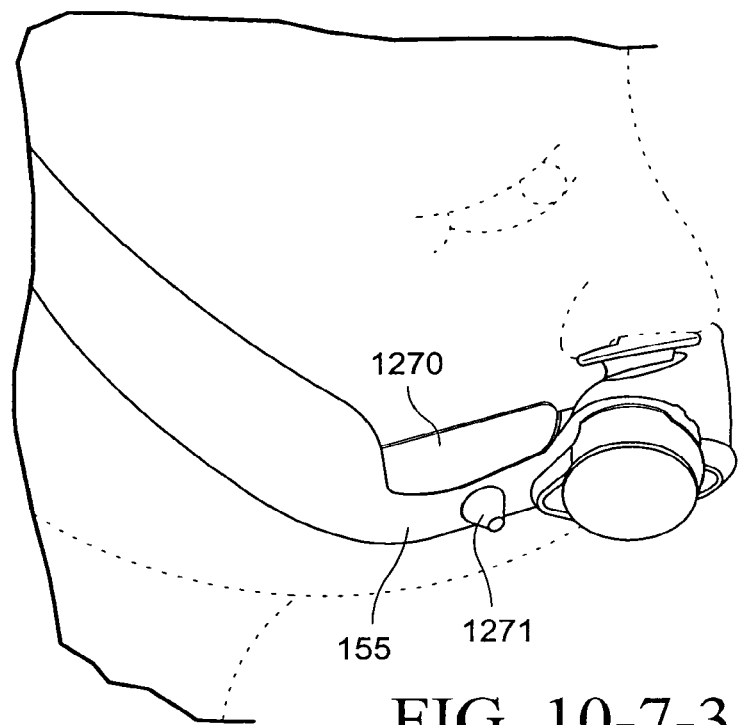
Figures 1, 8, 10:
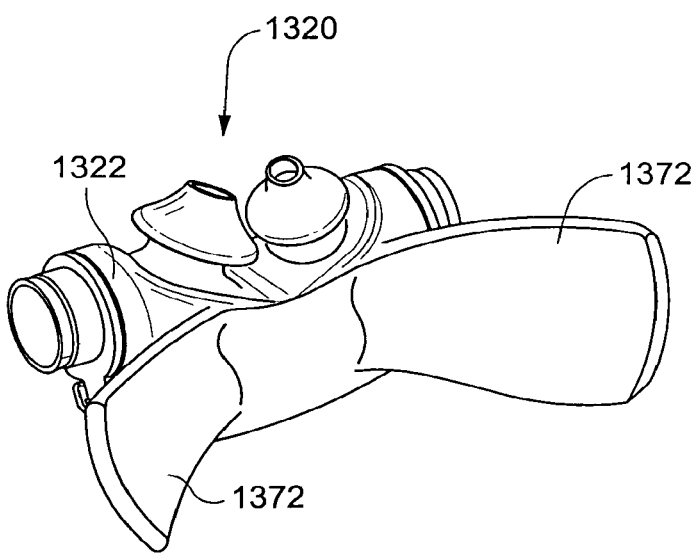
Figures 2, 8, 10:
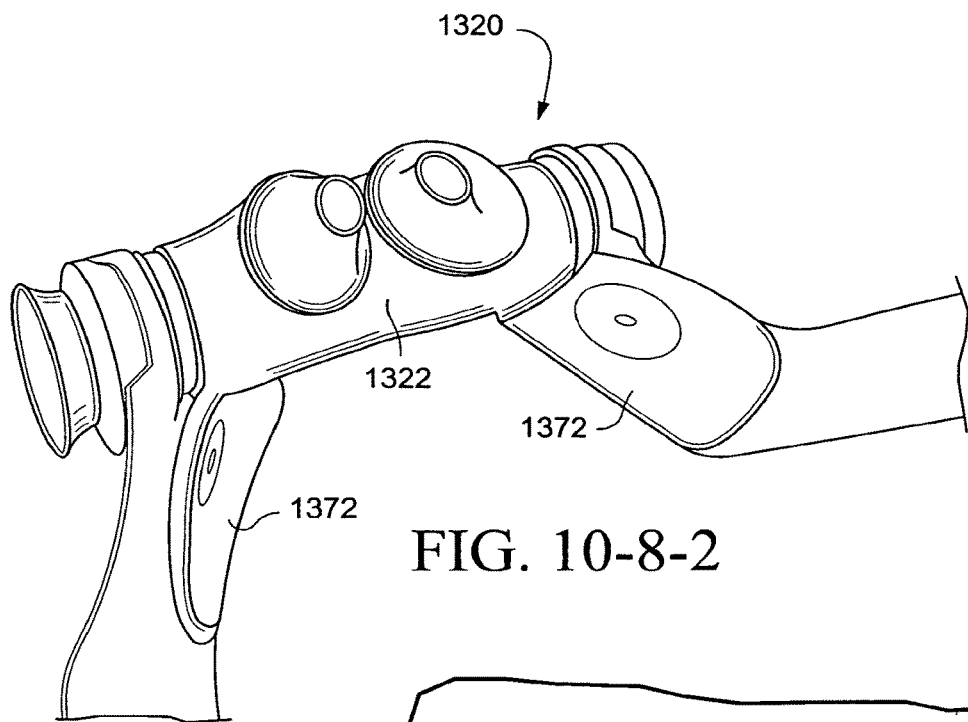
Figures 3, 8, 10:
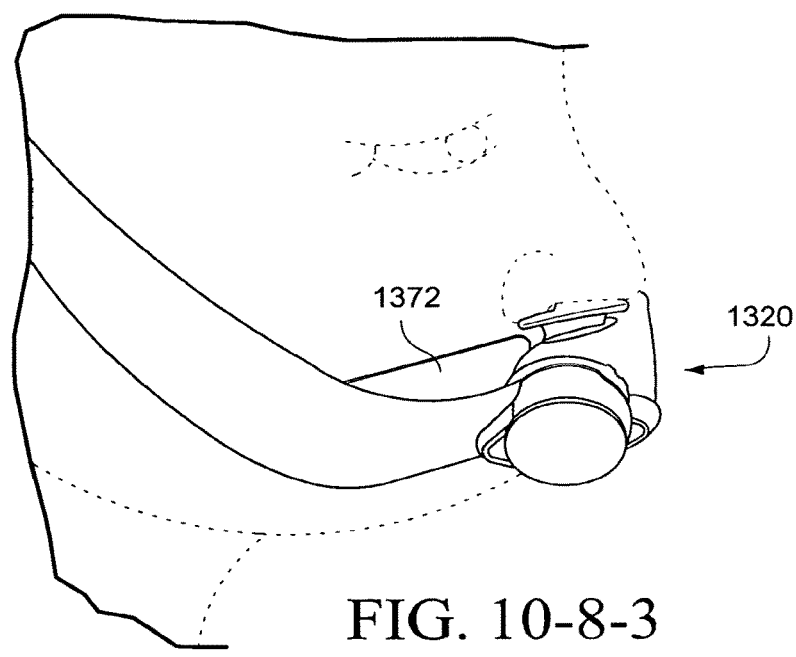
Figures 1, 9, 10:
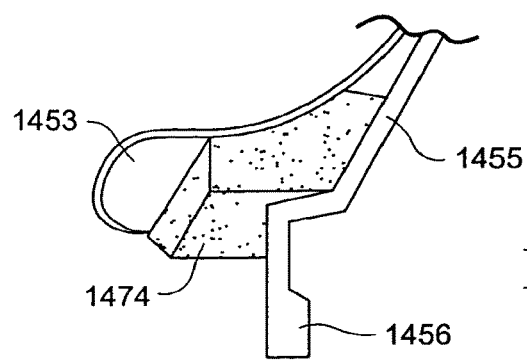
Figures 2, 9, 10:
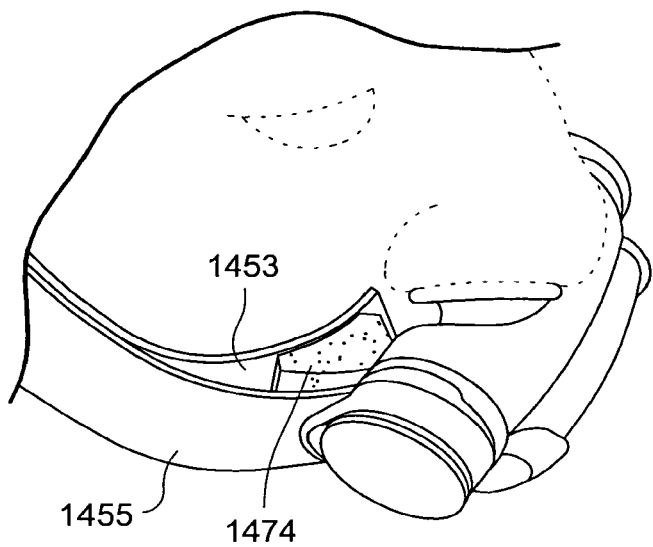
Figures 3, 9, 10:
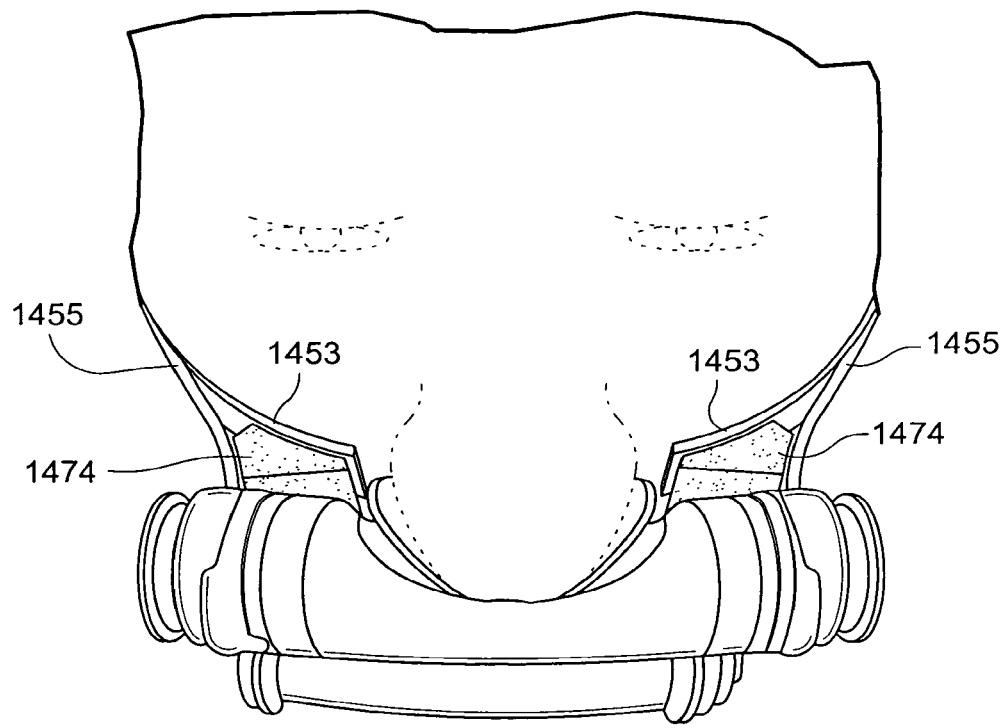
Figures 4, 9, 10:
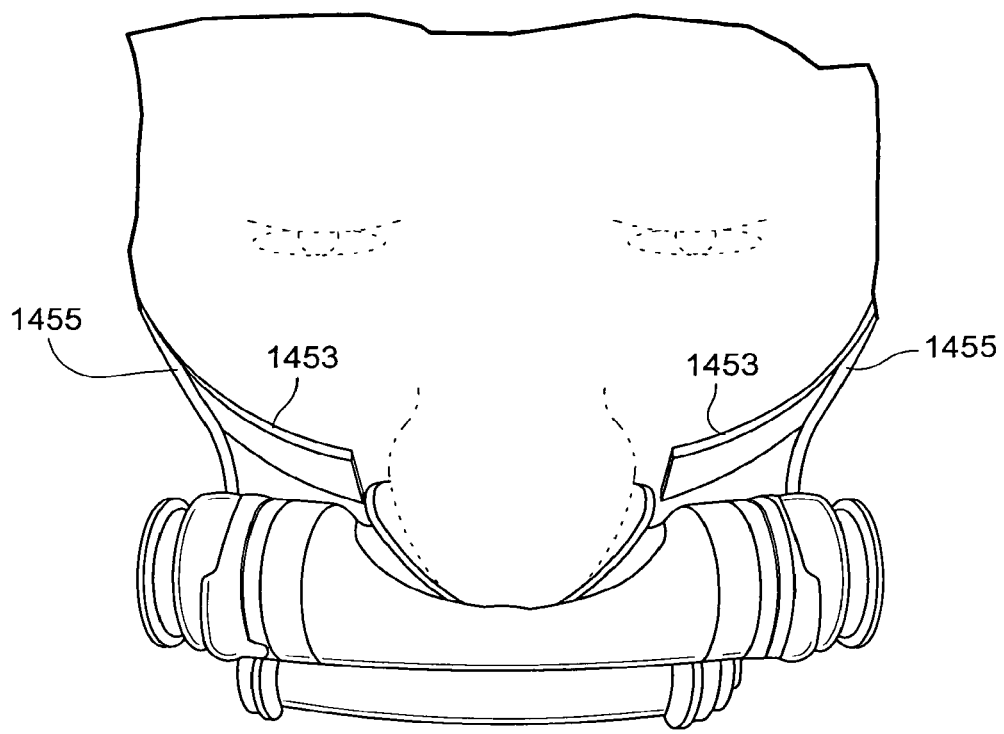
Figures 1, 11:
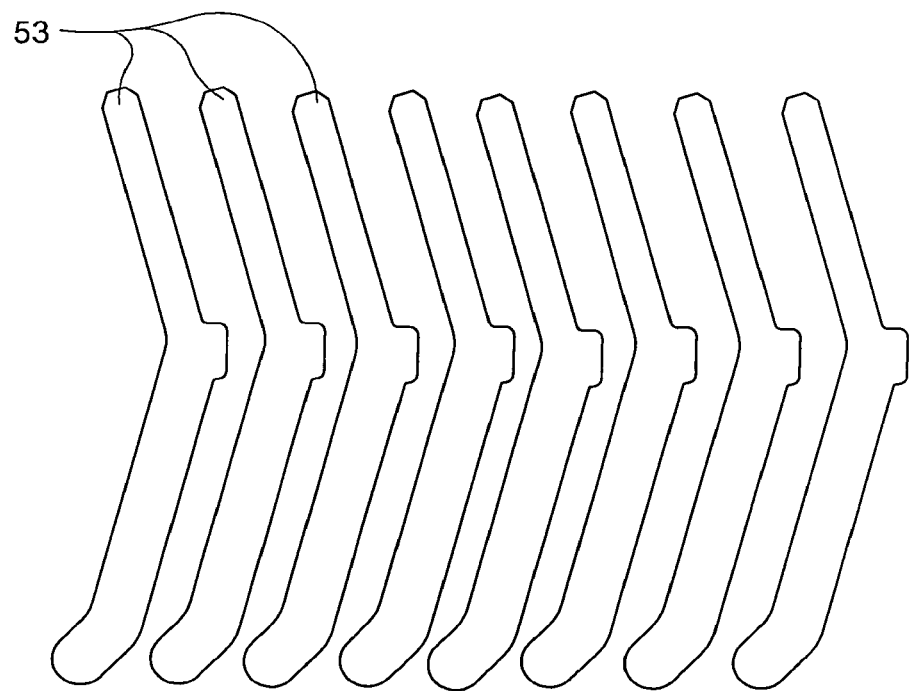
Figures 2, 11:
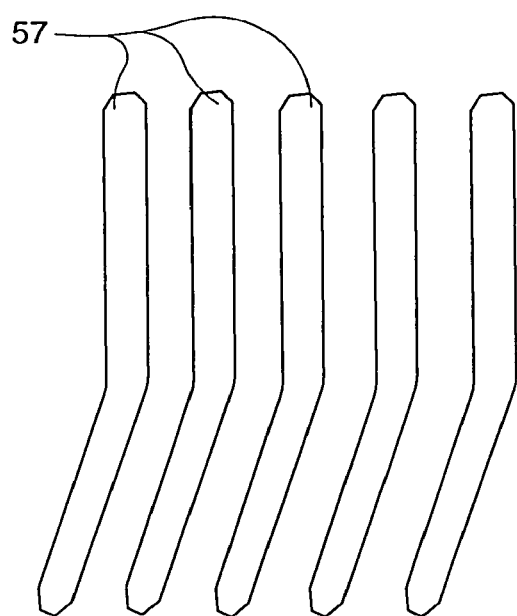
Figures 1, 12:
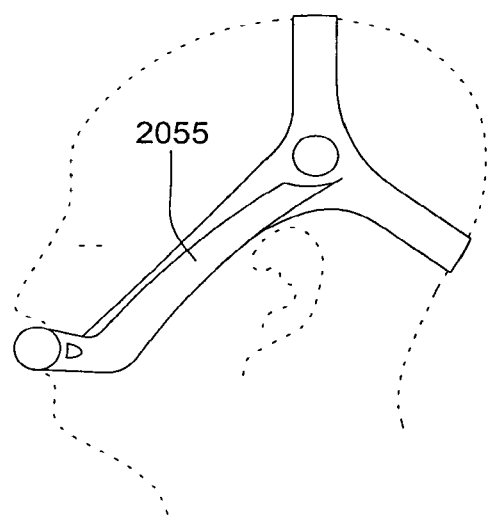
Figures 2, 12:
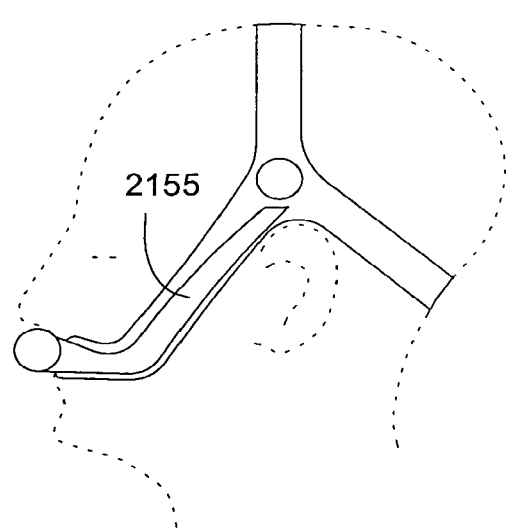
Figures 3, 4, 12:
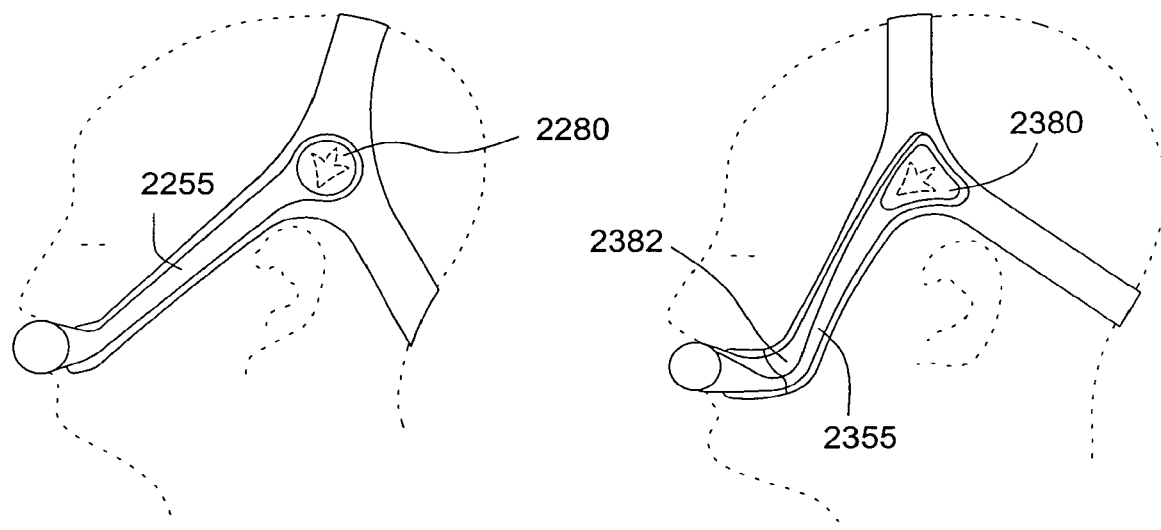
Figures 5, 12:
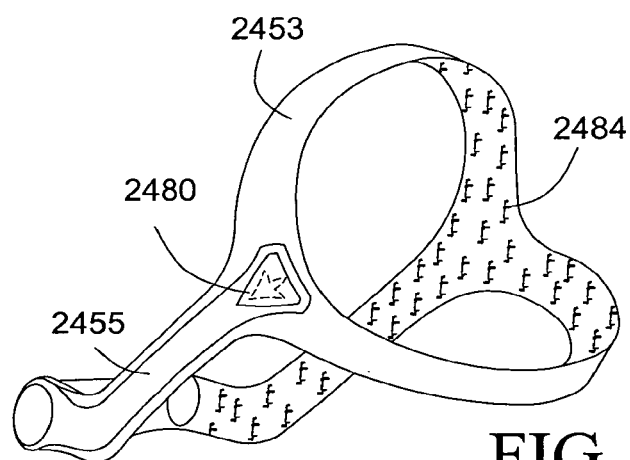
Figures 6, 12:
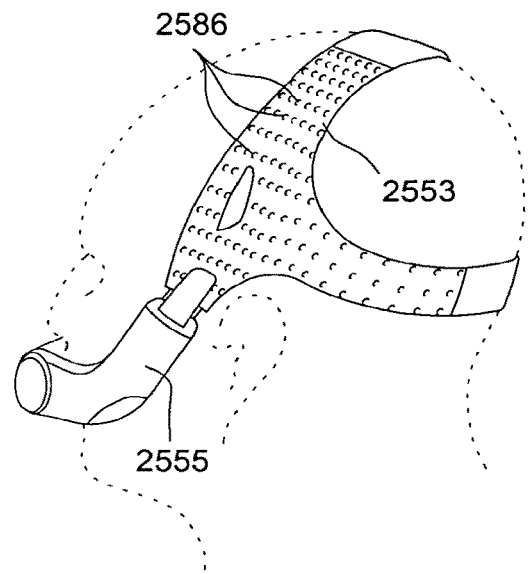
Figures 1, 7, 12:
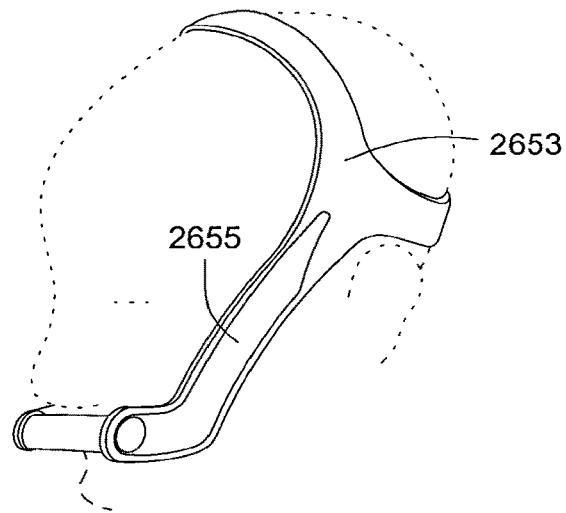
Figures 2, 7, 12:
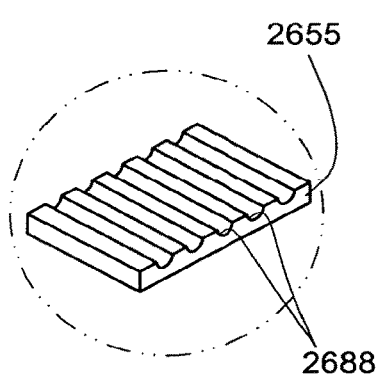
Figures 8, 12:
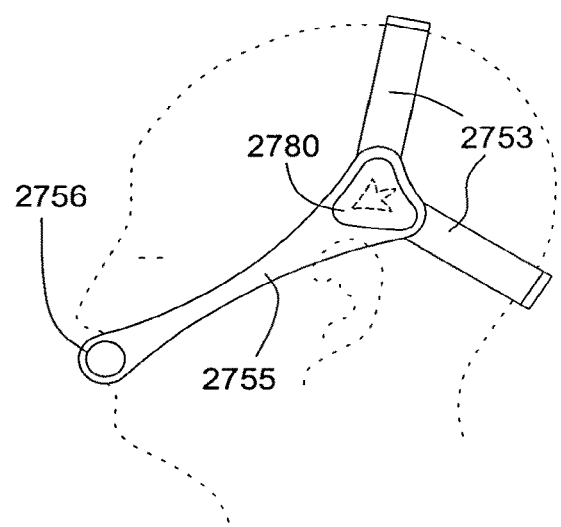
Figures 1, 9, 12:
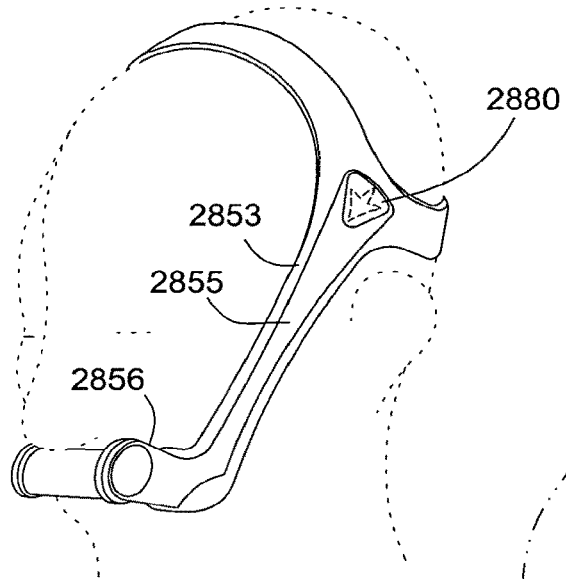
Figures 2, 9, 12:
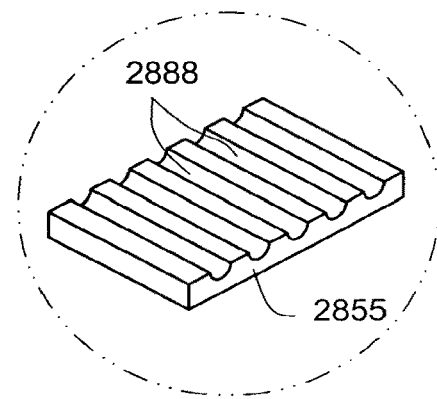
Figures 10, 12:
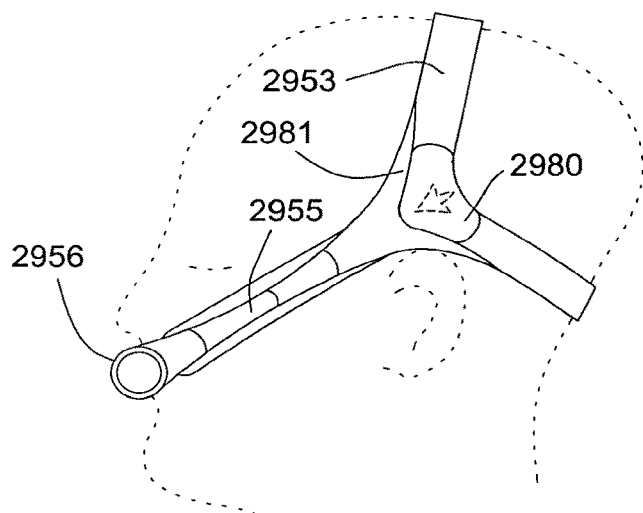
Figures 2, 11, 12:
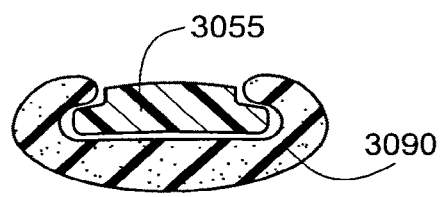
Figures 1, 11, 12:
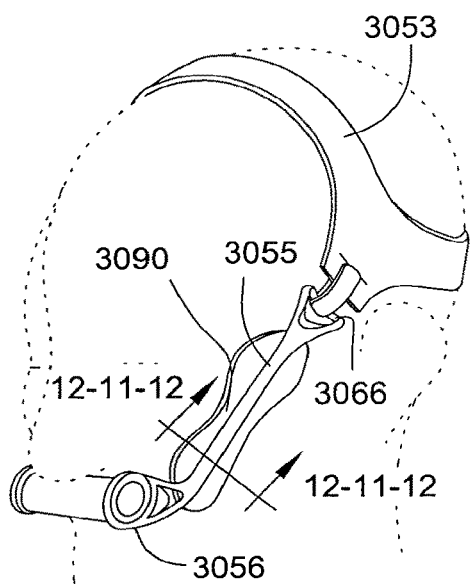
Figures 1, 12:
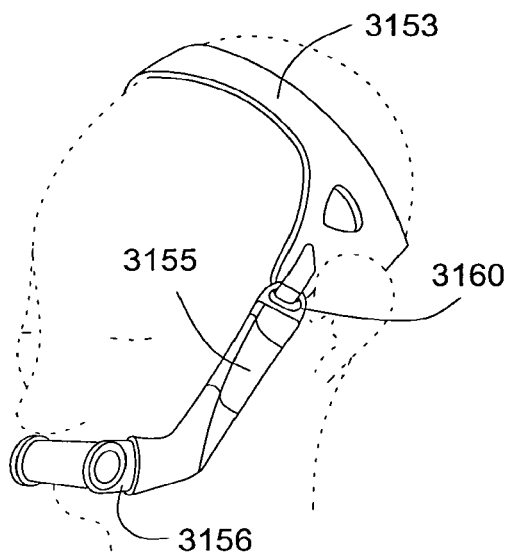
Figures 2, 12:
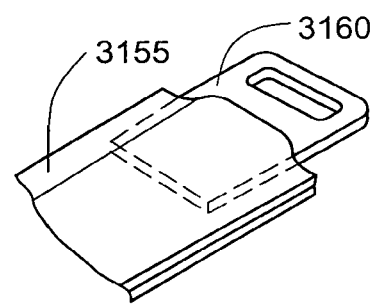
Figures 3, 12:
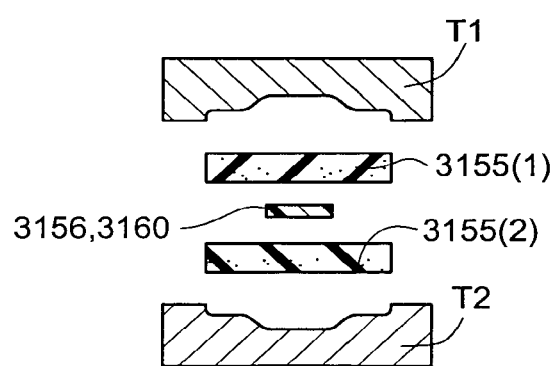
Figures 4, 12:
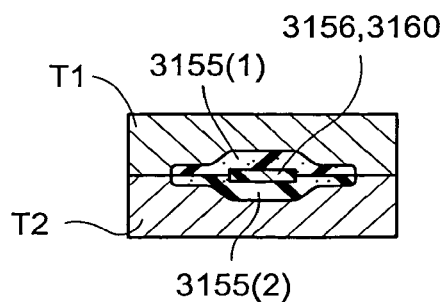
Figures 12, 13:
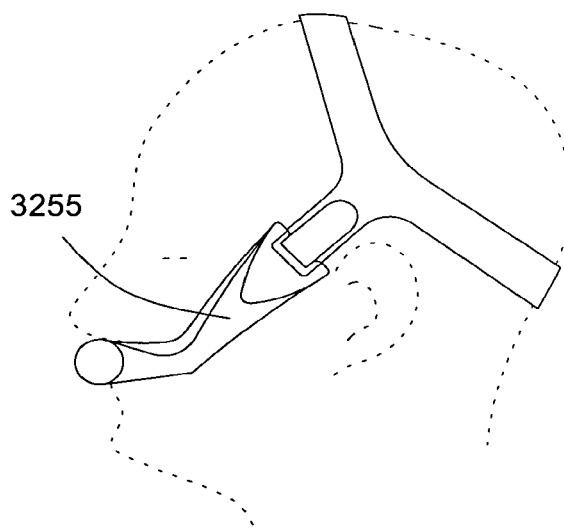
Figures 1, 12, 13, 14:
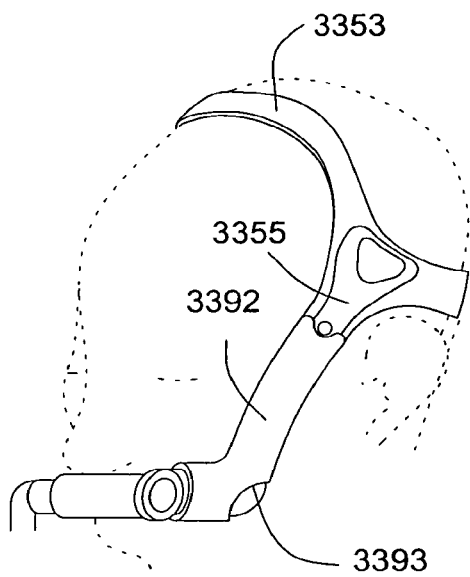
Figures 2, 12, 13, 14:
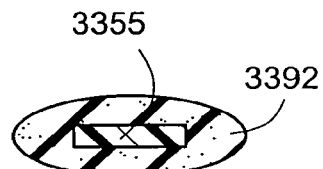
Figures 3, 12, 13, 14:
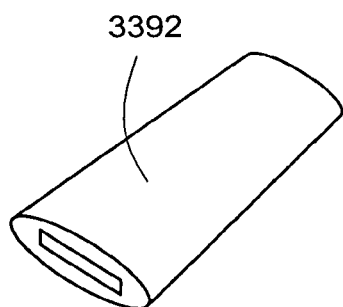
Figures 1, 12, 13, 14, 15:
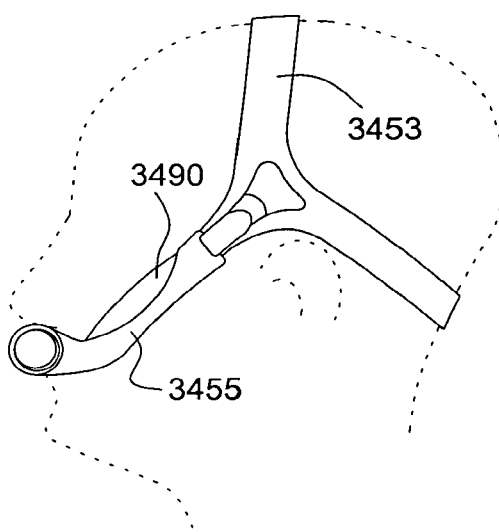
Figures 2, 12, 13, 14, 15:
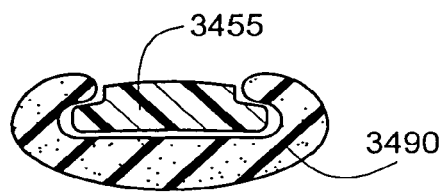
Figures 1, 12, 13, 14, 15, 16:
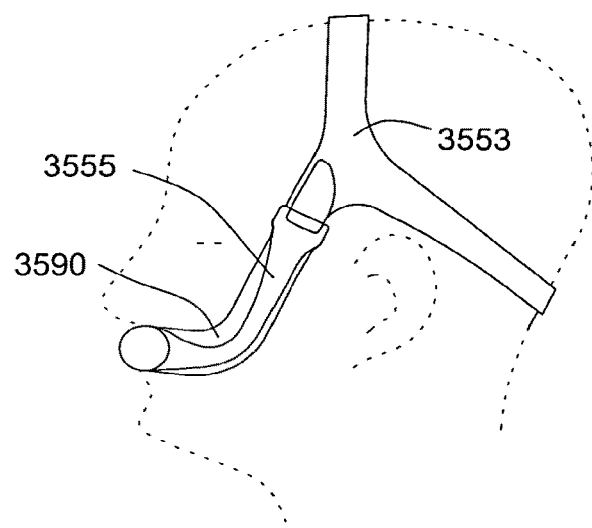
Figures 2, 12, 13, 14, 15, 16:
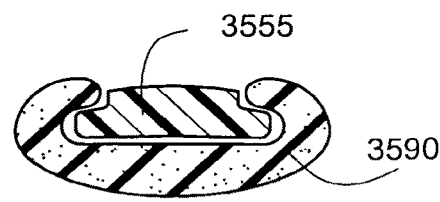
Figures 3, 12, 13, 14, 15, 16:
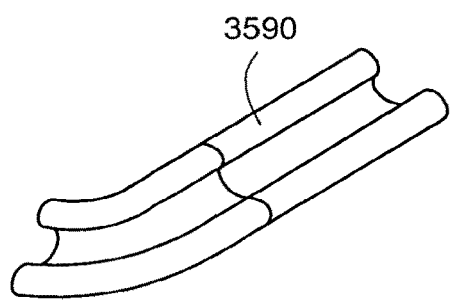
Figures 12, 13, 14, 15, 16, 17:
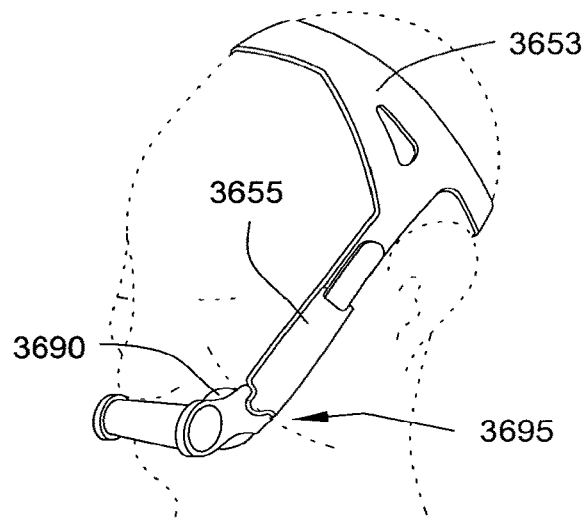
Figures 1, 12, 13, 14, 15, 16, 17, 18:
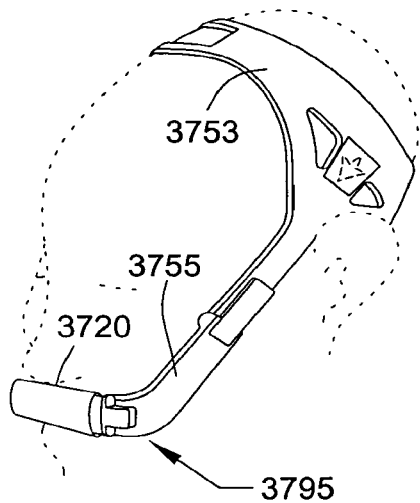
Figures 2, 12, 13, 14, 15, 16, 17, 18:
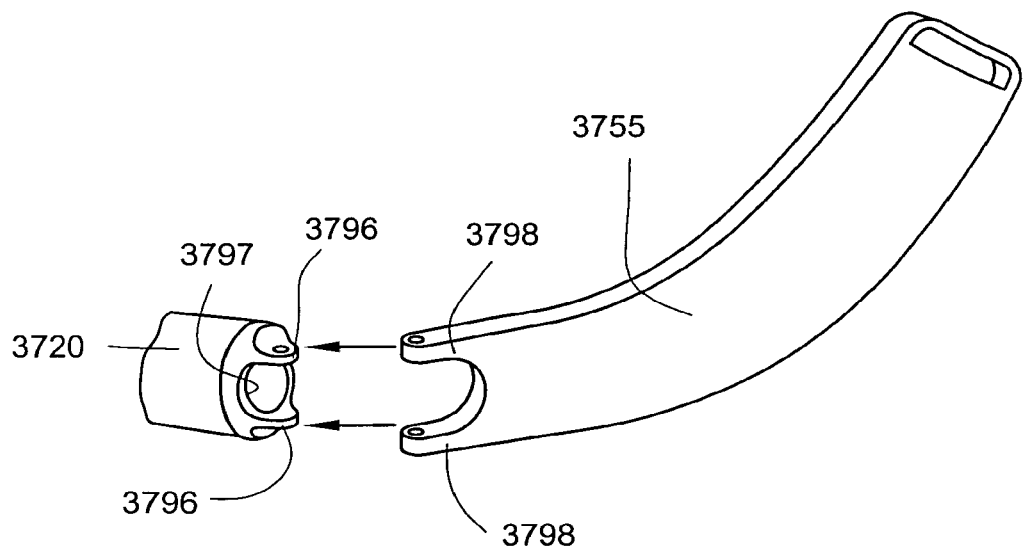
Figures 1, 2, 12, 13, 14, 15, 16, 17, 18, 19, 20:
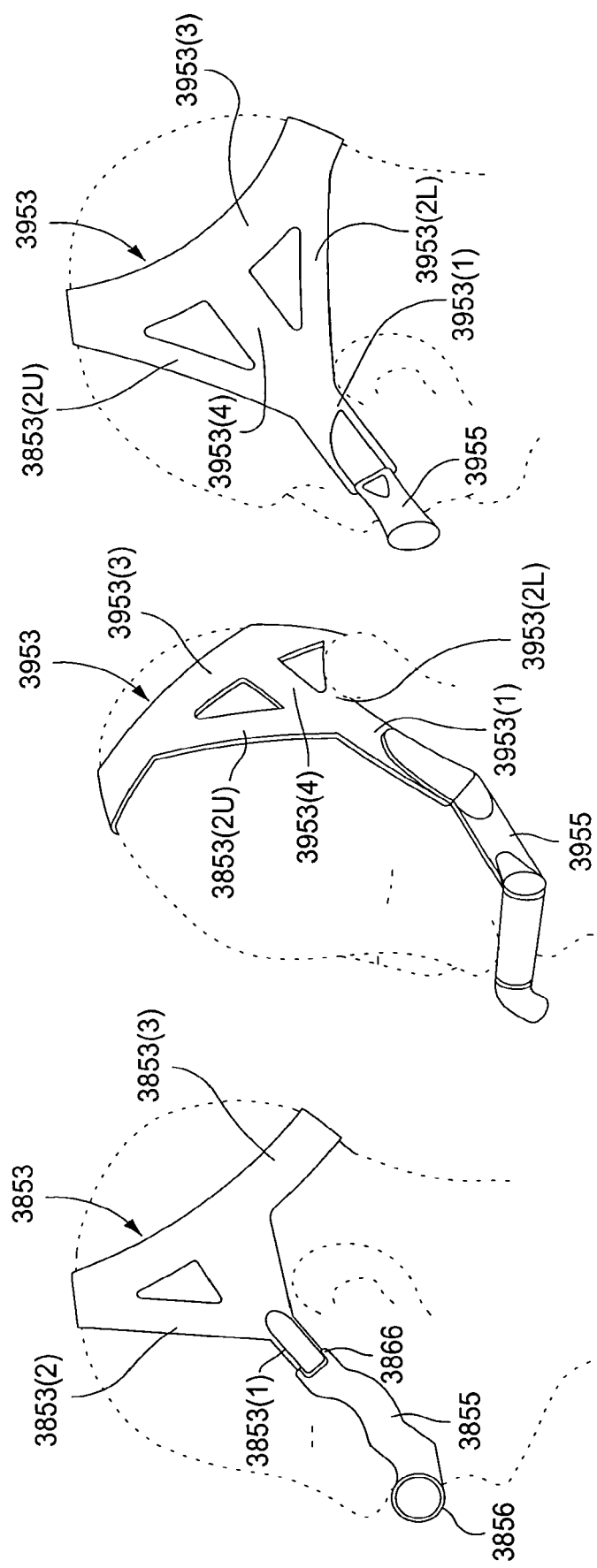
Figures 12, 13, 14, 15, 16, 17, 18, 19, 20, 21, 22:
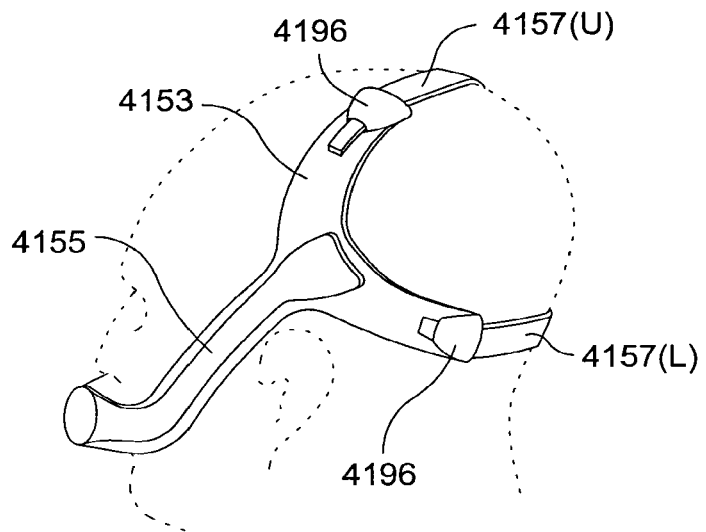
Figures 1, 12, 13, 14, 15, 16, 17, 18, 19, 20, 21, 22, 23:
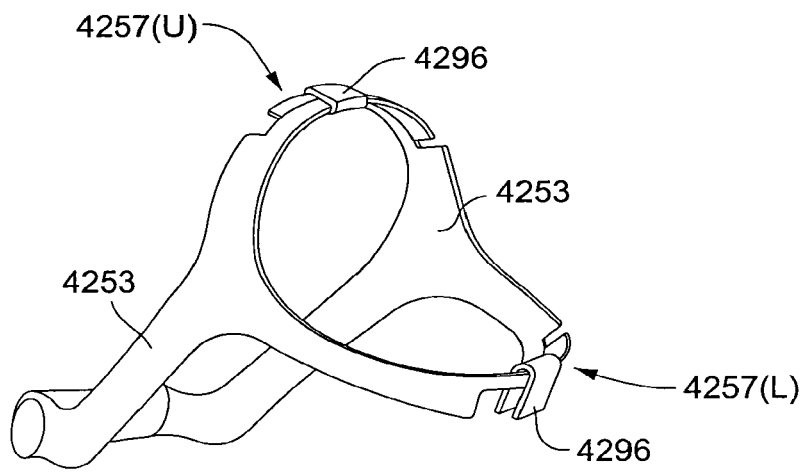
Figures 2, 12, 13, 14, 15, 16, 17, 18, 19, 20, 21, 22, 23:
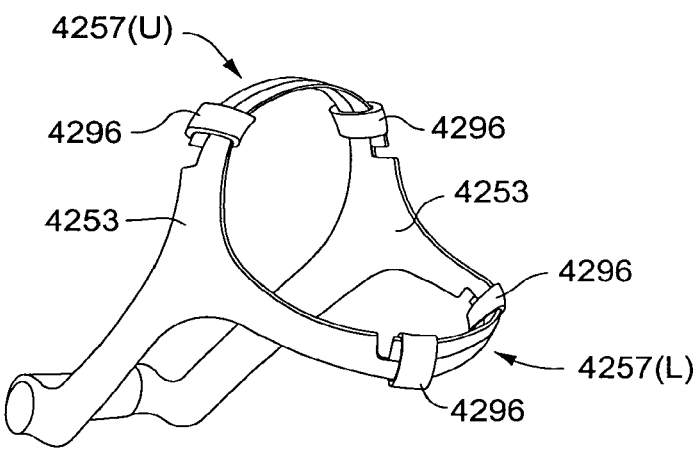
Figures 1, 12, 13, 14, 15, 16, 17, 18, 19, 20, 21, 22, 23, 24:
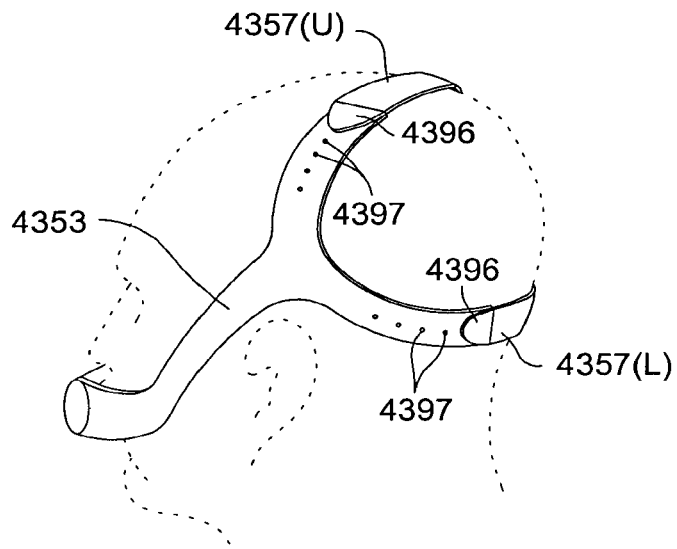
Figures 2, 12, 13, 14, 15, 16, 17, 18, 19, 20, 21, 22, 23, 24:
Figures 3, 12, 13, 14, 15, 16, 17, 18, 19, 20, 21, 22, 23, 24:
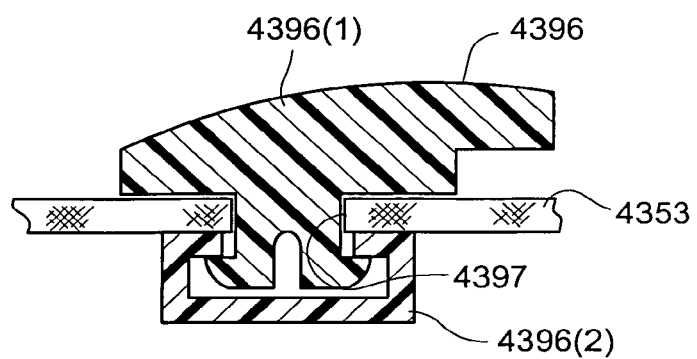
Figures 1, 13:
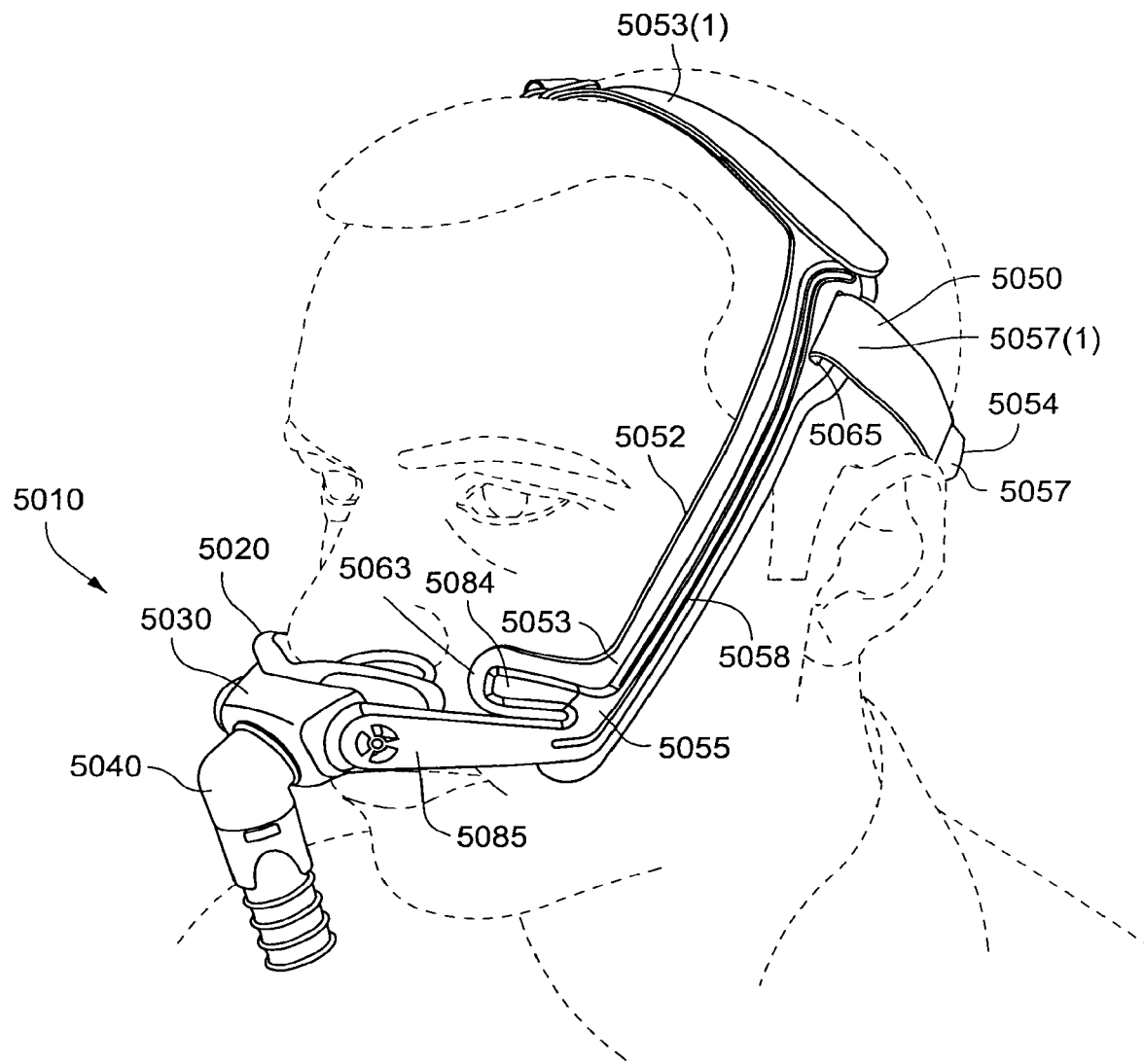
Figures 2, 13:
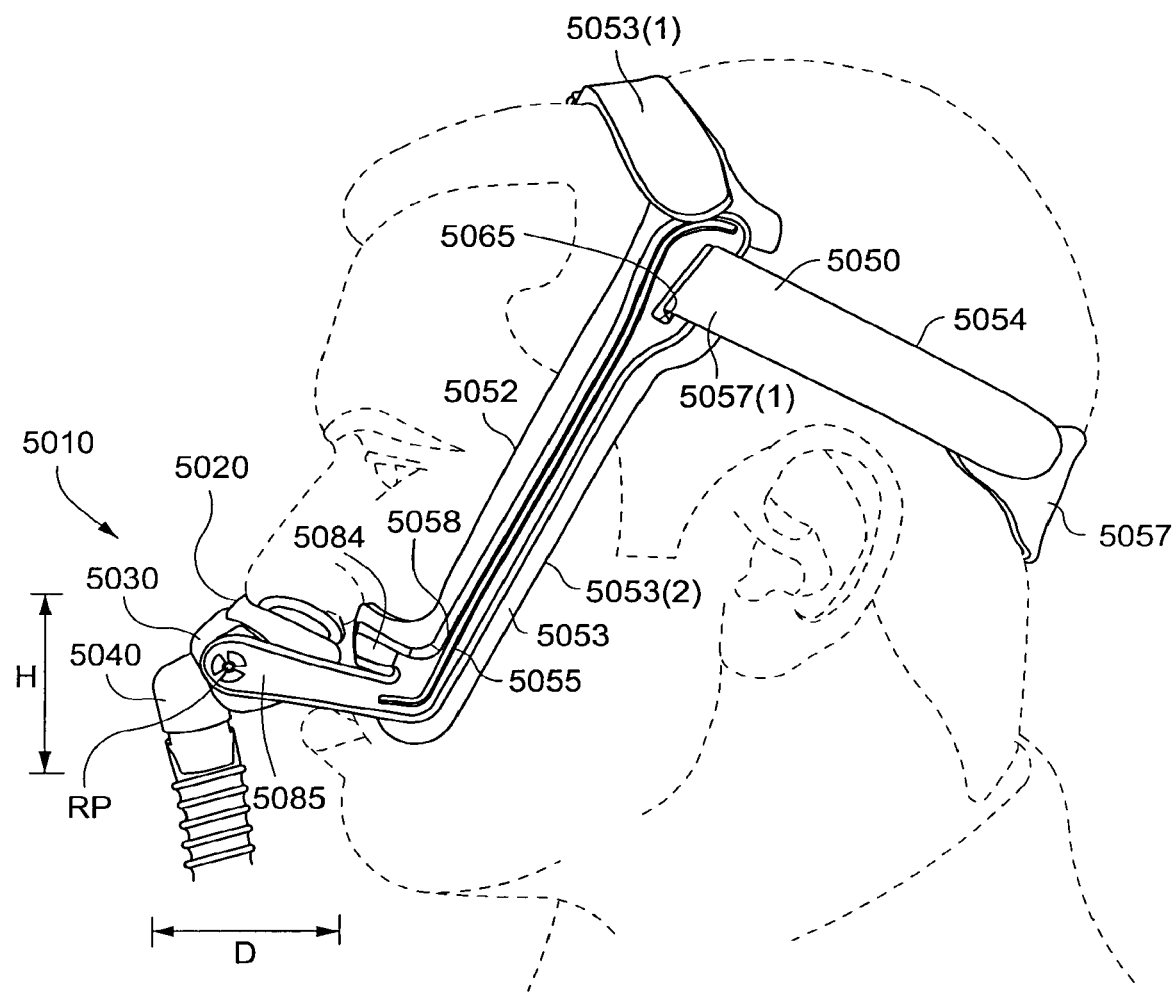
Figures 3, 13:
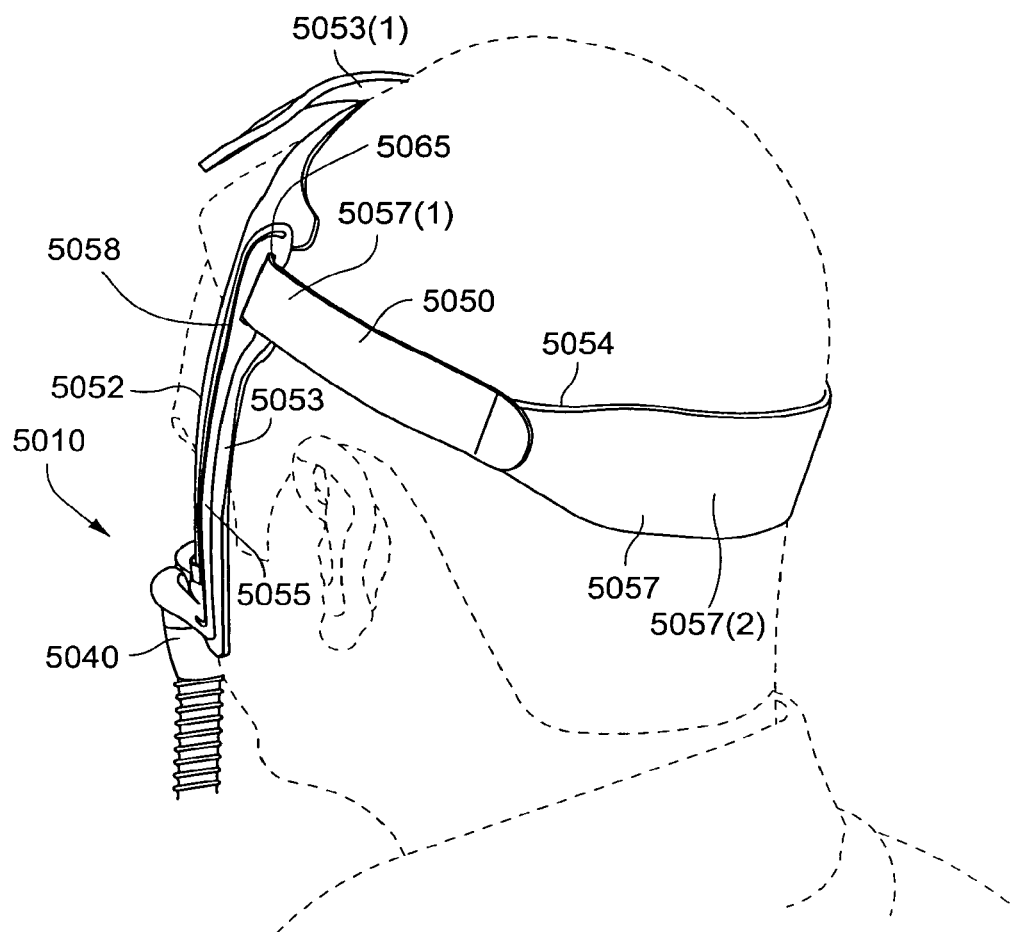
Figures 4, 13:
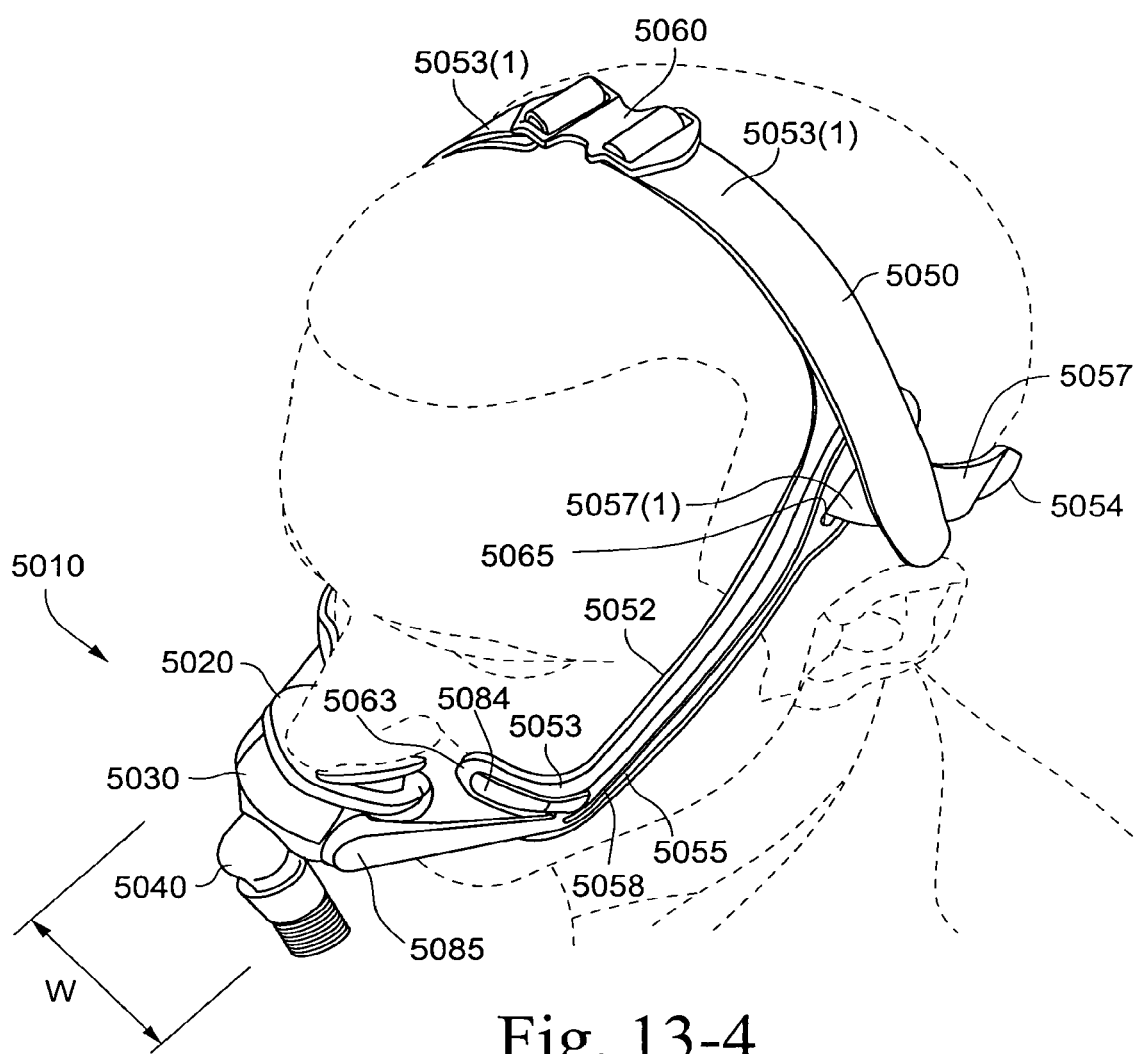
Figures 5, 13:
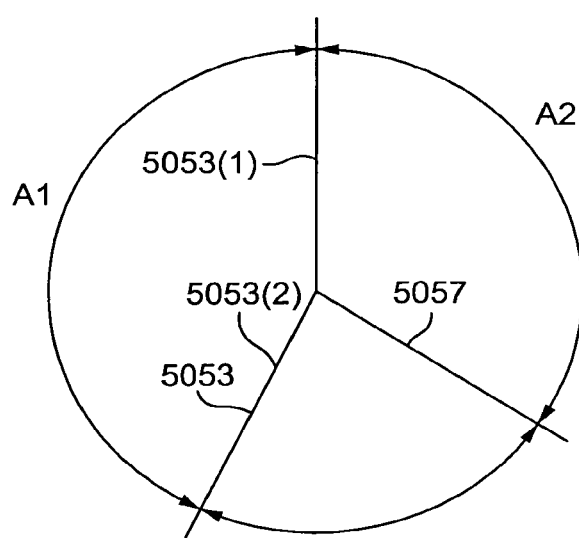
Figures 1, 14:
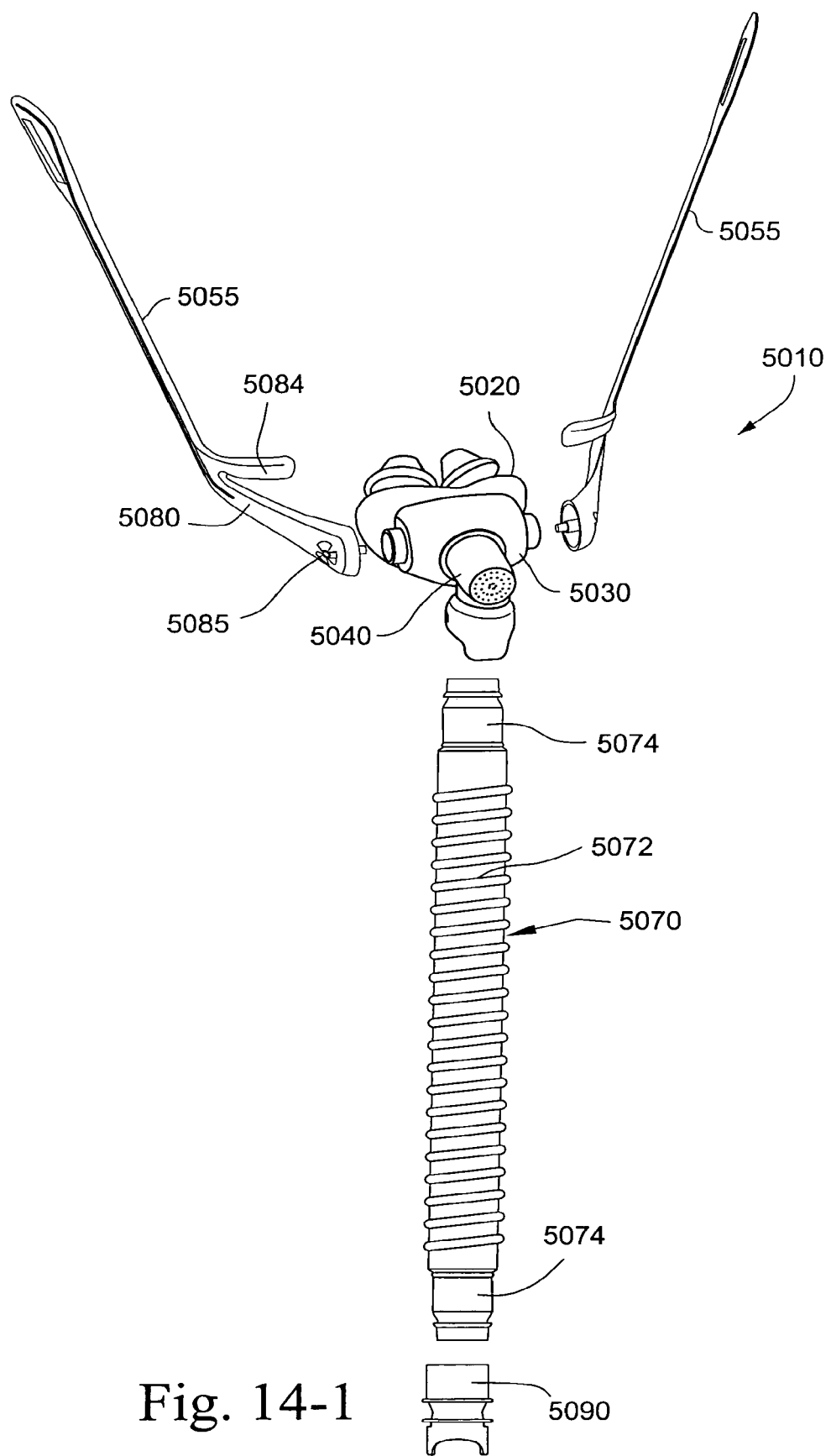
Figures 2, 14:
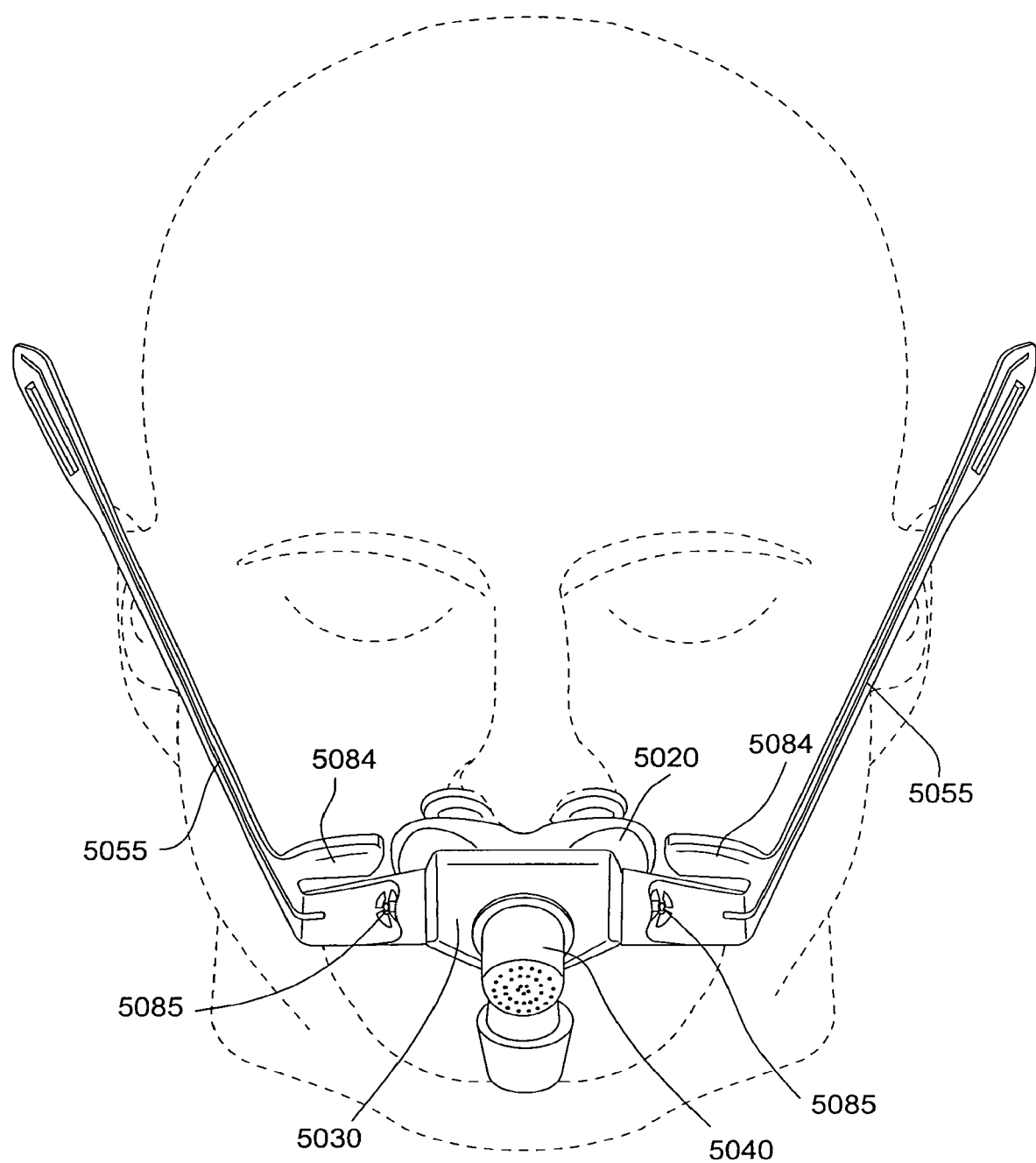
Figures 1, 15:
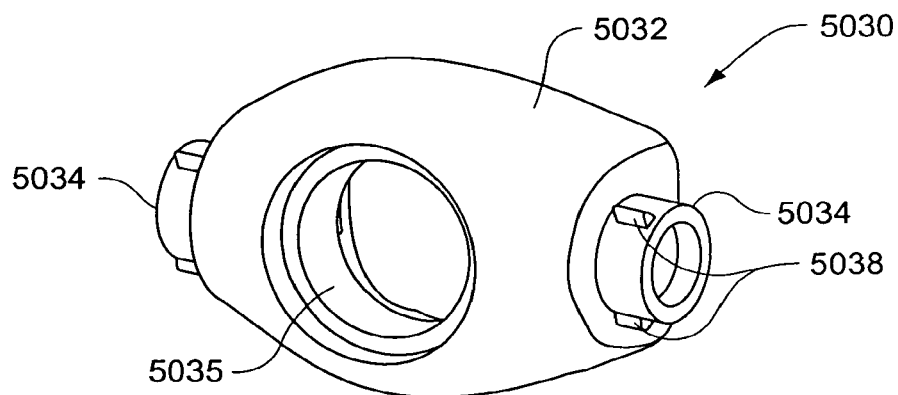
Figures 2, 15:
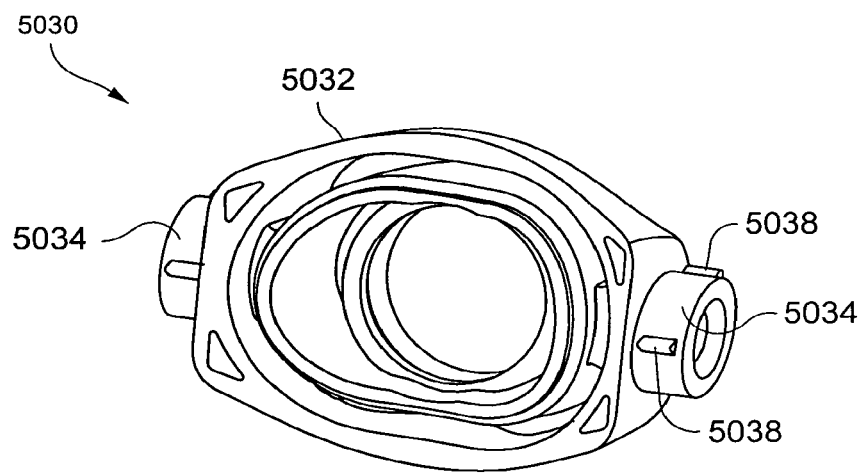
Figures 3, 15:
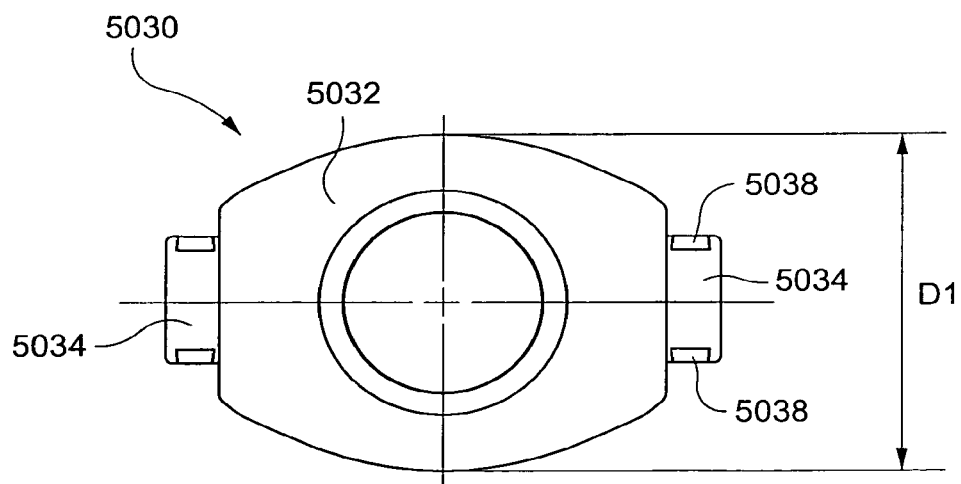
Figures 4, 15:
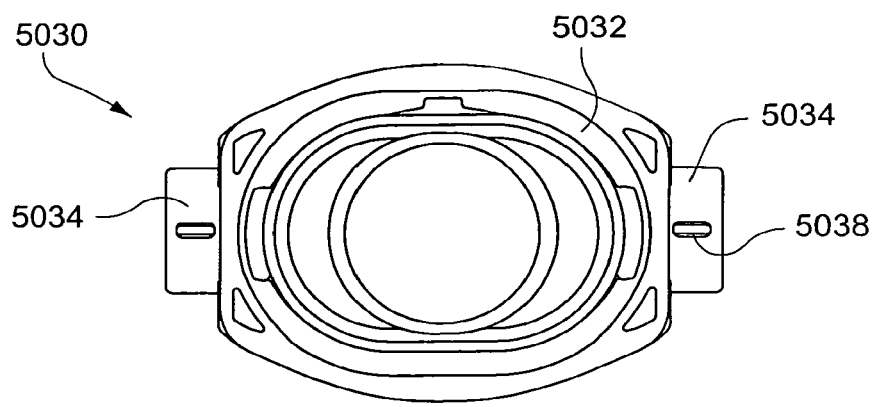
Figures 5, 15:
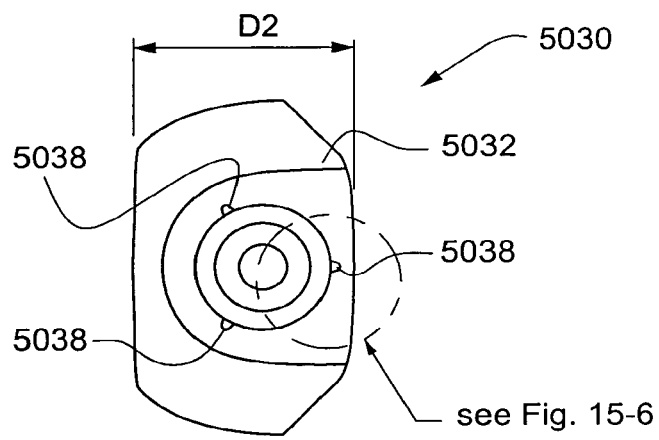
Figures 6, 15:
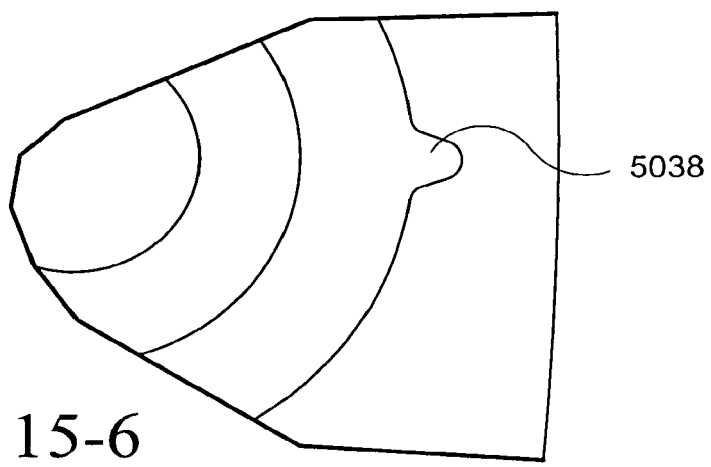
Figures 7, 15:
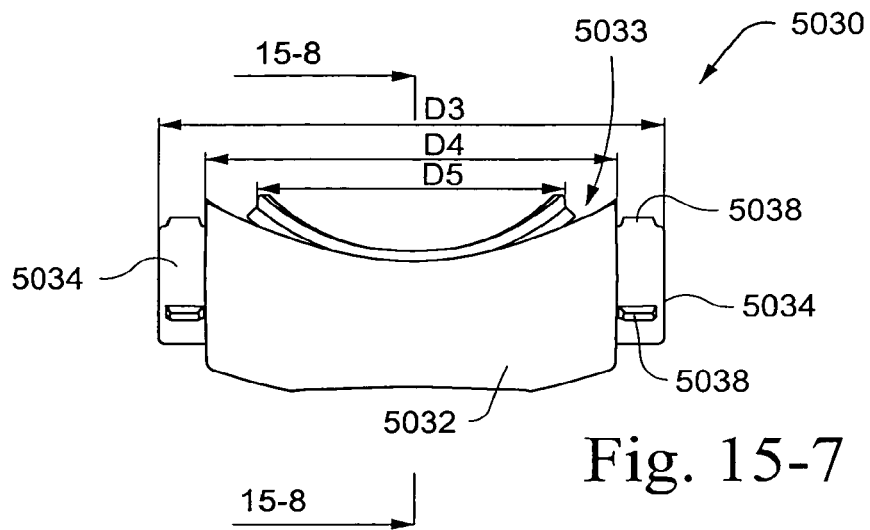
Figures 8, 15:
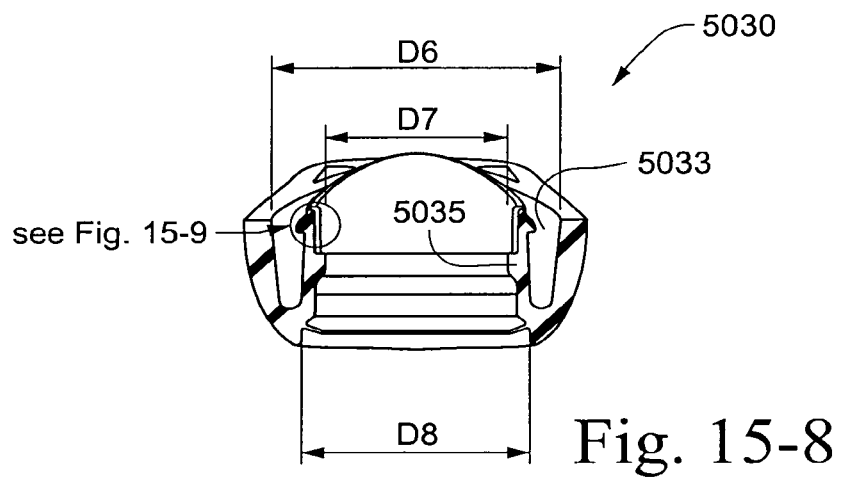
Figures 9, 15:
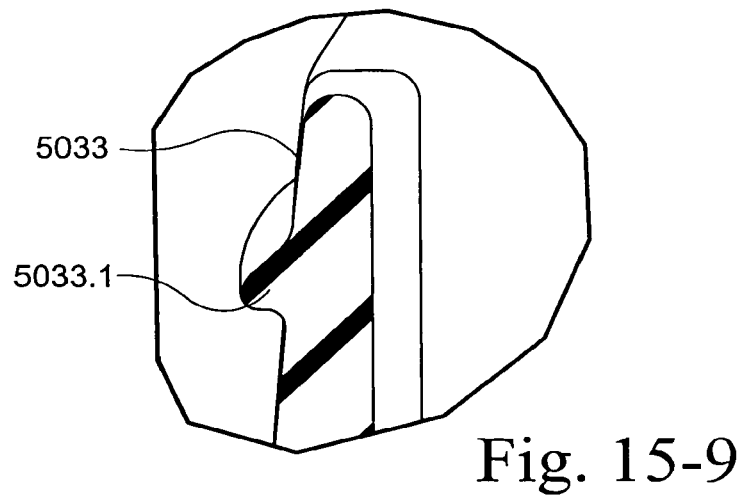
Figures 10, 15:
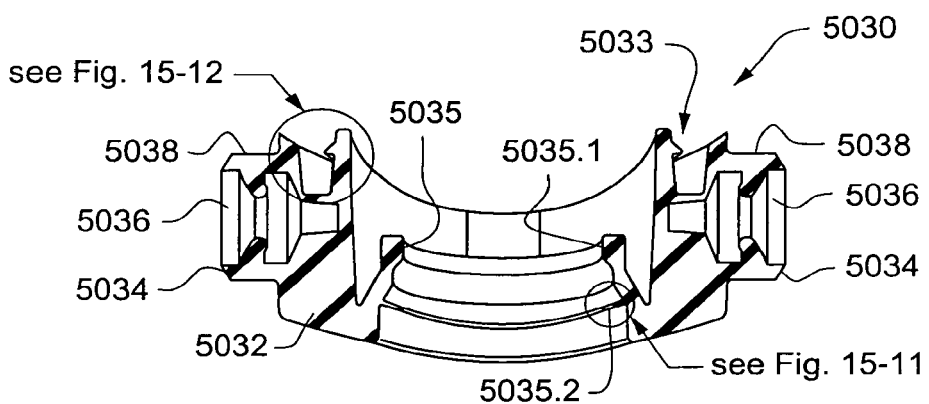
Figures 11, 15:
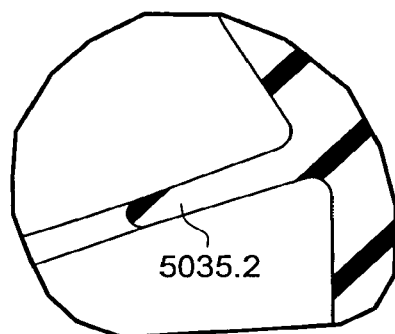
Figures 12, 15:
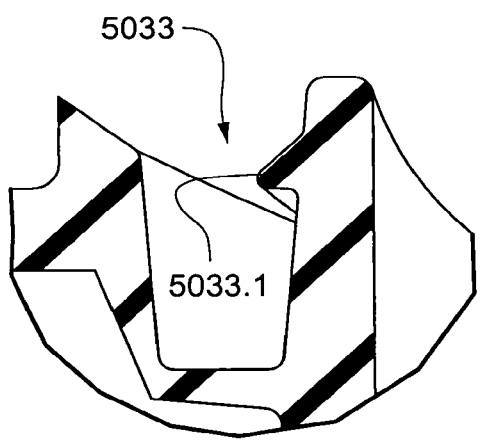
Figures 1, 16:
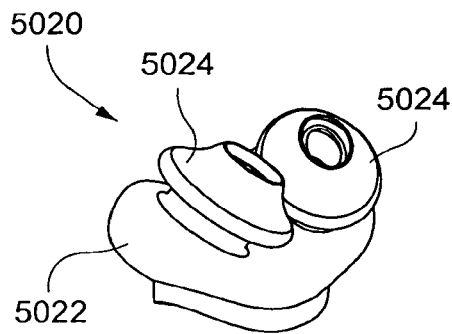
Figures 2, 16:
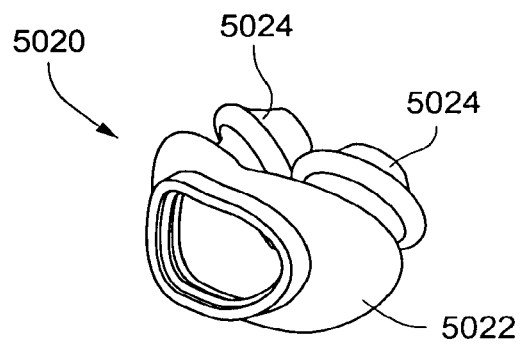
Figures 3, 16:
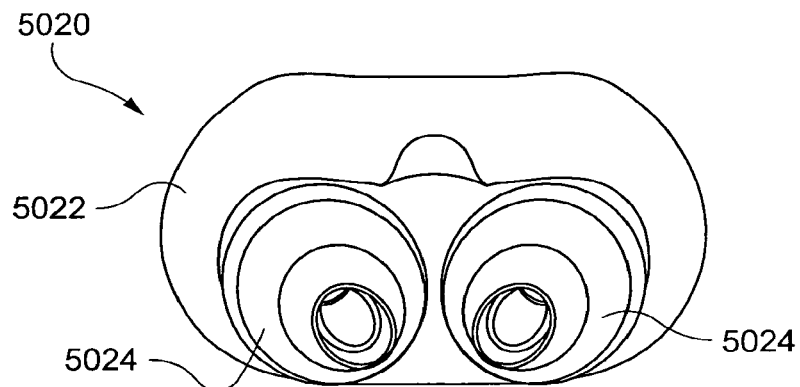
Figures 4, 16:
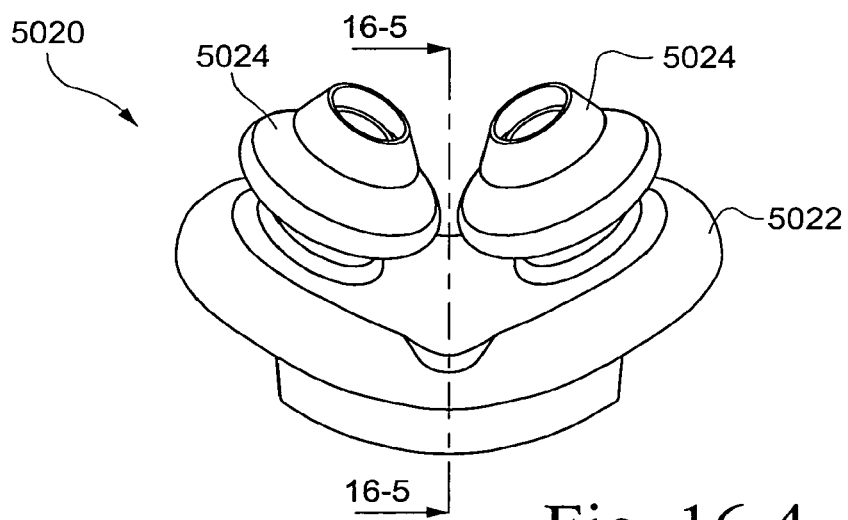
Figures 5, 16:
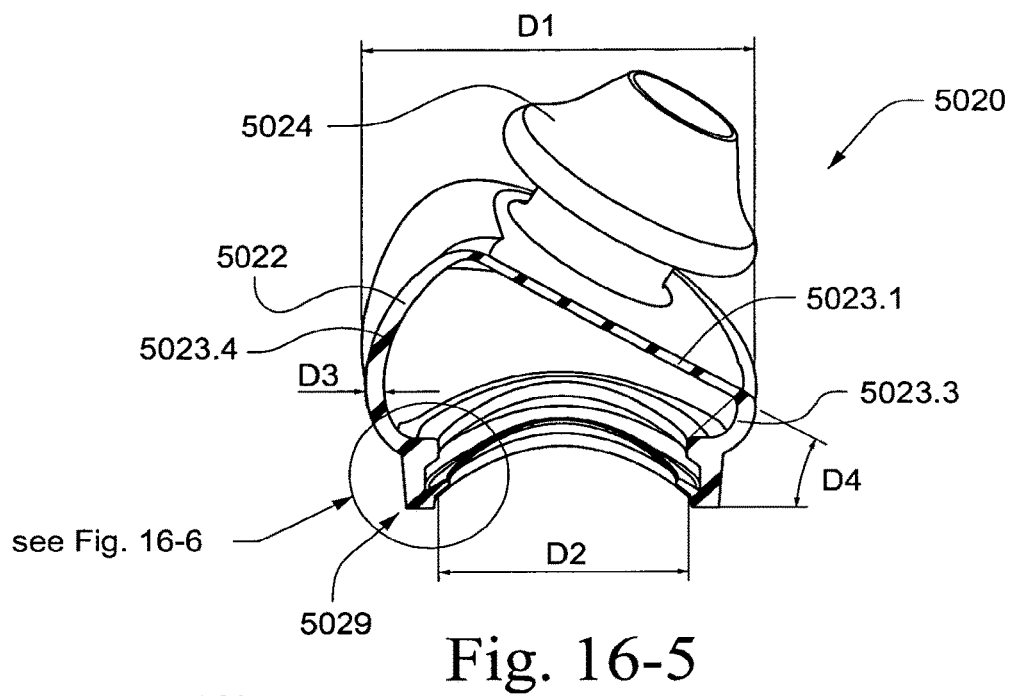
Figures 6, 16:
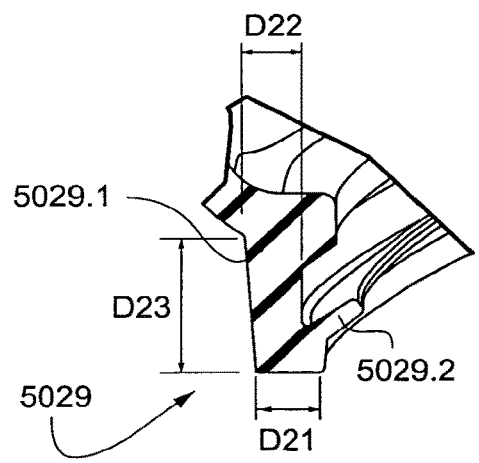
Figures 1, 6, 16:
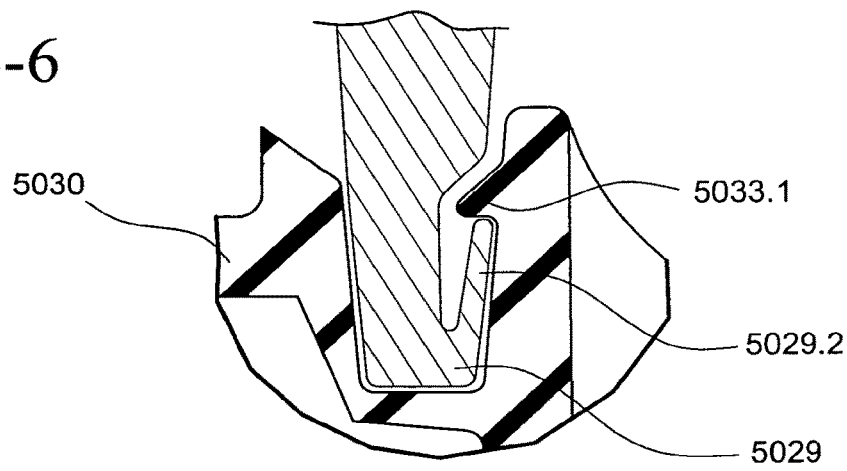
Figures 2, 6, 16:
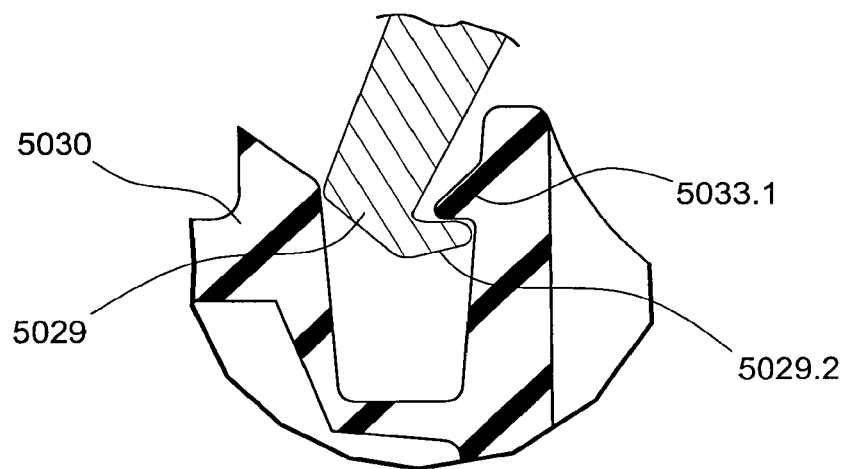
Figures 7, 16:
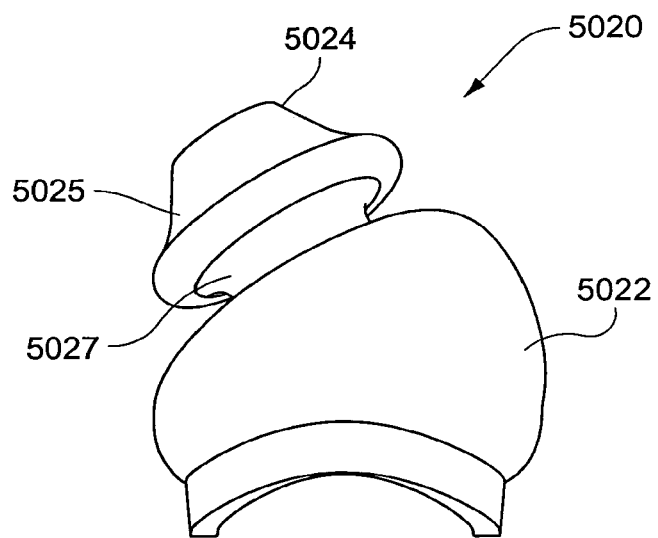
Figures 8, 16:
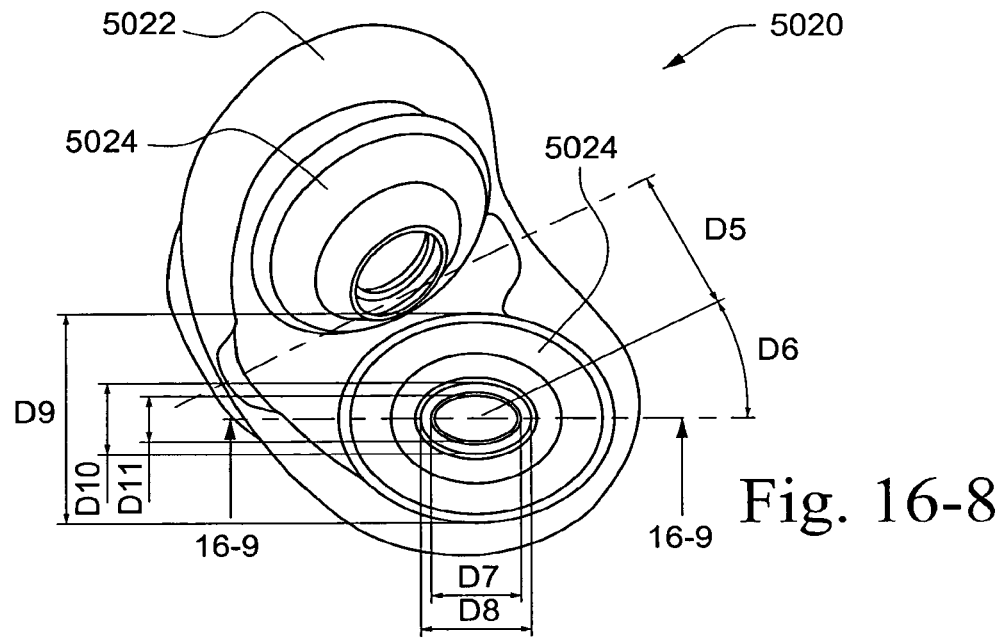
Figures 9, 16:
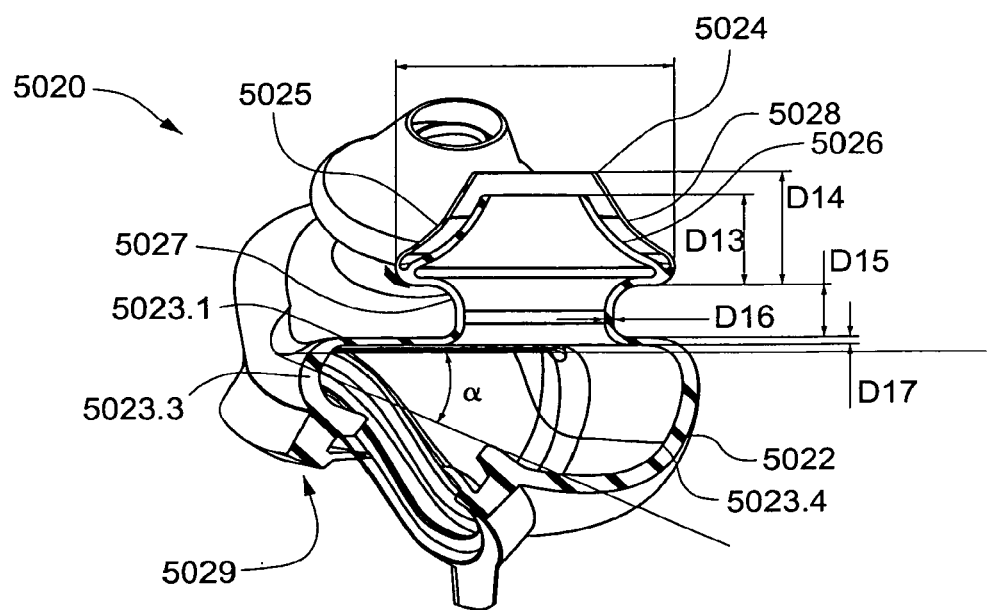
Figures 10, 16:
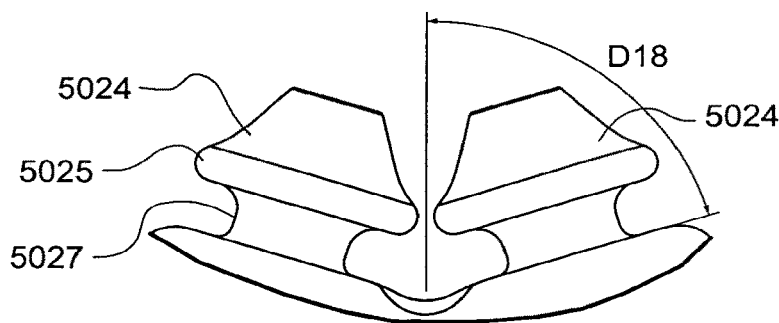
Figures 11, 16:
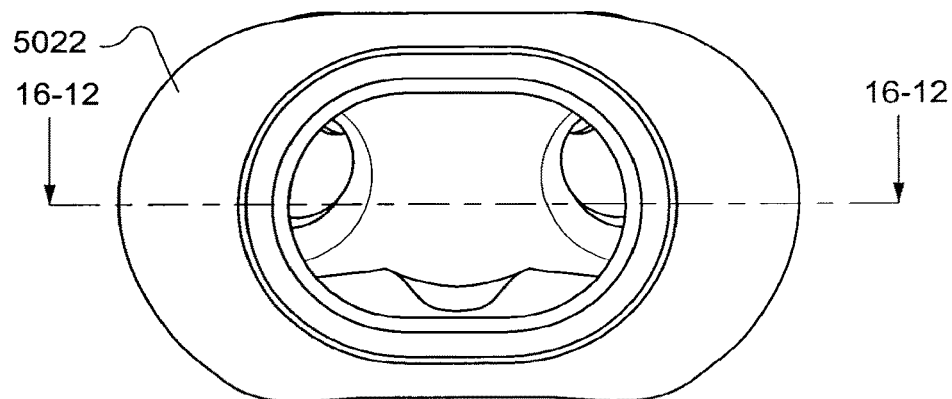
Figures 12, 16:
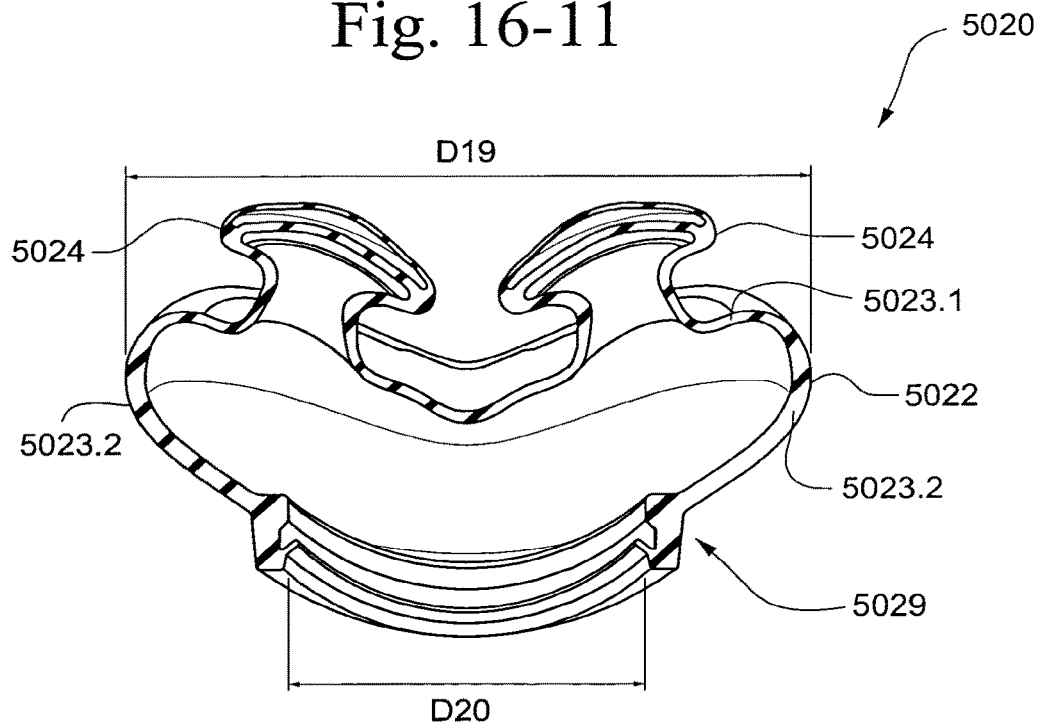
Figures 1, 13, 16:
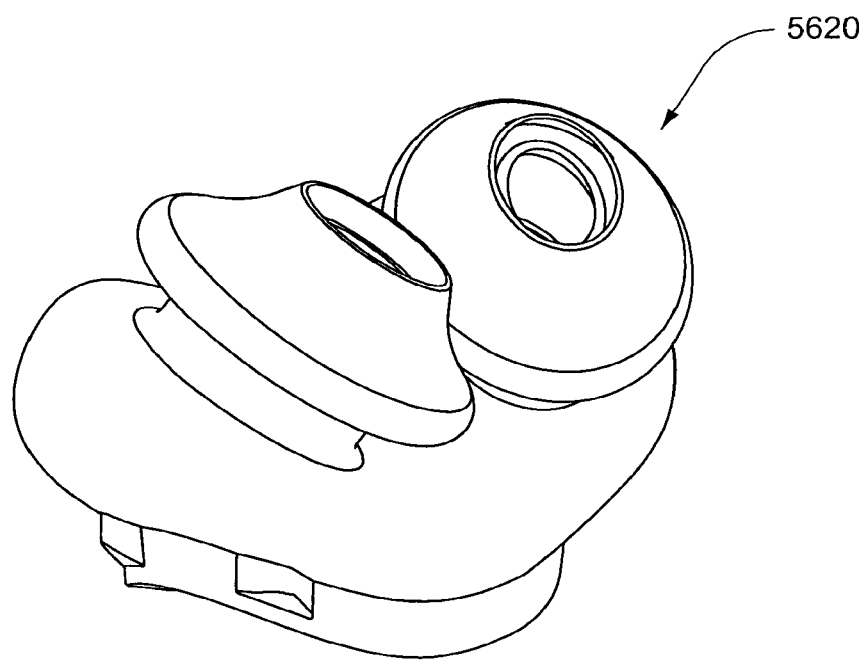
Figures 2, 13, 16:
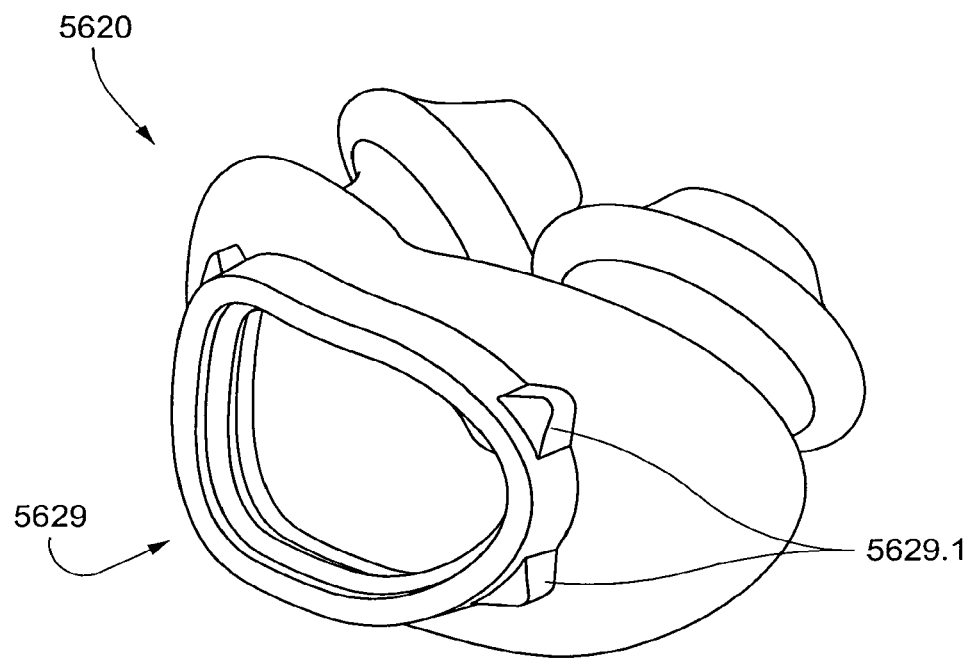
Figures 3, 13, 16:
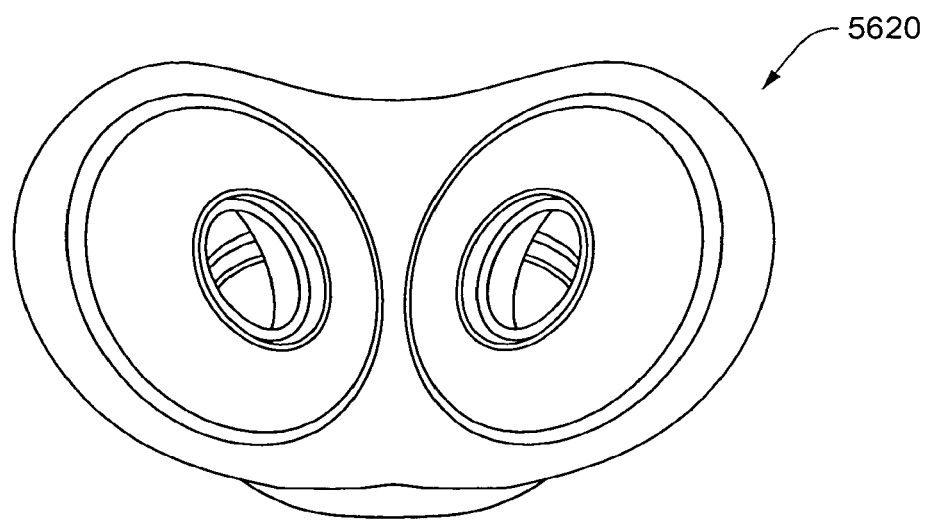
Figures 4, 13, 16:
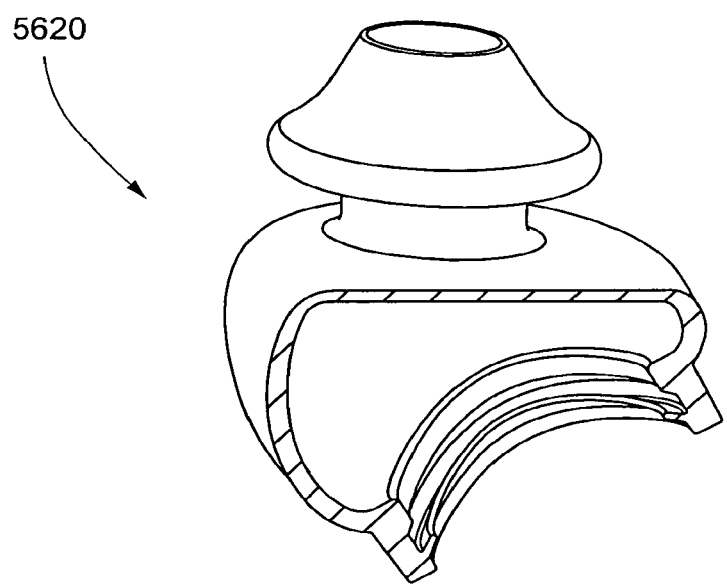
Figures 5, 13, 16:
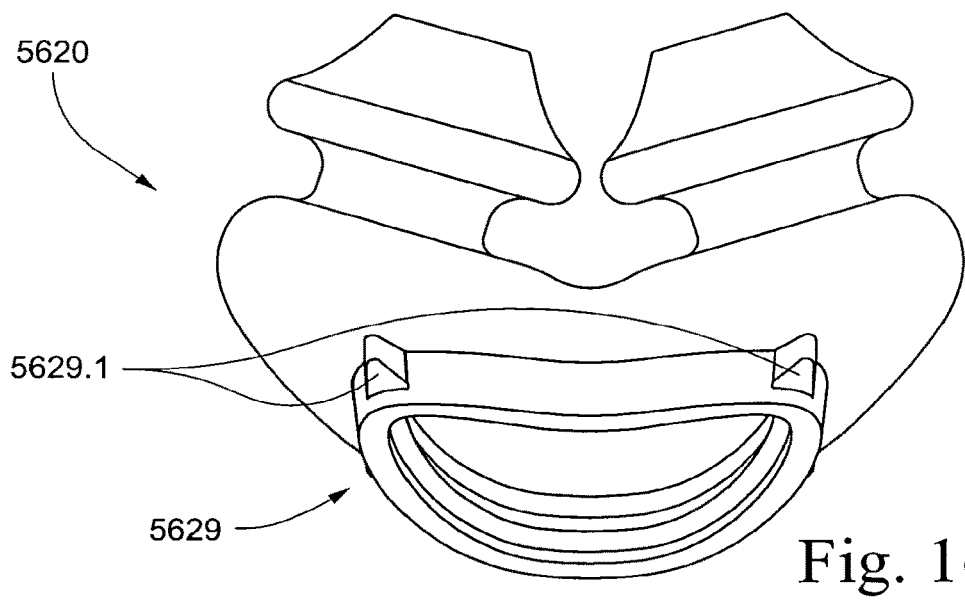
Figures 6, 13, 16:
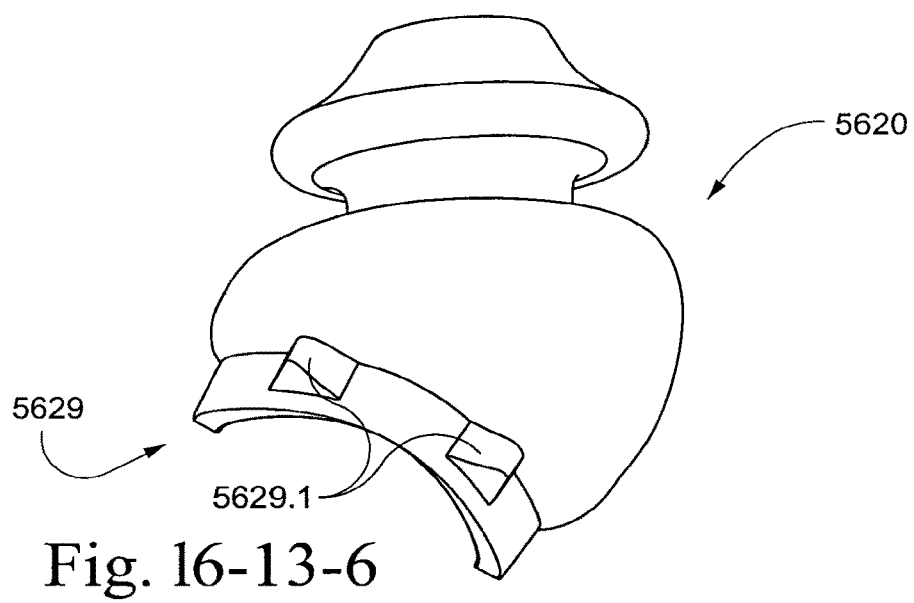
Figures 7, 13, 16:
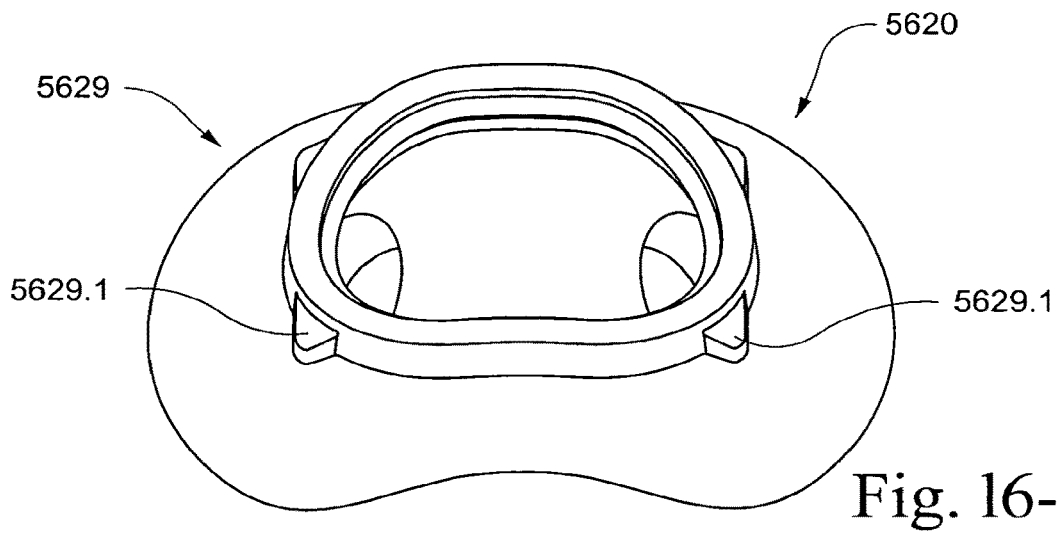
Figures 1, 14, 16:
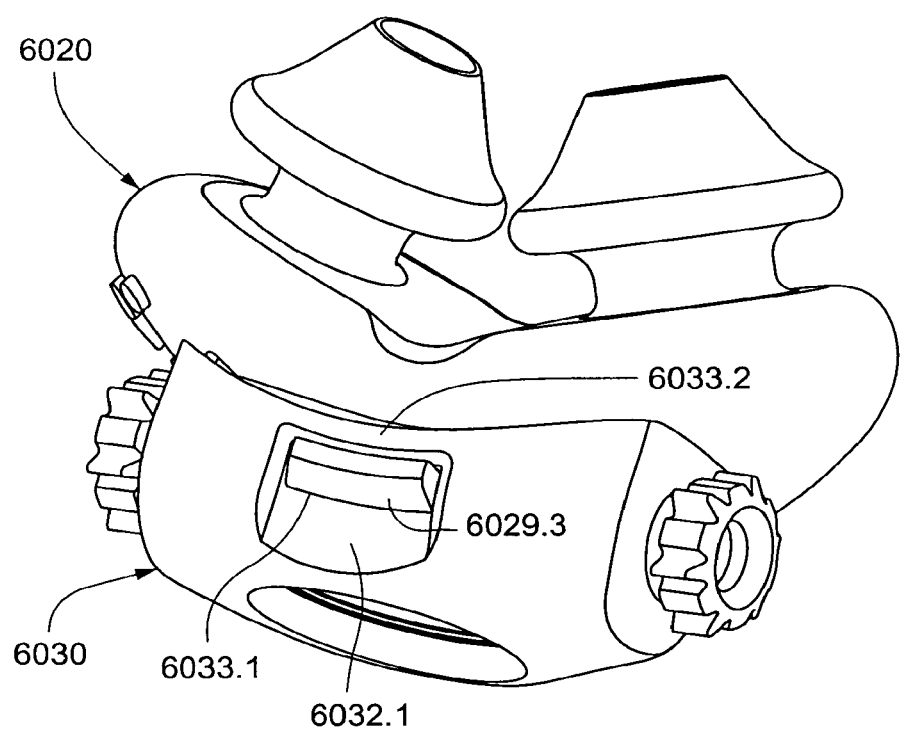
Figures 2, 14, 16:
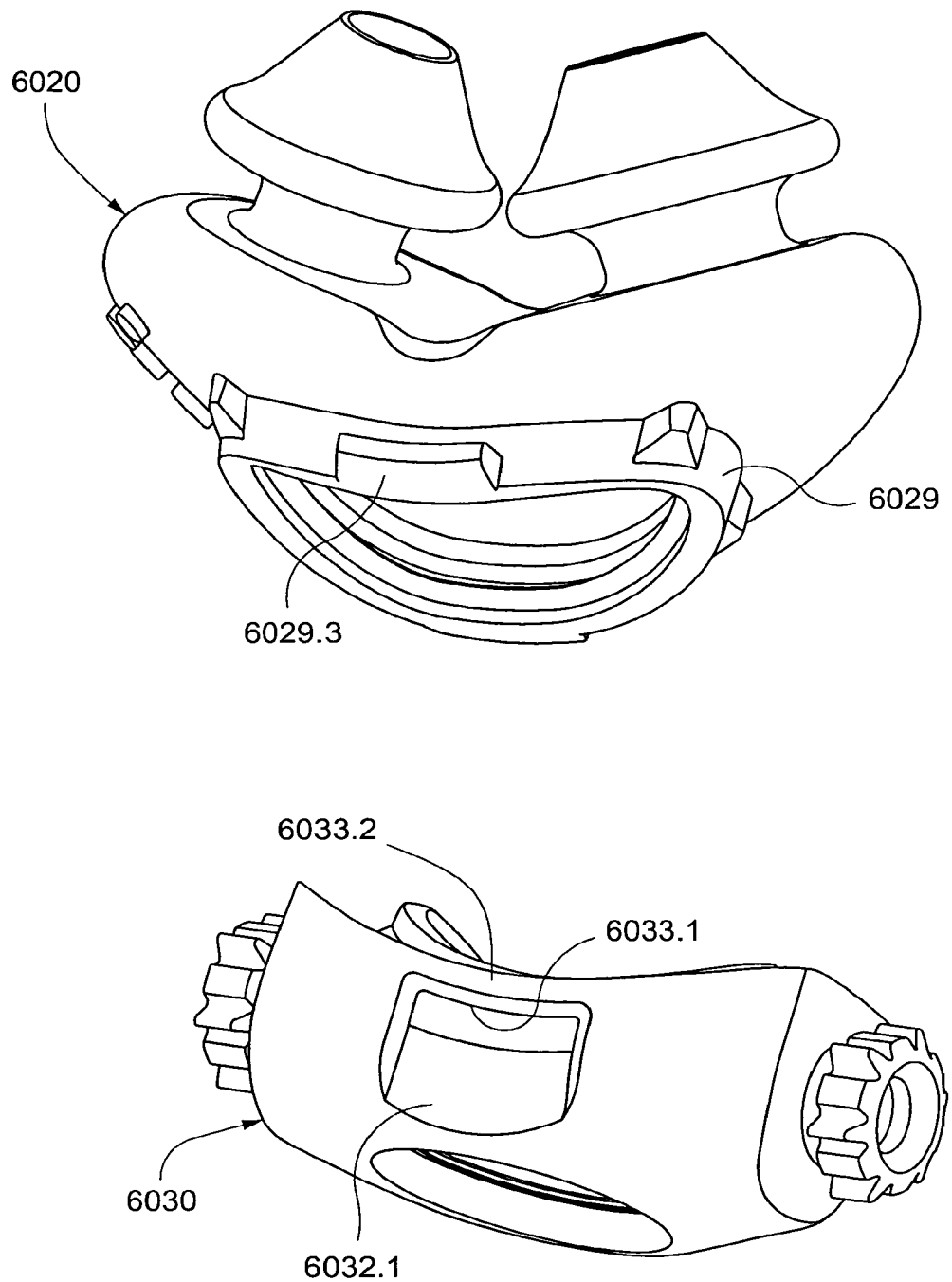
Figures 3, 14, 16:
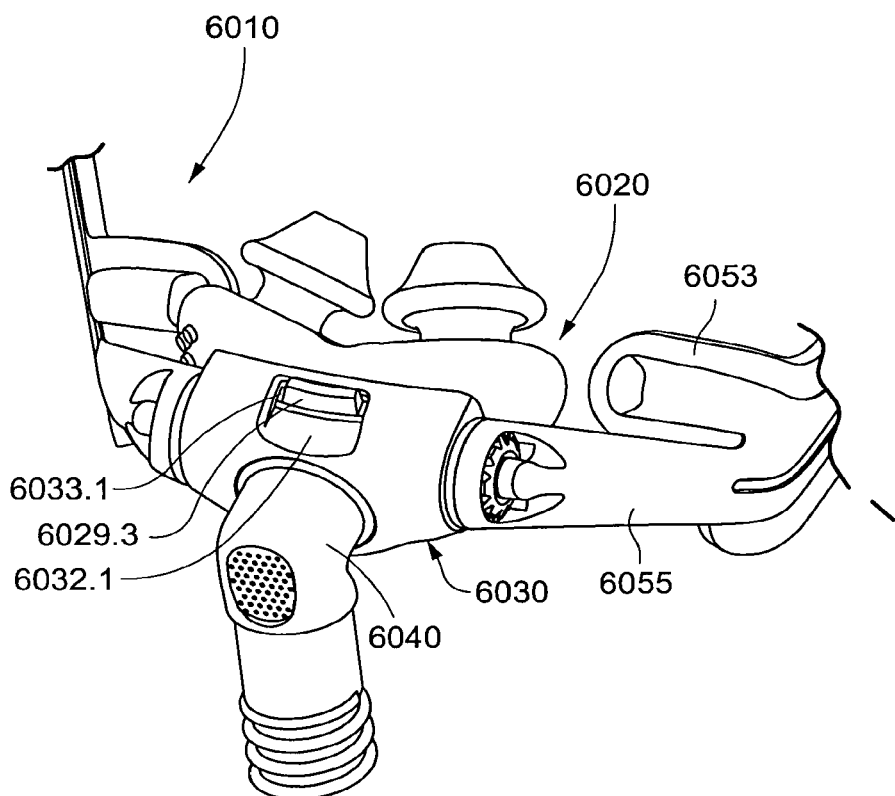
Figures 1, 15, 16:
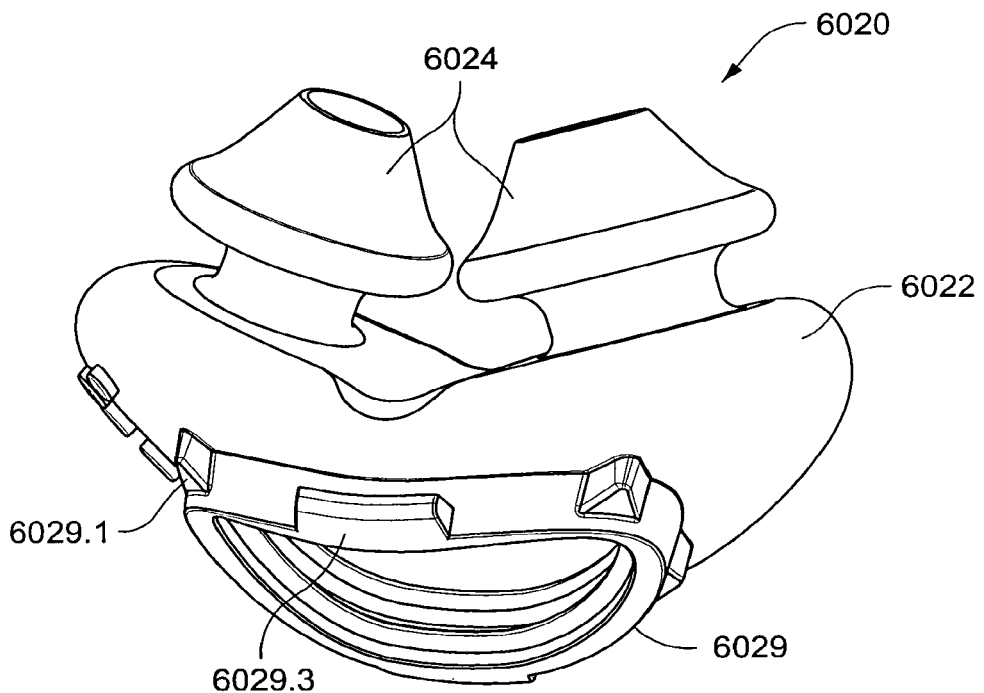
Figures 2, 15, 16:
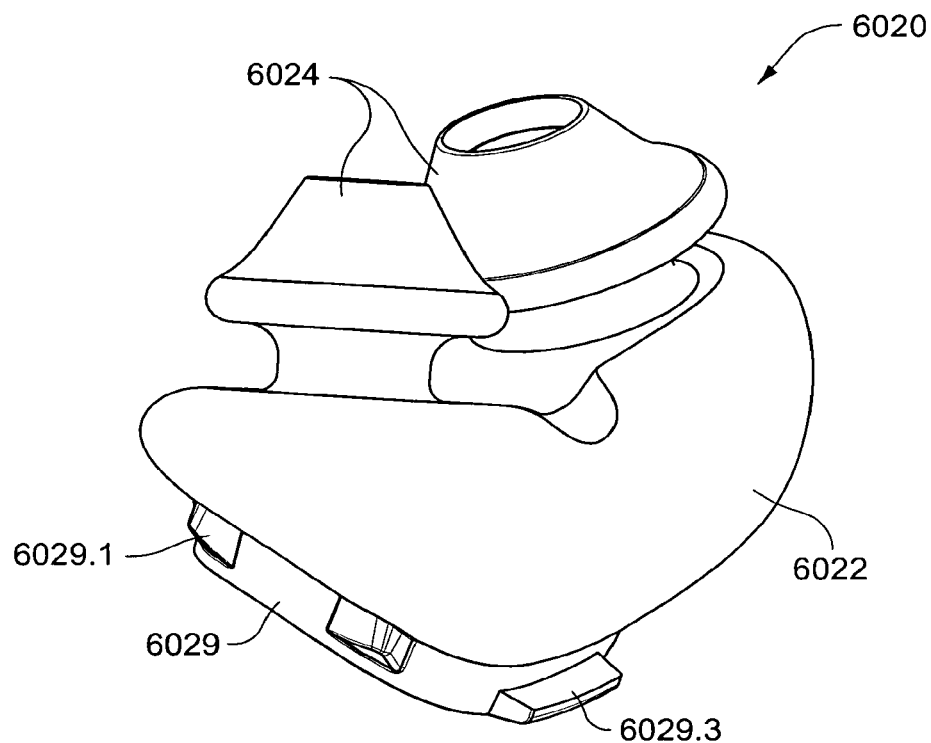
Figures 3, 15, 16:
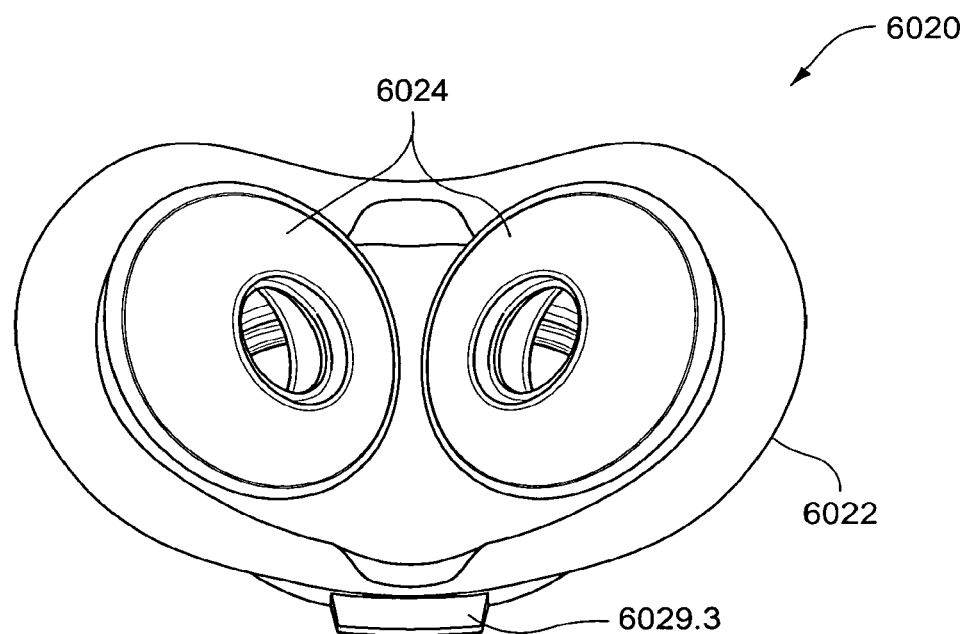
Figures 4, 15, 16:
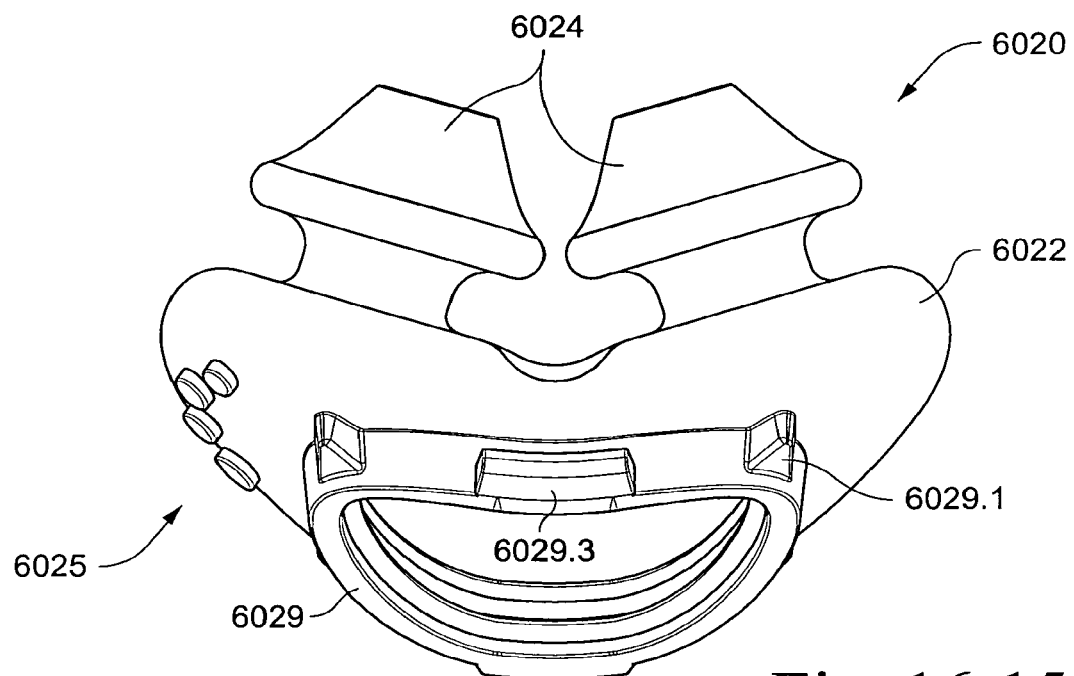
Figures 5, 15, 16:
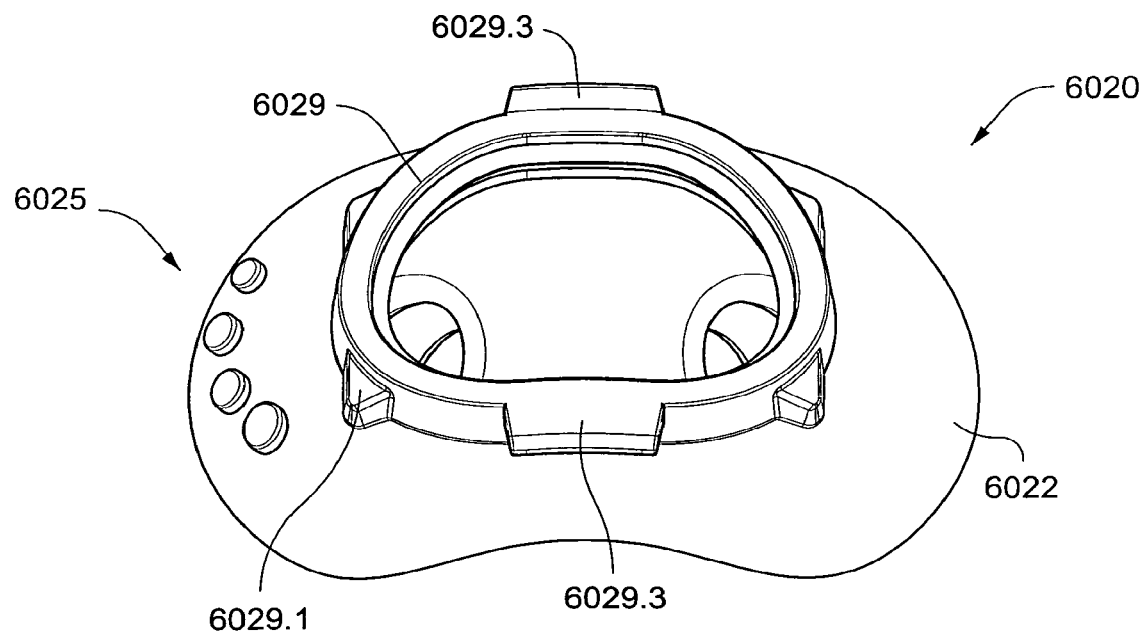
Figures 6, 15, 16:
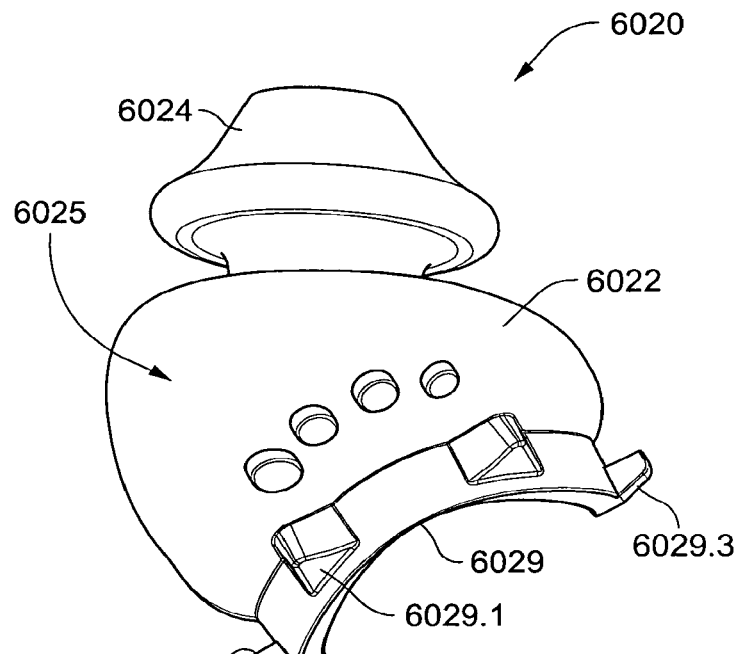
Figures 7, 15, 16:
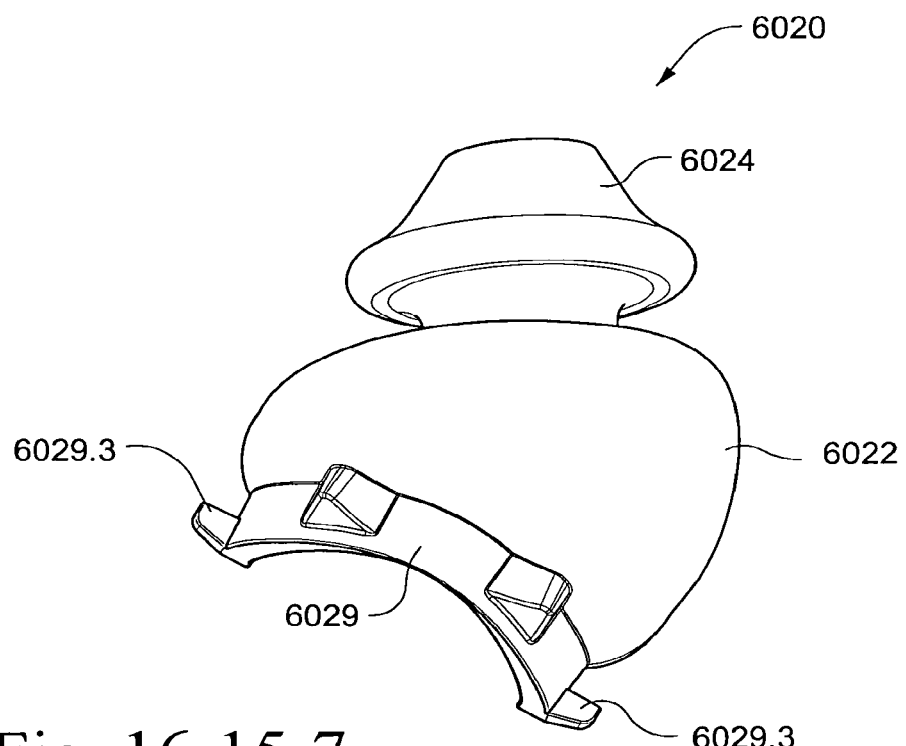
Figures 8, 15, 16:
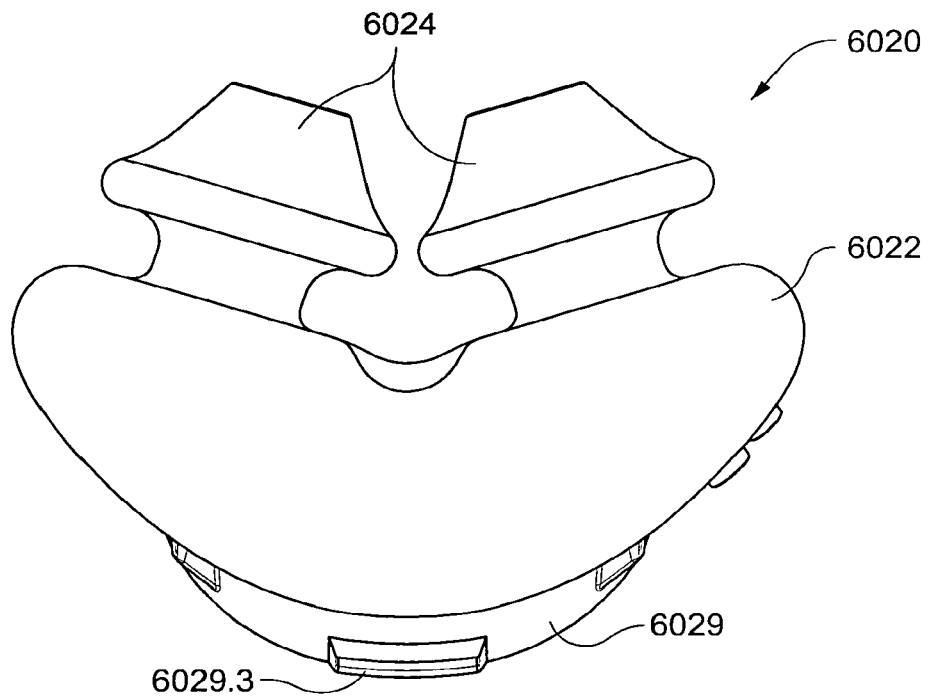
Figures 9, 15, 16:
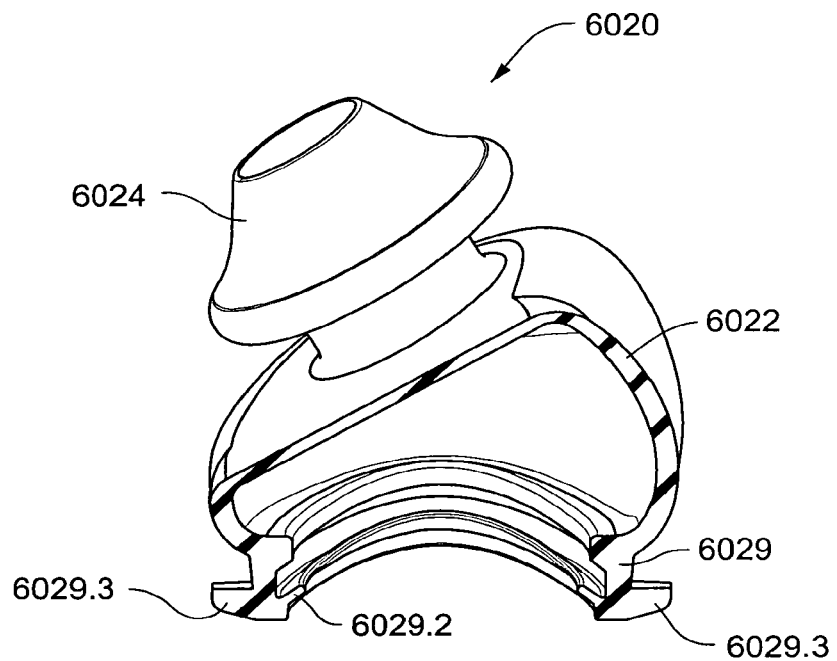
Figures 10, 15, 16:
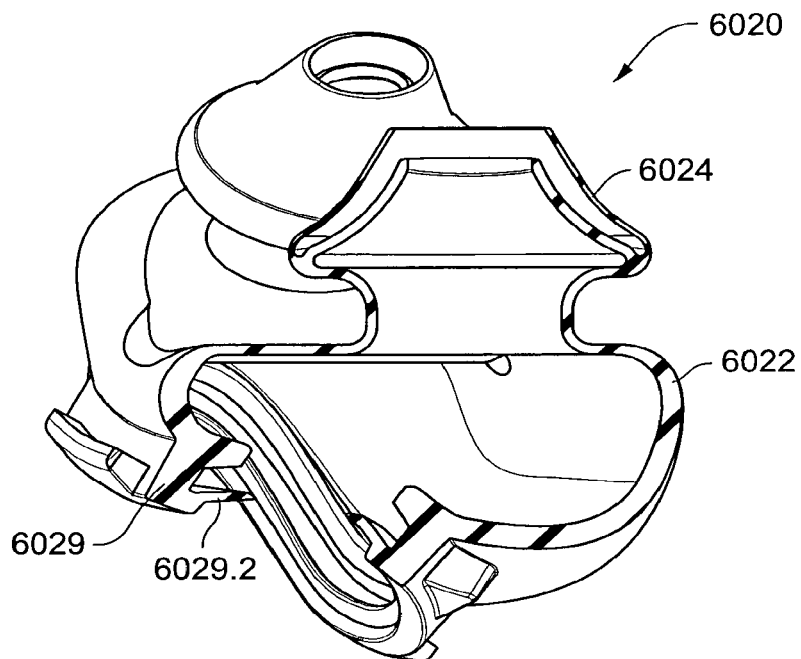
Figures 1, 16:
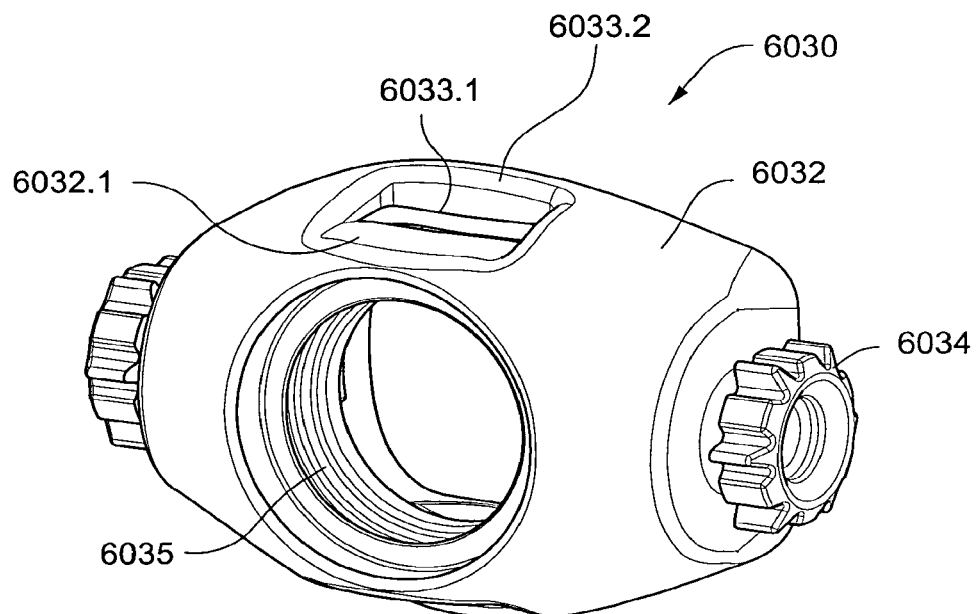
Figures 2, 16:
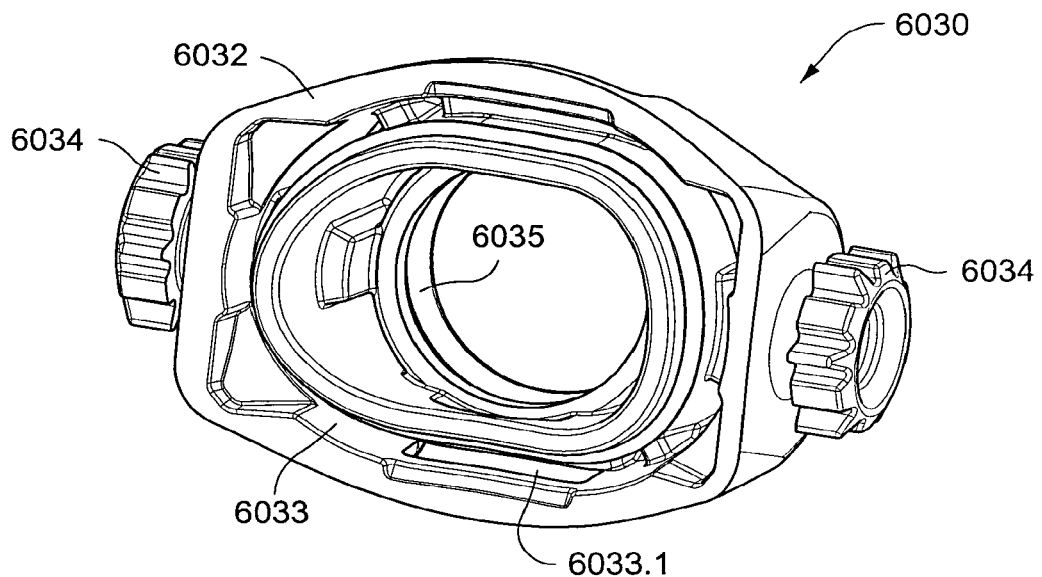
Figures 3, 16:
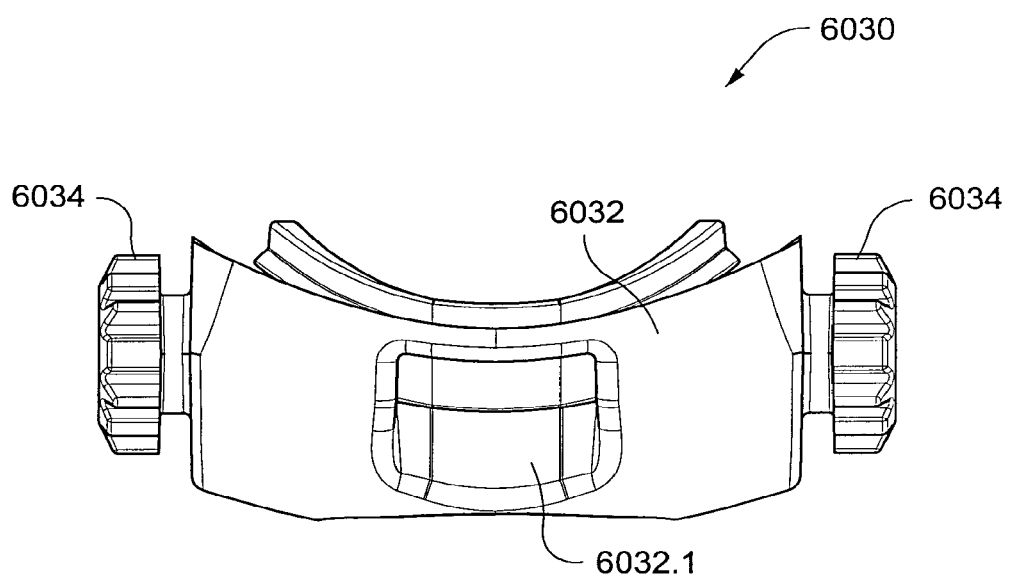
Figures 4, 16:
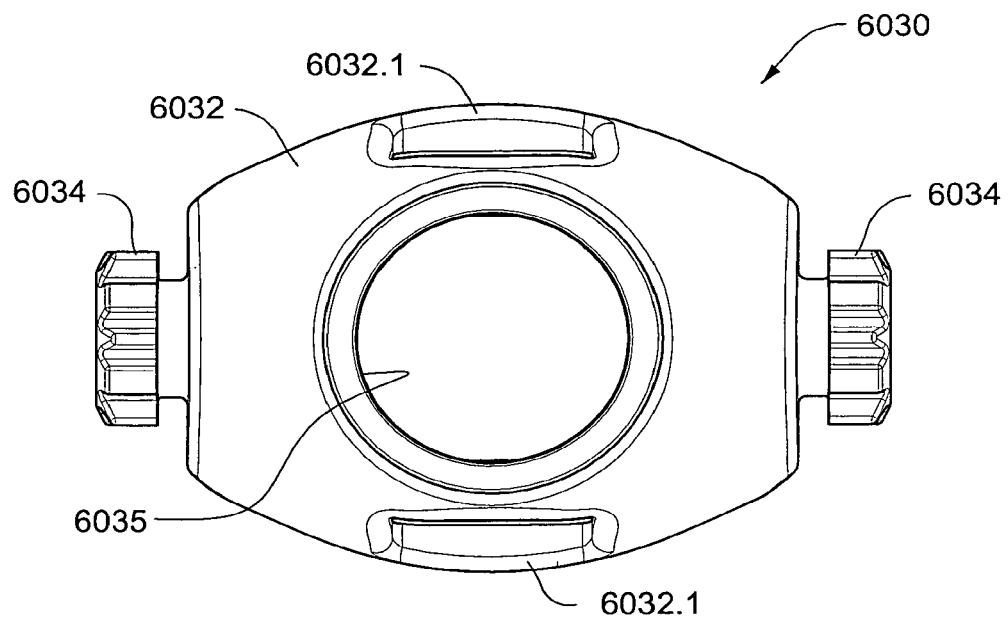
Figures 5, 16:
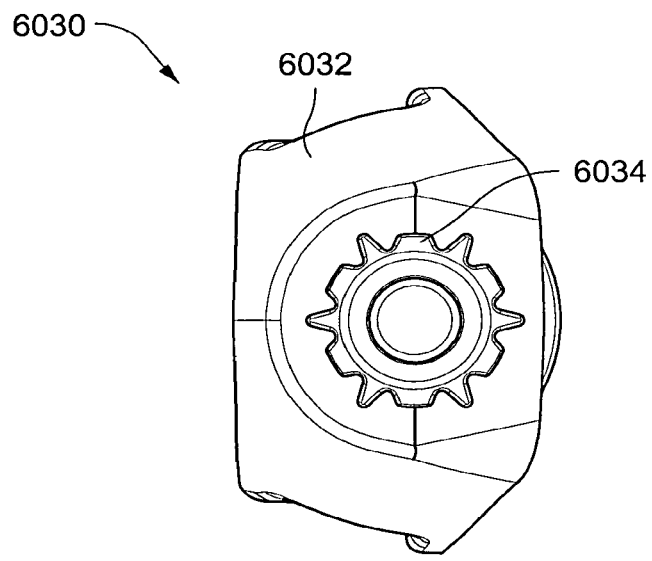
Figures 6, 16:
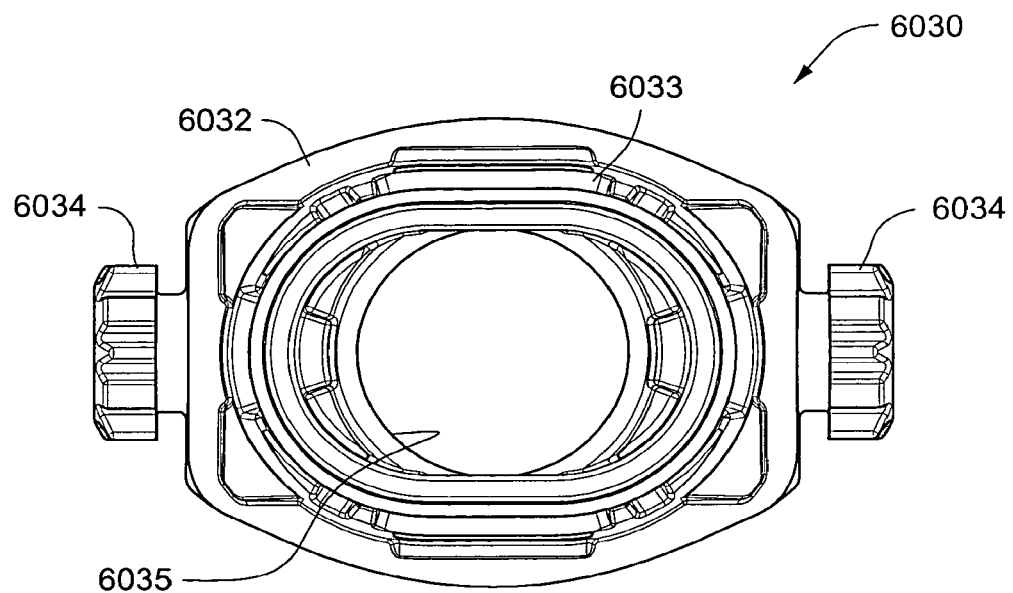
Figures 7, 16:
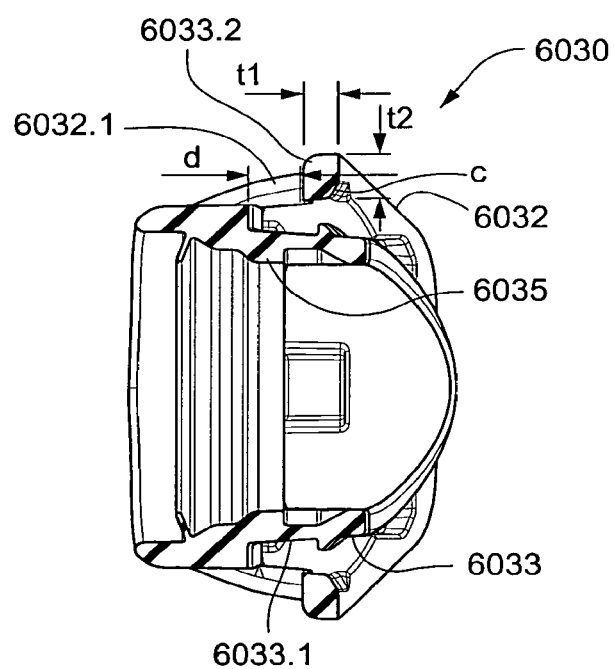
Figures 8, 16:
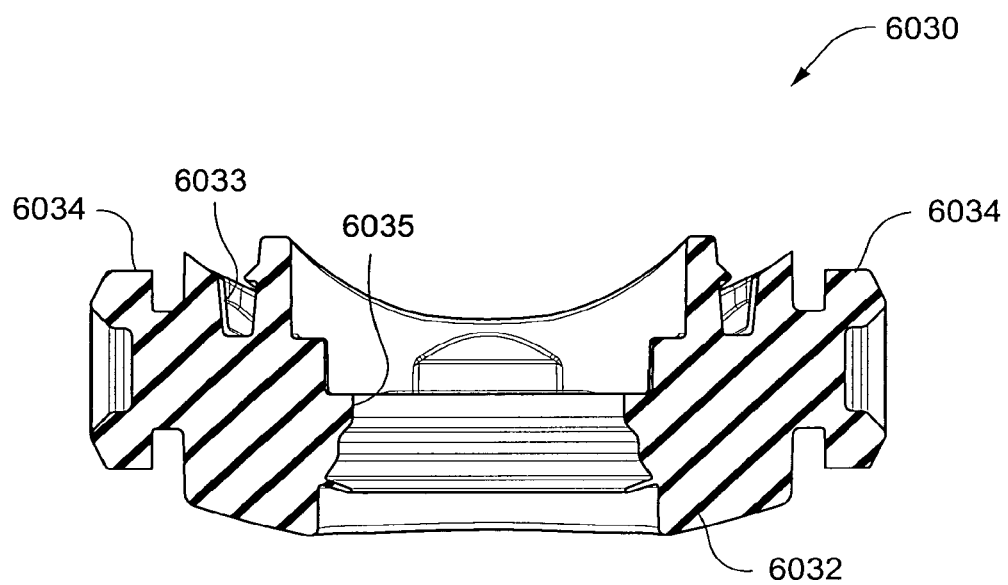
Figures 16, 17:
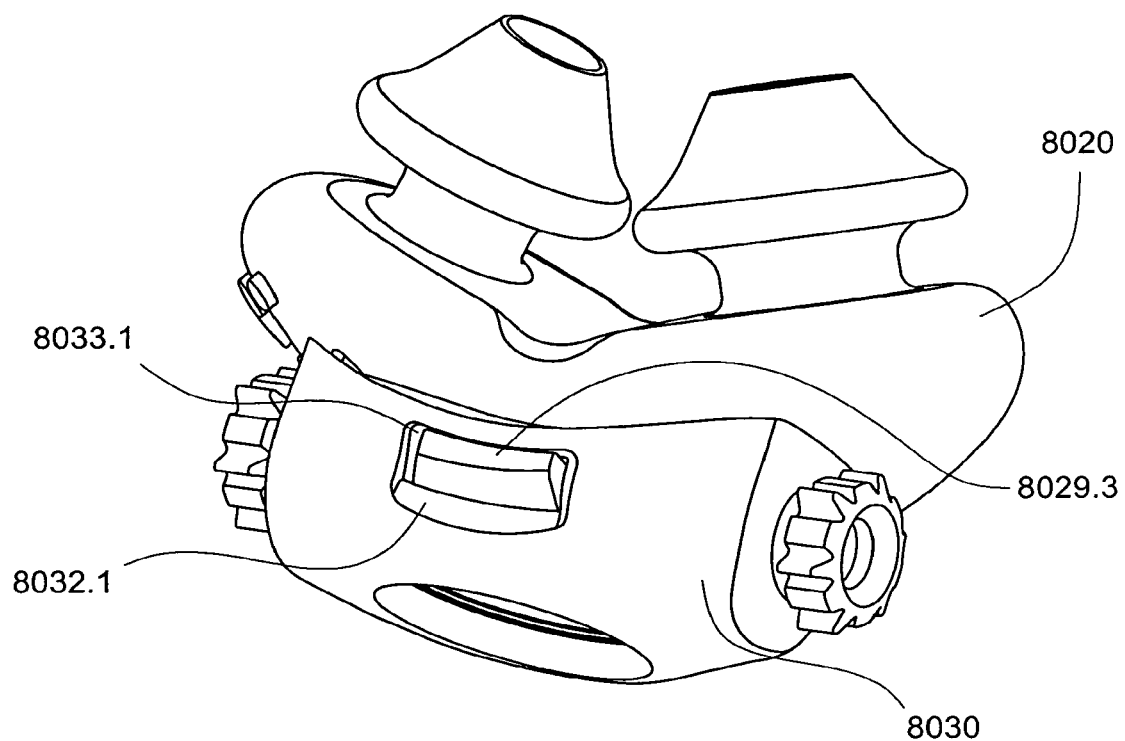
Figures 1, 16, 17, 18:
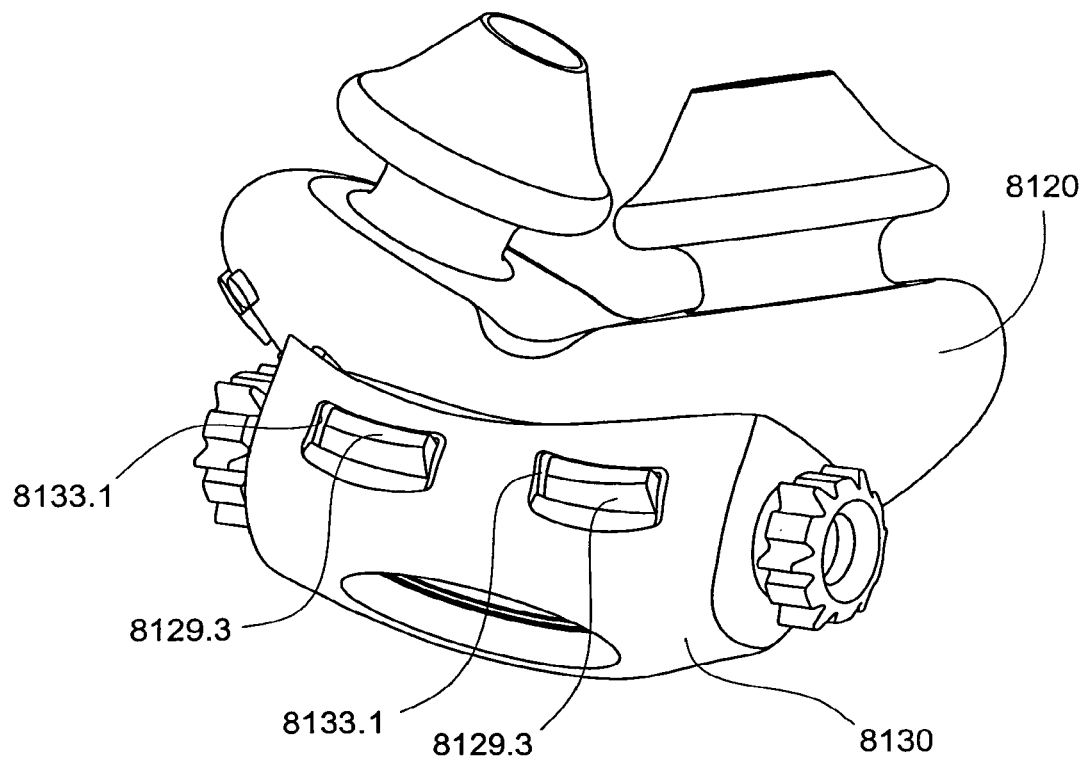
Figures 2, 16, 17, 18:
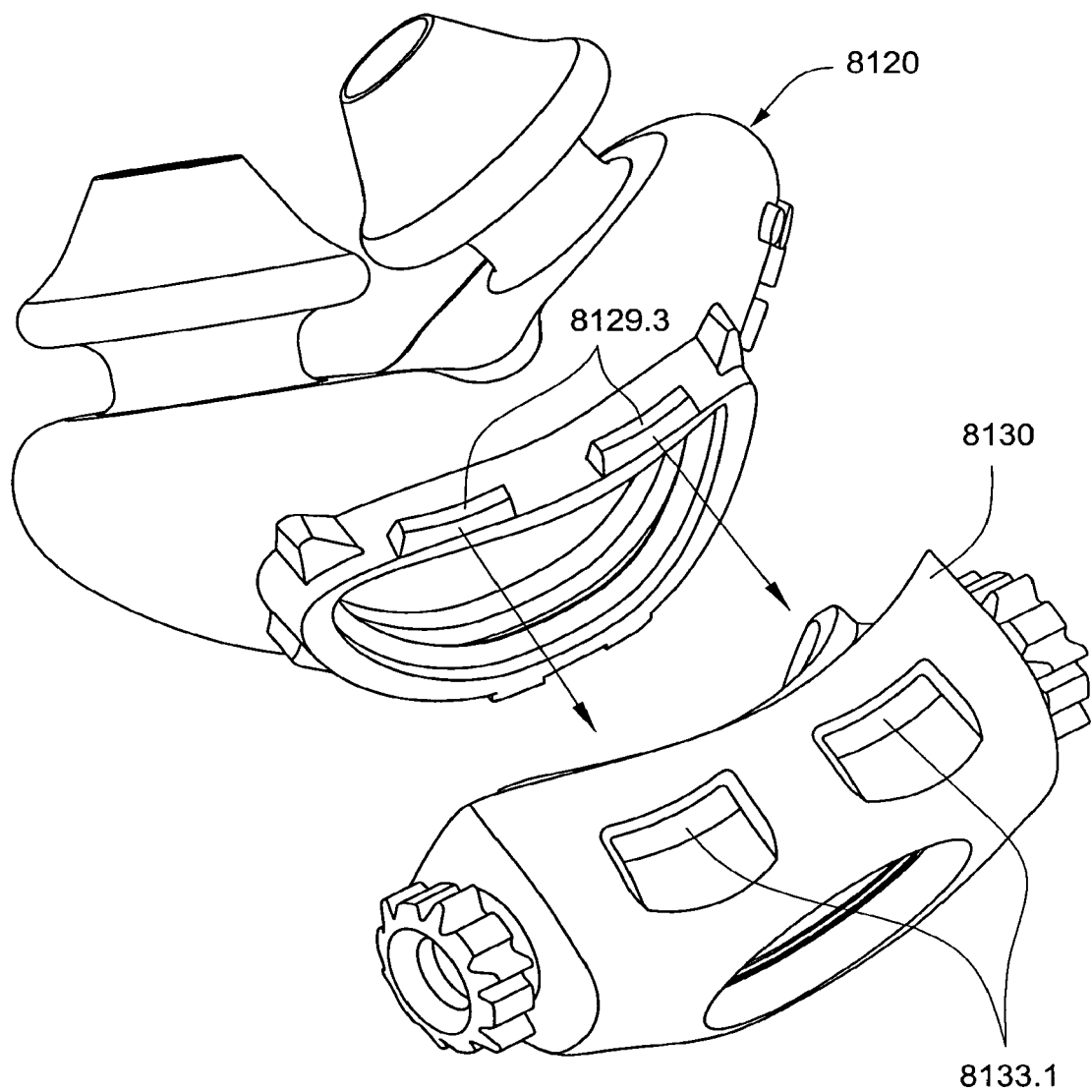
Figures 3, 16, 17, 18:
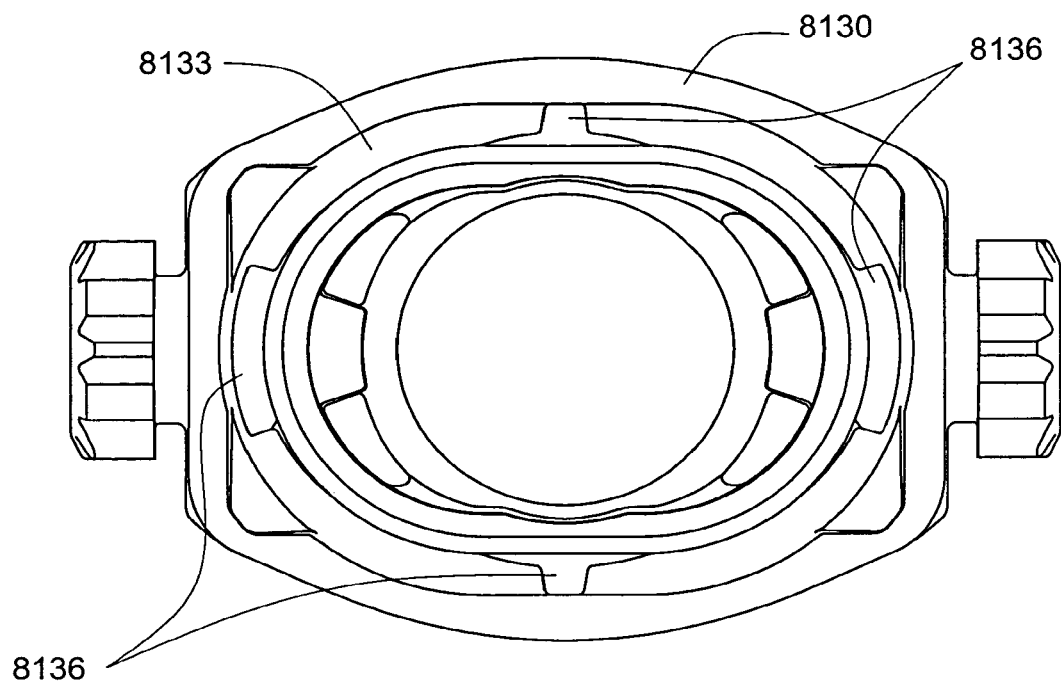
Figures 16, 17, 18, 19:
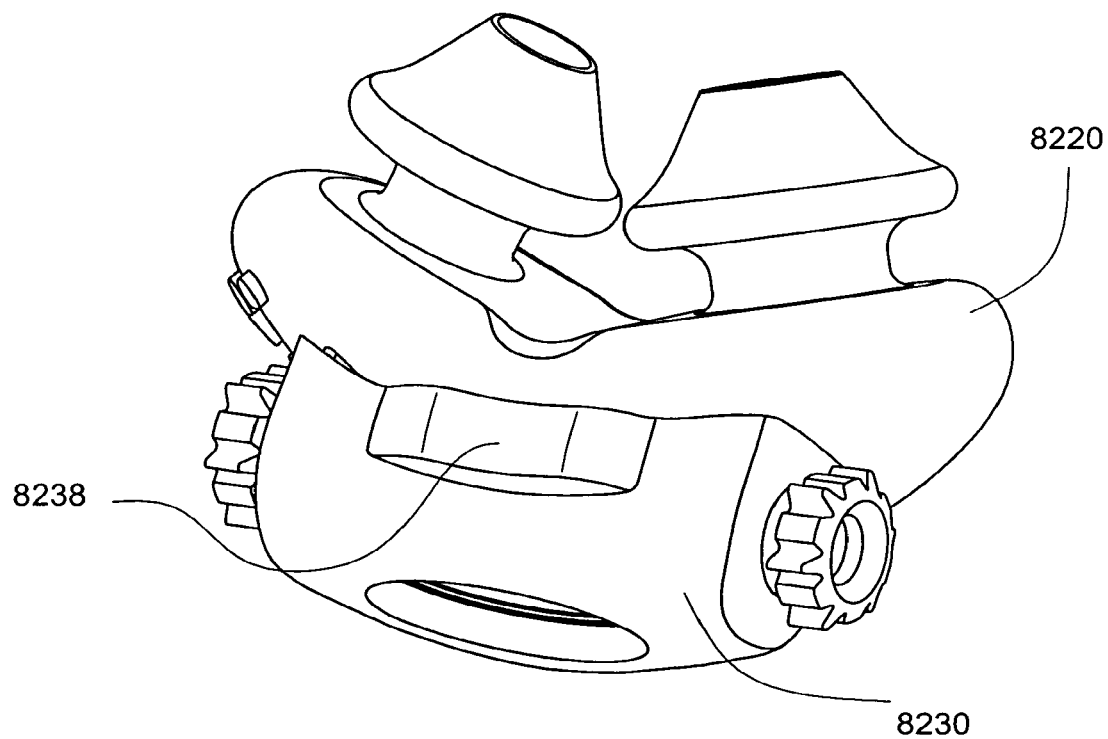
Figures 16, 17, 18, 19, 20:
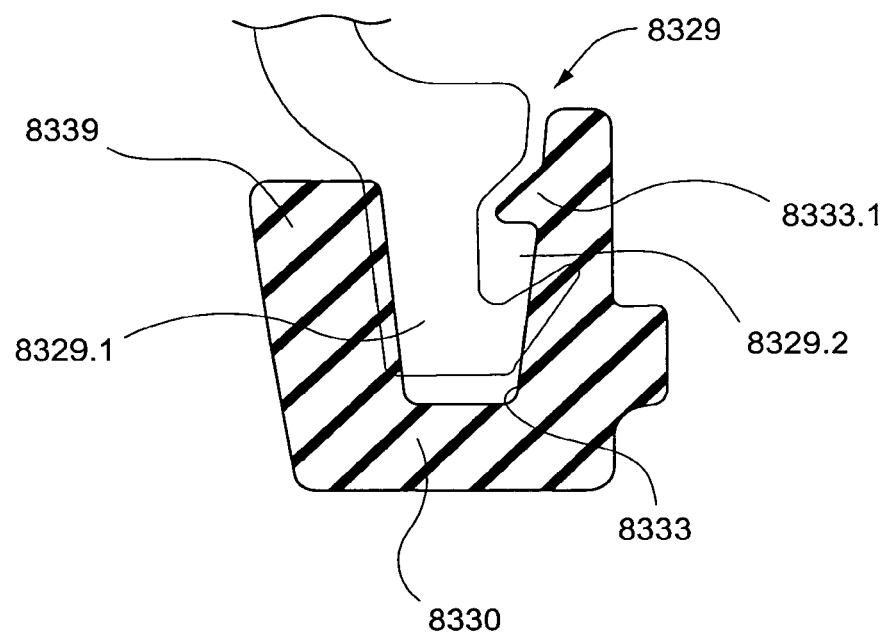
Figures 16, 17, 18, 19, 20, 21:
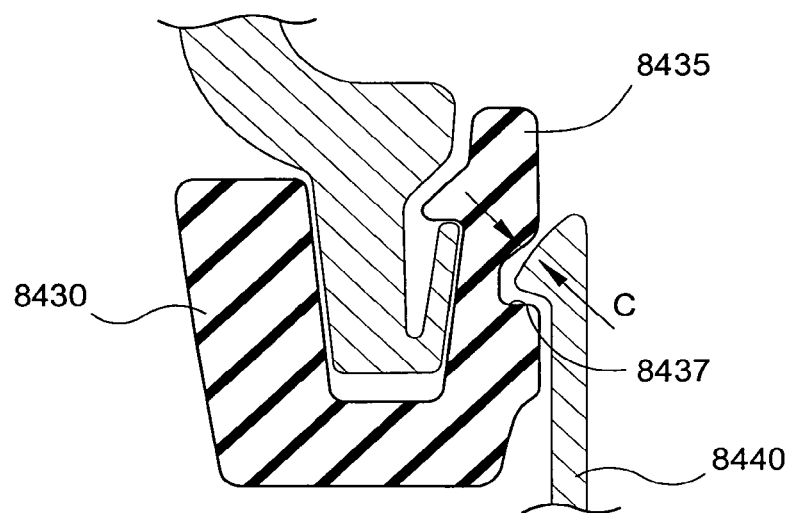
Figures 16, 17, 18, 19, 20, 21, 22:
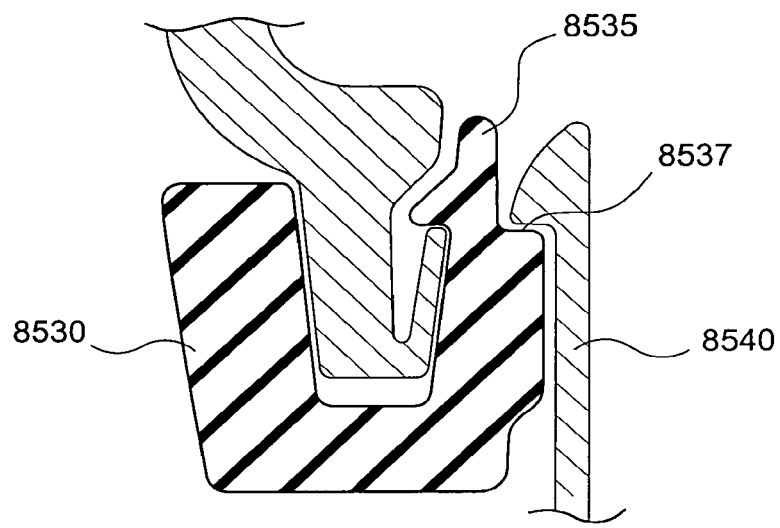
Figures 16, 17, 18, 19, 20, 21, 22, 23:
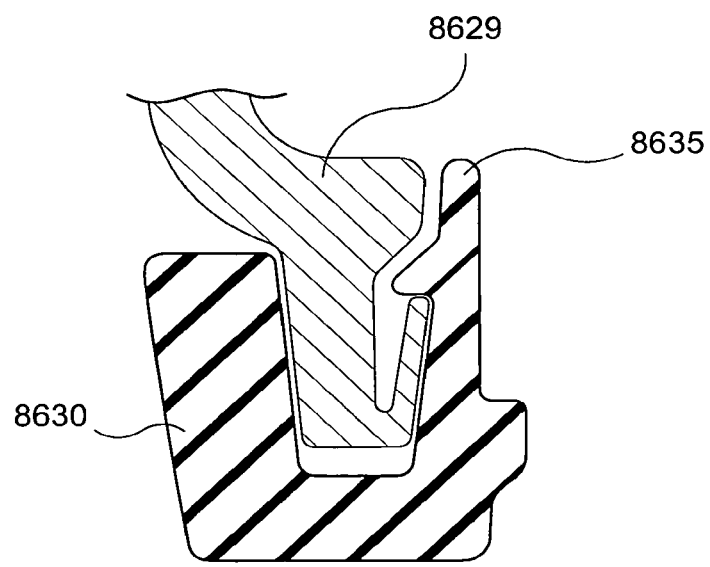
Figures 16, 17, 18, 19, 20, 21, 22, 23, 24:
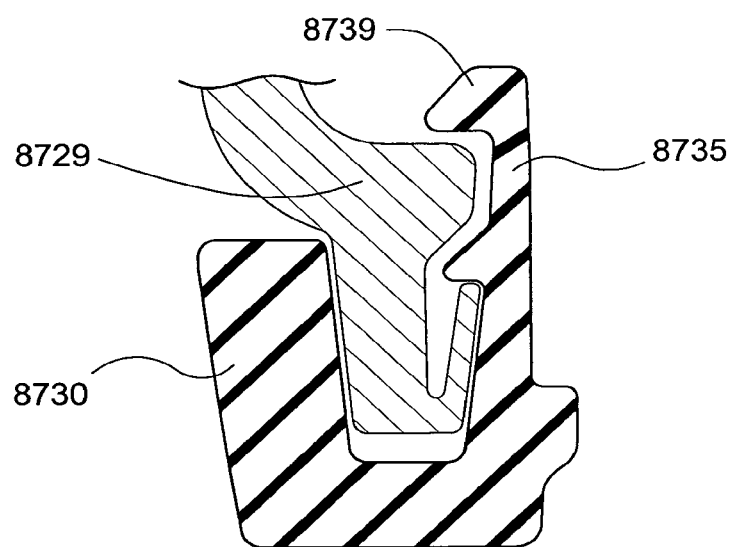
Figures 16, 17, 18, 19, 20, 21, 22, 23, 24, 25:
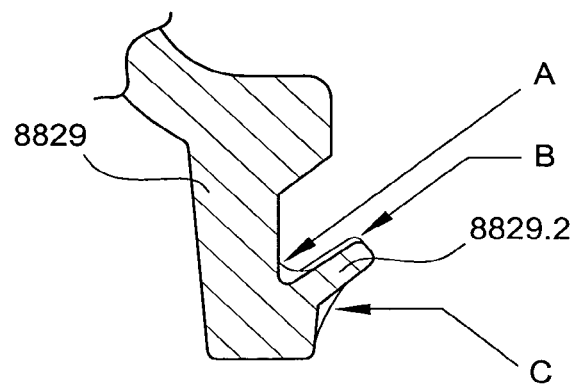
Figures 16, 17, 18, 19, 20, 21, 22, 23, 24, 25, 26:
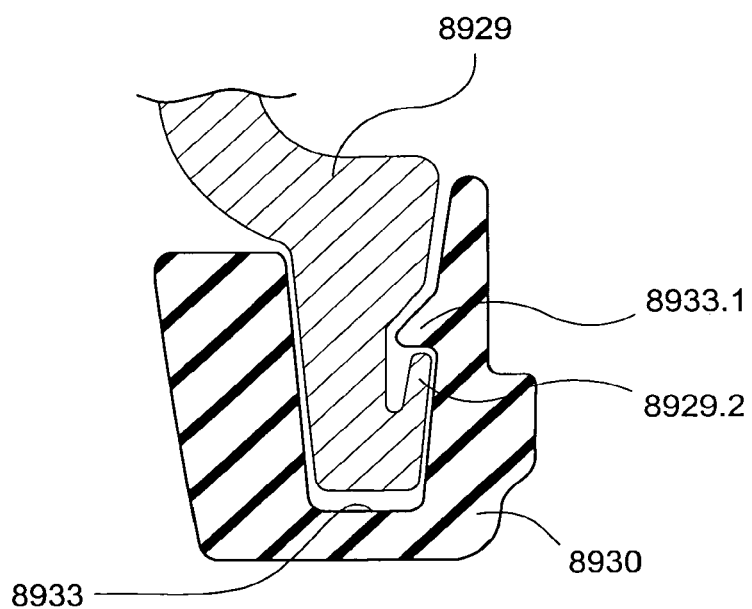
Figures 16, 17, 18, 19, 20, 21, 22, 23, 24, 25, 26, 27:
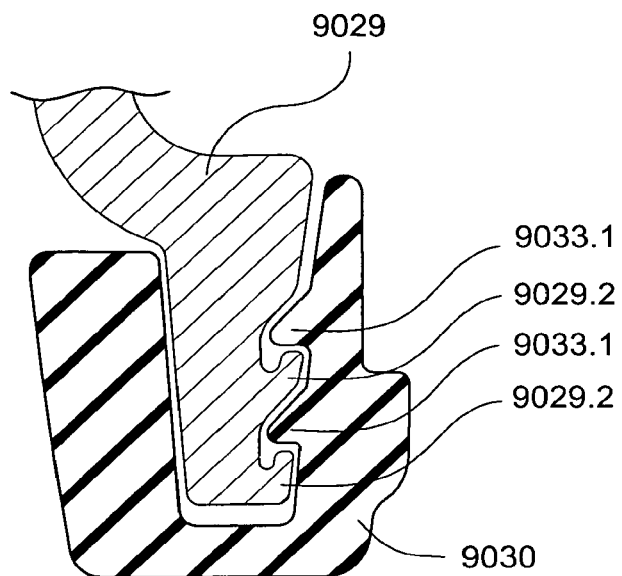
Figures 16, 17, 18, 19, 20, 21, 22, 23, 24, 25, 26, 27, 28:
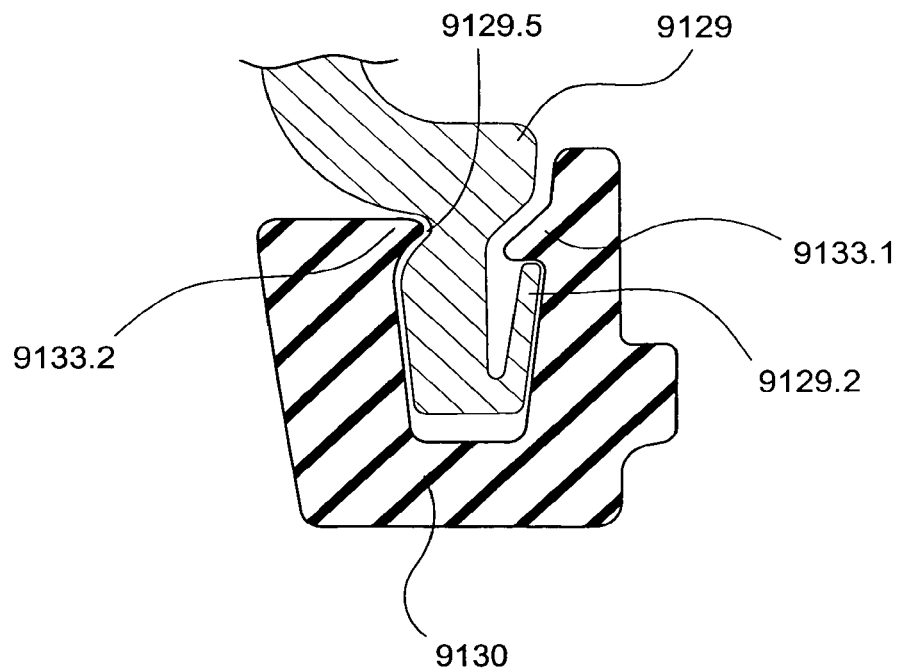
Figures 16, 17, 18, 19, 20, 21, 22, 23, 24, 25, 26, 27, 28, 29:
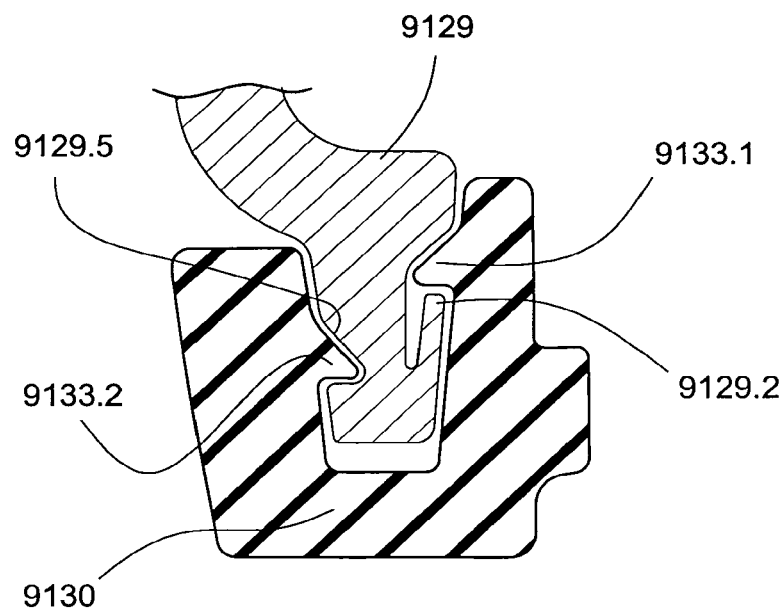
Figures 16, 17, 18, 19, 20, 21, 22, 23, 24, 25, 26, 27, 28, 29, 30:
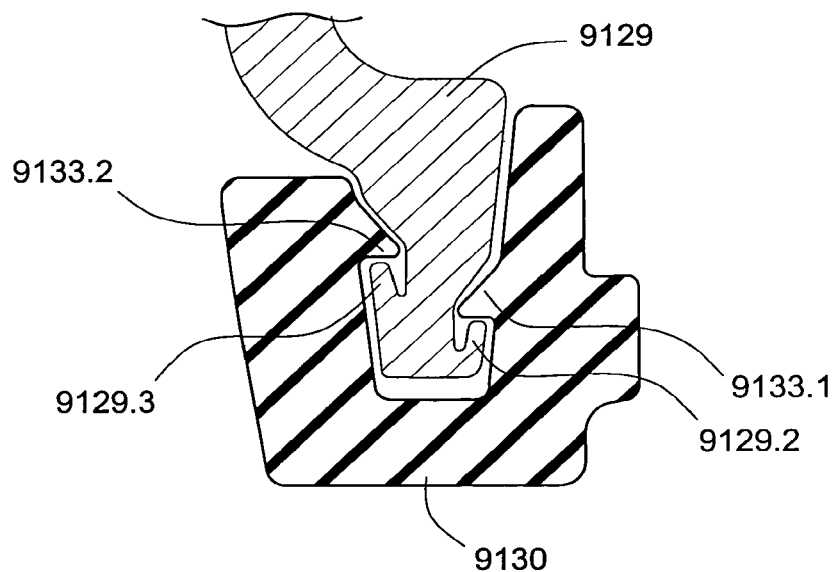
Figures 16, 17, 18, 19, 20, 21, 22, 23, 24, 25, 26, 27, 28, 29, 30, 31:
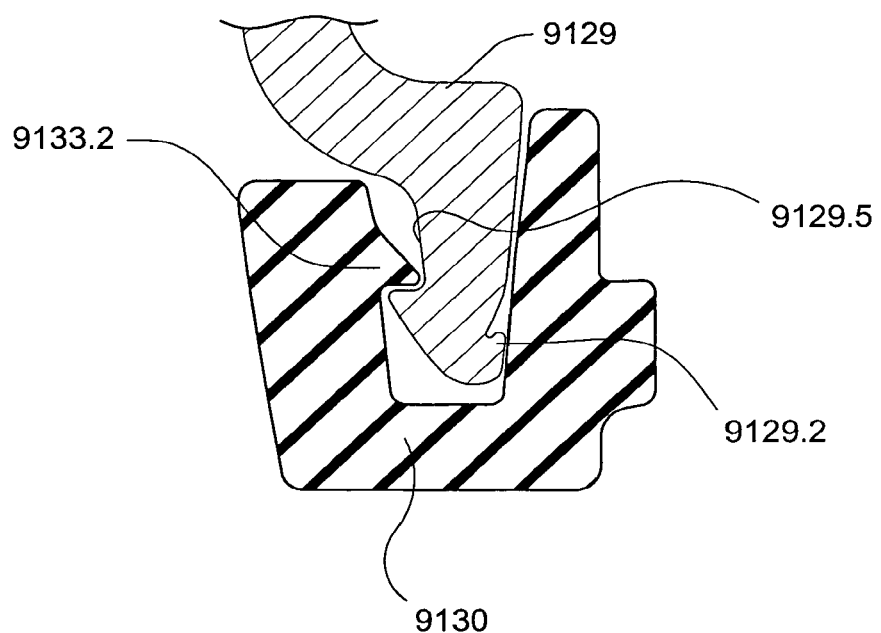
Figures 16, 17, 18, 19, 20, 21, 22, 23, 24, 25, 26, 27, 28, 29, 30, 31, 32:
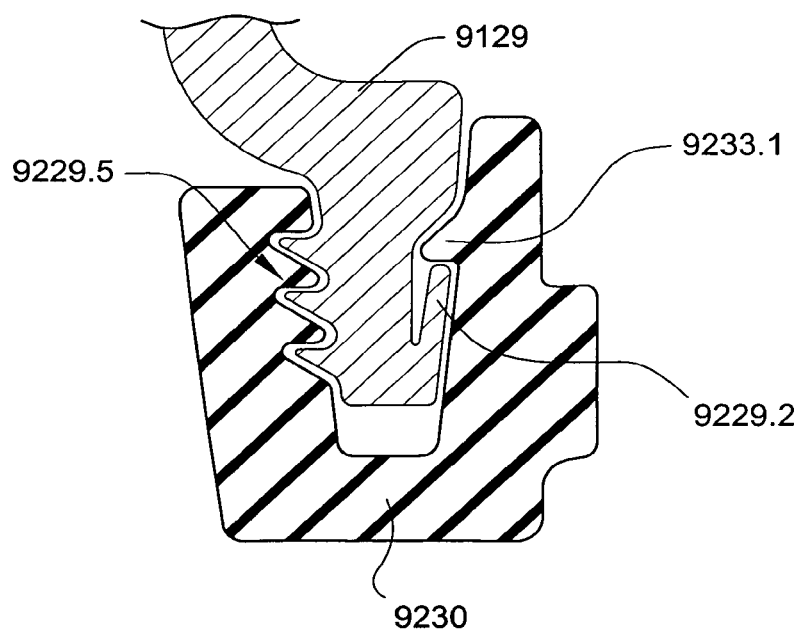
Figures 16, 17, 18, 19, 20, 21, 22, 23, 24, 25, 26, 27, 28, 29, 30, 31, 32, 33:
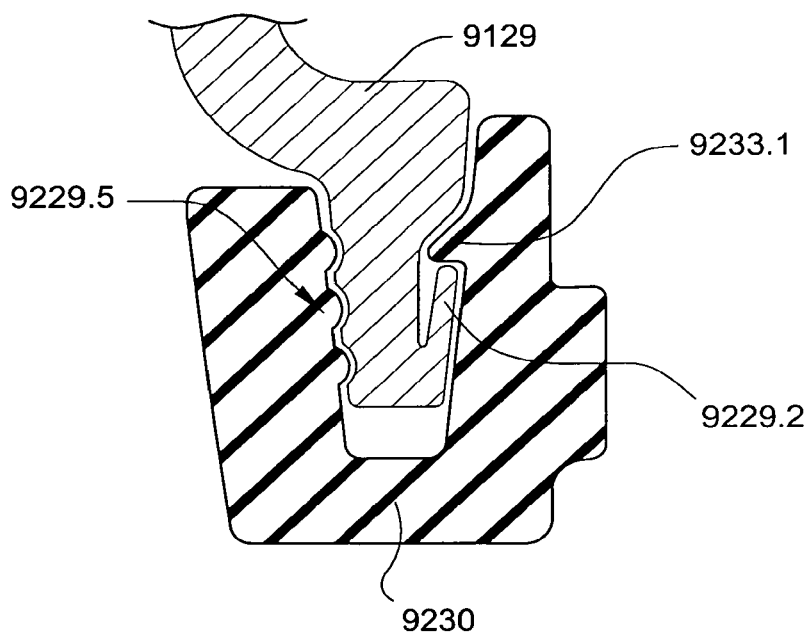
Figures 1, 2, 16, 17, 18, 19, 20, 21, 22, 23, 24, 25, 26, 27, 28, 29, 30, 31, 32, 33, 34:
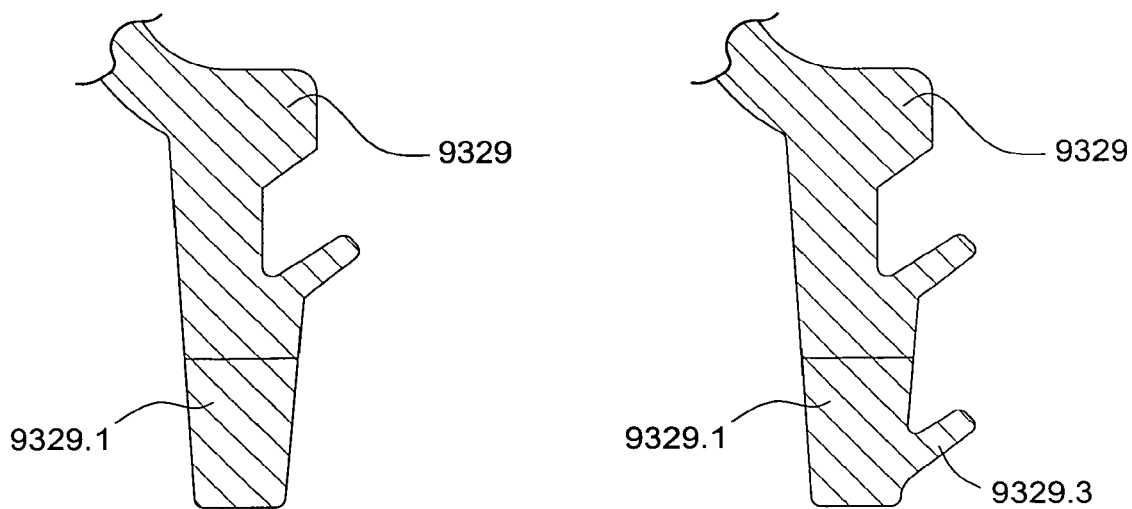
Figures 16, 17, 18, 19, 20, 21, 22, 23, 24, 25, 26, 27, 28, 29, 30, 31, 32, 33, 34, 35:
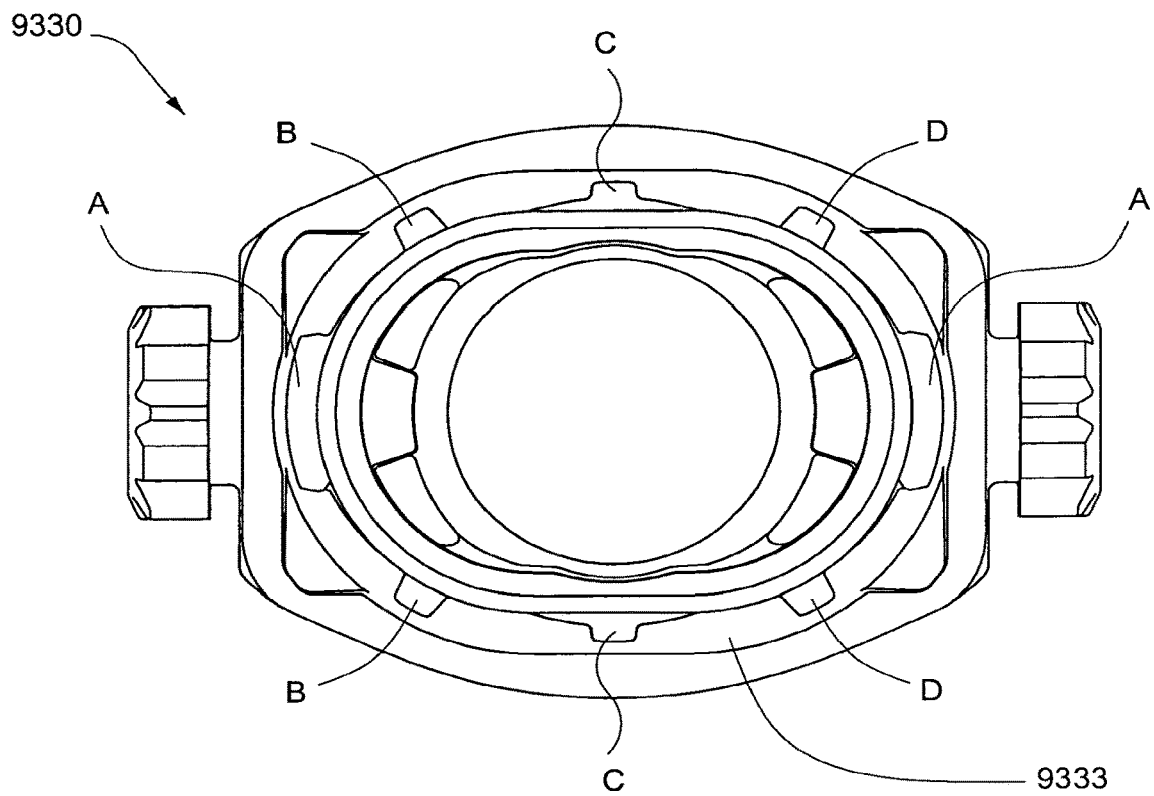
Figures 16, 17, 18, 19, 20, 21, 22, 23, 24, 25, 26, 27, 28, 29, 30, 31, 32, 33, 34, 35, 36:
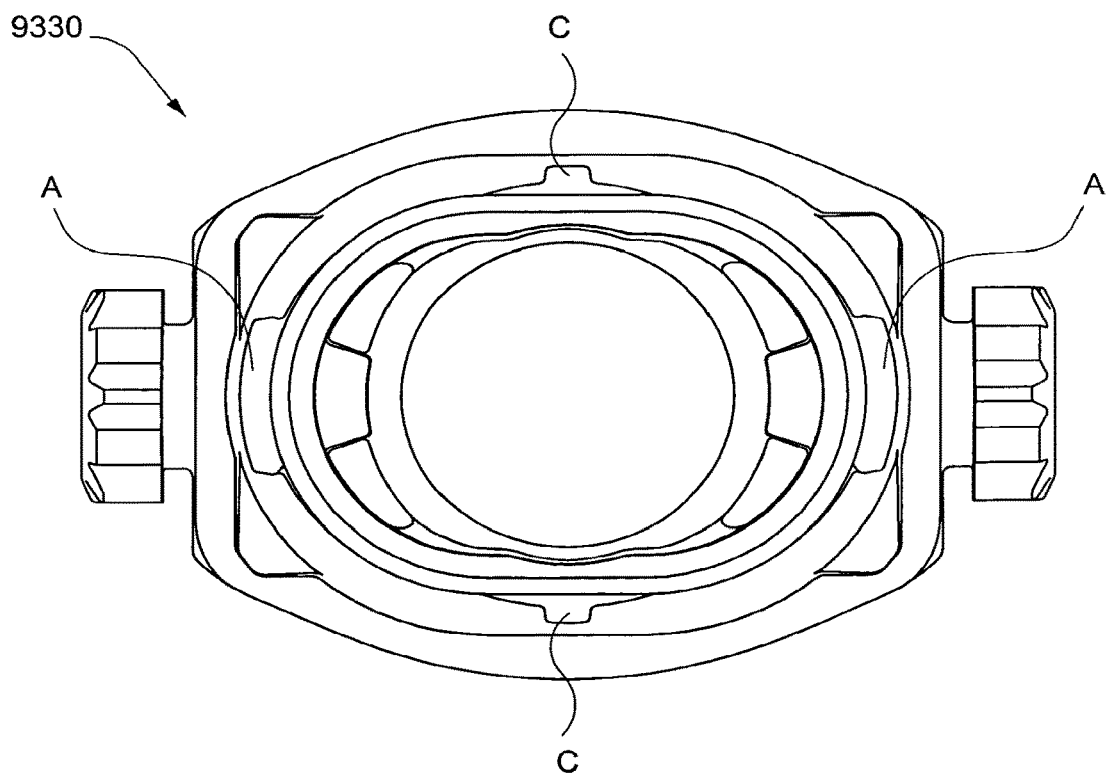
Figures 16, 17, 18, 19, 20, 21, 22, 23, 24, 25, 26, 27, 28, 29, 30, 31, 32, 33, 34, 35, 36, 37:
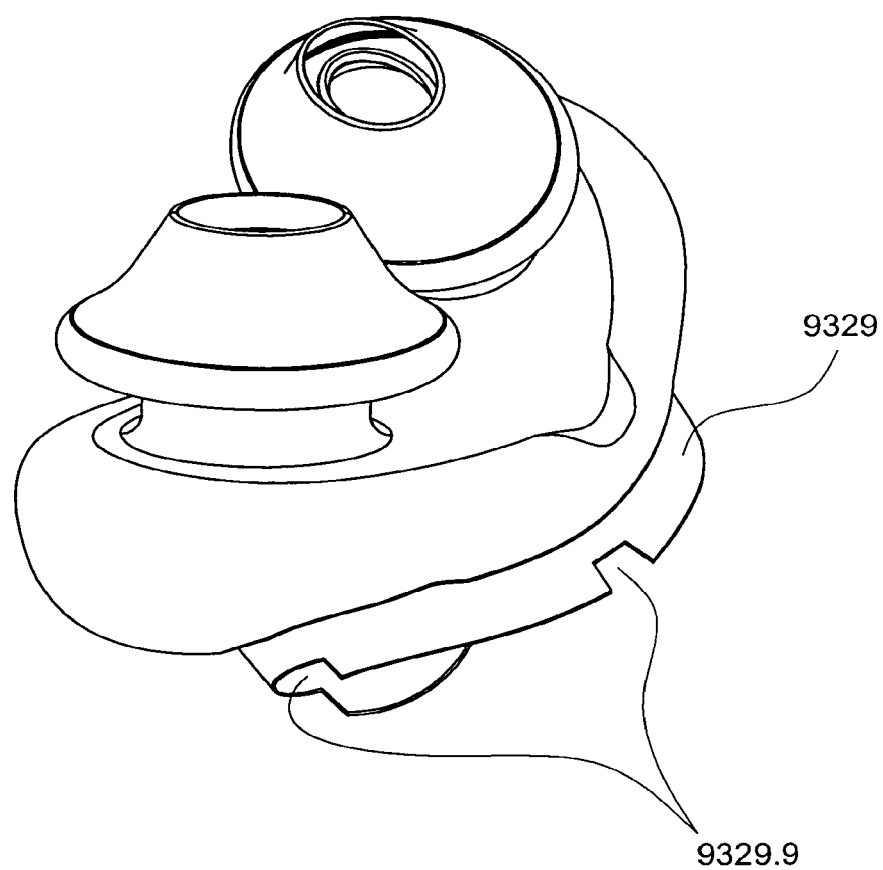
Figures 16, 17, 18, 19, 20, 21, 22, 23, 24, 25, 26, 27, 28, 29, 30, 31, 32, 33, 34, 35, 36, 37, 38:
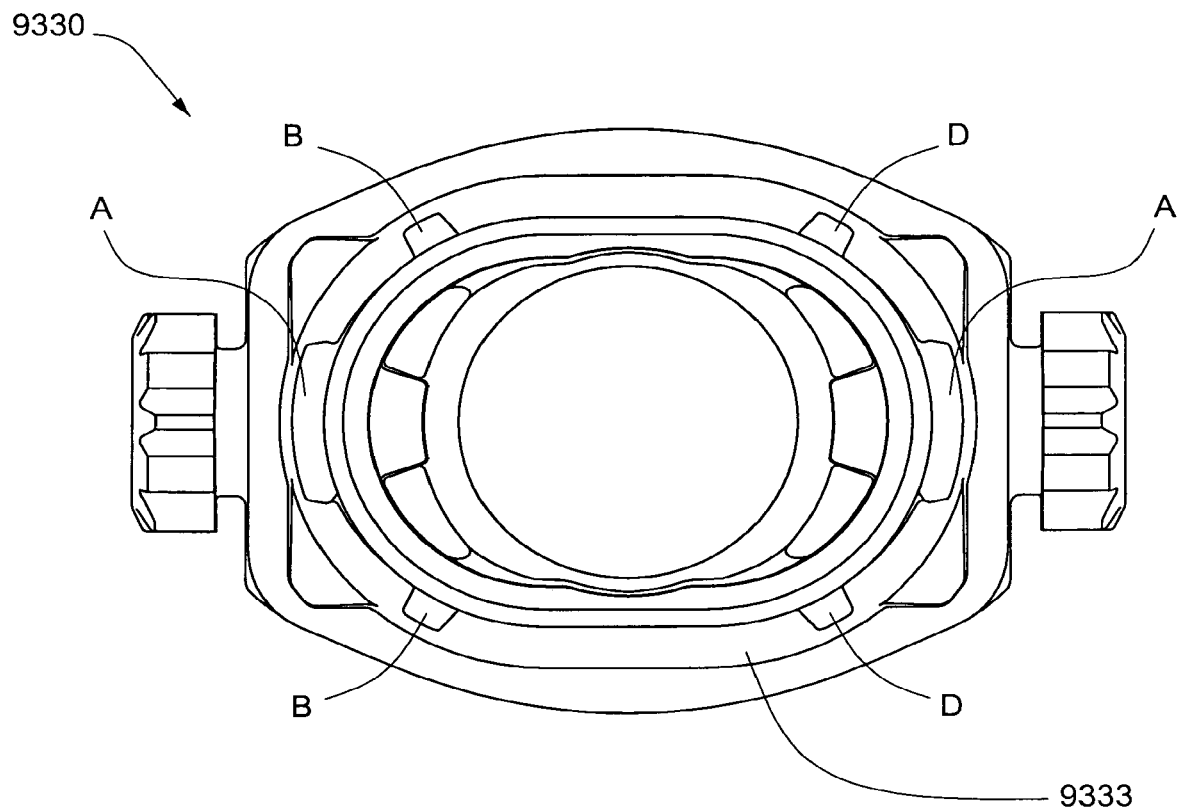
Figures 16, 17, 18, 19, 20, 21, 22, 23, 24, 25, 26, 27, 28, 29, 30, 31, 32, 33, 34, 35, 36, 37, 38, 39:
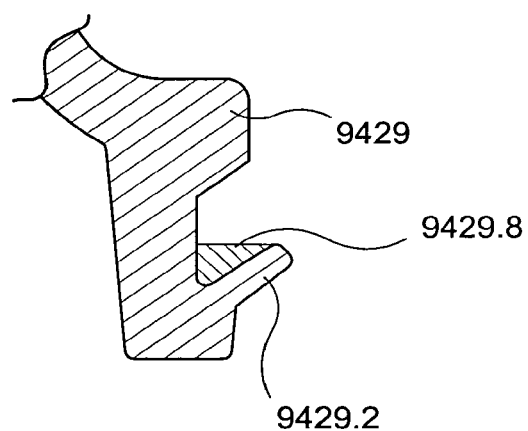
Figure 17:
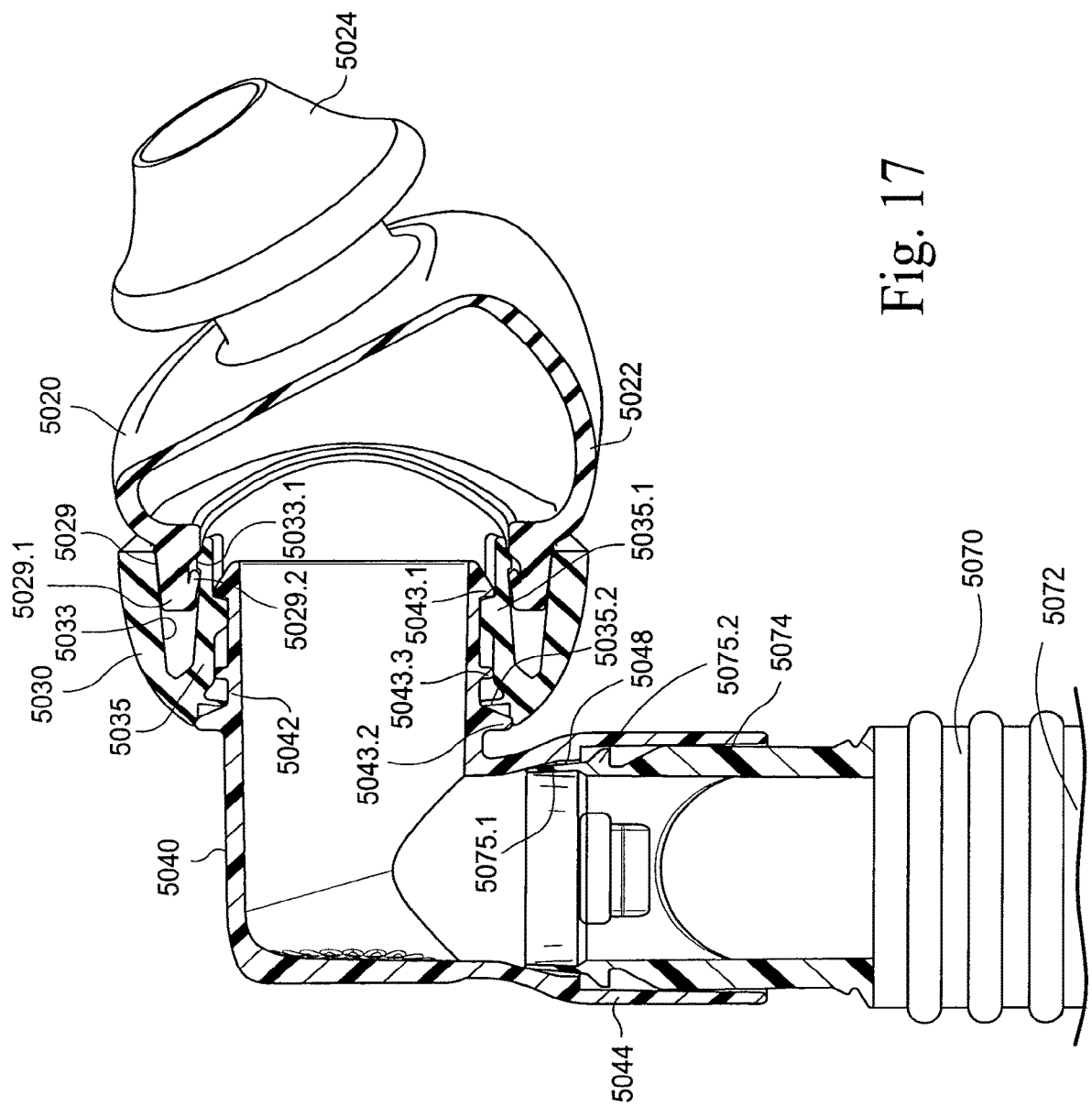
Figures 6, 18:
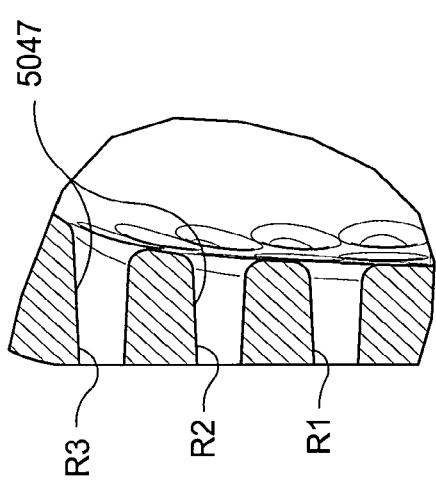
Figures 5, 18:
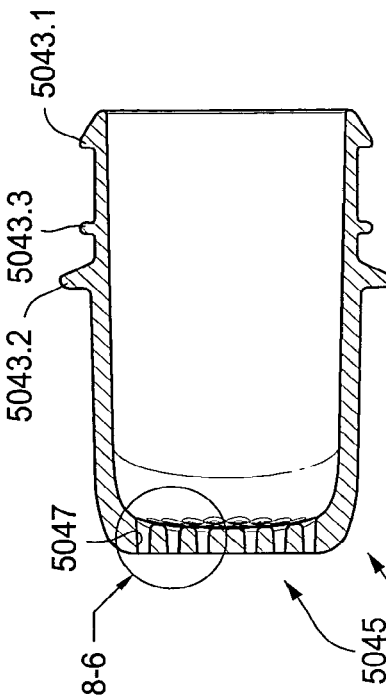
Figures 4, 18:
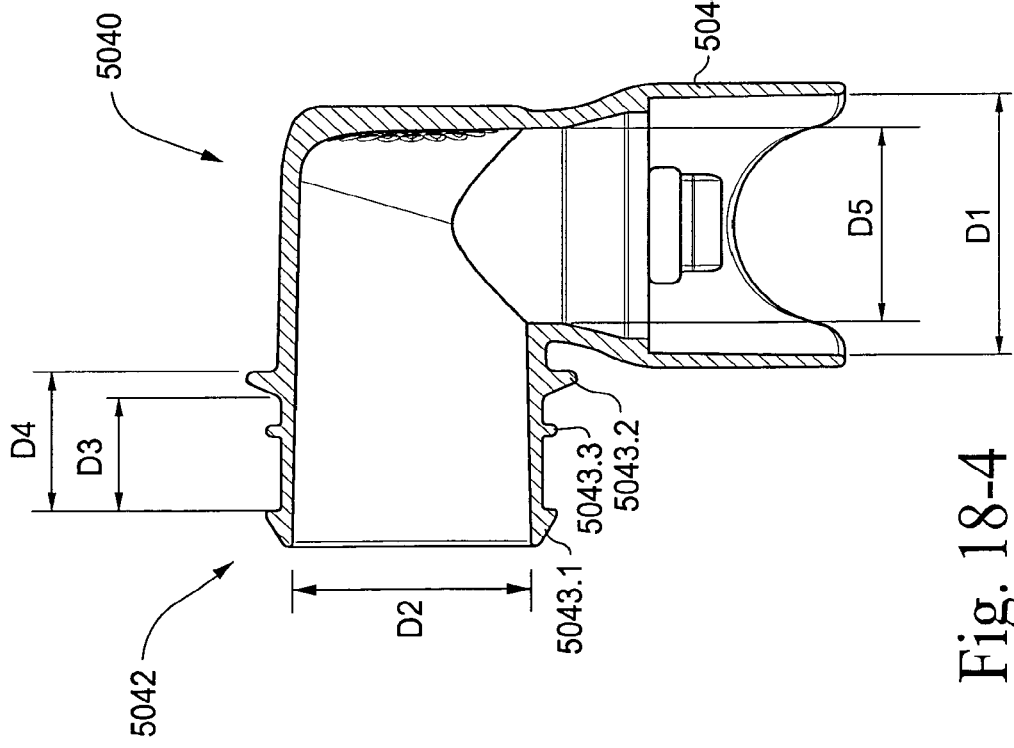
Figures 1, 8, 18:
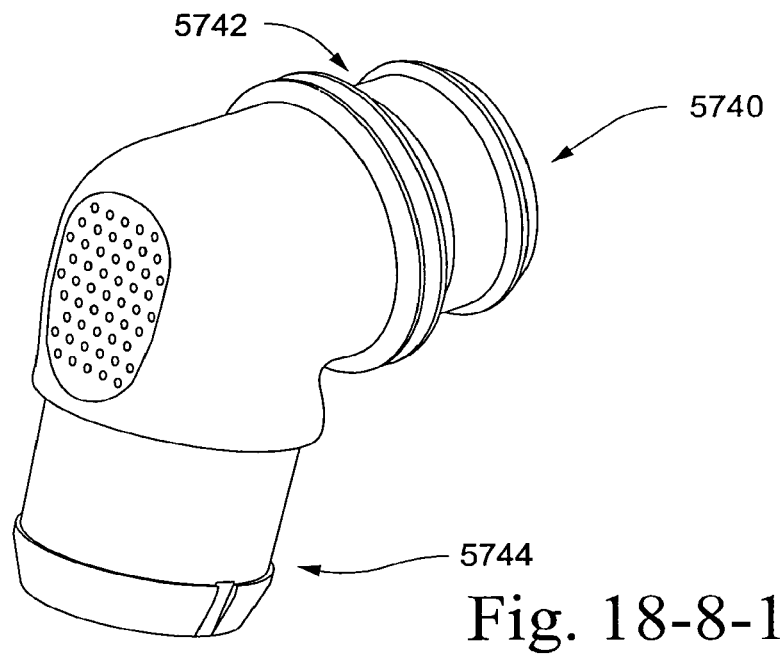
Figures 2, 8, 18:
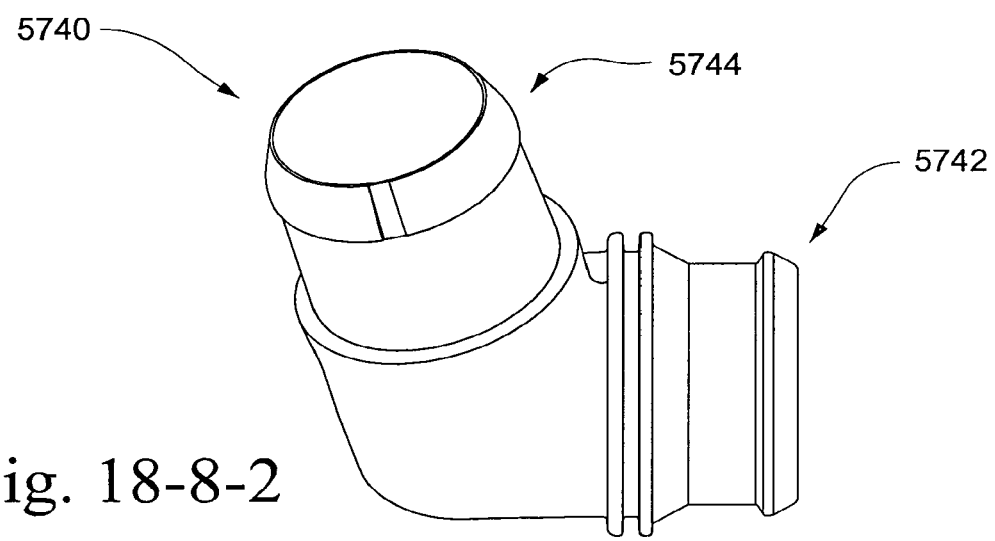
Figures 3, 8, 18:
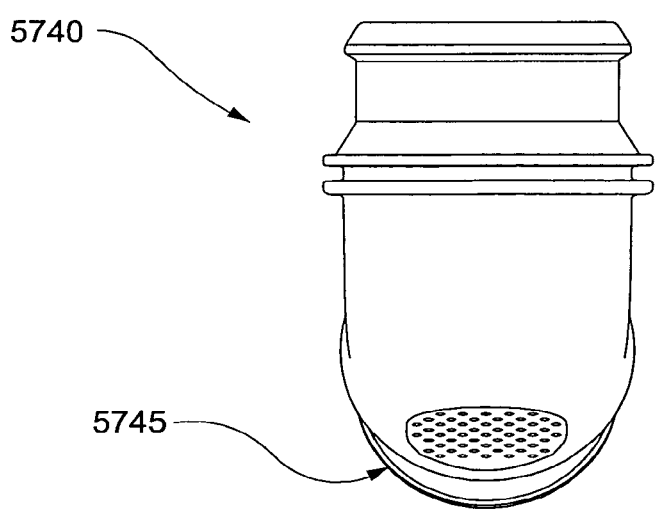
Figures 4, 8, 18:
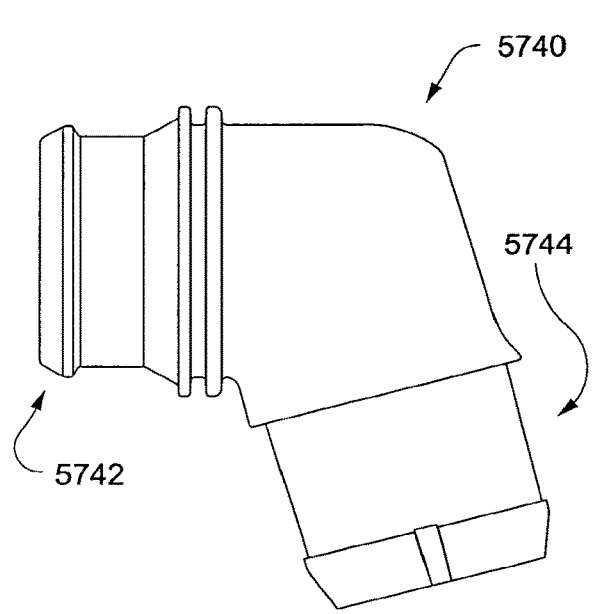
Figures 5, 8, 18:
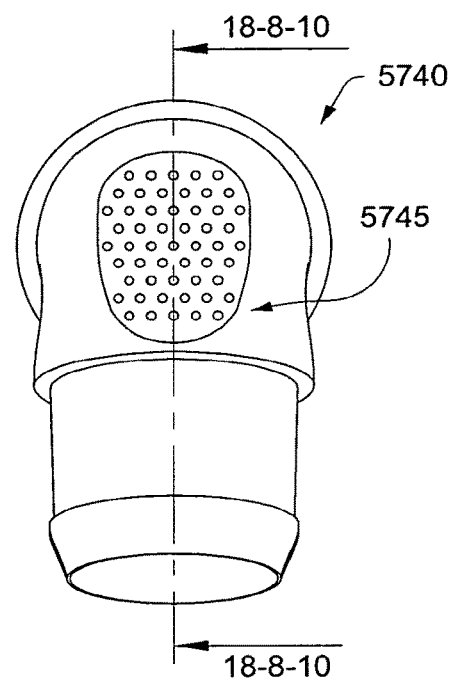
Figures 6, 8, 18:
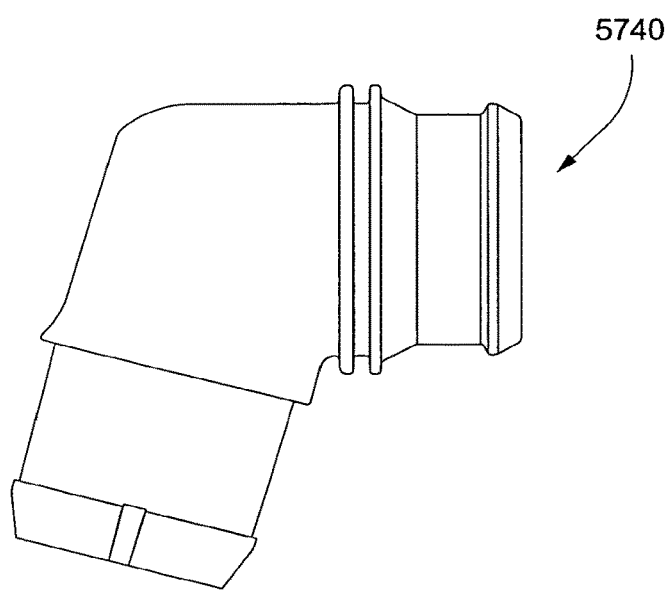
Figures 7, 8, 18:
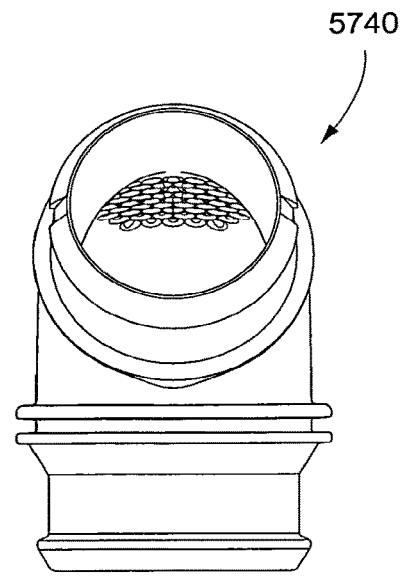
Figures 8, 18:
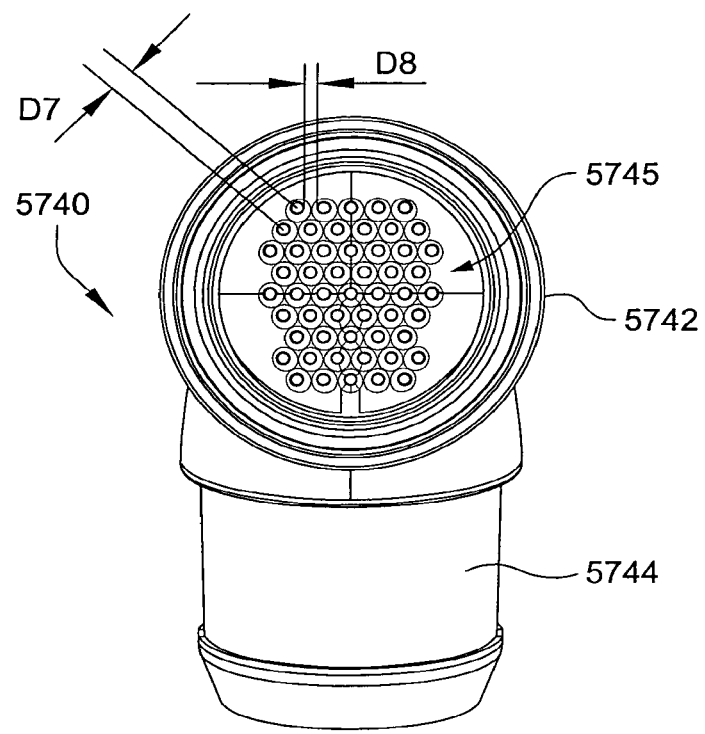
Figures 8, 9, 18:
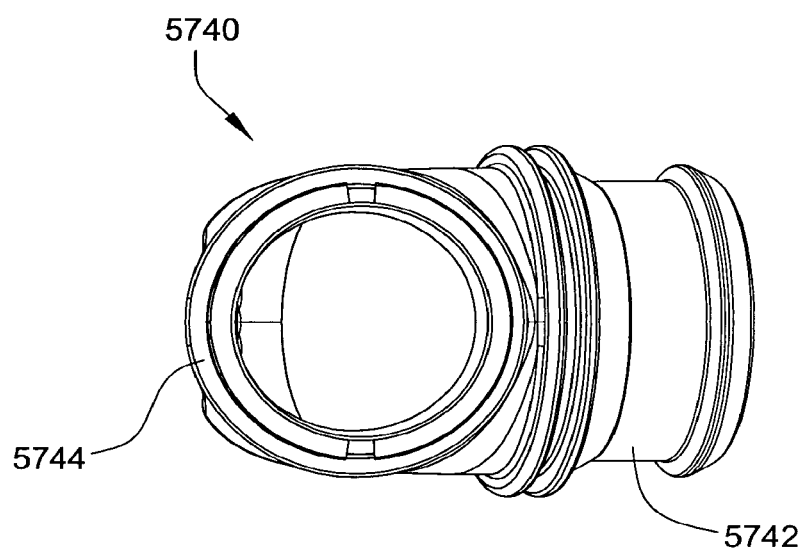
Figures 8, 10, 18:
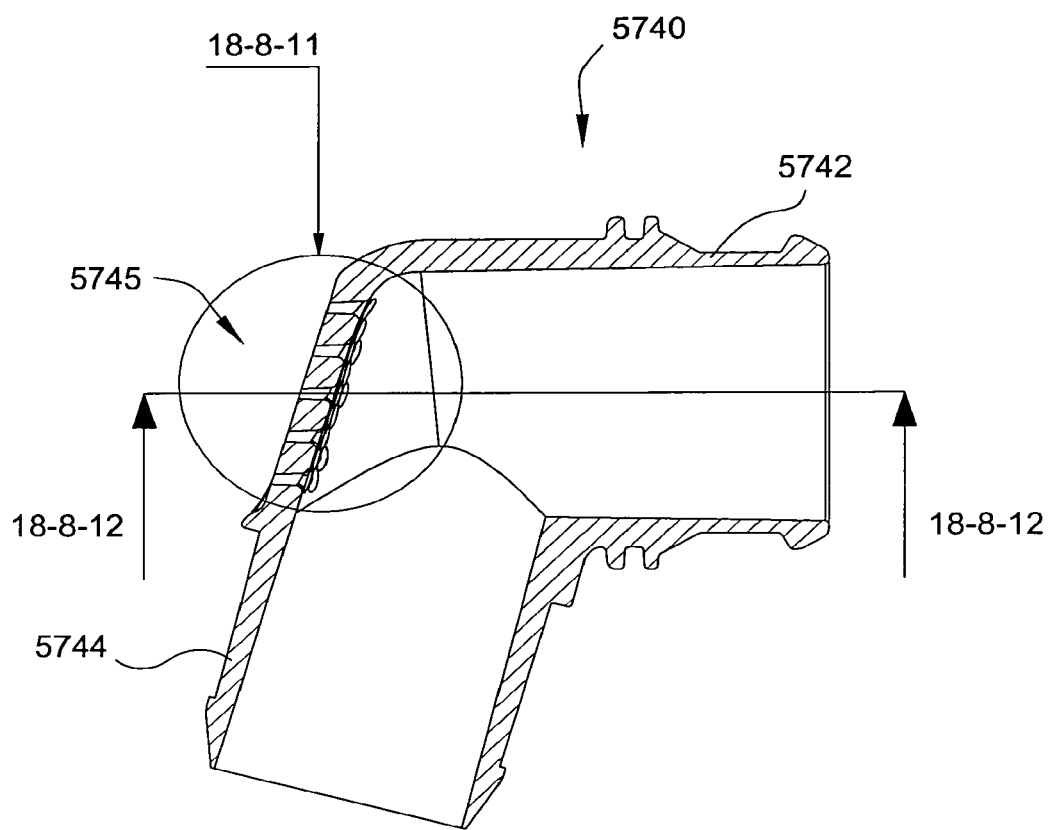
Figures 8, 11, 18:
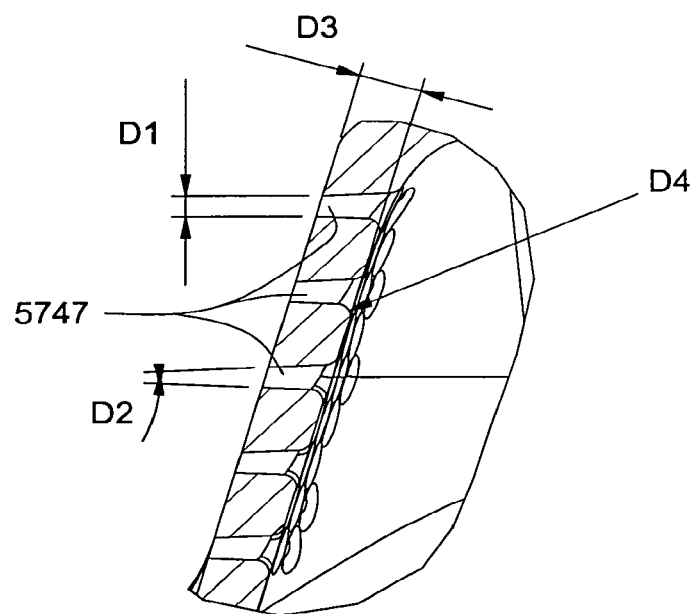
Figures 8, 12, 18:
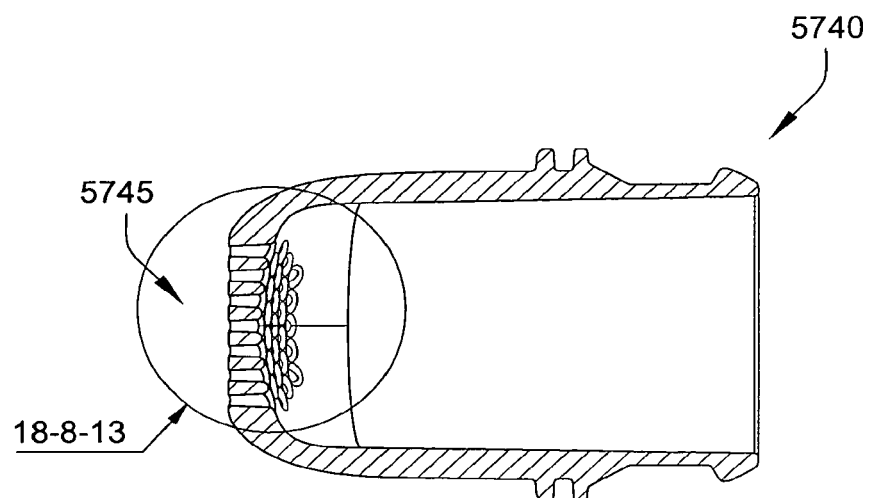
Figures 8, 13, 18:
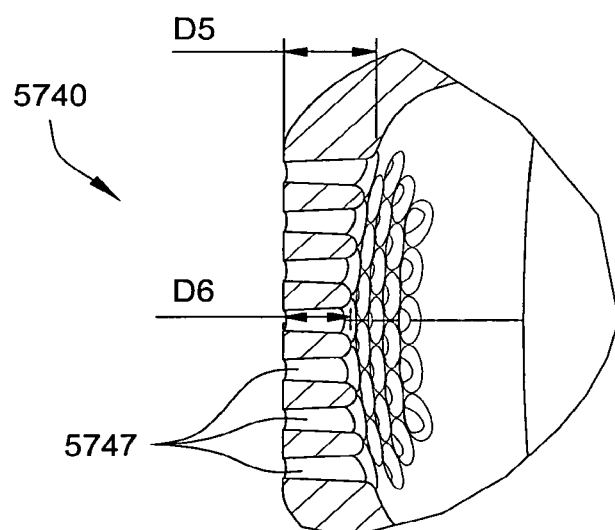
Figures 8, 14, 18:
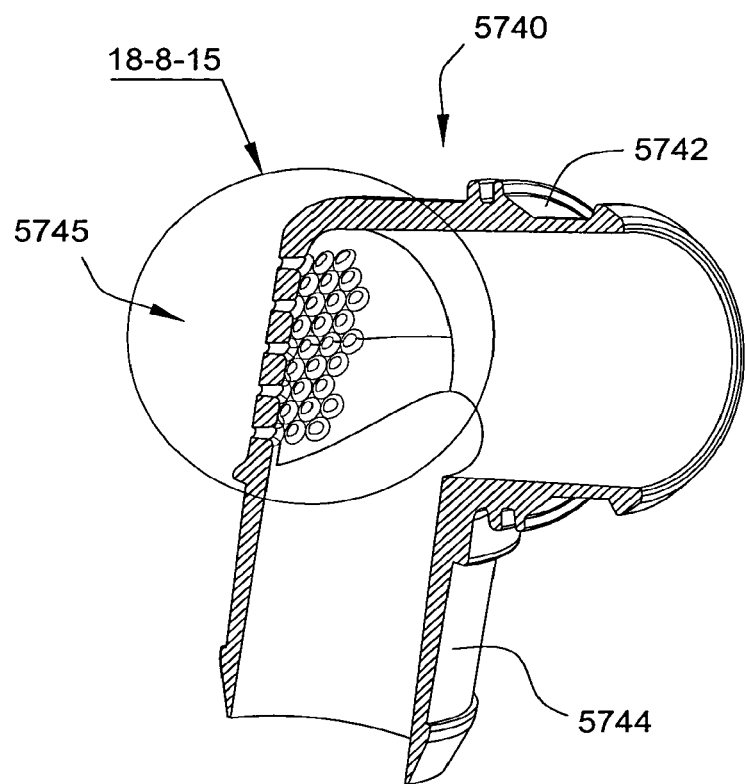
Figures 8, 15, 18:
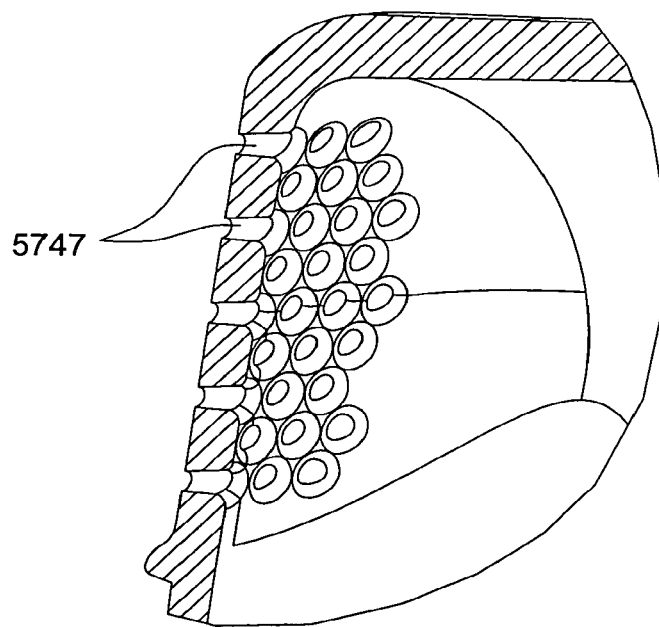
Figures 1, 2, 3, 10, 18:
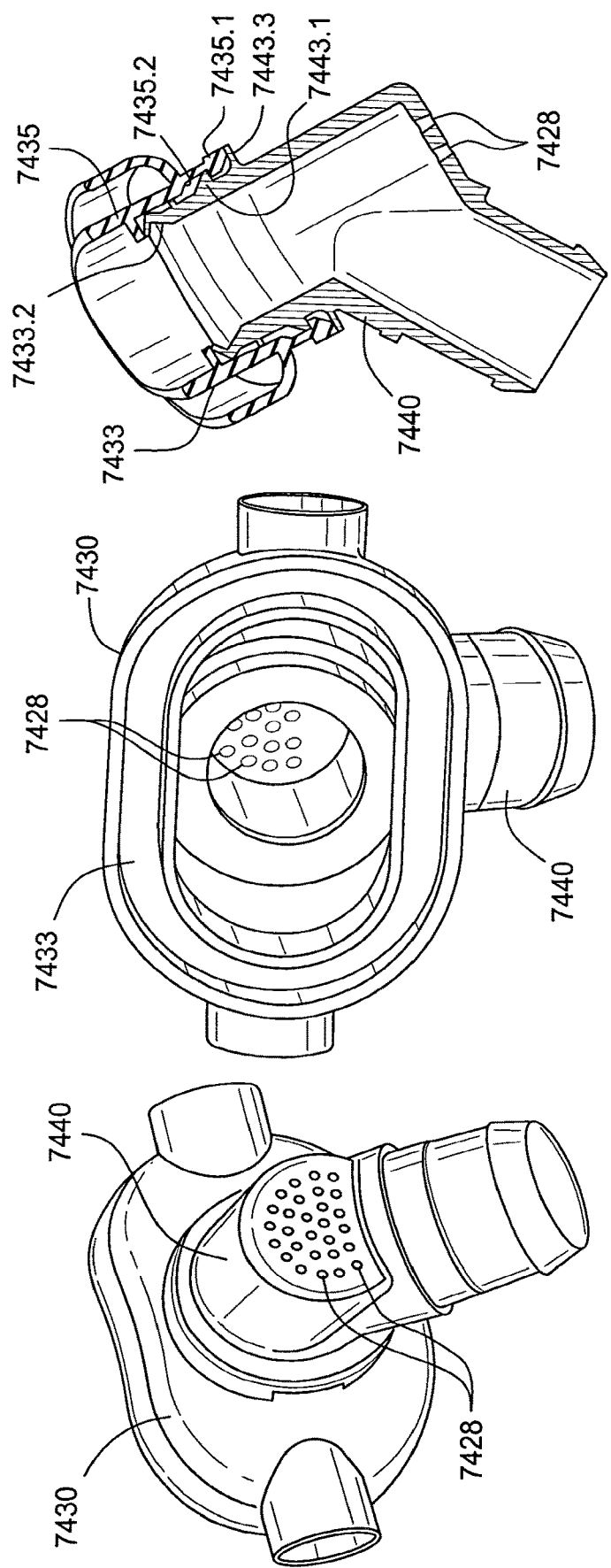
Figures 3, 11, 18:
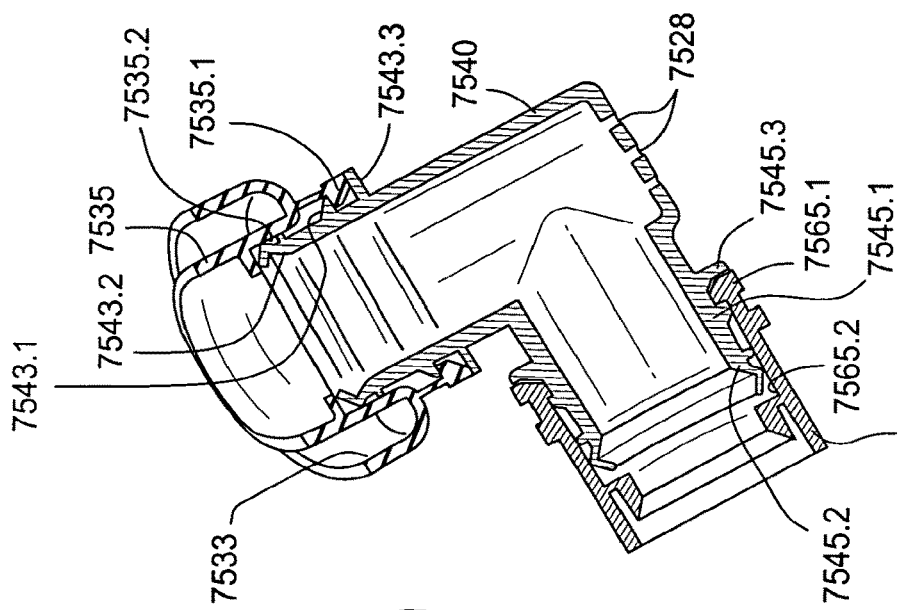
Figures 2, 11, 18:
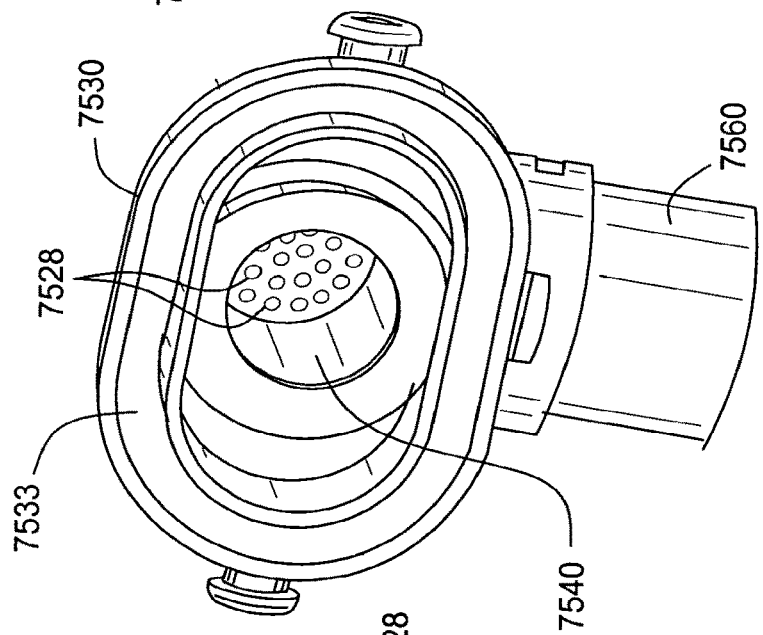
Figures 1, 11, 18:
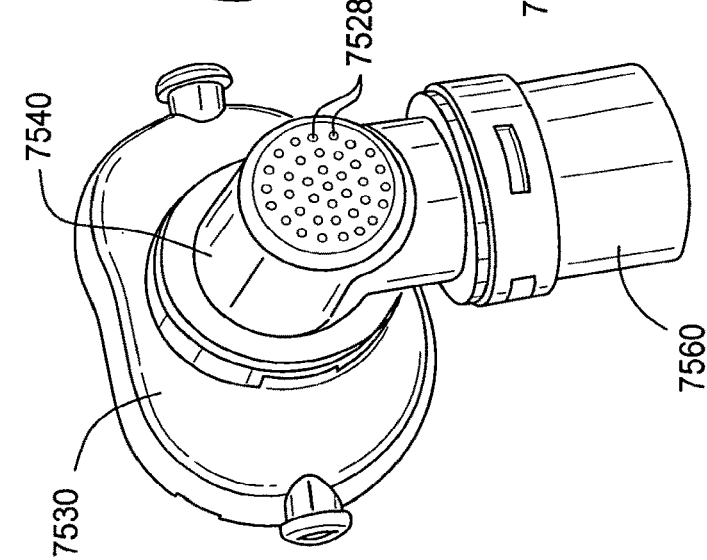
Figures 3, 12, 18:
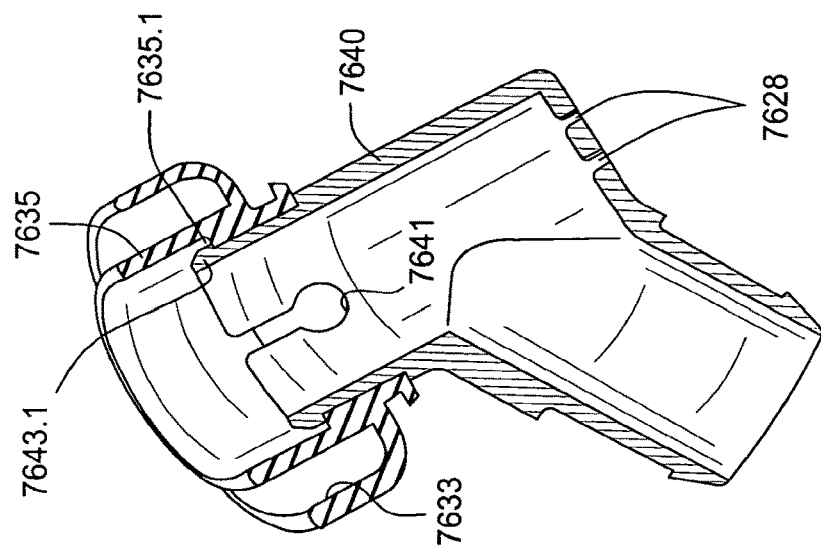
Figures 2, 12, 18:
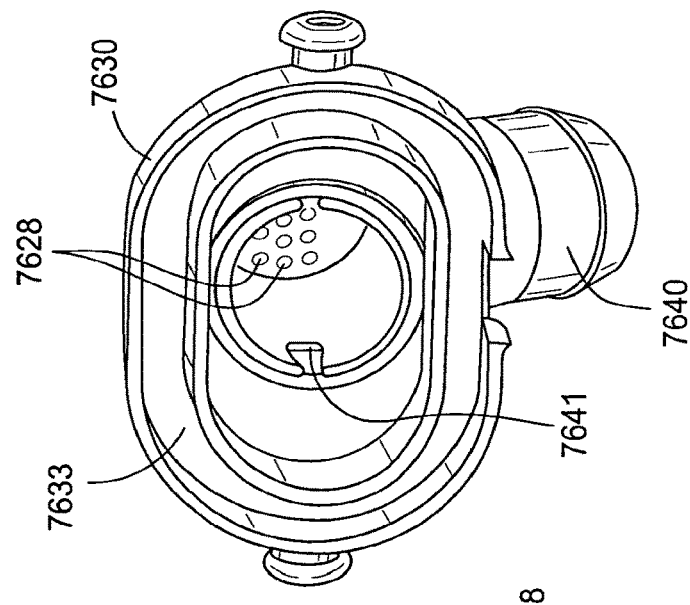
Figures 1, 12, 18:
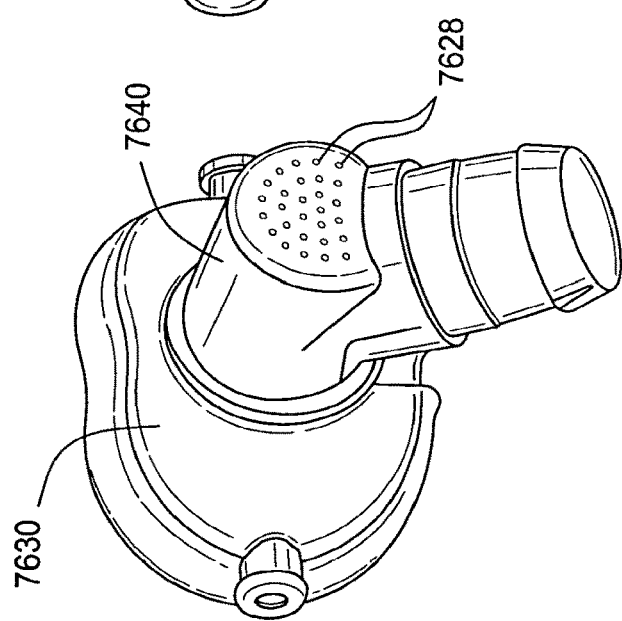
Figures 3, 13, 18:
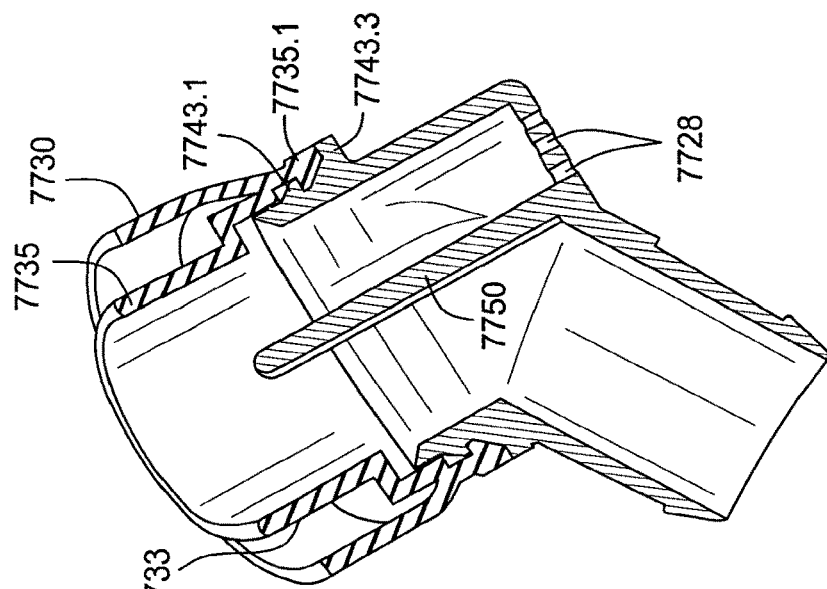
Figures 2, 13, 18:
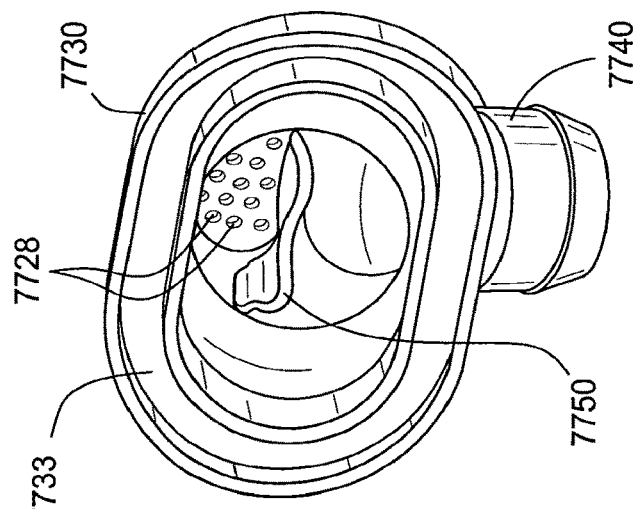
Figures 1, 13, 18:
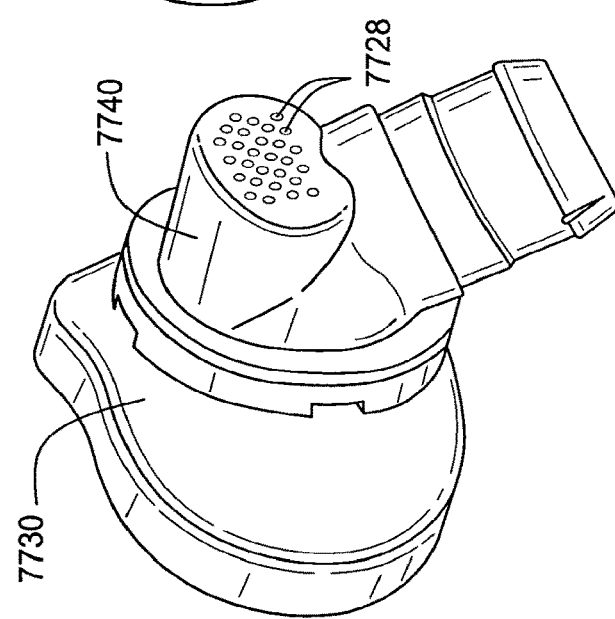
Figures 3, 14, 18:
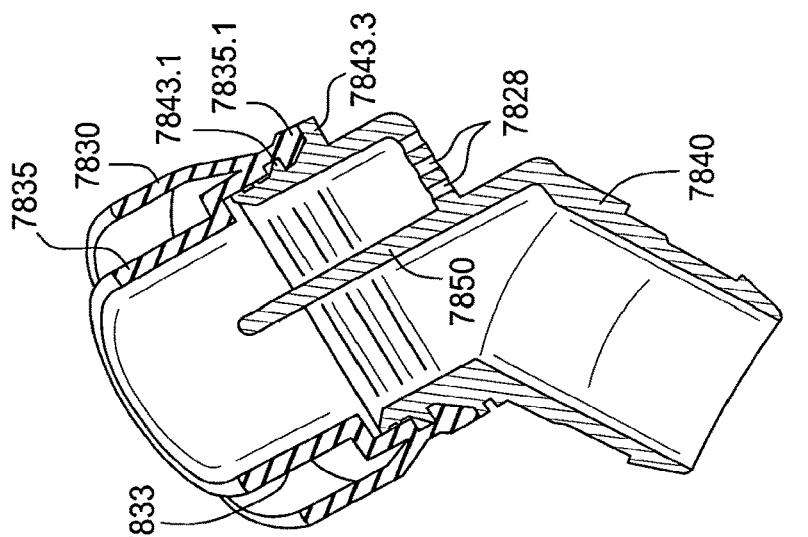
Figures 2, 14, 18:
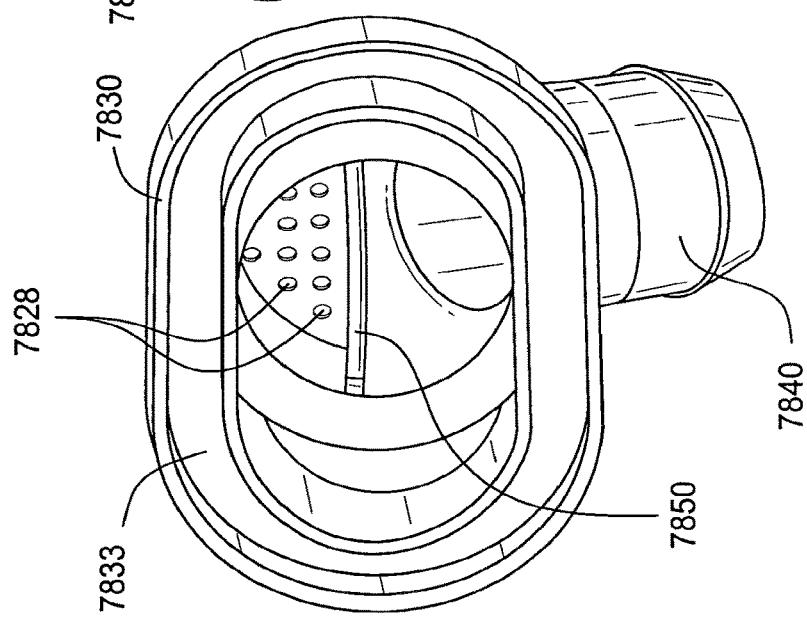
Figures 1, 14, 18:
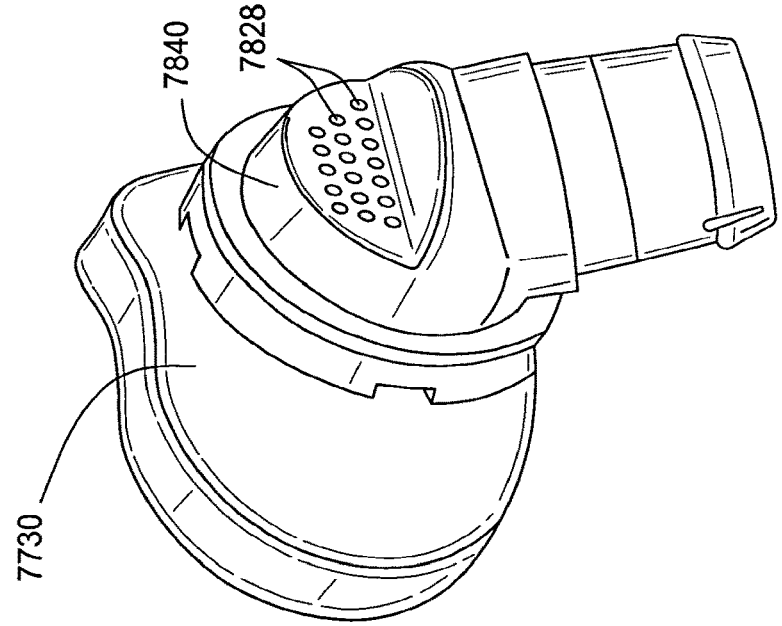
Figures 3, 18:
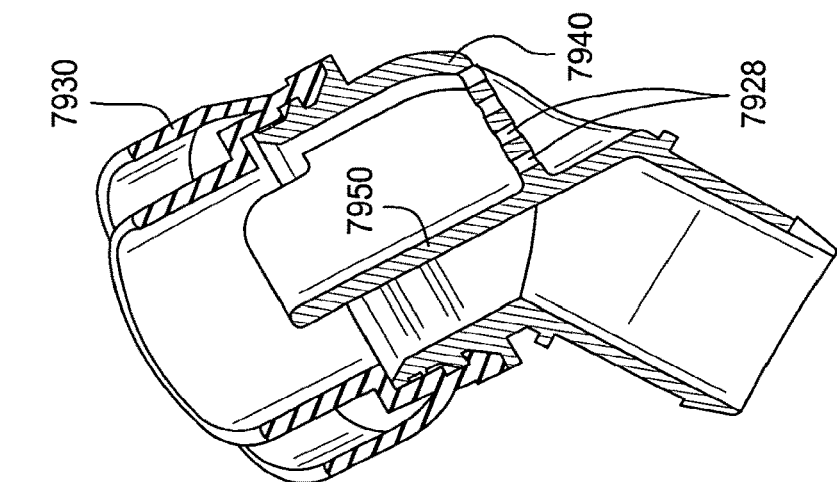
Figures 2, 18:
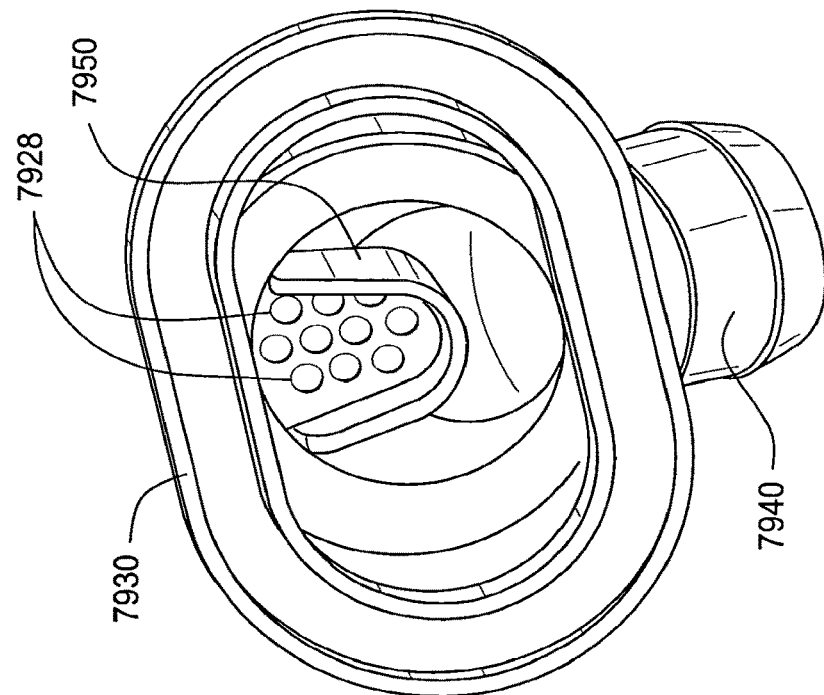
Figures 1, 18:
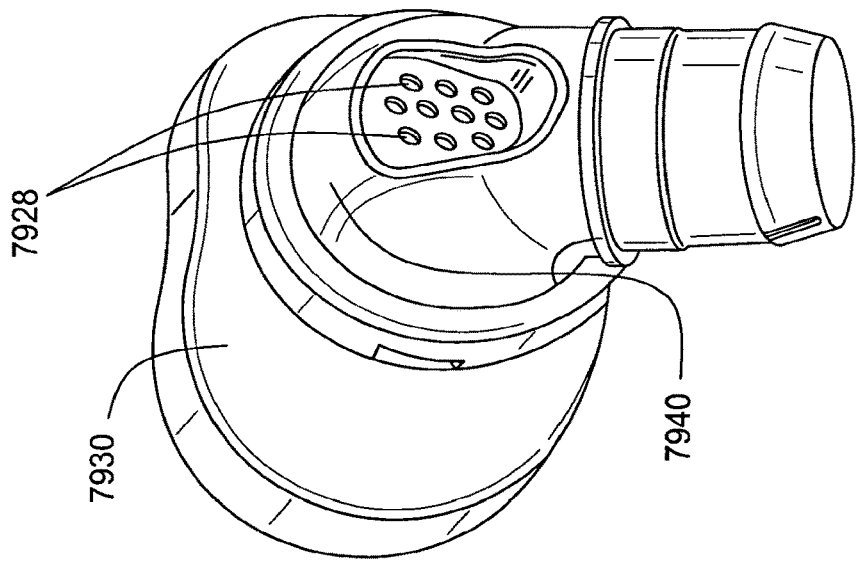
Figures 1, 19:
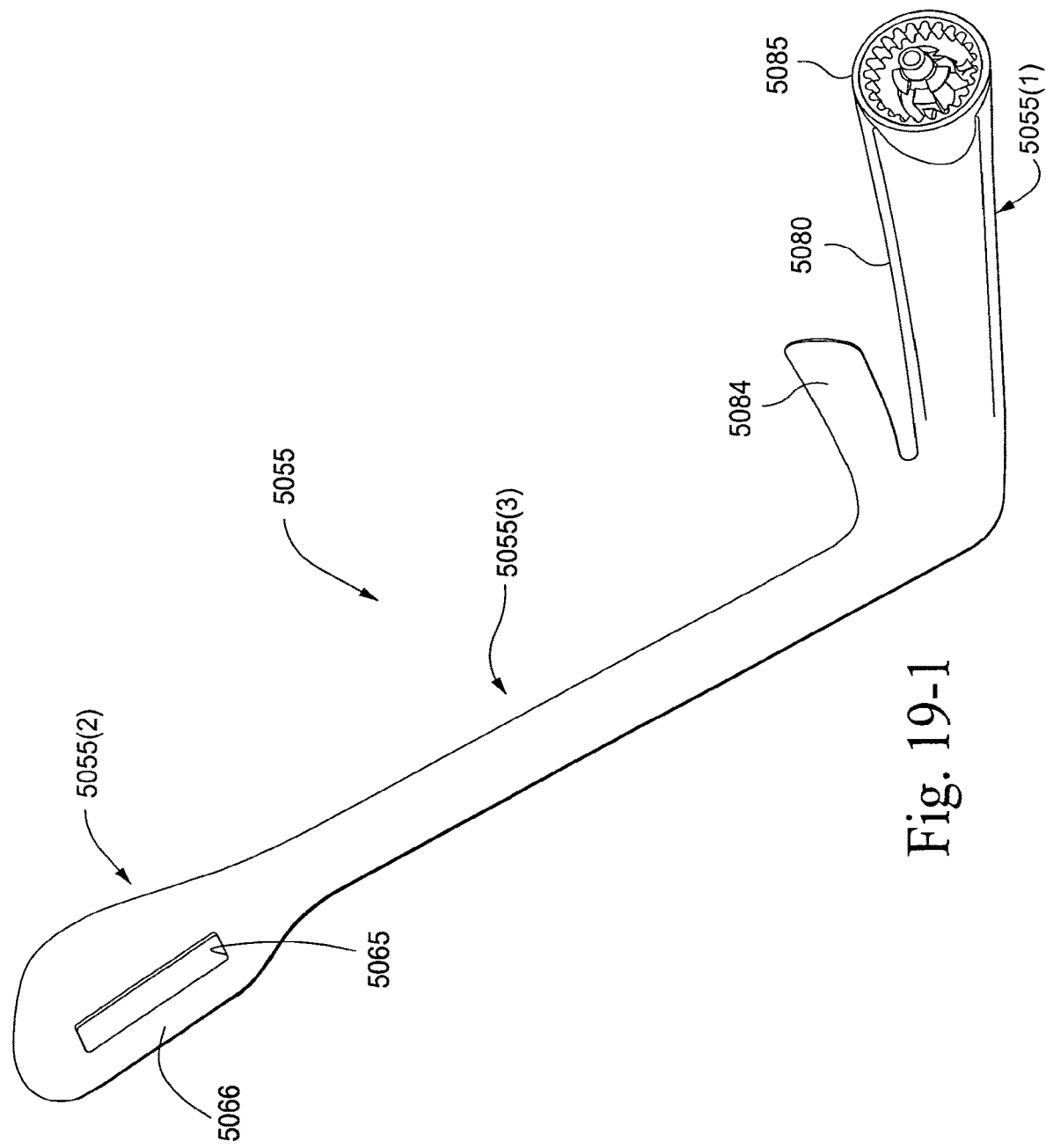
Figures 4, 19:
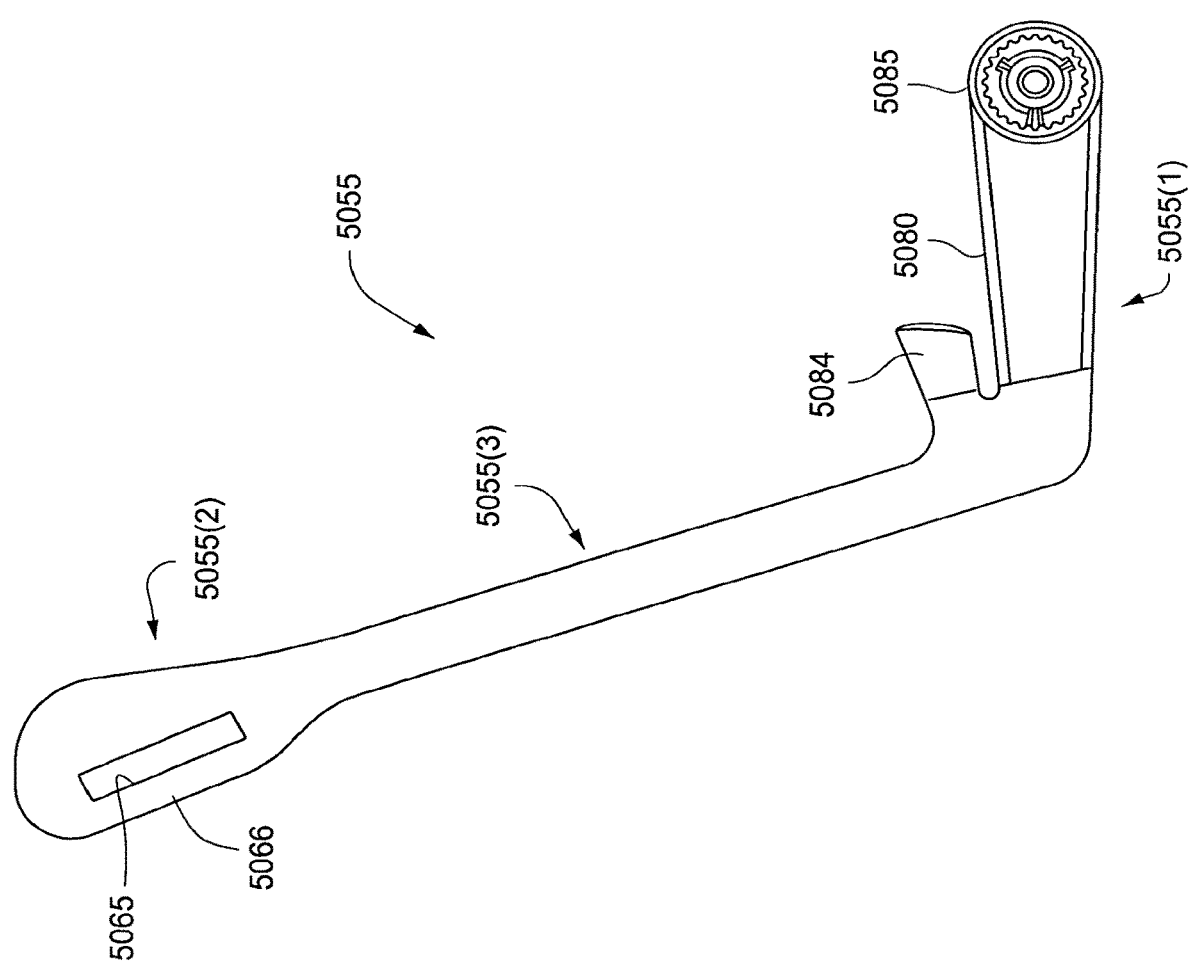
Figures 5, 19:
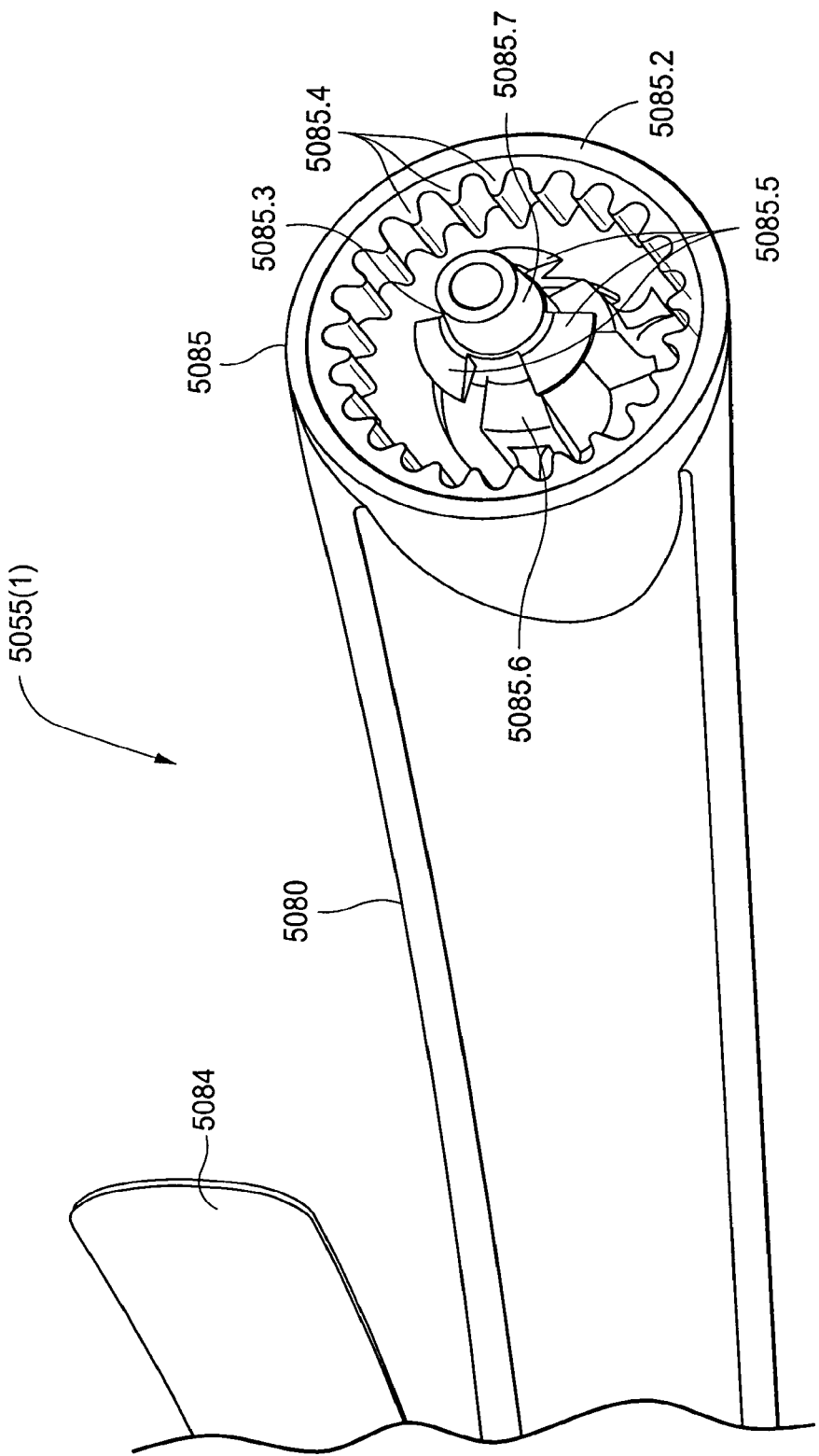
Figures 6, 19:
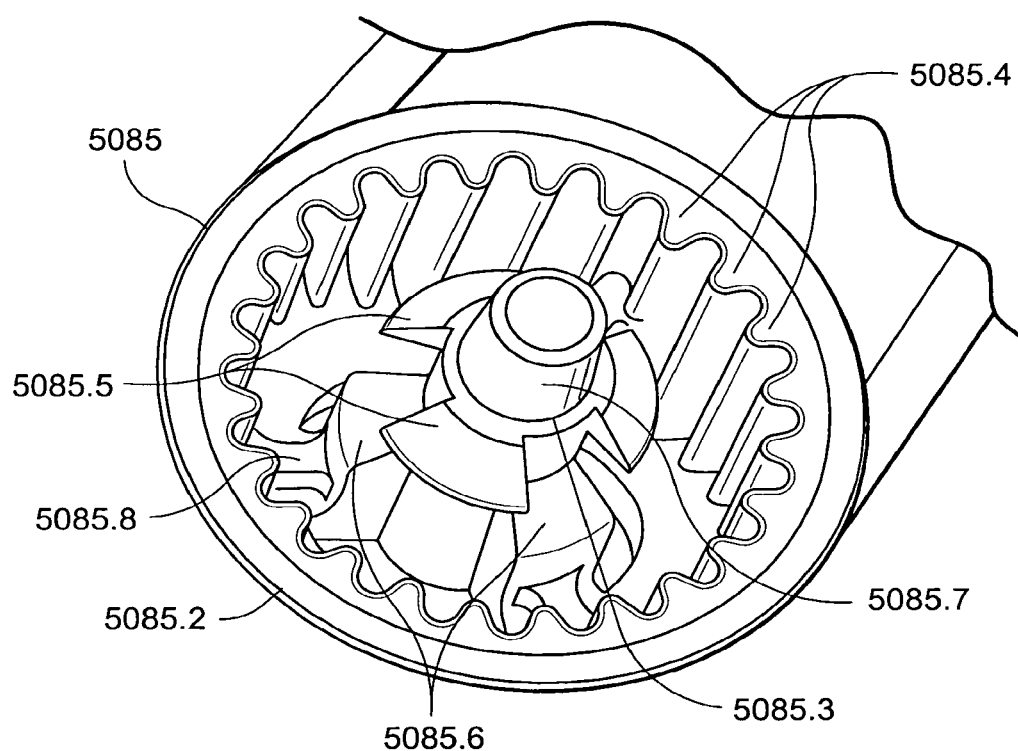
Figures 7, 19:
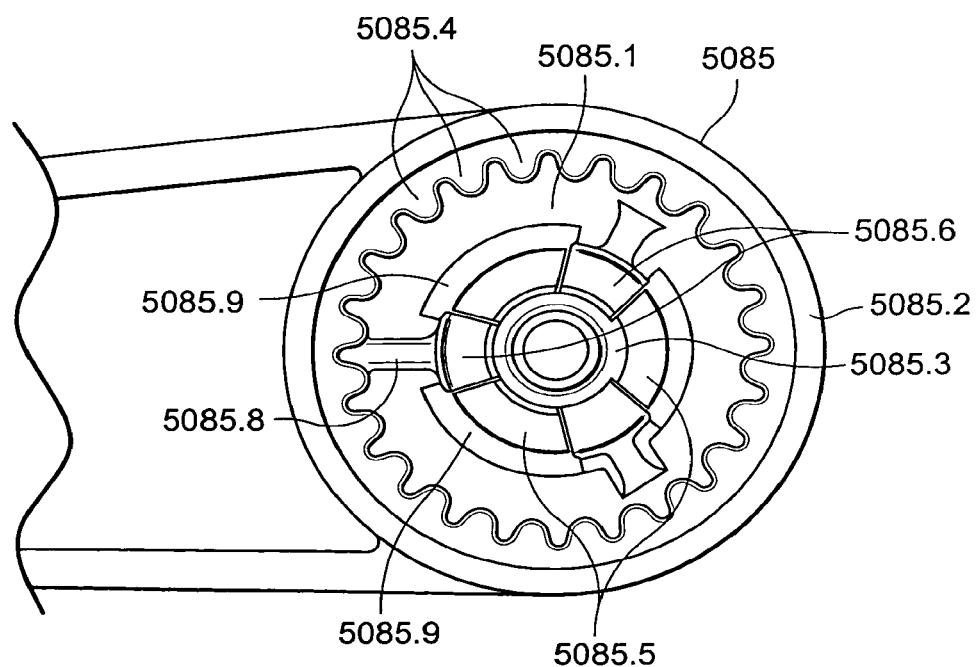
Figures 8, 19:
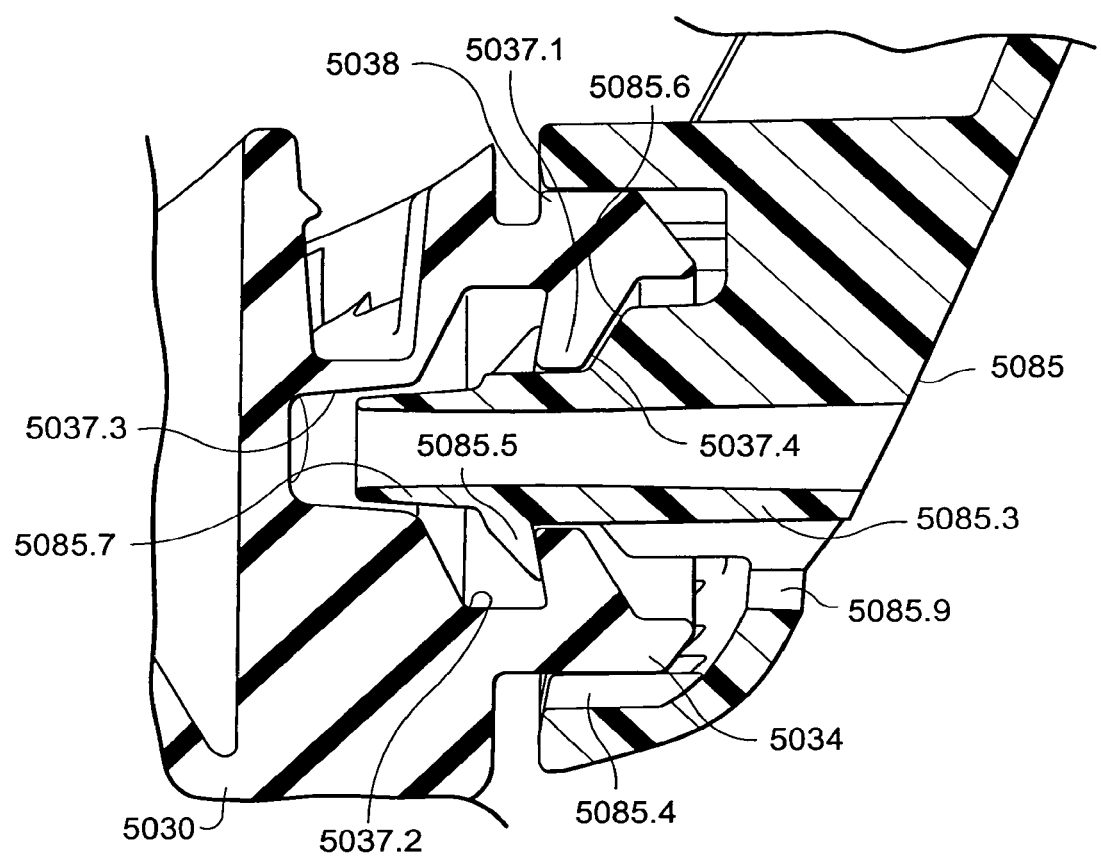
Figures 3, 9, 19:
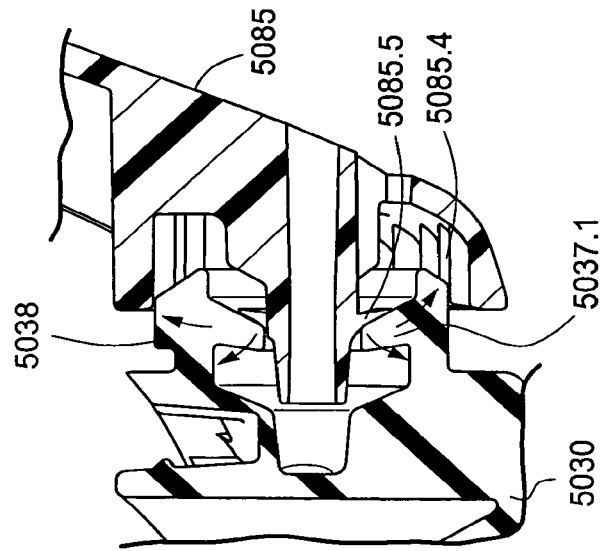
Figures 2, 9, 19:
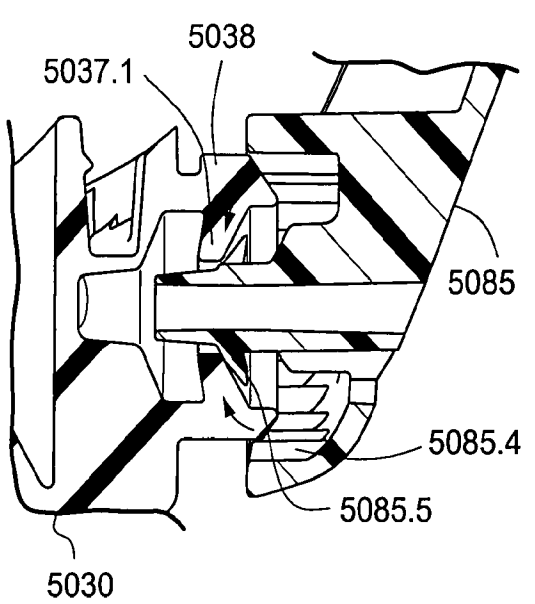
Figures 1, 9, 19:
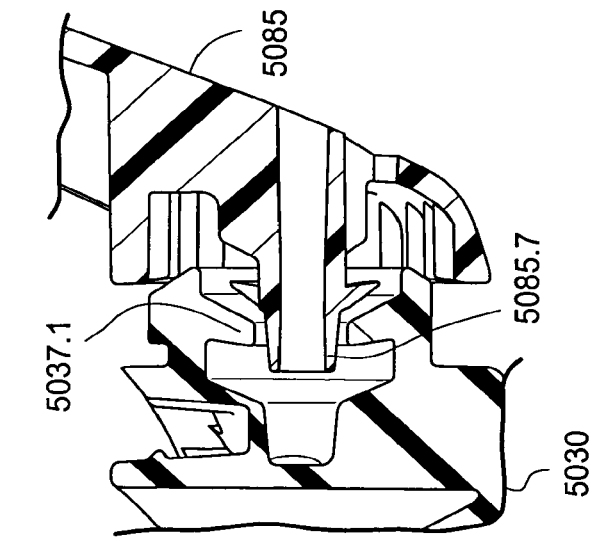
Figures 6, 9, 19:
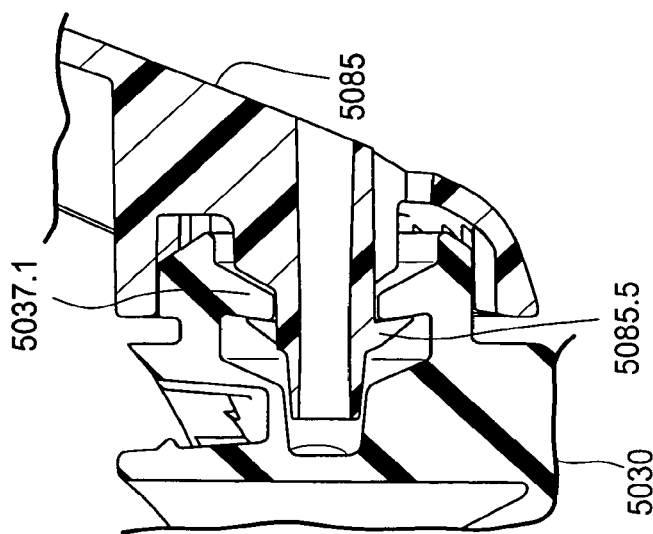
Figures 5, 9, 19:
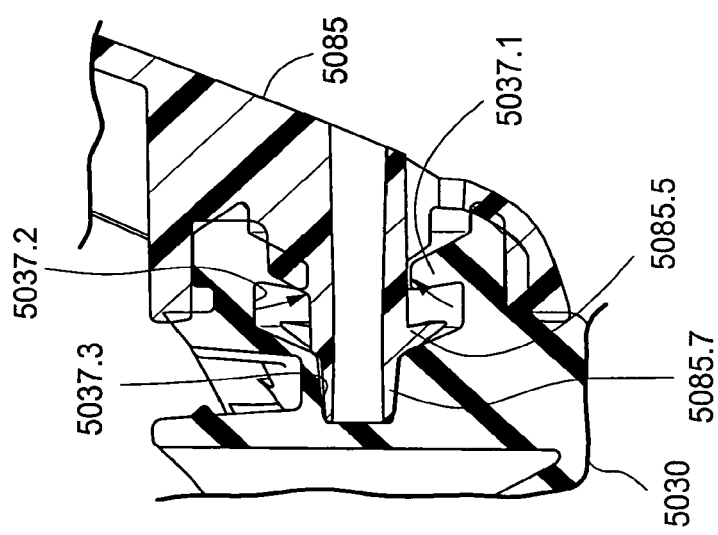
Figures 4, 9, 19:
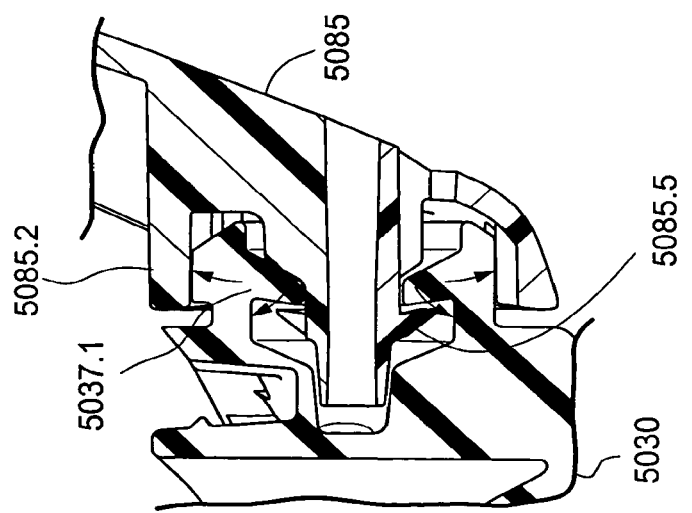
Figures 10, 19:
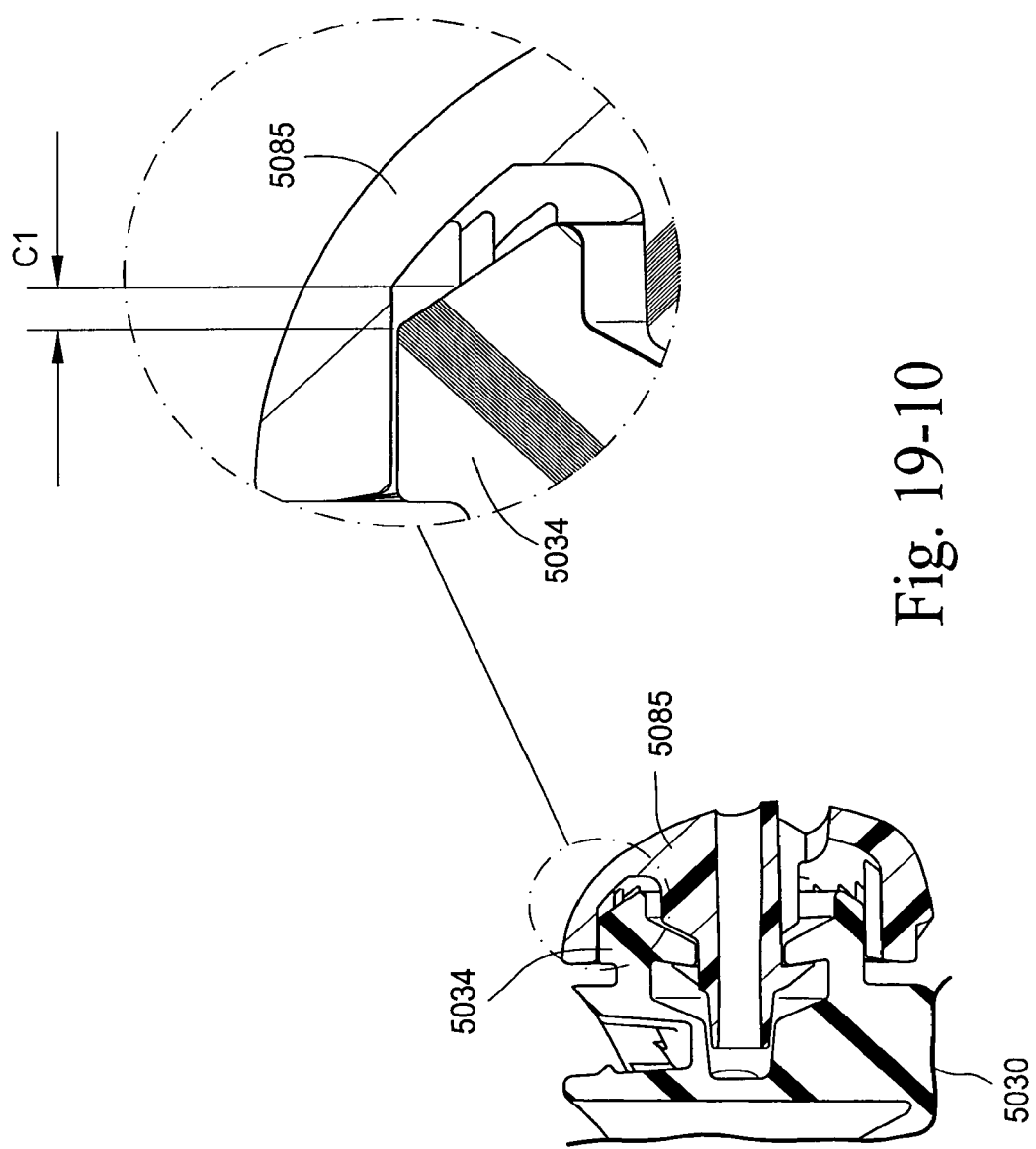
Figures 12, 19:
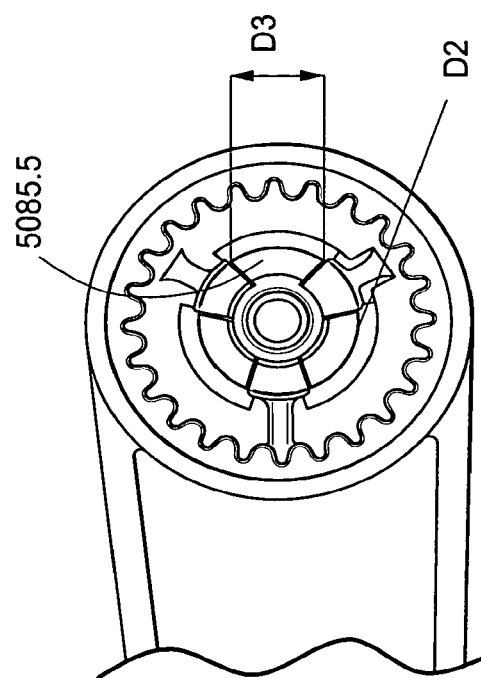
Figures 11, 19:
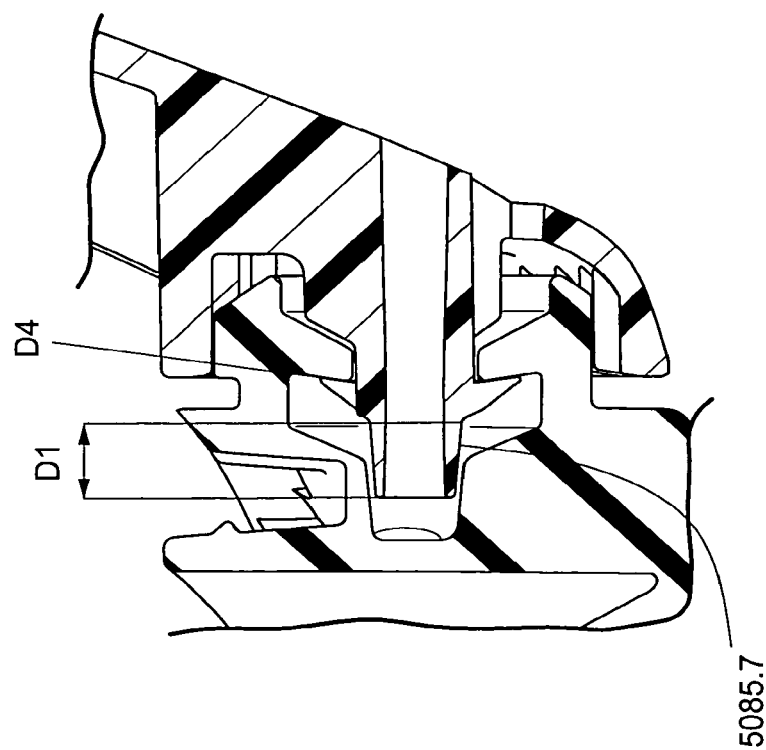
Figures 13, 19:
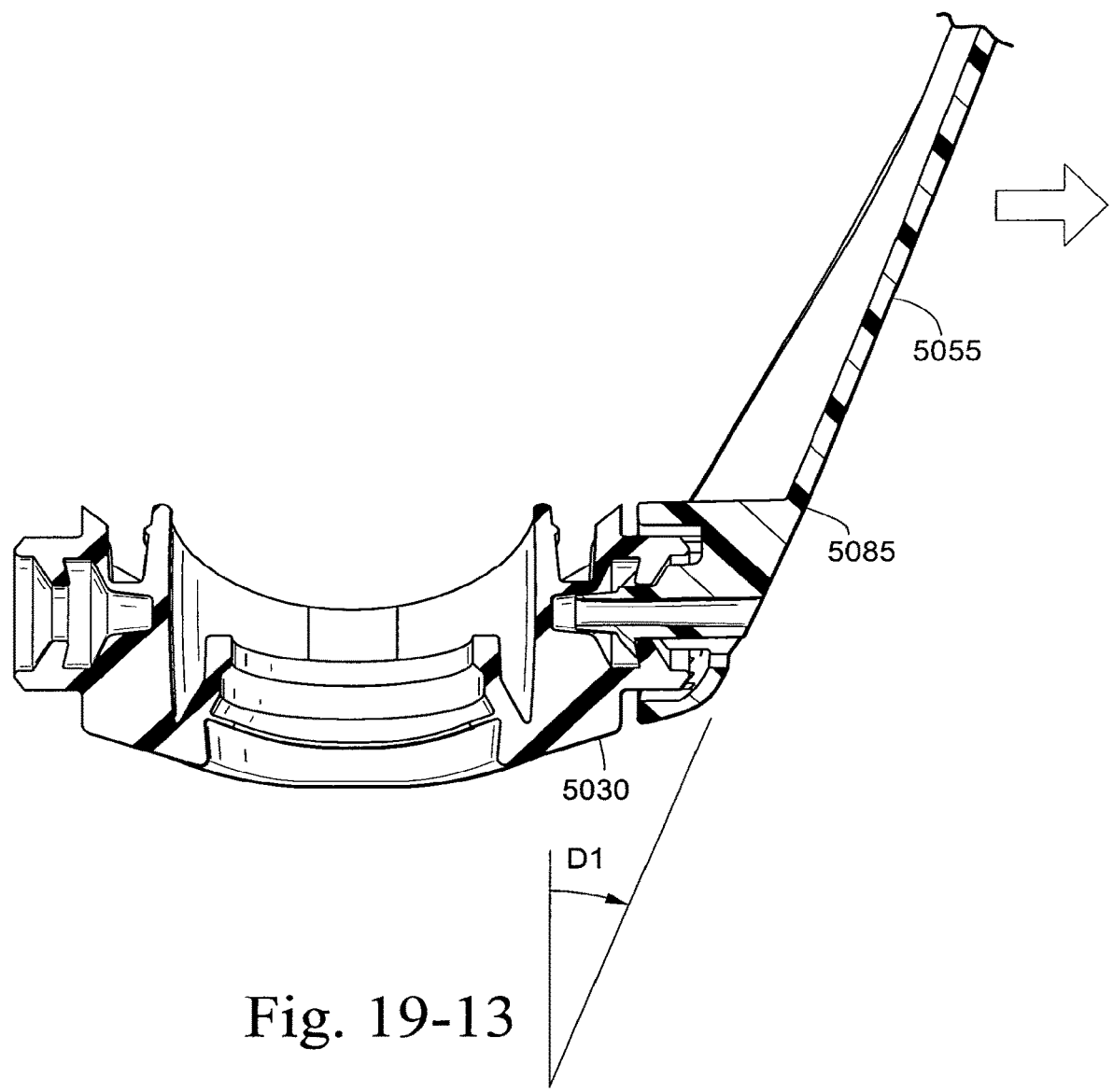
Figures 14, 19:
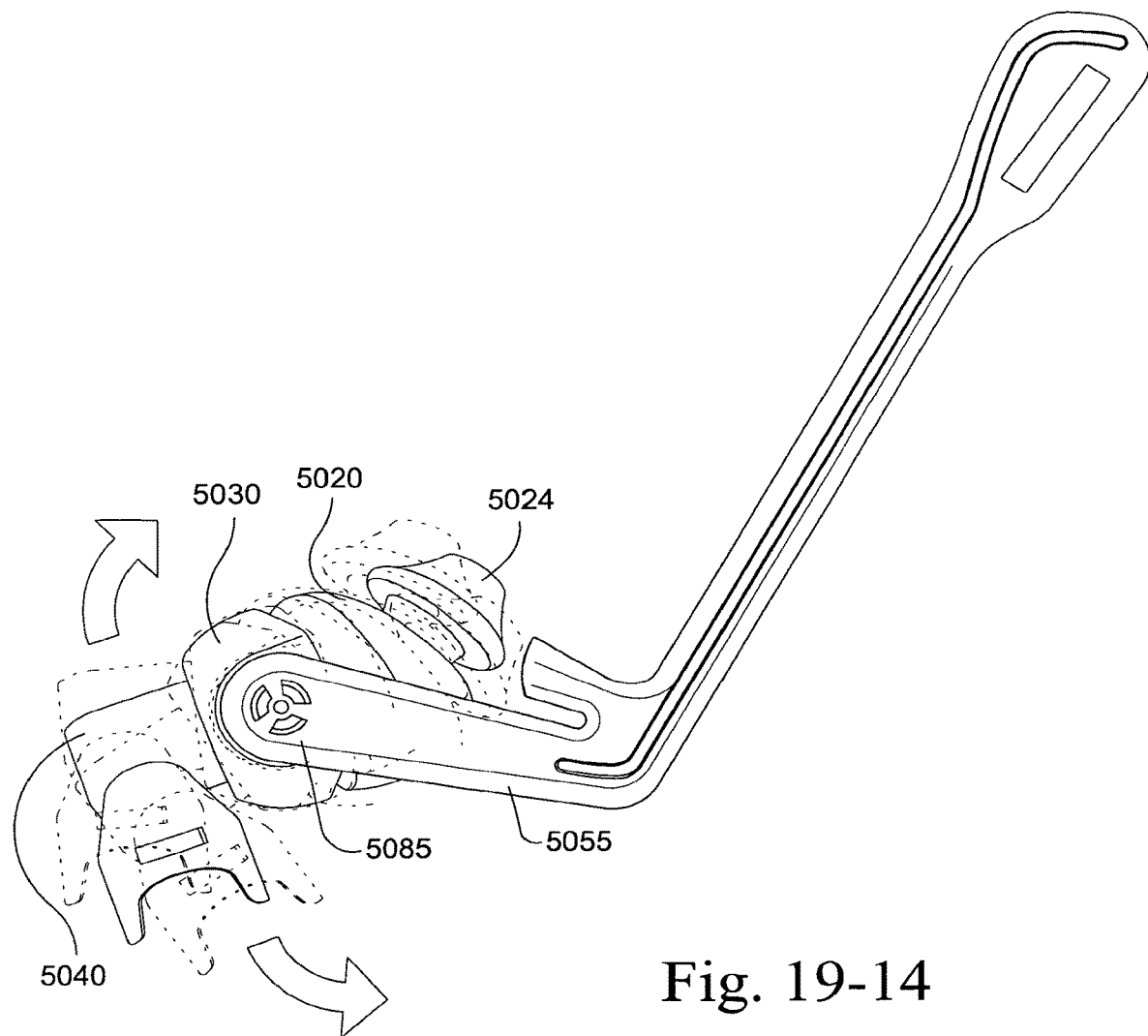
Figures 1, 15, 19:
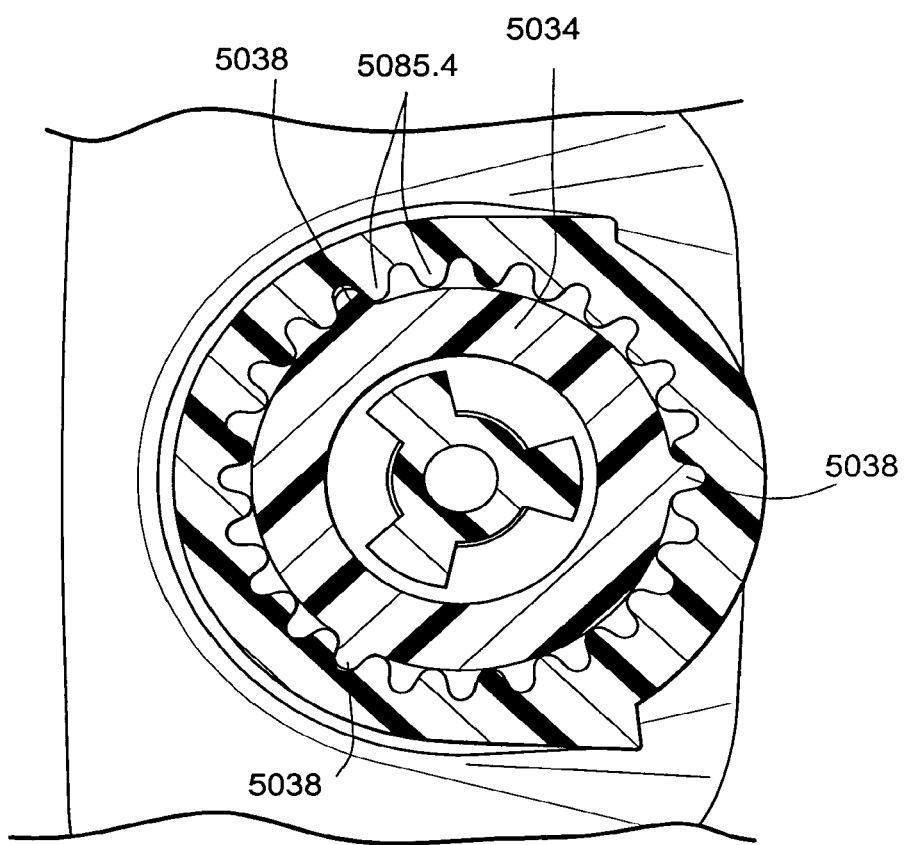
Figures 16, 19:
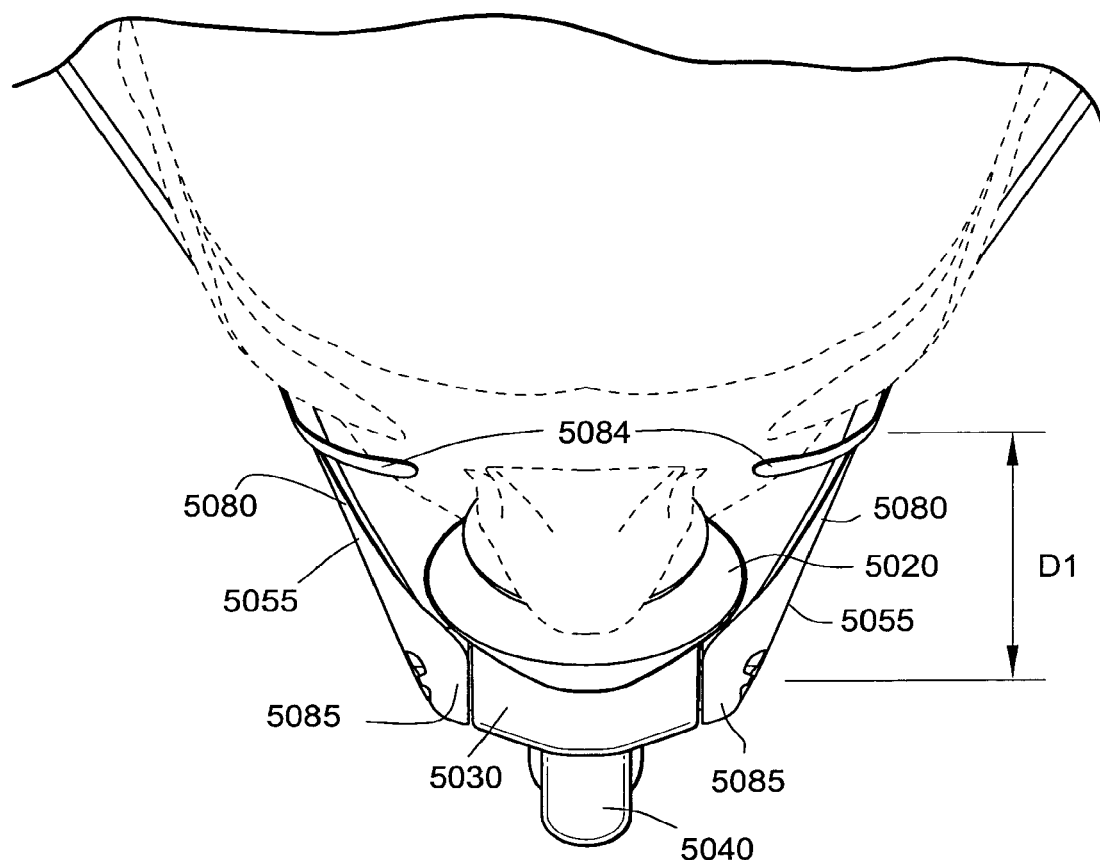
Figures 1, 17, 19:
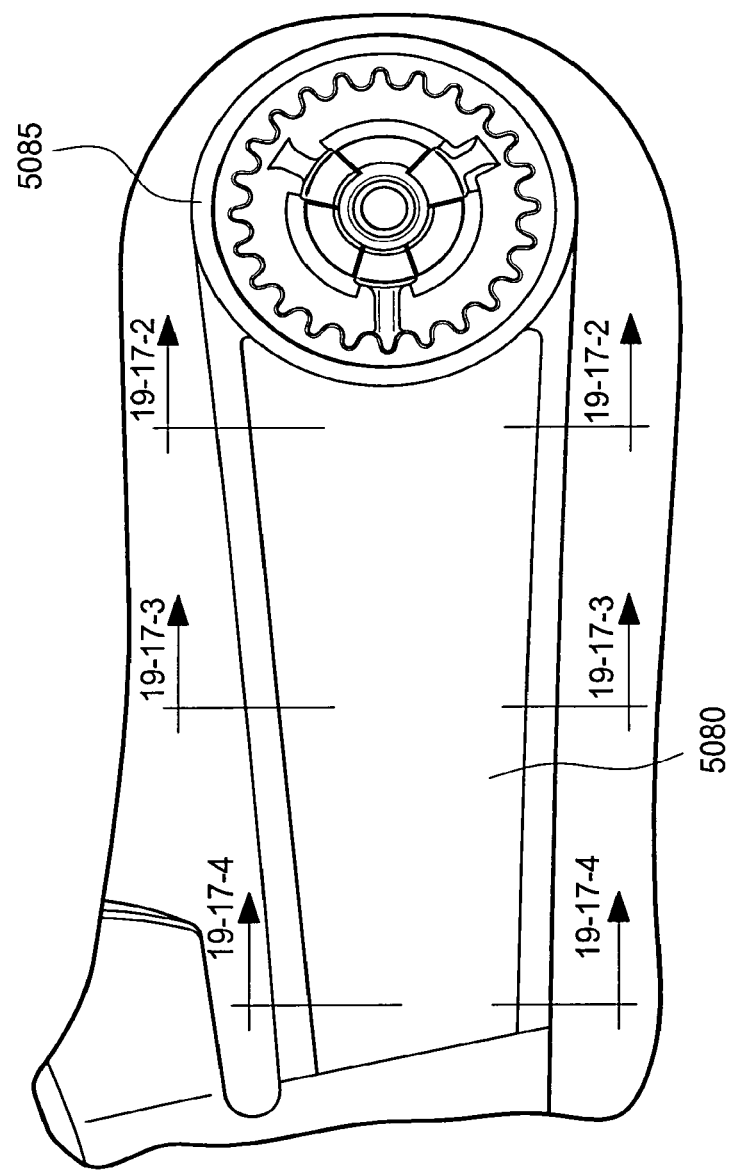
Figures 2, 17, 19:
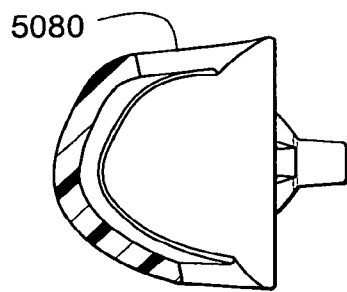
Figures 3, 17, 19:
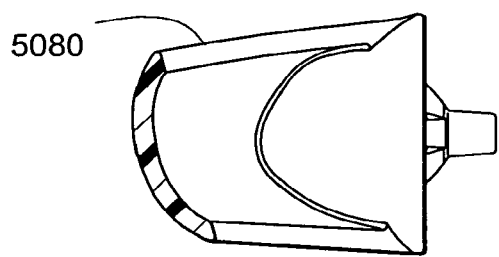
Figures 4, 17, 19:
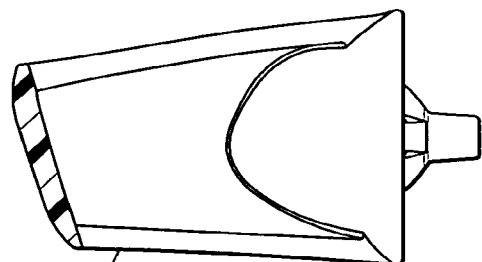
Figures 18, 19:
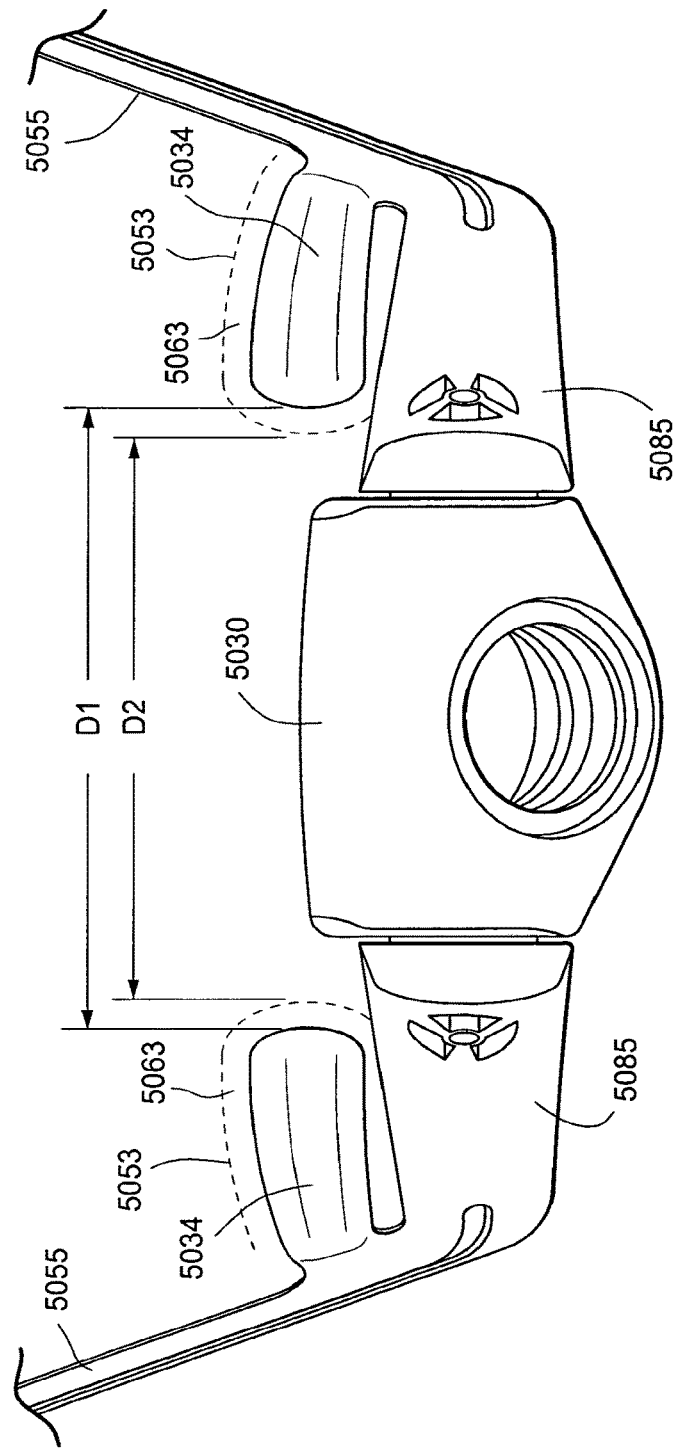
Figure 19:
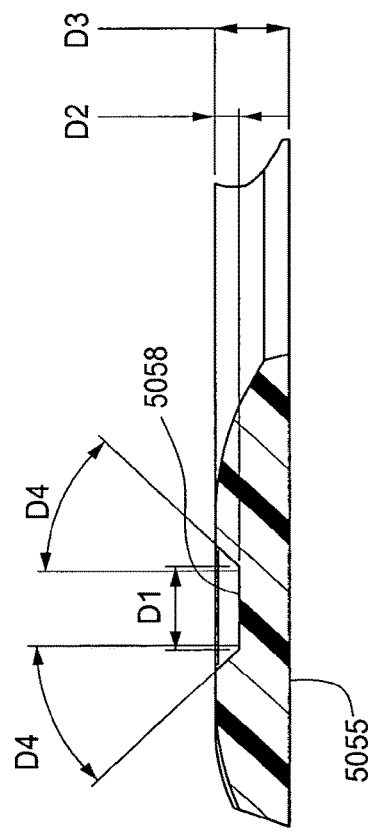
Figures 19, 20:
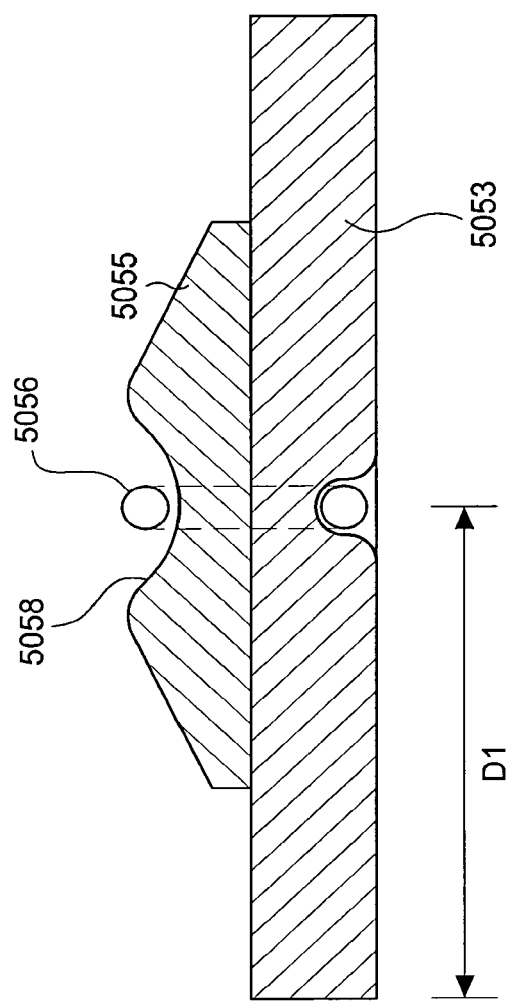
Figures 1, 19, 20, 21:
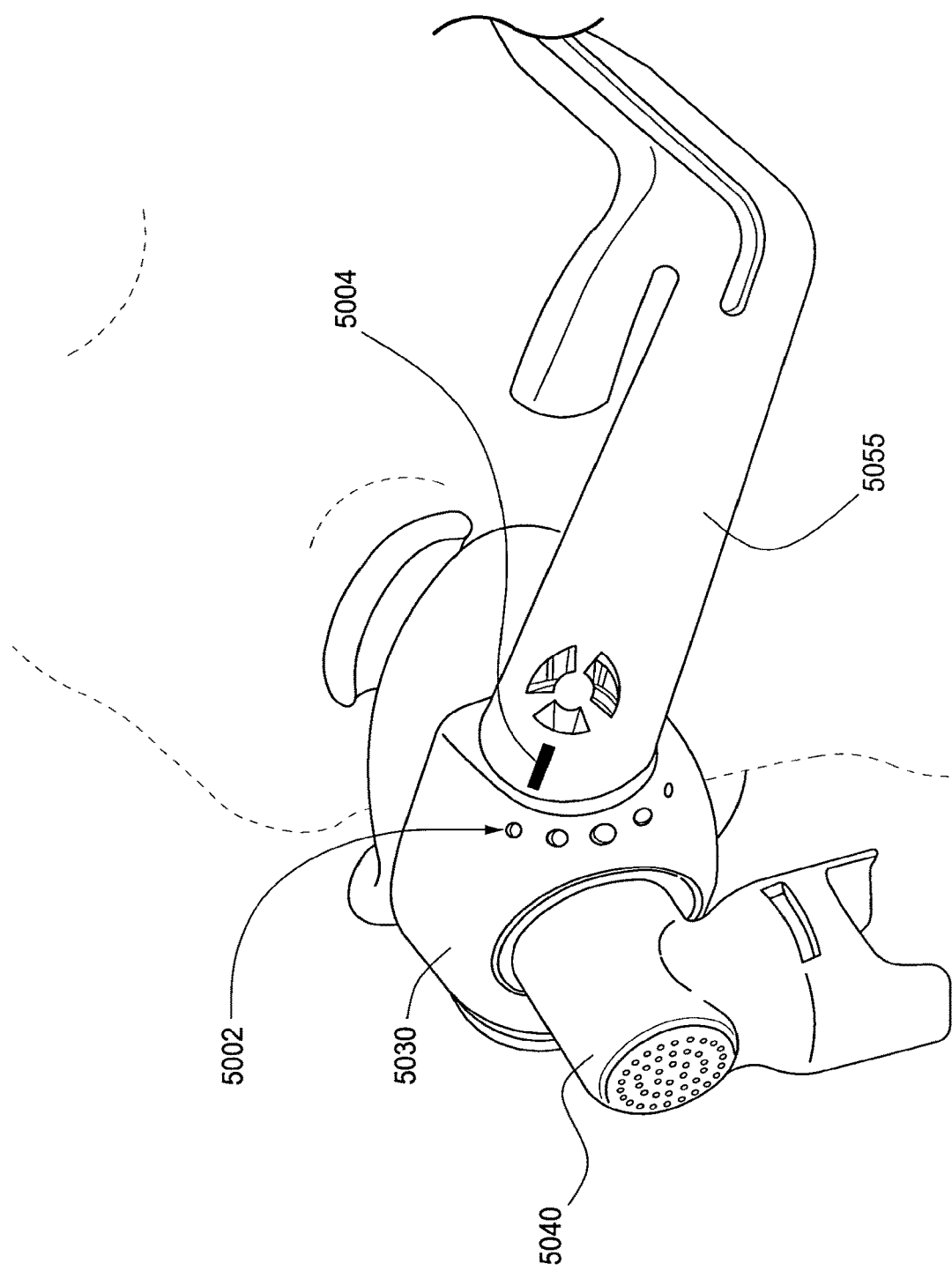
Figures 2, 19, 20, 21:
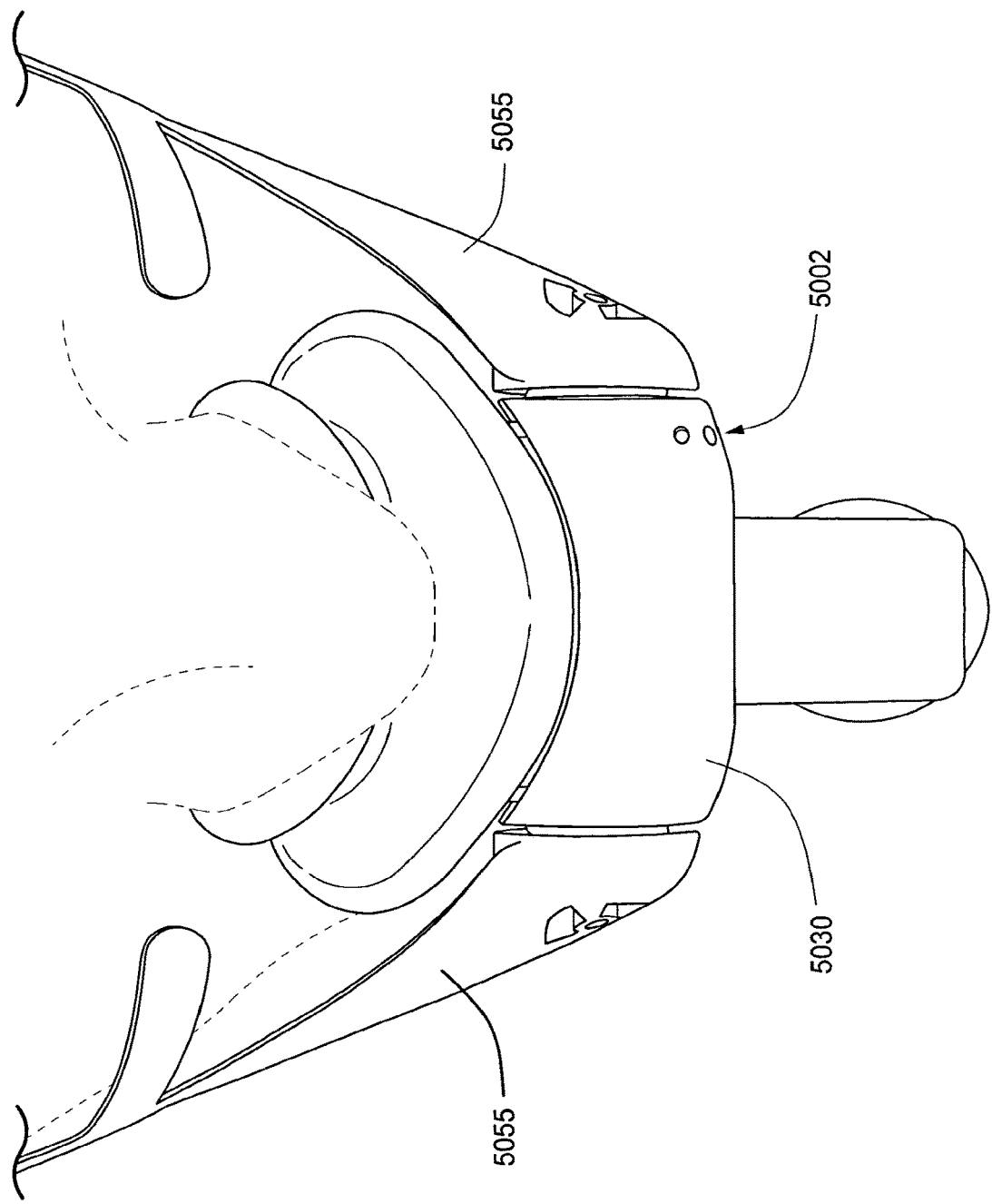
Figures 3, 19, 20, 21:
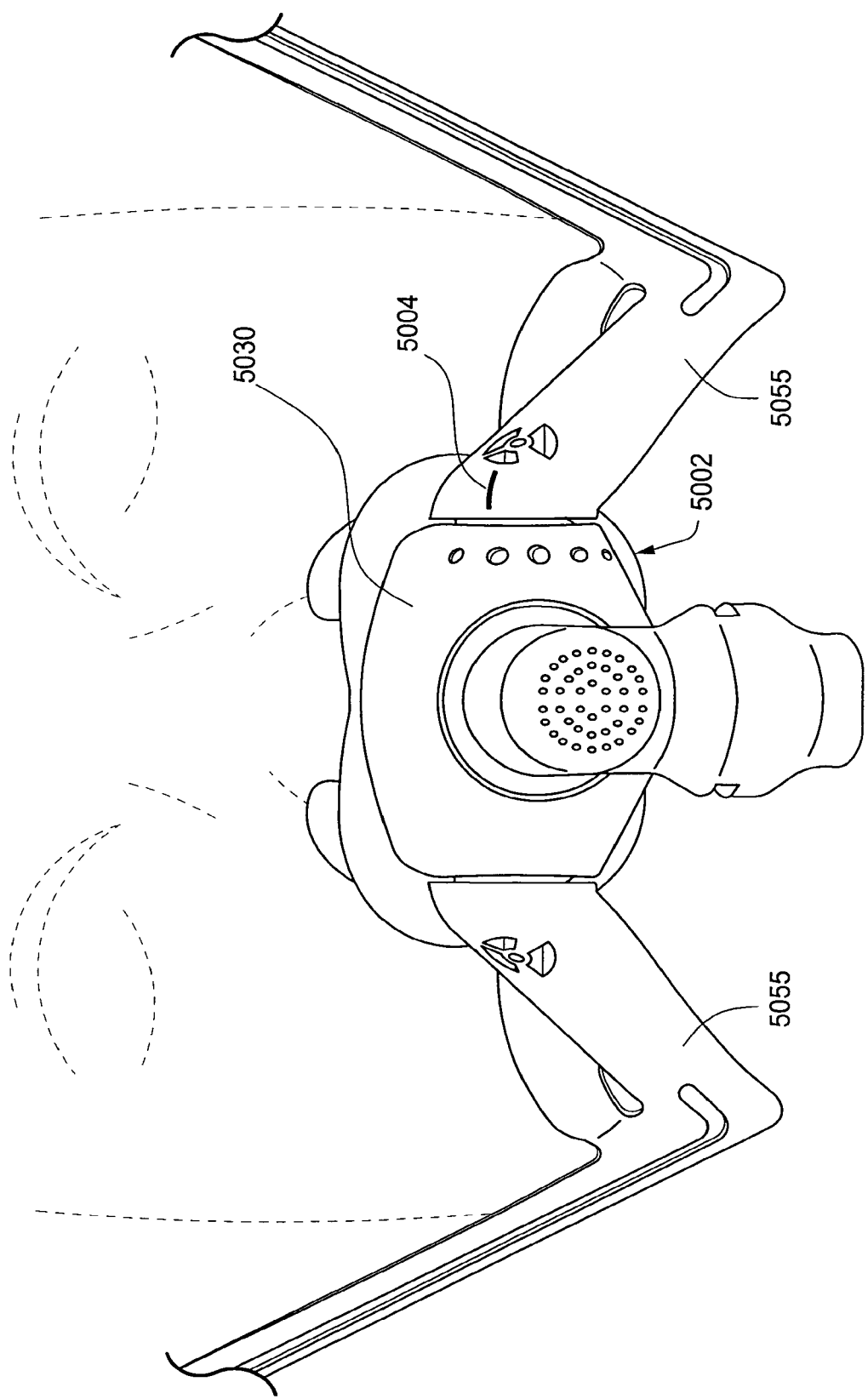
Figures 1, 19, 20, 21, 22:
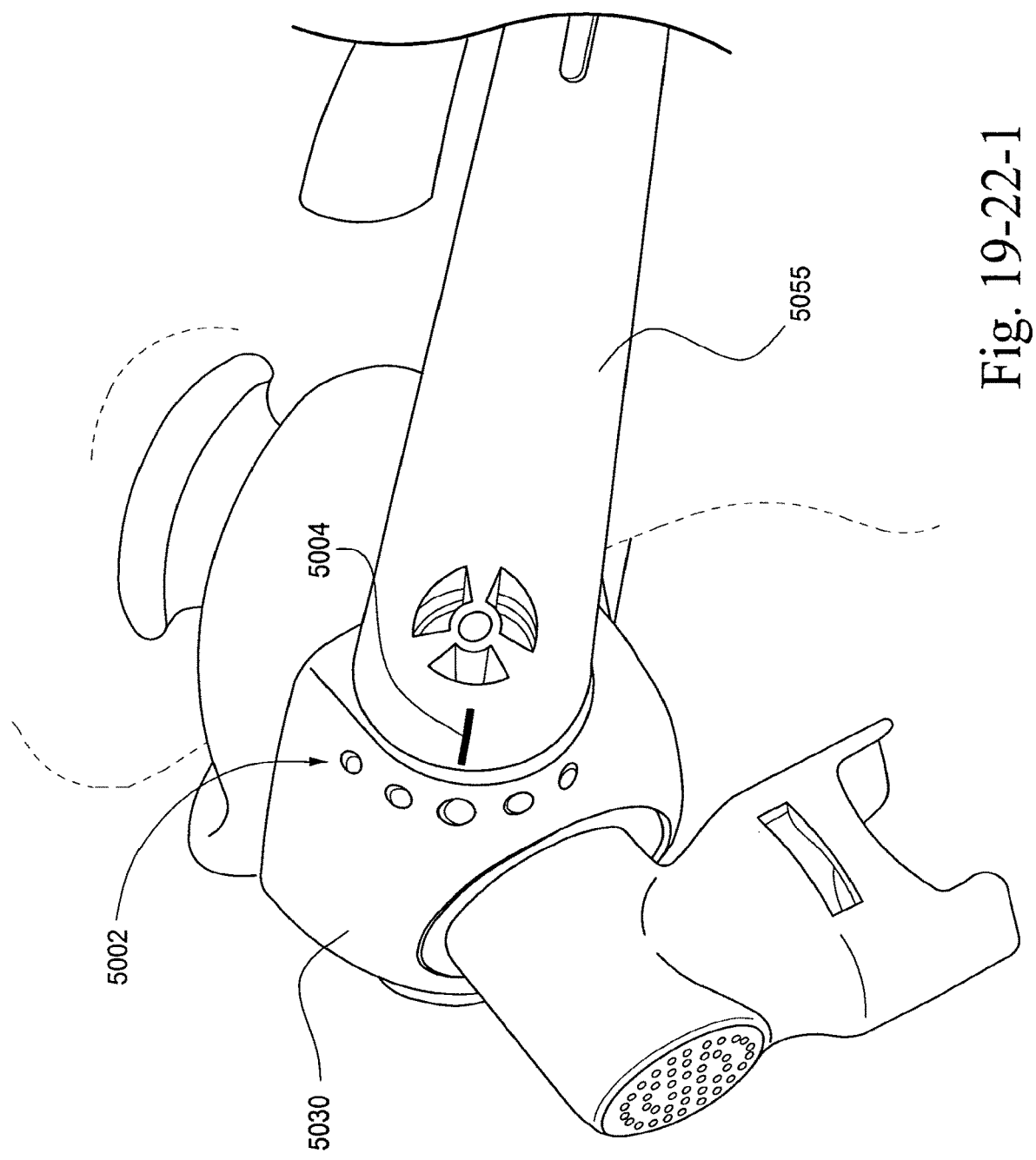
Figures 2, 19, 20, 21, 22:
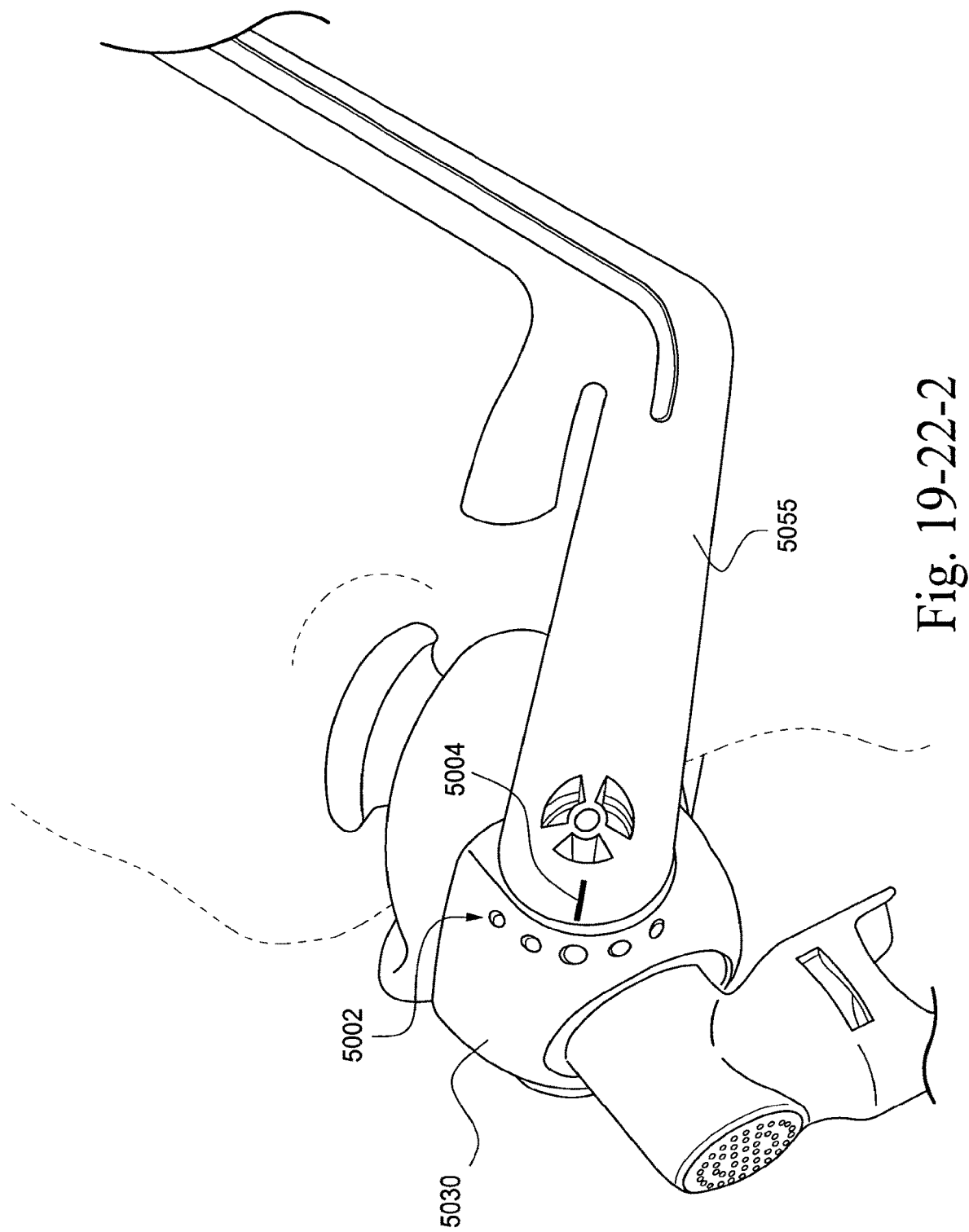
Figures 3, 19, 20, 21, 22:
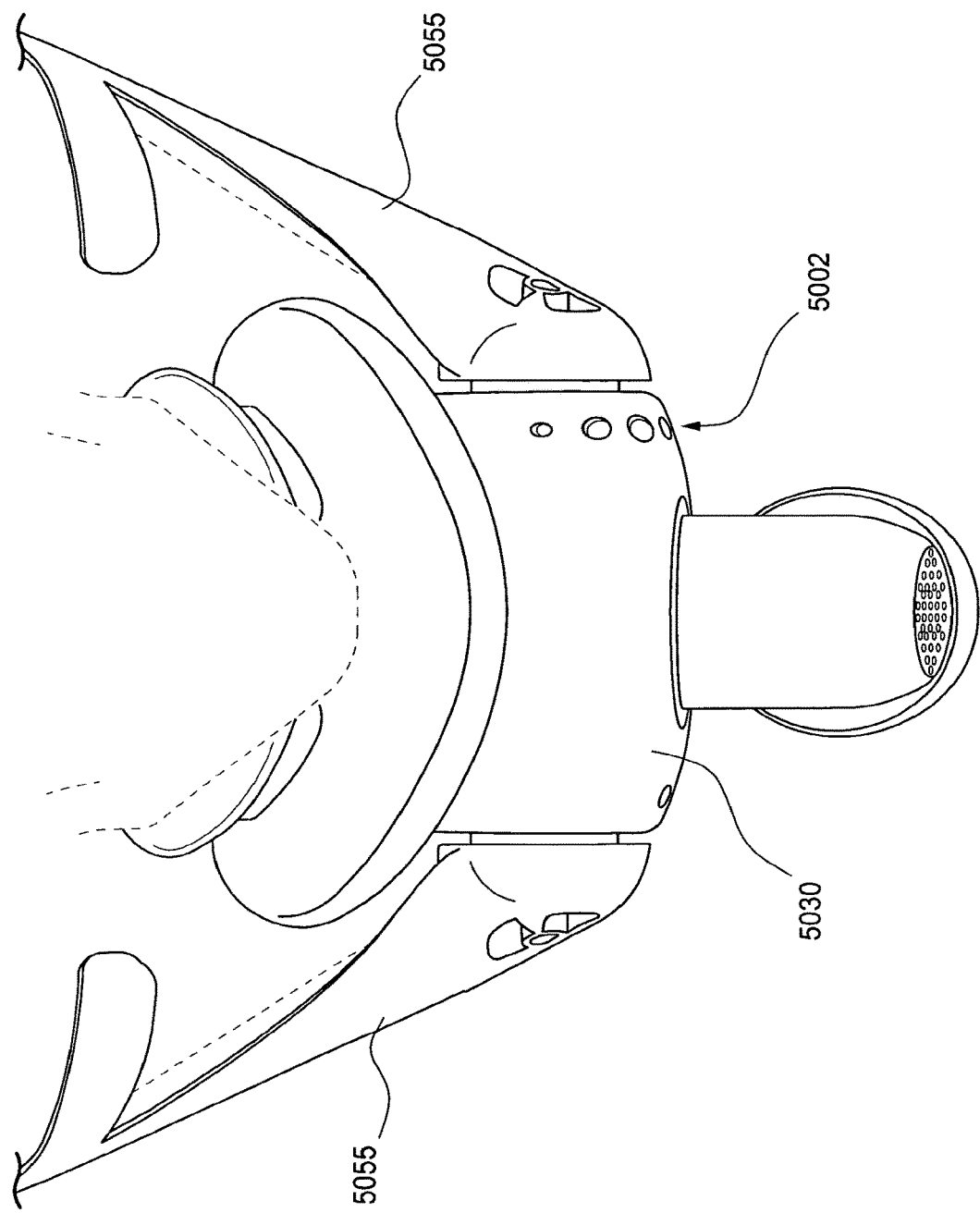
Figures 4, 19, 20, 21, 22:
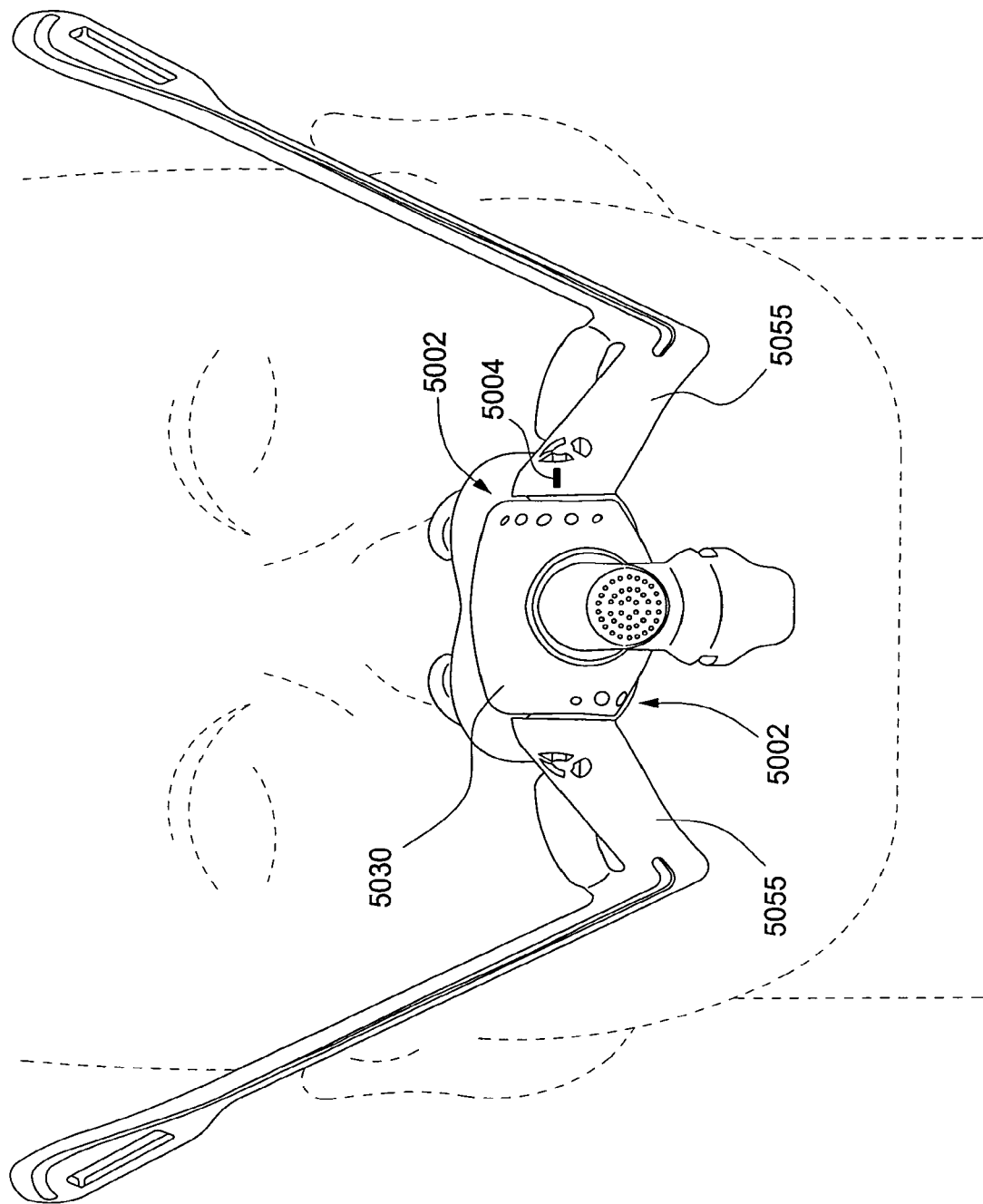
Figures 1, 19, 20, 21, 22, 23:
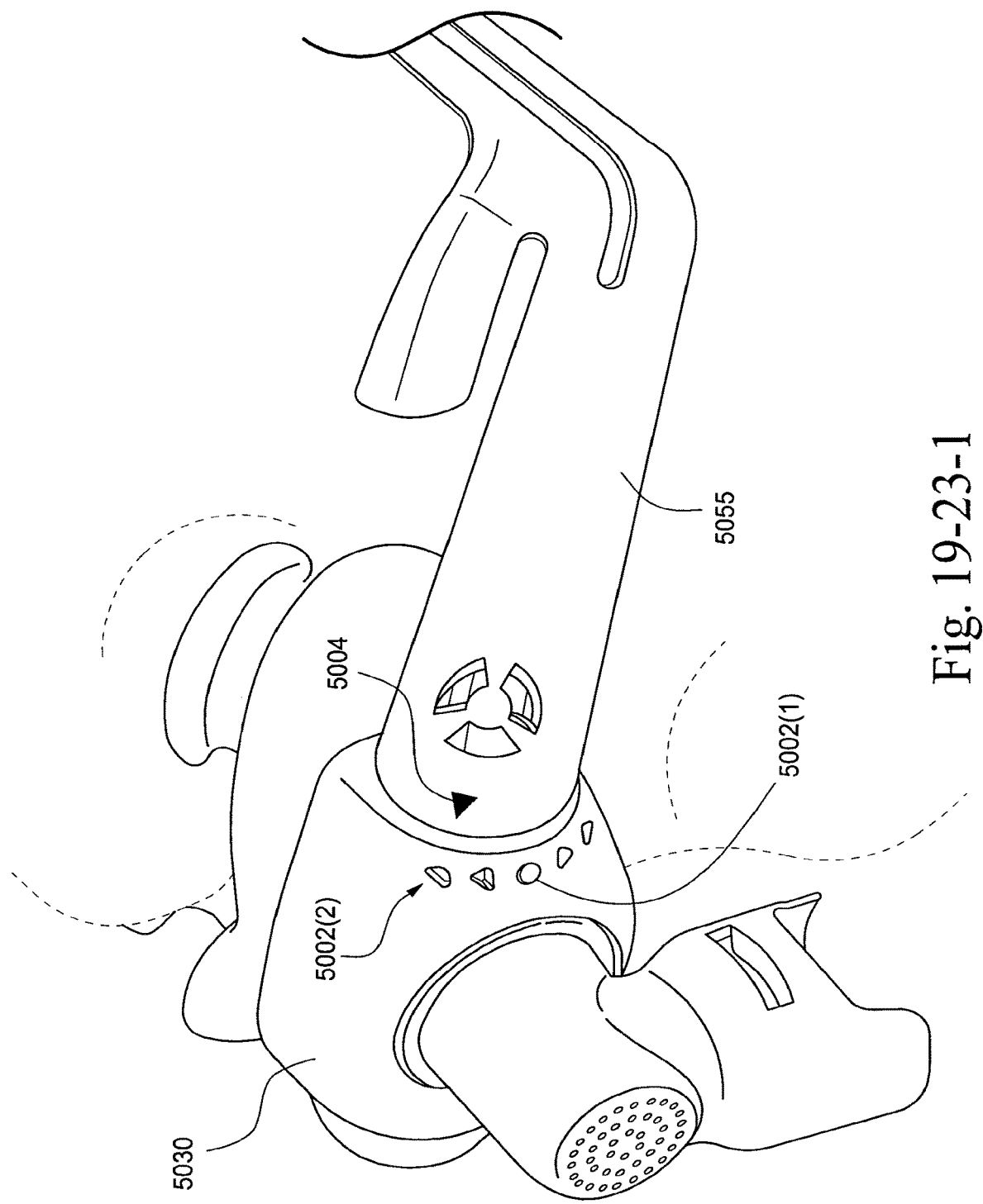
Figures 2, 19, 20, 21, 22, 23:
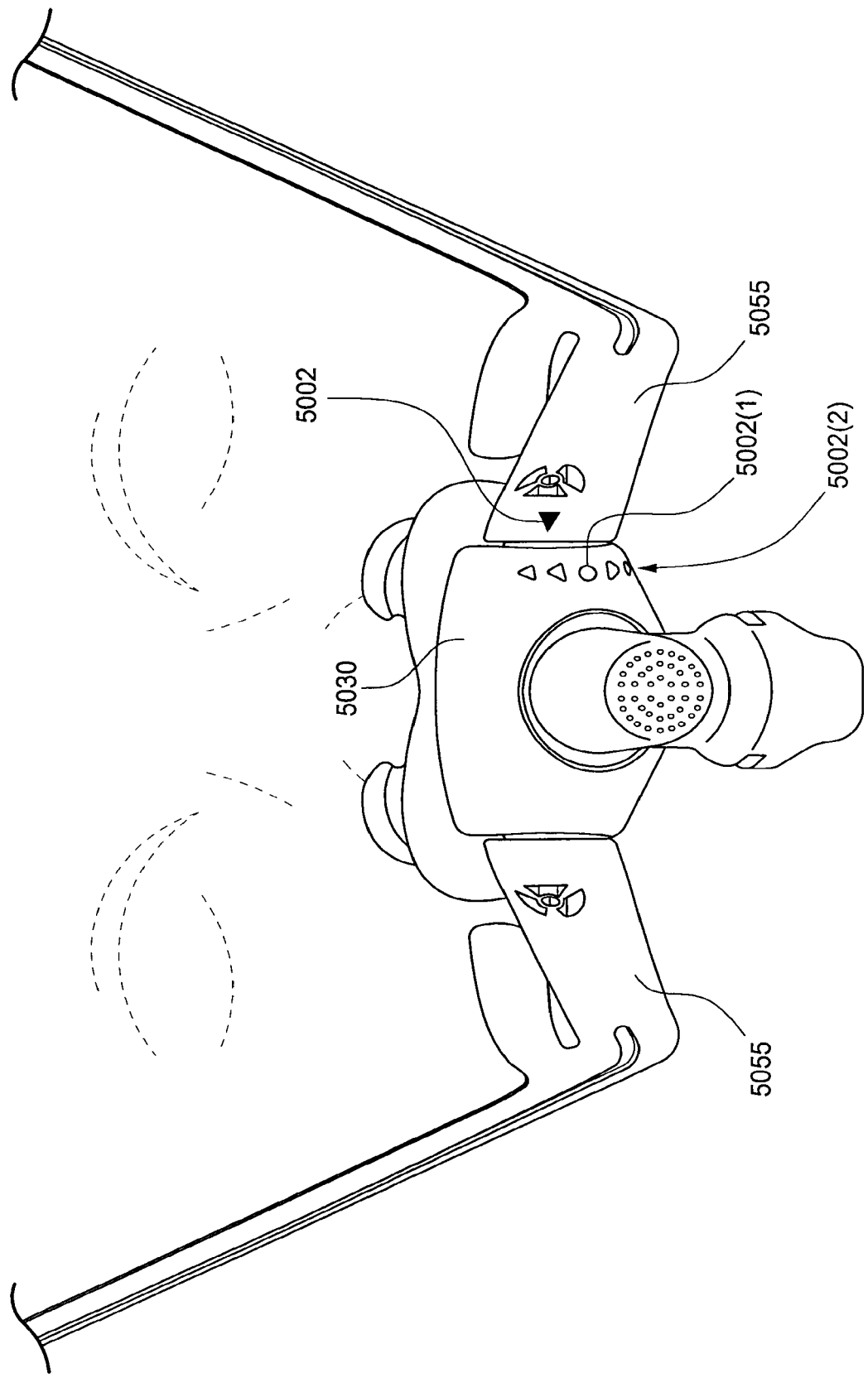
Figures 3, 19, 20, 21, 22, 23:
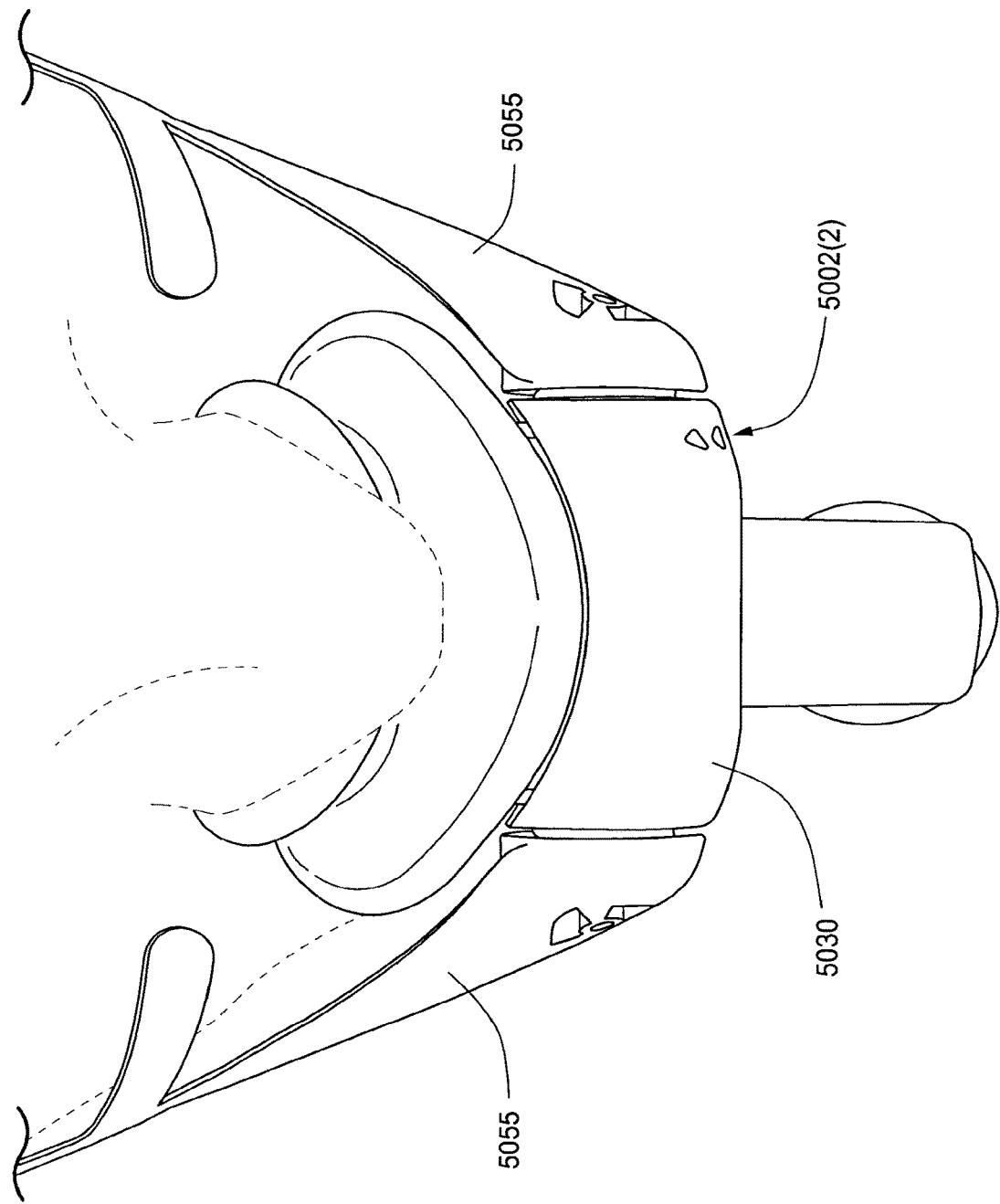
Figures 4, 19, 20, 21, 22, 23:
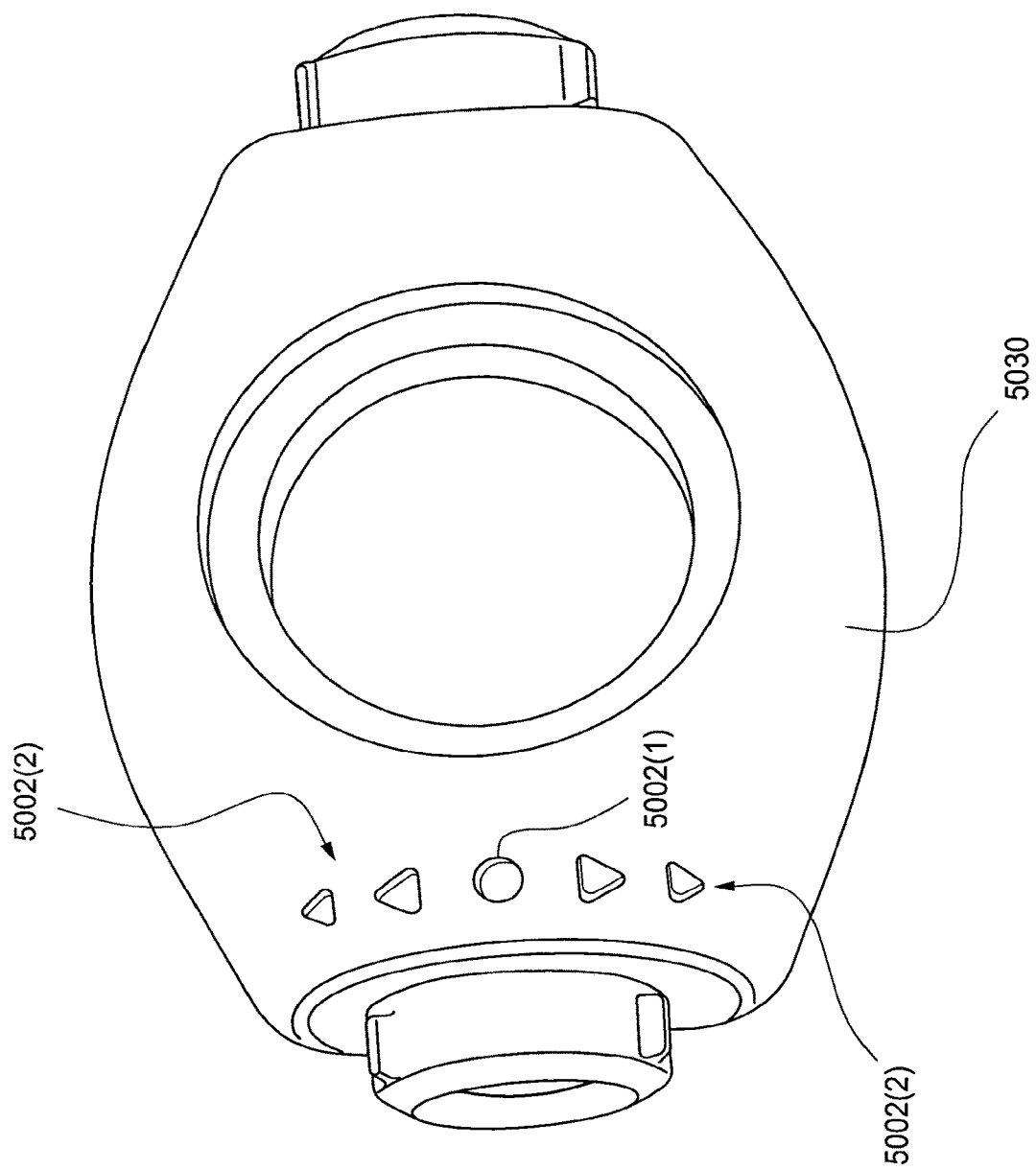
Figures 1, 20:
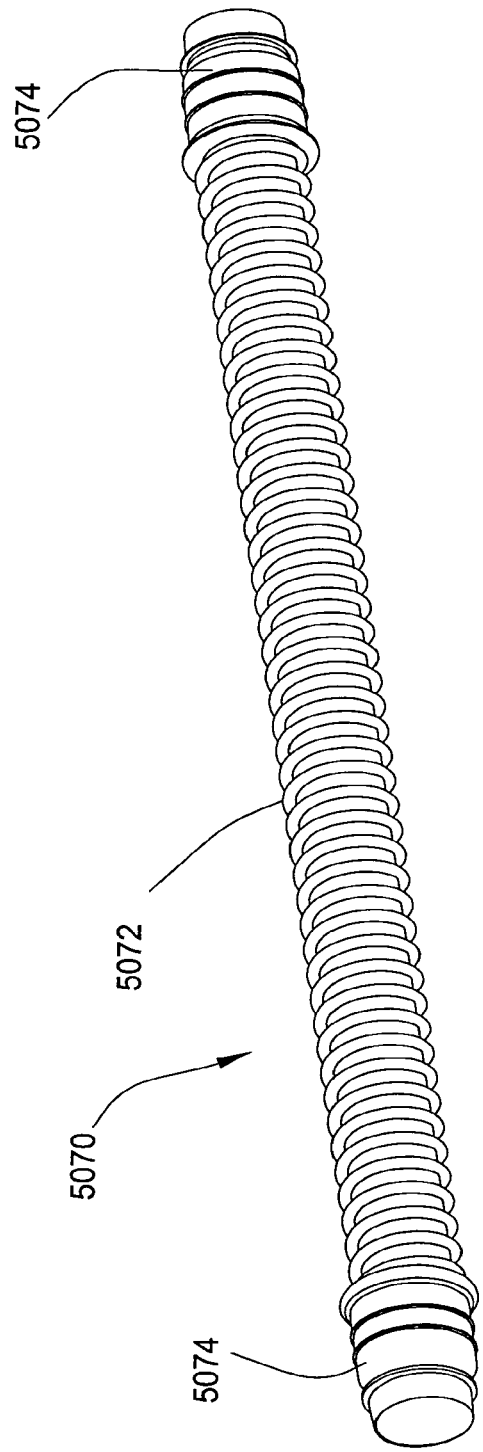
Figures 2, 20:
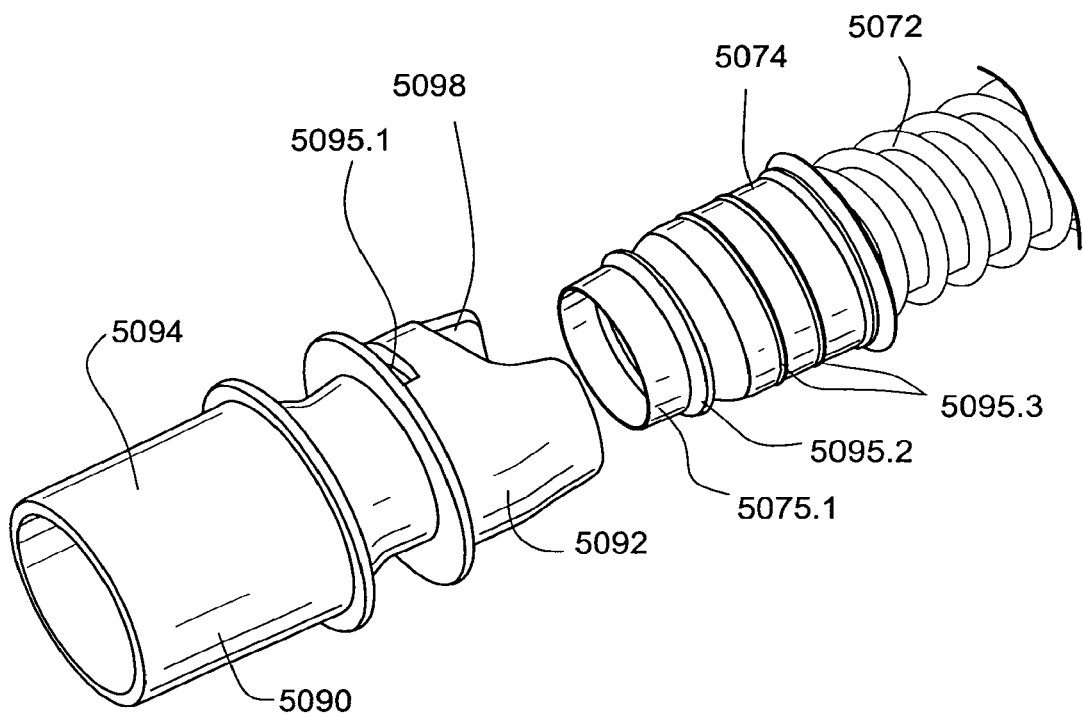
Figures 3, 20:
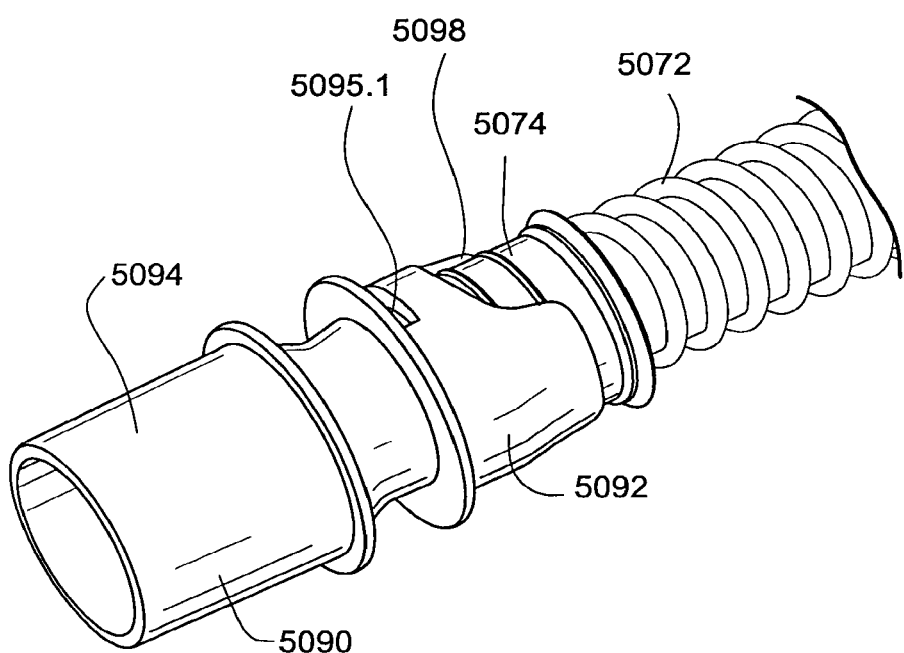
Figures 4, 20:
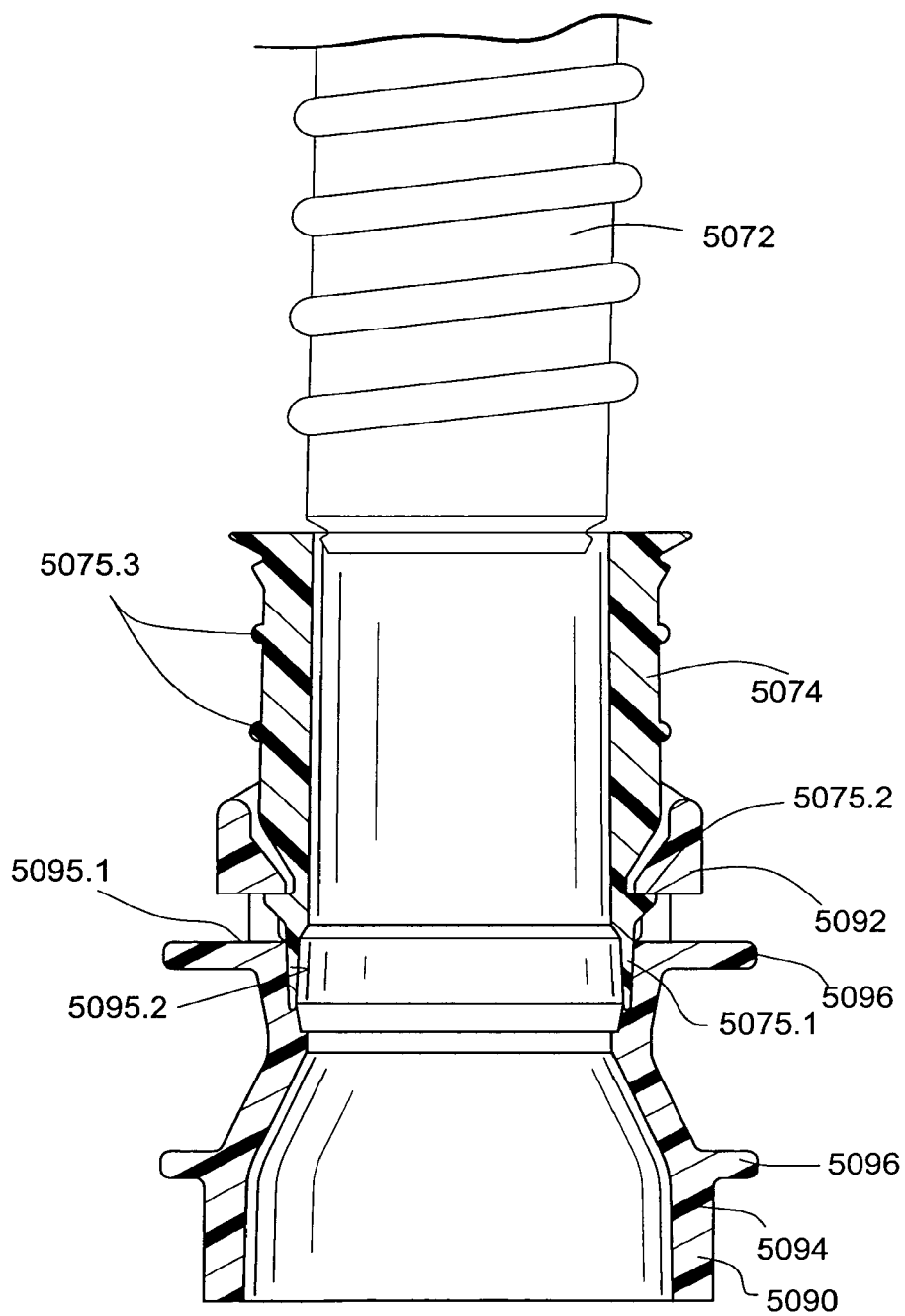
Figures 1, 21:
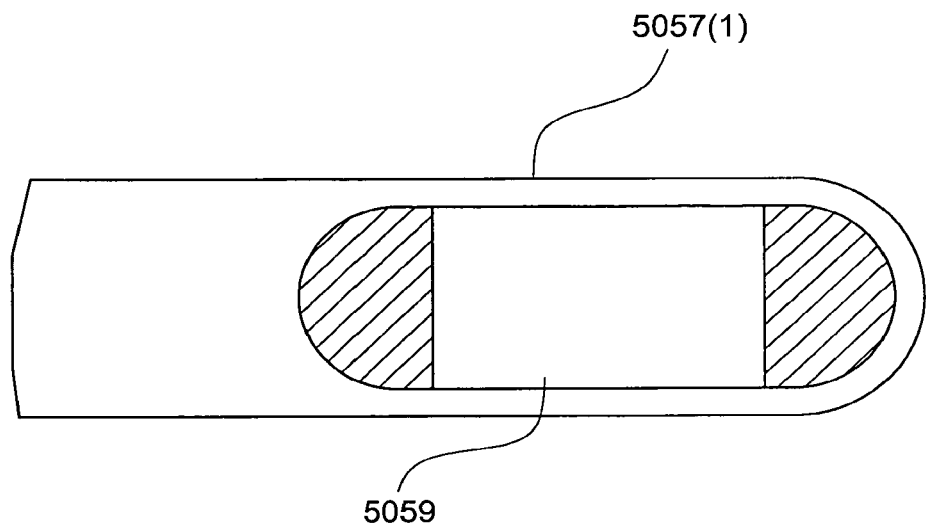
Figures 2, 21:
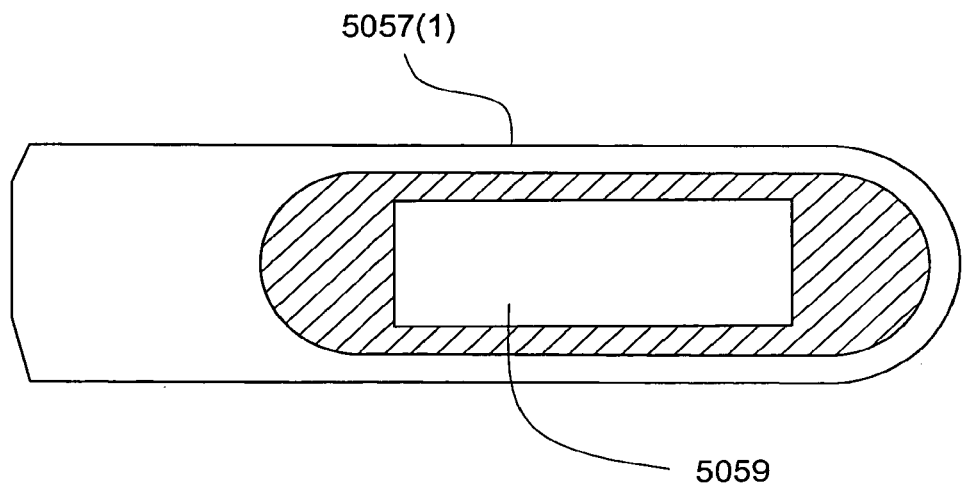
Figures 1, 22:
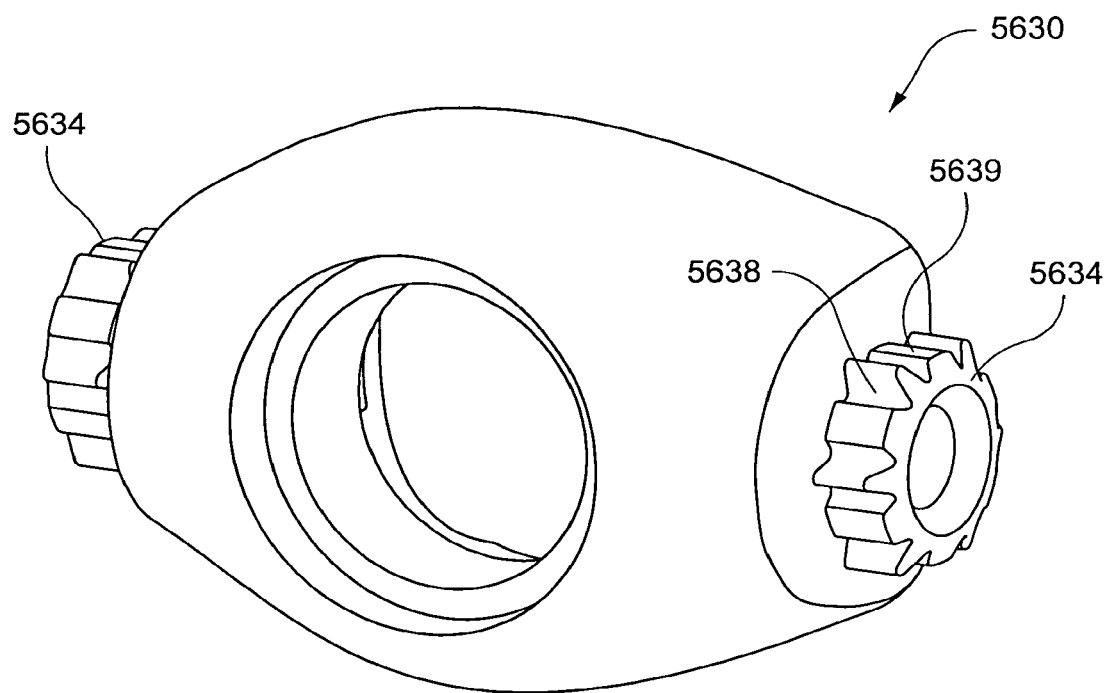
Figures 1, 2, 22:
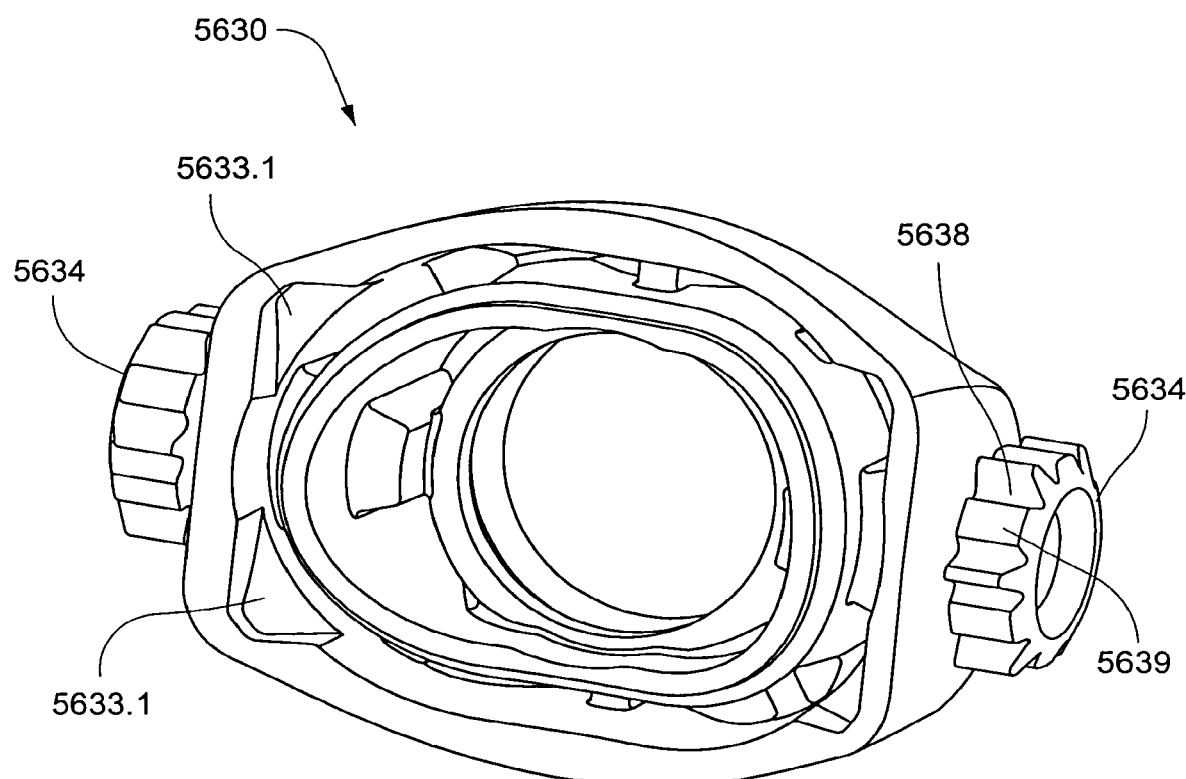
Figures 1, 3, 22:
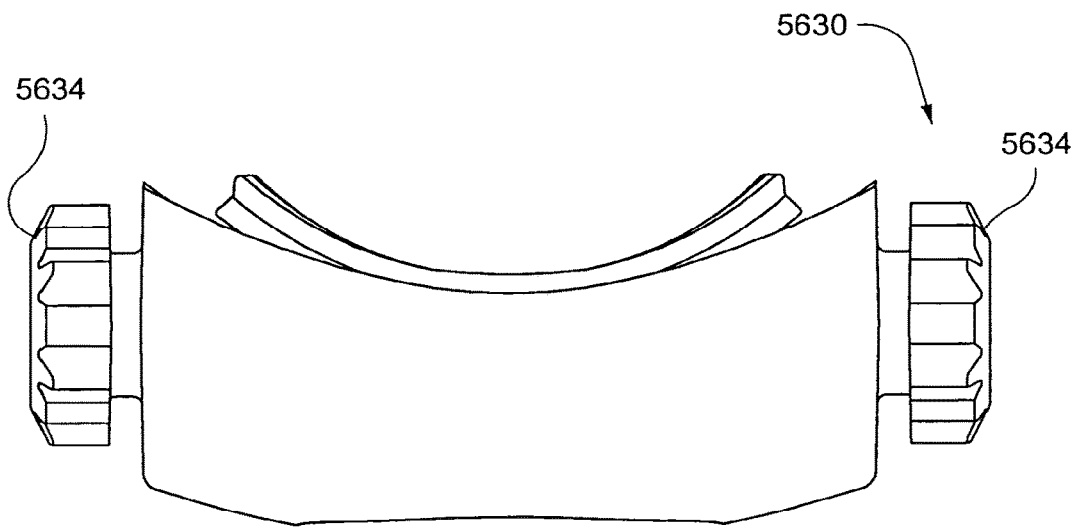
Figures 1, 4, 22:
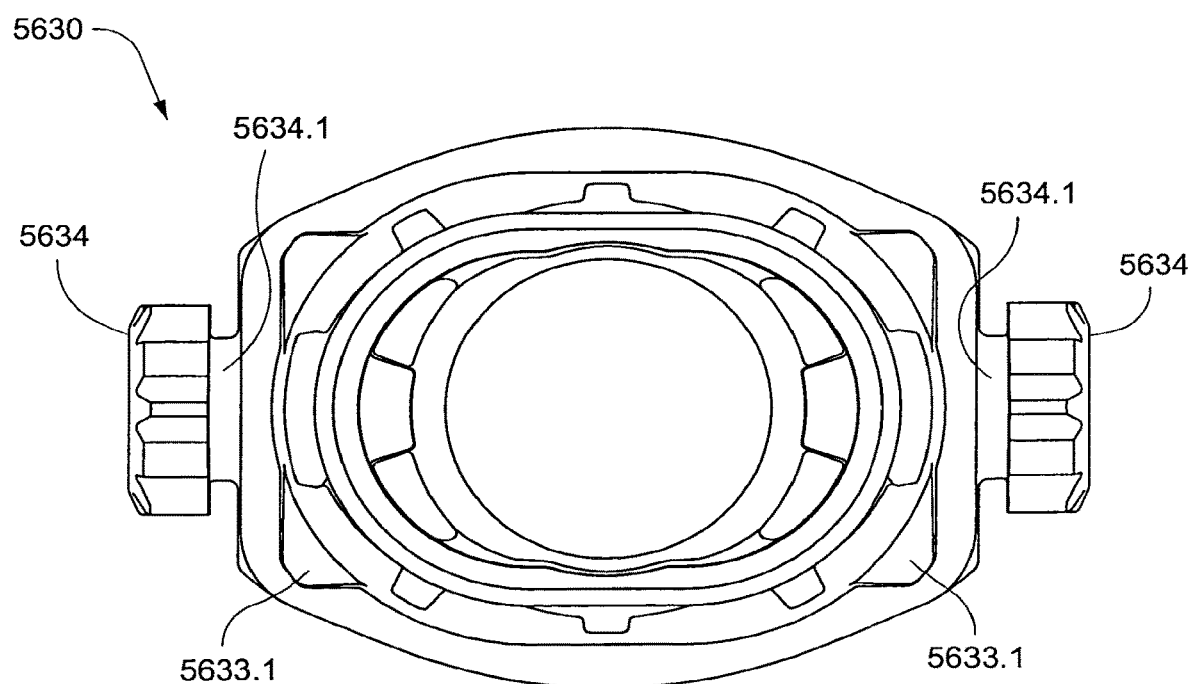
Figures 1, 5, 22:
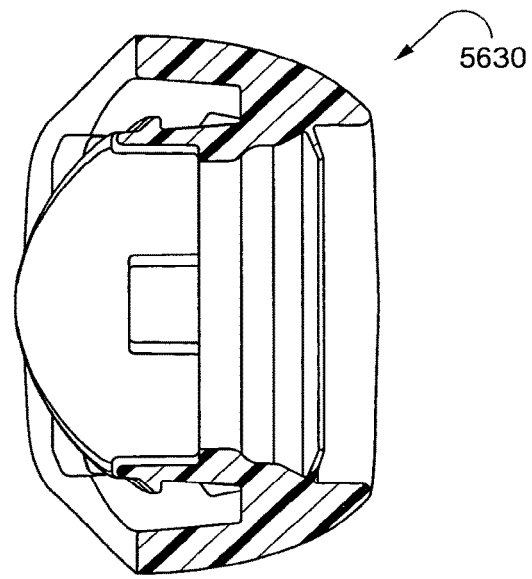
Figures 1, 6, 22:
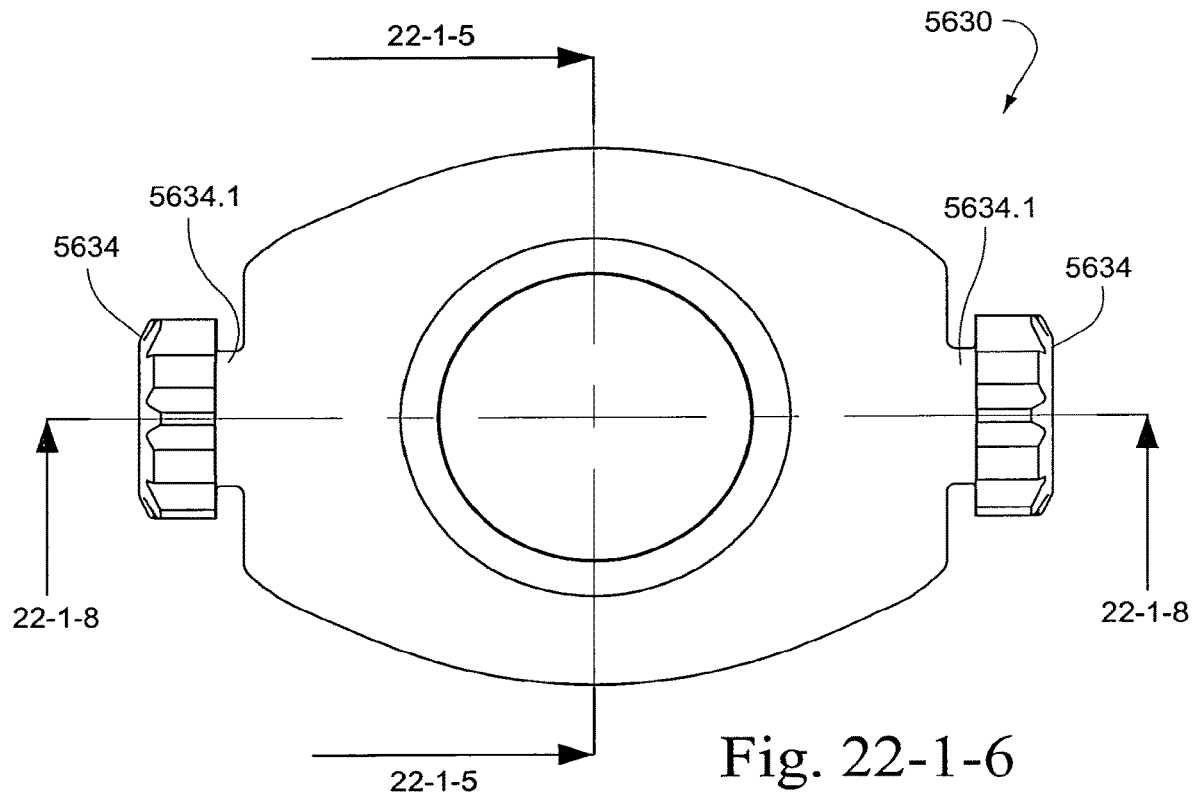
Figures 1, 7, 22:
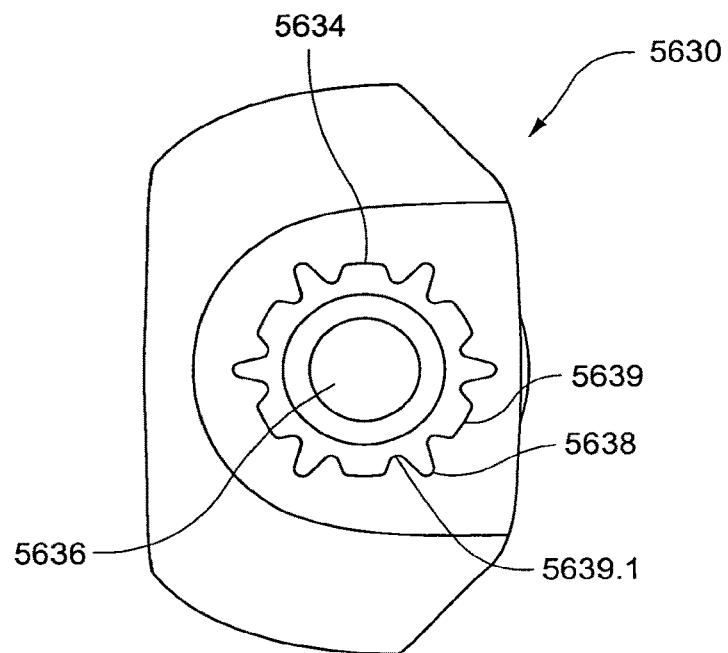
Figures 1, 8, 22:
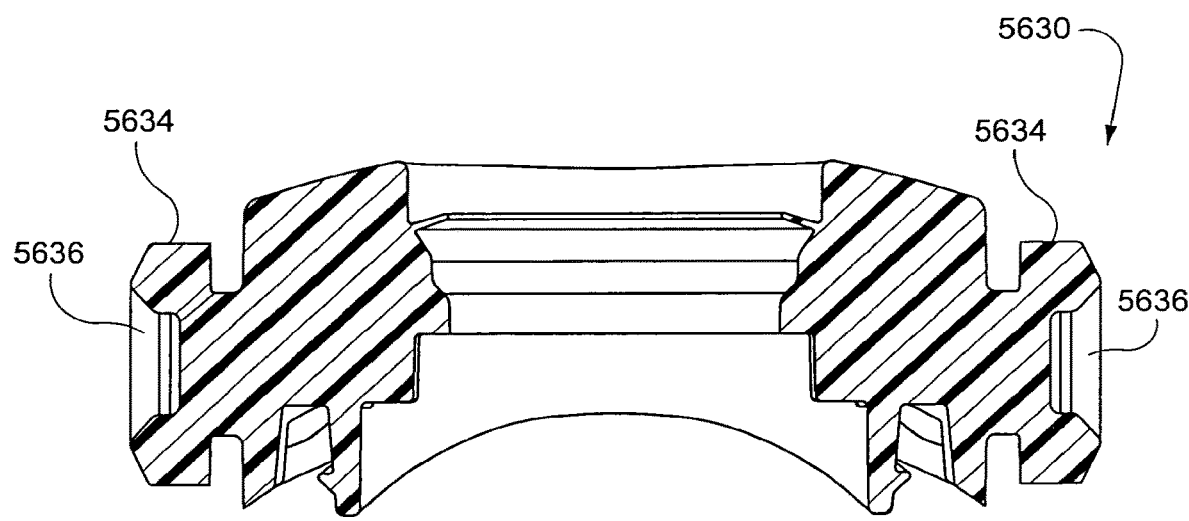
Figures 1, 9, 22:
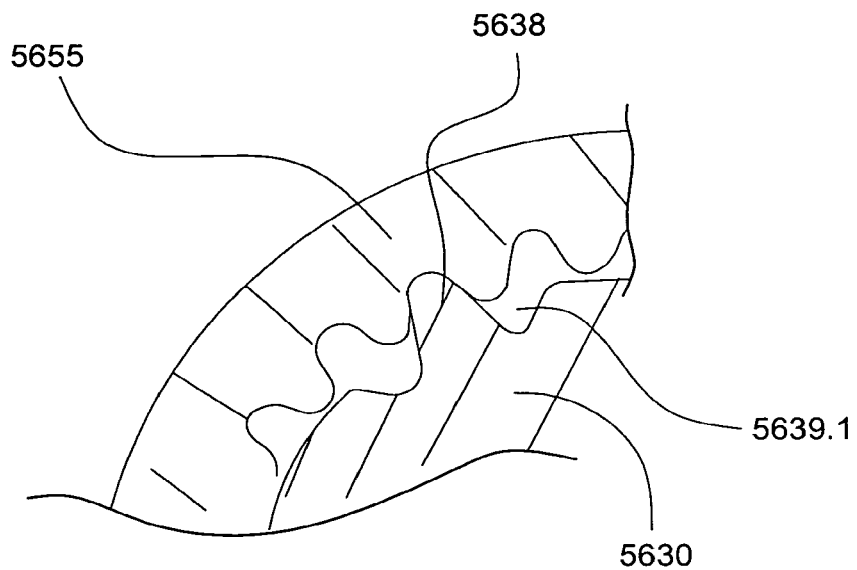
Figures 1, 10, 22:
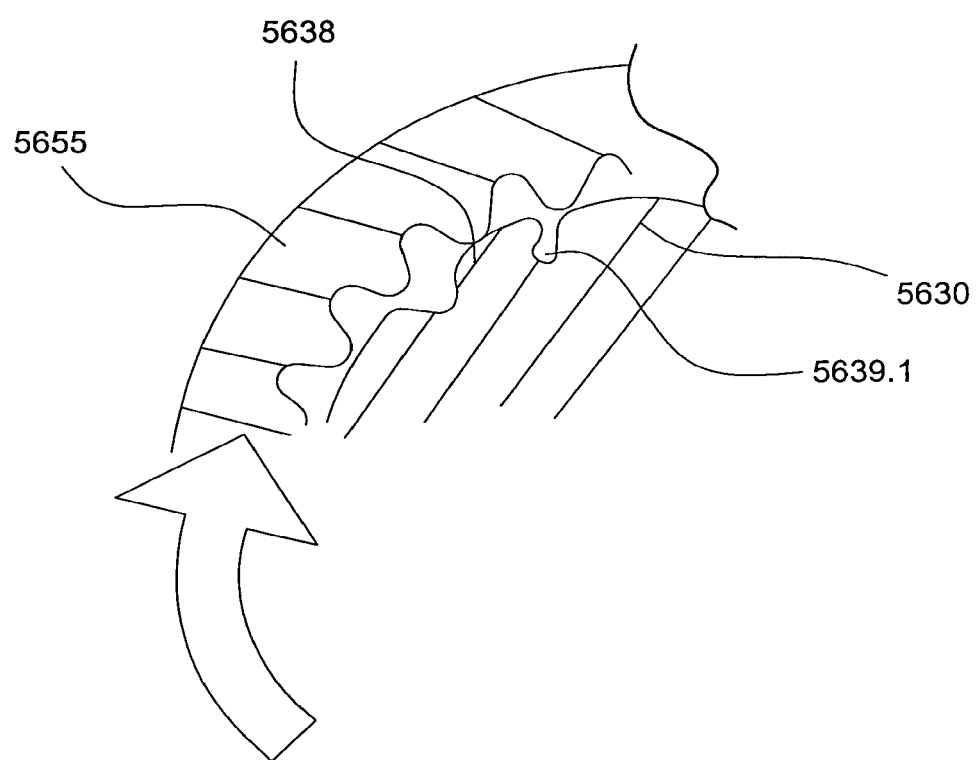
Figures 2, 22:
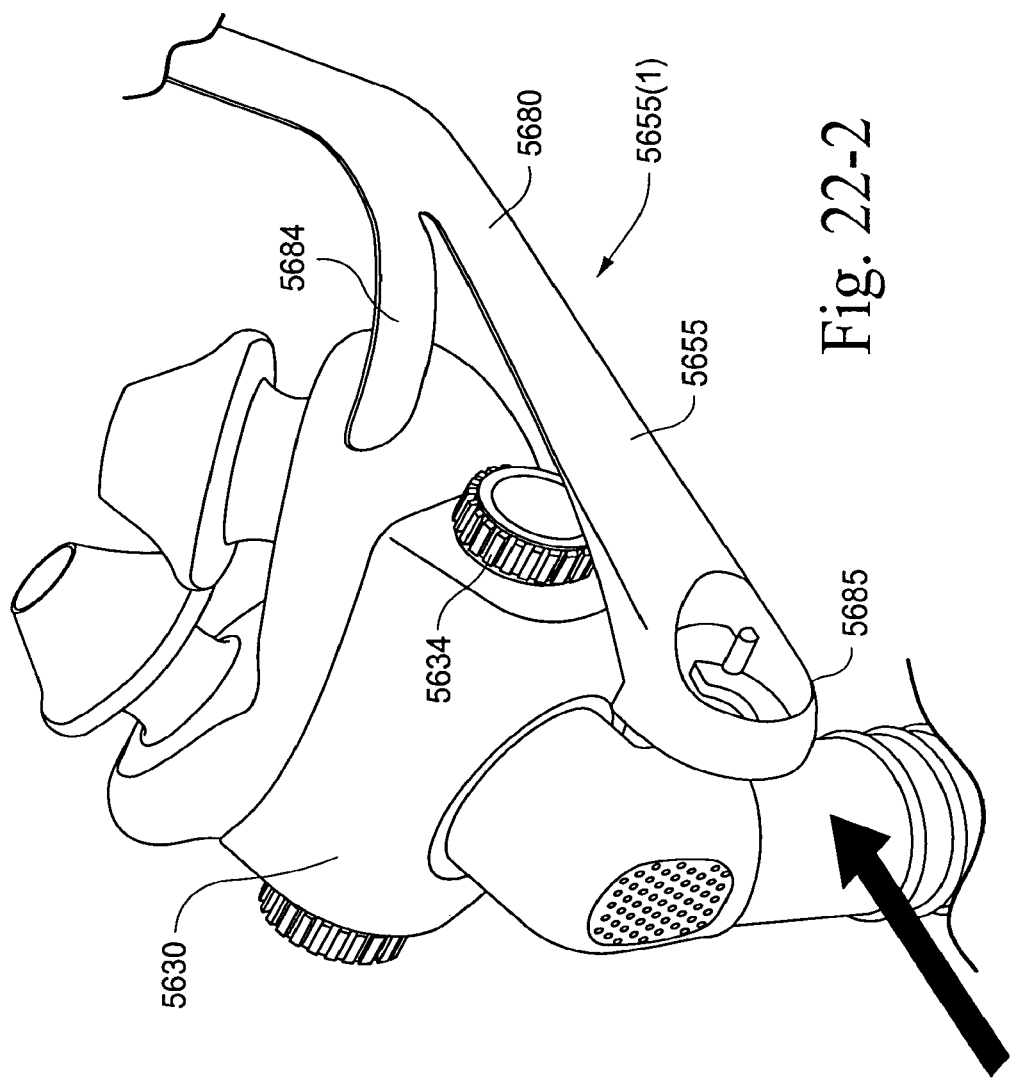
Figures 3, 22:
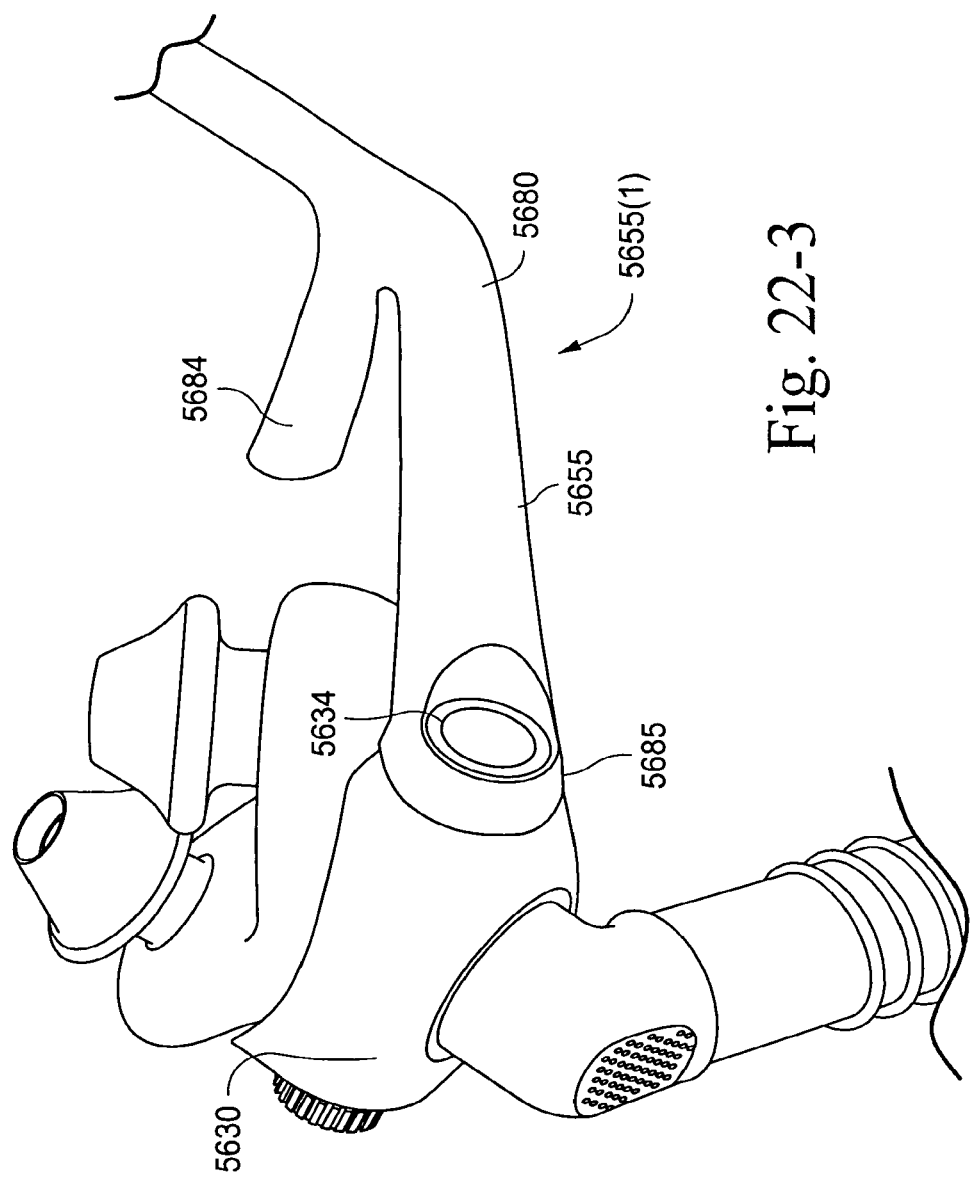
Figures 4, 22:
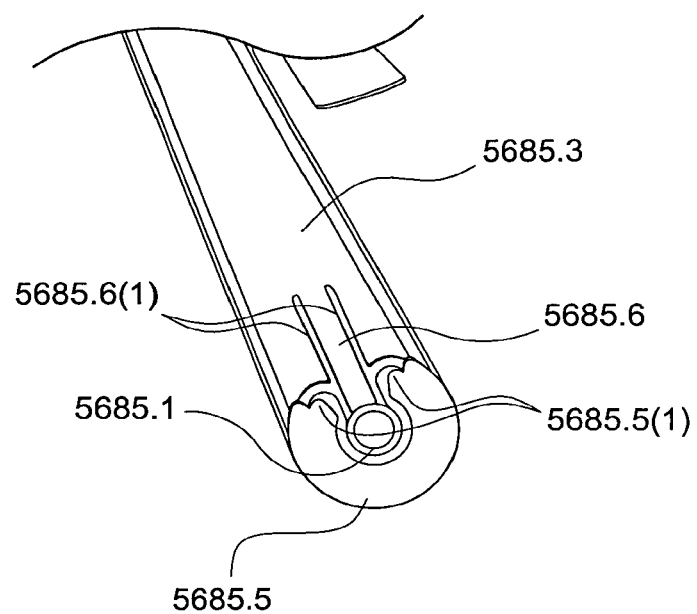
Figures 5, 22:
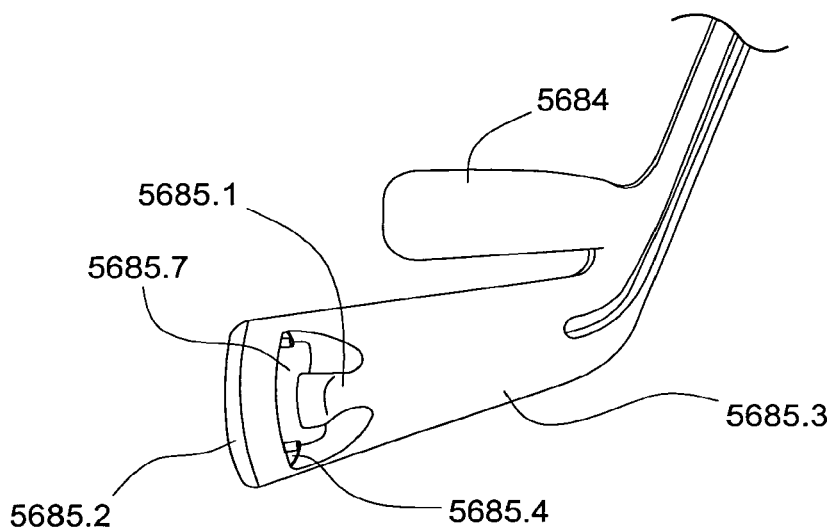
Figures 6, 22:
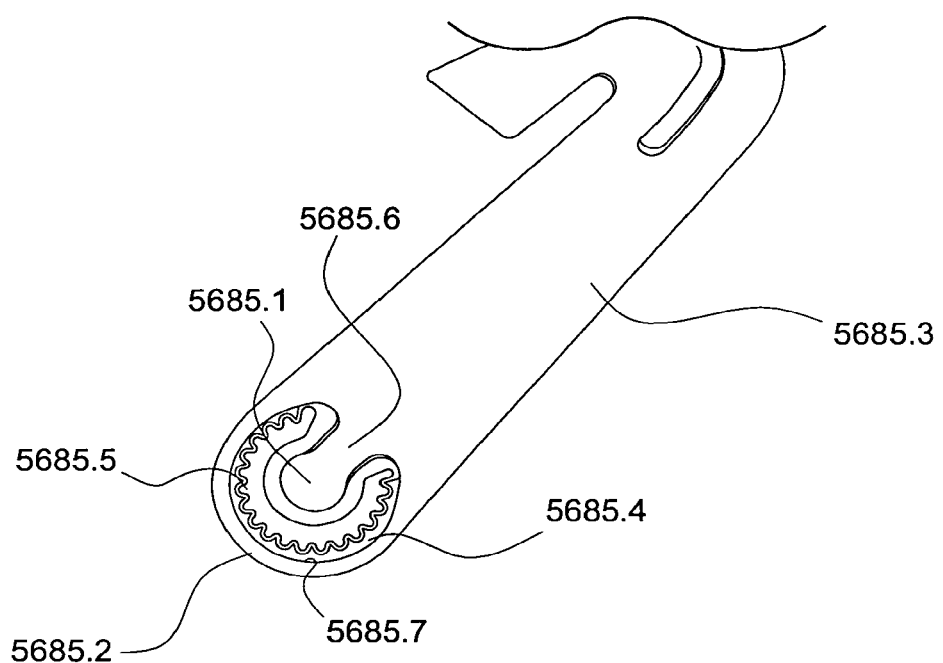
Figures 1, 7, 22:
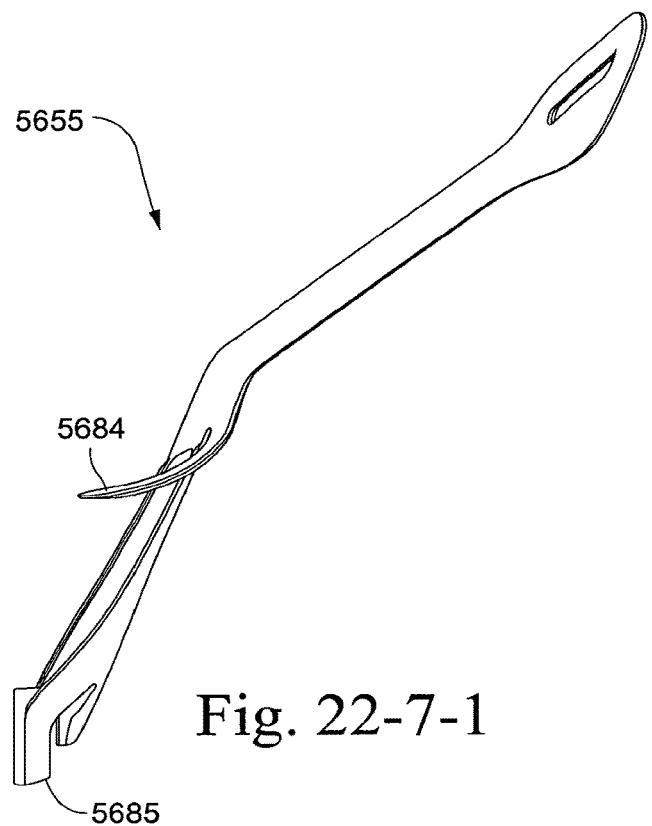
Figures 2, 7, 22:
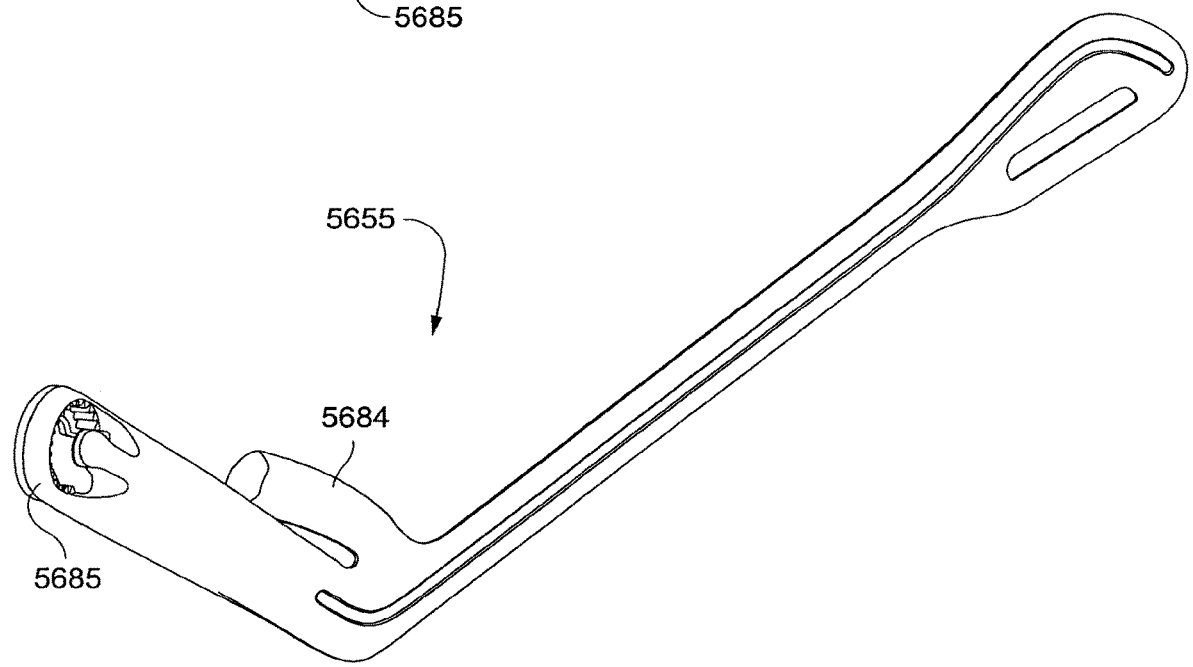
Figures 6, 7, 22:
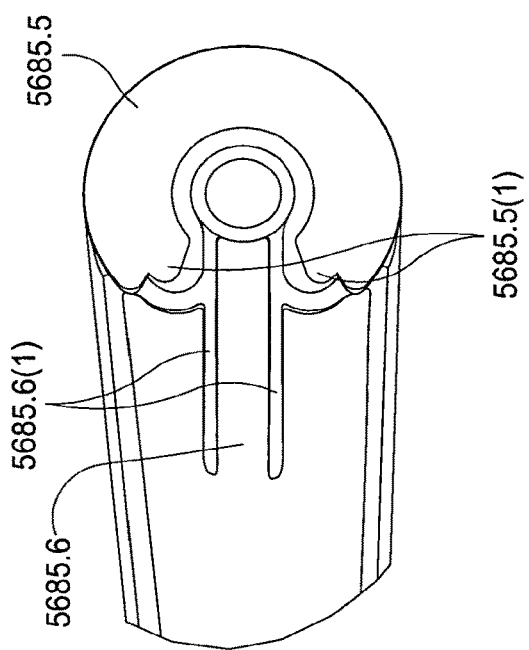
Figures 5, 7, 22:
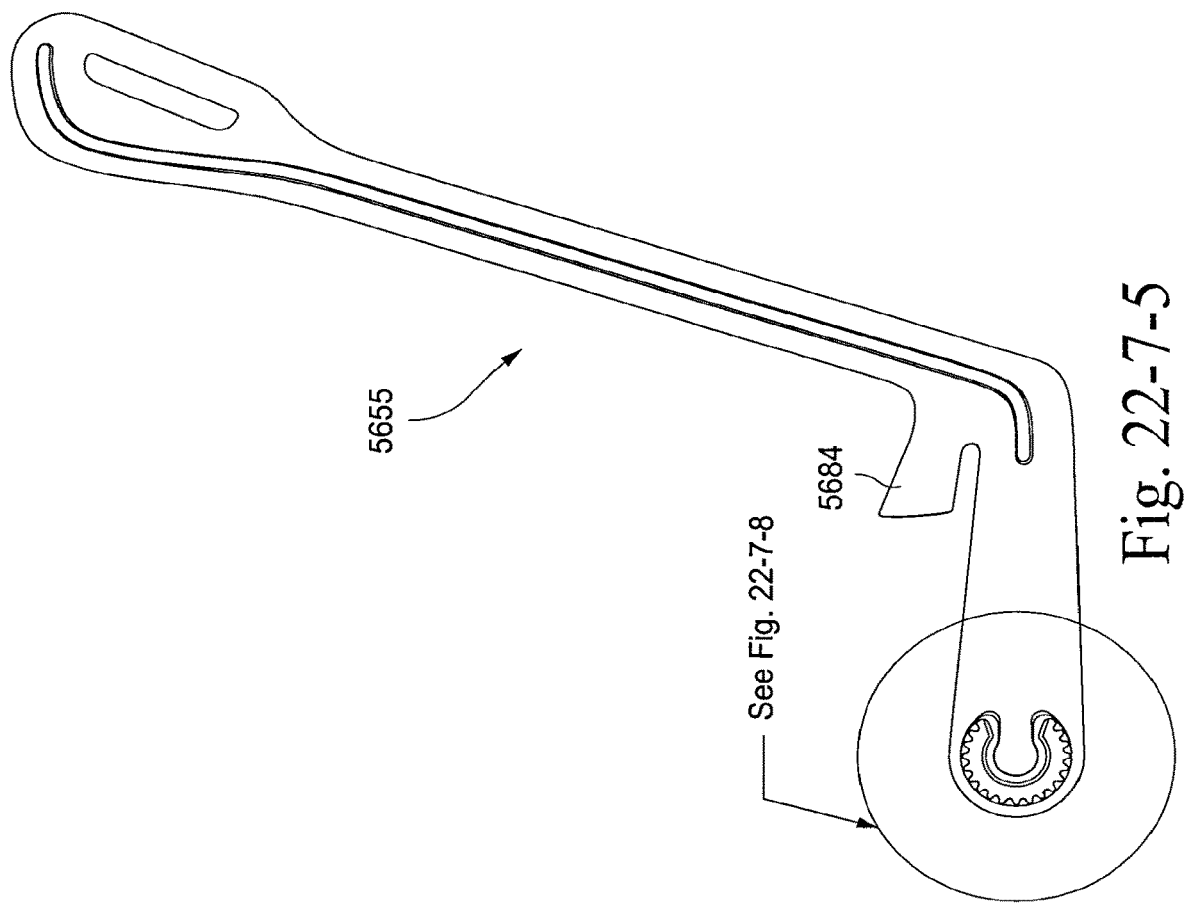
Figures 7, 22:
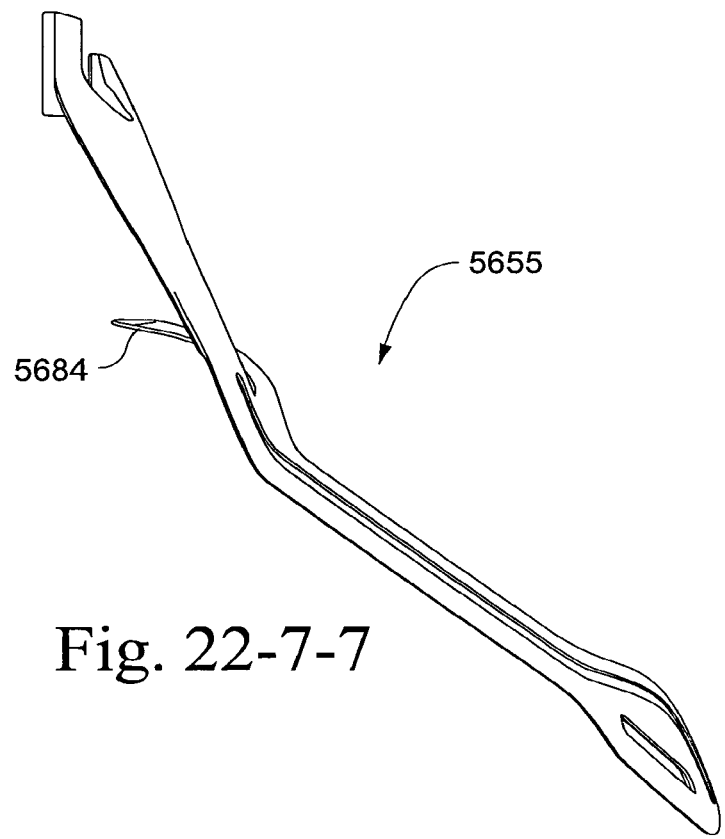
Figures 7, 8, 22:
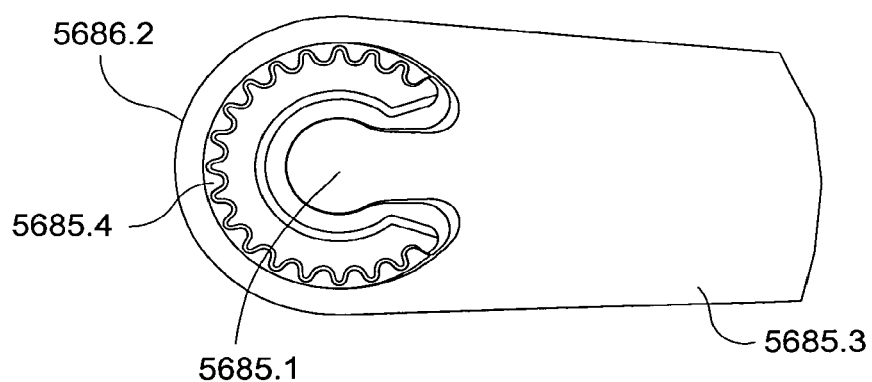
Figures 8, 22:
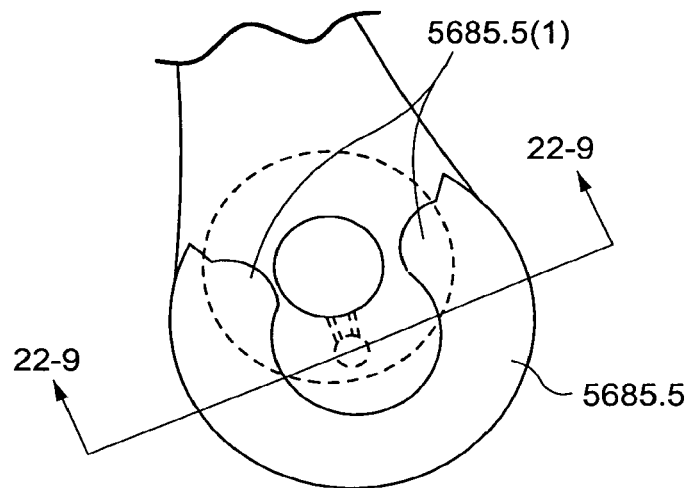
Figures 9, 22:
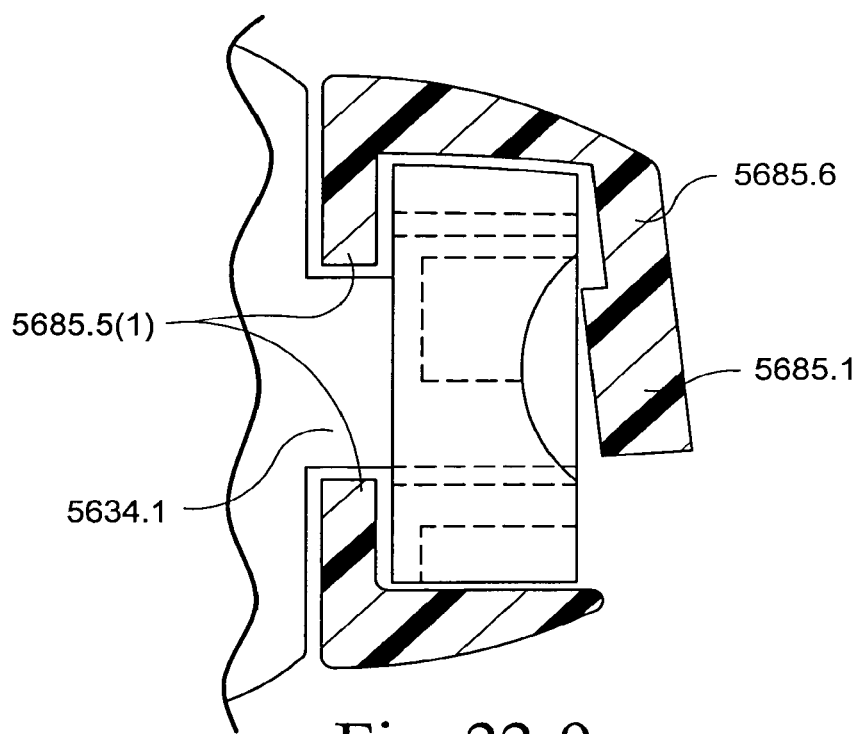
Figures 10, 22:
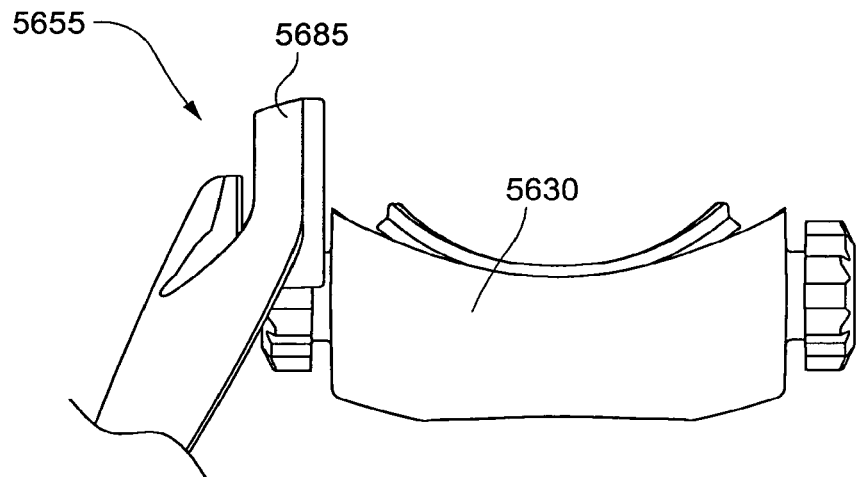
Figures 11, 22:
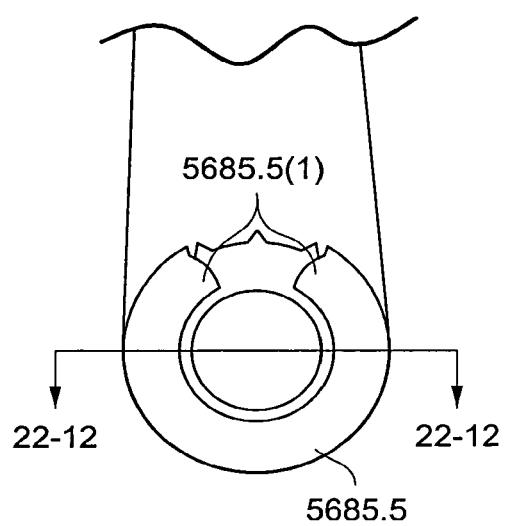
Figures 12, 22:
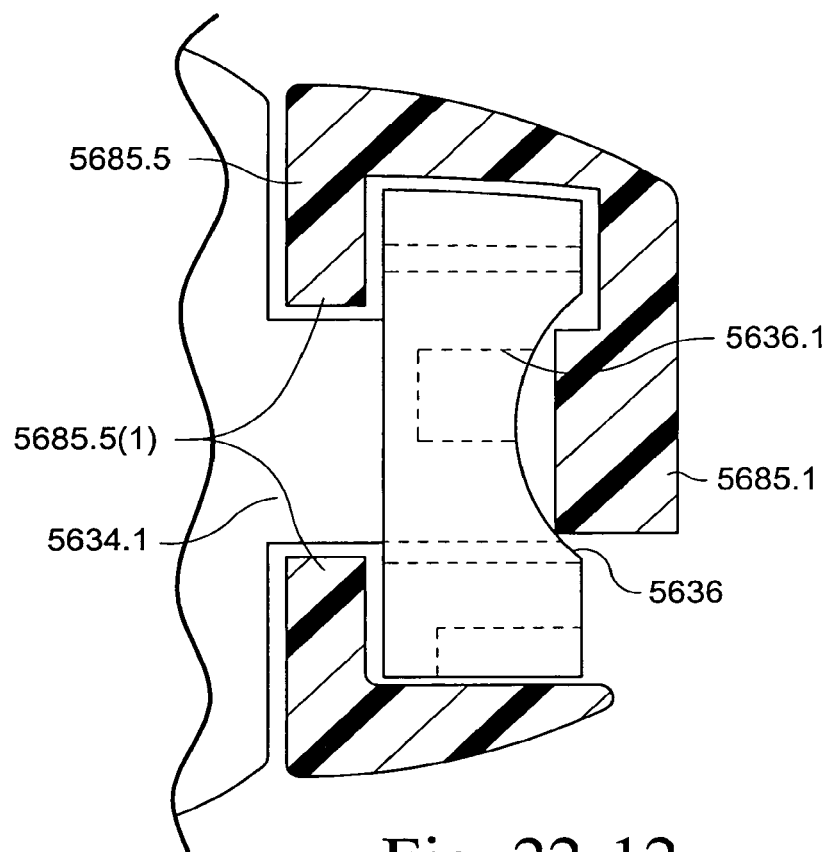
Figures 13, 22:
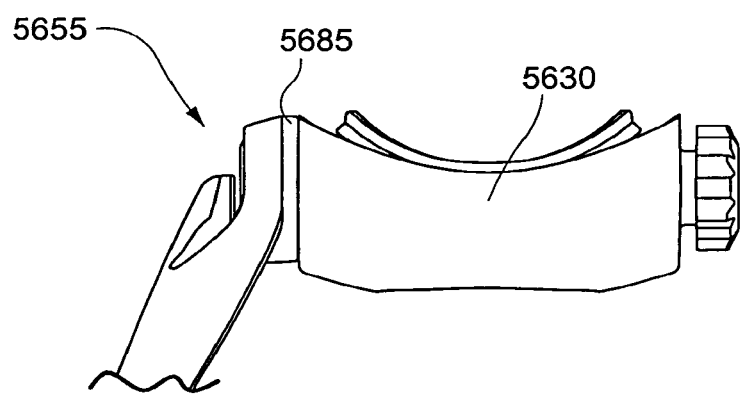
Figures 15, 22:
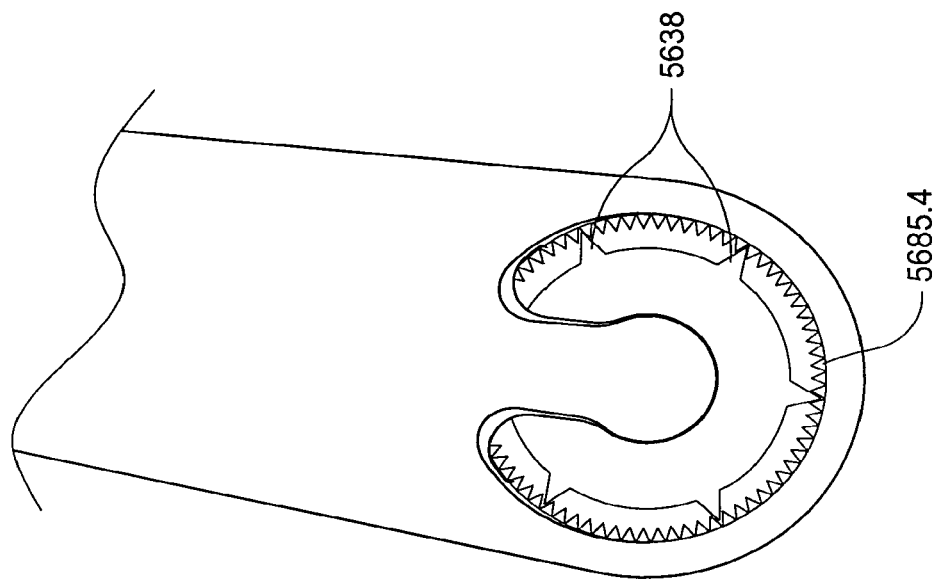
Figures 14, 22:
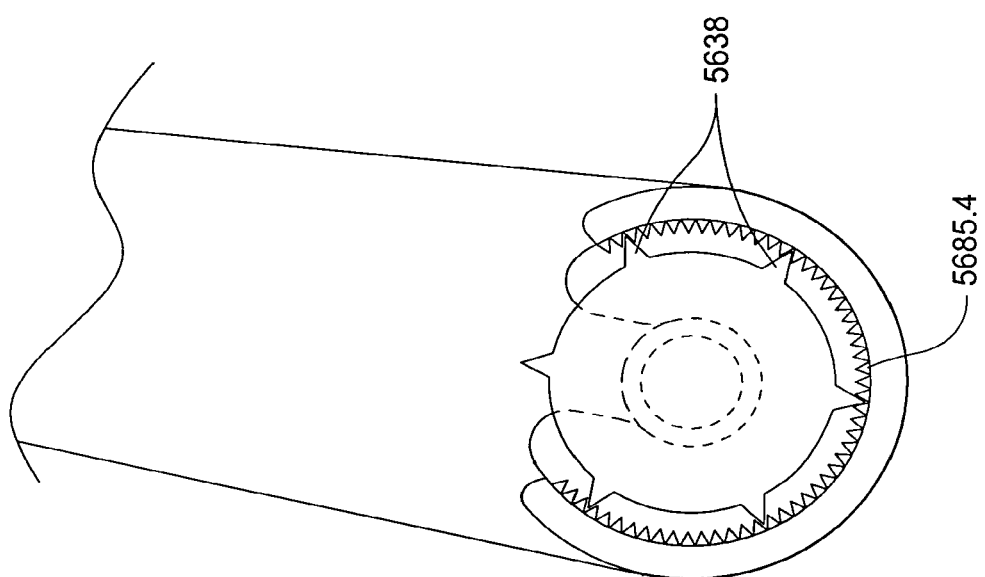
Figures 16, 22:
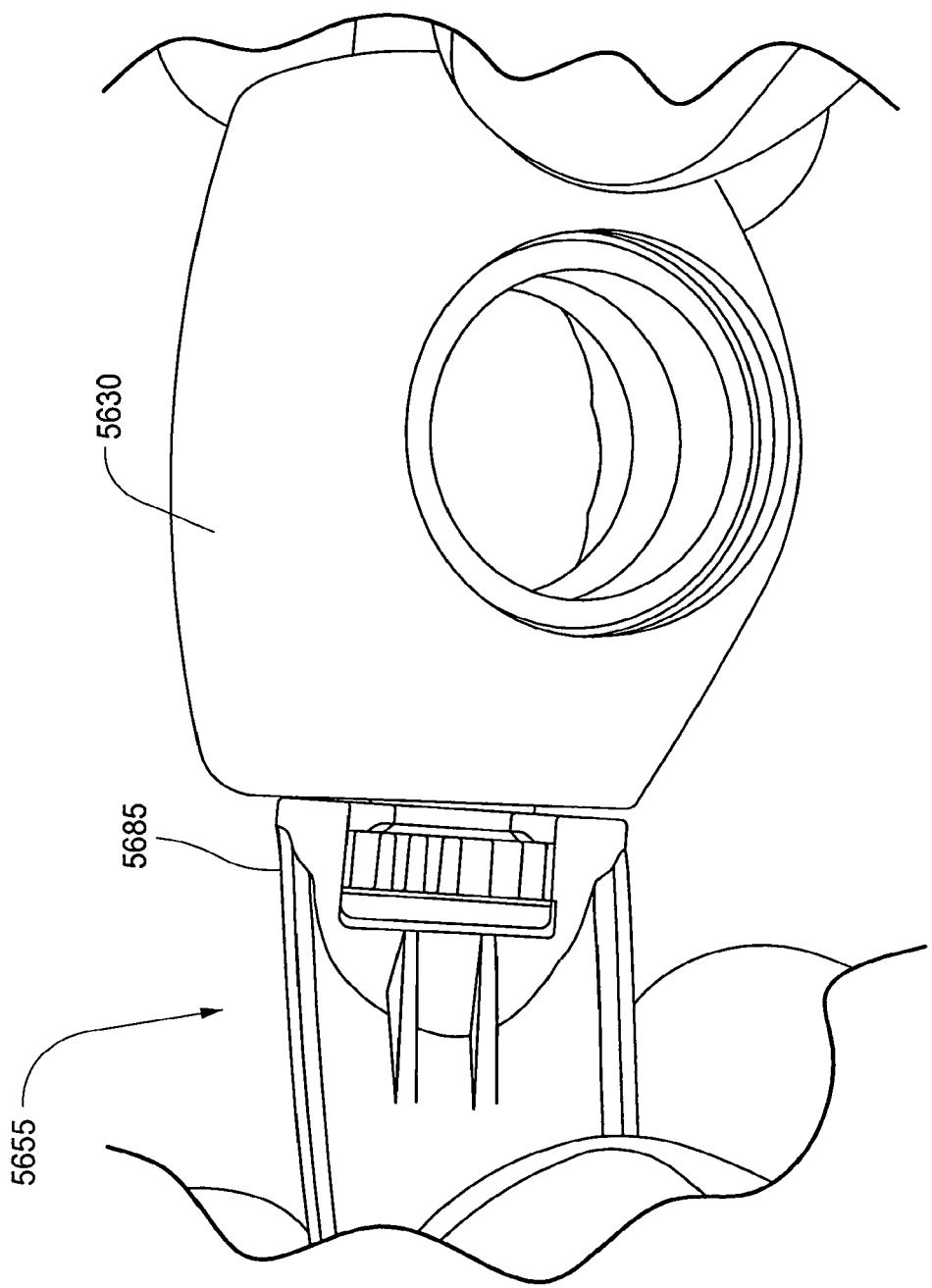
Figures 2, 16, 22:
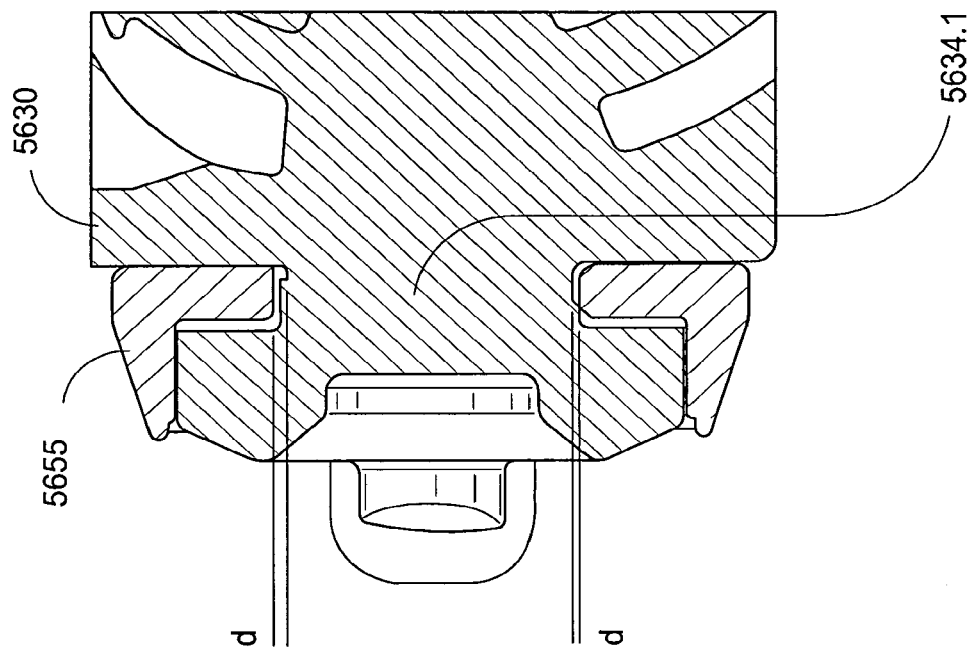
Figures 1, 16, 22:
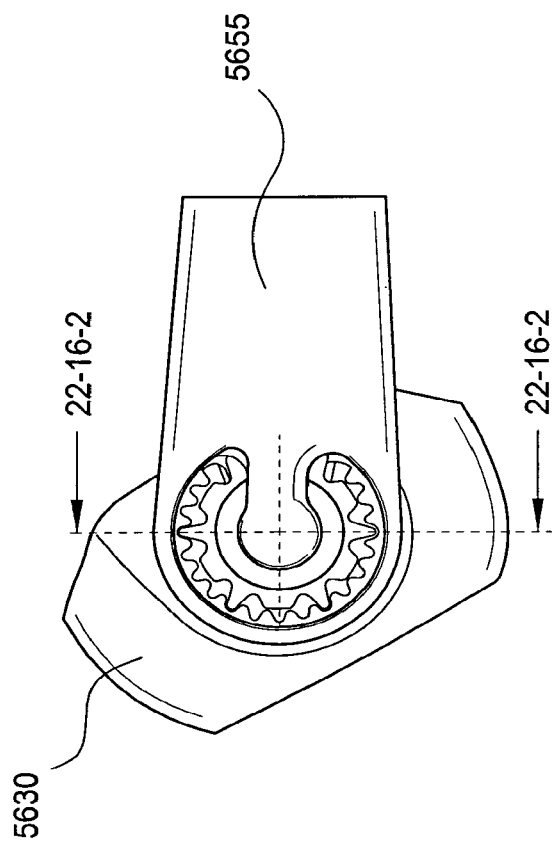
Figures 1, 18, 22:
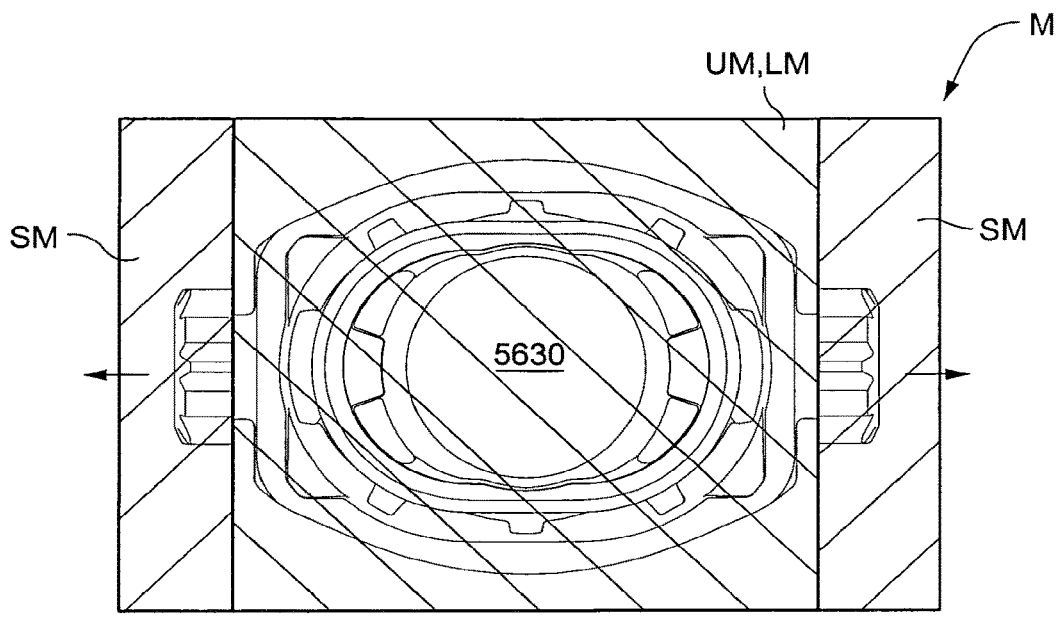
Figures 2, 18, 22:
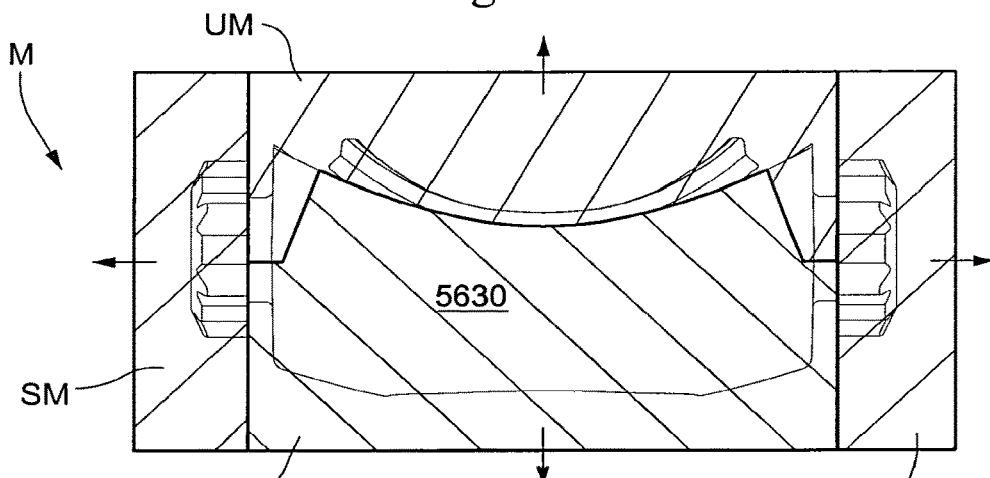
Figures 3, 18, 22:
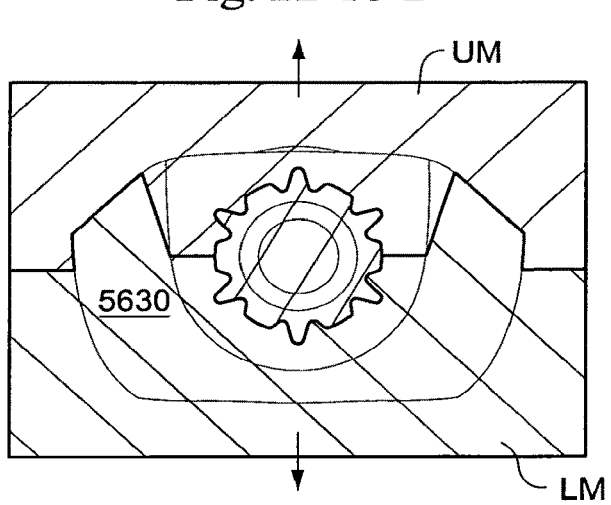
Figures 1, 19, 22:
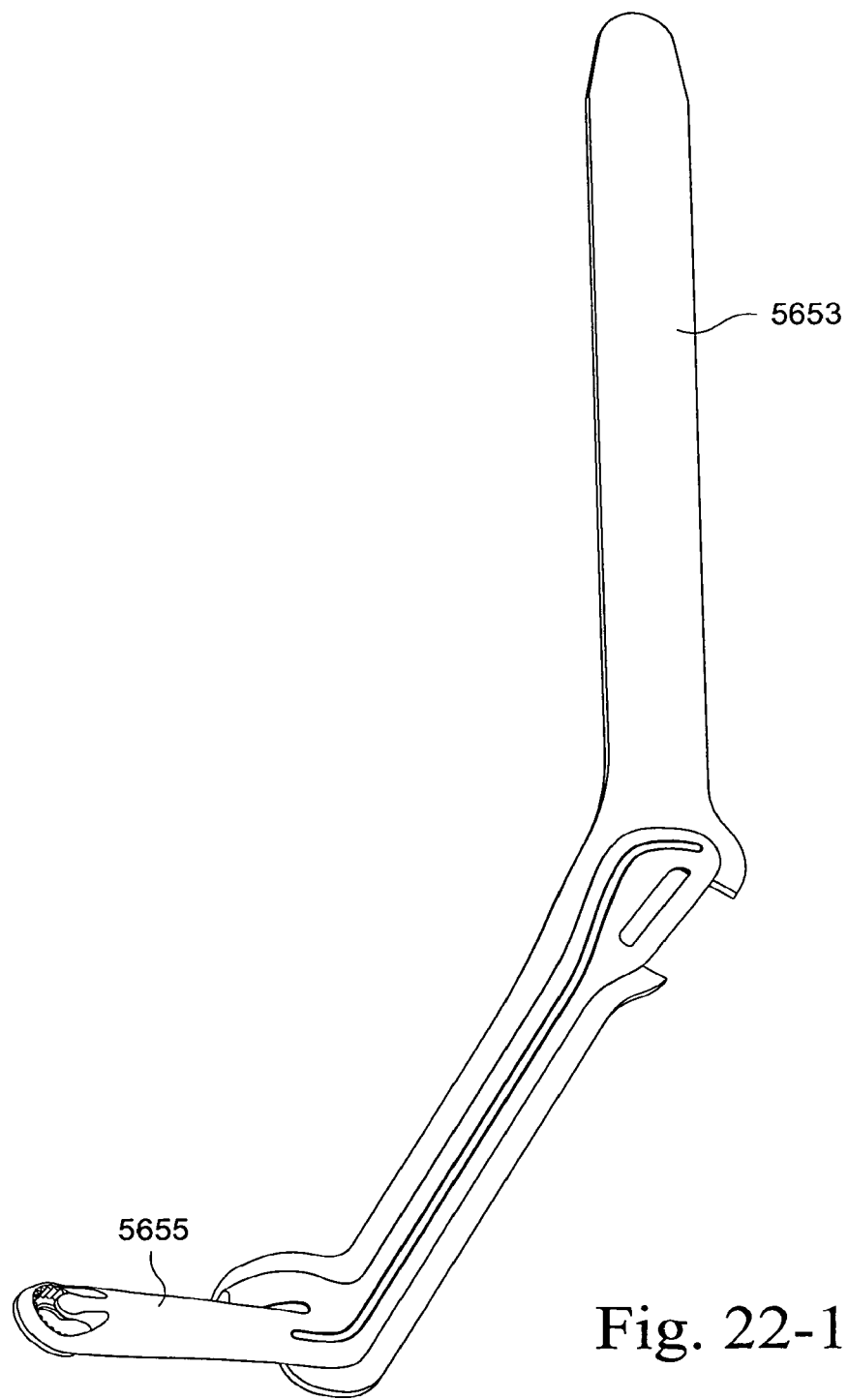
Figures 2, 19, 22:
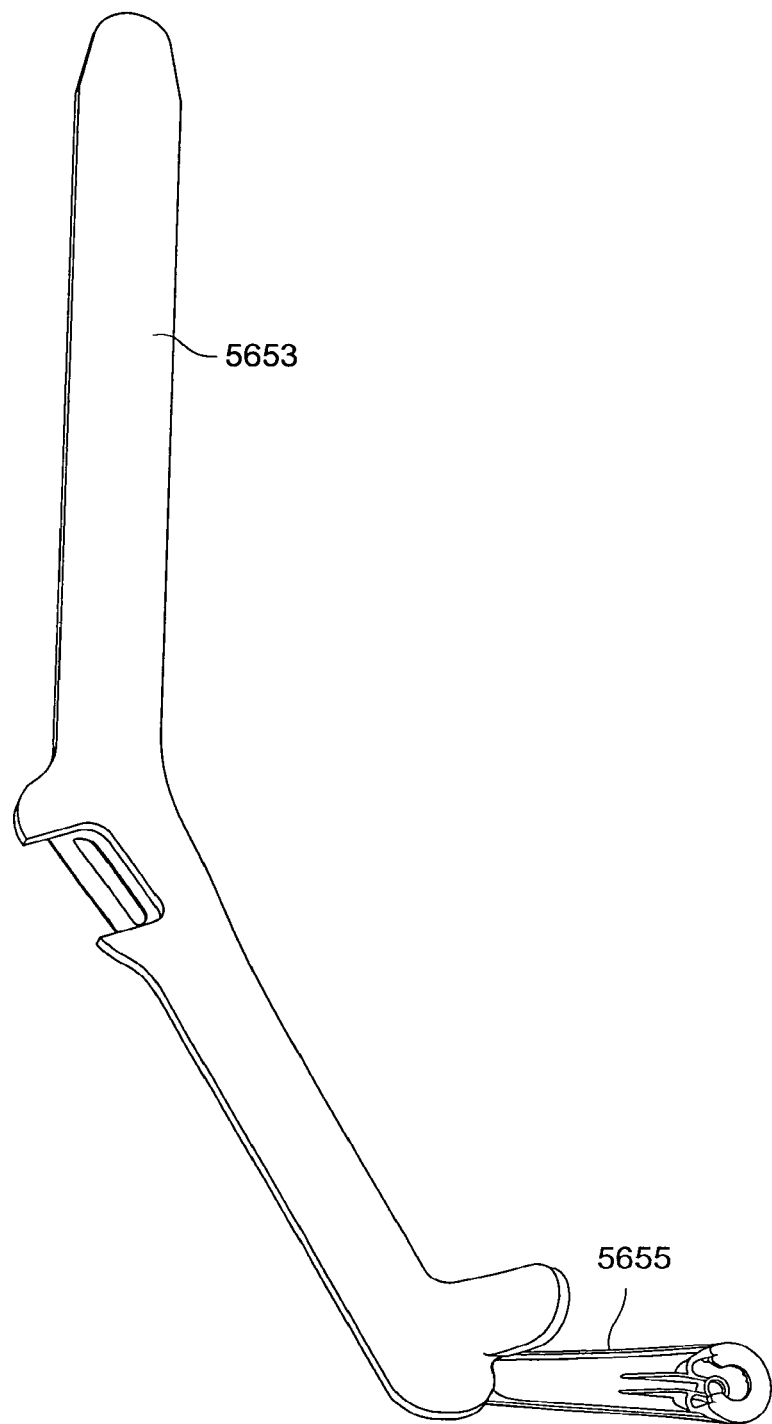
Figures 3, 19, 22:
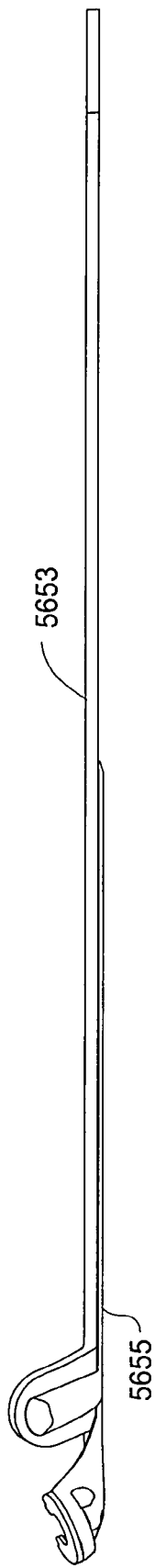
Figures 4, 19, 22:
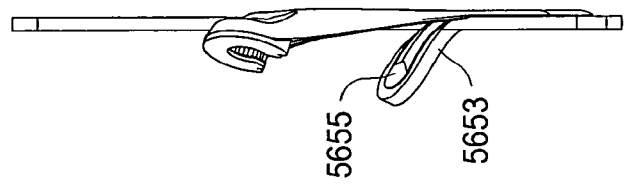
Figures 5, 19, 22:
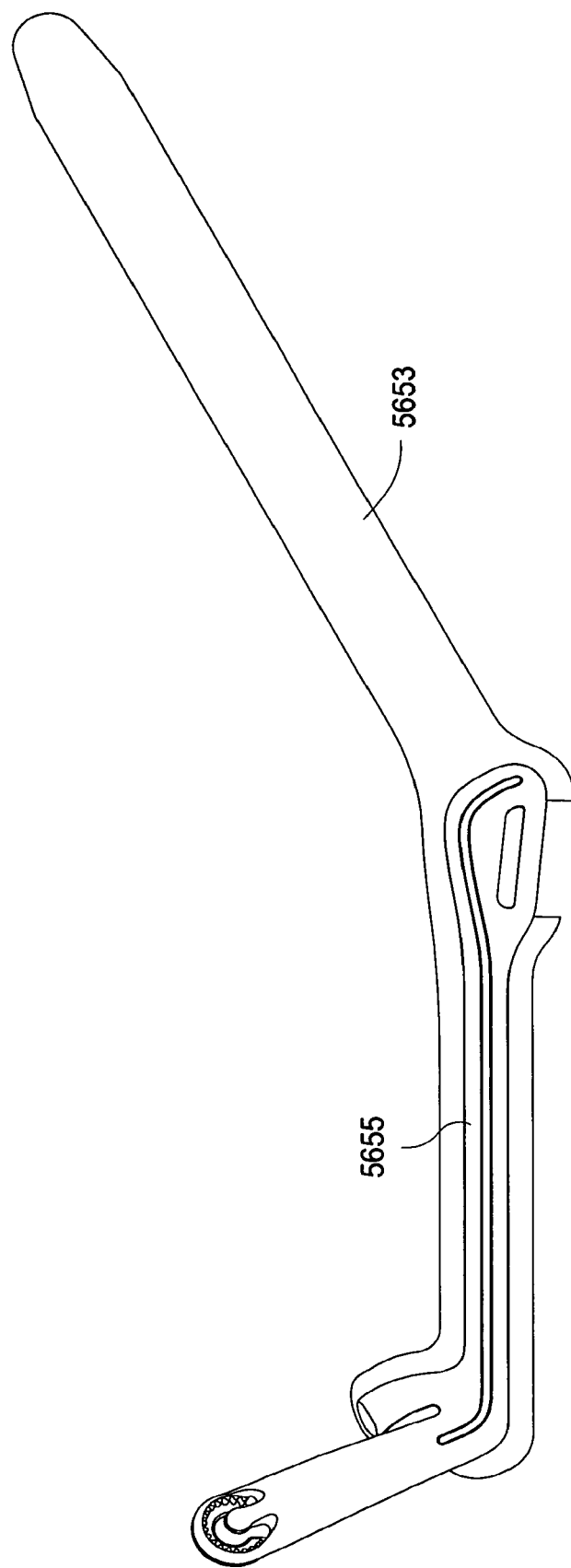
Figures 6, 19, 22:
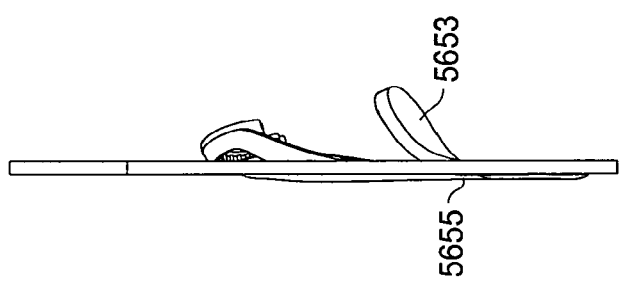
Figures 7, 19, 22:
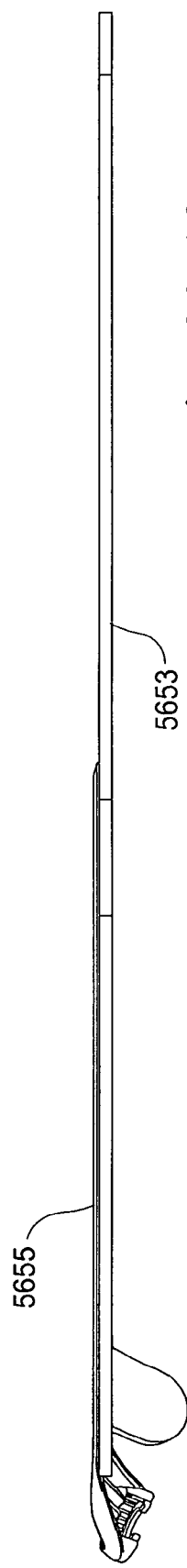
Figures 1, 20, 22:
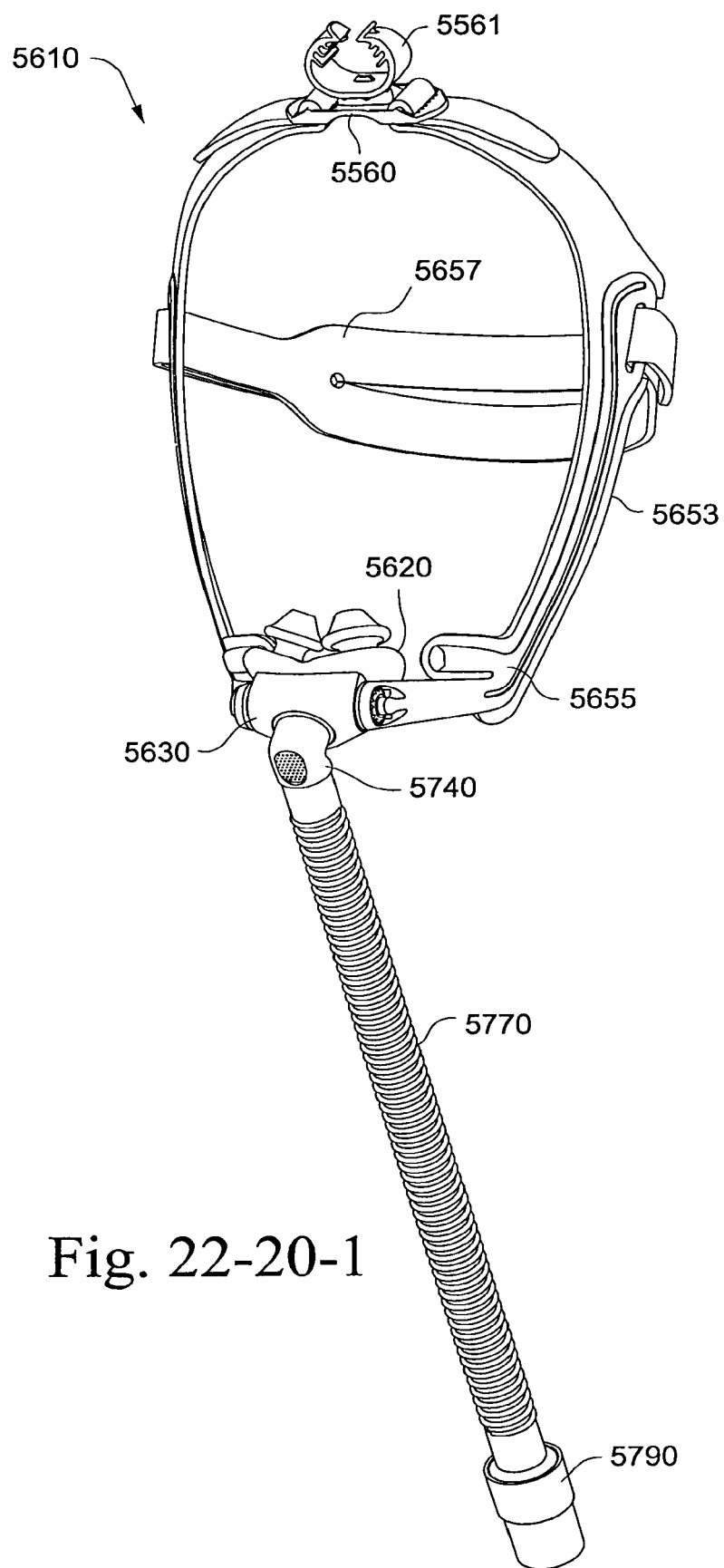
Figures 2, 20, 22:
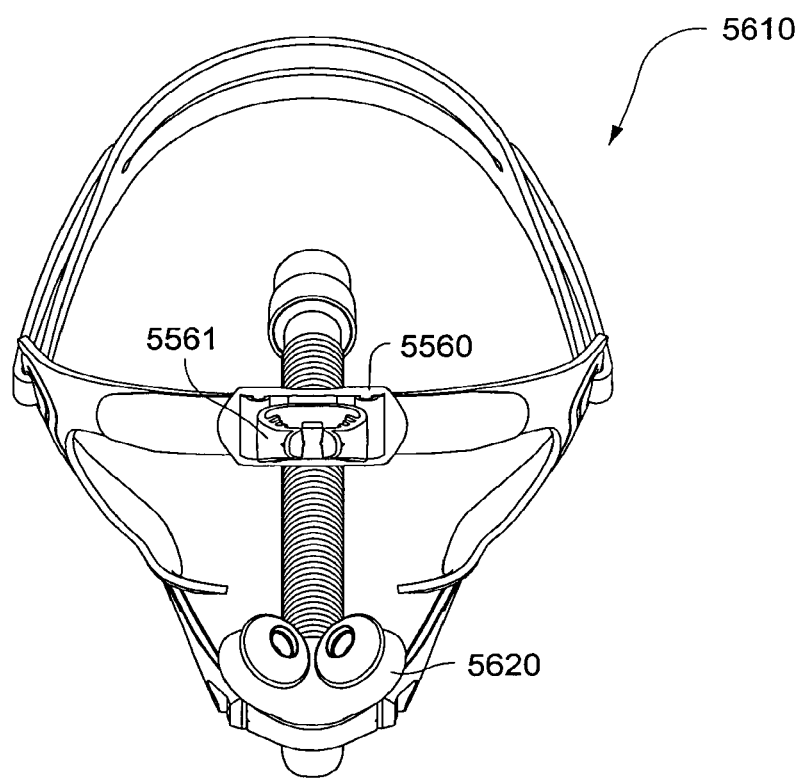
Figures 3, 20, 22:
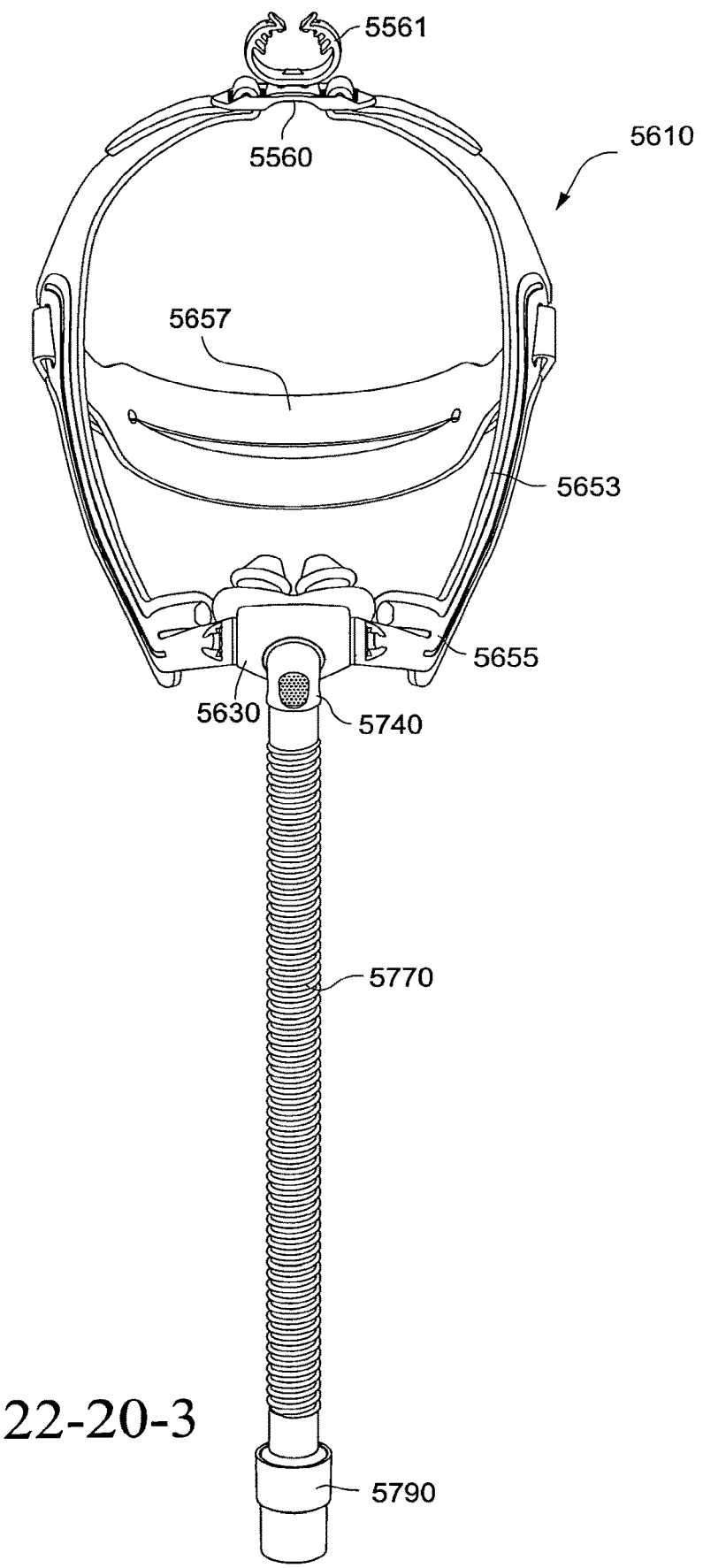
Figures 4, 20, 22:
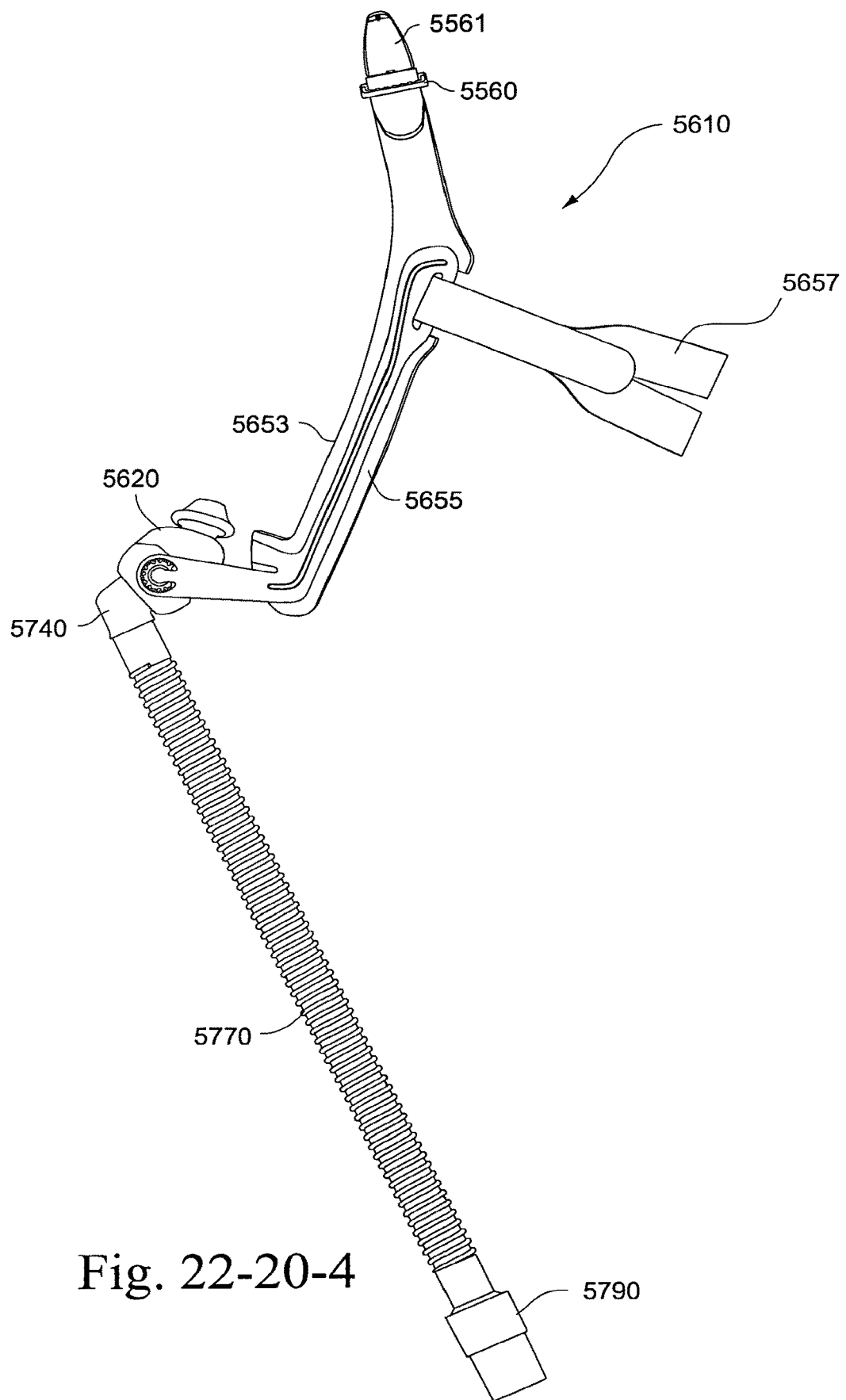
Figures 5, 20, 22:
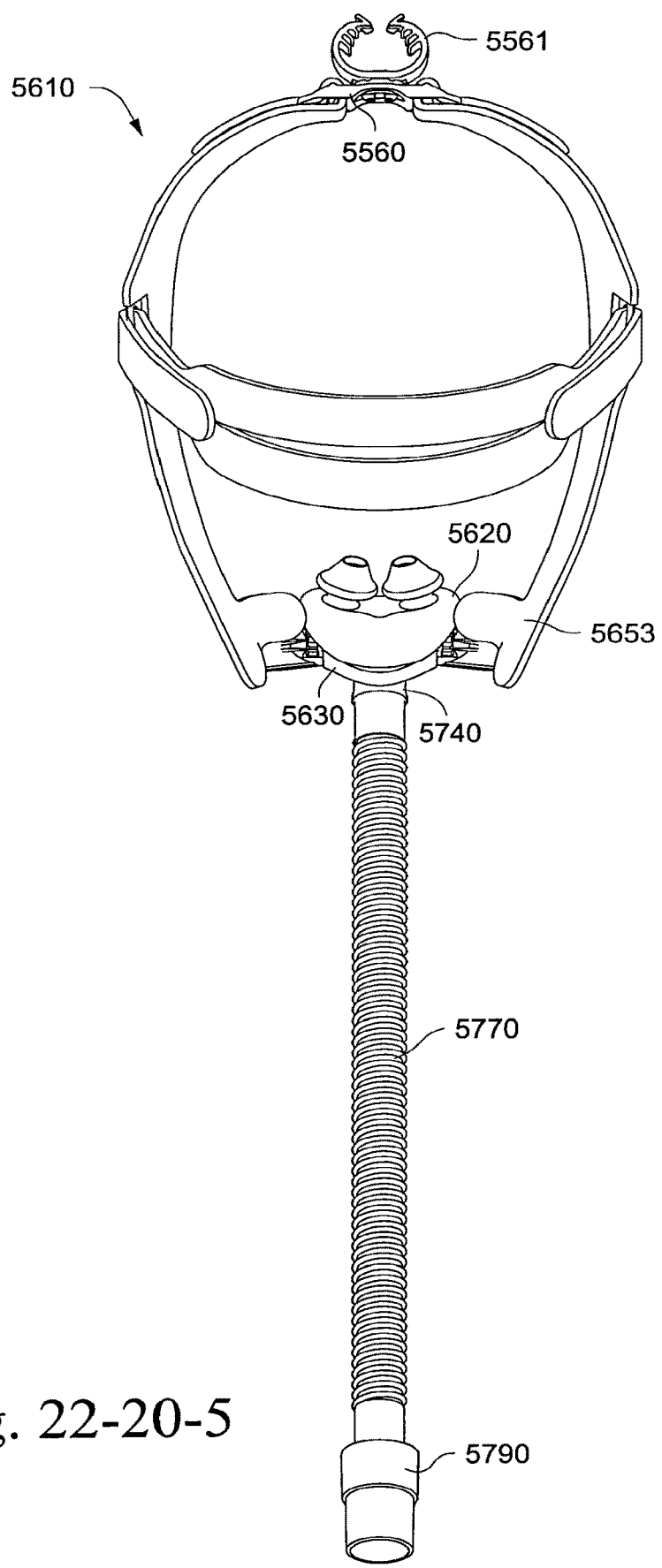
Figures 6, 20, 22:
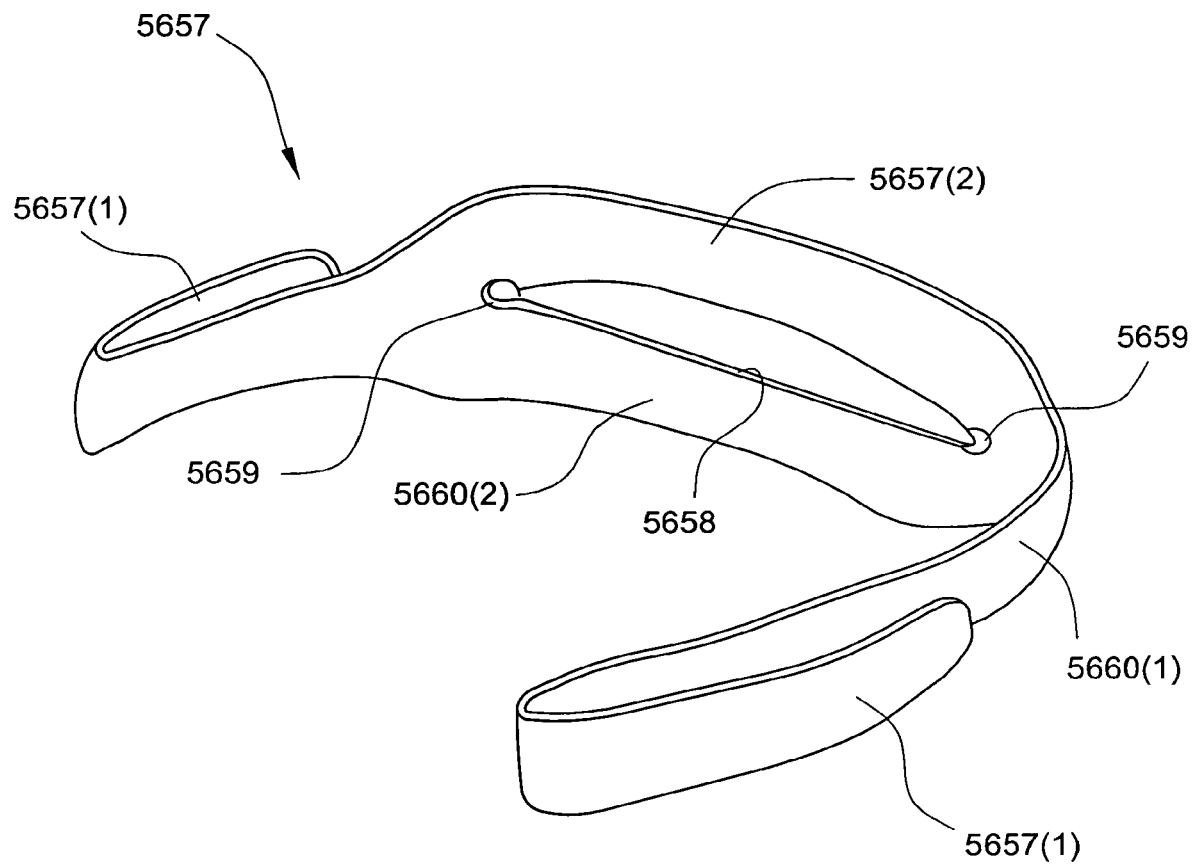
Figures 7, 20, 22:
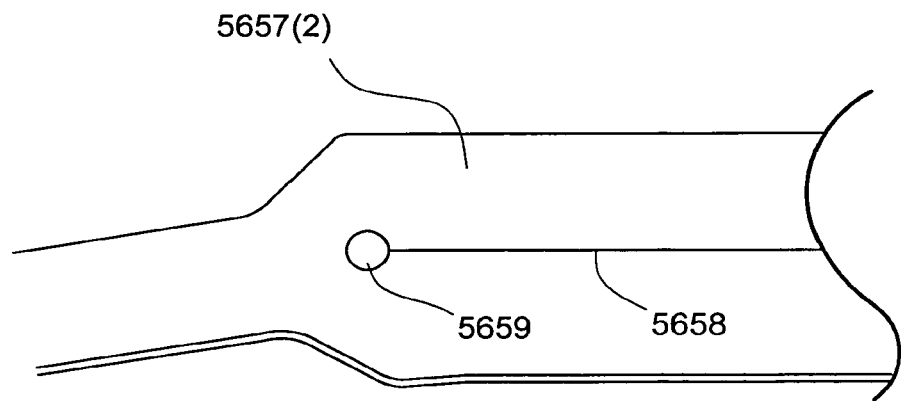
Figures 1, 21, 22:
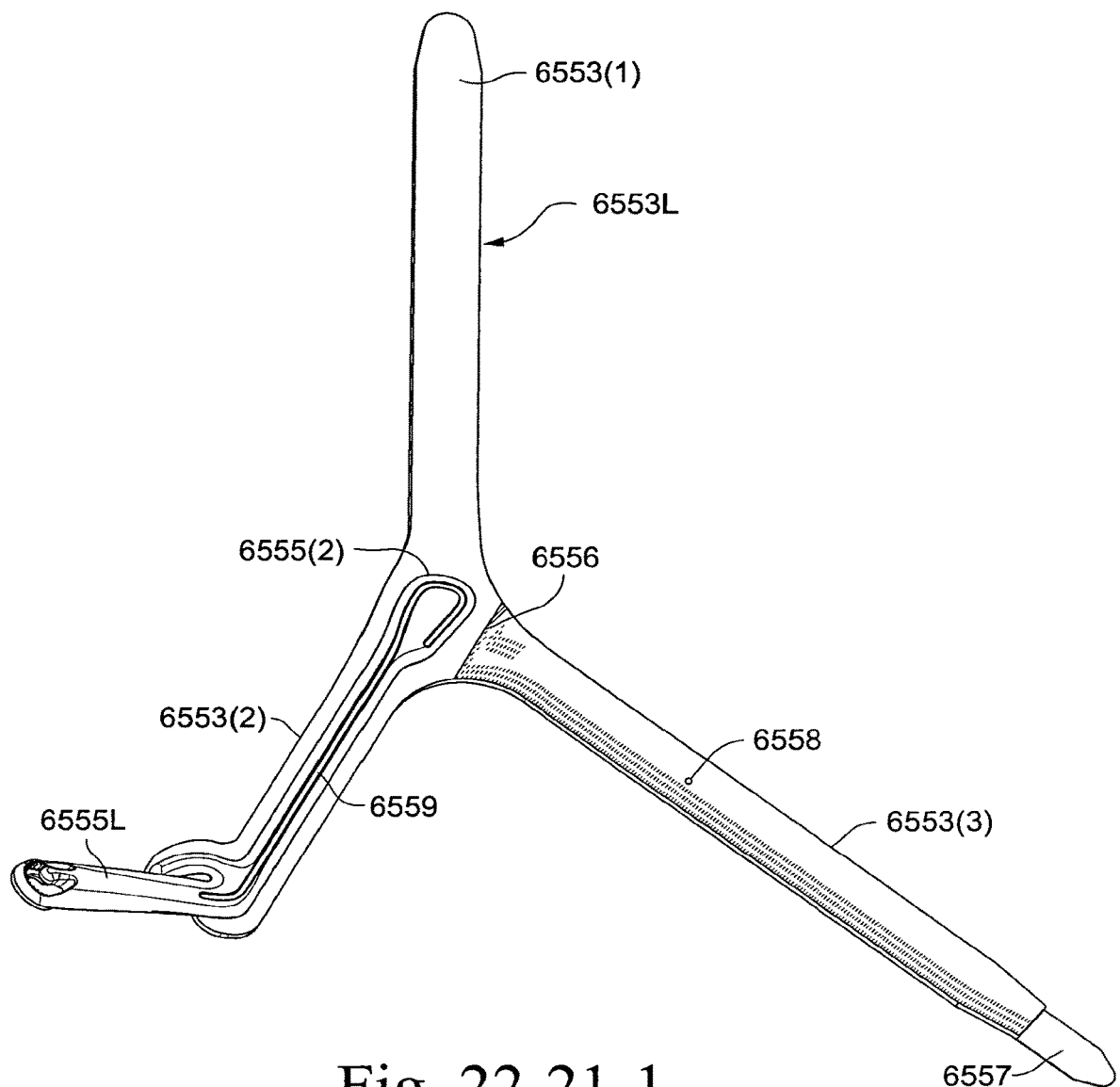
Figures 2, 21, 22:
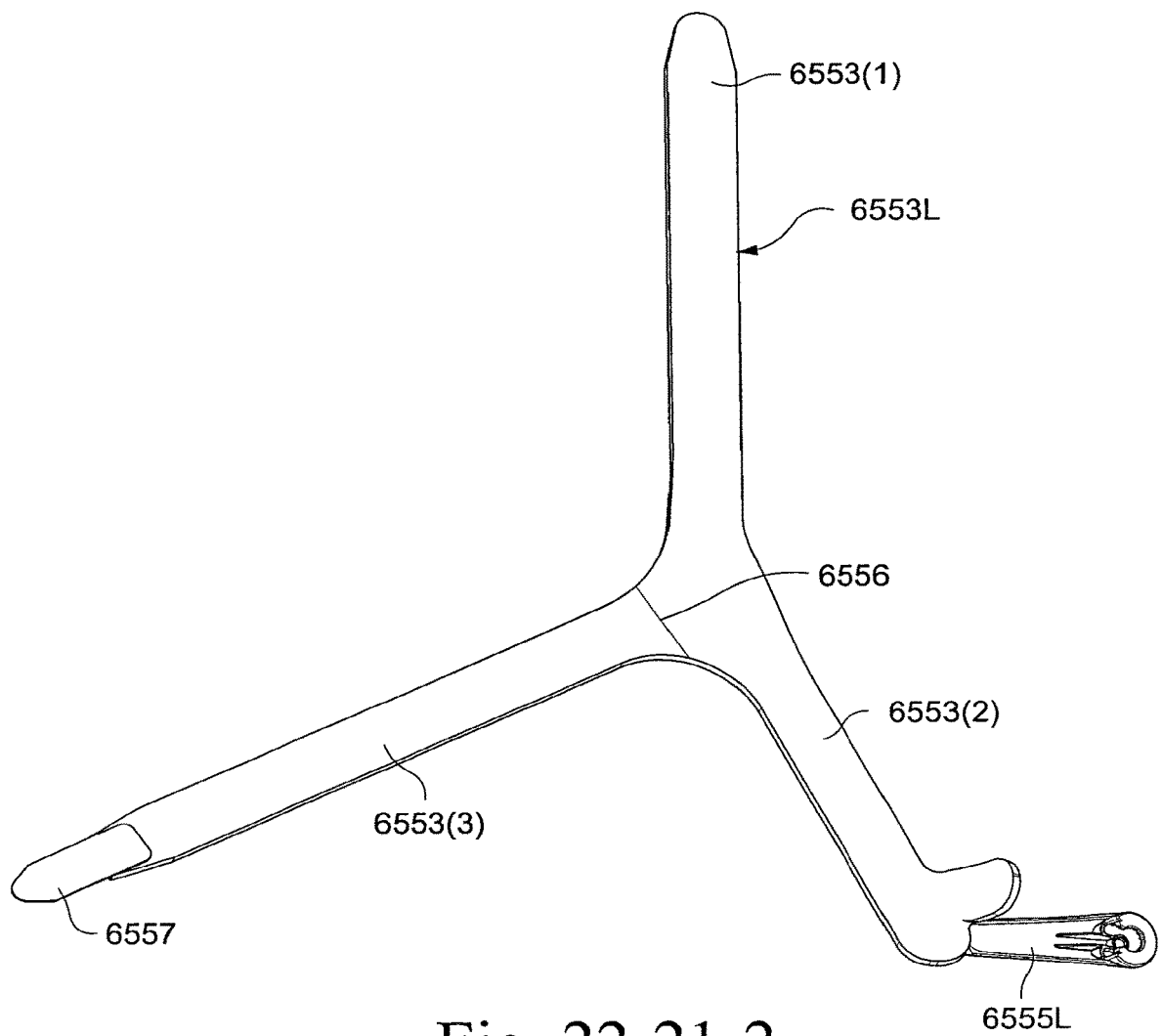
Figures 5, 21, 22:
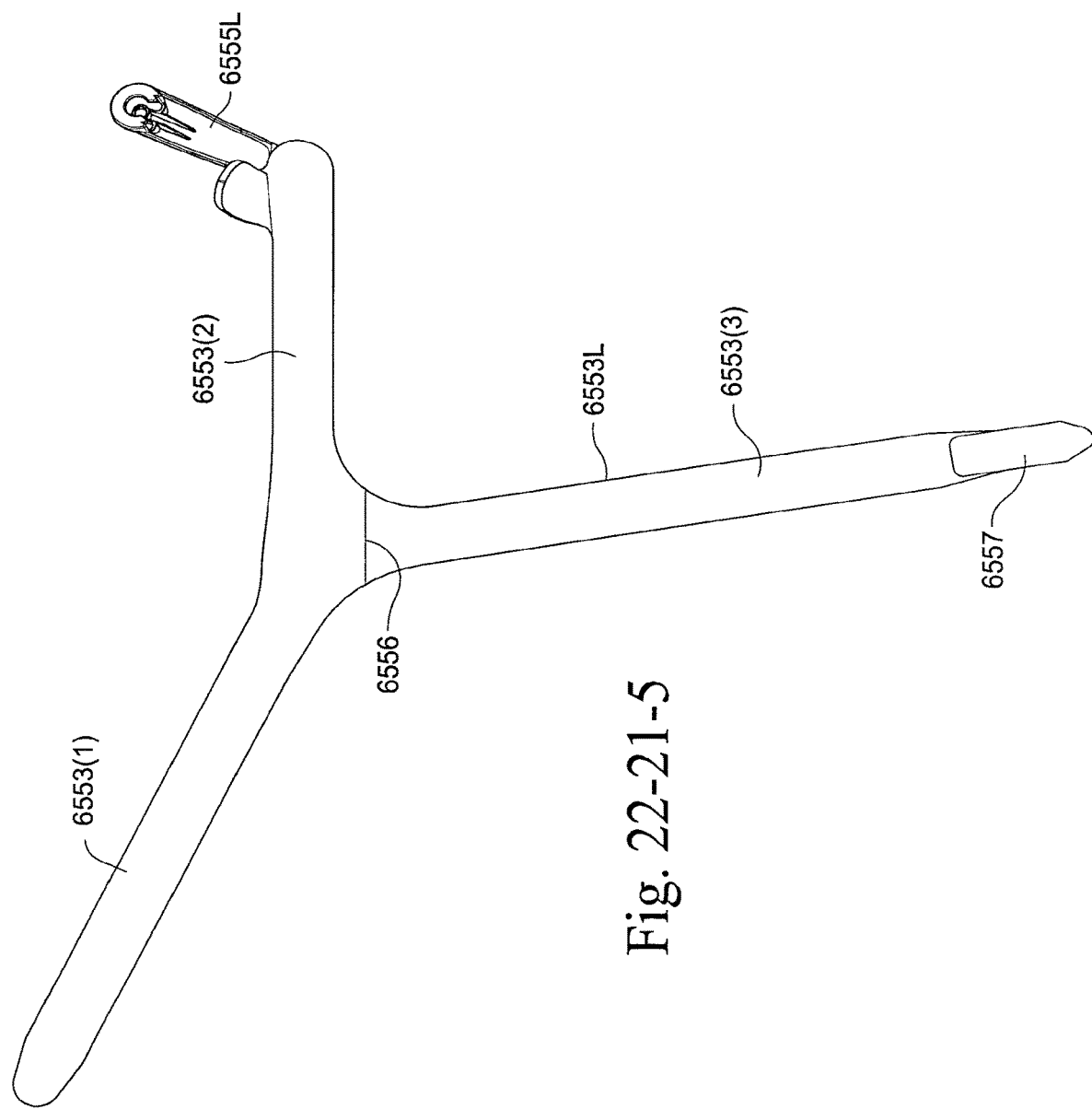
Figures 8, 21, 22:
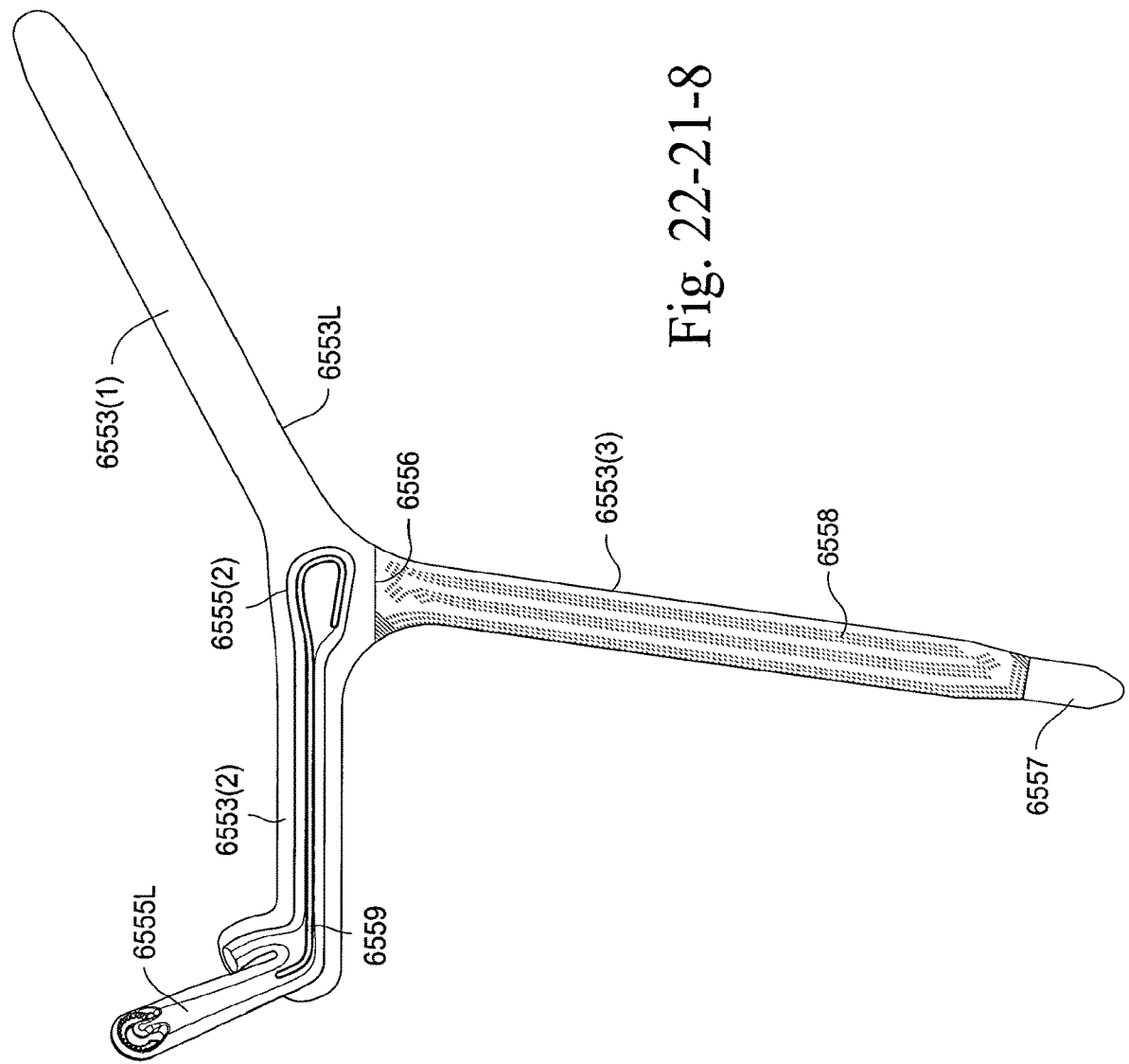
Figures 1, 22:
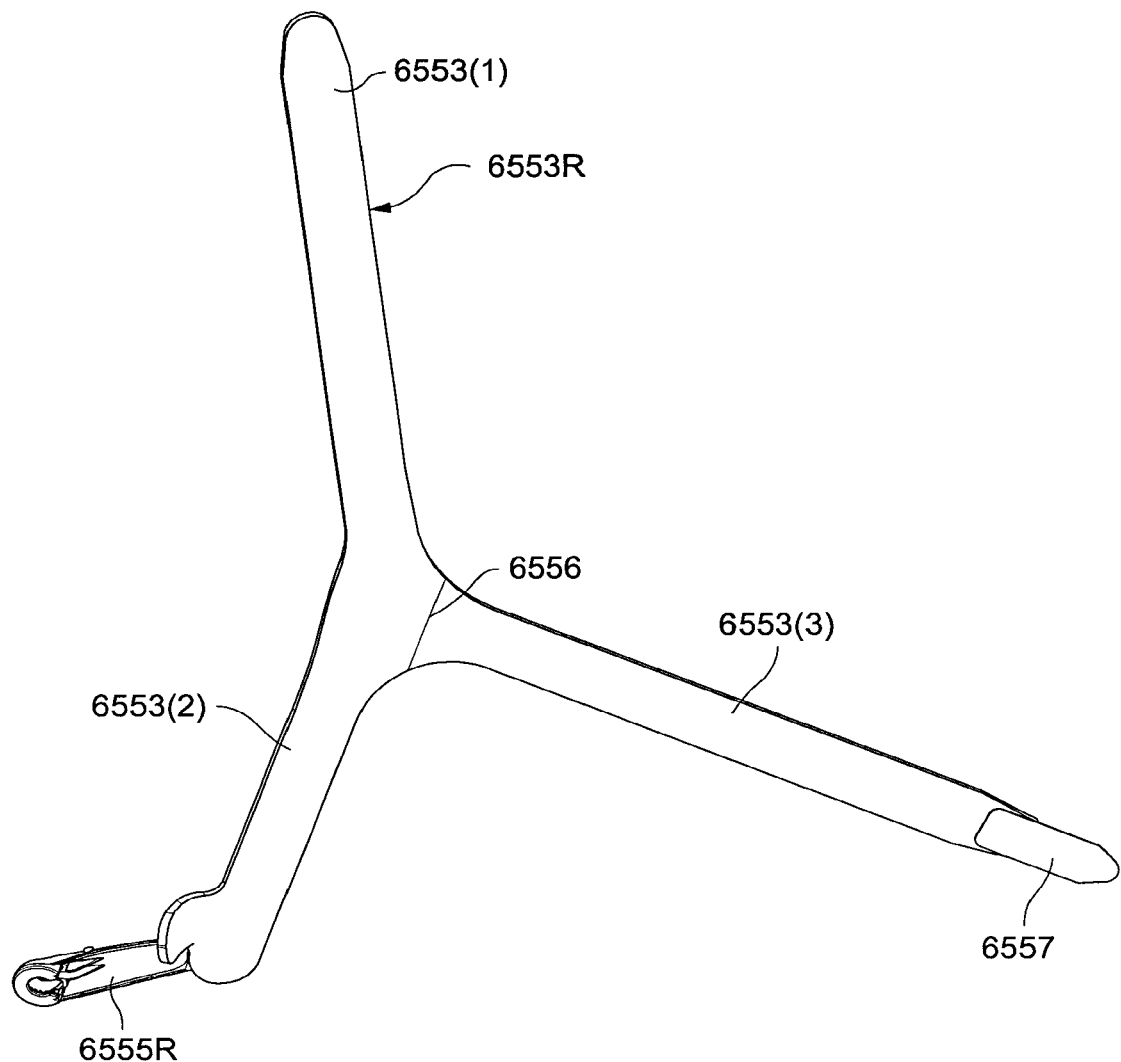
Figures 2, 22:
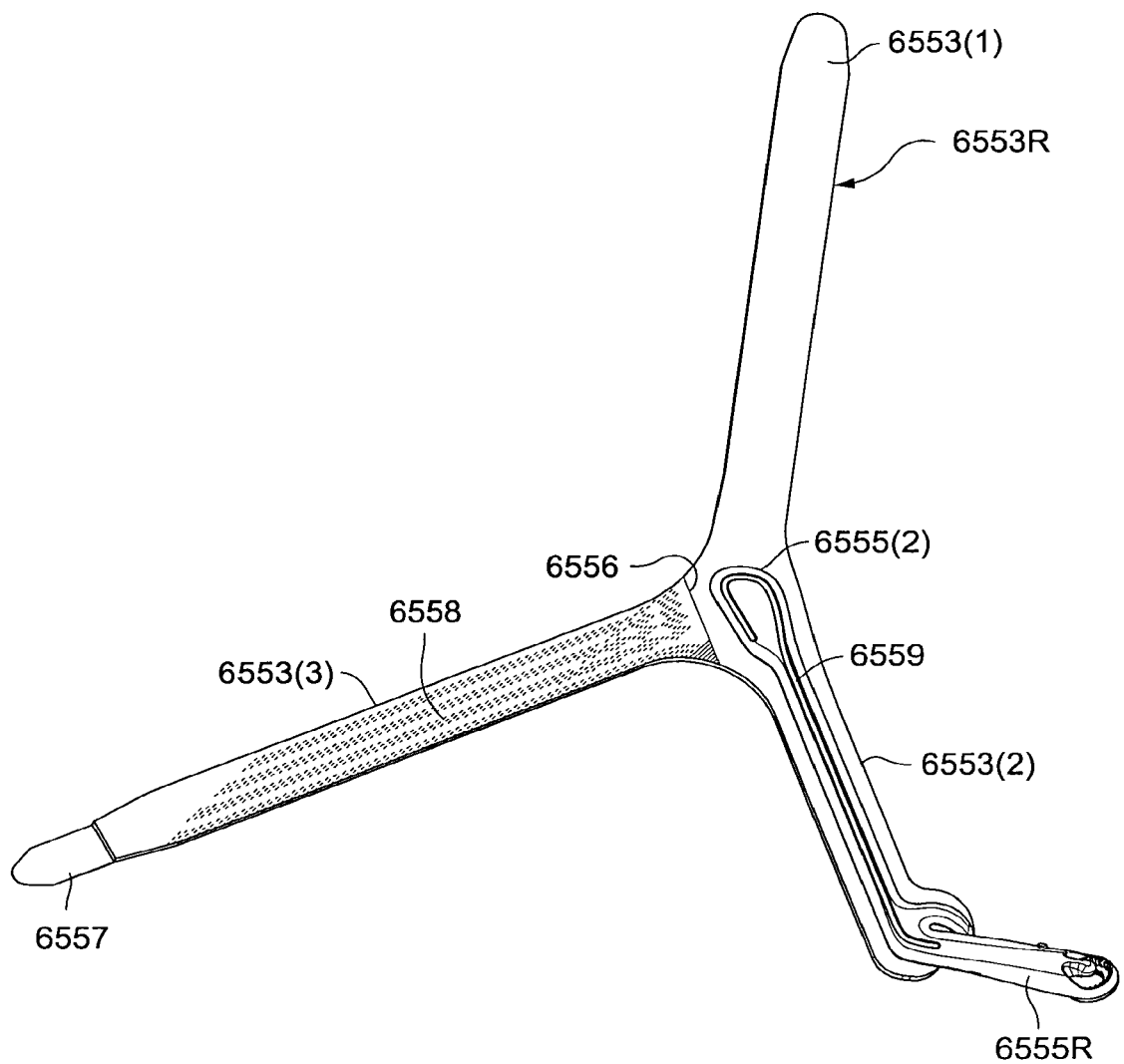
Figures 3, 22:
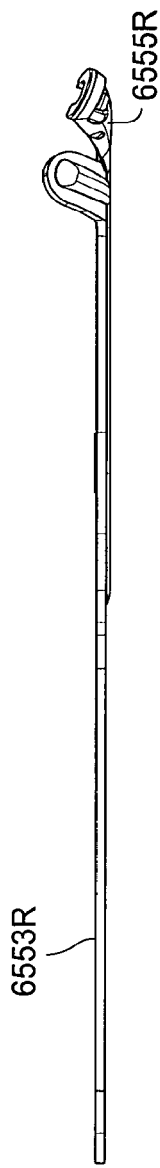
Figures 4, 22:
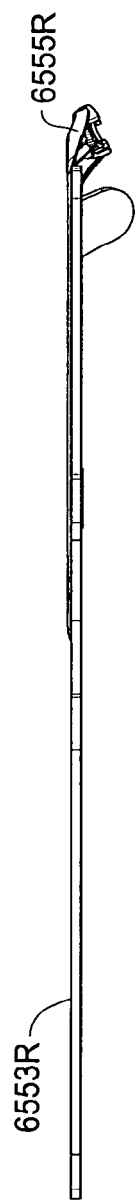
Figures 5, 22:
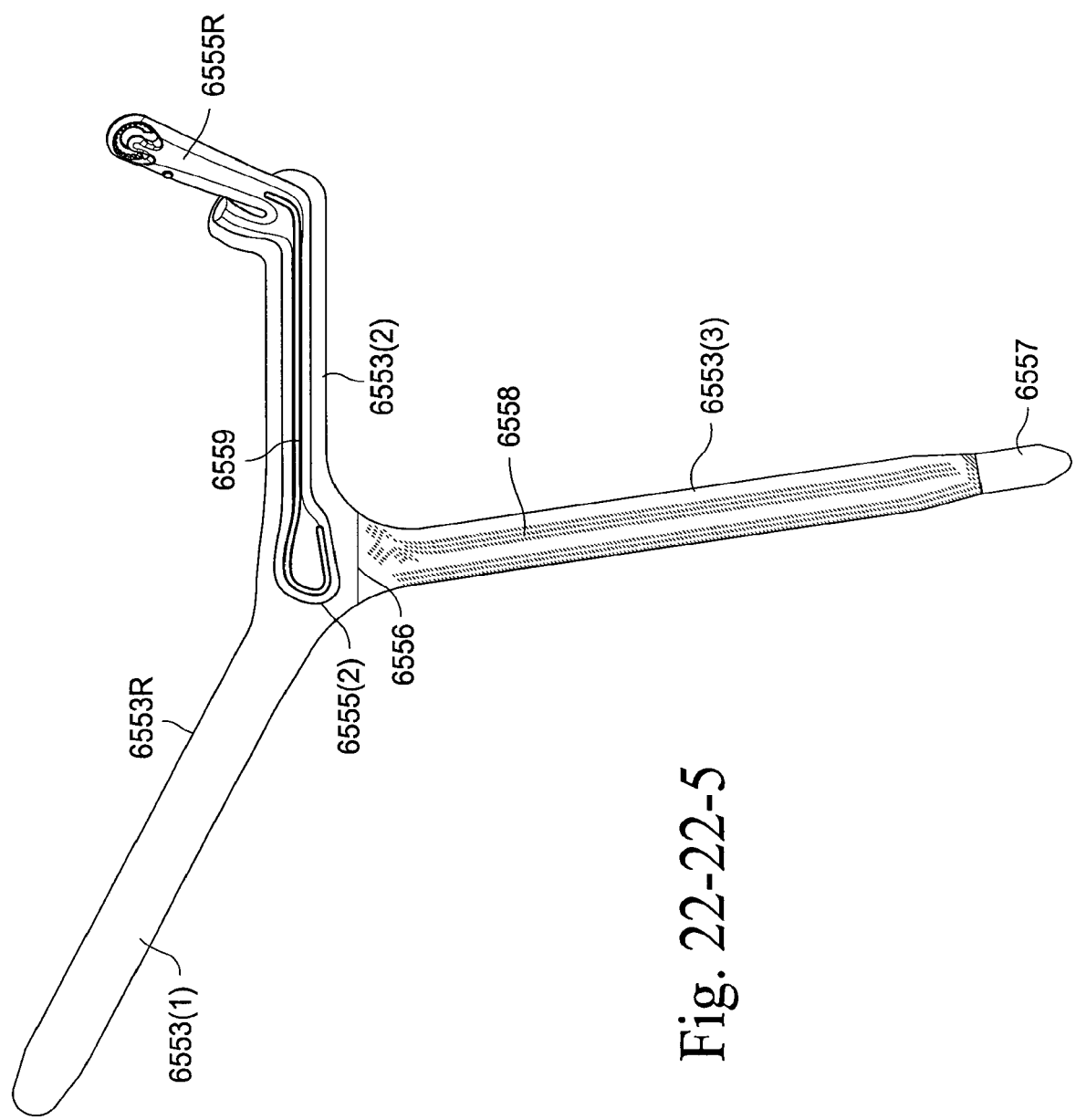
Figures 8, 22:
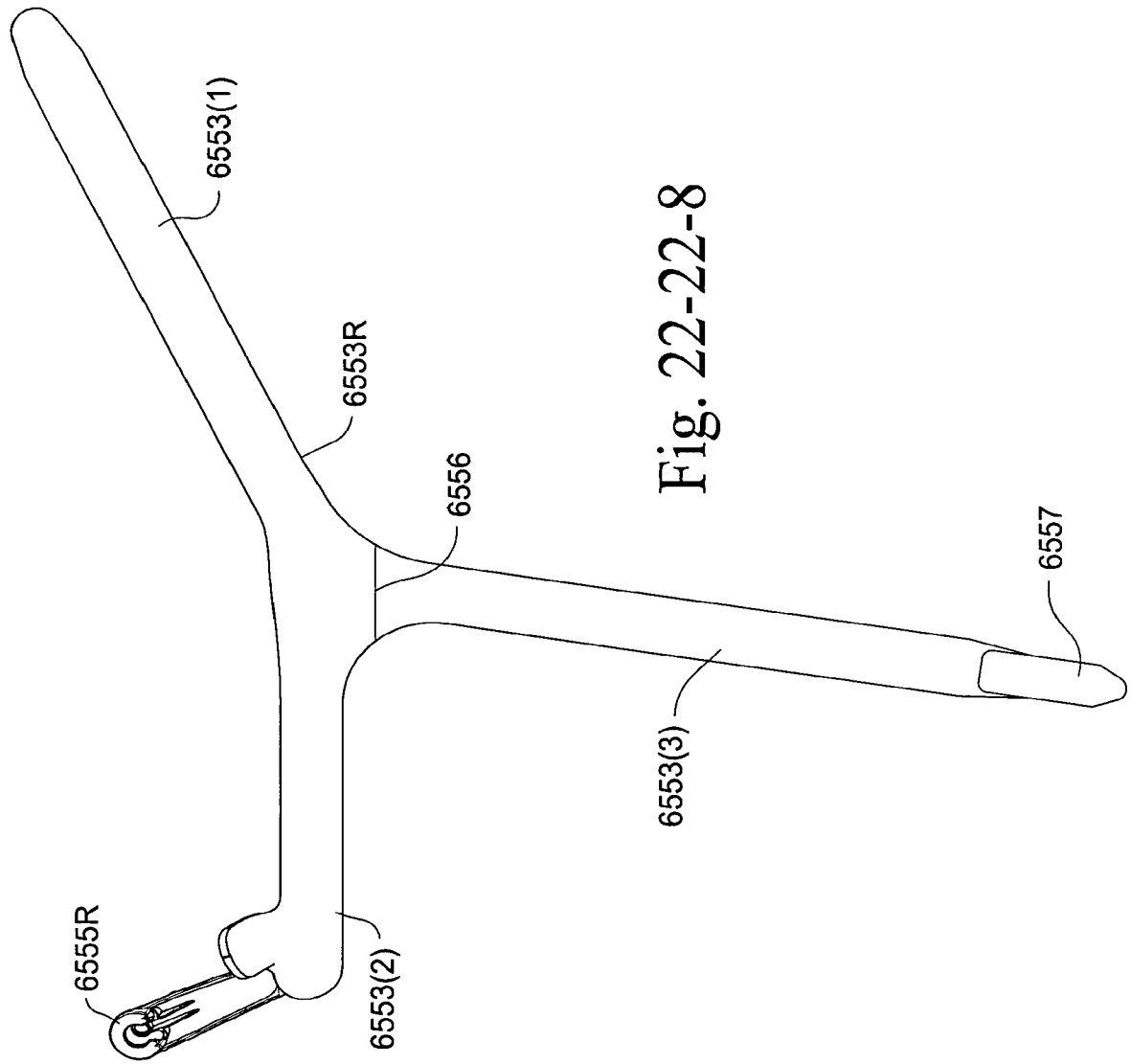
Figures 9, 22:
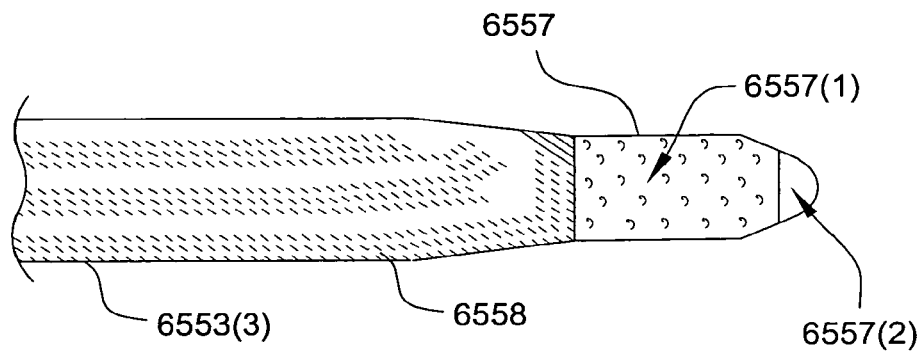
Figures 10, 22:
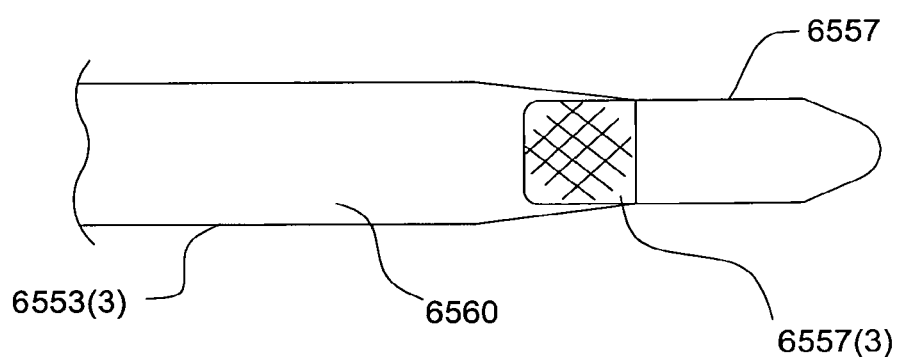
Figures 1, 22, 23:
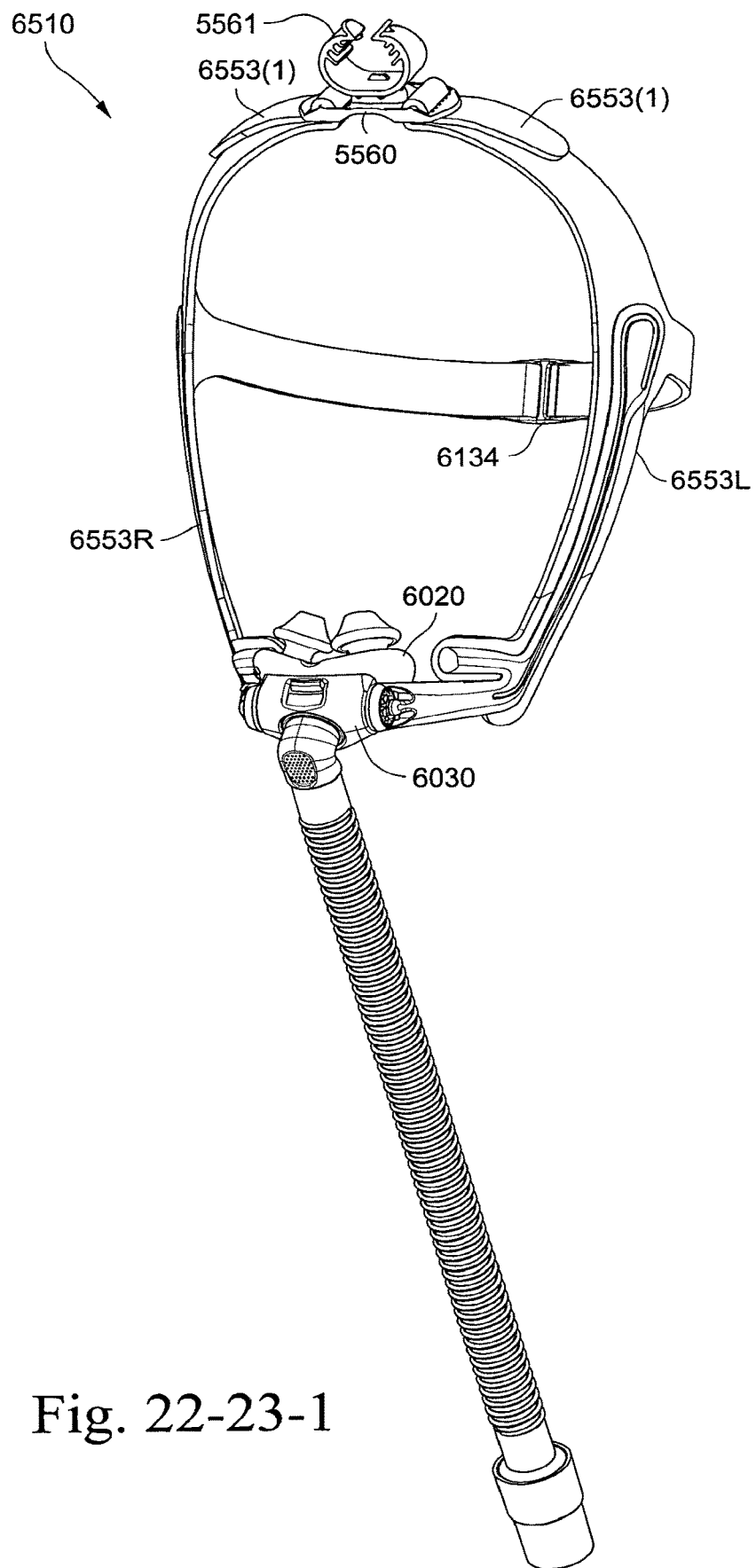
Figures 2, 22, 23:
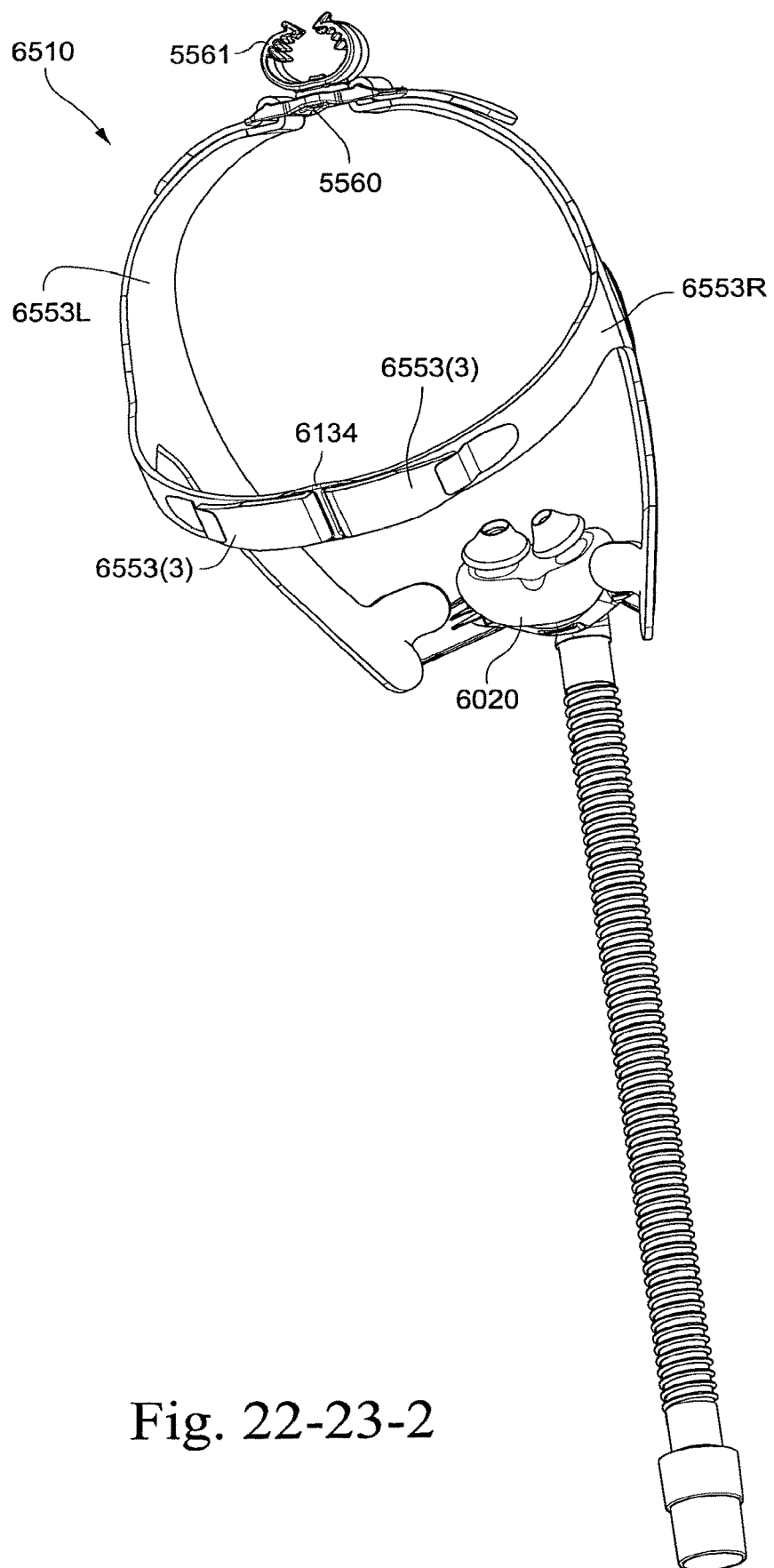
Figures 3, 22, 23:
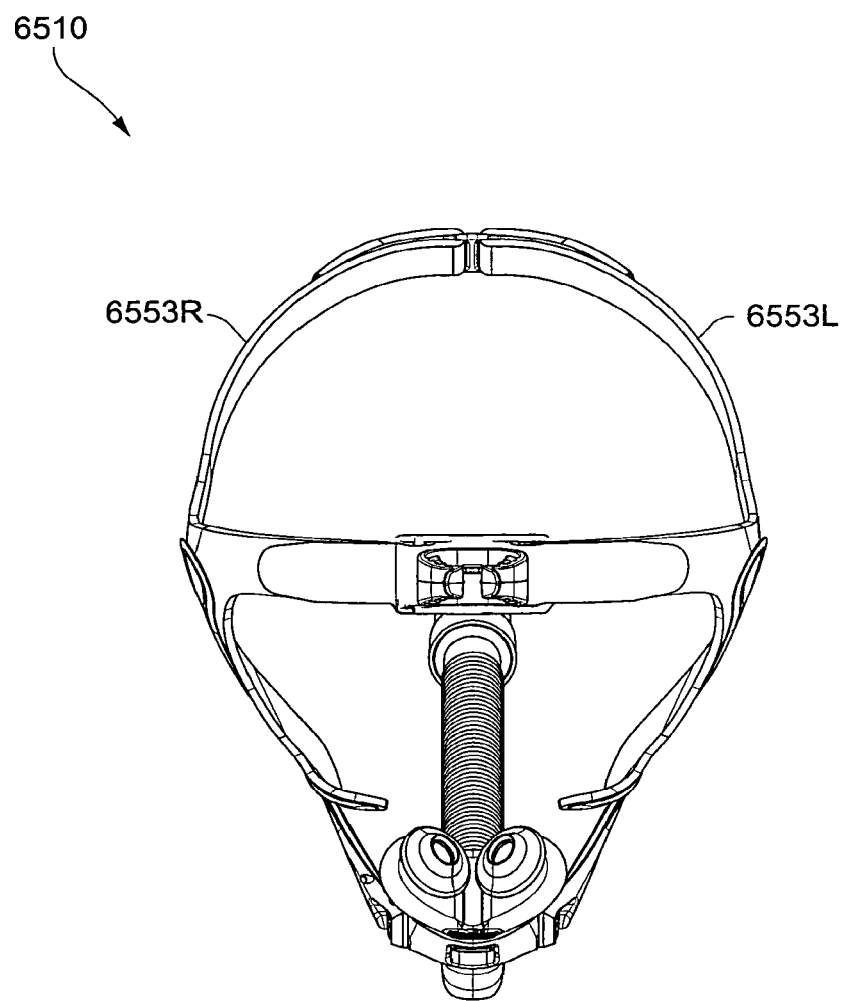
Figures 4, 22, 23:
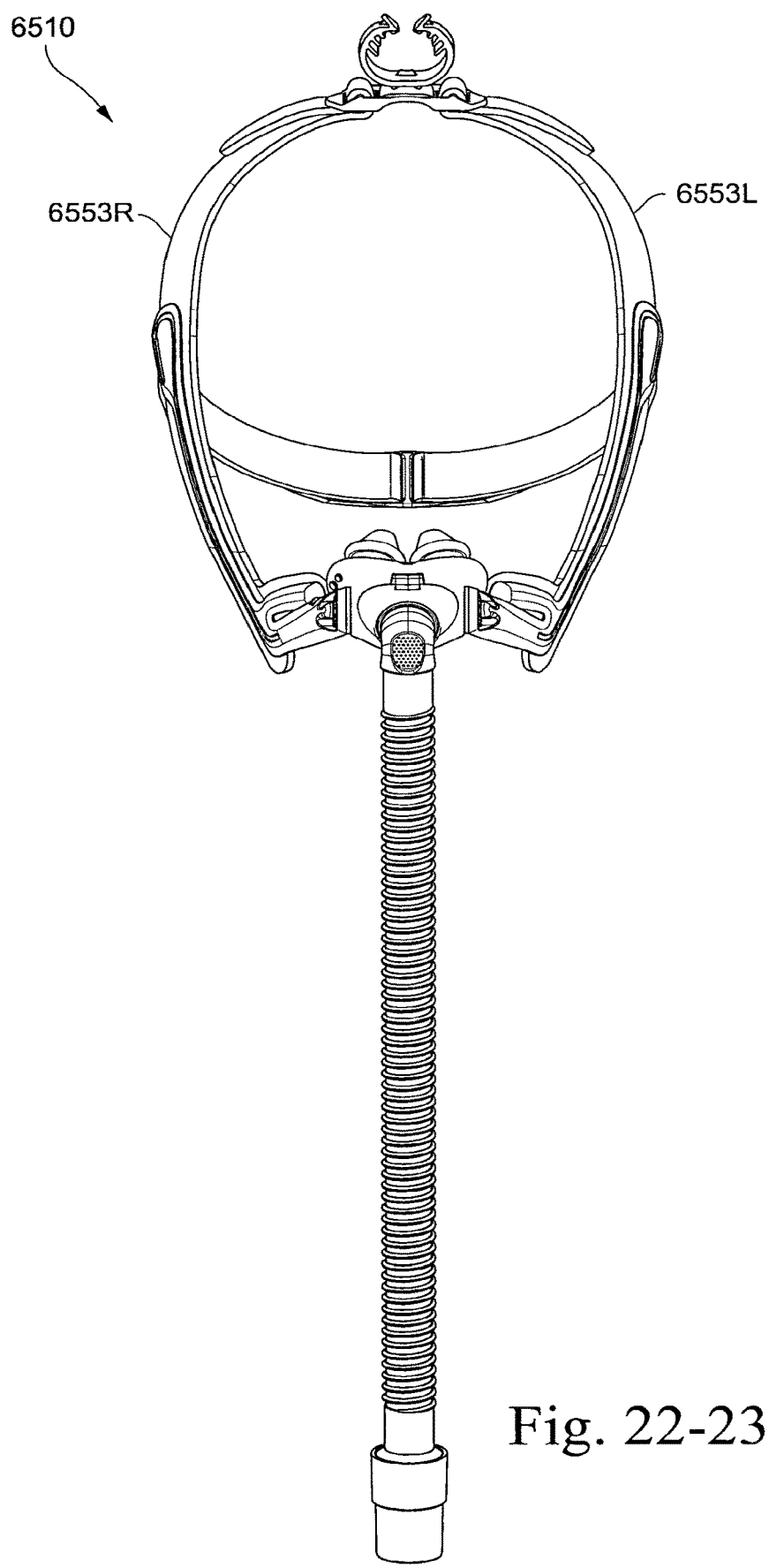
Figures 5, 22, 23:
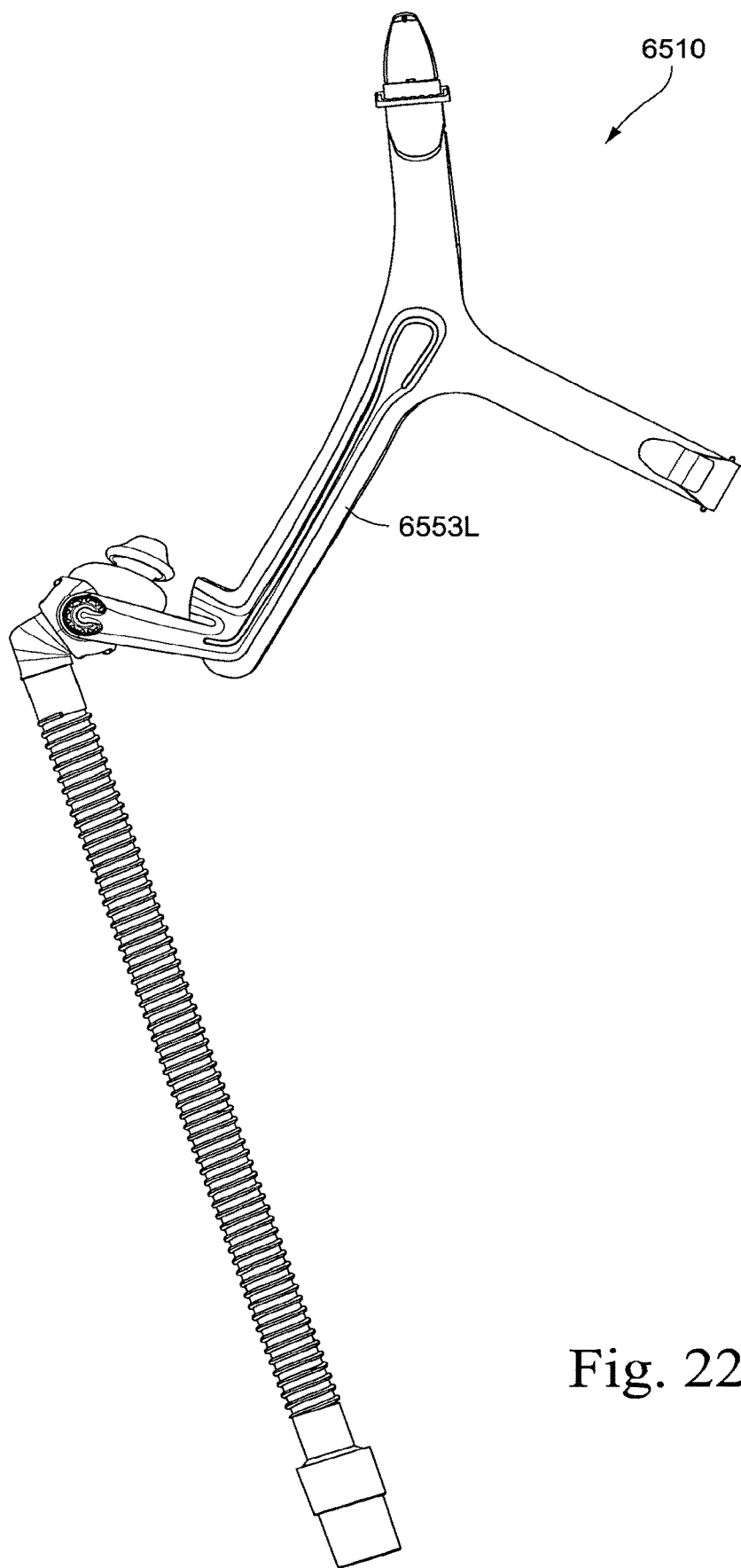
Figures 6, 22, 23:
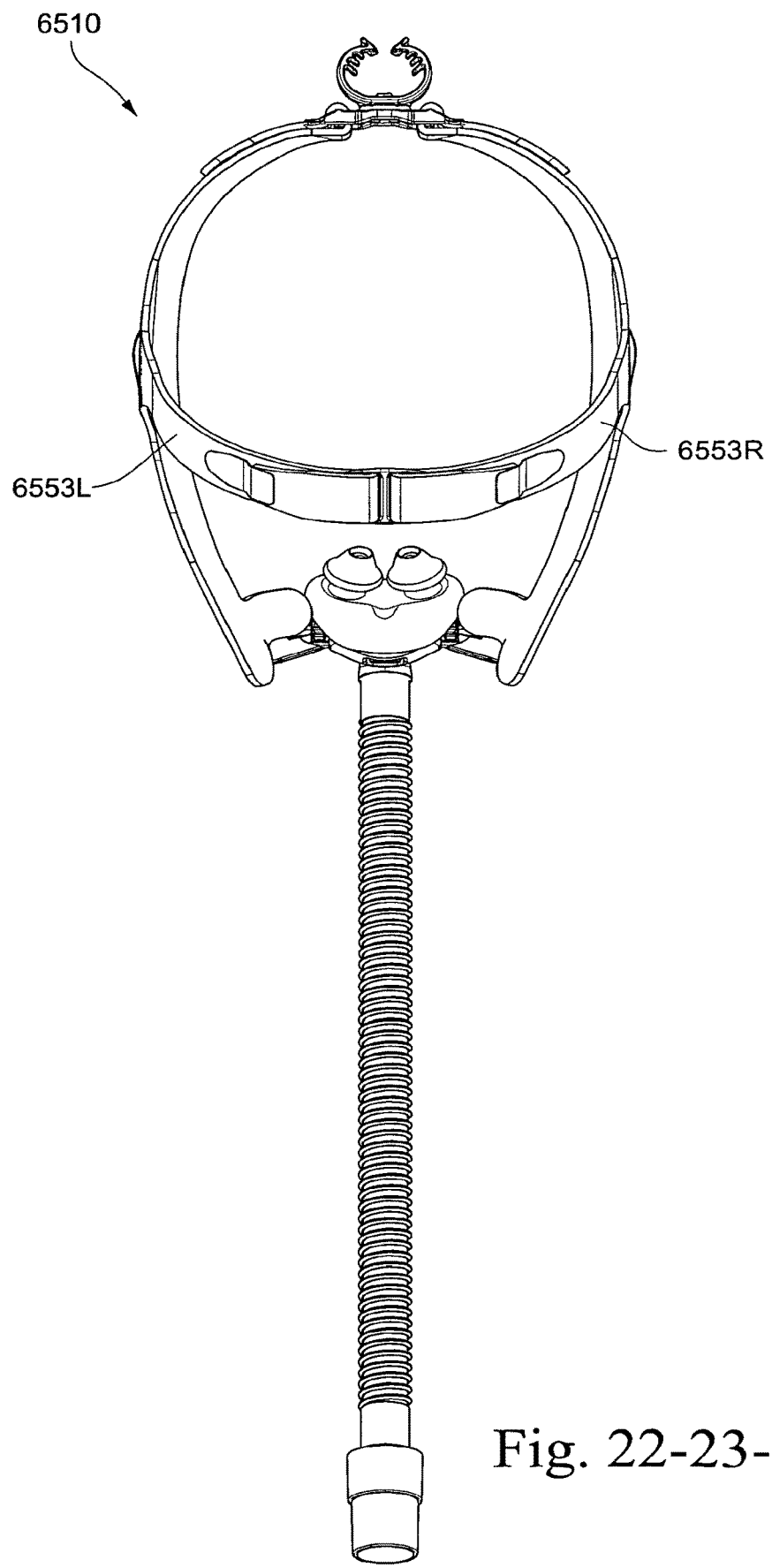
Figures 7, 22, 23:
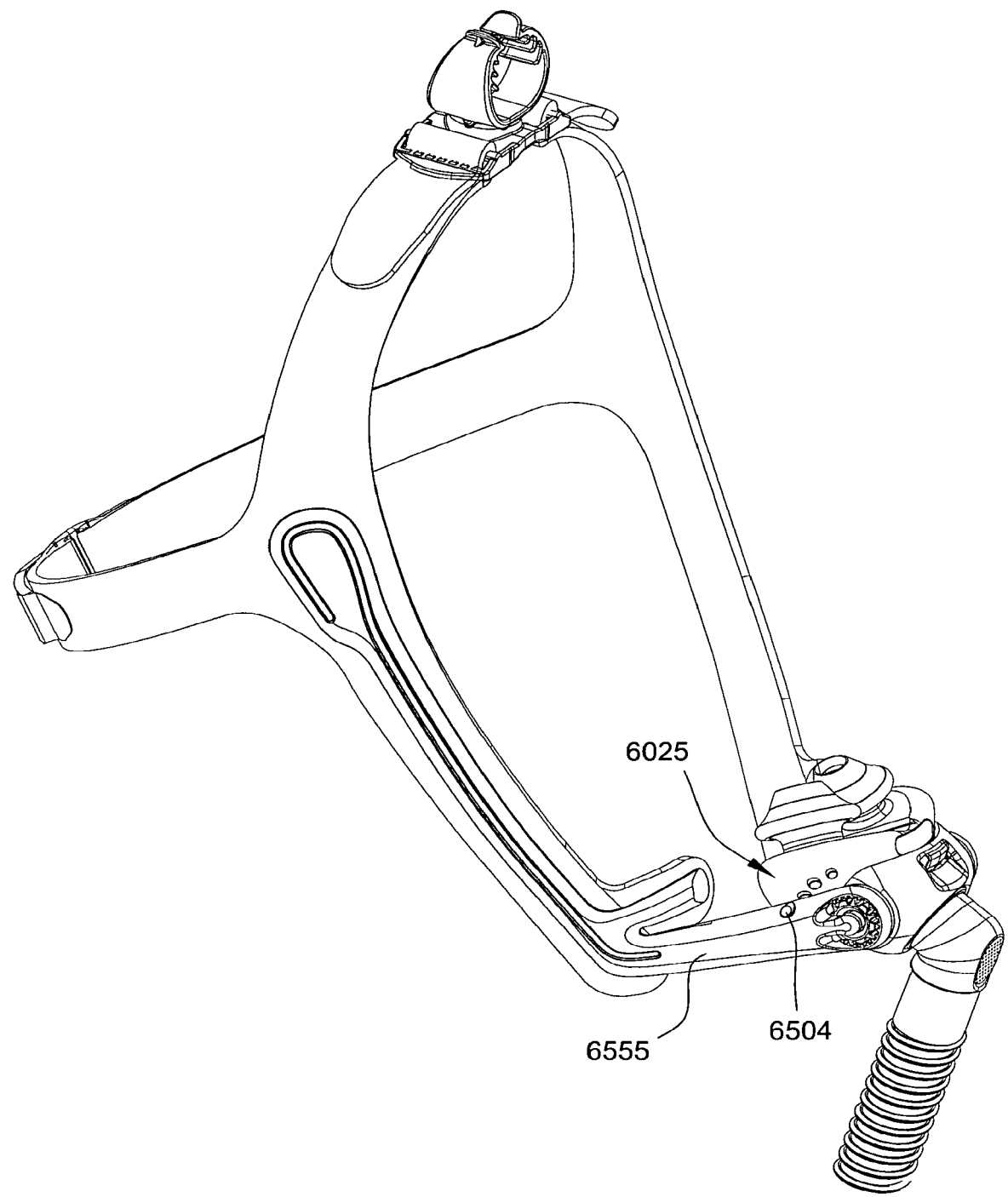
Figures 22, 23, 24:
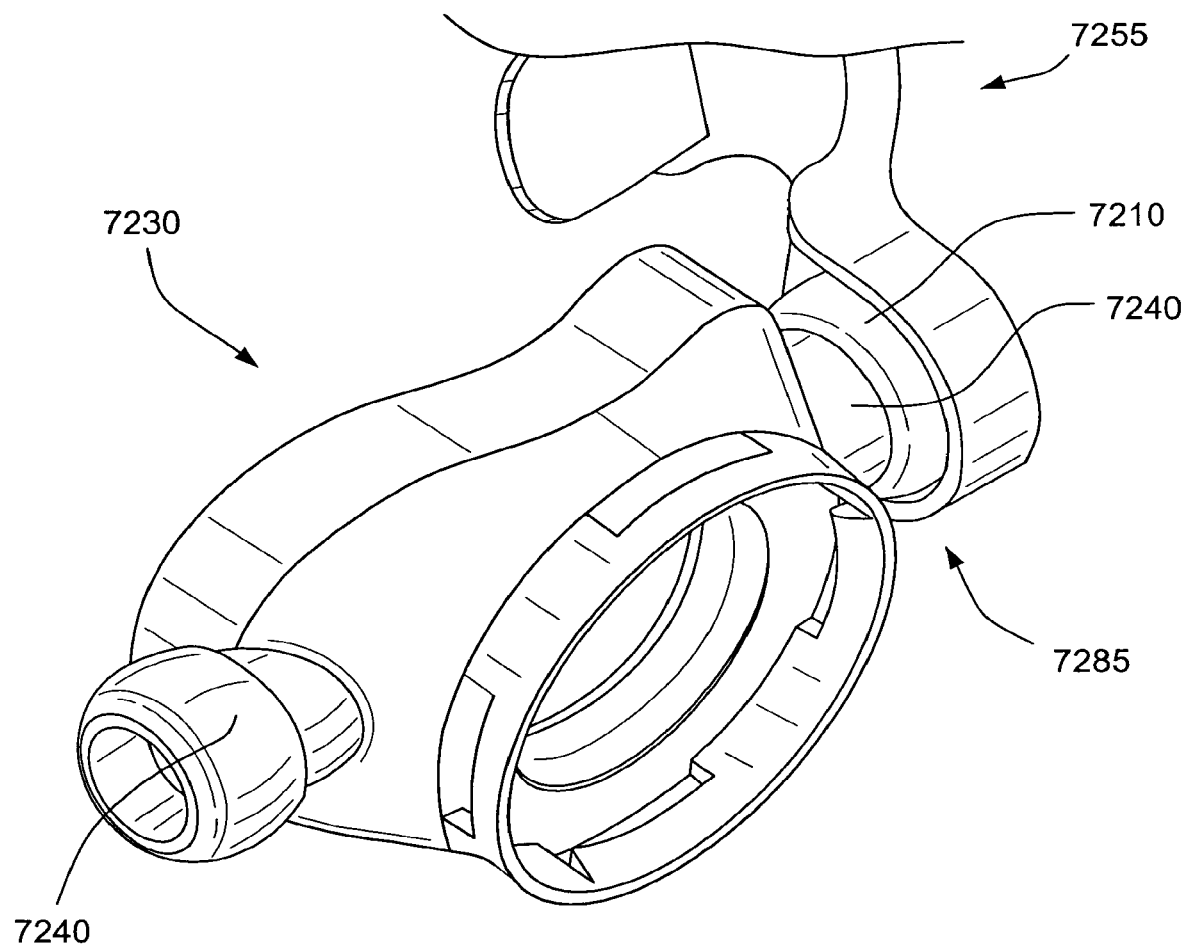
Figures 22, 23, 24, 25:
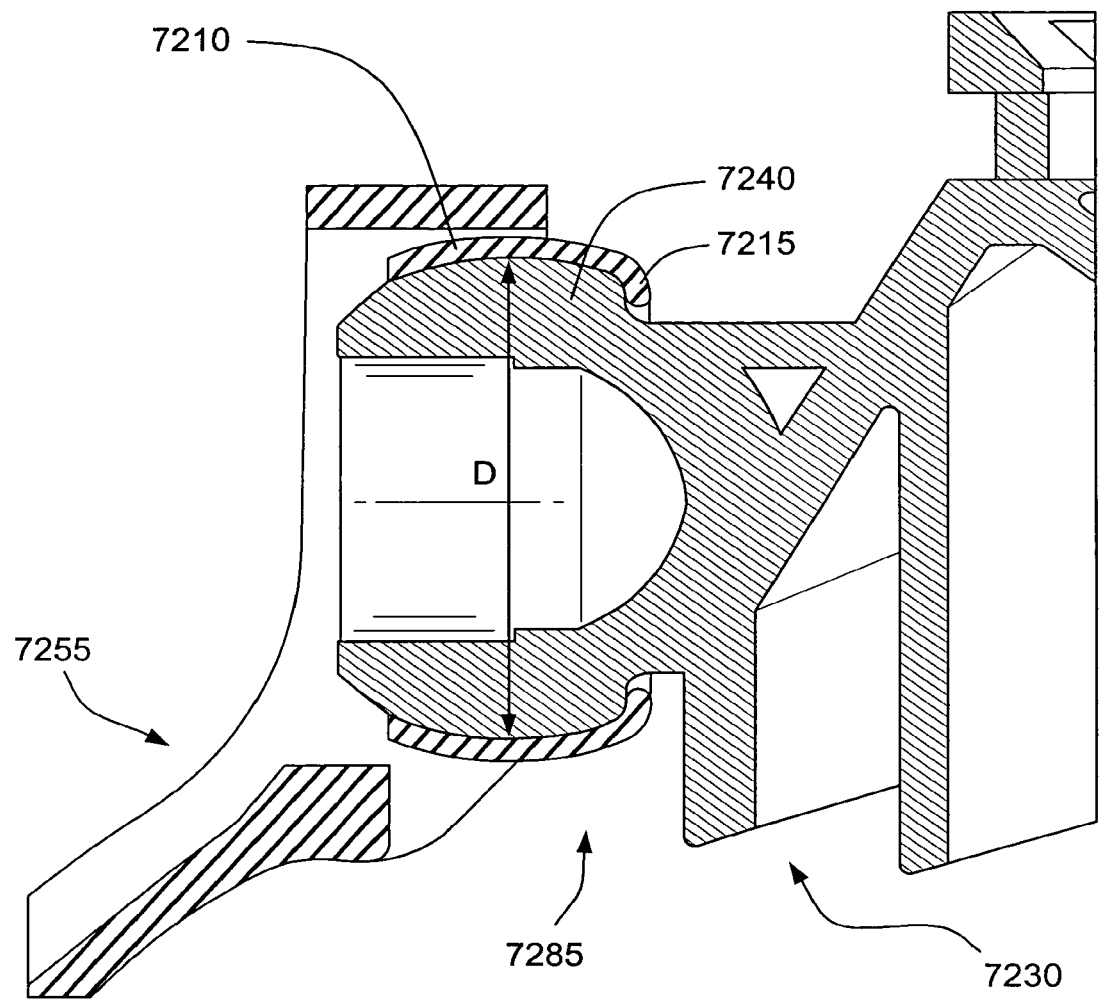
Figure 23:
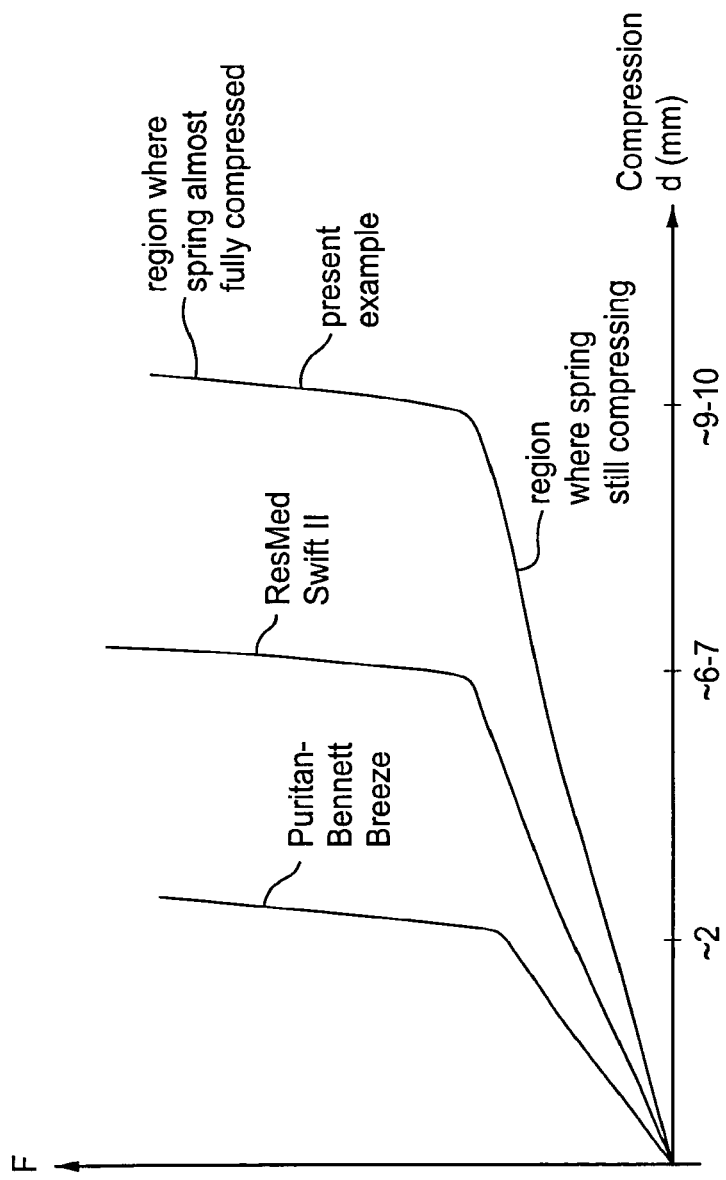
Figure 24:
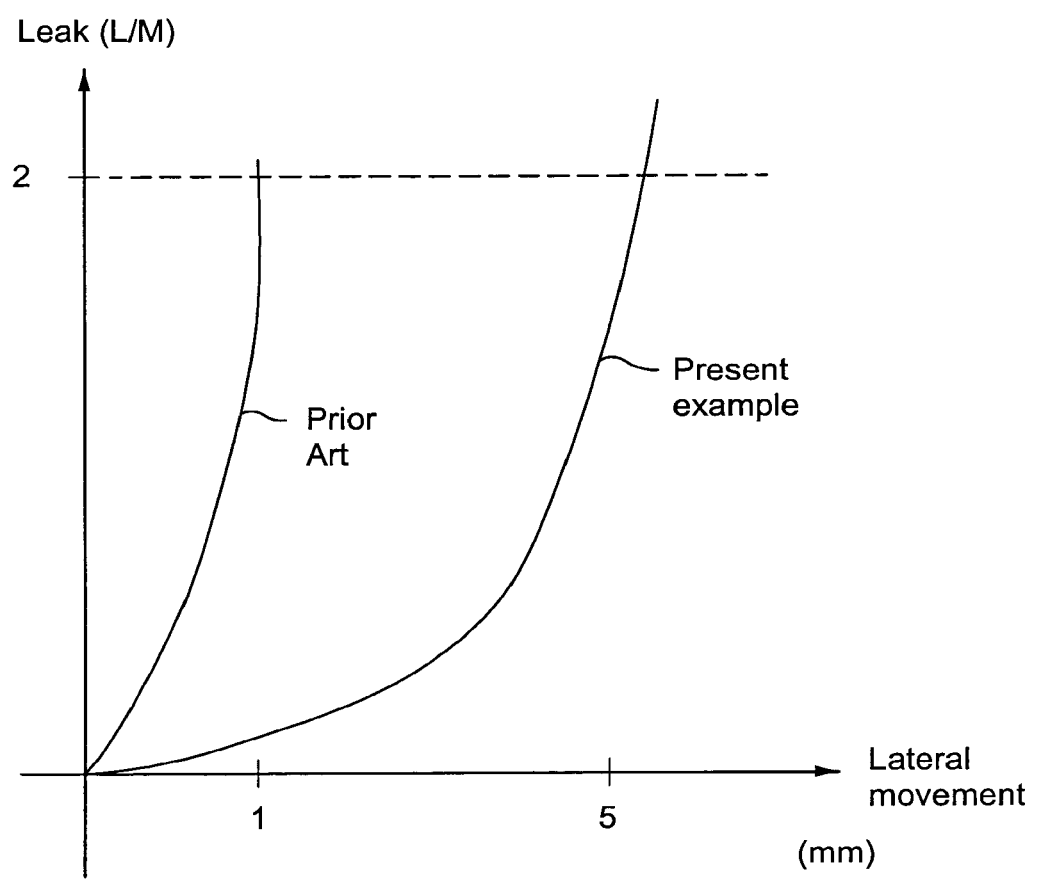
Figures 26, 27A:
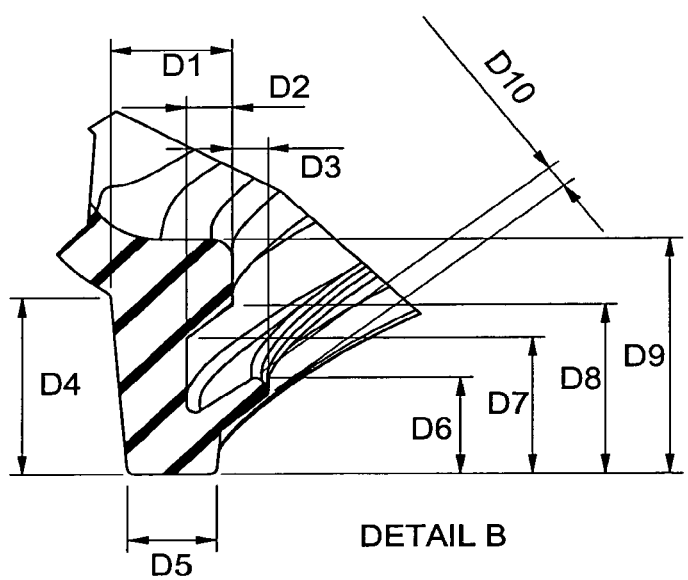

In the illustrated embodiments, each tube retainer 7100 has a tab 7160 at its base that is structured to engage with a keyhole 7060 provided to the buckle 7000. FIGS. 5-68 to 5-86 show several embodiments of tab 7160.

In an embodiment, the tab 7160 may be generally round as shown in FIG. 5-76. In an alternative embodiment, the tab 7160 may assume other suitable shapes, e.g., cross-like shape as shown in FIG. 5-82. In another form, the tab 7160 may have a fissure 7170 through its length (e.g., split configuration) as shown in FIG. 5-79. In another embodiment, the tab 7160 may include multiple fissures 7170 (e.g., multiple prong arrangement). The fissure 7170 may be any suitable shape, e.g., square, circular or elliptical. The fissure 7170 is provided to add flexion in tab 7160 to allow for easier engagement and disengagement with the buckle keyhole 7060. The flexion in tab 7160 also provides a snapping sound when the tab 7160 is locked in the buckle keyhole 7060, which provides tactile feedback that the system is correctly aligned. In another embodiment, the tab 7160 may have a cut out 7161 through a portion of its length as shown in FIG. 5-86. In embodiments, there may be one or more cut outs 7161 provided to the tab, e.g., 1, 2, 4, 7, or any other suitable number. The cut-out 7161 may be generally c-shaped or arcuate, or may have other suitable shapes. In use, the cut-out 7161 enables greater flexibility of the tab 7160.

In yet another embodiment, the tab 7160 may have a lip 7165 extending from its distal end as shown in FIG. 5-76. The lip 7165 is adapted to lock the tab 7160 in the buckle keyhole 7060 by an interference fit. In an embodiment, the lip 7165 may extend around the entire perimeter of the distal end of tab 7160 (e.g., as shown in FIGS. 5-76 and 5-85). In an alternative embodiment, the lip 7165 may extend around a portion or portions of the distal end of the tab 7160 (e.g., as shown in FIG. 5-83). In another embodiment, the depth and length of the lip 7165 may be varied. In an alternative embodiment, one or more finger tabs 7165.1 may be provided to the tab that extend upwards from the topside of the lip 7165 (as shown in FIG. 5-84). In an embodiment, the finger tabs 7165.1 may be generally rectangular, round, triangular, or any other suitable shape. In use. the finger tabs 7165.1 allow fixed rotation of the tube retainer 7100 once engaged with the buckle 7000.

In an embodiment, the tab 7160 may also have a joining ridge 7166 at its proximal end as shown in FIG. 5-76 (e.g., adjacent its interface with the arms 7130). In an embodiment, the joining ridge 7166 may be generally round but may have other suitable shapes. The joining ridge 7166 is provided to ensure a snug fit of the tab 7160 with the buckle keyhole 7060 so as to avoid lateral movement of the tube retainer 7100 with respect to the buckle 7000. In an alternative embodiment, one or more finger tabs 7166.1 may extend downwards from the underside of the joining ridge 7166 as shown in FIG. 5-85. In an embodiment, the finger tabs 7166.1 may be generally rectangular, round, triangular, or any other suitable shape. In use, the finger tabs 7166.1 allow fixed rotation of the tube retainer 7100 once engaged with buckle 7000.

Other alternatives to increase headgear flexibility to accommodate different sleep positions includes: integrate tubing into headgear through conduit system; and/or introduce an elbow that accommodates a wider range of movement through a ball and socket joint. The ball and socket joint elbow may also provide decoupling of forces due to shifts in tube position.

Other alternatives to increase decoupling of forces due to shifts in tube position include: provide a tube that has increased levels of flexibility in the axial directions; interrupt tube with highly flexible element (i.e., thin silicone element) below elbow; provide a tube that is constructed from an overall sifter material; and/or provide a tube that is constructed from an overall more lightweight material.

2.6 Other Aspects

Headgear Cost Reduction

To reduce the cost of the headgear, the headgear may incorporate one or more of the following: replace textile components with molded components; reduce part count for headgear; reduce materials used in headgear; reduce labor involved in assembling headgear; increase mechanization of assembly process; and/or new material cutting profile to reduce wastage.

FIGS. 11-1 and 11-2 illustrate an exemplary cutting profile for headgear straps to reduce wastage. In the illustrated embodiment, the headgear includes two strap configurations, i.e., one for the side strap 53 and one for the rear strap 57. FIG. 11-1 illustrates a cutting profile for the generally boomerang shaped side straps 53, and FIG. 11-2 illustrates a cutting profile for the generally straight rear strap 57. In each embodiment, the straps are arranged side by side to reduce material wastage.

Reducing Headgear Presence

Alternative embodiments to reduce the perceived presence of headgear (e.g., headgear made to feel more minimal/lightweight, provide minimal skin contact, and provide low intrusion into the field of view to reduce the likelihood of claustrophobia) include: providing a completely elastic headgear strap design; reducing the overall amount of skin contact that the headgear has with the user; introducing a skin toned or transparent headgear (e.g., chameleon headgear); eliminating all hard plastic components such as buckles and yokes; introducing cotton as the skin contact material (e.g., cotton may be better on skin and may be more synonymous with clothing); using a cup or parachute material section to capture the crown (e.g., a net like section that may be made from cotton); reducing the overall material thickness of all parts of the headgear; using two or three thin (e.g., 1 mm) wire-style strips of nylon to connect the frame to the headgear body (e.g., this arrangement may accommodate fine adjustments and may have a very fine appearance on the user, and this arrangement may be incorporated into a net style headgear which would appear almost invisible amongst the user's hair); eliminating the headgear and replacing its function with balloon style pillows that inflate up against the walls of the nasal passage to hold the pillows in place; and/or using an internal mouth guard which has magnets incorporated into it that will hold the pillow and frame assembly up against the upper lip and in position to retain a good seal (e.g., this arrangement may be incorporated with a balloon style prong system to completely eliminate the headgear).

Headgear Usability

Alternative embodiments to reduce the number/complexity of adjustments to achieve a correct fit/good seal include: introducing a single piece headgear that is highly flexible and provides sufficient breathability; introducing a highly flexible net style headgear system to capture the crown; and/or eliminating buckles and introducing a headgear that uses a simpler series of adjustment mechanisms.

Alternative embodiments to improve the intuitiveness of headgear adjustment include: introducing a 3D shape headgear that provides an obvious visual cue as to the correct fitting of the headgear; positioning the adjustment mechanisms closer to the region influenced by the adjustments (e.g., seal region) such that adjustments are more intuitive; introducing Velcro tabs that provide a more intuitive method of adjustment; and/or utilizing large Velcro tab sections as rigidizing elements to replace headgear yokes.

Alternative embodiments to improve the "set and forget" functionality of headgear (e.g., no need to reset/readjust after removal of headgear) include: incorporating a highly flexible element at points on the headgear that allow stretching to be isolated to aid rapid removal/replacement of headgear; and/or increasing the flexibility of the nasal pillows to accommodate the rapid removal/replacement of headgear.

Alternative embodiments to reduce the overall number of headgear parts include: providing single part headgear (e.g., textile or molded headgear); introducing Velcro tabs rather than having separate buckles; over-molding/insert molding the seal rings into the yokes; making the seal ring and yoke a single part; and/or utilizing large Velcro tab sections as rigidizing elements to replace the headgear yokes.

Alternative embodiments to improve ease of assembly/disassembly include: reducing overall number of parts; incorporating features that prevent disassembly (e.g., one time assembly); improving intuitiveness of assembly and disassembly (e.g., through color coding or physical locators/indicators); reducing the overall number of "open ends" (e.g., eliminate back buckle); introducing 2-tone headgear (e.g., different color on the inside surface to the outside surface which may reduce incidents of incorrect assembly in manufacturing; eliminating seal rings; and/or providing one-way assembly of headgear through headgear buckles (e.g., restricted by geometry).

Alternative embodiments to improve ease of cleaning all surfaces include: reducing overall number of parts; making headgear suitable for thermal disinfection so that the interface does not have to be completely disassembled to disinfect; and/or eliminating textile headgear (e.g., replace textile headgear with an elastomeric or thermoplastic material that does not collect oil and moisture which may allow the headgear to be wiped down as with other components of the interface and may increase durability).

Alternative embodiments to increase the overall durability of headgear include: eliminating textile headgear (e.g., replace textile headgear with an elastomeric or thermoplastic material that does not collect oil and moisture which may allow the headgear to be wiped down as with other components of the interface and may increase durability); reducing the need for adjustment; reducing the overall number of parts (e.g., interfacing parts); and/or creating headgear straps out of a single material structure rather than a laminated one (e.g., foam only headgear straps).

Headgear Alternatives

FIGS. 12-1 to 12-26-2 illustrate headgear alternatives for the patient interface. It should be appreciated that one or more features of any one embodiment may be combinable with one or more features of the other embodiments. In addition, any single feature or combination of features in any of the embodiments may constitute additional embodiments.

Mechanical Hinge

FIGS. 12-17 to 12-18-2 illustrate headgear with mechanical hinges. Such hinges are structured to reduce or eliminate the influence of lateral forces on the seal region. In addition, lateral hinges may help to reduce or eliminate marking on the cheeks as the hinges allow accommodation of users of varying facial widths and takes pressure off of the face.

In FIG. 12-17, the headgear includes headgear straps 3653 that cup the crown of the patient's head (e.g., similar to that shown in WO 2006/130903, which is incorporated herein by reference in its entirety), and yokes 3655 provided between the headgear straps 3653 and the nasal prong assembly. As illustrated, a lateral hinge 3695 is provided to an intermediate portion of the yoke 3655, e.g., offset to cheek region, to allow lateral movement of the yoke 3655 in use. A cheek pad 3690 (e.g., high friction silicone cheek pad) is provided to the yoke 3655 adjacent the hinge 3695 to support the hinge 3695 in a position off the patient's face. In an embodiment, the cheek pad 3690 may be comolded or insert molded to the yoke 3655. Also, the hinge 3695 may provide a quick-release function so that the hinge 3695 may be easily disconnected and allow quick removal of the headgear. The combination of the headgear strap arrangement and high friction silicone cheek pads may provide high levels of overall stability for the headgear.

In FIG. 12-18-1, a lateral hinge 3795 is provided to either end portion of the yoke 3755 (e.g., at the nasal prong assembly 3720 and/or at the headgear straps 3753) to allow lateral movement of the yoke 3755 in use. In the illustrated embodiment, the hinge 3795 is provided between the nasal prong assembly 3720 and the proximal end of the yoke 3755. A pad (not visible) is provided along the yoke 3755 to support the hinge 3795 in a position off the patient's face. As shown in FIG. 12-18-2, the end of the frame of the nasal prong assembly 3720 provides dimples 3796 and an aperture 3797 for engaging an elbow or end plug. The proximal end of the yoke 3755 provides spaced apart arms 3798 that snap into respective dimples 3796 on the end of frame to form the lateral hinge 3795. Also, the hinge 3795 may provide a quick-release function so that the hinge 3795 may be easily disconnected and allow quick removal of the headgear.

Headgear without "Dog Ear" Style Straps

FIGS. 12-22 to 12-25-2 illustrate headgear without "dog ear" style straps.

In FIG. 12-22, the headgear includes side strap portions 4153 (e.g., constructed of Breathoprene), headgear yoke 4155 provided to the side strap portions, and upper and lower connecting strap portions 4157(U), 4157(L) structured to connect the side strap portions. As illustrated, molded plastic crimps 4196 are positioned on ends of the side strap portions to engage respective ends of the connecting strap portions 4157(U), 4157(L) and allow length adjustment. The connecting strap portions 4157(U), 4157(L) may include a highly flexible elastic element to accommodate easy fitting/removal of the headgear. Also, the plastic crimps 4196 are positioned to avoid pressing into the patient's head in the most likely sleep positions, e.g., back and side of the head.

In FIGS. 12-23-1 and 12-23-2, the headgear includes side strap portions 4253 (e.g., constructed of Breathoprene), and upper and lower connecting strap portions 4257(U), 4257(L) structured to connect the side strap portions. As illustrated, molded plastic/silicone crimps 4296 are positioned to engage the connecting strap portions and allow length adjustment. The connecting strap portions 4257(U), 4257(L) may include a highly flexible elastic element to accommodate easy fitting/removal of the headgear. Also, the molded plastic/silicone crimps 4296 may be positioned anywhere along the connecting strap portions to avoid the patient's sleeping position, e.g., so patient does not lie on crimps. FIG. 12-23-1 illustrates one crimp 4296 provided to connect respective connecting strap portions 4257(U), 4257(L), and FIG. 12-23-2 illustrates two crimps 4296 provided to connect respective connecting strap portions 4257(U), 4257(L). In an embodiment, the crimp may be in the form of a hinged c-clip that may be opened to adjust and closed to crimp, e.g., such as that shown in FIG. 12-25-2.

In FIG. 12-24-1, the headgear includes side strap portions 4353 (e.g., constructed of Breathoprene), and upper and lower connecting strap portions 4357(U), 4357(L) structured to connect the side strap portions. As illustrated, each end of a connecting strap portion includes a two-part clip 4396 (e.g., constructed of plastic) adapted to engage a selected one of incremental holes 4397 provided along the side strap portions. As shown in FIGS. 12-24-2 and 12-14-3, each two-part clip 4396 includes a top section 4396(1) that protrudes through the selected hole 4397 in the strap portion and a bottom section 4396(2) that snaps onto the top section 4396(1) (e.g., via prongs provided on the top section) to fasten the clip in place. The connecting strap portion 4357(U), 4357(L) may be constructed of a highly flexible silicone/elastomeric material to accommodate easy fitting/removal of the headgear.

In FIG. 12-25-1, the headgear includes side strap portions 4453 (e.g., constructed of Breathoprene), and upper and lower connecting strap portions 4457(U), 4457(L) structured to connect the side strap portions. As illustrated, a single piece living hinge component 4496 (e.g., molded of plastic) is positioned on ends of the side strap portions to engage respective ends of the connecting strap portions and allow length adjustment. As shown in FIG. 12-25-2, the living hinge component 4496 provides first and second portions 4496(1), 4496(2) and a groove 4496(3) in each portion to receive the strap portions and crimp or clamp the strap portions in place. The connecting strap portions 4457(U), 4457(L) may include a highly flexible elastic element to accommodate easy fitting/removal of the headgear (e.g., highly flexible elastic element can elastically deform to allow headgear removal).

Incremental Lateral Adjustment

In FIG. 12-26-1, the headgear includes headgear straps 4553 that cup the crown of the patient's head, and yokes 4555 (e.g., silicone/molded plastic yokes) provided between the headgear straps 4553 and the nasal prong assembly 4520. In this embodiment, each yoke 4555 may be adjusted by a "cam" style lock or ratchet mechanism 4575 that is incorporated into a molded plastic section 4576 on the side of the headgear straps 4553. As shown in FIG. 12-26-2, the molded plastic section 4576 is structured to receive a end portion of the yoke 4555 therethrough, and the plastic section 4576 includes a locking arrangement to lock the end portion of the yoke in place. The locking arrangement includes a simple release button 4577 to release the yoke 4555. Also, the end portion of the yoke 4555 may have subtle ridges or teeth to provide tactile feedback to the user on strap tension adjustment.

This embodiment provides increased levels of usability (e.g., particularly during fitting and adjustment) for intuitive features such as single piece 3D shaped headgear and lateral headgear tension adjustments.

Alternative Headgear Embodiments to Improve Stability

Headgear stability may be improved by eliminating dislodging of the headgear on the head and/or capturing the crown region of the head.

Exemplary headgear embodiments for improving stability include: provide additional support around the head through a secondary strap which runs under the ears; provide additional support around the head through capturing the crown region with different headgear geometry; provide additional support around the head through one size fits all crown cap or a single piece of material that sits over the crown of the head (e.g., may be perforated to allow breathing or take the form of a netted section of material, may also take the form of a two strap parachute style headgear); increase stability of headgear through the incorporation of a high friction material such as textured rubber or textile (e.g., Velcro); increase stability through use of more silicone parts against the skin as this has a high friction coefficient; and/or alter the way in which the headgear captures the crown, e.g., sits further forward on the head and has a strap that runs along one plane to capture the crown (this aids in clearance of the ear lobes, etc.).

Headgear Properties

Each headgear embodiment described above may include one or more features to increase headgear fitting range, improve headgear comfort, reduce headgear cost, improve headgear aesthetics, and/or increase prominence of branding.

For example, headgear embodiments may increase overall comfort by eliminating potential ergonomic hotspots, eliminating sources of marking/irritation, creating a lightweight feel, and/or maintaining high levels of material breathability. Headgear embodiments may be designed in a manner that deviates from a "medical product" aesthetic but reflects a "lifestyle product" aesthetic, and creates a higher quality looking product overall. Also, headgear embodiments may incorporate and support more prominent branding through optimal branding locations and increased differentiation of branding from the surrounding material.

Additional Embodiments

Additional embodiments may be generated by combining one or more features of any one of the above-described embodiments with one or more features of the other of the above-described embodiments. Such additional embodiments may include one or more of the following features:

Stability
Captures the crown region of the head sufficiently;
Decouples headgear forces well;
Accommodates different sleeping positions;
Good stability on the face (hugs the face and uses the structure of the face for stability); and/or
Good stability of the headgear on the head (no slipping around).
Comfort
Reduce or eliminate irritation/marking on cheeks (swoosh marks);
Reduce or eliminate irritation caused by buckle;
Reduce or eliminate marking/irritation occurring on the upper ear lobes; and/or
Good tactile quality (soft feel wherever possible).
Usability
Intuitive fitting;
Simple and quick adjustment;
Minimal number of adjustments to achieve a good fit;
Ability to make precision adjustments to maintain a good seal;
Set and forget functionality; and/or
Minimal number of parts.
Unobtrusiveness
Low perceived presence by the user (avoids the user's line of sight);
Minimal overall size/visual impact of interface when on user; and/or
Minimal skin contact and low likelihood of overheating the patient or claustrophobia.
Aesthetics and Branding
Lifestyle product aesthetic ("non medical");
Improved overall function through aesthetics (e.g., visual cues for positioning and adjustment);
"High comfort" visual appearance;
Aesthetically pleasing and high quality user-product relationship building features (e.g., customizable features, colors, etc.);
Prominence of branding; and/or
High quality of branding.
Cleaning/Maintenance
Ease of assembly/disassembly (e.g., familiarity);
Ease of cleaning all surfaces (e.g., includes areas that do not become clogged or trap dirt); and/or
Overall durability.

3 Connection with Air Supply

Elbow

As shown in FIGS. 18-1 to 18-7, the elbow 5040 (e.g., constructed of a relatively hard plastic material such as polypropylene, Hytrel, HTPC) includes a first portion 5042 provided to the frame 5030 and a second portion 5044 provided to a short tube 5070 (e.g., see FIGS. 14-1 and 17) adapted to be connected to an air delivery tube.

The elbow 5040 is structured to provide easy assembly/disassembly to the frame, rotation with respect to the frame with acceptable level of torque, seal, and venting. In addition, the elbow directs air into the patient interface without significant flow restrictions.

In an embodiment of the elbow (see FIGS. 18-1 to 18-7), D1 may be about 15-20 mm, e.g., 17.99 mm, D2 may be about 10-20 mm, e.g., 15 mm, D3 may be about 5-10 mm, e.g., 7.8 mm, D4 may be about 5-15 mm, e.g., 9.6 mm, and D5 may be about 10-15 mm, e.g., 13.5 mm Although specific dimensions and ranges are indicated, it is to be understood that these dimensions and ranges are merely exemplary and other dimensions and ranges are possible depending on application. For example, the exemplary dimensions may vary by 10-20% or more or less depending on application.

As illustrated, the second portion 5044 tapers to a smaller internal diameter at D5 (e.g., about 13.5 mm), e.g., for sealing the lip 5075.1 of the tube against surface 5048 (e.g., see FIG. 17). Moreover, gas passes from a smaller diameter at D5 (e.g., about 13.5 mm) to a larger diameter at D2 (e.g., about 15 mm), which reduces the pressure drop through the elbow to maintain a sufficient impedance level.

In the illustrated embodiment, the first portion 5042 is angled about 90° with respect to the second portion 5044. This arrangement provides a low profile in use, e.g., 90° elbow and attached tubing does not stick outwardly when rotated, reduces mask size. In addition, the 90° elbow provides a quieter venting arrangement and is easier to tool/manufacture with a 90° flat blank at the surface for the vent hole pins. However, the first and second portions of the elbow may have other suitable angles with respect to one another, e.g., 120°. In an alternative embodiment, the elbow may include one or more baffles along its interior.

Frame Attachment

The first portion 5042 of the elbow 5040 includes a tapered retaining portion 5043.1, a circumferential flange 5043.2, and a circumferential rib 5043.3 between the retaining portion 5043.1 and the flange 5043.2. The first portion 5042 is engageable with the tube portion 5035 of the frame 5030. The tube portion 5035 include an inwardly facing circumferential rib 5035.1 at an inner end and an inwardly facing circumferential sealing lip 5035.2 at an outer end (e.g., see FIGS. 15-10 and 15-11).

The first portion 5042 of the elbow 5040 is inserted into the tube portion 5035 of the frame 5030 and the retaining portion 5043.1 engages the rib 5035.1 with a snap-fit (relatively hard elbow snaps into relatively soft frame). That is, the retaining portion 5043.1 deforms and compresses the rib 5035.1 inwardly until the retaining portion 5043.1 reaches its operative position in which the rib 5035.1 springs back to original form, as shown in FIG. 17. As illustrated, the sealing lip 5035.2 of the frame 5030 provides a seal around the perimeter of the first portion 5042 and/or the sloped surface of portion 5043.2 of the elbow 5040. Because the frame provides a relatively soft part to engage the relatively hard elbow, no additional seal ring is needed to seal between the frame and elbow.

The circumferential flange 5043.2 and circumferential rib 5043.3 (rib 5043.3 may be optional) provided to the elbow 5040 help prevent rotation of the elbow 5040 relative to the frame (e.g., prevents rocking or wiggle and keeps elbow and frame concentric). In an embodiment, the circumferential rib 5043.3 may be spaced apart ribs (rather than continuous) to reduce friction.

In the illustrated embodiment, a small clearance may be provided between the circumferential flange 5043.2 and the edge of the opening into the internal volume of the frame, e.g., only contact points are the sealing lip 5035.2 with the elbow and the retaining portion 5043.1 with the frame. Thus, the insertion length of the elbow into the frame is about the length of D4 (e.g., about 9-11 mm (e.g., 9.6 mm)), which provides sufficient length to securely retain the elbow to the frame. In addition, the elbow does not engage the frame along its entire length, so less friction is provided between the elbow and the frame. In an embodiment, the ratio of the insertion length (D4) to the related elbow diameter (D2) may be about 50-75%, e.g., 9.6/15 or about 65%.

Also, the sealing lip 5035.1 is angled towards the inlet of the frame opening and engages a lower end of the circumferential flange 5043.2, as shown in FIG. 17. This arrangement allows the sealing lip 5035.1 to maintain a seal with the elbow 5040, e.g., when tube drag or other force applied to elbow causes bending movement of the first portion with respect to the frame. For example, as the elbow pivots with respect to the frame due to an external force, the sealing lip 5035.1 resiliently maintains contact with the tapered surface of the circumferential flange 5043.2.

However, it should be appreciated that the elbow 5040 may be attached to the frame 5030 in other suitable arrangements, e.g., ball joint.

FIGS. 18-9-1 to 18-18-3 illustrate elbow to frame attachments according to alternative embodiments of the present invention.

FIGS. 18-9-1 to 18-9-3 illustrate an elbow 7340 attached to the frame 7330 by a ball and socket type joint. In the illustrated embodiment, the ball 7345 is provided to the elbow 7340 and the socket 7335 is provided to the frame 7330. However, it should be appreciated that the opposite arrangement is possible, i.e., socket on elbow and ball on frame.

As illustrated, the socket 7335 on frame 7330 provides a generally rounded inwardly facing surface, and the ball 7345 on elbow 7340 has a generally rounded or spherical outwardly facing surface adapted to engage the socket 7335 with an interference fit.

Also, the frame 7330 provides a channel 7333 structured to retain the nasal prong assembly, and the main body of the elbow 7340 includes a relatively flat portion for a vent arrangement. The vent arrangement includes a plurality of vent holes 7328 for gas washout. In the illustrated embodiment, the vent holes 7328 are arranged in a generally circular or arcuate manner. However, other suitable hole arrangements, hole numbers, and/or hole shapes on the elbow are possible.

FIGS. 18-10-1 to 18-10-3 illustrate a relatively soft elbow 7440 (e.g., relatively semi-rigid or soft plastic material (e.g., hard silicone (e.g., 30-80 shore A silicone))) attached to a frame 7430. As illustrated, the frame 7430 includes a tube portion 7435 with a rib 7435.1 and an inwardly facing sealing surface 7435.2. The elbow 7440 includes a retaining portion 7443.1 adapted to engage the rib 7435.1 (e.g., with a snap fit) and a sealing end portion 7443.2 adapted to engage the sealing surface 7435.2 to provide a seal. Also, the elbow 7440 includes a flange 7443.3 adapted to engage the end face of the tube portion 7435. Because the elbow provides a relatively soft part to engage the frame, no additional seal ring is provided to seal between the frame and elbow.

Also, the frame 7430 provides a channel 7433 structured to retain the nasal prong assembly, and the main body of the elbow 7440 includes a relatively flat portion for a vent arrangement. The vent arrangement includes a plurality of vent holes 7428 for gas washout. In the illustrated embodiment, the vent holes 7428 are arranged in a generally circular or arcuate manner. However, other suitable hole arrangements, hole numbers, and/or hole shapes on the elbow are possible.

FIGS. 18-11-1 to 18-11-3 illustrate a relatively soft elbow 7540 attached to a frame 7530 and to a relatively hard swivel 7560. As illustrated, the frame 7530 includes a tube portion 7535 with a rib 7535.1 and an inwardly facing sealing surface 7535.2. One end of the elbow 7540 includes a retaining portion 7543.1 adapted to engage the rib 7535.1 (e.g., with a snap fit) and a sealing end portion 7543.2 adapted to engage the sealing surface 7535.2 to provide a seal. Also, the elbow 7540 includes a flange 7543.3 adapted to engage the end face of the tube portion 7535.

The swivel 7560 includes a rib 7565.1 and an inwardly facing sealing surface 7565.2. The other end of the elbow 7540 includes a retaining portion 7545.1 adapted to engage the rib 7565.1 (e.g., with a snap fit) and a sealing end portion 7545.2 adapted to engage the sealing surface 7565.2 to provide a seal. Also, the elbow 7540 includes a flange 7545.3 adapted to engage the end face of the swivel 7560.

Because the elbow provides a relatively soft part to engage the frame and swivel, no additional seal ring is provided to seal between the frame and elbow or between the swivel and elbow.

Also, the frame 7530 provides a channel 7533 structured to retain the nasal prong assembly, and the main body of the elbow 7540 includes a relatively flat portion for a vent arrangement. The vent arrangement includes a plurality of vent holes 7528 for gas washout. In the illustrated embodiment, the vent holes 7528 are arranged in a generally circular manner (e.g., concentric circles). However, other suitable hole arrangements, hole numbers, and/or hole shapes on the elbow are possible.

FIGS. 18-12-1 to 18-12-3 illustrate a relatively hard elbow 7640 with a seal ring attached to a frame 7630. As illustrated, the frame 7630 includes a tube portion 7635 with a shoulder 7635.1. The elbow 7640 includes a retaining portion 7643.1 adapted to engage the shoulder 7635.1 (e.g., with a snap fit). A slot 7641 is provided to opposing sides of the elbow 7640 to facilitate deflection during its snap-fit attachment.

Also, the frame 7630 provides a channel 7633 structured to retain the nasal prong assembly, and the main body of the elbow 7640 includes a relatively flat portion for a vent arrangement. The vent arrangement includes a plurality of vent holes 7628 for gas washout. In the illustrated embodiment, the vent holes 7628 are arranged in a generally circular or arcuate manner. However, other suitable hole arrangements, hole numbers, and/or hole shapes on the elbow are possible.

FIGS. 18-13-1 to 18-13-3 illustrate a relatively soft elbow 7740 attached to a frame 7730 with a relatively large frame bore. As illustrated, the frame 7730 includes a tube portion 7735 with a rib 7735.1. The elbow 7740 includes a retaining portion 7743.1 adapted to engage the rib 7735.1 (e.g., with a snap fit). Also, the elbow 7740 includes a flange 7743.3 adapted to engage the end face of the tube portion 7735.

Also, the frame 7730 provides a channel 7733 structured to retain the nasal prong assembly, and the main body of the elbow 7740 includes a relatively flat portion for a vent arrangement. The vent arrangement includes a plurality of vent holes 7728 for gas washout. In the illustrated embodiment, the vent holes 7728 are arranged in offset rows (e.g., six offset rows). However, other suitable hole arrangements, hole numbers, and/or hole shapes on the elbow are possible.

In addition, the elbow 7740 includes a baffle 7750 that is arranged to divide the upper arm of the elbow into an air delivery passage and an exhaust passage. As illustrated, the baffle has a wavy or w-shaped configuration. However, other baffle shapes are possible.

FIGS. 18-14-1 to 18-14-3 illustrate a relatively soft elbow 7840 attached to a frame 7830 with a large frame bore. As illustrated, the frame 7830 includes a tube portion 7835 with a rib 7835.1. The elbow 7840 includes a retaining portion 7843.1 adapted to engage the rib 7835.1 (e.g., with a snap fit). Also, the elbow 7840 includes a flange 7843.3 adapted to engage the end face of the tube portion 7835.

Also, the frame 7830 provides a channel 7833 structured to retain the nasal prong assembly, and the main body of the elbow 7840 includes a relatively flat portion for a vent arrangement. The vent arrangement includes a plurality of vent holes 7828 for gas washout. In the illustrated embodiment, the vent holes 7828 are arranged in offset rows (e.g., three offset rows). However, other suitable hole arrangements, hole numbers, and/or hole shapes on the elbow are possible.

In addition, the elbow 7840 includes a baffle 7850 that is arranged to divide the upper arm of the elbow into an air delivery passage and an exhaust passage. As illustrated, the baffle has a generally flat or planar configuration. However, other baffle shapes are possible.

FIGS. 18-15-1 to 18-15-3 illustrate an elbow 7940 attached to a frame 7930 with a large frame bore. As illustrated, the frame 7930 includes a tube portion 7935 with a rib 7935.1. The elbow 7940 includes a retaining portion 7943.1 adapted to engage the rib 7935.1 (e.g., with a snap fit). Also, the elbow 7940 includes a flange 7943.3 adapted to engage the end face of the tube portion 7935.

Also, the frame 7930 provides a channel 7933 structured to retain the nasal prong assembly, and the main body of the elbow 7940 includes a relatively flat portion for a vent arrangement. The vent arrangement includes a plurality of vent holes 7928 for gas washout. In the illustrated embodiment, the vent holes 7928 are arranged in an arc and each vent hole includes a generally oval or capsule shape. However, other suitable hole arrangements, hole numbers, and/or hole shapes on the elbow are possible.

In addition, the elbow 7940 includes a baffle 7950 that is arranged to divide the upper arm of the elbow into an air delivery passage and an exhaust passage. As illustrated, the baffle has a generally inverse U-shaped configuration. However, other baffle shapes are possible.

FIGS. 18-16-1 to 18-16-3 illustrate an elbow to frame attachment similar to that shown in FIGS. 18-15-1 to 18-15-3 and indicated with similar reference numerals. In contrast, the vent holes 7928 are arranged in an arc with a larger radius of curvature, and the baffle 7950 has a larger radius of curvature (i.e., similar to the vent hole arc).

FIGS. 18-17-1 to 18-17-3 illustrate an elbow to frame attachment similar to that shown in FIGS. 18-15-1 to 18-15-3 and indicated with similar reference numerals. In contrast, each vent hole 7928 has a general U-shape and the vent holes are arranged on a flat portion that is recessed with respect to the exterior surface of the elbow. In addition, the baffle 7950 has a generally U-shaped configuration.

FIGS. 18-18-1 to 18-18-3 illustrate an elbow to frame attachment similar to that shown in FIGS. 18-15-1 to 18-15-3 and indicated with similar reference numerals. In contrast, the vent holes 7928 are arranged in offset columns and arranged on a flat portion that is recessed with respect to the exterior surface of the elbow. In addition, the baffle 7950 has a generally U-shaped configuration.

Vent Arrangement

A vent arrangement 5045 is positioned on a relatively flat portion of the elbow 5040. As illustrated, the relatively flat portion has a generally circular shape.

In the illustrated embodiment, the vent arrangement 5045 includes a plurality of holes 5047 arranged in concentric rings, e.g., three concentric rings R1, R2, R3. As shown in FIGS. 18-1, 18-2, and 18-7, the center ring R1 includes 3-10 holes, e.g., 6 holes, the intermediate ring R2 includes 5-30 holes, e.g., 14 holes, and the outside ring R3 includes 5-50 holes, e.g., 22 holes.

In the illustrated embodiment, each hole 5047 may have a generally part conic shape, including opposed walls that converge from a larger (inside) diameter to a smaller (outside) diameter, as viewed in the direction of exhausted gas (see FIGS. 18-5 and 18-6). In an embodiment, the maximum length of each hole 5047 may be about 2.5 mm, and the smaller outside diameter may be about 0.7 mm with a 5° draft angle.

However, it should be appreciated that the vent arrangement 5045 may include other suitable hole arrangements, hole numbers, and/or hole shapes.

Also, as shown in FIGS. 18-4, 18-5, and 18-7, the elbow provides rounded edges along its interior surface in order to reduce noise at the corners of the elbow. Such arrangement may result in the vent holes of the outside ring R3 being longer than the vent holes of the center and intermediate rings R1, R2 (e.g., see FIG. 18-6).

Elbow with Alternative Vent Arrangement

FIGS. 18-8-1 to 18-8-15 illustrate an elbow 5740 (e.g., constructed of polypropylene) according to another embodiment of the present invention. As illustrated, the first portion 5742 is angled about 90-130°, e.g., 105° with respect to the second portion 5744. In addition, the first and second end portions 5742, 5744 provide an alternative structure for engaging the frame and short tube respectively.

The vent arrangement 5745 is positioned on a relatively flat portion of the elbow 5740 and includes a plurality of holes 5747 arranged in offset rows. As shown in FIGS. 18-8-5 and 18-8-8, the arrangement 5745 may include 1-15 rows, e.g., 9 rows, with each row including 3-10 holes, e.g., 5, 6, or 7 holes. In an embodiment, the vent arrangement may include 40-70 total holes, e.g., 53 holes.

In the illustrated embodiment, each hole 5747 may have a generally part conic shape, including opposed walls that converge from a larger (inside) diameter to a smaller (outside) diameter, as viewed in the direction of exhausted gas (see FIGS. 18-8-11, 18-8-13, and 18-8-15). In an embodiment, the smaller outside diameter D1 may be about 0.6 mm with a draft angle D2 of about 5°. Edges of the larger (inside) diameter may be rounded, e.g., inlet radius D4 about 0.25-0.5 mm (e.g., 0.34 mm).

In this embodiment, each vent hole 5747 includes a diameter (about 0.6 mm) that is smaller than the diameter of each vent hole for ResMed's Swift II mask (about 0.7 mm).

Thus, in comparison to ResMed's Swift II mask, each vent hole 5747 provides a smaller venting area (venting area=number of holes×area of each hole), less vent flow, and a smaller pitch (distance between holes).

As shown in FIGS. 18-8-10, 18-8-12, and 18-8-14, tooling for the elbow 5740 provides a smooth inner path, e.g., the elbow includes rounded edges along its interior surface, e.g., in order to reduce noise. Such arrangement may result in outer vent holes being longer than inner vent holes, e.g., length D5 may be about 2-3 mm (e.g., 2.47 mm) and length D6 may be about 1.5-2.5 mm (e.g., 1.81 mm) as shown in FIG. 18-8-13. In FIG. 18-8-11, the vent holes along the vertical axis have a length D3 of about 1.5-2.5 mm, e.g., 1.7 mm.

However, it should be appreciated that the vent arrangement 5745 may include other suitable hole arrangements, hole numbers, hole sizes, and/or hole shapes.

The elbow 5740 is structured to provide an interface between the frame and the short tube assembly (e.g., see FIGS. 20-5-1 to 20-5-6). Venting of the mask system is provided by the array of small vent holes 5747 located in the elbow with a constant exhaust direction regardless of the elbow rotation position. The elbow decouples twisting forces from tubing to the frame by providing a 360 degree rotation with the frame. This rotation (in conjunction with the optional tube retainer) also allows the user to position the short tube and air delivery tubing in a preferred location for sleeping. The elbow to frame interface ensures that the elbow remains connected during use and allows the user to quickly assemble and disassemble tubing during the night and for easy cleaning.

The elbow includes one or more of the following functions: to provide a means of attaching tubing to the frame; to provide adequate area for a vent (due to limited space on the rest of the patient interface); to provide a total vent flow (in conjunction with the rest of the mask system) for safe use and flow generator compatibility; to provide an impedance (in conjunction with the rest of the mask system) within specification of ResMed's "Mirage" flow generator curve setting; to provide adequate $CO_2$ washout performance (in conjunction with the rest of the mask system); to provide adjustment of the tube position through 360 degree rotation; to provide a system of decoupling tube drag forces through rotation and/or swiveling actions; to provide easy assembly and disassembly with the mask; to provide adequate vent noise performance; to provide a vent direction that does not adversely affect the comfort of the patient or bed partner; to allow the user to easily clean the mask; to be unobtrusive and both visually and physically minimal in order to avoid the user feeling stifled or claustrophobic; and/or to be aesthetically pleasing and reflect high quality and style.

In an embodiment, the total flow specification for the patient interface of FIGS. 22-23-1 to 22-23-6 may be lower than the flow specification for ResMed's Swift II mask (e.g., minimum flow curve at 4 cmH2O to 20 cmH2O about 75% of Swift II nominal flow curve). The advantages of having a lower flow specification are reduced mask noise and reduced discomfort of jetting air inside the user's nose. In an embodiment, the length of the elbow inlet is sufficiently long to provide time for the flow to become laminar.

In the illustrated embodiment, the vent arrangement 5745 is located on the elbow 5740. Alternatively, vents may be located at other suitable locations, e.g., on the frame, short tube, etc. In the illustrated embodiment, the vent design consists of an array of 53 holes of nominal diameter of 0.6 mm to provide adequate vent flow.

Features of the vent arrangement will now be described in greater detail. The vent pin blankoff provides a flat surface with about 75° blankoff. The elbow angle of 105° improves aesthetics and optimizes range of tubing positioning. The 105° elbow may also be quieter than a 120° elbow, for example. The flat surface for blankoff minimizes tooling risk, tool life/maintenance and flash.

The smaller vent hole size of 00.6 mm produces less noise and provides acceptable $CO_2$ performance with humidification maintained.

The vent hole draft (i.e., converging vent hole with 5° included draft) produce less noise.

The vent hole inlet radius of about 0.34 mm is larger (than ResMed's Swift II, about 0.25 mm) for less noise (e.g., maximum possible between holes).

The vent hole length may range from about 1.7 mm for inner holes to 2.5 mm for outer holes. A longer vent hole length is provided for less noise. The hole length varies, e.g., due to the curvature of the elbow, e.g., curvature provided for a smoother internal wall transition between the inlet and outlet which produces less noise.

As shown in FIG. 18-8-8, the vent hole spacing includes D7 of about 1.45 mm and D8 of about 0.70 mm. The spacing between centers of about 1.45 mm corresponds to a minimum distance of approximately 0.7 mm between the tangency lines of the inlet radii, e.g., for tooling.

In an embodiment, the vent hole diameter, draft, inlet radius, length and spacing may be sized to fit in required space.

The internal elbow geometry provides an internal wall transition between the inlet and outlet that is relatively smooth. The smoother internal wall transition between the inlet and outlet produces less noise. As illustrated, the internal curvature is gradual while still maintaining an acceptable hole length for the outer holes due to the flat blank-off surface area.

The low mask noise of the patient interface may be achieved through one or more of the following features: lower flow specification (reduced flow means reduced noise); smaller vent hole diameter of 00.6 mm; increased vent hole length (for the outer holes) and larger inlet radius; elbow internal transition between inlet and outlet as gradual as possible; close spacing (high concentration) of vent holes leads to interaction between adjacent jets that reduces the noise; negligible leak in the rest of the patient interface which contributes to overall mask noise.

In an embodiment, the vent arrangement has a sound power of about 25 dBA (e.g., also due to the lower flow at the same pressure), which is significantly quieter than vents known in the art (e.g., ResMed's Swift II (28-29 dBA), Opus (31 dBA), OptiLife (34 dBA)).

As shown in FIG. 18-8-16, the vent direction of the elbow 5740 is in the same direction as ResMed's Swift II mask (indicated by darker portion S2). The vent direction does not change with elbow rotation but is fixed in an axial direction. The 30 degree angle between the nasal prong assembly to frame interface and the prong to patient interface enables a vent direction equivalent to ResMed's Swift II mask to be achieved. Also, minor adjustments to the vent direction are possible by adjusting the yoke-to-frame orientation (the prong to patient seal can be maintained due to the flexibility in the nasal prong assembly).

The smaller vent hole diameter and the lower flow specification assists in minimizing jetting. Also, because the vent exhausts in a narrow beam, the jetting is confined to a smaller area and therefore potentially less likely to affect (or more easily managed by) the patient or bed partner.

The elbow design has been structured to suit the impedance requirements of the ResMed's "Mirage" flow curve. Matching the impedance characteristics in this way assists with ensuring compatibility with ResMed flow generators. However, it should be appreciated that the elbow may be used with other suitable flow generators.

FIG. 18-8-16 shows the elbow 5740 attached to the frame 6030 and nasal prong assembly 6020 described above. In the illustrated embodiment, the elbow to frame interface is a continuous annular snap fit between a polypropylene elbow and a silicone frame (70-75 Shore A durometer). This hard-to-soft type interface has a number of advantages with respect to the elbow-to-frame interface as detailed below.

When the elbow is assembled to the frame a thin silicone lip 6035.2 (thickness of 0.3 to 0.4 mm or less) is deflected creating an interference seal with the elbow sealing surface 5741. The amount of interference is determined by both the axial stackup to the retention feature and the diametrical stackup. This interface effectively provides a zero leak interface under static operating conditions. The amount of interference has been designed to accommodate some tube drag.

The retention of the elbow to the frame is important to ensure that the short tube assembly does not inadvertently disconnect during use. A 10N tube drag load was considered to be sufficient retention force in all directions, e.g., at this force the mask seal to the patient is broken and likely to be completely clear of the face. The retention of the elbow is provided by a snap engagement of 0.7 mm all around the circumference. A 60 degree return angle A1 on the elbow barb 5743.1 was implemented to assist disassembly by the user while maintaining sufficient retention.

Assembly and disassembly should be easy enough to be performed by a typical user with limited dexterity considering the small size of the parts. Assembly of the elbow to the frame is assisted with a 30 degrees insertion angle A2 on the elbow barb 5743.1. The intent was to have an axial assembly force under about 40N. Subjectively assembly is actually easier as the user is more likely to manipulate the elbow into position with some angle or twist and this requires less force. Elbow disassembly is linked with elbow retention however disassembly is realistically easier than the retention force as the user can peel the elbow out with much less force.

The elbow can rotate 360 degrees within the frame to provide flexibility in tube positions and decouple tube drag forces during sleep movement. Due to the hard-to-soft interference for sealing of the elbow to frame, some rotational resistance may be provided. Some resistance may be preferable over freely rotating as the tube can be located in a certain direction without it inadvertently swinging around and disturbing the wearer. Factors influencing the rotation torque include the sealing lip interference, the sealing lip thickness, and/or the silicone frame hardness.

Sufficient clearance elsewhere in the interface (e.g., between the elbow flange 5749 and frame 6030) was ensured across tolerance ranges to ensure minimal contact and torque contribution. Clearance is controlled to some extent to minimize movement of the elbow within the frame that may lead to leakage under a tube drag load.

In an embodiment, the elbow rotation torque specification is less than 30 Nmm and subjectively is considered to be acceptable if the short tube can rotate under its own weight.

FIG. 18-8-17 shows the interface between the elbow 5740 and the short tube 5770, e.g., barbed, friction-type fit. The short tube material, e.g., made of Hytrel 5556, provides greater flexibility and durability and has a much higher thermal resistance enabling thermal disinfection at higher temperatures. The elbow/short tube interface may have other suitable arrangements, e.g., snap fit, swivel fit, etc.

The 105 degree angle elbow includes one or more of the following advantages: reduces the chance of the short tube impacting on the patient's chest while ensuring that the tube can be angled back far enough to route the tubing over the head; less noise; less obtrusive.

Wall thickness variation of the elbow was minimized however, some thicker wall sections were implemented to improve the aesthetics and unobtrusiveness of the elbow. The circular groove in the elbow flange 5749 was implemented to remove material bulk from this area of the elbow, improve molding quality, and/or dimensional control.

Short Tube and Swivel

The short tube 5070 is adapted to interconnect the patient interface with a standard air delivery tube (e.g., 22 mm tube). As shown in FIGS. 14-1 and 20-1, the short tube 5070 includes a tube portion 5072 and end fittings 5074 provided to respective ends of the tube portion 5072. The end fittings 5074 include the same structure, with one of the end fittings 5074 attachable to the second portion of the elbow 5040 and the other of the end fittings attachable to a swivel 5090 adapted to be connected to an air delivery tube. Such arrangement facilitates assembly and disassembly (e.g., for cleaning, disinfecting, etc.), provides a seal to reduce leak, and provides a limited number of parts to reduce assembly/disassembly steps.

The tube portion 5072 (e.g., 13-15 mm inner diameter (e.g., 13.5 mm inner diameter)) may have a reduced length (e.g., 30-40 mm (e.g., 35 mm)) to reduce impedance. Also, the width, height, pitch, and/or helical rib of the tube portion 5072 may be adjusted to adjust the flexibility of the short tube. For example, the size of the pitch of the helix around the tube portion may be adjusted to adjust the flexibility.

End Fittings

Each end fitting 5074 (e.g., constructed of a semi-rigid material such as TPE, silicone) may be integrally formed in one piece with the tube portion 5072 (e.g., constructed of a hard plastic material (e.g., 45-55 shore D hardness) such as polypropylene, PTE, Dupont Hybrid, Hytrel, Ritaflex, opaque ribs, translucent film, or combinations thereof) or may be formed separately from the tube portion 5072 and attached thereto (e.g., glued, welded). In an embodiment, the end fittings 5074 may be overmolded to respective ends of the tube portion 5072.

As best shown in FIGS. 20-2 and 20-4, each end fitting 5074 includes a sealing lip 5075.1 at its free end, an annular flange 5075.2 that provides a snap feature, and one or more annular ribs 5075.3 (e.g., two ribs) that provide finger grips.

Swivel Attachment

The swivel 5090 (e.g., constructed of a hard plastic material such as polypropylene, Hytrel, HTPC) includes a first portion 5092 adapted to connect to the short tube 5070 and second portion 5094 adapted to connect to an air delivery tube.

As shown in FIGS. 20-2 to 20-4, the first portion 5092 provides diametrically opposed windows 5095.1 through the swivel side wall and an inwardly facing tapered surface 5095.2. The second end portion 5094 provides a tapered side wall for connection to the air delivery tube. Also, spaced apart flanges 5096 are provided to the swivel 5090 which defines a space therebetween for a tube retainer clip adapted to retain the air delivery tube.

The end fitting 5074 of the short tube 5070 is structured to engage the first portion 5092 of the swivel 5090 with a snap or press fit, i.e., annular flange 5075.2 resiliently deflects into windows 5095.1. In addition, the sealing lip 5075.1 of the end fitting 5074 resiliently deflects into engagement with the inwardly facing tapered surface 5095.2 to provide an interference fit for sealing around the interior perimeter of the swivel. The first portion 5092 of the swivel 5090 also includes cut outs 5098 (see FIGS. 20-2 and 20-3) to provide finger clearance to facilitate assembly/disassembly of the end fitting 5074 to the swivel 5090.

In an alternative embodiment, the swivel may be overmolded to an end fitting of the short tube, e.g., to reduce the number of components, size, etc. In other alternatives, the swivel may be bonded with glue or welded to the end fitting.
Elbow Attachment The other of the end fittings 5074 of the short tube 5070 is attachable to the elbow 5040 in a similar manner as the swivel 5090. Specifically, as shown in FIG. 17, the end fitting 5074 of the short tube 5070 is structured to engage the second portion 5044 of the elbow 5040 with a snap fit, i.e., annular flange 5075.2 resiliently deflects into windows 5046 (see FIGS. 18-1 and 18-3). In addition, the sealing lip 5075.1 of the end fitting 5074 resiliently deflects into engagement with the inwardly facing tapered surface 5048 to provide an interference fit for sealing around the interior perimeter of the elbow. The second portion 5044 of the elbow 5040 also includes cut outs 5049 (see FIGS. 18-1 and 18-3) to provide finger clearance to facilitate assembly/disassembly of the end fitting 5074 to the elbow 5040.

FIGS. 20-5-1 to 20-5-6 illustrate a short tube 5770 with elbow 5740 and swivel 5790 according to another embodiment of the present invention. The elbow 5740 (described above in reference to FIGS. 18-8-1 to 18-8-7) and swivel 5790 may be attached to respective ends of the short tube 5770, e.g., by friction fit, mechanical interlock, and/or overmolding. In the illustrated embodiment, a small bore tube adaptor 5791 is provided to the short tube for coupling the swivel 5790, e.g., adaptor provides barbed connection.

The short tube includes one or more of the following functions: connects the air supply to the patient interface from the flow generator within an acceptable level of impedance level as specified by system requirement; reduces forces that may de-stabilize the mask and sealing because of the tube drag that weight of the flow generator tube and tangling of this tube may cause; reduces visual and physical obtrusiveness of the overall mask size; the inside of the tube is smooth to minimize generating noise due to air turbulence; the stiffness of the tube shall be sufficient to prevent kinking or stretched under normal usage conditions; tube fittings shall not have any smell; the tube shall have thermal insulation properties to reduce condensation build-up or "raining" in the tube; aesthetically pleasing and reflect high quality and style; the tube should be easy to assemble/disassemble from the mask; total leak in the short tube assembly should not cause the total mask flow to be outside the specified flow limit; the tube end fitting should have a finger grip area, an area that can hold on to during assembly and disassembly of the tube from the elbow or from the swivel.

In an embodiment, the length of the tube is about 200-400 mm, e.g., 300 mm, the elbow to tube retention is more than about 20N, and the swivel to tube retention is more than about 20N.

The short tube may also include one or more of the following features:

Through Impedance: The through impedance characteristics in the short tube assembly (e.g., short tube and end fittings or connectors) should not cause the mask system impedance to be elevated above acceptable limits. The length and the diameter of the short tube, surface finish inside the connectors and in the short tube, the shape of the elbow fitting, and amount of change in flow direction may be contributing factors that affect the through impedance in the short tube assembly. In addition, the position of the airflow inlet in relation to the nasal prong assembly may contribute to the airflow impedance.

Kinking and Occlusion: The short tube may be sufficiently rigid or constructed to minimize the possibility of kinking when placed over the top of bedrails or through the top of doors of incubators. The short tube may be structured to prevent occlusion when placed in areas around the patient, including when the patient's head or arm is on the short tube. The resistance to kinking and occlusion of the short tube can be based on the material strength of the short tube, the thickness of the short tube walls and the ribs, and the short tube dimensions such as the length, the pitch distance of the helix, and the diameter of the short tube.

Flexibility of the Short Tube: The short tube should be sufficiently flexible to reduce any forces applied to the mask system during any movement of the air tubes. Movement of the short tube towards different elbow positions should not cause extra leakage between the nasal prongs and nasal cavity.

Leakage in the Short Tube Assembly: In an embodiment, the leakage in the short tube assembly is less than 1 L/min @ 20 $cmH_2O$.

Tube Retention: In an embodiment, the short tube assembly is structured to withstand 30 $cmH_2O$ of pressure for about 12 hours without dislodgment of parts, and the connection of the parts is structured to withstand 20 N of pull force at various angles without fracturing or detaching from the mask elbow (force limit is about double the maximum bearable force which could be applied to person's face).

Swivel Rotational Requirements: The purpose of the swivel is to reduce application of any torsion forces to the mask system when the patient changes sleeping positions. The swivel can rotate through 360 degrees relative to the tube adaptor or lower swivel. In an embodiment, the swivel will not squeak during normal movement of the short tube or the mask system. In an embodiment, the swivel may securely snap-fit onto the lower swivel.

Comfort Factor: The short tube may be structured to optimize comfort when the patient moves during sleep. For example, all the parts in the short tube assembly may have a substantially smooth finish on its outer surface.

Assembly Integrity: In an embodiment, the short tube assembly does not have parts that are likely to catch bedclothes and dislodge the mask system or interrupt the seal.

Biocompatibility: In an embodiment, all short tube components are biocompatible.

Chemical Human Factors: In an embodiment, the tube assembly is easy to assemble and disassemble. For example, the components may be intuitive to assemble and disassemble, and may be fail safe (only able to be assembled in one way) if ends of the short tube assembly have different connection.

Dislodging: The mask system may be structured so that small parts cannot dislodge and be inhaled.

Durability During Use: The short tube assembly (including mask) may be durable or disposable.

In an embodiment, the short tube may have a diameter of about 13-13.5 mm (e.g., 13.5 mm) and a length of about 200-250 mm (e.g., 250 mm). However, other dimensions are possible as noted above.

The short tube may be manufactured from Polyolefin (e.g., which allows the tube to be made transparent), Hytrel (e.g., Hytrel 5556), or Riteflex materials. In an embodiment, the short tube and connectors may be made from a combination of Hytrel or Riteflex material to allow overmolding of the short tube on the connectors.

4 Other Aspects

Patient Interface

FIGS. 1-1 and 2-1 to 2-2 illustrate a patient interface or mask system according to an embodiment of the present invention. As illustrated, the patient interface includes a nasal prong assembly 20 (FIGS. 2-1 to 2-2) adapted to provide an effective seal or interface with the patient's nose and headgear 50 (FIG. 1-1) adapted to support the patient interface in a desired position on the patient's head.

Comfort and Seal

Embodiments of the invention are directed towards patient interfaces having structure to provide a comfortable and effective seal with the patient's face. Moreover, embodiments of the invention are directed towards patient interfaces having improved static sealing performance (e.g., the ability to allow lower strap tension from headgear to create a sealing force) and improved dynamic sealing performance (e.g., the ability to withstand macro-movement from a patient rolling around in bed and maintain a seal and/or to withstand changes in the patient's face in the short term (when the face relaxes and the cheeks fill will pressurized air) and in the long term (if the patient's facial features change, e.g., based on weight change, etc.). For example, embodiments of the invention are directed towards patient interfaces having one or more features that, either alone or in cooperation with other features, provide a unit that as a whole allows a range of movement without breaking seal or losing comfort (e.g., patient can sleep on side without dislodging nasal prongs from the patient's nose). Such interface properties are described in greater detail below.

Alternative Patient Interface Embodiment

FIGS. 13-1 to 13-4 and 14-1 to 14-2 illustrate a patient interface or mask system 5010 according to another embodiment of the present invention. As illustrated, the patient interface 5010 includes a frame 5030, a nasal prong assembly 5020 provided to the frame 5030 and adapted to provide an effective seal or interface with the patient's nose, an elbow 5040 provided to the frame 5030 and adapted to be connected to an air delivery tube that delivers breathable gas to the patient, and headgear 5050 adapted to support the patient interface in a desired position on the patient's head. As illustrated, the patient interface provides a relatively narrow configuration with a central swivel which provides a comfortable interface that allows a range of movement in use (described in greater detail below).

Comfort, Seal, and Allowing Range of Sleeping Positions

As illustrated, the patient interface 5010 provides an arrangement including a low number of components, a relatively small overall size including a relatively small, narrow frame (smaller profile, streamlined, less obtrusive), no seal rings, end caps, or vent caps, relatively thin headgear yokes with reduced obtrusiveness (e.g., less visual obtrusion), easy assembly, enhanced adjustability, and perceivable to be light and small. In addition, the patient interface 5010 provides an arrangement that may be more comfortable for side sleepers and may even allow the patient to be face down while maintaining a seal. For example, the patient interface 5010 allows a range of movement without breaking seal or loosing comfort (e.g., patient can sleep on side without dislodging nasal prongs from the patient's nose).

In an embodiment, as shown in FIGS. 13-2 and 13-4, the patient interface may include a width W (i.e., width of nasal prong assembly) of about 50-60 mm, e.g., 54 mm, a height H (i.e., height from tip of nasal prong to bottom of elbow) of about 65-75 mm, e.g., 69 mm, and a depth D (i.e., depth from edge of nasal prong assembly to edge of elbow) of about 35-45 mm, e.g., 39 mm. These dimensions are merely exemplary, and other dimension are possible depending on application.

Alternative Systems for Positioning and Supporting Nasal Prongs

FIGS. 31-1 to 45-2 illustrate alternative systems for positioning and supporting a pair of nasal prongs in a patient's nares for the provision of respiratory treatment, e.g., CPAP treatment. Aspects of the invention relate to reducing or minimizing the size of such a system.

For example, in an embodiment, ResMed's Swift mask may be reduced in width by relocating tube lugs on the frame to the inside of the frame, the elbow may be shortened, a seal ring may be added to the port plug or elbow (e.g., o-ring), and the yokes may be connected directly to the frame.

FIGS. 31-1 and 31-2 illustrate a mask system 9510 in which the yoke to frame interface 9585 is extended from the yoke 9555 and connected to a narrowed frame/nasal prong assembly 9520. As illustrated, a side tube exit is provided, e.g., to reduce the risk of seal compromise through tube drag.

FIGS. 32-1 and 32-2 illustrate another mask system 9610 in which the yoke to frame interface 9685 is extended from the yoke 9655 and connected to a narrowed frame 9630 and nasal prong assembly 9620. As illustrated, a side tube exit is provided, e.g., to reduce the risk of seal compromise through tube drag. In this embodiment, the yoke 9655 and frame 9630 may be integrally molded as a one piece structure or may be molded as two separate pieces.

FIGS. 33-1 and 33-2 illustrate a mask system 9710 in which nasal prong assembly 9720 is supported by a cradle 9759 provided to the yokes 9755. Such cradle arrangement reduces mask width by shifting rotational support from the ends of the nasal prong assembly (two locations) to the center of the nasal prong assembly (single location).

FIG. 34 illustrates a mask system 9810 in which a Y-piece inlet tube 9870 is provided to the mask for central mounting. The side tube exits on the mask may reduce the risk of seal compromise through tube drag. Such inlet tube may be used with the yoke to frame interfaces shown in FIGS. 32-1 to 33-2.

FIG. 35 illustrates a mask system 9910 in which a simple plastic frame 9930 supports or holds silicone molded prongs 9924 provided to an inlet tube 9970, e.g., prongs inserted through and retained within openings provided to frame. Such arrangement provides a mask system with low part count.

FIG. 36 illustrates a mask system 10010 in which a silicone nasal prong assembly 10020 includes an angular adjustment built into or integrated into the assembly. For example, the nasal prong assembly 10020 may include pins 10021 received in respective openings of the yokes 10055, e.g., friction fit. A cavity 10023 in respective sides of the nasal prong assembly 10020 allow for a degree of rotation.

FIG. 37 illustrates a mask system 10110 in which a silicone nasal prong assembly 10120 is wrapped around a rigid plastic tube 10130. The rigid tube 10130 acts as an air path and two holes 10131 in the rigid tube release pressurized air to the nasal prong assembly 10120. Such arrangement provides a reduction in parts and a reduction in mask width.

FIG. 38 illustrates a mask system 10210 including a rigid inner tube 10230, a flexible silicone outer frame 10231 provided to the tube 10230, and nasal prongs 10224 engaged or pushed into the rigid inner tube 10230. A side tube exit is provided, e.g., to reduce the risk of seal compromise through tube drag.

FIGS. 39-1 and 39-2 illustrate a mask system 10310 including a simple plastic frame 10330 that supports or holds a silicone molded prong interface 10320. As illustrated, the prong interface 10320 includes pins 10321 received in respective openings of the frame 10330, e.g., with a friction fit. Also, the prong interface 10320 includes a tube portion 13023 adapted to engage an inlet tube 10370. The frame 10330 includes openings for engaging respective headgear straps and may act as a rigidizer to headgear straps. Such arrangement provides a mask system with a minimalist design including a low part count and small/narrow footprint.

FIG. 40 illustrates a nasal prong 10424 that is free to rotate or translate along a curved path within a secondary rigid component 10440. Such prong arrangement may be integrated into one or more of the embodiments described above. In an embodiment, each nasal prong may be independently rotated or otherwise adjusted with respect to the secondary rigid component 10440.

In another embodiment, the nasal prong assembly may be reduced in width. For example, FIG. 41-1 illustrates a nasal prong assembly 10520 having a width W and FIG. 41-2 illustrates a nasal prong assembly 10620 having a width w which is about 40% less than that of nasal prong assembly 10520. As shown in FIG. 41-3, the nasal prong assembly 10620 may be secured in position by wrapping each end 10621 of the nasal prong assembly over a lip 10631 on the frame 10630 and then engaging the yoke 10655 over the end 10621.

FIG. 42 illustrates a mask system 10710 without a frame. As illustrated, ends of the nasal prong assembly 10720 (e.g., one piece arrangement) are retained by the yoke 10755 which also supports the elbow 10740.

FIG. 43 illustrates nasal prongs 10824 push-fit to a frame 10830. In an embodiment, overmolded seal rings 10858 may be provided to ends of the frame 10830.

FIG. 44 illustrates another embodiment of a mask system 10910 without a frame. As illustrated, ends of the nasal prong assembly 10920 wrap around the yokes 10955 to seal. The nasal prong assembly 10920 may self seal or a clip may provided to facilitate a seal. The elbow or short tube 10940 may be sealed to the yoke 10955 via an o-ring 10941 (e.g., overmolded to the elbow). In the illustrated embodiment, each side of the mask includes an inlet port (i.e., double sided port) in which one side may be blocked off. Alternatively, only one side of the mask may include a port (i.e., single sided port), therefore no plug may be necessary. The side mounted elbow-to-yoke arrangement may improve stability of the mask, e.g., compared to a front mounted elbow-to-frame/nasal prong assembly arrangement.

FIG. 45-1 illustrates a nasal prong assembly 11020 having a central axis A and FIG. 45-2 illustrates a nasal prong assembly 11120 having a central axis a which is shifted to make the prongs longer in the nose to reduce width. This arrangement may also improve comfort by lifting the prongs off the patient's top lip in use. In an embodiment, the mask system may be provided without a frame so that the yokes 11155 support the nasal prong assembly 11120.

Range of Movement

In an embodiment, the patient interface may be broadly broken down into a pair of nasal prongs adapted to provide an effective seal or interface with the patient's nose and a support arrangement to support the nasal prongs in an operative position on the patient's face. The support arrangement is structured to provide a range of rotational, axial, and lateral movement to the nasal prongs while maintaining a sufficient seal and resisting the application of tube drag and headgear tension to the nasal prongs. In an embodiment, the support arrangement may include everything besides the nasal prongs and even parts of the nasal prongs, e.g., a gusset, a frame, and/or headgear as described above. Thus, the patient interface provides one or more features that, either alone or in cooperation, allow a range of movement without breaking seal or loosing comfort.

While the invention has been described in connection with what are presently considered to be the most practical and preferred embodiments, it is to be understood that the invention is not to be limited to the disclosed embodiments, but on the contrary, is intended to cover various modifications and equivalent arrangements included within the spirit and scope of the invention. Also, the various embodiments described above may be implemented in conjunction with other embodiments, e.g., aspects of one embodiment may be combined with aspects of another embodiment to realize yet other embodiments. Further, each independent feature or component of any given assembly may constitute an additional embodiment. In addition, while the invention has particular application to patients who suffer from OSA, it is to be appreciated that patients who suffer from other illnesses (e.g., congestive heart failure, diabetes, morbid obesity, stroke, bariatric surgery, etc.) can derive benefit from the above teachings. Moreover, the above teachings have applicability with patients and non-patients alike in non-medical applications.

What is claimed is:

1. A patient interface for delivering breathable gas to a patient, the patient interface comprising:
   a substantially rigid frame, the rigid frame comprising,
      a main body including an opening configured to receive a flow of pressurized gas,
      a projection extending from the main body and forming a closed perimeter, the projection having an inner surface configured to direct the flow of pressurized gas and an external surface including a lip, and
      a chamfer;
   a nasal seal assembly comprising,
      a first end having a pair of nasal prongs structured to sealingly communicate with nasal passages of the patient's nose in use,
      a second end opposite the first end, the second end having an opening with a closed perimeter corresponding to the closed perimeter of the projection, wherein an interior surface of the second end includes a complementary lip configured to removably engage the lip of the projection; and
   a positioning and stabilising structure connected to the frame at two discrete points, the positioning and stabilising structure comprising,
      a pair of rigidizers each having a first end connected to the frame and configured to have an inner surface extend at least partially along the patient's cheeks and a second end including a slot, wherein the inner surface of each rigidizer includes a first curvature proximate to the first end and a second curvature transitioning from the first curvature toward the second end, and wherein the first curvature and the second curvature are in opposite directions, and a headgear strap receivable through the slots and configured to contact the patient's head and maintain the pair of nasal prongs in a sealing position on the patient's head.

2. The patient interface of claim 1, wherein a textile material is attached to at least a portion of an inner surface of each rigidizer of the pair of rigidizers, and wherein the textile material is configured to contact the patient.

3. The patient interface of claim 1, wherein the nasal seal assembly is stretchable relative to the frame when connecting or disconnecting the nasal seal assembly from the frame, and wherein the nasal seal assembly is connectable to the frame in only one orientation.

4. The patient interface of claim 1, wherein the chamfer is disposed at a free end of the projection, and wherein the second end of the nasal seal assembly is configured to slide over the chamfer when the nasal seal assembly connects to the frame.

5. The patient interface of claim 1, wherein the first curvature is configured to form a convex shape with respect to the patient in use and the second curvature is configured to form a concave shape with respect to the patient in use.

6. The patient interface of claim 1, further comprising an elbow connected to the frame, wherein the elbow includes a plurality of vent holes configured to allow for gas washout.

7. The patient interface of claim 1, further comprising a short tube that includes a first end and a second end, the first end connected to the patient interface and the second end adapted to connect to an air delivery tube.

8. The patient interface of claim 1, wherein,
the nasal seal assembly is stretchable relative to the frame when connecting or disconnecting the nasal seal assembly from the frame;
a majority of each rigidizer arm is formed with the second curvature, the second curvature configured to conform to a contour of the patient's cheek;
the first curvature is configured to form a convex shape with respect to the patient in use and the second curvature is configured to form a concave shape with respect to the patient in use;
the main body of the frame includes an outer perimeter and wherein an outer perimeter of the lip is less than the outer perimeter of the main body; and
the pair of rigidizers are each connected to the main body at the outer perimeter of the main body.

9. A patient interface for delivering breathable gas to a patient, the patient interface comprising:
a substantially rigid frame, the rigid frame comprising,
a main body including an opening configured to receive a flow of pressurized gas, and
a projection extending from the main body and forming a closed shape, the projection having an inner surface configured to direct the flow of pressurized gas, and an external surface including a lip and a groove, wherein the lip is disposed at a free end of the projection, and wherein the groove is disposed between the lip and the main body;
a nasal seal assembly comprising,
a first end having a pair of nasal prongs structured to sealingly communicate with nasal passages of the patient's nose in use,
a second end opposite the first end, the second end having an opening with a closed shape corresponding to the closed shape of the projection, wherein an interior surface of the second end includes a frame contacting portion configured to be removably receivable within the groove and removably engage the frame, wherein the frame contacting portion includes an inner surface configured to engage the lip in use; and
a positioning and stabilising structure connected to the frame at two discrete points, the positioning and stabilising structure comprising,
a pair of rigidizers each having a first end connected to the frame and configured to extend at least partially along the patient's cheeks and a second end including a slot, and
a headgear strap receivable through the slots and configured to contact the patient's head and maintain the pair of nasal prongs in a sealing position on the patient's head.

10. The patient interface of claim 9, wherein,
the second end of the nasal seal assembly is thicker than the first end of the nasal seal assembly;
the closed shape is a non-circular shape;
the nasal seal assembly is connectable to the frame in only one orientation; and
the nasal seal assembly includes a curved shape, and wherein each nasal prong extends toward the other nasal prong of the pair of nasal prongs.

11. The patient interface of claim 9, wherein each rigidizer of the pair of rigidizers includes a compound curvature having a first curvature and a second curvature in an opposite direction from the first curvature, and wherein each rigidizer includes the first curvature proximate to the first end and the second curvature transitioning from the first curvature toward the second end.

12. The patient interface of claim 9, wherein the external surface of the projection further includes a chamfer, and wherein the second end of the nasal seal assembly is configured to slide over the chamfer when the nasal seal assembly connects to the frame.

13. The patient interface of claim 9, wherein the closed shape is a non-circular shape with a top side, a bottom side, and two connecting sides connecting the top side and the bottom side, wherein the top side is larger than the bottom side, and wherein the nasal seal assembly is connectable to the frame in only one orientation.

14. The patient interface of claim 9, wherein the main body of the frame includes an outer perimeter and wherein an outer perimeter of the lip is less than the outer perimeter of the main body.

15. The patient interface of claim 14, wherein the pair of rigidizers are each connected to the main body at the outer perimeter of the main body.

16. The patient interface of claim 9, wherein the main body includes a slot, and wherein each rigidizer of the pair of rigidizer is received within the slot.

17. The patient interface of claim 9, wherein the nasal seal assembly is stretchable relative to the frame when connecting or disconnecting the nasal seal assembly from the frame.

18. A patient interface for delivering breathable gas to a patient, the patient interface comprising:
a substantially rigid frame, the rigid frame comprising,
a main body including an opening configured to receive a flow of pressurized gas, and
a projection extending from the main body and forming a closed shape, the projection having an inner surface configured to direct the flow of pressurized gas;

a nasal seal assembly comprising,
- a first end having a pair of nasal prongs structured to sealingly communicate with nasal passages of the patient's nose in use,
- a second end opposite the first end, the second end having an opening with a closed shape corresponding to the closed shape of the projection, wherein an interior surface of the second end is configured to removably engage an external surface of the projection; and a positioning and stabilising structure connected to the frame at two discrete points, the positioning and stabilising structure comprising,
- a pair of rigidizers each having a first end connected to the frame and configured to have an inner surface extend at least partially along the patient's cheeks and a second end opposite to the first end, wherein the inner surface of each rigidizer includes a compound curvature having a first curvature proximate to the first end and a second curvature transitioning from the first curvature toward the second end, wherein the first curvature and the second curvature are in opposite directions, and wherein the first curvature is configured to form a convex shape with respect to the patient in use and the second curvature is configured to form a concave shape with respect to the patient in use, and
- a headgear strap connectable to the pair of rigidizers and configured to contact the patient's head and maintain the pair of nasal prongs in a sealing position on the patient's head.

19. The patient interface of claim 18, wherein the main body includes a slot, and wherein each rigidizer of the pair of rigidizer is received within the slot.

20. The patient interface of claim 18, further comprising an elbow connected to the frame, wherein the elbow includes a plurality of vent holes configured to allow for gas washout.

21. The patient interface of claim 18, further comprising a short tube that includes a first end and a second end, the first end connected to the patient interface and the second end adapted to connect to an air delivery tube.

22. The patient interface of claim 18, wherein a textile material is attached to at least a portion of the inner surface of each rigidizer of the pair of rigidizers, and wherein the textile material is configured to contact the patient.

23. The patient interface of claim 18, wherein
the rigid frame further comprises, the external surface of the projection extending from the main body includes a lip and a groove, wherein the lip is disposed at a free end of the projection, and wherein the groove is disposed between the lip and the main body;
an interior surface of the second end of the nasal seal assembly includes a frame contacting portion configured to be removably receivable within the groove and removably engage the frame, wherein the frame contacting portion includes an inner surface configured to engage the lip in use; and
the nasal seal assembly is stretchable relative to the frame when connecting or disconnecting the nasal seal assembly from the frame.

24. The patient interface of claim 23, wherein the closed shape is a non-circular shape with a top side, a bottom side, and two connecting sides connecting the top side and the bottom side, wherein the top side is larger than the bottom side, and wherein the nasal seal assembly is connectable to the frame in only one orientation.

25. The patient interface of claim 18, wherein the main body of the frame includes an outer perimeter and wherein an outer perimeter of the lip is less than the outer perimeter of the main body.

26. The patient interface of claim 18, further comprising a conduit opening passing through the main body and configured to direct the flow of pressurized gas into the nasal seal assembly, wherein the projection is wider than the conduit opening.

27. The patient interface of claim 18, wherein the first curvature includes a smaller radius of curvature than the second curvature.

28. The patient interface of claim 18, wherein,
the main body of the frame includes an outer perimeter and wherein an outer perimeter of the lip is less than the outer perimeter of the main body;
the pair of rigidizers are each connected to the main body at the outer perimeter of the main body, the outer perimeter includes a slot, and wherein each rigidizer of the pair of rigidizer is received within the slot; and
the first curvature includes a smaller radius of curvature than the second curvature.

29. The patient interface of claim 18, wherein the second end of each rigidizer arm includes an eyelet, and wherein the headgear straps are receivable through the eyelets.

30. The patient interface of claim 18, wherein,
a textile material is attached to at least a portion of the inner surface of each rigidizer of the pair of rigidizers, and wherein the textile material is configured to contact the patient;
the first curvature includes a smaller radius of curvature than the second curvature;
a short tube that includes a first end and a second end, the first end connected to the patient interface and the second end adapted to connect to an air delivery tube; and
the second end of the nasal seal assembly includes a frame contacting portion configured to be removably engaged to the frame.

* * * * *